US012612403B2

(12) United States Patent
Deng et al.

(10) Patent No.: US 12,612,403 B2
(45) **Date of Patent: *Apr. 28, 2026**

(54) NITROGEN-CONTAINING HETEROCYCLIC DERIVATIVE INHIBITOR, AND PREPARATION METHOD THEREFOR AND USE THEREOF

(71) Applicants: SHANGHAI HANSOH BIOMEDICAL CO., LTD., Shanghai (CN); JIANGSU HANSOH PHARMACEUTICAL GROUP CO., LTD., Jiangsu (CN)

(72) Inventors: Xinxian Deng, Shanghai (CN); Jiaqiang Dong, Shanghai (CN); Wensheng Yu, Shanghai (CN); Fangfang Jin, Shanghai (CN); Tingjun Wang, Shanghai (CN)

(73) Assignees: SHANGHAI HANSOH BIOMEDICAL CO., LTD., Shanghai (CN); JIANGSU HANSOH PHARMACEUTICAL GROUP CO., LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/309,669

(22) Filed: Aug. 26, 2025

(65) Prior Publication Data

US 2025/0388578 A1 Dec. 25, 2025

Related U.S. Application Data

(63) Continuation-in-part of application No. PCT/CN2024/103568, filed on Jul. 4, 2024.

(51) Int. Cl.

| | |
|---|---|
| ***C07D 471/04*** | (2006.01) |
| ***A61K 31/444*** | (2006.01) |
| ***A61K 31/4985*** | (2006.01) |
| ***A61K 31/513*** | (2006.01) |
| ***A61K 31/519*** | (2006.01) |
| ***C07D 519/00*** | (2006.01) |

(52) U.S. Cl.

CPC .......... *C07D 471/04* (2013.01); *A61K 31/444* (2013.01); *A61K 31/4985* (2013.01); *A61K 31/513* (2013.01); *A61K 31/519* (2013.01); *C07D 519/00* (2013.01)

(58) Field of Classification Search

None

See application file for complete search history.

(56) References Cited

U.S. PATENT DOCUMENTS 11,248,001 B2 * 2/2022 Serrano-Wu ......... C07D 471/04

FOREIGN PATENT DOCUMENTS

| | | | | |
|---|---|---|---|---|
| CN | 113412258 A | 9/2021 | | |
| CN | 113574055 A | 10/2021 | | |
| WO | 2014150326 A1 | 9/2014 | | |
| WO | 2014170786 A1 | 10/2014 | | |
| WO | 2020150473 A2 | 7/2020 | | |
| WO | 2022133529 A1 | 6/2022 | | |
| WO | 2023084449 A1 | 5/2023 | | |
| WO | 2024078620 A1 | 4/2024 | | |
| WO | WO 2025/007915 * | 1/2025 | ........... | C07D 213/74 |

OTHER PUBLICATIONS

English translation of PCT application PCT/CN2024/103568.

Oct. 5, 2024 International Search Report issued in International Patent Application No. PCT/CN2024/103568.

Oct. 5, 2024 Written Opinion of the International Searching Authority issued in International Patent Application No. PCT/CN2024/103568.

* cited by examiner

*Primary Examiner* — Craig D Ricci

(74) *Attorney, Agent, or Firm* — Houston Beshining Law Office PLLC; Liangang Ye

(57) ABSTRACT

The present invention relates to a nitrogen-containing heterocyclic derivative inhibitor, and a preparation method therefor and the use thereof. In particular, the present invention relates to a compound as represented by general formula (I), a preparation method therefor, a pharmaceutical composition containing the compound, and the use thereof as an inhibitor in the treatment of diseases such as cardiovascular diseases and cerebrovascular diseases, wherein the definition of each substituent in general formula (I) is the same as that defined in the description.

(I)

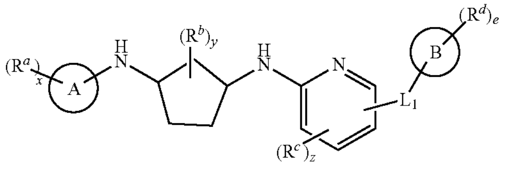

26 Claims, No Drawings

NITROGEN-CONTAINING HETEROCYCLIC DERIVATIVE INHIBITOR, AND PREPARATION METHOD THEREFOR AND USE THEREOF

CROSS-REFERENCE TO RELATED APPLICATIONS

The present application is a Continuation-in-part Application of International Application No. PCT/CN2024/103568, filed on Jul. 4, 2024, which claims the priority of CN202310818758.5 filed on Jul. 4, 2023; CN 202311011109.0 filed on Aug. 10, 2023; CN 202311227801.7 filed on Sep. 21, 2023; CN 202311552677.1 filed on Nov. 17, 2023; CN 202410052828.5 filed on Jan. 12, 2024; CN 202410173281.4 filed on Feb. 6, 2024; CN 202410407937.4 filed on Apr. 3, 2024; and CN 202410426055.2 filed on Apr. 9, 2024.

TECHNICAL FIELD

The present disclosure belongs to the field of drug synthesis and specifically relates to a nitrogen-containing heterocyclic derivative inhibitor, and a preparation method therefor and the use thereof.

BACKGROUND

Cardiovascular disease (CVD) is the leading cause of death in the world, and a high level of low-density lipoprotein cholesterol (LDL-C) is the main risk factor. The accumulation of LDL-C on the inner wall of arteries leads to atherosclerosis and may cause an inflammatory response, leading to cardiovascular events such as heart attack and stroke. Statins can reduce serum LDL-C and are main lipid-lowering drugs in clinic at present. However, patients who are intolerant to statins or who fail to achieve the therapeutic goal when receiving a tolerant dose of treatment, e.g., patients with familial hypercholesterolemia, are still at risk. The discovery of PCSK9 inhibitors provides a more positive treatment method for homozygous and heterozygous patients with familial hypercholesterolemia. Non-statin Ezetimibe combined with a statin can reduce LDL-C by 15-20%, whereas a PCSK9 inhibitor combined with a statin can significantly reduce LDL-C by 54-74%. PCSK9 inhibitors can also overcome unbearable side effects of statins, e.g., symptoms such as muscle pain.

PCSK9 (Proprotein convertase subtilisin kexin type 9) is a serine protease, which is highly expressed in liver. Loss-of-function mutation in PCSK9 gene is related to a low level of LDL-C and a reduced cardiovascular risk (Cohen, J. C., 2006) and has been clinically confirmed to be a therapeutic target for hyperlipidemia. PCSK9 is synthesized as an enzyme precursor that, after synthesis, undergoes autocatalytic cleavage in a cell, and the mature PCSK9 binds to a propeptide and is secreted to the extracellular space. The binding to the propeptide blocks the catalytic activity of PCSK9.

PCSK9 is a main regulator for the level of low-density lipoprotein receptor (LDLR) on the surface of hepatocytes and can inhibit the circulating pathway of LDLR. The function of LDLR is the key to maintain cholesterol homeostasis, and it is responsible for the uptake and degradation of low-density lipoprotein. Circulating LDL binds to an N-terminal ligand binding domain of LDLR via apolipoprotein B100, and the LDL/LDLR complex is internalized by means of receptor-mediated endocytosis. A low-pH environment in the cell causes the LDLR to release LDL, the LDLR circulates back to the cell membrane, and the intracellular free LDL is sent to lysosomes and degraded. Secreted PCSK9 interferes with the circulating ability of LDLR by binding to LDLR on the surface of hepatocytes. After the PCSK9/LDLR complex migrates to acidic endosomal compartments via clathrin-coated pits, the conformational change of LDLR leads to the formation of additional binding sites with PCSK9. Therefore, PCSK9 accompanies LDLR to lysosomes for degradation, preventing LDLR circulation, thus up-regulating the LDL-C level.

Familial hypercholesterolemia (FH) is a genetic disease of low-density lipoprotein cholesterol metabolism, which affects one in every 250 people and is characterized by a significant increase in the LDL-C level. The risk of coronary heart disease (CAD) in heterozygous patients with FH is 3-4 times that in normal people, and CAD often occurs 10 years earlier than in normal people on average. Statins can reduce the low-density lipoprotein cholesterol in heterozygous patients with FH. In Besseling's research, it is believed that a high-intensity statin therapy can reduce the risk and mortality of coronary heart disease by 44%. However, in many cases, the reduction of LDL-C is considered insufficient. The compensatory mechanism of statins involves up-regulating sterol regulatory element-binding protein 2 (SREBP-2) to thus activate LDL receptor and PCSK9, increase the expression and secretion of PCSK9 which will bind to LDLR, leading to an elevated LDL-C level in blood. Therefore, although statins can reduce LDL by inhibiting HMGCoA, the effect thereof on SREPB counteracts and balances this reduction. Adding a PCSK9 inhibitor to a statin therapy can help overcome this mechanism. Considering that patients with familial hypercholesterolemia may not fully benefit from statin therapies, alternative treatment approaches such as PCSK9 inhibitors are needed.

Macromolecular PCSK9 inhibitors, Alirocumab and Evolocumab based on monoclonal antibodies, which can selectively bind to extracellular PCSK9 and prevent the interaction thereof with LDLR, have been approved by FDA for reducing the LDL-C level with good safety. Studies have shown that in heterozygous patients with FH who failed to achieve the LCL-C target after a statin therapy alone, injection of Alirocumab once every two weeks can minimize the cardiovascular risk. Alirocumab has also been shown to moderately increase "good" cholesterol (HDL-C). In addition, there is a PCSK9 siRNA drug Inclisiran currently available on the market, which can reduce lipids for an extended period with good safety by reducing the expression level of PCSK9 protein. However, the above two drugs both need to be administered by injection, and the production cost is high and expensive. To date, there has been no PCSK9 small molecule inhibitors on the market, so there is a high demand for oral PCSK9 small molecule inhibitor drugs.

PCSK9 small molecule inhibitors have been reported in patents, such as: WO 2014170786 (Pfizer), WO 2014150326 (Shifa), WO 2020150473 (AZ), and WO 2022133529 (Nyrada). At present, AZD-0780, which has the fastest progress, is in clinical phase I, while others are in preclinical development phase. There are also some polypeptides reported, with the most advanced ones in clinical phase II. In the present disclosure, there is a need to develop an oral PCSK9 small molecule inhibitor.

BRIEF SUMMARY OF THE INVENTION

The objective of the present disclosure is to provide a compound as represented by general formula (I), or a stereoisomer or pharmaceutically acceptable salt thereof, wherein the compound as represented b general formula (I) has a structure as follows:

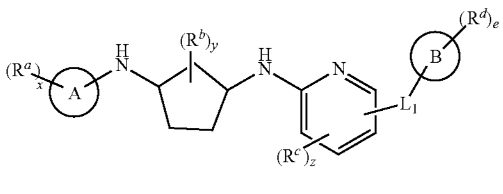

(I)

wherein ring A is selected from cycloalkyl, heterocyclyl, aryl, or heteroaryl;

ring B is selected from cycloalkyl, heterocyclyl, aryl, or heteroaryl;

$L_1$ is selected from a bond, $-(CH_2)_n-$, $-(CH_2)_nC(O)(CR_{aa}R_{bb})_{n1}-$, $-(CH_2)_nC(O)NR_{aa}(CH_2)_{n1}-$, $-(CH_2)_n(CR_{aa}R_{bb})_{n2}-$, $-(CR_{aa}R_{bb})_nO(CH_2)_{n1}-$, $-(CH_2)_nO(CR_{aa}R_{bb})_{n1}-$, $-(CR_{aa}R_{bb})_{n3}S(CH_2)_{n4}-$, $-(CH_2)_nS(CR_{aa}R_{bb})_{n3}-$, $-(CR_{aa}R_{bb})_{n3}(CH_2)_nNR_{cc}-$, $-(CH_2)_nNR_{aa}(CR_{bb}R_{cc})_n-$, $-(CH_2)_nNR_{aa}C(O)-$, $-(CH_2)_nP(O)_pR_{aa}-$, $-(CH_2)_nS(O)_m-$, $-(CH_2)_nC(O)NR_{aa}R_{bb}-$, $-(CH_2)_nNR_{cc}C(O)R_{dd}-$, $-(CH_2)_nS(O)_mN-R_{aa}R_{bb}-$, and $-(CH_2)_nNR_{cc}S(O)_mR_{dd}-$;

$R_{aa}$, $R_{bb}$, $R_{cc}$ and $R_{dd}$ are each independently selected from hydrogen, deuterium, halogen, amino, hydroxyl, cyano, nitro, alkyl, alkenyl, alkynyl, deuteroalkyl, haloalkyl, alkoxy, haloalkoxy, hydroxyalkyl, cycloalkyl, heterocyclyl, aryl, or heteroaryl, wherein the amino, alkyl, alkenyl, alkynyl, deuteroalkyl, haloalkyl, alkoxy, haloalkoxy, hydroxyalkyl, cyano-substituted alkyl, cycloalkyl, heterocyclyl, aryl, and heteroaryl can be optionally further substituted; alternatively, any two adjacent or non-adjacent substituents are connected to form cycloalkyl, heterocyclyl, aryl, or heteroaryl, wherein the cycloalkyl, heterocyclyl, aryl, or heteroaryl can be optionally further substituted;

preferably, $L_1$ is selected from a bond, $-C(O)-$, or $-C(O)NH-$;

$R^a$ is selected from hydrogen, deuterium, halogen, amino, hydroxyl, cyano, nitro, alkyl, alkenyl, alkynyl, oxo, thio, alkylthio, deuteroalkyl, haloalkyl, alkoxy, haloalkoxy, hydroxyalkyl, cyano-substituted alkyl, cycloalkyl, heterocyclyl, aryl, heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, alkyl, alkenyl, alkynyl, alkylthio, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

$R_{A1}$—$R_{A3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

preferably, $R^a$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$—$R_{A3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^a$ are connected to form cycloalkyl, heterocyclyl, aryl, or heteroaryl, wherein the cycloalkyl, heterocyclyl, aryl, and heteroaryl can be optionally further substituted;

$R^b$ is selected from hydrogen, deuterium, halogen, amino, hydroxyl, cyano, nitro, alkyl, alkenyl, alkynyl, oxo, thio, deuteroalkyl, haloalkyl, alkoxy, haloalkoxy, hydroxyalkyl, cyano-substituted alkyl, cycloalkyl, het erocyclyl, aryl, heteroaryl, —$(CH_2)_nR_{B1}$, —$(CH_2)_nOR_{B1}$, —$(CH_2)_nC(O)$ $R_{B1}$, —$(CH_2)_nC(O)O$ $R_{B1}$, —$(CH_2)_nS(O)_mR_{B1}$, —$(CH_2)_nNR_{B2}R_{B3}$, —$(CH_2)_nNR_{B2}C(O)OR_{B3}$, —$(CH_2)_nNR_{B2}C(O)(CH_2)_{n1}R_{B3}$, —$(CH_2)_nNR_{B2}C(O)NR_{B2}R_{B3}$, —$(CH_2)_nC(O)NR_{B2}(CH_2)_{n1}R_{B3}$, —$OC(R_{B1}R_{B2})_n(CH_2)_{n1}R_{B3}$, or —$(CH_2)_nNR_{B2}S(O)_mR_{B3}$, wherein the amino, alkyl, alkenyl, alkynyl, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

$R_{B1}$—$R_{B3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

preferably, $R^b$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, —$(CH_2)_nR_{B1}$, —$(CH_2)_nOR_{B1}$, —$(CH_2)_nC(O)R_{B1}$, —$(CH_2)_nC(O)OR_{B1}$, —$(CH_2)_nS(O)_mR_{B1}$, —$(CH_2)_nNR_{B2}R_{B3}$, —$(CH_2)_nNR_{B2}C(O)OR_{B3}$, —$(CH_2)_nNR_{B2}C(O)(CH_2)_{n1}R_{B3}$, —$(CH_2)_nNR_{B2}C(O)NR_{B2}R_{B3}$, —$(CH_2)_nC(O)NR_{B2}(CH_2)_{n1}R_{B3}$, —$OC(R_{B1}R_{B2})_n(CH_2)_{n1}R_{B3}$, or —$(CH_2)_nNR_{B2}S(O)_mR_{B3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{B1}$—$R_{B3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^b$ are connected to form cycloalkyl, heterocyclyl, aryl, or heteroaryl, wherein the cycloalkyl, heterocyclyl, aryl, and heteroaryl can be optionally further substituted;

preferably, alternatively, any two $R^a$ and $R^b$ are connected to form heterocyclyl or heteroaryl, wherein the heterocyclyl and heteroaryl can be optionally further substituted with one or more substituents of deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

$R^c$ is selected from hydrogen, deuterium, halogen, amino, hydroxyl, cyano, nitro, alkyl, alkenyl, alkynyl, oxo, thio, deuteroalkyl, haloalkyl, alkoxy, haloalkoxy, hydroxyalkyl, cyano-substituted alkyl, cycloalkyl, heterocyclyl, aryl, heteroaryl, —$(CH_2)_nR_{C1}$, —$(CH_2)_nOR_{C1}$, —$(CH_2)_nC(O)$ $R_{C1}$, —$(CH_2)_nC(O)O$ $R_{c1}$, —$(CH_2)_nS(O)_m$ Rci, —$(CH_2)_nNR_{C2}R_{C3}$, —$(CH_2)_nNR_{C2}C(O)OR_{C3}$, —$(CH_2)_nNR_{C2}C(O)(CH_2)_{n1}R_{C3}$, —$(CH_2)_nNR_{C2}C(O)NR_{C2}R_{C3}$, —$(CH_2)_nC(O)NR_{C2}(CH_2)_{n1}R_{C3}$, —$OC(R_{C1}R_{C2})_n(CH_2)_{n1}R_{C3}$, or —$(CH_2)_nNR_{C2}S(O)_mR_{C3}$, wherein the amino, alkyl, alkenyl, alkynyl, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

$R_{C1}$—$R_{C3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

preferably, $R^c$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, —$(CH_2)_nR_{C1}$, —$(CH_2)_nOR_{C1}$, —$(CH_2)_nC(O)R_{C1}$, —$(CH_2)_nC(O)OR_{C1}$, —$(CH_2)_nS(O)_mR_{C1}$, —$(CH_2)_nNR_{C2}R_{C3}$, —$(CH_2)_nNR_{C2}C(O)OR_{C3}$, —$(CH_2)_nNR_{C2}C(O)(CH_2)_{n1}R_{C3}$, —$(CH_2)_nNR_{C2}C(O)NR_{C2}R_{C3}$, —$(CH_2)_nC(O)NR_{C2}(CH_2)_{n1}R_{C3}$, —$OC(R_{C1}R_{C2})_n(CH_2)_{n1}R_{C3}$, or —$(CH_2)_nNR_{C2}S(O)_mR_{C3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{C1}$—$R_{C3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroal kyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^c$ are connected to form cycloalkyl, heterocyclyl, aryl, or heteroaryl, wherein the cycloalkyl, heterocyclyl, aryl, and heteroaryl can be optionally further substituted;

$R^d$ is selected from hydrogen, deuterium, halogen, amino, hydroxyl, cyano, nitro, alkyl, alkenyl, alkynyl, oxo, thio, deuteroalkyl, haloalkyl, alkoxy, haloalkoxy, hydroxyalkyl, cyano-substituted alkyl, cycloalkyl, heterocyclyl, aryl, heteroaryl, $—(CH_2)_nR_{D1}$, $—(CH_2)_nOR_{D1}$, $—(CH_2)_nC(O)\ R_{D1}$, $—(CH_2)_nC(O)OR_{D1}$, $—(CH_2)_nS(O)_mR_{D1}$, $—(CH_2)_nNR_{D2}R_{D3}$, $—(CH_2)_nNR_{D2}C(O)OR_{D3}$, $—(CH_2)_nNR_{D2}C(O)(CH_2)_{n1}R_{D3}$, $—(CH_2)_nNR_{D2}C(O)NR_{D2}R_{D3}$, $—(CH_2)_nC(O)NR_{D2}(CH_2)_{n1}R_{D3}$, $—OC(R_{D1}R_{D2})_n(CH_2)_{n1}R_{D3}$, or $—(CH_2)_nNR_{D2}S(O)_mR_{D3}$, wherein the amino, alkyl, alkenyl, alkynyl, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

$R_{D1}—R_{D3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

preferably, $R^d$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $—(CH_2)_nR_{D1}$, $—(CH_2)_nOR_{D1}$, $—(CH_2)_nC(O)R_{D1}$, $—(CH_2)_nC(O)OR_{D1}$, $—(CH_2)_nS(O)_mR_{D1}$, $—(CH_2)_nNR_{D2}R_{D3}$, $—(CH_2)_nNR_{D2}C(O)OR_{D3}$, $—(CH_2)_nNR_{D2}C(O)(CH_2)_{n1}R_{D3}$, $—(CH_2)_nNR_{D2}C(O)NR_{D2}R_{D3}$, $—(CH_2)_nC(O)NR_{D2}(CH_2)_{n1}R_{D3}$, $—OC(R_{D1}R_{D2})_n(CH_2)_{n1}R_{D3}$, or $—(CH_2)_nNR_{D2}S(O)_mR_{D3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{D1}—R_{D3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^d$ are connected to form cycloalkyl, heterocyclyl, aryl, or heteroaryl, wherein the cycloalkyl, heterocyclyl, aryl, and heteroaryl can be optionally further substituted;

alternatively, any two $R^c$ and $R^d$ are connected to form cycloalkyl, heterocyclyl, aryl, or heteroaryl, wherein the cycloalkyl, heterocyclyl, aryl, and heteroaryl can be optionally further substituted;

x is 0, 1, 2, or 3; y is 0, 1, 2, or 3; z is 0, 1, 2, or 3; e is 0, 1, 2, or 3; m is 0, 1, or 2; n is 0, 1, 2, 3, or 4; n1 is 0, 1, 2, 3, or 4; n2 is 0, 1, 2, 3, or 4; n3 is 0, 1, 2, 3, or 4; and n4 is 0, 1, 2, 3, or 4.

In a preferred embodiment of the present disclosure, the compound is further as represented by general formula (I-A):

(I-A)

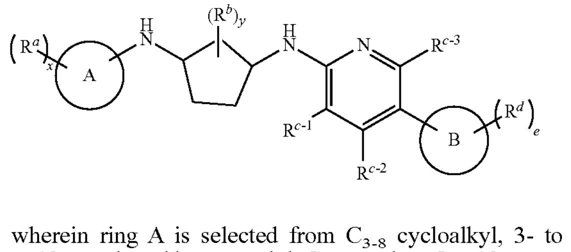

wherein ring A is selected from $C_{3-8}$ cycloalkyl, 3- to 12-membered heterocyclyl, $C_{6-10}$ aryl, or 5 to 12-membered heteroaryl; preferably, ring A is selected from 5-membered nitrogen-containing heteroaryl, 5-membered fused 5-membered bicyclic nitrogen-containing heteroaryl, 5-membered fused 6-membered bicyclic nitrogen-containing heteroaryl, 6-membered nitrogen-containing heteroaryl, 6-membered fused 5-membered bicyclic nitrogen-containing heteroaryl or 6-membered fused 6-membered bicyclic nitrogen-containing heteroaryl;

ring B is selected from $C_{3-8}$ cycloalkyl, 5- to 12-membered heterocyclyl, $C_{6-10}$ aryl or 5- to 12-membered heteroaryl; preferably, ring B is selected from $C_{3-6}$ cycloalkyl, phenyl, 5-membered nitrogen-containing heterocyclyl, 6-membered nitrogen-containing heterocyclyl, 5-membered nitrogen-containing heteroaryl, 6-membered nitrogen-containing heteroaryl, 5-membered fused 5-membered bicyclic nitrogen-containing heteroaryl, 5-membered fused 6-membered bicyclic nitrogen-containing heteroaryl, 6-membered fused 5-membered bicyclic nitrogen-containing heteroaryl, 6-membered fused 6-membered bicyclic nitrogen-containing heteroaryl, 5-membered fused 5-membered bicyclic nitrogen-containing heterocyclyl, 5-membered fused 6-membered bicyclic nitrogen-containing heterocyclyl, 6-membered fused 5-membered bicyclic nitrogen-containing heterocyclyl, or 6-membered fused 6-membered bicyclic nitrogen-containing cycloaryl;

$R^{c-1}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{C1}$, $-(CH_2)_nOR_{C1}$, $-(CH_2)_nC(O)R_{C1}$, $-(CH_2)_nC(O)OR_{C1}$, $-(CH_2)_nS(O)_mR_{C1}$, $-(CH_2)_nNR_{C2}R_{C3}$, $-(CH_2)_nNR_{C2}C(O)OR_{C3}$, $-(CH_2)_nNR_{C2}C(O)(CH_2)_{n1}R_{C3}$, $-(CH_2)_nNR_{C2}C(O)NR_{C2}R_{C3}$, $-(CH_2)_nC(O)NR_{C2}(CH_2)_{n1}R_{C3}$, $-OC(R_{C1}R_{C2})_n(CH_2)_{n1}R_{C3}$, or $-(CH_2)_nNR_{C2}S(O)_mR_{C3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{C1}$—$R_{C3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl; preferably, $R^{c-1}$ is selected from —H, —F, —Cl, —O—$CH_3$, —CN, —$CF_3$, —$CH_3$, —O—$CF_3$, —O—$CH_3$, —O—$CH(CH_3)_2$,

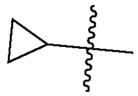
or
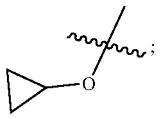
;

alternatively, preferably, $R^{c-1}$ is selected from halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{C1}$, $-(CH_2)_nOR_{C1}$, $-(CH_2)_nC(O)R_{C1}$, $-(CH_2)_nC(O)OR_{C1}$, $-(CH_2)_nS(O)_mR_{C1}$, $-(CH_2)_nNR_{c2}R_{C3}$, $-(CH_2)_nNR_{c2}C(O)OR_{c3}$, $-(CH_2)_nNR_{c2}C(O)(CH_2)_{n1}R_{C3}$, $-(CH_2)_nNR_{C2}C(O)NR_{C2}R_{C3}$, $-(CH_2)_nC(O)NR_{C2}(CH_2)_{n1}R_{C3}$, $-OC(R_{C1}R_{C2})_n(CH_2)_{n1}R_{C3}$, or $-(CH_2)_nNR_{C2}S(O)_mR_{C3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{C1}$—$R_{C3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{c-1}$ is selected from —F, —Cl, —O—$CH_3$, —CN, —$CF_3$, —$CH_3$, —O—$CF_3$, —O—$CH_3$, —O—$CH(CH_3)_2$,

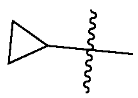
or
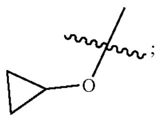
;

further preferably, $R^{c-1}$ is —F;

$R^{c-2}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{C1}$, $-(CH_2)_nOR_{C1}$, $-(CH_2)_nC(O)R_{C1}$, $-(CH_2)_nC(O)OR_{C1}$, $-(CH_2)_nS(O)_mR_{C1}$, $-(CH_2)_nNR_{C2}R_{C3}$, $-(CH_2)_nNR_{C2}C(O)OR_{C3}$, $-(CH_2)_nNR_{C2}C(O)(CH_2)_{n1}R_{C3}$, $-(CH_2)_nNR_{C2}C(O)NR_{C2}R_{C3}$, $-(CH_2)_nC(O)NR_{C2}(CH_2)_{n1}R_{C3}$, $-OC(R_{C1}R_{C2})_n(CH_2)_{n1}R_{C3}$, or $-(CH_2)_nNR_{C2}S(O)_mR_{C3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{C1}$—$R_{C3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{c-2}$ is selected from —H, —F, —Cl, —O—$CH_3$, —CN, —$CF_3$, —$CH_3$, —O—$CF_3$, —O—$CH_3$, —O—$CH(CH_3)_2$,

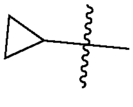 or 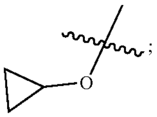;

$R^{c-3}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{C1}$, $-(CH_2)_nOR_{C1}$, $-(CH_2)_nC(O)R_{C1}$, $-(CH_2)_nC(O)OR_{C1}$, $-(CH_2)_nS(O)_mR_{C1}$, $-(CH_2)_nNR_{C2}R_{C3}$, $-(CH_2)_nNR_{C2}C(O)OR_{C3}$, $-(CH_2)_nNR_{C2}C(O)(CH_2)_{n1}R_{C3}$, $-(CH_2)_nNR_{C2}C(O)NR_{C2}R_{C3}$, $-(CH_2)_nC(O)NR_{C2}(CH_2)_{n1}R_{C3}$, $-OC(R_{C1}R_{C2})_n(CH_2)_{n1}R_{C3}$, or $-(CH_2)_nNR_{C2}S(O)_mR_{C3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{C1}$—$R_{C3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{c-3}$ is selected from —H, —F, —Cl, —O—$CH_3$, —CN, —$CF_3$, —$CD_3$, —$CH_3$, —O—$CF_3$, —O—$CH_3$, —O—$CH(CH_3)_2$,

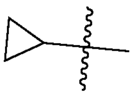 or 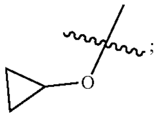;

more preferably, $R^{c-3}$ is selected from —H, —F, —Cl, —O—$CH_3$, —CN, —$CF_3$, —$CH_3$, —O—$CF_3$, —O—$CH_3$, —O—$CH(CH_3)_2$,

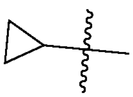 or 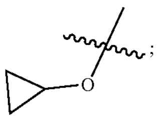;

m is 0, 1, or 2; n is 0, 1, 2, 3, or 4; and n1 is 0, 1, 2, 3, or 4;

the other groups are as defined above.

In a preferred embodiment of the present disclosure, the compound is further as represented by general formula (I-A-1):

(I-A-1)

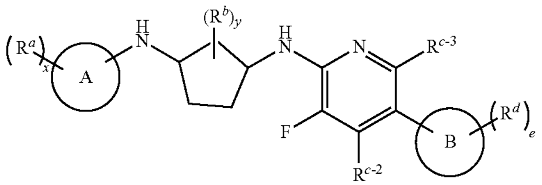

the groups are as defined above.

In a more preferred embodiment of the present disclosure, ring A described in the present disclosure is selected from 5-membered monoheterary, 5-membered fused 5-membered bicyclic heteroaryl, 5-membered fused 6-membered bicyclic heteroaryl, 6-membered monoheteraryl, 6-membered fused 5-membered bicyclic heteroaryl, or 6-membered fused 6-membered bicyclic heteroaryl;

further preferably, ring A is selected from

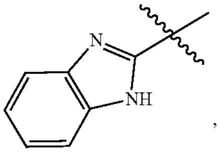
,
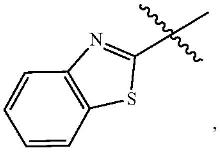
,
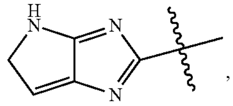
,
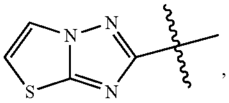
,
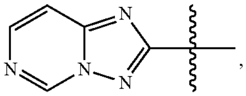
,
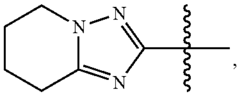
,
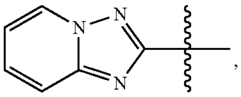
,
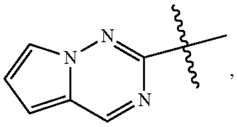
,
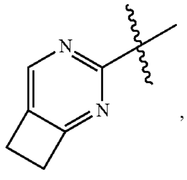
,
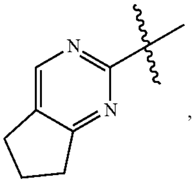
,
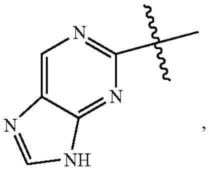
,
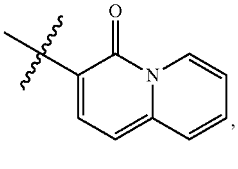
,
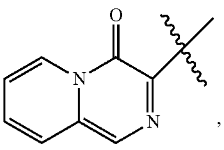
,
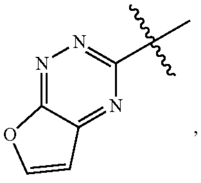
, -continued

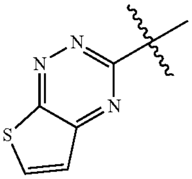
,
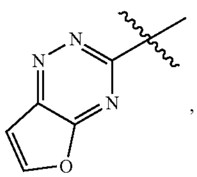
,
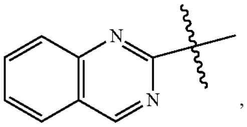
,
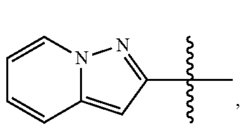
,
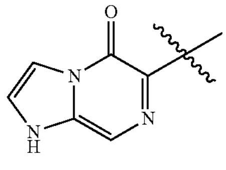
or
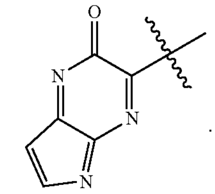
.

In a preferred embodiment of the present disclosure, the compound is further as represented by general formula (I-2'):

(I-2')

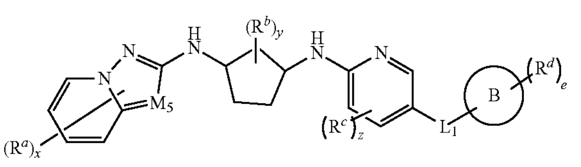

$L_1$ is selected from a bond, —C(O)—, —C(O)NH—, —C(O)NCH$_3$—, or —C(O)N(CH$_3$)$_2$; $M_5$ is selected from N or CR$_5$;

$R_5$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the other groups are as defined above.

In a preferred embodiment of the present disclosure, the compound is further as represented by general formula (I-1-a):

(I-1-a)

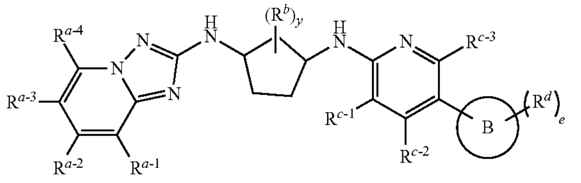

wherein $R^{a-1}$—$R^{a-4}$ are each independently selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$—$R_{A3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents of deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

the other groups are as defined above;

m is 0, 1, or 2; n is 0, 1, 2, 3, or 4; and n1 is 0, 1, 2, 3, or 4.

In a preferred embodiment of the present disclosure, the compound is further as represented by general formula (I-1-a'):

(I-1-a')

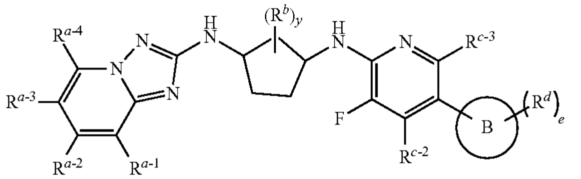

the groups are as defined above.

In a more preferred embodiment of the present disclosure, ring B described in the present disclosure is selected from $C_{3-6}$ cycloalkyl, phenyl, 3- to 8-membered heterocyclyl, 7- to 10-membered bicyclic heterocyclyl, 5-membered heteroaryl, 6-membered heteroaryl, 5-membered fused 5-membered bicyclic heteroaryl, 5-membered fused 6-membered bicyclic heteroaryl, 6-membered fused 5-membered bicyclic heteroaryl, or 6-membered fused 6-membered bicyclic heteroaryl;

more preferably, ring B is selected from $C_{3-6}$ cycloalkyl, phenyl, 5-membered nitrogen-containing heterocyclyl, 6-membered nitrogen-containing heterocyclyl, 7- to 10-membered bicyclic heterocyclyl, 5-membered nitrogen-containing heteroaryl, 6-membered nitrogen-containing heteroaryl, 5-membered fused 5-membered bicyclic nitrogen-containing heteroaryl, 5-membered fused 6-membered bicyclic nitrogen-containing heteroaryl, 6-membered fused 5-membered bicyclic nitrogen-containing heteroaryl, or 6-membered fused 6-membered bicyclic nitrogen-containing heteroaryl;

further preferably, ring B is selected from pyridine, pyrimidine, benzene,

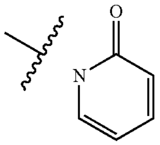, 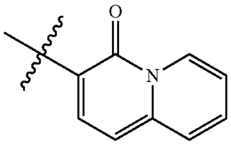,

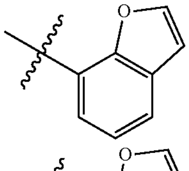, 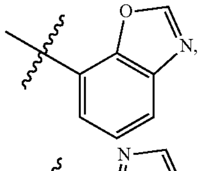,

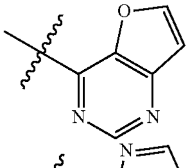, 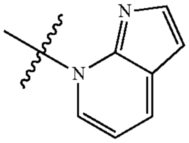,

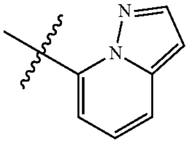, 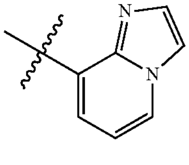,

-continued
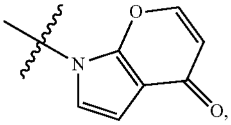 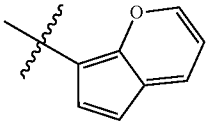 ,
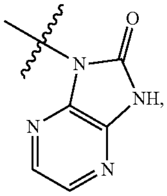 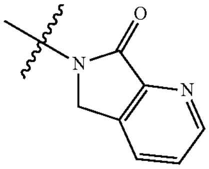 ,
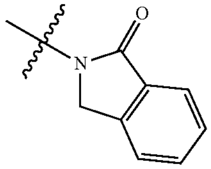 , 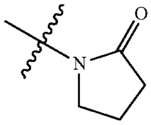 ,
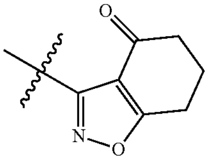 , 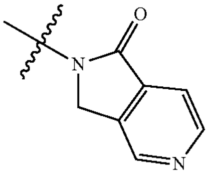 ,
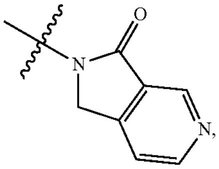 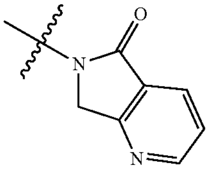 ,
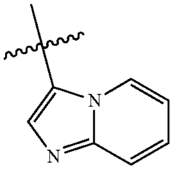 , 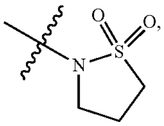 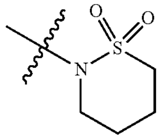 ,
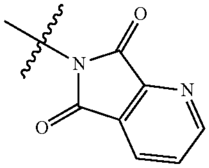 , 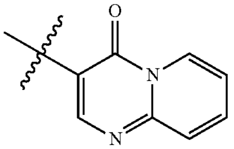 ,
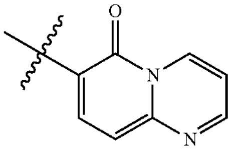 , 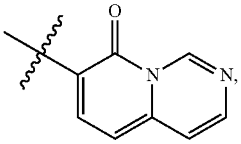
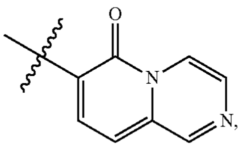 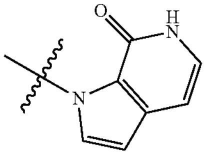 ,
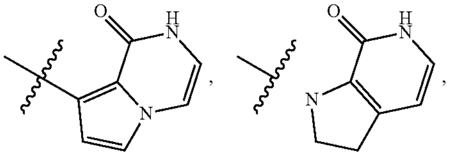 ,
-continued
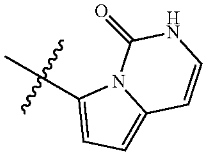 , 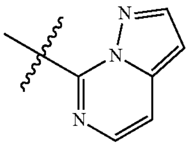 ,
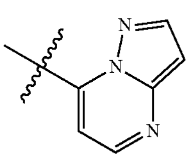 , 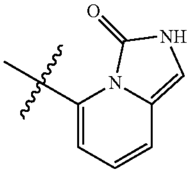 ,
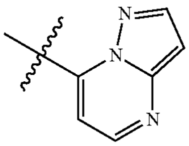 , 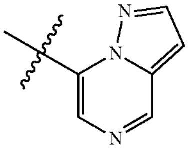 ,
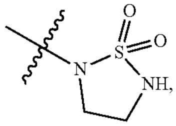 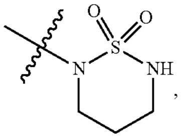 ,
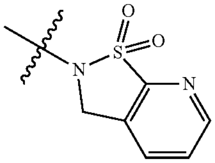 , 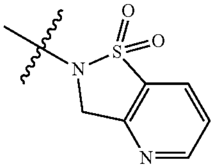 ,
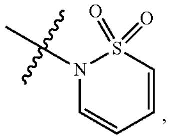 , 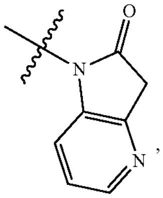 , 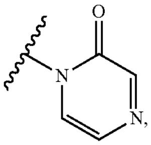
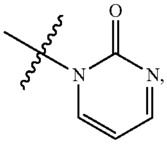 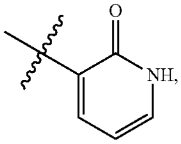
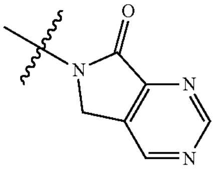 , 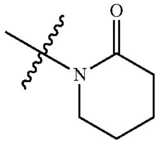 ,
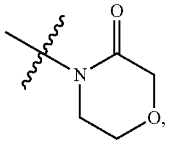 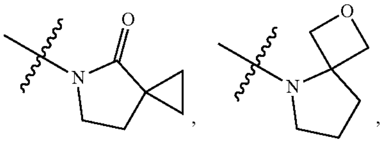 ,
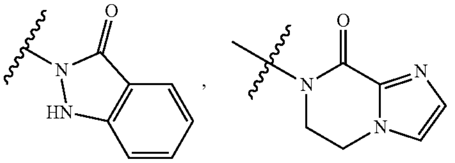 , -continued
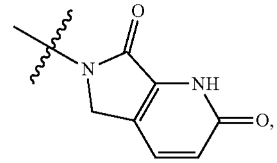, 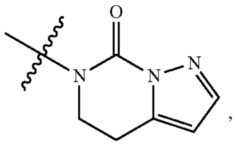, 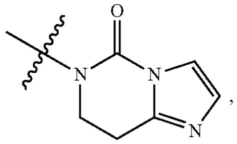, 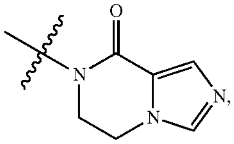, 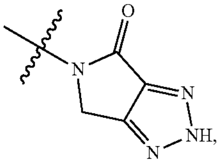, 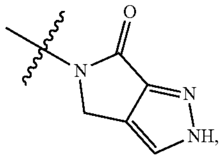, 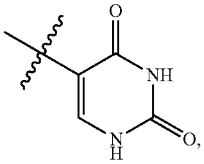, 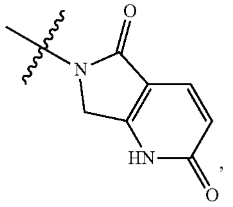, 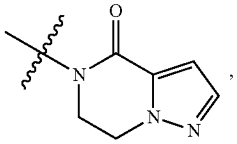, 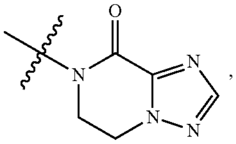, 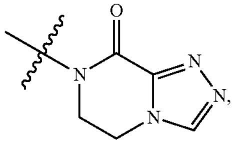, 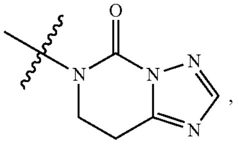, 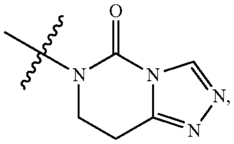, 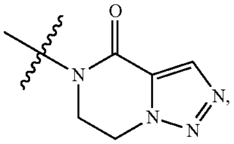, 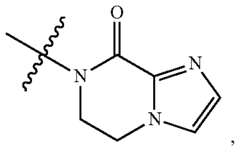, 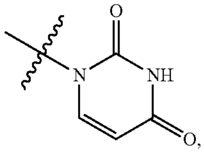, 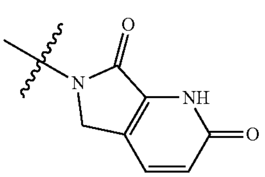 or 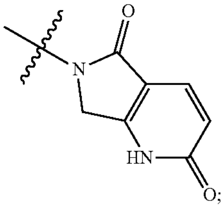;
further preferably, ring B is selected from pyridine, pyrimidine, pyridone, or pyrimidinone;
further preferably, ring B is selected from pyridine, pyrimidine, benzene,
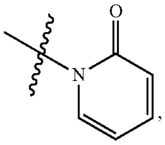, 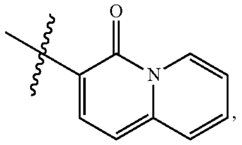, 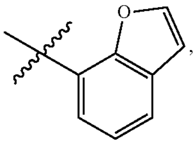, 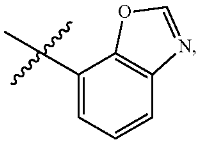, 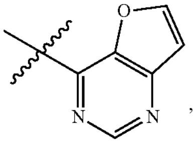, 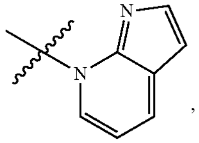, 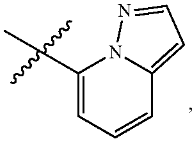, 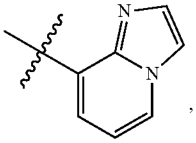, 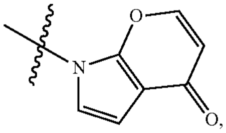, 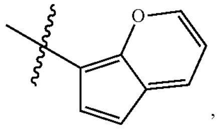, 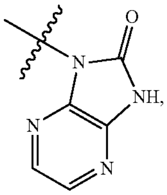, 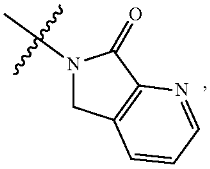, 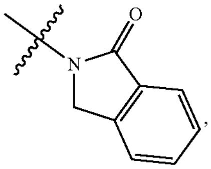, 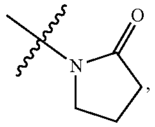, 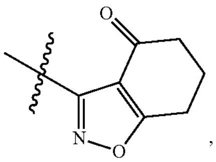, 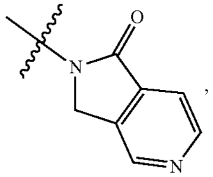, 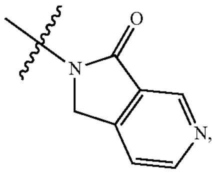, 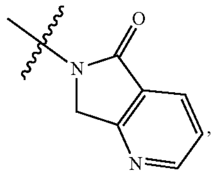, 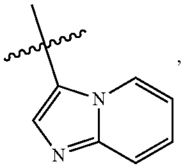, 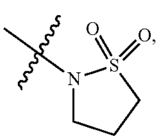, 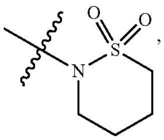, -continued

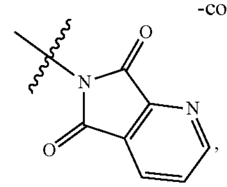, 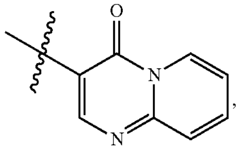,

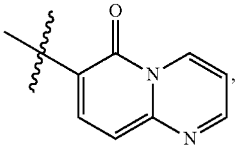, 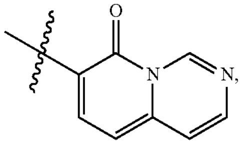

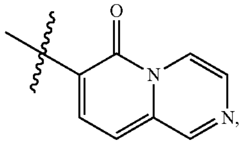, 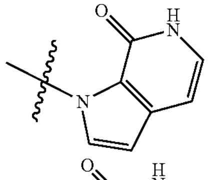,

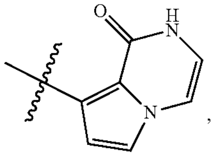, 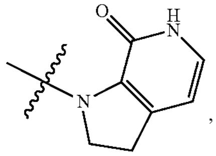,

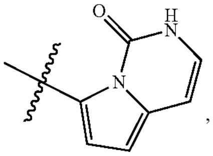, 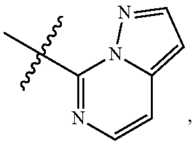,

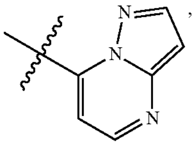, 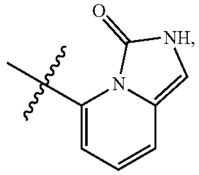

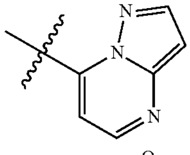, 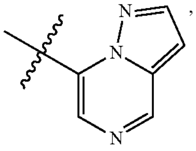,

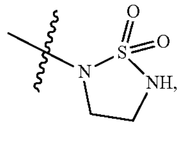 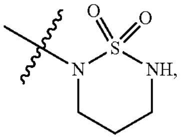

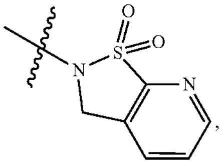, 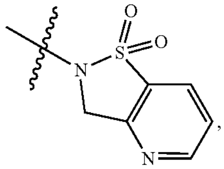,

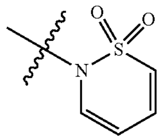 or 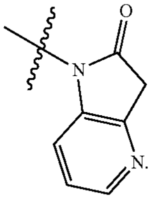

In a further preferred embodiment of the present disclosure, $R^a$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$—$R_{A3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^a$ is selected from —H, $-O-CHF_2$, $-O-CF_3$, $-O-CF_2Cl$, $-O-CF_2Br$, $-O-CH_2-CHF_2$, $-O-CH_2-CF_3$, $-CHF_2$, $-CF_3$, $-CD_3$, $-CH_2-OH$, $-CH_2-CHF_2$, $-CH(CH_3)-OH$, $-(CH_2)_3-OH$, $-C(CH_3)_2-OH$, —OH, $-O-CH_3$, $-CH_3$, $-CF_3$, —F, —Cl, —CN, $-NHCH_3$, $-NH_2$, $-CH_2-CF_3$, —

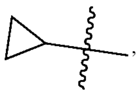, 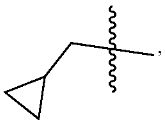, 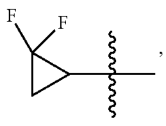,

-continued

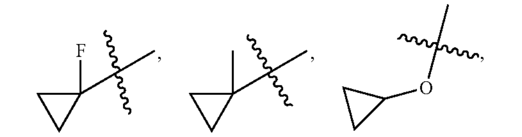

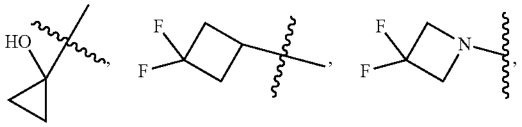

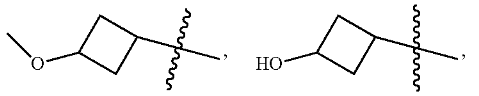

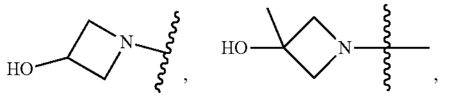

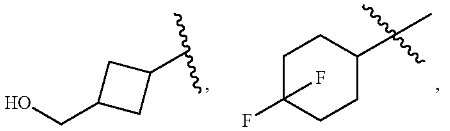

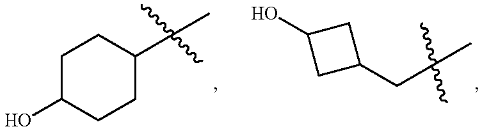

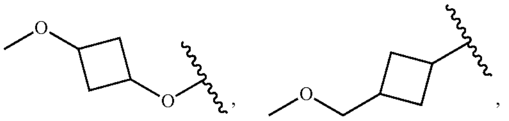

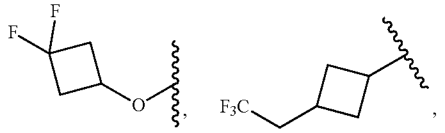

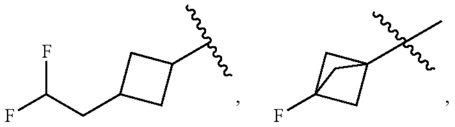

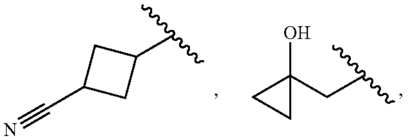

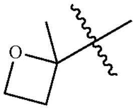 or 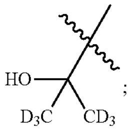 ;

further preferably, $R^a$ is selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CH_2$—OH, —$CH_2$—$CHF_2$, —CH($CH_3$)—OH, —$(CH_2)_3$—OH, —C$(CH_3)_2$—OH, —OH, —O—$CH_3$, —$CH_3$, —$CF_3$, —F, —Cl, —CN, —$NHCH_3$, —$NH_2$, —$CH_2$—$CF_3$,

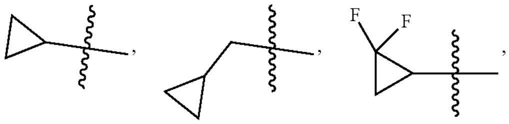

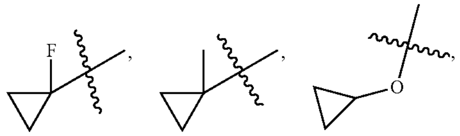

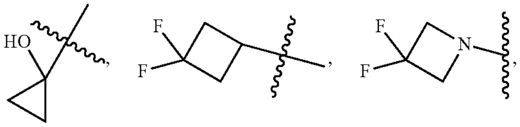

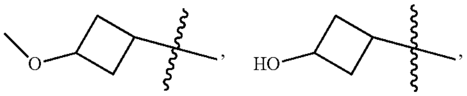

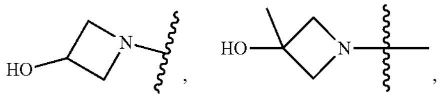

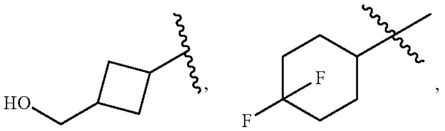

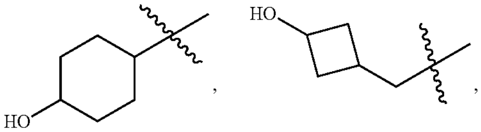

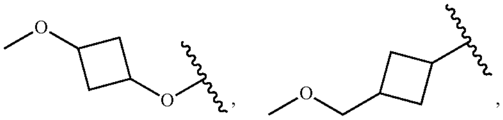

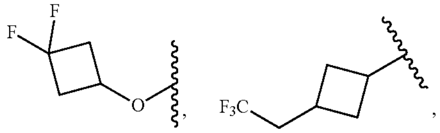

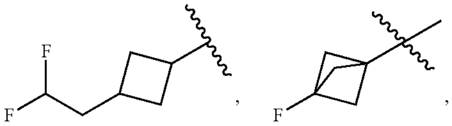

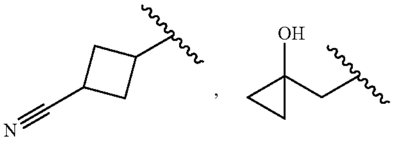 or

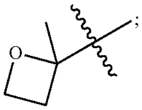 ;

more further preferably, R is selected from —H, —O—$CHF_2$, —O—$CF_3$, —O—$CF_2Cl$, —O—$CF_2Br$, —O—$CH_2$—$CHF_2$, —O—$CH_2$—$CF_3$—$CHF_2$, —$CF_3$, —$CH_2$—OH, —$CH_2$—$CHF_2$, —CH($CH_3$)—OH, —$(CH_2)_3$—OH, —C$(CH_3)_2$—OH, —OH, —O—$CH_3$, —$CH_3$, —$CF_3$, —F, —Cl, —CN, —$NHCH_3$, —$NH_2$,

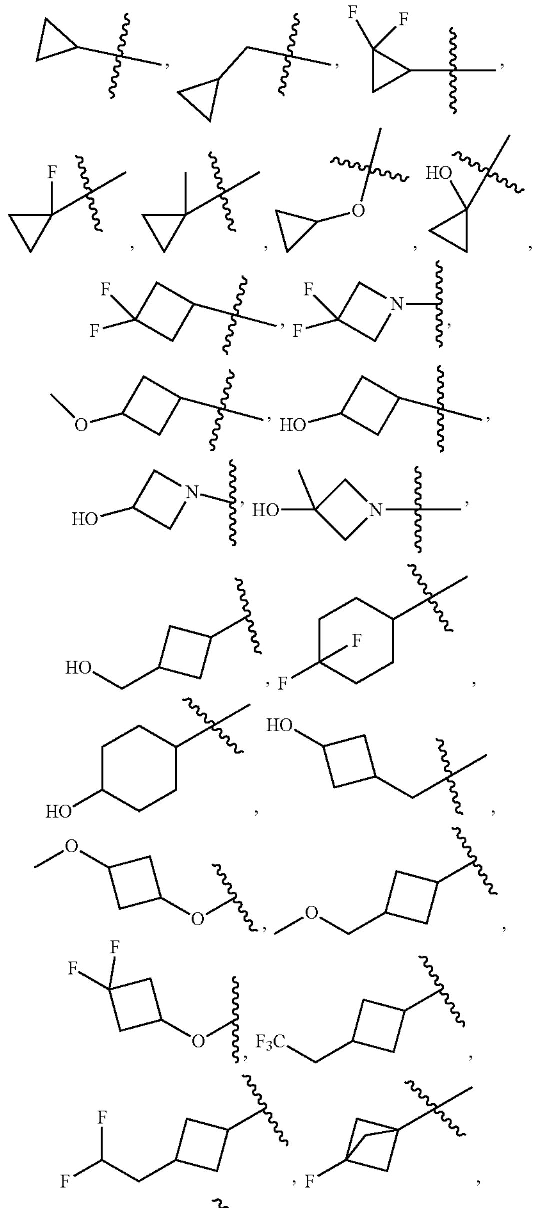

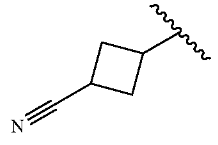

or

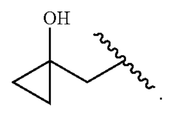

In a further preferred embodiment of the present disclosure, $R^{a-1}$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; $R_{A1}$—$R_{A3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{a-1}$ is selected from —H, $-O-CHF_2$, $-O-CF_3$, $-O-CF_2Cl$, $-O-CF_2Br$, $-O-CH_2-CHF_2$, $-O-CH_2-CF_3$, $-CHF_2$, $-CF_3$, $-CD_3$, $-CH_2-OH$, $-CH_2-CHF_2$, $-CH(CH_3)-OH$, $-(CH_2)_3-OH$, $-C(CH_3)_2-OH$, —OH, $-O-CH_3$, $-CH_3$, $-CF_3$, —F, —Cl, —CN, $-NHCH_3$, $-NH_2$, $-CH_2-CF_3$,

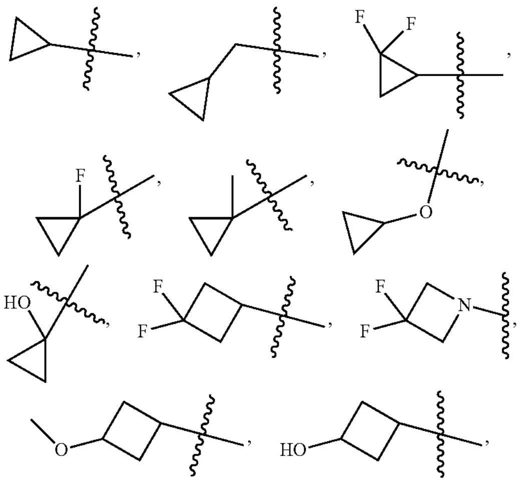

-continued

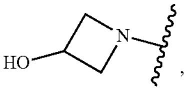, 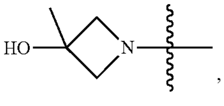,

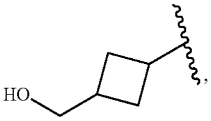, 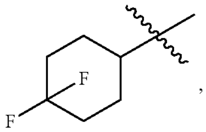,

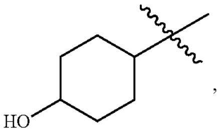, 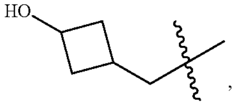,

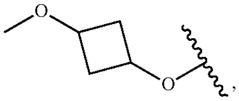, 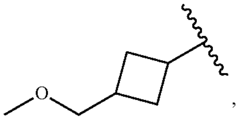,

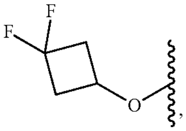, 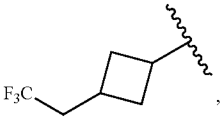,

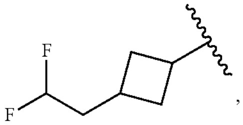, 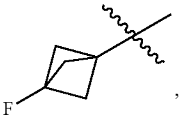,

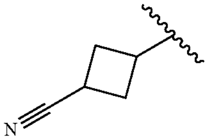, 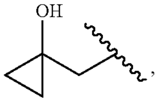,

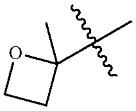 or 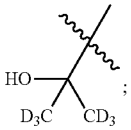;

further preferably, $R^{a-1}$ is selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, —$CH_2$—$CF_3$,

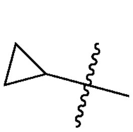, 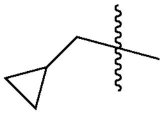, 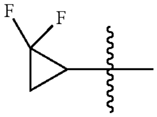,

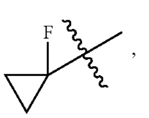, 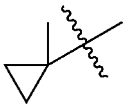, 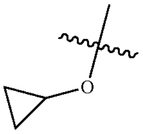,

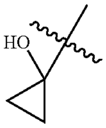, 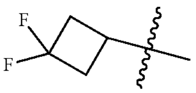, 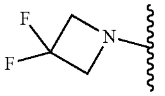,

-continued

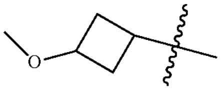, 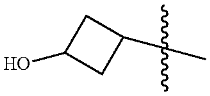,

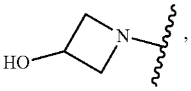, 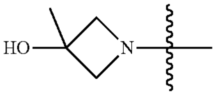,

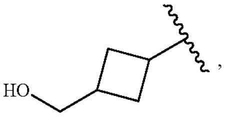, 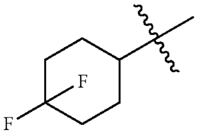,

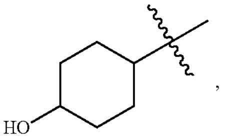, 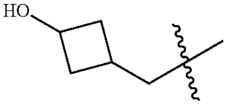,

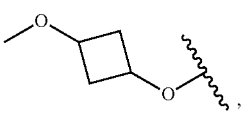, 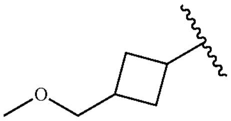,

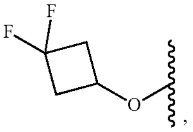, 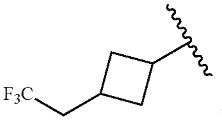,

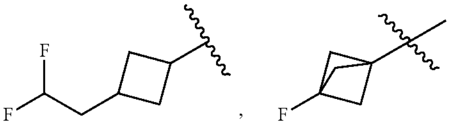,

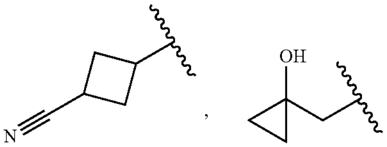 or

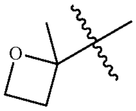.

In a further preferred embodiment of the present disclosure, $R^{a-2}$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, —$(CH_2)_n R_{A1}$, —$(CH_2)_n OR_{A1}$, —$(CH_2)_n C(O)R_{A1}$, —$(CH_2)_n C(O)OR_{A1}$, —$(CH_2)_n S(O)_m R_{A1}$, —$(CH_2)_n NR_{A2}R_{A3}$, —$(CH_2)_n NR_{A2}C(O)OR_{A3}$, —$(CH_2)_n NR_{A2}C(O)(CH_2)_{n1}R_{A3}$, —$(CH_2)_n NR_{A2}C(O)NR_{A2}R_{A3}$, —$(CH_2)_n C(O)NR_{A2}(CH_2)_{n1}R_{A3}$, —$OC(R_{A1}R_{A2})_n$ $(CH_2)_{n1}R_{A3}$, or —$(CH_2)_n NR_{A2}S(O)_m R_{A3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$—$R_{A3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{a-2}$ is selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CD_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, —$CH_2$—$CF_3$,

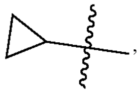 , 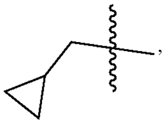 , 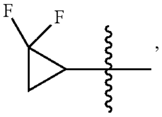 ,

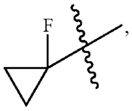 , 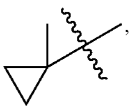 , 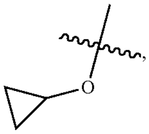 ,

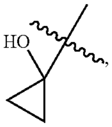 , 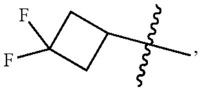 , 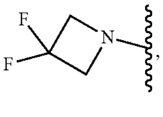 ,

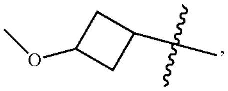 , 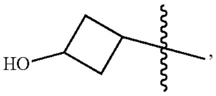 ,

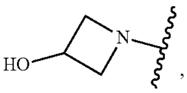 , 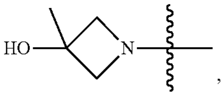 ,

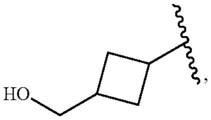 , 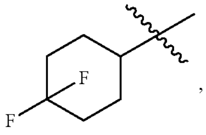 ,

-continued

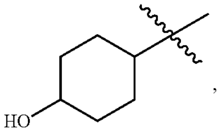 , 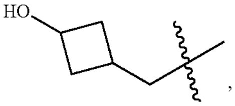 ,

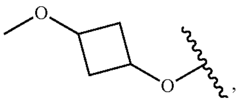 , 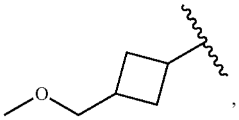 ,

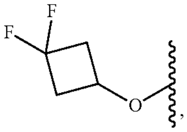 , 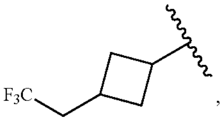 ,

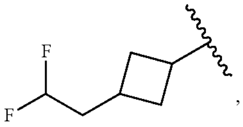 , 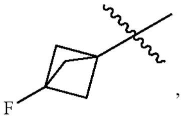 ,

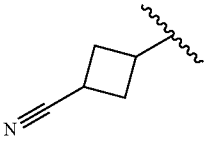 , 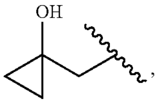 ,

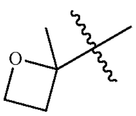 or 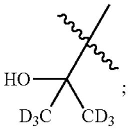 ;

further preferably, $R^{a-2}$ is selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, —$CH_2$—$CF_3$,

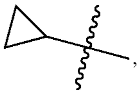 , 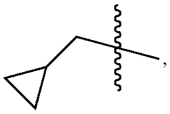 , 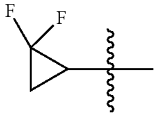 ,

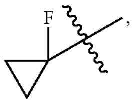 , 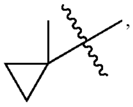 , 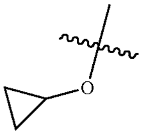 , 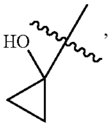 ,

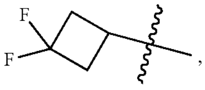 , 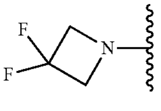 ,

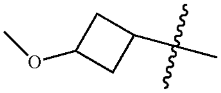 , 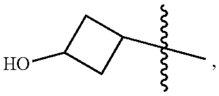 ,

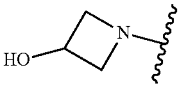 , 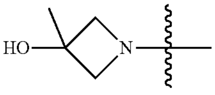 ,

-continued

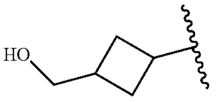, 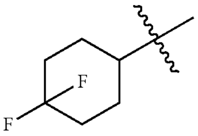,

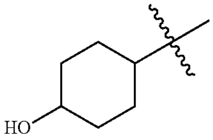, 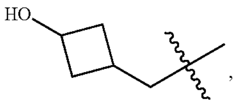,

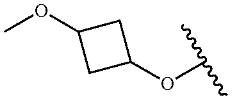, 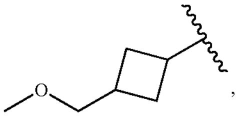,

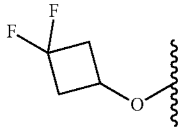, 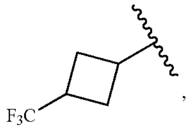,

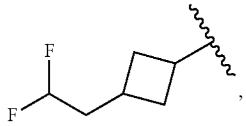, 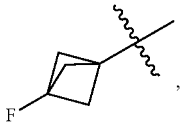,

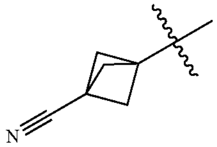, 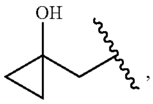, or

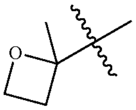.

In a further preferred embodiment of the present disclosure, $R^{a-3}$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$—$R_{A3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{a-3}$ is selected from —H, $-O-CHF_2$, $-O-CF_3$, $-O-CF_2Cl$, $-O-CF_2Br$, $-O-CH_2-CHF_2$, $-O-CH_2-CF_3$, $-CHF_2$, $-CF_3$, $-CD_3$, $-CH_2-OH$, $-CH_2-CHF_2$, $-CH(CH_3)-OH$, $-(CH_2)_3-OH$, $-C(CH_3)_2-OH$, —OH, $-O-CH_3$, $-CH_3$, $-CF_3$, —F, —Cl, —CN, $-NHCH_3$, $-NH_2$, $-CH_2-CF_3$,

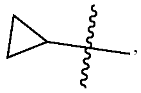, 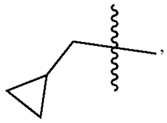, 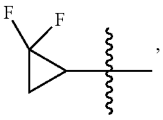,

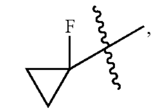, 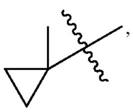, 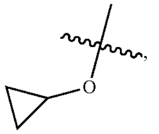,

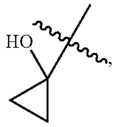 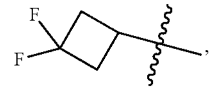, 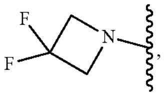,

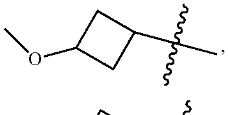, 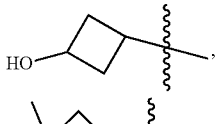,

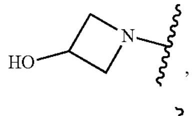, 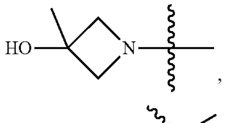,

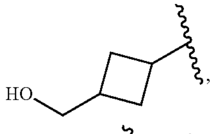, 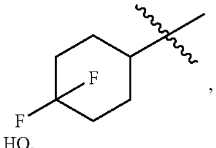,

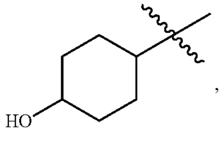, 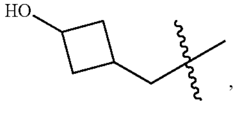,

-continued

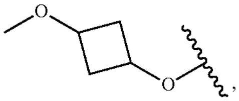,
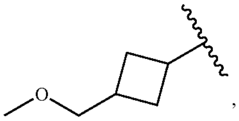,
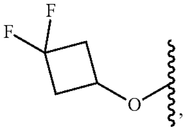,
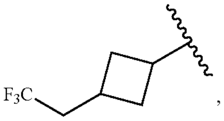,
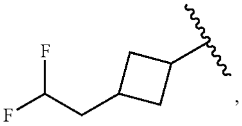,
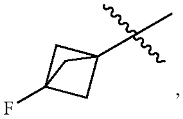,
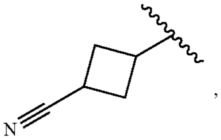,
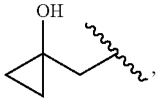,
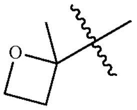 or 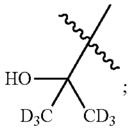;

further preferably, $R^{a-3}$ is selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, —$CH_2$—$CF_3$,

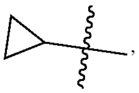,
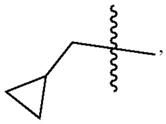,
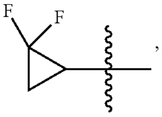,
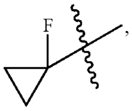,
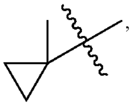,
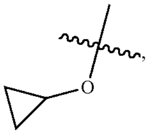,
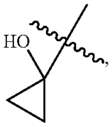
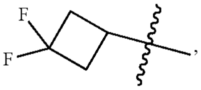,
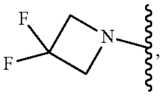,
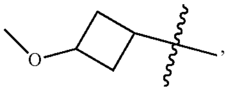,
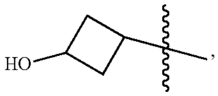,
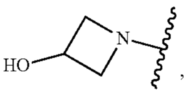,
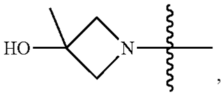,
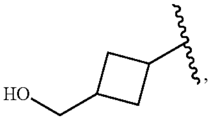,
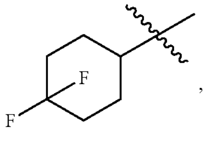, -continued

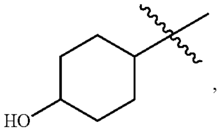,
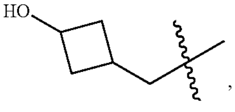,
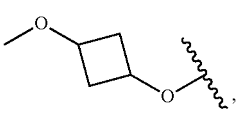,
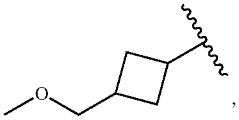,
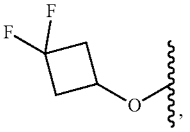,
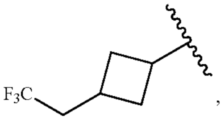,
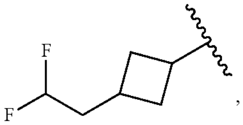,
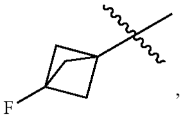,
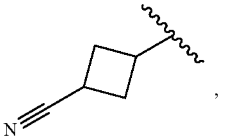,
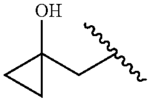 or
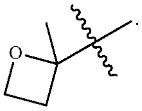.

In a further preferred embodiment of the present disclosure, $R^{a-4}$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, —$(CH_2)_nR_{A1}$, —$(CH_2)_nOR_{A1}$, —$(CH_2)_nC(O)R_{A1}$, —$(CH_2)_nC(O)OR_{A1}$, —$(CH_2)_nS(O)_mR_{A1}$, —$(CH_2)_nNR_{A2}R_{A3}$, —$(CH_2)_nNR_{A2}C(O)OR_{A3}$, —$(CH_2)_nNR_{A2}C(O)(CH_2)_{n1}R_{A3}$, —$(CH_2)_nNR_{A2}C(O)NR_{A2}R_{A3}$, —$(CH_2)_nC(O)NR_{A2}(CH_2)_{n1}R_{A3}$, —$OC(R_{A1}R_{A2})_n(CH_2)_{n1}R_{A3}$, or —$(CH_2)_nNR_{A2}S(O)_mR_{A3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$—$R_{A3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{a-4}$ is selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CD_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, —$CH_2$—$CF_3$,

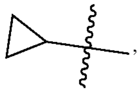, 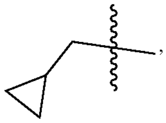, 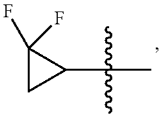,

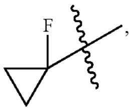, 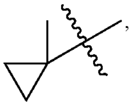, 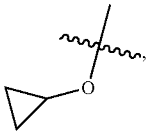,

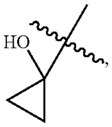, 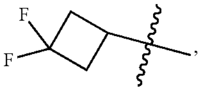, 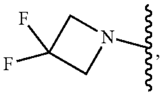,

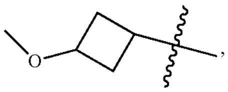, 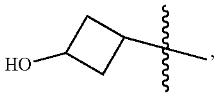,

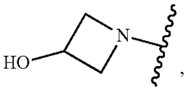, 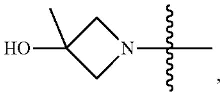,

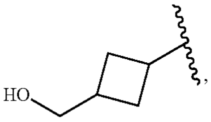, 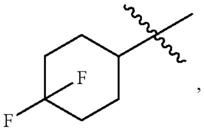,

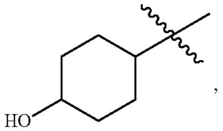, 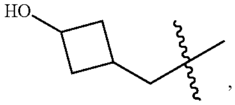,

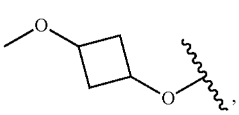, 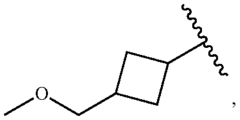,

-continued

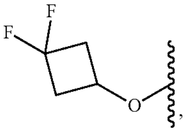, 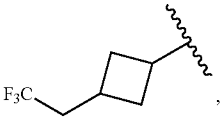,

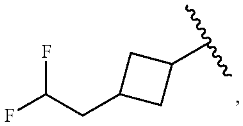, 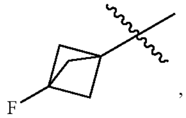,

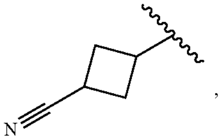, 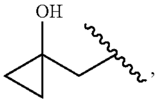,

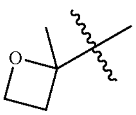 or 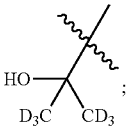;

further preferably, $R^{a-4}$ is selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, —$CH_2$—$CF_3$,

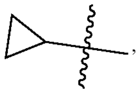, 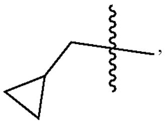, 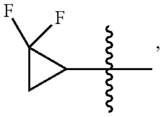,

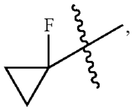, 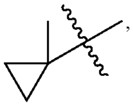, 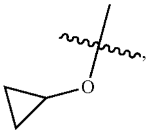,

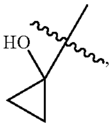, 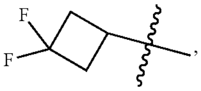, 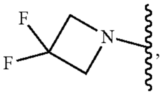,

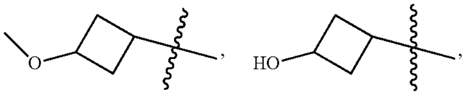,

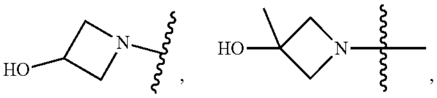,

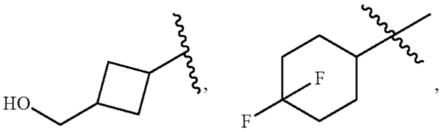,

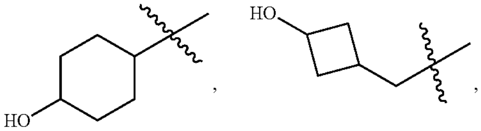,

-continued

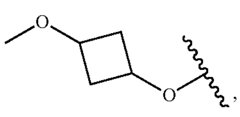, 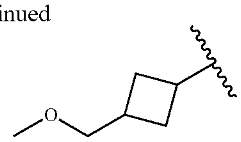,

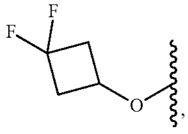, 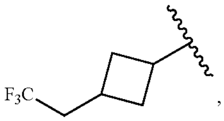,

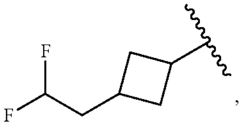, 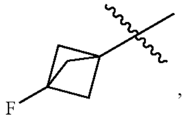,

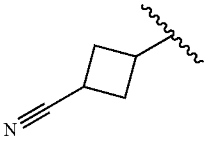, 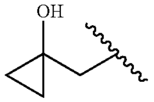 or

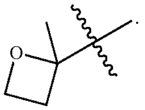.

In a further preferred embodiment of the present disclosure, $R^b$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{B1}$, $-(CH_2)_nOR_{B1}$, $-(CH_2)_nC(O)R_{B1}$, $-(CH_2)_nC(O)OR_{B1}$, $-(CH_2)_nS(O)_mR_{B1}$, $-(CH_2)_nNR_{B2}R_{B3}$, $-(CH_2)_nNR_{B2}C(O)OR_{B3}$, $-(CH_2)_nNR_{B2}C(O)(CH_2)_{n1}R_{B3}$, $-(CH_2)_nNR_{B2}C(O)NR_{B2}R_{B3}$, $-(CH_2)_nC(O)NR_{B2}(CH_2)_{n1}R_{B3}$, $-OC(R_{B1}R_{B2})_n(CH_2)_{n1}R_{B3}$, or $-(CH_2)_nNR_{B2}S(O)_mR_{B3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{B1}$—$R_{B3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^b$ is selected from —H or —F.

In a further preferred embodiment of the present disclosure, any two $R^b$ described in the present disclosure are linked to an adjacent atom to form $C_{3-8}$ cycloalkyl, 3- to 8-membered heterocyclyl, $C_{6-10}$ aryl or 5- to 12-membered heteroaryl.

In a further preferred embodiment of the present disclosure, $R^a$ and $R^b$ described in the present disclosure are connected to form 5- to 12-membered heterocyclyl or 5- to 12-membered heteroaryl, wherein the 5- to 12-membered heterocyclyl or 5- to 12-membered heteroaryl can be optionally further substituted with one or more substituents of deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl.

In a further preferred embodiment of the present disclosure, $R^c$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{C1}$, $-(CH_2)_nOR_{C1}$, $-(CH_2)_nC(O)R_{C1}$, $-(CH_2)_nC(O)OR_{C1}$, $-(CH_2)_nS(O)_mR_{C1}$, $-(CH_2)_nNR_{C2}R_{C3}$, $-(CH_2)_nNR_{C2}C(O)OR_{C3}$, $-(CH_2)_nNR_{C2}C(O)(CH_2)_{n1}R_{C3}$, $-(CH_2)_nNR_{C2}C(O)NR_{C2}R_{C3}$, $-(CH_2)_nC(O)NR_{C2}(CH_2)_{n1}R_{C3}$, $-OC(R_{C1}R_{C2})_n(CH_2)_{n1}R_{C3}$, or $-(CH_2)_nNR_{C2}S(O)_mR_{C3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{C1}$—$R_{C3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^c$ is selected from —H, —F, —Cl, —O—$CH_3$, —CN, —$CF_3$, —$CD_3$, —$CH_3$, —O—$CF_3$, —O—$CH_3$, —O—$CH(CH_3)_2$,

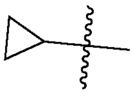 or 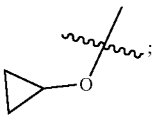;

more preferably, $R^c$ is selected from —H, —F, —Cl, —O—$CH_3$, —CN, —$CF_3$, —$CH_3$, —O—$CF_3$, —O—$CH_3$, —O—$CH(CH_3)_2$,

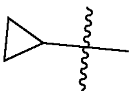 or 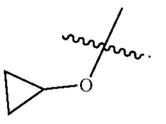.

In a further preferred embodiment of the present disclosure, $R^d$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, —$(CH_2)_nR_{D1}$, —$(CH_2)_nOR_{D1}$, —$(CH_2)_nC(O)R_{D1}$, —$(CH_2)_nC(O)OR_{D1}$, —$(CH_2)_nS(O)_mR_{D1}$, —$(CH_2)_nNR_{D2}R_{D3}$, —$(CH_2)_nNR_{D2}C(O)OR_{D3}$, —$(CH_2)_nNR_{D2}C(O)(CH_2)_{n1}R_{D3}$, —$(CH_2)_nNR_{D2}C(O)NR_{D2}R_{D3}$, —$(CH_2)_nC(O)NR_{D2}(CH_2)_{n1}R_{D3}$, —$OC(R_{D1}R_{D2})_n(CH_2)_{n1}R_{D3}$, or —$(CH_2)_nNR_{D2}S(O)_mR_{D3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{D1}$—$R_{D3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents of deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^d$ is selected from —H, -D, —F, —Cl, —CN, —$CH_3$, —$CF_3$, —$CD_3$, —$CH(CH_3)_2$, —$C(CH_3)_3$, —$C(CH_3)_2$—OH, —$C(CH_3)_2$—$CH_2$—OH, —O—$CH_3$, —$CH_2$—$NH_2$, —$CH_2$—OH, —$NH_2$, —OH, —C(O)OH,

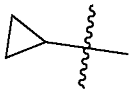, 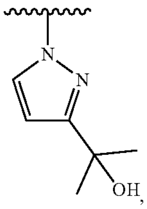 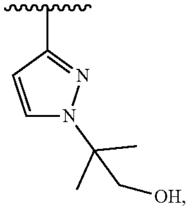

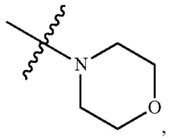, 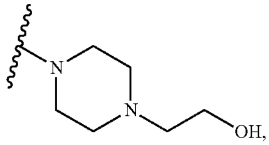

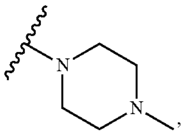, 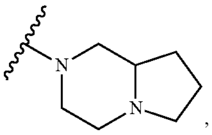,

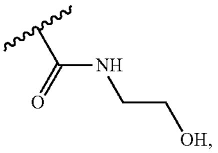 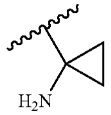, 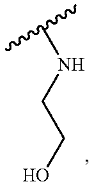,

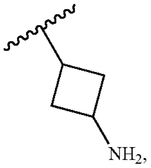 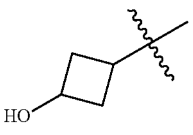, 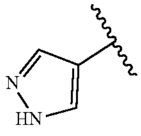,

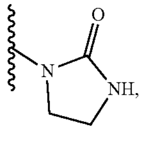 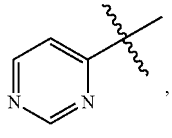, 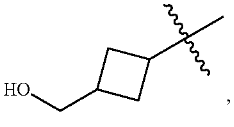,

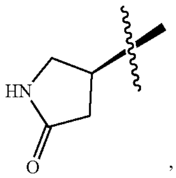, 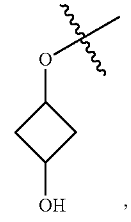, 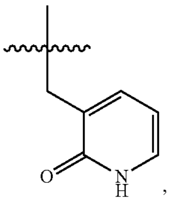,

-continued
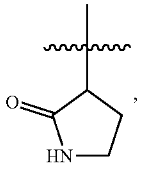, 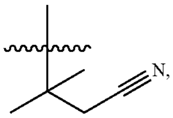 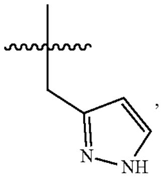,
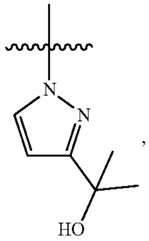, 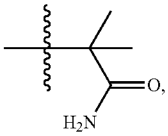 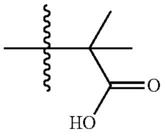 or
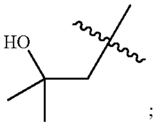;
further preferably, $R^d$ is selected from —H, -D, —F, —Cl, —CN, —$CH_3$, —$CF_3$, —$CH(CH_3)_2$, —$C(CH_3)_3$, —$C(CH_3)_2$—OH, —$C(CH_3)_2$—$CH_2$—OH, —O—$CH_3$, —$CH_2$—$NH_2$, —$CH_2$—OH, —$NH_2$, —OH, —C(O)OH,
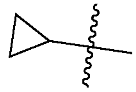, 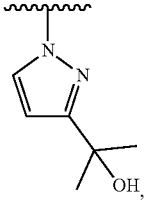 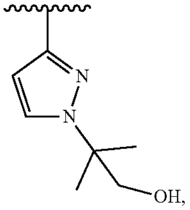
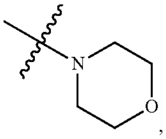, 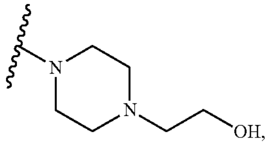
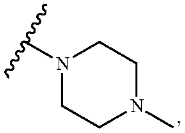 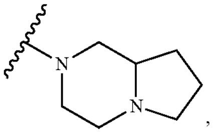,
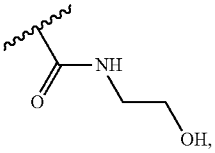 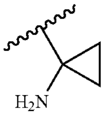, 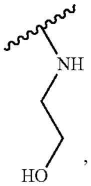,
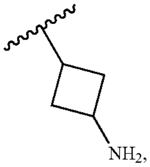 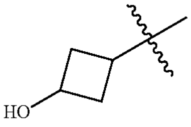, 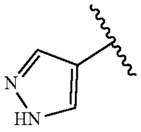,
-continued
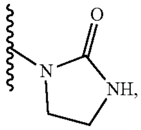 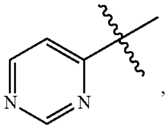, 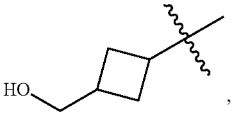,
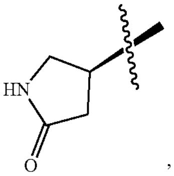, 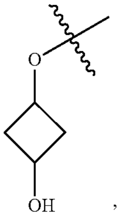, 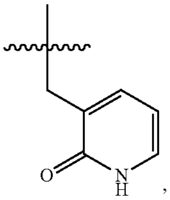,
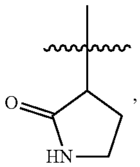, 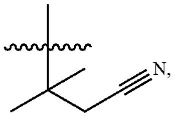 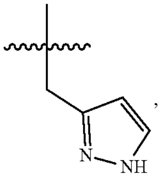,
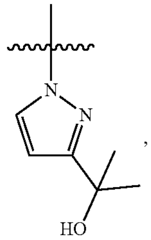, 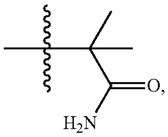 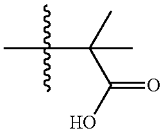 or
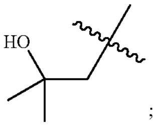;
more further preferably, $R^d$ is selected from —H, -D, —F, —Cl, —CN, —$CH_3$, —$CF_3$, —$CH(CH_3)_2$, —$C(CH_3)_3$, —$C(CH_3)_2$—OH, —$C(CH_3)_2$—$CH_2$—OH, —O—$CH_3$, —$CH_2$—$NH_2$, —$CH_2$—OH, —$NH_2$, —OH,
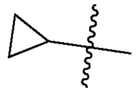, 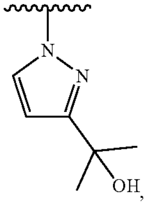 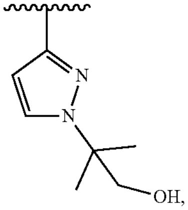
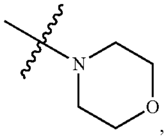 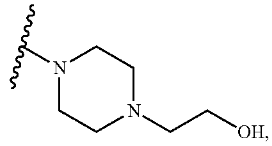
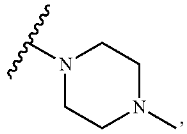 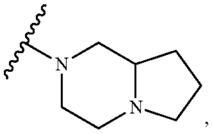, -continued

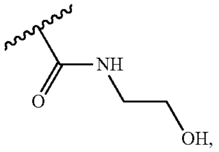 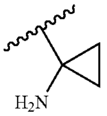 , 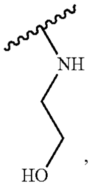 ,

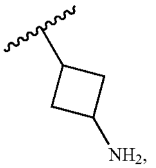 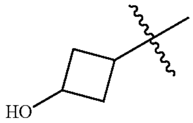 , 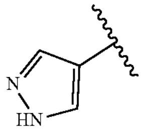 ,

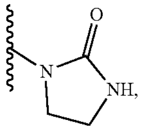 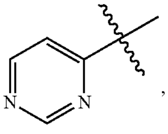 , 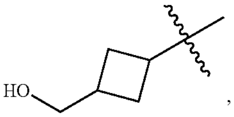 ,

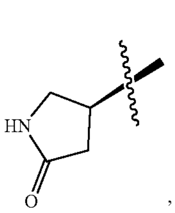 , 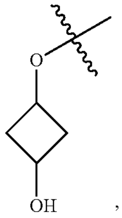 , 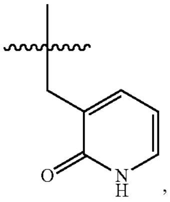 ,

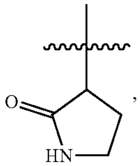 , 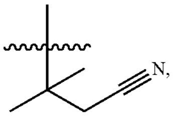

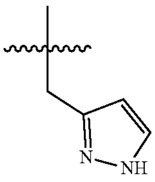 or 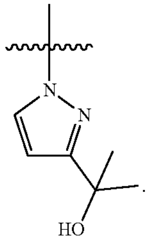

In a further preferred embodiment of the present disclosure,

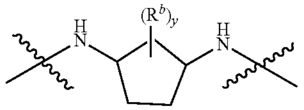

in the compound is preferably

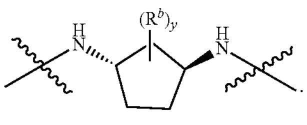

In a further preferred embodiment of the present disclosure,

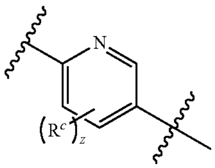

in the compound is

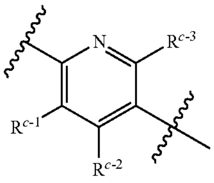

wherein $R^{c-1}$, $R^{c-2}$ and $R^{c-3}$ are as defined for $R^c$; preferably, $R^{c-1}$, $R^{c-2}$ and $R^{c-3}$ are as defined above for $R^{c-1}$, $R^{c-2}$ and $R^{c-3}$.

The present disclosure further provides a compound as represented by general formula (IV) or a stereoisomer or pharmaceutically acceptable salt thereof:

(IV)

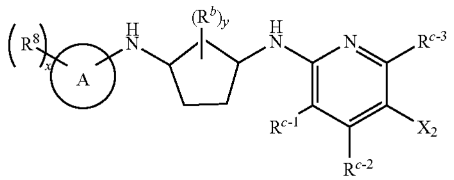

wherein $X_2$ is amino, nitro, halogen, boronic acid, or boronate; the other groups are each as defined above;

preferably, the compound as represented by general formula (IV) is further as represented by (IV-A), (IV-B) or (IV-C):

(IV-A)

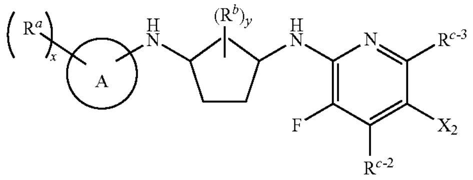

(IV-B)

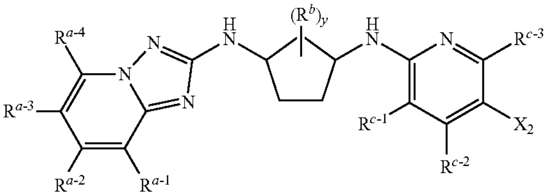 or

-continued (IV-C)

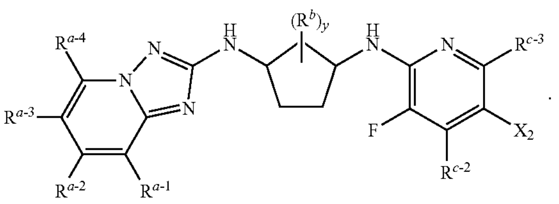

In a further preferred embodiment of the present disclosure, provided is the compound as represented by general formula (IV) or the stereoisomer or pharmaceutically acceptable salt thereof, wherein the compound is selected from the following compounds:

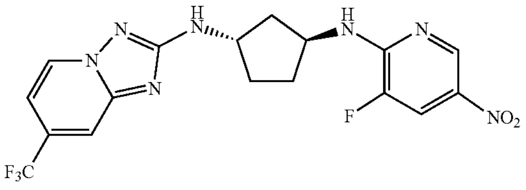

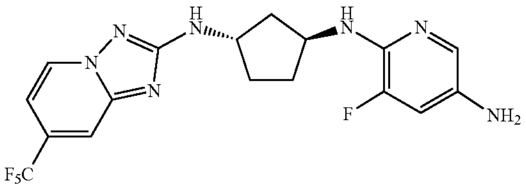

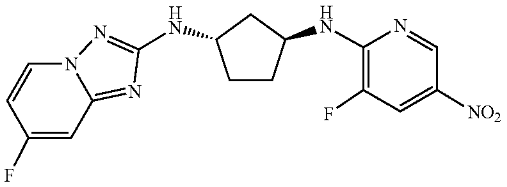

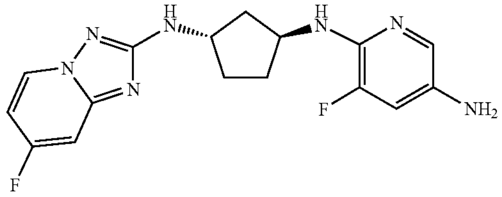

or

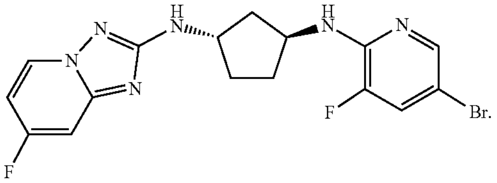

The present disclosure further provides a method for a compound as represented by general formula (I-A), comprising the following step:

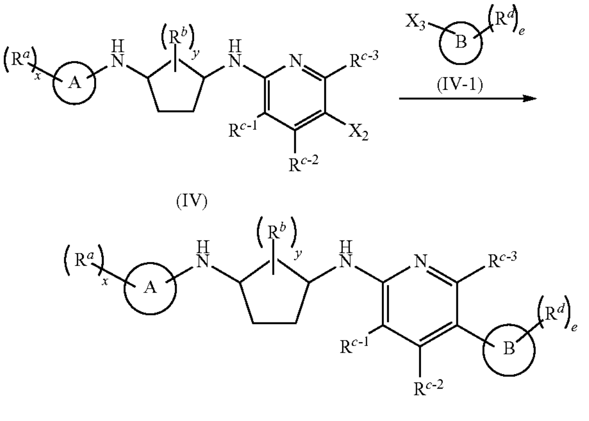

(IV)

(I-A)

wherein $X_3$ is hydroxyl, amino, halogen, boronic acid or boronate;

a compound as represented by general formula (IV) reacts with a compound as represented by general formula (IV-1) to obtain the compound as represented by general formula (I-A); and the other groups are each as defined above;

preferably, the compound as represented by general formula (I-A) is further as represented by (I-A-1), (I-1-a) or (I-1-a'):

(I-A-1)

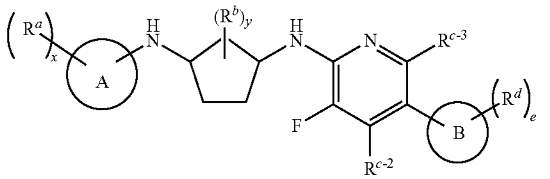

(I-1-a)

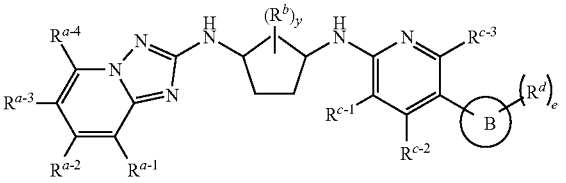

or (I-1-a')

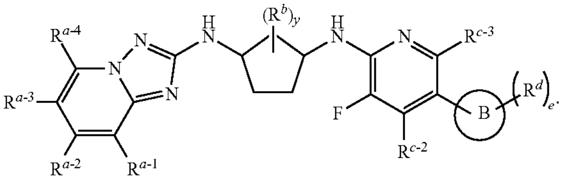

The present disclosure further relates to a pharmaceutical composition comprising a therapeutically effective dose of any compound as represented by general formula (I) or the stereoisomer or pharmaceutically acceptable salt thereof and one or more pharmaceutically acceptable carriers, diluents or excipients.

The present disclosure further relates to the use of any compound as represented by general formula (I) or the stereoisomer or pharmaceutically acceptable salt thereof or the pharmaceutical composition in the preparation of a PCSK9 inhibitor drug.

The present disclosure further relates to the use of any compound as represented by general formula (I) or the stereoisomer or pharmaceutically acceptable salt thereof or the pharmaceutical composition in the preparation of an LDL-lowering drug; preferably, the LDL is LDL-C.

The present disclosure further relates to the use of the compound as represented by general formula (I) or the stereoisomer or pharmaceutically acceptable salt thereof or the pharmaceutical composition thereof in the preparation of a drug for treating a cardiovascular disease, a cerebrovascular disease, atherosclerosis and/or a related disease thereof or a symptom thereof; preferably in the preparation of a drug for stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease.

The present disclosure further relates to the use of the compound as represented by general formula (I) or the stereoisomer or pharmaceutically acceptable salt thereof or the pharmaceutical composition thereof in the preparation of a method for treating a cardiovascular disease, a cerebrovascular disease, atherosclerosis and/or a related disease thereof or a symptom thereof; preferably in the preparation for treating stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease.

The present disclosure further relates to a method for preventing and/or treating stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease, comprising administering a therapeutically effective dose of the compound or the stereoisomer or pharmaceutically acceptable salt thereof, or the pharmaceutical composition thereof according to the present disclosure to a patient.

Furthermore, the weight percentage of the compound or the stereoisomer or pharmaceutically acceptable salt thereof in the composition is 0.1-95%, preferably 0.5-85%, more preferably 1-60%, further preferably 10-50%, more further preferably 15-40%, more further preferably 20-30%, and more further preferably 20-25% (based on the total weight of the pharmaceutical composition).

The present disclosure further provides a method for treating a disease condition with the compound or pharmaceutical composition of the present disclosure. The disease condition includes, but is not limited to, conditions related to PCSK9.

The present disclosure further relates to a method for treating stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease condition in a mammal, comprising administering a therapeutically effective amount of the compound or a pharmaceutically acceptable salt, ester, prodrug, solvate, hydrate or derivative thereof according to the present disclosure to the mammal.

DETAILED DESCRIPTION OF THE INVENTION

Unless stated to the contrary, the terms used in the description and claims have the following meanings.

The term "alkyl" refers to a saturated aliphatic hydrocarbon group, which is a linear or branched group containing 1 to 20 carbon atoms, preferably alkyl containing 1 to 8 carbon atoms, more preferably alkyl containing 1 to 6 carbon atoms, and most preferably alkyl containing 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, etc. More preferably, the alkyl is a lower alkyl group containing 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. Alkyl can be substituted or unsubstituted, and when substituted, the substituent can be substituted at any available connection point, and the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or a carboxylate group. In the present disclosure, alkyl is preferably methyl, ethyl, isopropyl, tert-butyl, haloalkyl, deuteroalkyl, alkoxy-substituted alkyl and hydroxyl-substituted alkyl.

The term "alkylene" refers to one hydrogen atom of alkyl being further substituted, for example: "methylene" refers to $-CH_2-$, "ethylene" refers to $-(CH_2)_2-$, "propylene" refers to $-(CH_2)_3-$, and "butylene" refers to $-(CH_2)_4-$, etc. The term "alkenyl" refers to an alkyl group as defined above consisting of at least two carbon atoms and at least one carbon-carbon double bond, such as ethenyl, 1-propenyl, 2-propenyl, 1-, 2- or 3-butenyl, etc. Alkenyl can be substituted or unsubstituted. When the alkenyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, or heterocycloalkylthio.

The term "cycloalkyl" refers to a saturated or partially unsaturated monocyclic or polycyclic cyclic hydrocarbon substituent. The cycloalkyl ring contains 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclopentenyl, cyclohexyl, cyclohexenyl, cyclohexadienyl, cycloheptyl, cycloheptatrienyl, cyclooctyl, etc.; and polycyclic cycloalkyl includes spiro, fused and bridged cycloalkyl, preferably cyclopropyl, cyclobutyl, cyclohexyl, cyclopentyl, and cycloheptyl.

The term "spirocycloalkyl" refers to a polycyclic group with 5- to 20-membered monocyclic rings sharing one carbon atom (called a spiro atom). It may contain one or more double bonds, but no ring has a completely conjugated n electron system. Preferably, the bridged heterocyclyl is 6- to 14-membered, and more preferably 7- to 10-membered. According to the number of shared spiro atoms between the rings, the spirocycloalkyl is divided into monospirocycloalkyl, bispirocycloalkyl or polyspirocycloalkyl, preferably monospirocycloalkyl and bispirocycloalkyl. More preferably, it is a 3-membered/6-membered, 3-membered/5-membered, 4-membered/4-membered, 4-membered/5-membered, 4-membered/6-membered, 5-membered/5-membered or 5-membered/6-membered monospirocycloalkyl. Non-limiting examples of spirocycloalkyl include;

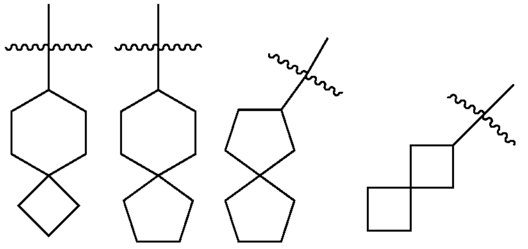

and

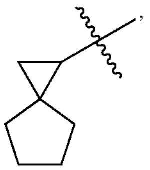

, etc.

Also included are spirocycloalkyl groups in which monospirocycloalkyl and heterocycloalkyl share a spiro atom. Non-limiting examples include:

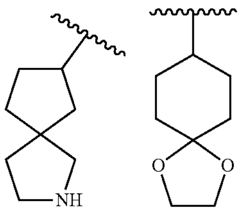

and

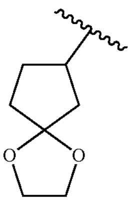

etc.

The term "fused cycloalkyl" refers to a 5- to 20-membered all-carbon polycyclic group in which each ring in the system shares an adjacent pair of carbon atoms with other rings in the system, one or more ring of which may contain one or more double bonds, but no ring has a fully conjugated n electron system. Preferably, the bridged heterocyclyl is 6- to 14-membered, and more preferably 7- to 10-membered. According to the number of constituent rings, it can be divided into bicyclic, tricyclic, tetracyclic or polycyclic fused cycloalkyl, preferably bicyclic or tricyclic, and more preferably 5-membered/5-membered or 5-membered/6-membered bicyclic cycloalkyl. Non-limiting examples of fused cycloalkyl include:

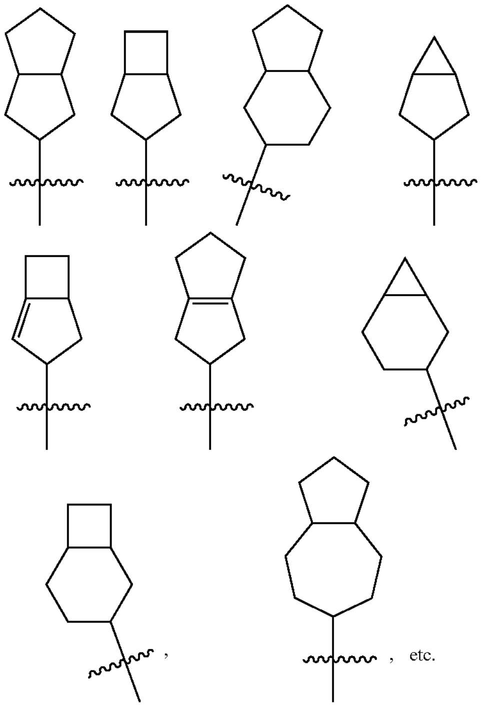

, etc.

The term "bridged cycloalkyl" refers to a 5- to 20-membered all-carbon polycyclic group with any two rings sharing two carbon atoms that are not directly connected. It may contain one or more double bonds, but no ring has a fully conjugated n electron system. Preferably, the bridged heterocyclyl is 6- to 14-membered, and more preferably 7- to 10-membered. According to the number of constituent rings, it can be divided into bicyclic, tricyclic, tetracyclic or polycyclic bridged cycloalkyl, preferably bicyclic, tricyclic or tetracyclic, and more preferably bicyclic or tricyclic. Non-limiting examples of bridged cycloalkyl include;

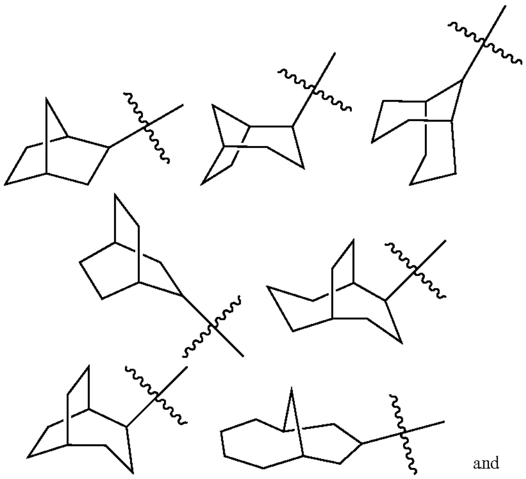

and

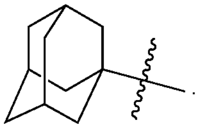

.

The cycloalkyl ring can be fused to an aryl, heteroaryl or heterocycloalkyl ring, wherein the ring connected to the parent structure is cycloalkyl, and non-limiting examples include indanyl, tetrahydronaphthyl, benzocycloheptanyl, etc. Cycloalkyl can be optionally substituted or unsubstituted. When the cycloalkyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or a carboxylate group.

The term “heterocyclyl” refers to a saturated or partially unsaturated monocyclic or polycyclic cyclic hydrocarbon substituent, which comprises 3 to 20 ring atoms, wherein one or more ring atoms are heteroatoms selected from nitrogen, oxygen or $S(O)_m$ (wherein m is an integer of 0 to 2), but excluding ring moieties of —O—O—, —O—S— or —S—S—, and the remaining ring atoms are carbon. Preferably, the heterocyclyl comprises 3 to 12 ring atoms, among which 1-4 are heteroatoms; more preferably, the heterocyclyl comprises 3 to 8 ring atoms; most preferably, the heterocyclyl comprises 3 to 8 ring atoms; further preferably, the heterocyclyl is 3-membered, 4-membered, 5-membered, 6-membered, 7-membered, or 8-membered heterocyclyl comprising 1-3 nitrogen atoms, optionally substituted with 1-2 oxygen atoms, sulfur atoms, or oxo, including nitrogen-containing monocyclic heterocyclyl, nitrogen-containing spiro heterocyclyl, or nitrogen-containing fused heterocyclyl; alternatively, preferably, the heterocyclyl comprises 5 to 12 ring atoms, among which 1-4 are heteroatoms and is further preferably 5-membered, 6-membered, 7-membered, 8-membered, 9-membered, 10-membered, 11-membered, or 12-membered heterocyclyl comprising 1-3 nitrogen and/or oxygen atoms.

Non-limiting examples of monocyclic heterocyclyl include pyrrolidinyl, imidazolidinyl, tetrahydrofuryl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl, azepinyl, 1,4-diazacycloheptyl, pyranyl, etc., preferably pyrrolidinyl, morpholinyl, piperidinyl, azepinyl, 1,4-diazacycloheptyl and piperazinyl. Polycyclic heterocyclyl includes spiro, fused and bridged heterocyclyl, wherein the spiro, fused and bridged heterocyclyl groups are optionally connected to other groups through a single bond, or further fused to other cycloalkyl, heterocyclyl, aryl and heteroaryl through any two or more atoms on the ring.

The term “spiroheterocyclyl” refers to a 5- to 20-membered polycyclic heterocyclyl with monocyclic rings sharing one atom (called a spiro atom), wherein one or more ring atoms are heteroatoms selected from nitrogen, oxygen, or $S(O)_m$ (wherein m is an integer of 0 to 2), and the remaining ring atoms are carbon. Spiroheterocyclyl may contain one or more double bonds, but no ring has a fully conjugated n electron system. Preferably, the bridged heterocyclyl is 6- to 14-membered, and more preferably 7- to 10-membered. According to the number of shared spiro atoms between the rings, the spiro heterocyclyl is divided into monospiroheterocyclyl, bispiroheterocyclyl or polyspiroheterocyclyl, preferably monospiroheterocyclyl and bispiroheterocyclyl. More preferably, it is a 3-membered/5-membered, 3-membered/6-membered, 4-membered/4-membered, 4-membered/5-membered, 4-membered/6-membered, 5-membered/5-membered or 5-membered/6-membered monospiro heterocyclyl. Non-limiting examples of spiro heterocyclyl include:

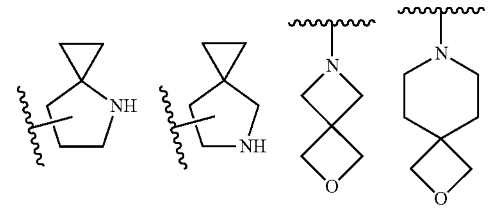

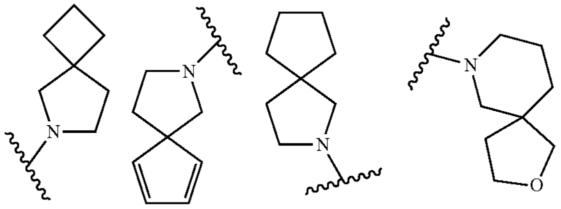

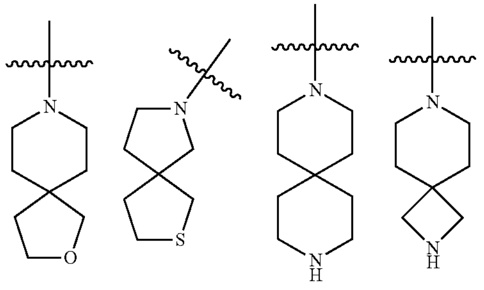

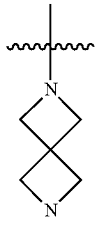

etc.

The term “fused heterocyclyl” refers to a 5- to 20-membered polycyclic heterocyclyl with each ring in the system sharing a pair of atoms neighboring other rings in the system, and one or more rings may contain one or more double bonds, but no ring has a fully conjugated n electron system, wherein one or more ring atoms are heteroatoms selected from nitrogen, oxygen, or $S(O)_m$ (wherein m is an integer of 0 to 2), and the remaining ring atoms are carbon. Preferably, the bridged heterocyclyl is 6- to 14-membered, and more preferably 7- to 10-membered. According to the number of constituent rings, it can be divided into bicyclic, tricyclic, tetracyclic or polycyclic fused heterocyclyl, preferably bicyclic or tricyclic, more preferably 5-membered fused 5-membered or 5-membered fused 6-membered bicyclic heterocyclyl. Non-limiting examples of fused heterocyclyl include:

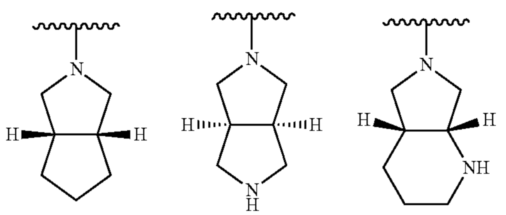

-continued

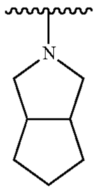
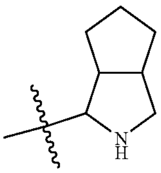
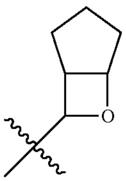
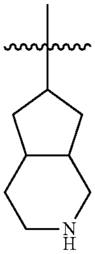
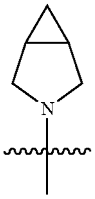
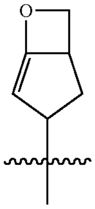
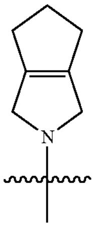
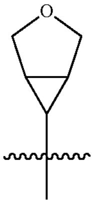
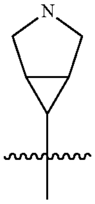
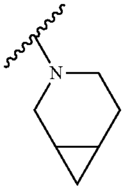
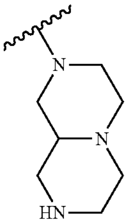
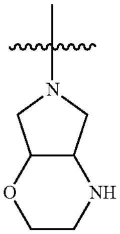
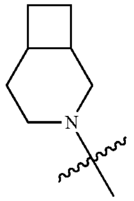
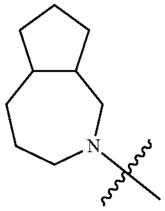
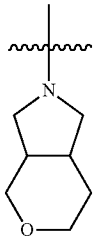
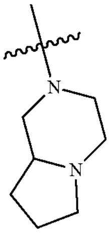
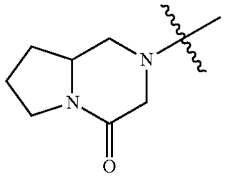

etc.

The term "bridged heterocyclyl" refers to a 5- to 14-membered polycyclic heterocyclyl with any two rings sharing two atoms that are not directly connected. It may contain one or more double bonds, but no ring has a fully conjugated n electron system, wherein one or more ring atoms are heteroatoms selected from nitrogen, oxygen, or $S(O)_m$ (wherein m is an integer of 0 to 2), and the remaining ring atoms are carbon. Preferably, the bridged heterocyclyl is 6- to 14-membered, and more preferably 7- to 10-membered. According to the number of constituent rings, it can be divided into bicyclic, tricyclic, tetracyclic or polycyclic bridged heterocyclyl, preferably bicyclic, tricyclic or tetracyclic, and more preferably bicyclic or tricyclic. Non-limiting examples of bridged heterocyclyl include:

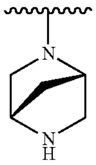
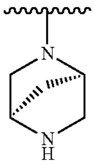
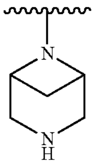
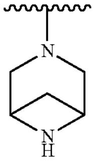
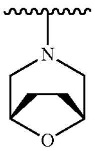
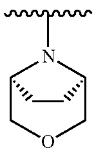
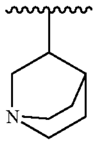
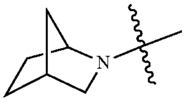
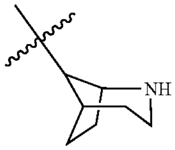
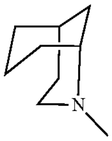
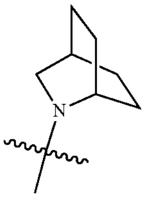
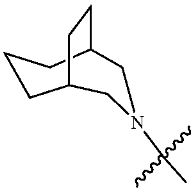
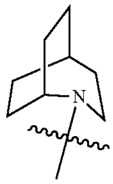
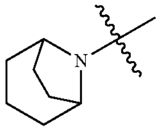

and

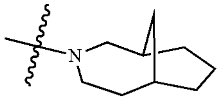

etc.

The heterocyclyl ring can be fused to an aryl, heteroaryl or cycloalkyl ring, wherein the ring connected to the parent structure is heterocyclyl, and the non-limiting examples thereof include:

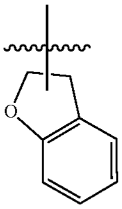
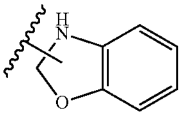
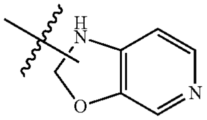
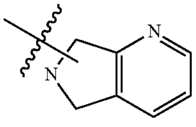
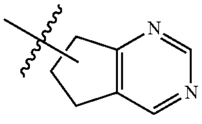
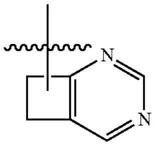
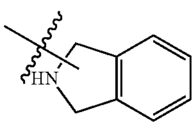

-continued

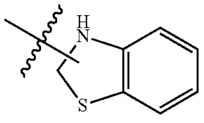

etc.

Heterocyclyl can be optionally substituted or unsubstituted. When the heterocyclyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or a carboxylate group.

The term "aryl" refers to a 6- to 14-membered all-carbon monocyclic or fused polycyclic (i.e., rings sharing an adjacent pair of carbon atoms) group having a conjugated n electron system, preferably 6- to 12-membered aryl, such as phenyl and naphthyl, and more preferably phenyl. The aryl ring can be fused to heteroaryl, heterocyclyl or cycloalkyl ring, including benzo 5- to 10-membered heteroaryl, benzo 3- to 8-membered cycloalkyl and benzo 3- to 8-membered heteroalkyl, preferably benzo 5- to 6-membered heteroaryl, benzo 3- to 6-membered cycloalkyl and benzo 3- to 6-membered heteroalkyl, wherein the heterocyclyl is heterocyclyl containing 1-3 nitrogen atoms, oxygen atoms, or sulfur atoms; or further including a three-membered nitrogen-containing fused ring containing a benzene ring, wherein the ring connected to the parent structure is aryl ring, and the non-limiting examples thereof include:

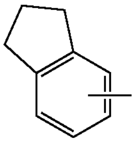 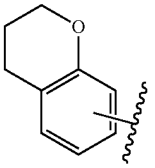 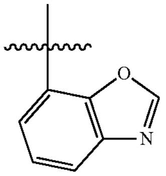

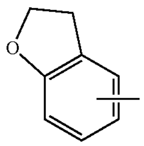 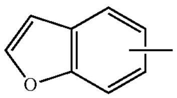 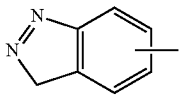

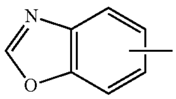 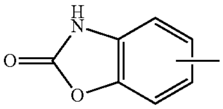

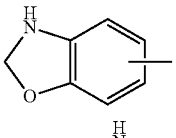 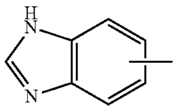 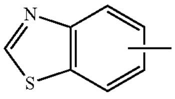

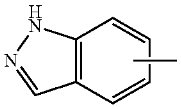 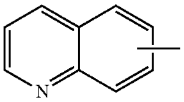

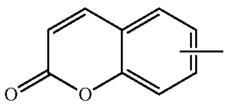 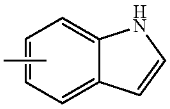

-continued

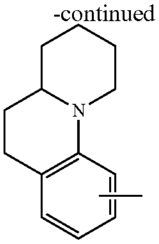

etc.

Aryl can be substituted or unsubstituted. When the aryl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, oxo, heterocycloalkyl, aryl, heteroaryl, cycloalkoxy, heterocycloalkoxy, cycloalkylthio, heterocycloalkylthio, carboxyl or a carboxylate group.

The term "heteroaryl" refers to a heteroaromatic system containing 1 to 4 heteroatoms and 5 to 14 ring atoms, wherein the heteroatoms are selected from oxygen, sulfur and nitrogen. The heteroaryl is preferably 5- to 12-membered, more preferably 5-membered or 6-membered monocyclic heteroaryl or 8- to 12-membered bicyclic heteroaryl, such as imidazolyl, furyl, thienyl, thiazolyl, pyrazolyl, oxazolyl, oxadiazolyl, pyrrolyl, triazolyl, tetrazolyl, pyridinyl, pyrimidinyl, thiadiazole, pyrazinyl, triazinyl, pyridazinyl, etc., preferably triazolyl, thienyl, imidazolyl, pyrazolyl, oxazolyl, pyrimidinyl, or thiazolyl; more preferably, pyrazolyl, pyrrolyl and oxazolyl.

The bicyclic heteroaryl is preferably 5-membered fused 5-membered bicyclic heteroaryl, 5-membered fused 6-membered bicyclic heteroaryl, 6-membered fused 5-membered bicyclic heteroaryl, or 6-membered fused 6-membered bicyclic heteroaryl, and non-limiting examples thereof include:

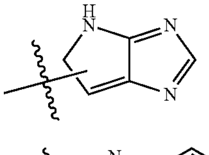 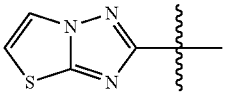

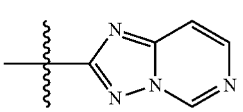 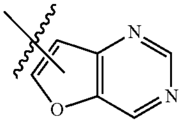

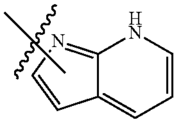 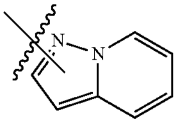 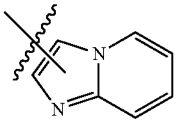

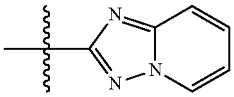 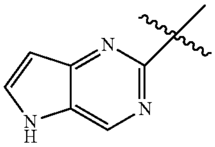

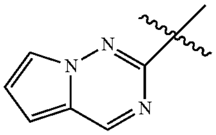 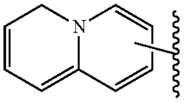

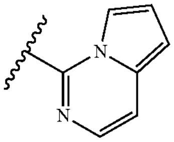 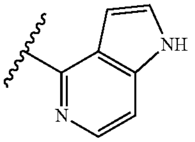

-continued
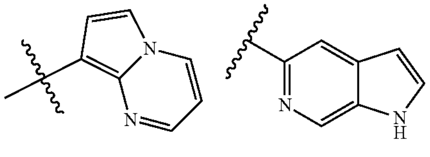
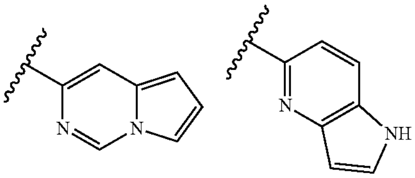
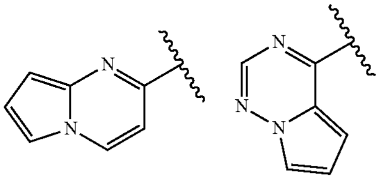
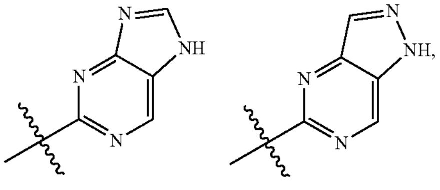
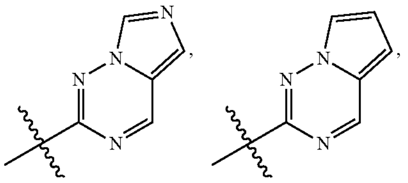
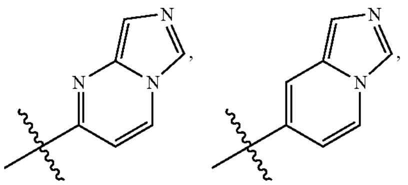
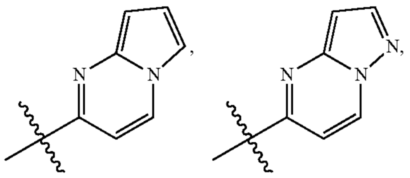
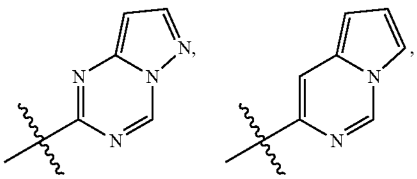
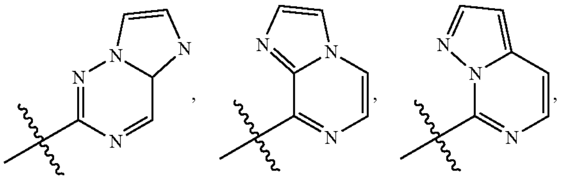
-continued
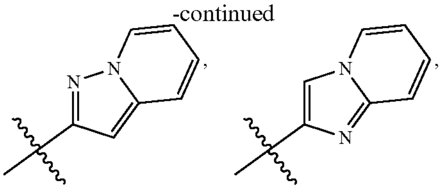
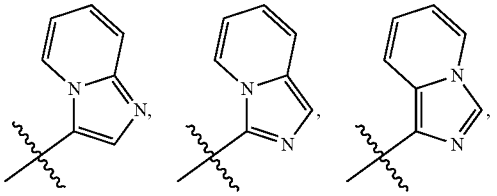
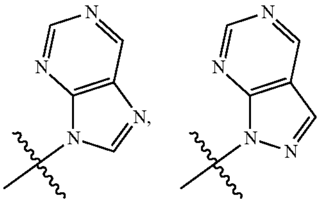
or
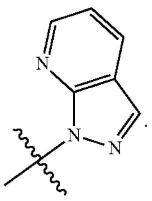
The heteroaryl ring can be fused to an aryl, heterocyclyl or cycloalkyl ring, wherein the ring connected to the parent structure is heteroaryl ring, and the non-limiting examples thereof include:
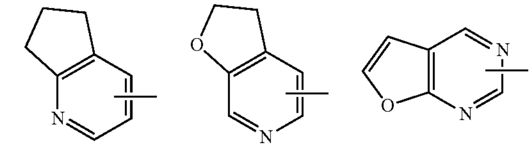
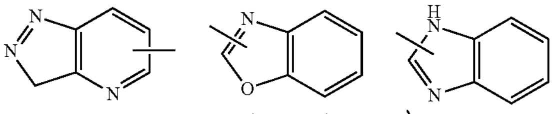
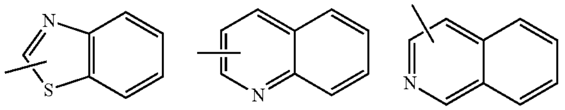
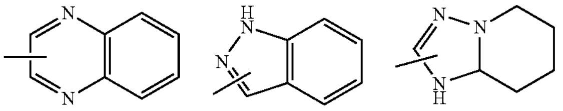
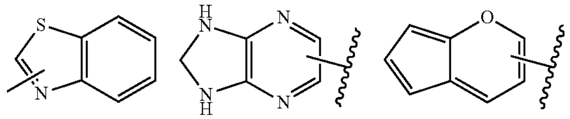
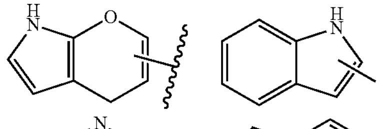
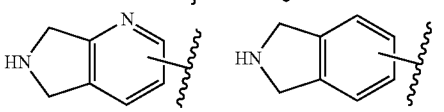
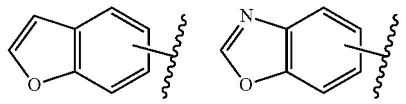
etc.
Heteroaryl can be optionally substituted or unsubstituted. When the heterocyclyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl, oxo, or a carboxylate group.

The term "alkoxy" refers to —O-(alkyl) and —O-(unsubstituted cycloalkyl), where the alkyl is as defined above. Non-limiting examples of alkoxy include: methoxy, ethoxy, propoxy, butoxy, cyclopropoxy, cyclobutoxy, cyclopentoxy, and cyclohexoxy. Alkoxy can be optionally substituted or unsubstituted. When the alkoxy is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

"Haloalkyl" refers to alkyl substituted with one or more halogen, wherein alkyl is defined as above.

"Haloalkoxy" refers to alkoxy substituted with one or more halogen, wherein alkoxy is defined as above.

"Hydroxyalkyl" refers to alkyl substituted with hydroxyl, wherein alkyl is defined as above.

"Alkenyl" is also known as alkylene, wherein the alkenyl can be further substituted with other related groups, such as: alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

"Alkynyl" refers to (CH≡C—), wherein the alkynyl can be further substituted with other related groups, such as: alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

The term "alkenylcarbonyl" refers to —C(O)-(alkenyl), wherein alkenyl is defined as above. Non-limiting examples of alkenylcarbonyl include: ethenylcarbonyl, propenylcarbonyl, and butenylcarbonyl. Alkenylcarbonyl can be optionally substituted or unsubstituted. When the alkenylcarbonyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

"Halogen" refers to fluorine, chlorine, bromine or iodine.

Different terms such as "X is selected from A, B, or C", "X is selected from A, B and C", "X is A, B or C", and "X is A, B and C" all express the same meaning, i.e., X can be any one or more of A, B, and C.

The enol structure and the lactam structure in the compound of the present disclosure are tautomers, and a person skilled in the art should know that they are the same molecule, such as,

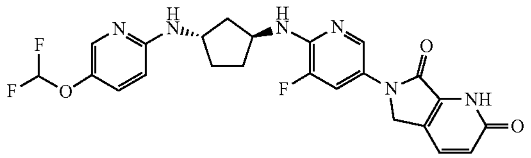

and

-continued

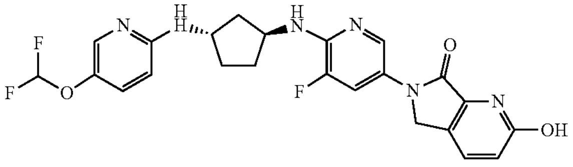

are the same molecule.

The hydrogen atoms of the present disclosure can be replaced with its isotope deuterium, and any hydrogen atom in the example compounds involved in the present disclosure can also be replaced with a deuterium atom.

"Optional" or "optionally" means that the event or circumstance subsequently described may but need not to occur, and the description includes the occasion where the event or circumstance occurs or does not occur. For example, "heterocyclic group optionally substituted with alkyl" means the alkyl may but need not be present, and the description includes the case where the heterocyclic group is substituted with alkyl and the case where the heterocyclic group is not substituted with alkyl.

"Substituted" means that one or more hydrogen atoms, preferably at most 5, more preferably 1-3 hydrogen atoms in the group are each independently substituted with a corresponding number of substituents. It goes without saying, the substituents may be only in their possible chemical positions, a person skilled in the art can determine the possible or impossible substitutions (by experiment or theory) without paying too much effort. For example, the amino group having a free hydrogen or a hydroxyl group may be unstable when combined the carbon atoms having an unsaturated (e.g., olefinic) bond.

"Pharmaceutical composition" denotes a mixture containing one or more compounds described herein or physiologically/pharmaceutically acceptable salts or prodrug thereof and other chemical components, as well as other components, such as physiologically/pharmaceutically acceptable carriers and excipients. The purpose of pharmaceutical compositions is to facilitate administration to living organisms and facilitate the absorption of active ingredients to exert biological activity.

"Pharmaceutically acceptable salts" refer to salts of the compounds of the present disclosure, which are safe and effective when used in mammals, and have appropriate biological activity.

DETAILED DESCRIPTION OF EMBODIMENTS

The present disclosure will be further described below in conjunction with examples, but these examples are not meant to limit the scope of the present disclosure.

EXAMPLES

The structure of the compound of the present disclosure is determined by nuclear magnetic resonance (NMR) or/and liquid chromatography-mass spectrometry (LC-MS). NMR chemical shift (δ) is given in parts per million (ppm). NMR was determined using Bruker AVANCE-400 nuclear magnetic instrument. The solvent for the determination is deuterated dimethyl sulfoxide (DMSO-$d_6$), deuterated methanol ($CD_3OD$), deuterated chloroform ($CDCl_3$), or deuterium water ($D_2O$), and the internal standard, if any, is tetramethylsilane (TMS).

Agilent 1200 Infinity Series mass spectrometer is used for measurement by liquid chromatography-mass chromatography (LC-MS). For determination by HPLC, Agilent 1200DAD high-pressure liquid chromatograph (Sunfire C18 150×4.6 mm chromatographic column) and Waters 2695-2996 high-pressure liquid chromatograph (Gimini $C_{18}$ 150×4.6 mm chromatographic column) are used.

Yantai Huanghai HSGF254 or Qingdao GF254 silica gel plate is used as a thin layer chromatography silica plate, and TLC is of the specification of 0.15-0.20 mm, and the specification when separating and purifying a product by thin layer chromatography is 0.4-0.5 mm. For column chromatography, Yantai Huanghai silica gel of 200-300 mesh silica gel is generally used as a carrier.

The compound of the present disclosure has significant advantages in druggability such as solubility, permeability and safety.

The starting materials in the examples of the present disclosure are known and can be purchased on the market, or can be synthesized using or according to methods known in the art.

Unless otherwise specified, all reactions in the present disclosure are carried out under continuous magnetic stirring in a dry nitrogen or argon atmosphere, the solvent is a dry solvent, and the reaction temperature unit is degrees Celsius.

Eluent systems for silica gel column chromatography and developer systems for thin layer chromatography, which are used for the purification of compounds in the intermediates and examples, include: A: dichloromethane and methanol system, B: n-hexane and ethyl acetate system, and C: dichloromethane and acetone system, wherein the volume ratio between the solvents could be adjusted depending on the polarity of the compound, or could also be adjusted by adding a small amount of basic or acidic reagents such as triethylamine and acetic acid.

Unless otherwise specified, in the examples of the present disclosure, ratios in mobile phases in HPLC chiral resolution conditions and HPLC chiral analysis conditions were volume ratios.

Intermediate 1

(1S,3S)-N1-(5-(difluoromethoxy)pyrimidin-2-yl) cyclopentane-1,3-diamine

Intermediate 1

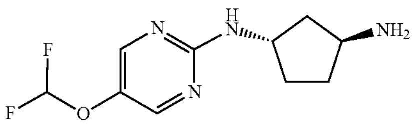

By reference to the preparation method of patent WO 2020150473 A2, intermediate 1 was synthesized.

MS m/z (ESI): 245.1 [M+H]+.

Intermediate 1 could also be obtained by the following method:

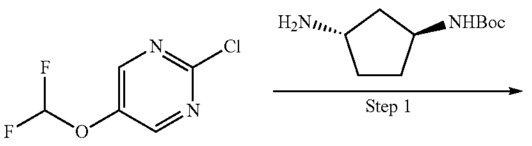

1A

-continued

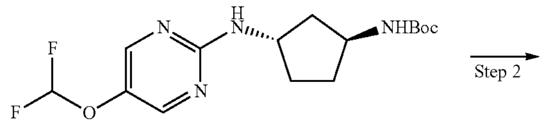

1B

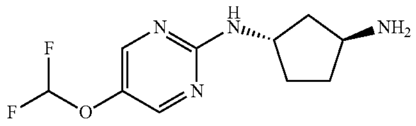

Intermediate 1

Step 1: 2-Chloro-5-(difluoromethoxy)pyrimidine 1A (2.0 g, 11.1 mmol), tert-butyl (1S,3S)-3-aminocyclopentylcarbamate (2.44 g, 12.2 mmol), and diisopropylethylamine (2.86 g, 14.08 mmol) were dissolved in dimethyl sulfoxide (10 mL), and the reaction was heated to 100° C. and stirred for 5 hours. The reaction liquid was cooled to room temperature and poured into water (50 mL), and the aqueous phase was extracted with ethyl acetate (100 mL×2). The organic phases were combined, washed successively with water (50 mL) and a saturated sodium chloride solution (50 mL), dried, and concentrated, and the residue was purified by silica gel chromatography (elution system B) to separate tert-butyl (1S,3S)-3-((5-(difluoromethoxy)pyrimidin-2-yl) amino)cyclopentylcarboxylate 1B (2.1 g), yield: 55.1%. MS m/z (ESI): 345.2 [M+H]+.

Step 2: 1B (2.1 g, 6.1 mmol) was dissolved in methanol (10 mL), a solution of hydrogen chloride in dioxane (4 M, 20 mL) was added, and the reaction was stirred at room temperature for 2 hours. The reaction liquid was concentrated, and the pH was adjusted to weak alkalinity by adding an ammonia methanol solution (7 M, 10 mL). After concentration again, the residue was purified by silica gel chromatography (elution system A) to separate intermediate 1, (1S,3S)—N1-(5-(difluoromethoxy)pyrimidin-2-yl)cyclopentane-1,3-diamine (1.3 g), yield: 87.3%. MS m/z (ESI): 245.1 [M+H]+.

Intermediate 2

6'-(((1S,3S)-3-aminocyclopentyl)amino)-2H-[1,3'-bipyridine]-2-one

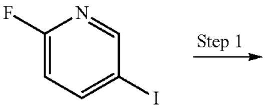

2A

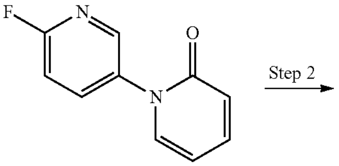

2B

-continued

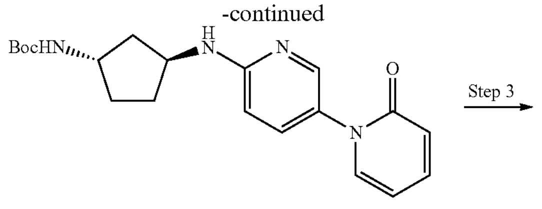

2C

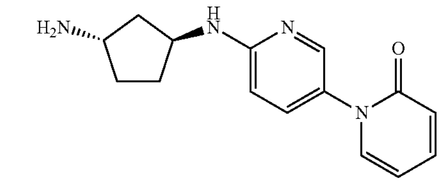

Intermediate 2

Step 1: 2-Fluoro-5-iodopyridine 2A (5 g, 22.4 mmol), 2-hydroxypyridine (2.35 g, 24.7 mmol), cuprous iodide (427 mg, 2.24 mmol), trans-(1R,2R)—N,N'-dimethyl 1,2-cyclohexanediamine (159 mg, 1.12 mmol), and cesium carbonate (9.5 g, 29.2 mmol) were dissolved in 1,4-dioxane (75 mL), and the reaction was heated to 100° C. and stirred for 16 hours. The reaction liquid was cooled to room temperature and poured into 100 mL of water, and the aqueous phase was extracted with ethyl acetate (100 mL×2). The organic phases were combined, washed successively with water (100 mL) and a saturated sodium chloride solution (100 mL), dried, and concentrated, and the residue was purified by silica gel chromatography (elution system B) to obtain 6'-fluoro-2H-[1,3'-bipyridine]-2-one 2B (3.1 g), yield: 72.7%. MS m/z (ESI): 191.1 [M+H]$^+$.

Step 2: Tert-butyl (1S,3S)-3-aminocyclopentylcarbamate (2.0 g, 9.99 mmol), 6'-fluoro-2H-[1,3'-bipyridine]-2-one 2B (2.85 g, 14.9 mmol), and N,N-diisopropylethylamine (3.87 g, 30.0 mmol) were dissolved in dimethyl sulfoxide (30 mL), and the reaction was heated to 130° C. and stirred for 16 hours. The reaction liquid was cooled to room temperature and poured into water (100 mL), and the aqueous phase was extracted with ethyl acetate (100 mL×2). The organic phases were combined, washed successively with water (100 mL) and a saturated sodium chloride solution (100 mL), dried, and concentrated, and the residue was purified by silica gel chromatography (elution system B) to obtain tert-butyl ((1S,3S)-3-((2-carbonyl-2H-[1,3'-bipyridin]-6'-yl)amino)cyclopentyl)carbamate 2C (2.9 g), yield: 78.4%. MS m/z (ESI): 371.2 [M+H]$^+$.

Step 3: Tert-butyl ((1S,3S)-3-((2-carbonyl-2H-[1,3'-bipyridin]-6'-yl)amino)cyclopentyl)carbamate 2C (2.9 g, 7.83 mmol) was dissolved in a solution of 4 M hydrogen chloride in dioxane (30 mL), and the reaction was stirred at room temperature for 3 hours. The reaction liquid was concentrated, and the residue was purified by a reversed-phase chromatographic column (eluent system C) to obtain intermediate 2,6'-(((1S,3S)-3-aminocyclopentyl)amino)-2H-[1,3'-bipyridine]-2-one (1.5 g), yield: 70.9%. MS m/z (ESI): 271.2 [M+H]$^+$.

Reference Example 1

6'-((3-(((1S,3S)-7-fluoro-[1,2,4]triazolo[1,5-a]pyridin-2-yl)amino)cyclopentyl)amino)-2H-[1,3'-bipyridine]-2-one

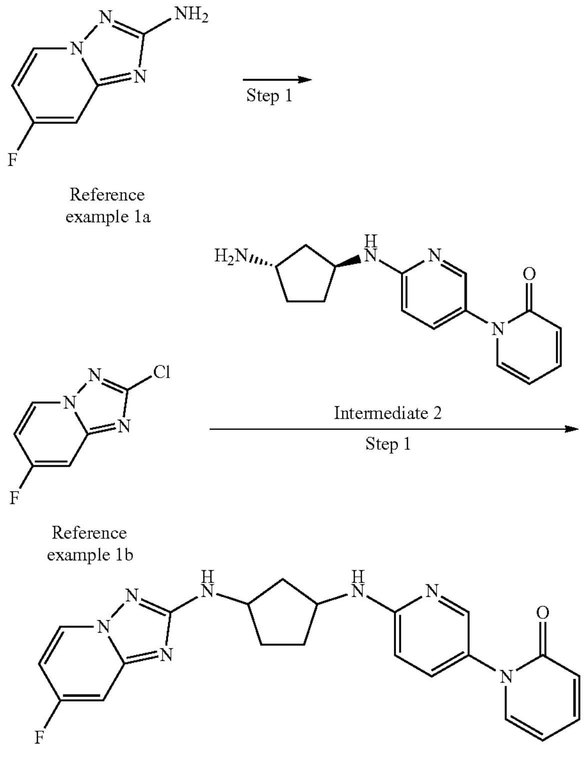

Reference example 1a

Reference example 1b

Reference example 1

Step 1: In an ice bath, 7-fluoro-[1,2,4]triazolo[1,5-a]pyridin-2-amine reference example 1a (100 mg, 0.657 mmol) was dissolved in acetonitrile and stirred, sodium nitrite (91 mg, 1.31 mmol) was added to the reaction liquid, and stirring was continued for 1 minute. Hydrochloric acid (4 M, 0.41 mL) was dropwise added to the reaction liquid, the reaction was heated to room temperature and continued to be stirred, and the completion of the reaction was detected by a thin layer chromatography plate. A saturated sodium bicarbonate solution was dropwise added to the reaction liquid until pH=7. The reaction liquid was extracted with dichloromethane (10 mL×3). The organic phase was dried and concentrated, and the residue was separated by silica gel column chromatography (eluent system A) to obtain 2-chloro-7-fluoro-[1,2,4]triazolo[1,5-a]pyridine reference example 1b (65 mg), yield: 77.5%. MS m/z (ESI): 172.1 [M+H]$^+$.

Step 2: Under nitrogen protection, reference example 1b (80 mg, 0.37 mmol), 27c (100 mg, 0.37 mmol), cesium carbonate (241.3 mg, 0.74 mmol), $Pd_2dba_3$ (67.8 mg, 0.074 mmol), and xantphos (85.7 mg, 0.15 mmol) were dissolved in 1'4-dioxane (2 mL). The reaction liquid was heated to 130° C. and reacted for 2 hours by microwave. The reaction liquid was heated to 130° C. under nitrogen protection and reacted for 16 hours. The reaction liquid was filtered and concentrated. The residue was subjected to preparative HPLC (basic system) to obtain 6'-(((1S,3S)-3-((7-fluoro-[1,2,4]triazolo[1,5-a]pyridin-2-yl)amino)cyclopentyl)amino)-

2H-[1,3'-bipyridine]-2-one reference example 1 (6.6 mg), yield: 4.08%. MS m/z (ESI): 406.2 [M+H]$^+$.

$^1$H NMR (400 MHz, DMSO-$d_6$) δ 8.69-6.59 (m, 1H), 7.92 (d, 1H), 7.60 (dd, 1H), 7.51-7.35 (m, 2H), 7.27 (dd, 1H), 6.97-6.82 (m, 2H), 6.74 (d, 1H), 6.52 (d, 1H), 6.44 (d, 1H), 6.26 (t, 1H), 4.35-4.28 (m, 1H), 4.20-4.10 (m, 1H), 2.20-2.07 (m, 2H), 2.00-1.82 (m, 2H), 1.60-1.42 (m, 2H).

Reference Example 2

6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one

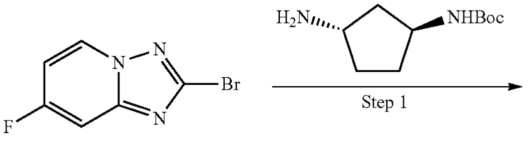

Reference example 2a

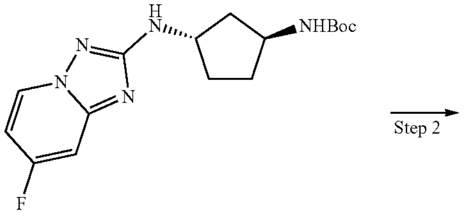

Reference example 2b

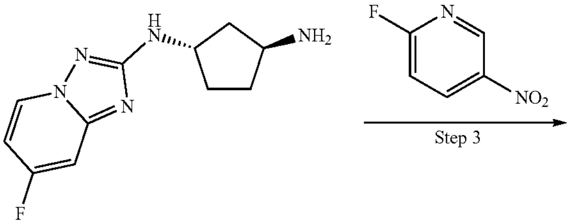

Reference example 2c

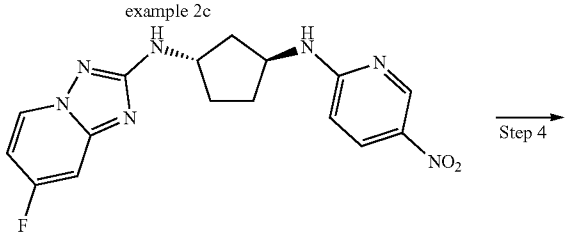

Reference example 2d

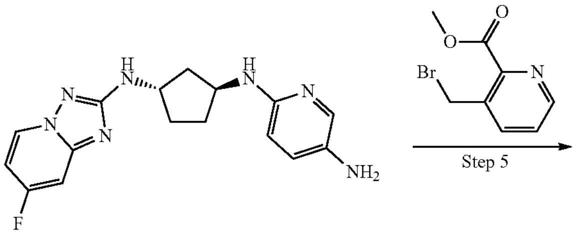

Reference example 2e

-continued

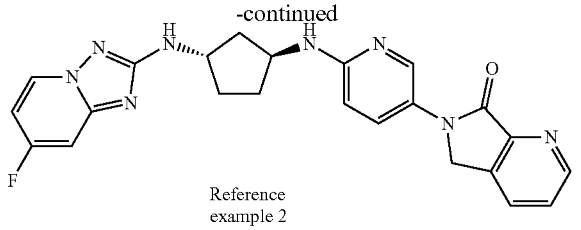

Reference example 2

Step 1: Under nitrogen protection, 2-bromo-7-fluoro-[1,2,4]triazolo[1,5-a]pyridine reference example 2a (500 mg, 2.31 mmol), tert-butyl N-[(1S,3S)-3-aminocyclopentyl]carbamate (510 mg, 2.55 mmol), cesium carbonate (1.51 g, 4.63 mmol), tris(dibenzylideneacetone)dipalladium (424 mg, 0.46 mmol), and 4,5-bis(diphenylphosphino)-9,9-dimethylxanthene (536 mg, 0.92 mmol) were dissolved in 1,4-dioxane (15 mL), heated to 130° C. by microwave and stirred for 2 hours. The reaction liquid was filtered, and the filtrate was concentrated. The residue was subjected to silica gel column chromatography (elution system B) and preparative HPLC (formic acid system) to obtain tert-butyl N-[(1S,3S)-3-[(7-fluoro-[1,2,4]triazolo[1,5-a]pyridin-2-yl)amino]cyclopentyl]carbamate reference example 2b (240 mg), yield: 30.9%. MS m/z (ESI): 336.0 [M+H]$^+$.

Step 2: At room temperature, reference example 2b (202 mg, 0.60 mmol) was dissolved in methanol (2 mL) and stirred, and a solution of hydrogen chloride in 1,4-dioxane (4 M, 5 mL) was added to the reaction liquid. The reaction liquid was stirred at room temperature for 1 hour. The reaction liquid was concentrated, and the residue was purified by preparative HPLC (aqueous ammonia system) to obtain (1S,3S)-N1-(7-fluoro-[1,2,4]triazolo[1,5-a]pyridin-2-yl)cyclopentane-1,3-diamine reference example 2c (140 mg), yield: 98.6%. MS m/z (ESI): 236.2 [M+H]$^+$.

Step 3: Reference example 2c (150 mg, 0.64 mmol), 2-fluoro-5-nitro-pyridine (91 mg, 0.64 mmol), and cesium carbonate (416 mg, 1.28 mmol) were dissolved in acetonitrile (2 mL), and the reaction was heated to 80° C. and stirred for 16 hours. The reaction liquid was filtered, the filtrate was concentrated, and the residue was purified by silica gel column chromatography (elution system B) to obtain (1S,3S)-N1-(7-fluoro-[1,2,4]triazolo[1,5-a]pyridin-2-yl)-N3-(5-nitropyridin-2-yl)cyclopentane-1,3-diamine reference example 2d (190 mg), yield: 83.4%. MS m/z (ESI): 358.1 [M+H]$^+$.

Step 4: In a hydrogen atmosphere at room temperature, reference example 2d (190 mg, 0.53 mmol) and palladium on carbon (28 mg, 0.026 mmol, content: 10%) were dissolved in methanol (5 mL) and stirred for 1 hour. The reaction liquid was filtered, and the filtrate was concentrated to obtain N2-((1S,3S)-3-((7-fluoro-[1,2,4]triazolo[1,5-a]pyridin-2-yl)amino)cyclopentyl)pyridine-2,5-diamine reference example 2e (170 mg), yield: 97.7%. MS m/z (ESI): 328.1 [M+H]$^+$.

Step 5: At room temperature, reference example 2e (80 mg, 0.24 mmol), methyl 3-(bromomethyl)picolinate (62 mg, 0.27 mmol), and potassium carbonate (101.2 mg, 0.73 mmol) were dissolved in N,N-dimethylformamide (2 mL), stirred for 1 hour, then heated to 50° C., and stirred for 4 hours. The reaction liquid was filtered, and the filtrate was purified by preparative HPLC (ammonium bicarbonate system) to obtain 6-(6-(((1S,3S)-3-((7-fluoro-[1,2,4]triazolo[1,5-a]pyridin-2-yl)amino)cyclopentyl)amino)pyridin-3-yl)-5, 6-dihydro-7H-pyrrolo[3,4-b]pyridin-7-one reference example 2 (24.3 mg), yield: 22.4%. MS m/z (ESI): 445.2 [M+H]$^+$.

$^1$H NMR (400 MHz, DMSO-d$_6$) δ 8.75 (d, 1H), 8.66 (t, 1H), 8.35 (d, 1H), 8.11 (d, 1H), 7.88 (dd, 1H), 7.62 (dd, 1H), 7.27 (dd, 1H), 6.86 (td, 1H), 6.75 (d, 1H), 6.70 (d, 1H), 6.56 (d, 1H), 4.93 (s, 2H), 4.38-4.24 (m, 1H), 4.22-4.09 (m, 1H), 2.24-2.10 (m, 2H), 2.03-1.82 (m, 2H), 1.66-1.39 (m, 2H).

Reference Example 3

6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one

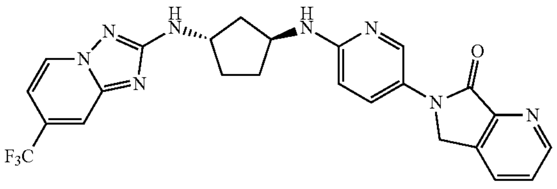 [SMILES: O=C1c2ncccc2CN1c1ccc(N[C@H]2CC[C@H](Nc3nc4cc(C(F)(F)F)ccn4n3)C2)nc1]

Reference Example 3

By reference to the synthesis method of reference example 2, 6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one reference example 3 was synthesized. MS m/z (ESI): 495.2 [M+H]$^+$.

$^1$H NMR (400 MHz, DMSO-d$_6$) δ 8.83 (d, 1H), 8.75 (dd, 1H), 8.35 (d, 1H), 8.15-8.06 (m, 1H), 7.88 (dd, 1H), 7.86 (s, 1H), 7.62 (dd, 1H), 7.15 (dd, 1H), 7.04 (d, 1H), 6.71 (d, 1H), 6.57 (d, 1H), 4.93 (s, 2H), 4.36-4.15 (m, 2H), 2.23-2.10 (m, 2H), 2.05-1.83 (m, 2H), 1.65-1.42 (m, 2H).

Reference example 3 could also be prepared by reference to the following method.

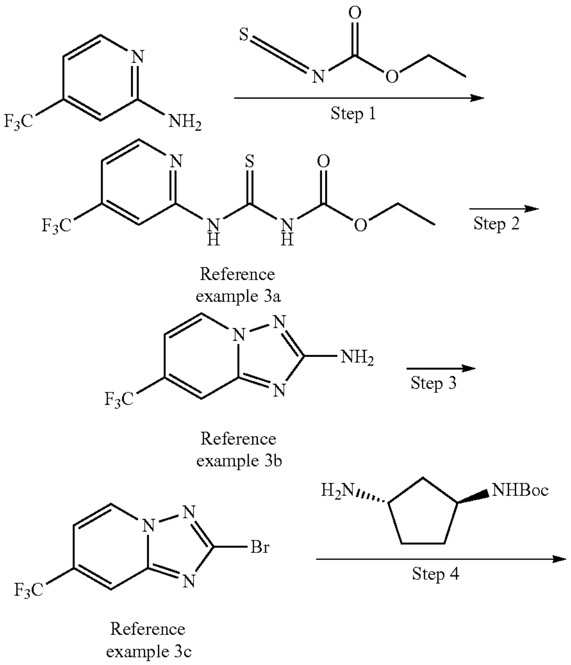

-continued

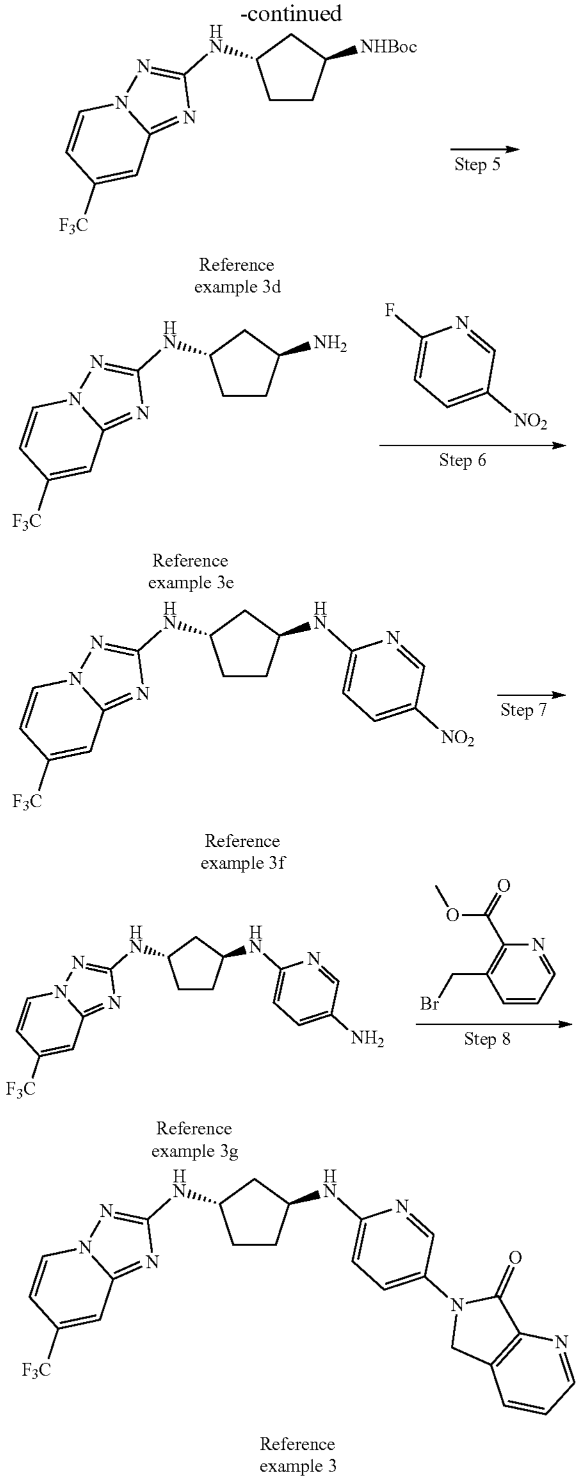

Step 1: At room temperature, 4-(trifluoromethyl)pyridin-2-amine (5 g, 30.84 mmol) and ethyl N-(thiomethylene) carbamate (4.85 g, 37.01 mmol) were dissolved in 1,2-dichloroethane (50 mL), and stirred for 16 hours. The reaction liquid was concentrated to obtain ethyl N-[[4-(trifluoromethyl)-2-pyridinyl]carbamothioyl]carbamate reference example 3a (9.05 g). The product was directly used in the next reaction without purification. MS m/z (ESI): 294.1 [M+H]$^+$.

Step 2: At room temperature, reference example 3a (9 g, 30.69 mmol), hydroxylamine hydrochloride (10.66 g, 153.44 mmol) and N,N-diisopropylethylamine (11.90 g, 92.07 mmol) were dissolved in methanol (100 mL), stirred for 20 minutes, then heated to 65° C., and stirred for 3 hours. The reaction liquid was concentrated, and the residue was purified by silica gel column chromatography (elution system A) to obtain 7-(trifluoromethyl)-[1,2,4]triazolo[1,5-a]pyridin-2-amine reference example 3b (5.0 g), yield: 80.60%. MS m/z (ESI): 203.1 $[M+H]^+$.

Step 3: Reference example 3b (5 g, 24.74 mmol) and copper bromide (5.52 g, 24.74 mmol) were dissolved in acetonitrile (50 mL), and tert-butyl nitrite (12.75 g, 123.68 mmol) was added. The reaction was stirred at room temperature for 0.5 hours, then heated to 70° C., and stirred for 2 hours. The reaction liquid was concentrated, and the residue was diluted with ethyl acetate (150 mL) and filtered. The organic phase was washed with water (100 mL) and concentrated, and the residue was purified by silica gel column chromatography (elution system A) to obtain 2-bromo-7-(trifluoromethyl)-[1,2,4]triazolo[1,5-a]pyridine reference example 3c (5 g), yield: 75.99%. MS m/z (ESI): 266.0, 268.0 $[M+H]^+$.

Step 4: Under nitrogen protection, reference example 3c (4.5 g, 16.92 mmol), tert-butyl N-[(1S,3S)-3-aminocyclopentyl]carbamate (3.39 g, 16.92 mmol), cesium carbonate (11.02 g, 33.83 mmol), tris(dibenzylideneacetone)dipalladium (2.32 g, 2.54 mmol), and 4,5-bis(diphenylphosphino)-9,9-dimethylxanthene (2.94 g, 5.07 mmol) were dissolved in 1'4-dioxane (120 mL). The reaction was heated to 130° C. and stirred for 16 hours. The reaction liquid was filtered and concentrated. The residue was purified by silica gel column chromatography (elution system A) to obtain tert-butyl N-[(1S,3S)-3-[[7-(trifluoromethyl)-[1,2,4]triazolo[1,5-a]pyridin-2-yl]amino]cyclopentyl]carbamate reference example 3d (3.7 g), yield: 56.76%. MS m/z (ESI): 386.2 $[M+H]^+$.

Step 5: At room temperature, reference example 3d (3.7 g, 9.60 mmol) and hydrogen chloride (4 M in dioxane, 36.00 mL) were dissolved in methanol (10 mL), and stirred for one hour. The reaction liquid was concentrated, and the residue was diluted with methanol, and adjusted to pH=8-10 with a saturated sodium bicarbonate solution. After concentration, the residue was purified by silica gel column chromatography (elution system A) to obtain (1S,3S)-N1-(7-(trifluoromethyl)-[1,2,4]triazolo[1,5-a]pyridin-2-yl)cyclopentane-1,3-diamine reference example 3e (2.74 g), yield: 100%. MS m/z (ESI): 286.2 $[M+H]^+$.

Step 6: Reference example 3e (2.74 g, 9.61 mmol), 2-fluoro-5-nitro-pyridine (1.50 g, 10.57 mmol), and cesium carbonate (7.82 g, 24.01 mmol) were dissolved in N,N-dimethylformamide (40 mL), heated to 80° C. and stirred for 16 hours. The reaction liquid was filtered, and the filtrate was concentrated. The residue was purified by silica gel column chromatography (elution system B) to obtain (1S, 3S)-N1-(5-nitropyridin-2-yl))-N3-(7-(trifluoromethyl)-[1,2,4]triazolo[1,5-a]pyridin-2-yl)cyclopentane-1,3-diamine reference example 3f (3.8 g), yield: 97.12%. MS m/z (ESI): 408.1 $[M+H]^+$.

Step 7: In a hydrogen atmosphere, reference example 3f (3.8 g, 9.33 mmol) and palladium on carbon (993 mg, 0.93 mmol, purity: 10%) were dissolved in methanol (60 mL), and stirred for 2 hours at room temperature. The reaction liquid was filtered, and concentrated to obtain N2-((1S,3S)-3-((7-(trifluoromethyl)-[1,2,4]triazolo[1,5-a]pyridin-2-yl)amino)cyclopentyl)pyridine-2,5-diamine reference example 3g (3.2 g). The product was directly used in the next reaction without purification. MS m/z (ESI): 378.1 $[M+H]^+$ Step 8: Reference example 3g (2.0 g, 5.30 mmol), methyl 3-(bromomethyl)pyridine-2-carboxylate (1.30 g, 4.24 mmol) and N,N-diisopropylethylamine (2.05 g, 15.90 mmol) were dissolved in a mixed solvent of tert-butanol (20 mL) and N,N-dimethylformamide (4 mL), stirred for 1 hour at room temperature, then heated to 40° C. and stirred for 16 hours, further heated to 80° C. and stirred for 1 hour. The reaction liquid was filtered, and the filtrate was purified by preparative HPLC (ammonium bicarbonate system) to obtain 6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one reference example 3 (1.2 g), yield: 45.79%. MS m/z (ESI): 495.2 $[M+H]^+$ $^1$H NMR (400 MHz, DMSO-$d_6$) δ 8.82 (d, 1H), 8.75 (dd, 1H), 8.35 (d, 1H), 8.10 (d, 1H), 7.92-7.82 (m, 2H), 7.61 (dd, 1H), 7.15 (dd, 1H), 7.02 (d, 1H), 6.69 (d, 1H), 6.56 (d, 1H), 4.92 (s, 2H), 4.32-4.13 (m, 2H), 2.23-2.10 (m, 2H), 2.04-1.85 (m, 2H), 1.67-1.43 (m, 2H).

Reference Example 4

1-(6-(((1S,3S)-3-((5-(difluoromethoxy)pyrimidin-2-yl)amino)cyclopentyl)amino)pyridin-3-yl)-3-methyl-1,3-dihydro-2H-imidazolo[4,5-b]pyrazin-2-one

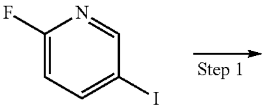

Reference example 4a

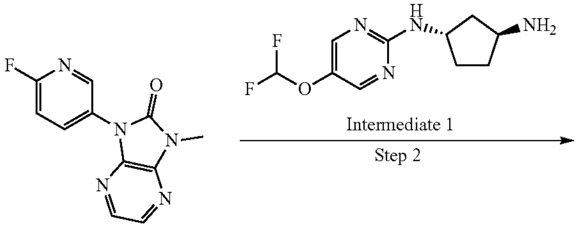

Reference example 4b

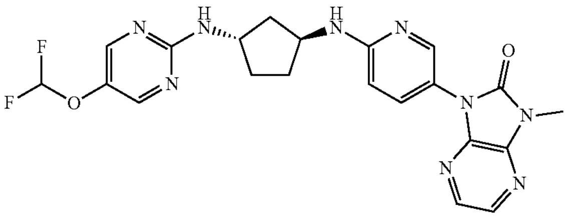

Reference example 4

Step 1: Under nitrogen protection, 2-fluoro-5-iodopyridine reference example 4a (2.2 g, 9.87 mmol), 1-methyl-1H-imidazo[4,5-b]pyrazin-2(3H)-one (1.78 g, 11.84 mmol), cuprous iodide (188 mg, 0.99 mmol), N,N'-dimethyl-1,2-cyclohexanediamine (281 mg, 1.97 mmol), and potassium phosphate (4.19 g, 19.73 mmol) were dissolved in dimethyl sulfoxide (40 mL), and the reaction was heated to 100° C. and stirred for 3 hours. The reaction liquid was brought back to room temperature, and a saturated sodium chloride solution (120 mL) was added to the reaction liquid. The aqueous phase was extracted with ethyl acetate (40 mL×3). The organic phases were combined, dried, and concentrated, and the residue was separated by silica gel column chromatography to obtain 1-(6-fluoropyridin-3-yl)-3-methyl-1,3-dihydro-2H-imidazolo[4,5-b]pyrazin-2-one reference example 4b (1.4 g, light yellow solid), yield: 57.87%. MS m/z (ESI): 246.1 $[M+H]^+$.

Step 2: Intermediate 1 (70 mg, 0.29 mmol), 1-(6-fluoropyridin-3-yl)-3-methyl-1,3-dihydro-2H-imidazolo[4,5-b]pyrazin-2-one reference example 4b (77 mg, 0.32 mmol), and cesium carbonate (280 mg, 0.86 mmol) were dissolved in dimethyl sulfoxide (3 mL), and the reaction was heated to 130° C. and stirred for 48 hours. The reaction liquid was cooled to room temperature and filtered, and the filtrate was subjected to preparative separation by reversed-phase HPLC (ammonium bicarbonate system) to obtain 1-(6-(((1S,3S)-3-((5-(difluoromethoxy)pyrimidin-2-yl)amino)cyclopentyl)amino)pyridin-3-yl)-3-methyl-1,3-dihydro-2H-imidazolo[4,5-b]pyrazin-2-one reference example 4 (41 mg, white solid), yield: 30.47%. MS m/z (ESI): 470.1 $[M+H]^+$.

$^1$H NMR (400 MHz, DMSO-$d_6$) δ 8.24 (s, 2H), 8.11 (d, 1H), 8.01 (d, 1H), 7.91 (d, 1H), 7.57-7.45 (m, 2H), 7.26-6.82 (m, 1H), 6.97 (d, 1H), 6.59 (d, 1H), 4.42-4.19 (m, 2H), 3.40 (s, 3H), 2.22-2.05 (m, 2H), 1.95-1.82 (m, 2H), 1.61-1.42 (m, 2H).

Reference Example 5

6-(6-(((1S,3S)-3-((5-(difluoromethoxy)pyrimidin-2-yl)amino)cyclopentyl)amino)pyridin-3-yl)-5,6-dihydro-7H-pyrrolo[3,4-b]pyridin-7-one Step 1: Under nitrogen protection, 2-fluoro-5-iodopyridine reference example 4a (2.2 g, 9.87 mmol), 5,6-dihydro-7H-pyrrolo[3,4-b]pyridin-7-one (1.59 g, 11.84 mmol), cuprous iodide (188 mg, 0.99 mmol), N,N'-dimethyl-1,2-cyclohexanediamine (281 mg, 1.97 mmol), and potassium phosphate (4.19 g, 19.73 mmol) were dissolved in dimethyl sulfoxide (40 mL), and the reaction was heated to 100° C. and stirred for 3 hours. The reaction liquid was brought back to room temperature, and a saturated sodium chloride solution (120 mL) was added to the reaction liquid. The aqueous phase was extracted with ethyl acetate (40 mL×3). The organic phases were combined, dried, and concentrated, and the residue was separated by silica gel column chromatography (eluent system A) to obtain 6-(6-fluoropyridin-3-yl)-5,6-dihydro-7H-pyrrolo[3,4-b]pyridin-7-one reference example 5b (1.3 g), yield: 57.49%. MS m/z (ESI): 230.1 $[M+H]^+$.

Step 2: Intermediate 1 (70 mg, 0.29 mmol), 6-(6-fluoropyridin-3-yl)-5,6-dihydro-7H-pyrrolo[3,4-b]pyridin-7-one reference example 5b (72 mg, 0.32 mmol), and cesium carbonate (280 mg, 0.86 mmol) were dissolved in dimethyl sulfoxide (3 mL), and the reaction was heated to 130° C. and stirred for 48 hours. The reaction liquid was cooled to room temperature and filtered, and the filtrate was subjected to preparative separation by reversed-phase HPLC (formic acid system) to obtain 6-(6-(((1S,3S)-3-((5-(difluoromethoxy)pyrimidin-2-yl)amino)cyclopentyl)amino)pyridin-3-yl)-5,6-dihydro-7H-pyrrolo[3,4-b]pyridin-7-one reference example 5 (46 mg), yield: 35.4%. MS m/z (ESI): 454.1 $[M+H]^+$.

$^1$H NMR (400 MHz, DMSO-$d_6$) δ 8.76 (d, 1H), 8.35 (d, 1H), 8.24 (s, 2H), 8.11 (d, 1H), 7.88 (d, 1H), 7.66-7.57 (m, 1H), 7.48 (d, 1H), 7.25-6.82 (m, 1H), 6.71 (s, 1H), 6.57 (d, 1H), 4.93 (s, 2H), 4.37-4.19 (m, 2H), 2.22-2.04 (m, 2H), 1.96-1.80 (m, 2H), 1.60-1.41 (m, 2H).

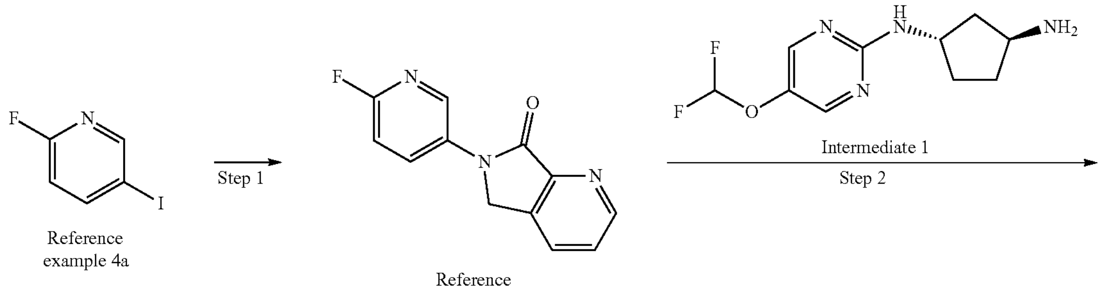

Reference example 4a

Reference example 5b

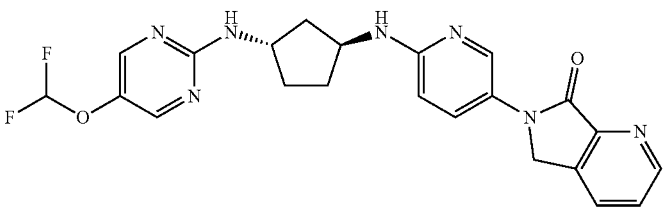

Reference example 5

Reference Example 6

6-(6-(((1S,3S)-3-((5-(difluoromethoxy)pyrimidin-2-yl)amino)cyclopentyl)amino)pyridin-3-yl)-5,5-dimethyl-5,6-dihydro-7H-pyrrolo[3,4-b]pyridin-7-one

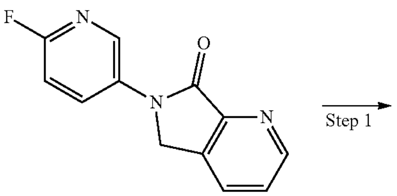

Reference example 5b

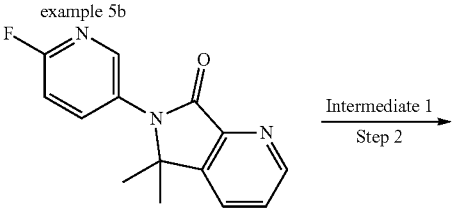

Reference example 6a

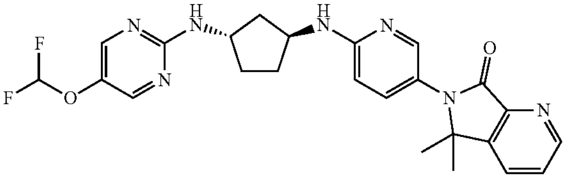

Reference example 6

Step 1: At 0° C., lithium bis(trimethylsilyl)amide (1 M, 3.6 mL) was added to a solution of reference example 5b (167 mg, 0.73 mmol) and iodomethane (517 mg, 3.64 mmol) in tetrahydrofuran (3 mL), and the reaction was heated to room temperature and stirred for 3 hours. At 0° C., a saturated ammonium chloride solution was added to the reaction liquid. The aqueous phase was extracted with ethyl acetate (20 mL×2). The organic phases were combined, dried, and concentrated, and the residue was separated by silica gel column chromatography to obtain 6-(6-fluoropyridin-3-yl)-5,5-dimethyl-5,6-dihydro-7H-pyrrolo[3,4-b]pyridin-7-one reference example 6a (110 mg), yield: 58.69%. MS m/z (ESI): 258.1 $[M+H]^+$.

Step 2: Under nitrogen protection, intermediate 1 (100 mg, 0.41 mmol), reference example 6a (70 mg, 0.27 mmol), and diisopropylethylamine (106 mg, 0.82 mmol) were dissolved in dimethyl sulfoxide (1.5 mL), and the reaction was heated to 130° C. and stirred for 48 hours. A saturated sodium chloride solution was added to the reaction liquid. The aqueous phase was extracted with ethyl acetate (15 mL×2). The organic phases were combined, dried, and concentrated, and the residue was subjected to reversed-phase HPLC to prepare 6-(6-(((1S,3S)-3-((5-(difluoromethoxy)pyrimidin-2-yl)amino)cyclopentyl)amino)pyridin-3-yl)-5,5-dimethyl-5,6-dihydro-7H-pyrrolo[3,4-b]pyridin-7-one reference example 6 (32.1 mg), yield: 24.50%. MS m/z (ESI): 482.3 $[M+H]^+$.

$^1$H NMR (400 MHz, DMSO-$d_6$) δ 8.79-8.69 (m, 1H), 8.29-8.19 (m, 3H), 7.86 (d, 1H), 7.68-7.59 (m, 1H), 7.49 (d, 1H), 7.32-7.26 (m, 1H), 7.23-6.82 (m, 1H), 6.90 (d, 1H), 6.57 (d, 1H), 4.42-4.20 (m, 2H), 2.23-2.03 (m, 2H), 2.01-1.78 (m, 2H), 1.64-1.34 (m, 8H).

Example 1

6'-(((1S,3S)-3-((7-(difluoromethyl)-[1,2,4]triazolo[1,5-a]pyridin-2-yl)amino)cyclopentyl)amino)-2H-[1,3'-bipyridine]-2-one

1

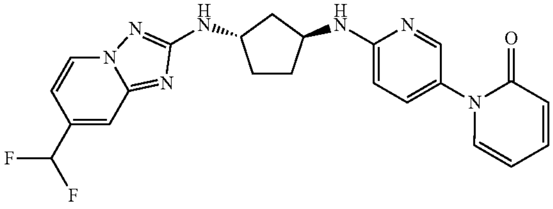

By reference to the synthesis method of reference example 1, 6'-(((1S,3S)-3-((7-(difluoromethyl)-[1,2,4]triazolo[1,5-a]pyridin-2-yl)amino)cyclopentyl)amino)-2H-[1,3'-bipyridine]-2-one 1 was synthesized. MS m/z (ESI): 438.2 $[M+H]^+$.

$^1$H NMR (400 MHz, DMSO-$d_6$) δ 8.73 (d, 1H), 7.92 (d, 1H), 7.66-7.54 (m, 2H), 7.52-7.36 (m, 2H), 7.09 (t, 1H), 7.01 (dd, 1H), 6.91 (dd, 2H), 6.53 (d, 1H), 6.44 (d, 1H), 6.27 (td, 1H), 4.38-4.11 (m, 2H), 2.21-2.09 (m, 2H), 2.03-1.84 (m, 2H), 1.63-1.44 (m, 2H).

Example 3

6'-(((1S,3S)-3-((7-(1-hydroxyethyl)-[1,2,4]triazolo[1,5-a]pyridin-2-yl)amino)cyclopentyl)amino)-2H-[1,3'-bipyridine]-2-one Example 3 could also be obtained by the following method:

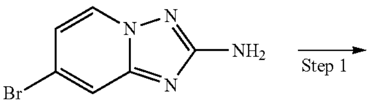

3a

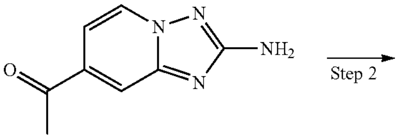

3b

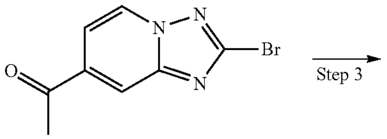

3c

-continued

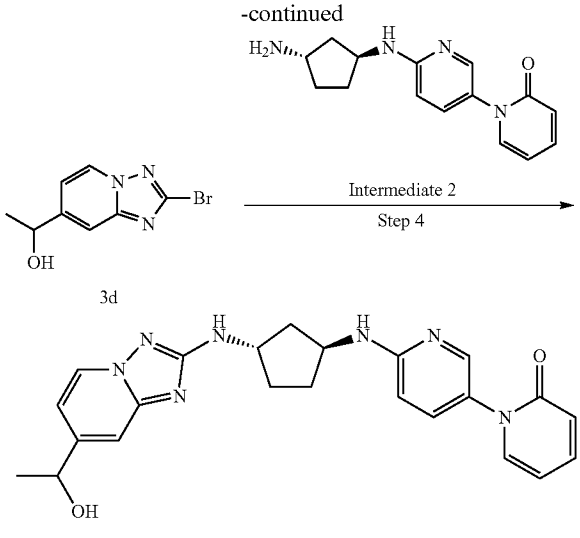

3d

3

Step 1: Under nitrogen protection, 7-bromo-[1,2,4]triazolo[1,5-a]pyridin-2-amine 3a (800 mg, 3.76 mmol), tributyl(1-ethoxyvinyl)stannane (1.76 g, 4.88 mmol) and bis(triphenylphosphine)palladium chloride (264 mg, 0.38 mmol) were dissolved in dioxane (8 mL), and the reaction was heated to 125° C. and stirred for 5 hours. The reaction was brought back to room temperature, dilute hydrochloric acid (3 mL, 3 M) was added to the reaction liquid, and the mixture was stirred for 2 hours. A saturated sodium bicarbonate solution was added to the reaction liquid, and the aqueous phase was extracted with ethyl acetate (25 mL×6). The organic phases were combined, dried, and concentrated, and the residue was separated by silica gel column chromatography to obtain 1-(2-amino-[1,2,4]triazolo[1,5-a]pyridin-7-yl)ethan-1-one 3b (445 mg), yield: 67.26%. MS m/z (ESI): 177.1 $[M+H]^+$.

Step 2: 3b (460 mg, 2.61 mmol) and copper bromide (583 mg, 2.61 mmol) were dissolved in acetonitrile (10 mL), and the reaction was heated to 70° C. Tert-butyl nitrite (458 mg, 4.44 mmol) was added to the above reaction liquid, and the mixture was stirred at 70° C. for 1.5 hours. A saturated ammonium chloride solution was added to the reaction liquid, and the aqueous phase was extracted with ethyl acetate (20 mL×2). The organic phases were combined, dried, and concentrated to remove most of the solvent. To the residue was added (petroleum ether/ethyl acetate=1/1, 10 mL), and the mixture was stirred at 0° C. for 15 minutes, and filtered to obtain 1-(2-bromo-[1,2,4]triazolo[1,5-a]pyridin-7-yl)ethan-1-one 3c (320 mg), yield: 51.05%. MS m/z (ESI): 240.0 $[M+H]^+$.

Step 3: At 0° C., sodium borohydride (29 mg, 0.76 mmol) was added to a solution of 3c (140 mg, 0.58 mmol) in methanol (4 mL), and the mixture was stirred for 1 hour. A saturated ammonium chloride solution was slowly added dropwise into the reaction liquid, and the aqueous phase was extracted with ethyl acetate (20 mL×2). The organic phases were combined, dried, and concentrated, and the residue was separated by silica gel column chromatography to obtain 1-(2-bromo-[1,2,4]triazolo[1,5-a]pyridin-7-yl)ethan-1-ol 3d (136 mg), yield: 96.33%. MS m/z (ESI): 242.0 $[M+H]^+$ Step 4: Under nitrogen protection, 3d (66 mg, 0.27 mmol), intermediate 2 (57 mg, 0.21 mmol), Ruphos Pd G4 (18 mg, 0.002 mmol) and sodium tert-butoxide (61 mg, 0.63 mmol) were dissolved in 1,4-dioxane (2 mL), and the reaction was heated to 130° C. and stirred for 16 hours. A saturated sodium chloride solution was added to the reaction liquid, and the aqueous phase was extracted with ethyl acetate (15 mL×2). The organic phases were combined, dried, and concentrated, and the residue was subjected to reversed-phase HPLC to prepare 6'-(((1S,3S)-3-((7-(1-hydroxyethyl)-[1,2,4]triazolo[1,5-a]pyridin-2-yl)amino)cyclopentyl)amino)-2H-[1,3'-bipyridine]-2-one 3 (1 mg), yield: 1.10%. MS m/z (ESI): 432.2 $[M+H]^+$.

$^1H$ NMR (400 MHz, DMSO-$d_6$) δ 8.49 (d, 1H), 7.92 (d, 1H), 7.61-7.56 (m, 1H), 7.51-7.44 (m, 1H), 7.42-7.36 (m, 1H), 7.26 (s, 1H), 6.92 (d, 1H), 6.86-6.81 (m, 1H), 6.57 (d, 1H), 6.53 (d, 1H), 6.44 (d, 1H), 6.30-6.23 (m, 1H), 5.42 (d, 1H), 4.81-4.69 (m, 1H), 4.39-4.24 (m, 1H), 4.22-4.09 (m, 1H), 2.20-2.09 (m, 2H), 2.02-1.82 (m, 2H), 1.62-1.43 (m, 2H), 1.34 (d, 3H).

Example 4

6-(6-(((1S,3S)-3-((7-fluoro-[1,2,4]triazolo[1,5-a]pyridin-2-yl)amino)cyclopentyl)amino)pyridin-3-yl)-6,7-dihydro-5H-pyrrolo[3,4-b]pyridin-5-one

4

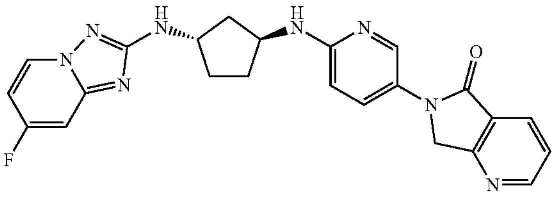

By reference to the synthesis method of reference example 2, 6-(6-(((1S,3S)-3-((7-fluoro-[1,2,4]triazolo[1,5-a]pyridin-2-yl)amino)cyclopentyl)amino)pyridin-3-yl)-6,7-dihydro-5H-pyrrolo[3,4-b]pyridin-5-one 4 was synthesized. MS m/z (ESI): 445.2 $[M+H]^+$.

$^1H$ NMR (400 MHz, DMSO-$d_6$) δ 8.80 (d, 1H), 8.65 (d, 1H), 8.36 (d, 1H), 8.14 (d, 1H), 7.87 (dd, 1H), 7.56 (dd, 1H), 7.27 (dd, 1H), 6.86 (td, 1H), 6.74 (d, 1H), 6.67 (d, 1H), 6.54 (d, 1H), 4.97 (s, 2H), 4.34-4.22 (m, 1H), 4.20-4.07 (m, 1H), 2.22-2.06 (m, 2H), 2.00-1.81 (m, 2H), 1.63-1.43 (m, 2H).

Example 5

6-(6-(((1S,3S)-3-((7-methyl-[1,2,4]triazolo[1,5-a]pyridin-2-yl)amino)cyclopentyl)amino)pyridin-3-yl)-6,7-dihydro-5H-pyrrolo[3,4-b]pyridin-5-one

5

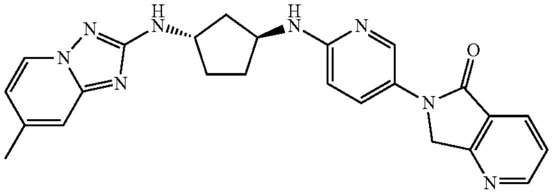

By reference to the synthesis method of reference example 2, 6-(6-(((1S,3S)-3-((7-methyl-[1,2,4]triazolo[1,5- a]pyridin-2-yl)amino)cyclopentyl)amino)pyridin-3-yl)-6,7-dihydro-5H-pyrrolo[3,4-b]pyridin-5-one 5 was synthesized. MS m/z (ESI): 441.2 $[M+H]^+$.

$^1$H NMR (400 MHz, DMSO-$d_6$) δ 8.80 (d, 1H), 8.43 (d, 1H), 8.36 (d, 1H), 8.14 (dd, 1H), 7.87 (dd, 1H), 7.56 (dd, 1H), 7.16 (s, 1H), 6.73-6.62 (m, 2H), 6.54 (t, 2H), 4.97 (s, 2H), 4.38-4.22 (m, 1H), 4.20-4.07 (m, 1H), 2.34 (s, 3H), 2.22-2.06 (m, 2H), 2.02-1.79 (m, 2H), 1.62-1.38 (m, 2H).

Example 6

6'-(((1S,3S)-3-((7-(difluoromethoxy)-[1,2,4]triazolo[1,5-a]pyridin-2-yl)amino)cyclopentyl)amino)-2H-[1,3'-bipyridine]-2-one

6

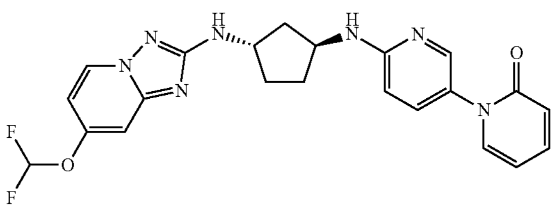

By reference to the synthesis method of reference example 1, 6'-(((1S,3S)-3-((7-(difluoromethoxy)-[1,2,4]triazolo[1,5-a]pyridin-2-yl)amino)cyclopentyl)amino)-2H-[1,3'-bipyridine]-2-one 6 was synthesized. MS m/z (ESI): 454.1 $[M+H]^+$.

$^1$H NMR (400 MHz, DMSO-$d_6$) δ 8.63 (d, 1H), 7.91 (d, 1H), 7.62-7.56 (m, 1H), 7.47 (ddd, 1H), 7.42 (s, 1H), 7.39 (dd, 1H), 7.13 (d, 1H), 6.92 (d, 1H), 6.78-6.69 (m, 2H), 6.52 (d, 1H), 6.44 (dd, 1H), 6.27 (td, 1H), 4.37-4.25 (m, 1H), 4.20-4.07 (m, 1H), 2.19-2.08 (m, 2H), 2.00-1.82 (m, 2H), 1.63-1.41 (m, 2H).

Example 7

6'-(((1S,3S)-3-((7-(trifluoromethoxy)-[1,2,4]triazolo[1,5-a]pyridin-2-yl)amino)cyclopentyl)amino)-2H-[1,3'-bipyridine]-2-one

7

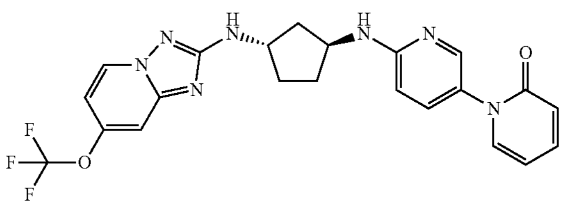

By reference to the synthesis method of reference example 1, 6'-(((1S,3S)-3-((7-(trifluoromethoxy)-[1,2,4]triazolo[1,5-a]pyridin-2-yl)amino)cyclopentyl)amino)-2H-[1,3'-bipyridine]-2-one 7 was synthesized. MS m/z (ESI): 472.2 $[M+H]^+$.

$^1$H NMR (400 MHz, DMSO-$d_6$) δ 8.74 (d, 1H), 7.92 (d, 1H), 7.60 (dd, 1H), 7.51-7.44 (m, 2H), 7.40 (dd, 1H), 6.98-6.87 (m, 3H), 6.52 (d, 1H), 6.44 (dd, 1H), 6.27 (td, 1H), 4.37-4.26 (m, 1H), 4.22-4.11 (m, 1H), 2.20-2.07 (m, 2H), 2.00-1.82 (m, 2H), 1.61-1.43 (m, 2H).

Example 8

6'-(((1S,3S)-3-((7-(3-hydroxyazetidin-1-yl)-[1,2,4]triazolo[1,5-a]pyridin-2-yl)amino)cyclopentyl)amino)-2H-[1,3'-bipyridine]-2-one

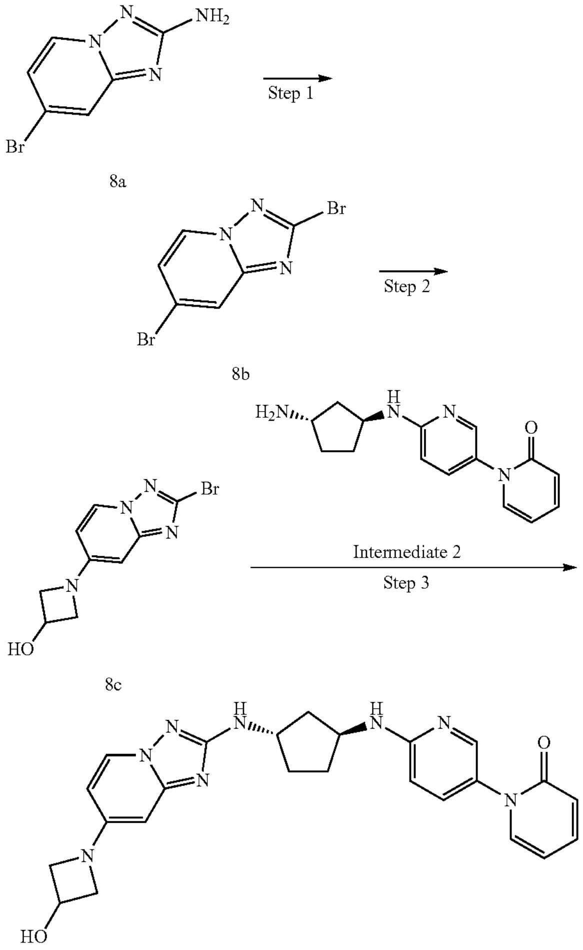

8a

8b

8c

8

Step 1: At room temperature, tert-butyl nitrite (1.45 g, 14.08 mmol) and copper bromide (3.15 g, 14.08 mmol) were dissolved in acetonitrile (50 mL) and stirred. The reaction was heated to 70° C., 7-bromo-[1,2,4]triazolo[1,5-a]pyridin-2-amine 8a (2.0 g, 9.39 mmol) were added to the reaction liquid in portions, and the mixture was further stirred for 2 hours. The reaction liquid was concentrated, and the residue was separated by silica gel column chromatography (eluent system B) to obtain 2,7-dibromo-[1,2,4]triazolo[1,5-a]pyridine 8b (2.5 g), yield: 96.2%. MS m/z (ESI): 275.9 $[M+H]^+$.

Step 2: Under nitrogen protection, 8b (500 mg, 1.81 mmol), 3-hydroxyazetidine hydrochloride (989 mg, 1.07 mmol), (2-dicyclohexylphosphino-3,6-dimethoxy-2',4',6'-triisopropyl-1,1'-biphenyl)(2'-amino-1,1'-biphenyl-2-yl)palladium(II) methanesulfonate (163.7 mg, 0.18 mmol), and cesium carbonate (1.76 g, 5.42 mmol) were dissolved in 1,4-dioxane (20 mL), heated to 100° C. and stirred for 16 hours. The reaction liquid was concentrated, and the residue was separated by silica gel column chromatography (eluent system A) to obtain 1-(2-bromo-[1,2,4]triazolo[1,5-a]pyridin-7-yl)azetidine-3-hydroxy 8c (100 mg), yield: 20.6%. MS m/z (ESI): 269.0 $[M+H]^+$.

Step 3: Under nitrogen protection, 8c (100 mg, 0.372 mmol), intermediate 2 (100.5 mg, 0.372 mmol), tris(dibenzylideneacetone)dipalladium (34 mg, 0.037 mmol), 2-dicyclohexylphosphino-2',6'-diisopropylbiphenyl (35 mg, 0.074 mmol), and cesium carbonate (363 mg, 1.11 mmol) were dissolved in 1,4-dioxane (10 mL), heated to 130° C. and stirred for 16 hours. The reaction liquid was concentrated, and the residue was purified by preparative HPLC (ammonium bicarbonate system) to obtain the target product 6'-(((1S,3S)-3-((7-(3-hydroxyazetidin-1-yl)-[1,2,4]triazolo[1,5-a]pyridin-2-yl)amino)cyclopentyl)amino)-2H-[1,3'-bipyridine]-2-one 8 (10 mg), yield: 5.87%. MS m/z (ESI): 459.2 $[M+H]^+$.

$^1$H NMR (400 MHz, DMSO-$d_6$) δ 8.14 (d, 1H), 7.92 (d, 1H), 7.60 (dd, 1H), 7.48 (td, 1H), 7.41 (dd, 1H), 6.97 (d, 1H), 6.62 (d, 1H), 6.53 (d, 1H), 6.44 (dd, 1H), 6.32 (dd, 1H), 6.27 (td, 1H), 6.17 (d, 1H), 5.60 (d, 1H), 4.53 (m, 1H), 4.37-4.26 (m, 1H), 4.10 (t, 2H), 3.90 (d, 1H), 3.67 (d, 2H), 2.22-2.14 (m, 2H), 1.93-1.90 (m, 2H), 1.55-1.51 (m, 2H).

Example 9

6'-(((1S,3S)-3-((7-(3-hydroxy-3-methylazetidin-1-yl)-[1,2,4]triazolo[1,5-a]pyridin-2-yl)amino)cyclopentyl)amino)-2H-[1,3'-bipyridine]-2-one

9

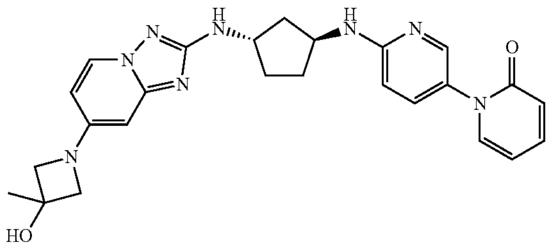

By reference to the synthesis method of example 8, the target product 6'-(((1S,3S)-3-((7-(3-hydroxy-3-methylazetidin-1-yl)-[1,2,4]triazolo[1,5-a]pyridin-2-yl)amino)cyclopentyl)amino)-2H-[1,3'-bipyridine]-2-one 9 was synthesized. MS m/z (ESI): 473.2 $[M+H]^+$.

$^1$H NMR (400 MHz, DMSO-$d_6$) δ 8.15 (d, 1H), 7.92 (d, 1H), 7.60 (dd, 1H), 7.48 (td, 1H), 7.41 (dd, 1H), 6.98 (d, 1H), 6.62 (d, 1H), 6.53 (d, 1H), 6.44 (dd, 1H), 6.32 (dd, 1H), 6.27 (td, 1H), 6.18 (d, 1H), 5.52 (d, 1H), 4.33 (t, 1H), 3.95-3.86 (m, 1H), 3.82-3.74 (m, 4H), 2.24-2.10 (m, 2H), 1.91 (t, 2H), 1.57-1.48 (m, 2H), 1.41 (s, 3H).

Example 11

6'-(((1S,3S)-3-((7-(2-hydroxypropan-2-yl)-[1,2,4]triazolo[1,5-a]pyridin-2-yl)amino)cyclopentyl)amino)-2H-[1,3'-bipyridine]-2-one

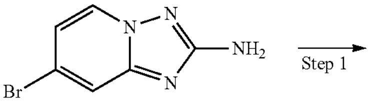

11a

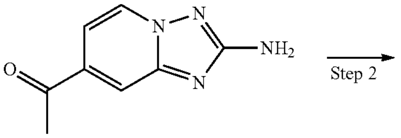

11b

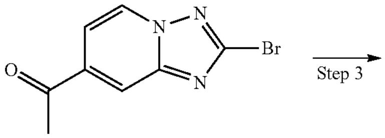

11c

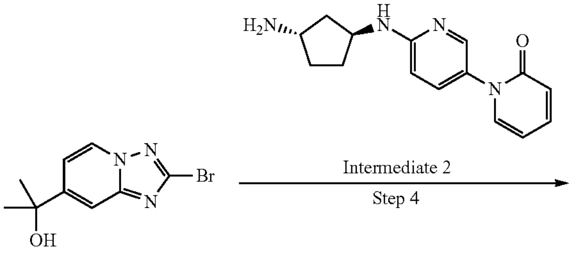

11d

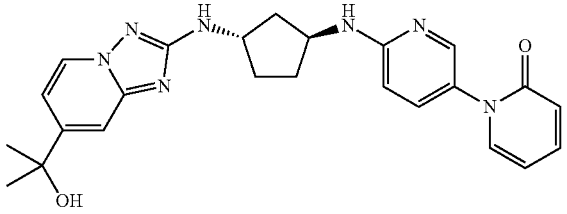

11

Step 1: Under nitrogen protection, 7-bromo-[1,2,4]triazolo[1,5-a]pyridin-2-amine 11a (800 mg, 3.76 mmol), tributyl(1-ethoxyvinyl)stannane (1.76 g, 4.88 mmol) and bis(triphenylphosphine)palladium chloride (264 mg, 0.38 mmol) were dissolved in dioxane (8 mL), and the reaction was heated to 125° C. and stirred for 5 hours. The reaction was brought back to room temperature, dilute hydrochloric acid (3 mL, 3 M) was added to the reaction liquid, and the mixture was stirred for 2 hours. A saturated sodium bicarbonate solution was added to the reaction liquid, and the aqueous phase was extracted with ethyl acetate (25 mL×6). The organic phases were combined, dried, and concentrated, and the residue was separated by silica gel column chromatography to obtain 1-(2-amino-[1,2,4]triazolo[1,5-a]pyridin-7-yl)ethan-1-one 11b (445 mg), yield: 67.26%. MS m/z (ESI): 177.1 $[M+H]^+$.

Step 2: 11b (460 mg, 2.61 mmol) and copper bromide (583 mg, 2.61 mmol) were dissolved in acetonitrile (10 mL), heated to 70° C. and stirred. Tert-butyl nitrite (458 mg, 4.44 mmol) was added to the above reaction liquid, and the reaction was further stirred at 70° C. for 1.5 hours. A saturated ammonium chloride solution was added to the reaction liquid, and the aqueous phase was extracted with ethyl acetate (20 mL×2). The organic phases were combined, dried, and concentrated to remove most of the solvent. To the residue was added (PE/EA=1/1, 10 mL), and the mixture was stirred at 0° C. for 15 minutes, and filtered to obtain 1-(2-bromo-[1,2,4]triazolo[1,5-a]pyridin-7-yl)ethan-1-one 11c (320 mg), yield: 51.05%. MS m/z (ESI): 240.0 [M+H]$^+$.

Step 3: At 0° C., methyl magnesium bromide (1 M, 0.7 mL) was dropwise added to a solution of 11c (80 mg, 0.33 mmol) in tetrahydrofuran (2 mL), and the reaction was heated to room temperature and stirred for 1 hour. At 0° C., a saturated sodium chloride solution was added to the reaction liquid, and the aqueous phase was extracted with ethyl acetate (15 mL×2). The organic phases were combined, dried, and concentrated, and the residue was separated by silica gel column chromatography to obtain 2-(2-bromo-[1,2,4]triazolo[1,5-a]pyridin-7-yl)propan-2-ol 11d (60 mg), yield: 70.30%. MS m/z (ESI): 256.0 [M+H]$^+$.

Step 4: Under nitrogen protection, 11d (50 mg, 0.2 mmol), intermediate 2 (63 mg, 0.23 mmol), Ruphos Pd G4 (17 mg, 0.02 mmol) and sodium tert-butoxide (56 mg, 0.59 mmol) were dissolved in dioxane (1 mL), and the reaction was heated to 130° C. and stirred for 16 hours. The reaction liquid was brought back to room temperature, a saturated sodium chloride solution was added to the reaction liquid, and the aqueous phase was extracted with ethyl acetate (15 mL×2). The organic phases were combined, dried, and concentrated, and the residue was subjected to reversed-phase HPLC to prepare 6'-(((1S,3S)-3-((7-(2-hydroxypropan-2-yl)-[1,2,4]triazolo[1,5-a]pyridin-2-yl)amino)cyclopentyl)amino)-2H-[1,3'-bipyridine]-2-one 11 (8.7 mg), yield: 10.00%. MS m/z (ESI): 446.2 [M+H]$^+$.

$^1$H NMR (400 MHz, DMSO-d$_6$) δ 8.47 (d, 1H), 7.92 (d, 1H), 7.63-7.57 (m, 1H), 7.50-7.44 (m, 1H), 7.42-7.37 (m, 1H), 7.35 (d, 1H), 6.98-6.86 (m, 2H), 6.60-6.49 (m, 2H), 6.44 (d, 1H), 6.31-6.21 (m, 1H), 5.27 (s, 1H), 4.35-4.26 (m, 1H), 4.20-4.10 (m, 1H), 2.22-2.07 (m, 2H), 2.02-1.80 (m, 2H), 1.62-1.37 (m, 8H).

Example 12

6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one

12

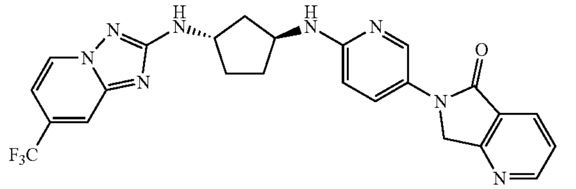

By reference to the synthesis method of reference example 2, 6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one 12 was synthesized. MS m/z (ESI): 495.2 [M+H]$^+$.

$^1$H NMR (400 MHz, DMSO-d$_6$) δ 8.85-8.74 (m, 2H), 8.36 (d, 1H), 8.14 (dd, 1H), 7.91-7.83 (m, 2H), 7.56 (dd, 1H), 7.15 (dd, 1H), 7.04 (d, 1H), 6.69 (d, 1H), 6.55 (d, 1H), 4.97 (s, 2H), 4.36-4.15 (m, 2H), 2.23-2.10 (m, 2H), 2.05-1.83 (m, 2H), 1.65-1.42 (m, 2H).

Example 13

2-(6-(((1S,3S)-3-((7-fluoro-[1,2,4]triazolo[1,5-a]pyridin-2-yl)amino)cyclopentyl)amino)pyridin-3-yl)pyridazin-3(2H)-one Example 13 could also be prepared by reference to the following method.

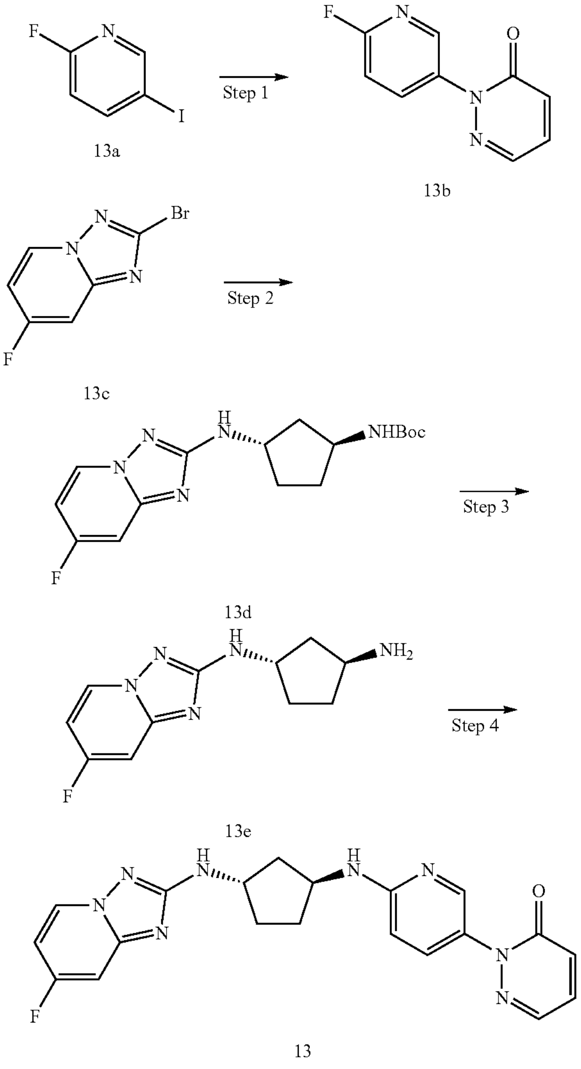

13a

13b

13c

13d

13e

13

Step 1: Under nitrogen protection, 2-fluoro-5-iodopyridine 13a (2 g, 8.97 mmol), 3-pyridazinone (948.00 mg, 9.87 mmol), cuprous iodide (342 mg, 1.79 mmol), trans-(1S, 2S)—N,N'-dimethylcyclohexanediamine (255 mg, 1.79 mmol) and potassium carbonate (2.48 g, 17.94 mmol) were dissolved in dimethyl sulfoxide (30 mL), heated to 130° C. and stirred for 16 hours. The reaction liquid was filtered, and the filtrate was diluted with a saturated sodium chloride solution and extracted with ethyl acetate (30 mL×2). The organic phases were combined, dried, and concentrated, and the residue was separated by silica gel column chromatography to obtain 2-(6-fluoropyridin-3-yl)pyridazin-3(2H)-one 13b (856 mg), yield: 49.93%. MS m/z (ESI): 192.0 $[M+H]^+$.

Step 2: Under nitrogen protection, 2-bromo-7-fluoro-[1,2,4]triazolo[1,5-a]pyridine 13c (710 mg, 3.29 mmol), tert-butyl ((1S,3S)-3-aminocyclopentyl)carbamate (856 mg, 4.27 mmol), tris(dibenzylideneacetone)dipalladium (150 mg, 0.16 mmol), 4,5-bis(diphenylphosphino)-9,9-dimethylxanthene (228 mg, 0.39 mmol), and cesium carbonate (3.21 g, 9.86 mmol) were dissolved in 1,4-dioxane (25 mL), and the reaction was heated to 130° C. and stirred for 3 hours. The reaction liquid was filtered, the filtrate was concentrated, and the residue was separated by silica gel column chromatography to obtain tert-butyl ((1S,3S)-3-((7-fluoro-[1,2,4]triazolo[1,5-a]pyridin-2-yl)amino)cyclopentyl)carbamate 13d (473 mg), yield: 42.91%. MS m/z (ESI): 336.2 $[M+H]^+$.

Step 3: Hydrogen chloride/1,4-dioxane solution (4 M, 3.53 mL) was added to a solution of 13d (473 mg, 1.41 mmol) in dichloromethane (4 mL), and the mixture was stirred at room temperature for 2 hours. The reaction liquid was concentrated, and the residue was dissolved with a small amount of dichloromethane and methanol, then adjusted to pH as alkalinity with a saturated sodium bicarbonate solution, and concentrated. The residue was separated by silica gel column chromatography to obtain (1S,3S)-N1-(7-fluoro-[1,2,4]triazolo[1,5-a]pyridin-2-yl)cyclopentane-1,3-diamine 13e (310 mg), yield: 93.43%. MS m/z (ESI): 236.1 $[M+H]^+$ Step 4: Under nitrogen protection, 13e (74 mg, 0.31 mmol), 13b (50 mg, 0.26 mmol), and diisopropylethylamine (101 mg, 0.78 mmol) were dissolved in dimethyl sulfoxide (1.5 mL), and the reaction was heated to 130° C. and stirred for 48 hours. The reaction liquid was filtered, and the filtrate was subjected to reversed-phase HPLC to prepare 2-(6-(((1S,3S)-3-((7-fluoro-[1,2,4]triazolo[1,5-a]pyridin-2-yl)amino)cyclopentyl)amino)pyridin-3-yl)pyridazin-3(2H)-one 13 (16.8 mg), yield: 15.80%. MS m/z (ESI): 407.1 $[M+H]^+$.

$^1$H NMR (400 MHz, DMSO-$d_6$) δ 8.69-8.62 (m, 1H), 8.10 (d, 1H), 8.04-7.98 (m, 1H), 7.55-7.49 (m, 1H), 7.48-7.43 (m, 1H), 7.30-7.23 (m, 1H), 7.05-6.99 (m, 1H), 6.94 (d, 1H), 6.89-6.82 (m, 1H), 6.75 (d, 1H), 6.53 (d, 1H), 4.39-4.26 (m, 1H), 4.22-4.07 (m, 1H), 2.21-2.09 (m, 2H), 2.01-1.83 (m, 2H), 1.63-1.42 (m, 2H).

Example 14

6'-(((1S,3S)-3-((6-methyl-[1,2,4]triazolo[1,5-a]pyridin-2-yl)amino)cyclopentyl)amino)-2H-[1,3'-bipyridine]-2-one

14

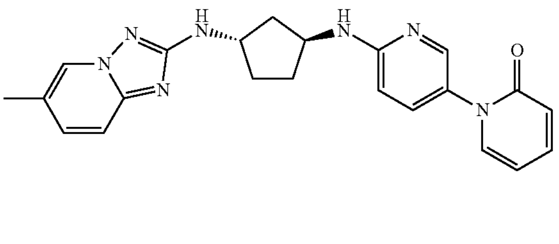

By reference to the synthesis method of reference example 1, 6'-(((1S,3S)-3-((6-methyl-[1,2,4]triazolo[1,5-a]pyridin-2-yl)amino)cyclopentyl)amino)-2H-[1,3'-bipyridine]-2-one 14 was synthesized. MS m/z (ESI): 402.2 $[M+H]^+$.

$^1$H NMR (400 MHz, DMSO-$d_6$) δ 8.42 (s, 1H), 7.91 (d, 1H), 7.60 (dd, 1H), 7.47 (ddd, 1H), 7.39 (dd, 1H), 7.28 (d, 2H), 6.92 (d, 1H), 6.53 (d, 2H), 6.44 (d, 1H), 6.26 (td, 1H), 4.36-4.26 (m, 1H), 4.22-4.08 (m, 1H), 2.27 (s, 3H), 2.20-2.09 (m, 2H), 1.99-1.82 (m, 2H), 1.59-1.44 (m, 2H).

Example 15

6'-(((1S,3S)-3-((6,7-difluoro-[1,2,4]triazolo[1,5-a]pyridin-2-yl)amino)cyclopentyl)amino)-2H-[1,3'-bipyridine]-2-one

15

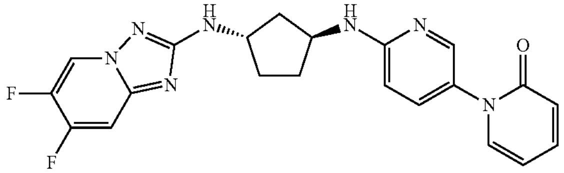

By reference to the synthesis method of reference example 1, 6'-(((1S,3S)-3-((6,7-difluoro-[1,2,4]triazolo[1,5-a]pyridin-2-yl)amino)cyclopentyl)amino)-2H-[1,3'-bipyridine]-2-one 15 was synthesized. MS m/z (ESI): 424.2 $[M+H]^+$.

$^1$H NMR (400 MHz, DMSO-$d_6$) δ 9.22 (dd, 1H), 8.15 (s, 1H), 7.91 (d, 1H), 7.63-7.54 (m, 2H), 7.47 (ddd, 1H), 7.39 (dd, 1H), 6.92 (d, 1H), 6.80 (d, 1H), 6.52 (d, 1H), 6.47-6.41 (m, 1H), 6.27 (td, 1H), 4.38-4.26 (m, 1H), 4.20-4.08 (m, 1H), 2.20-2.08 (m, 2H), 2.03-1.83 (m, 2H), 1.63-1.42 (m, 2H).

Example 18

6'-(((1S,3S)-3-((7-methoxy-[1,2,4]triazolo[1,5-a]pyridin-2-yl)amino)cyclopentyl)amino)-2H-[1,3'-bipyridine]-2-one

18

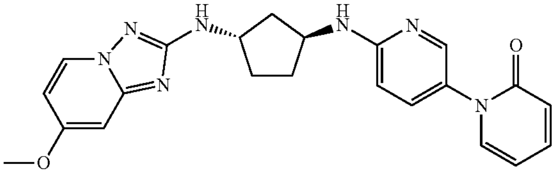

By reference to the synthesis method of reference example 1, 6'-(((1S,3S)-3-((7-methoxy-[1,2,4]triazolo[1,5-a]pyridin-2-yl)amino)cyclopentyl)amino)-2H-[1,3'-bipyridine]-2-one 18 was synthesized. MS m/z (ESI): 418.2 $[M+H]^+$.

$^1$H NMR (400 MHz, DMSO-$d_6$) δ 8.40 (d, 1H), 7.91 (d, 1H), 7.60 (dd, 1H), 7.47 (ddd, 1H), 7.39 (dd, 1H), 6.91 (d, 1H), 6.81 (d, 1H), 6.55-6.41 (m, 4H), 6.26 (td, 1H), 4.37-

4.25 (m, 1H), 4.19-4.05 (m, 1H), 3.82 (s, 3H), 2.20-2.07 (m, 2H), 2.01-1.82 (m, 2H), 1.61-1.43 (m, 2H).

Example 19

6-(6-(((1S,3S)-3-((7-fluoro-[1,2,4]triazolo[1,5-a]pyridin-2-yl)amino)cyclopentyl)amino)pyridin-3-yl)-5,5-dimethyl-5,6-dihydro-7H-pyrrolo[3,4-b]pyridin-7-one Example 19 could also be prepared by reference to the following method.

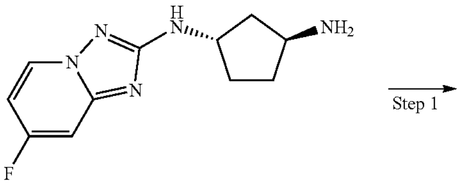

13e

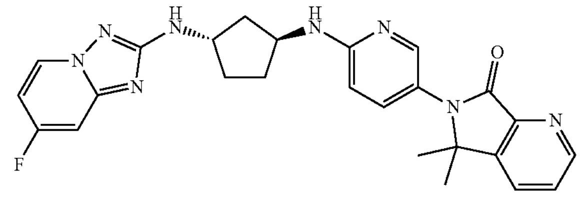

19

Step 1: Under nitrogen protection, 13e (48 mg, 0.2 mmol), reference example 6a (40 mg, 0.16 mmol), and diisopropylethylamine (60 mg, 0.47 mmol) were dissolved in dimethyl sulfoxide (1 mL), and the reaction was heated to 130° C. and stirred for 48 hours. The reaction liquid was filtered, the filtrate was concentrated, and the residue was subjected to reversed-phase HPLC to prepare 6-(6-(((1S,3S)-3-((7-fluoro-[1,2,4]triazolo[1,5-a]pyridin-2-yl)amino)cyclopentyl)amino)pyridin-3-yl)-5,5-dimethyl-5,6-dihydro-7H-pyrrolo[3,4-b]pyridin-7-one 19 (7.3 mg), yield: 9.94%. MS m/z (ESI): 473.3 $[M+H]^+$.

$^1$H NMR (400 MHz, DMSO-$d_6$) δ 8.80-8.72 (m, 1H), 8.70-8.62 (m, 1H), 8.27-8.19 (m, 1H), 7.85 (d, 1H), 7.69-7.60 (m, 1H), 7.34-7.23 (m, 2H), 6.93-6.81 (m, 2H), 6.75 (d, 1H), 6.57 (d, 1H), 4.37-4.26 (m, 1H), 4.22-4.10 (m, 1H), 2.22-2.08 (m, 2H), 2.02-1.84 (m, 2H), 1.64-1.34 (m, 8H).

Example 20

3-fluoro-6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one

20

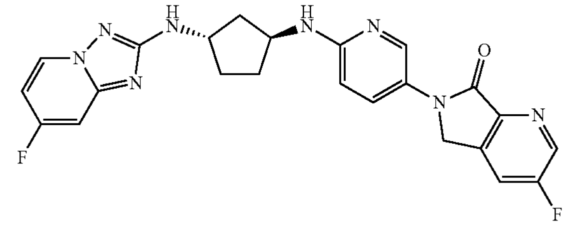

By reference to the synthesis method of reference example 2, 3-fluoro-6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one 20 was synthesized. MS m/z (ESI): 463.2 $[M+H]^+$.

$^1$H NMR (400 MHz, DMSO-$d_6$) δ 8.76 (s, 1H), 8.66 (dd, 1H), 8.33 (d, 1H), 8.09 (dd, 1H), 7.85 (dd, 1H), 7.27 (dd, 1H), 6.88-6.84 (m, 1H), 6.74 (d, 1H), 6.71 (d, 1H), 6.55 (d, 1H), 4.93 (s, 2H), 4.32-4.27 (m, 1H), 4.18-4.13 (m, 1H), 2.19-2.09 (m, 2H), 2.01-1.93 (m, 1H), 1.90-1.83 (m, 1H), 1.59-1.46 (m, 2H).

Example 21

6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-d]pyrimidin-7-one

21

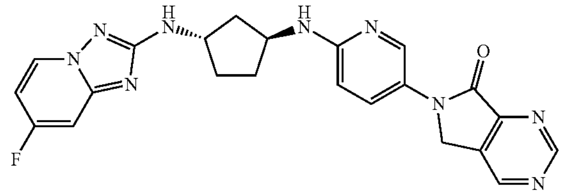

By reference to the synthesis method of reference example 2, 6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-d]pyrimidin-7-one 21 was synthesized. MS m/z (ESI): 446.2 $[M+H]^+$.

$^1$H NMR (400 MHz, DMSO-$d_6$) δ 8.86-8.79 (m, 2H), 8.66 (dd, 1H), 8.40 (d, 1H), 7.91 (dd, 1H), 7.27 (dd, 1H), 6.88-6.81 (m, 1H), 6.74 (dd, 2H), 6.56 (d, 1H), 5.02 (s, 2H), 4.37-4.23 (m, 1H), 4.21-4.08 (m, 1H), 2.21-2.06 (m, 2H), 1.99-1.83 (m, 2H), 1.62-1.44 (m, 2H).

Example 22

6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-d]pyrimidin-7-one

22

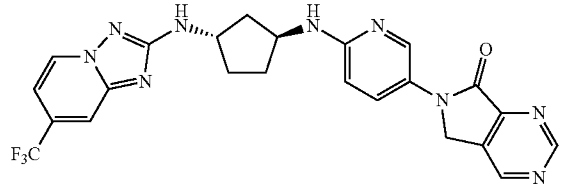

By reference to the synthesis method of reference example 3, 6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-d]pyrimidin-7-one 22 was synthesized. MS m/z (ESI): 496.2 $[M+H]^+$.

$^1$H NMR (400 MHz, DMSO-$d_6$) δ 9.41 (s, 1H), 9.23 (s, 1H), 8.82 (d, 1H), 8.37 (d, 1H), 7.89-7.85 (m, 2H), 7.15 (dd,

1H), 7.04 (d, 1H), 6.80 (d, 1H), 6.57 (d, 1H), 5.02 (s, 2H), 4.34-4.29 (m, 1H), 4.24-4.18 (m, 1H), 2.20-2.13 (m, 2H), 2.01-1.89 (m, 2H), 1.62-1.46 (m, 2H).

Example 23

6-(6-(((1S,3S)-3-((7-fluoro-[1,2,4]triazolo[1,5-a]pyridin-2-yl)amino)cyclopentyl)amino)pyridin-3-yl)-2-(2-hydroxypropan-2-yl)-5,6-dihydro-7H-pyrrolo[3,4-b]pyridin-7-one

23

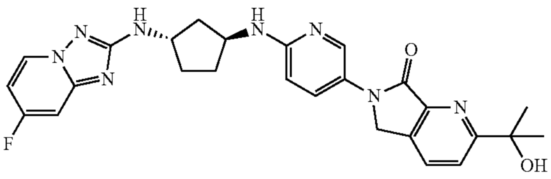

By reference to the synthesis method of reference example 2, 6-(6-(((1S,3S)-3-((7-fluoro-[1,2,4]triazolo[1,5-a]pyridin-2-yl)amino)cyclopentyl)amino)pyridin-3-yl)-2-(2-hydroxypropan-2-yl)-5,6-dihydro-7H-pyrrolo[3,4-b]pyridin-7-one 23 was synthesized. MS m/z (ESI): 503.2 $[M+H]^+$.

$^1$H NMR (400 MHz, DMSO-$d_6$) δ 8.70-8.62 (m, 1H), 8.34 (d, 1H), 8.06 (d, 1H), 7.90 (d, 1H), 7.87-7.81 (m, 1H), 7.30-7.23 (m, 1H), 6.90-6.82 (m, 1H), 6.75 (d, 1H), 6.69 (d, 1H), 6.56 (d, 1H), 5.40 (s, 1H), 4.88 (s, 2H), 4.37-4.23 (m, 1H), 4.21-4.07 (m, 1H), 2.21-2.05 (m, 2H), 2.01-1.81 (m, 2H), 1.62-1.39 (m, 8H).

Example 25

2-(6-(((1S,3S)-3-((7-fluoro-[1,2,4]triazolo[1,5-a]pyridin-2-yl)amino)cyclopentylamino)pyridin-3-yl)-7-(trifluoromethyl)isoindol-1-one

25

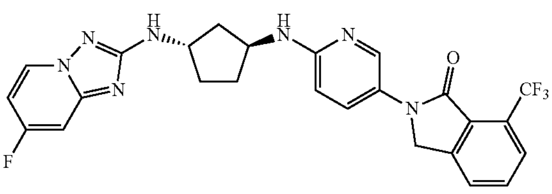

By reference to the synthesis method of reference example 2, 2-(6-(((1S,3S)-3-((7-fluoro-[1,2,4]triazolo[1,5-a]pyridin-2-yl)amino)cyclopentylamino)pyridin-3-yl)-7-(trifluoromethyl)isoindol-1-one 25 was synthesized. MS m/z (ESI): 512.2 $[M+H]^+$.

$^1$H NMR (400 MHz, DMSO-$d_6$) δ 8.66 (dd, 1H), 8.30 (d, 1H), 7.95 (d, 1H), 7.90-7.77 (m, 3H), 7.27 (dd, 1H), 6.86 (t, 1H), 6.75 (d, 1H), 6.68 (d, 1H), 6.54 (d, 1H), 4.98 (s, 2H), 4.29 (q, 1H), 4.15 (q, 1H), 2.15 (dd, 2H), 2.01-1.84 (m, 2H), 1.61-1.44 (m, 2H).

Example 26

2-(6-(((1S,3S)-3-((7-fluoro-[1,2,4]triazolo[1,5-a]pyridin-2-yl)amino)cyclopentylamino)pyridin-3-yl)-4-(trifluoromethyl)isoindol-1-one

26

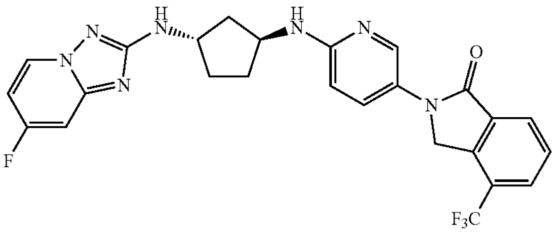

By reference to the synthesis method of reference example 2, 2-(6-(((1S,3S)-3-((7-fluoro-[1,2,4]triazolo[1,5-a]pyridin-2-yl)amino)cyclopentylamino)pyridin-3-yl)-4-(trifluoromethyl)isoindol-1-one 26 was synthesized. MS m/z (ESI): 512.1 $[M+H]^+$.

$^1$H NMR (400 MHz, DMSO-$d_6$) δ 8.66 (dd, 1H), 8.36 (d, 1H), 8.03 (dd, 2H), 7.89-7.70 (m, 2H), 7.27 (dd, 1H), 6.86 (t, 1H), 6.72 (dd, 2H), 6.54 (d, 1H), 5.10 (d, 2H), 4.22 (d, 2H), 2.21-2.06 (m, 2H), 2.00-1.81 (m, 2H), 1.64-1.42 (m, 2H).

Example 27

3-Fluoro-6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one

27

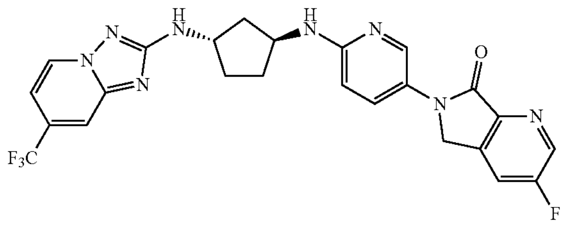

By reference to the synthesis method of reference example 3, 3-fluoro-6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one 27 was synthesized. MS m/z (ESI): 513.2 $[M+H]^+$.

$^1$H NMR (400 MHz, DMSO-$d_6$) δ 8.82 (d, 1H), 8.75 (s, 1H), 8.33 (d, 1H), 8.09 (dd, 1H), 7.87-7.83 (m, 2H), 7.15 (dd, 1H), 7.04 (d, 1H), 6.72 (d, 1H), 6.56 (d, 1H), 4.93 (s, 2H), 4.35-4.29 (m, 1H), 4.25-4.17 (m, 1H), 2.20-2.13 (m, 2H), 2.00-1.86 (m, 2H), 1.62-1.48 (m, 2H).

Example 28

3-(6-(((1S,3S)-3-((7-fluoro-[1,2,4]triazolo[1,5-a]pyridin-2-yl)amino)cyclopentyl)amino)pyridin-3-yl)pyrimidin-4(3H)-one

28

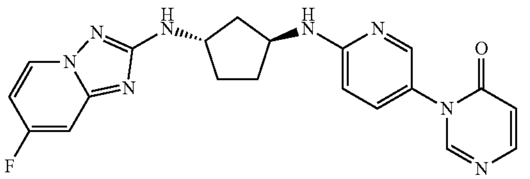

By reference to the synthesis method of reference example 1, the target product 3-(6-(((1S,3S)-3-((7-fluoro-[1,2,4]triazolo[1,5-a]pyridin-2-yl)amino)cyclopentyl)amino)pyridin-3-yl)pyrimidin-4(3H)-one 28 could also be synthesized. MS m/z (ESI): 407.2 $[M+H]^+$.

$^1$H NMR (400 MHz, DMSO-$d_6$) δ 8.73-8.58 (m, 1H), 8.39 (s, 1H), 8.01-7.90 (m, 2H), 7.48-7.40 (m, 1H), 7.30-7.23 (m, 1H), 7.03 (d, 1H), 6.90-6.82 (m, 1H), 6.75 (d, 1H), 6.55 (d, 1H), 6.47 (d, 1H), 4.39-4.26 (m, 1H), 4.24-4.09 (m, 1H), 2.21-2.08 (m, 2H), 2.02-1.80 (m, 2H), 1.65-1.40 (m, 2H).

Example 29

1-(6-(((1S,3S)-3-((7-fluoro-[1,2,4]triazolo[1,5-a]pyridin-2-yl)amino)cyclopentyl)amino)pyridin-3-yl)pyrazin-2(1H)-one

29

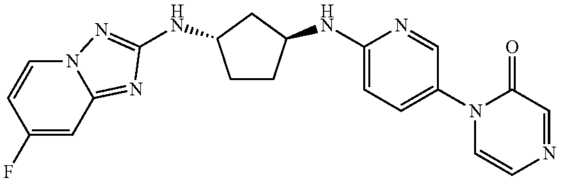

By reference to the synthesis method of reference example 1, the target product 1-(6-(((1S,3S)-3-((7-fluoro-[1,2,4]triazolo[1,5-a]pyridin-2-yl)amino)cyclopentyl)amino)pyridin-3-yl)pyrazin-2(1H)-one 29 could also be synthesized. MS m/z (ESI): 407.1 $[M+H]^+$.

$^1$H NMR (400 MHz, DMSO-$d_6$) δ 8.70-8.61 (m, 1H), 8.07 (s, 1H), 8.02 (d, 1H), 7.63 (d, 1H), 7.52-7.45 (m, 1H), 7.36 (d, 1H), 7.31-7.23 (m, 1H), 7.04 (d, 1H), 6.90-6.81 (m, 1H), 6.75 (d, 1H), 6.55 (d, 1H), 4.39-4.26 (m, 1H), 4.22-4.10 (m, 1H), 2.21-2.06 (m, 2H), 2.02-1.80 (m, 2H), 1.64-1.42 (m, 2H).

Example 31

6'-(3-((7-fluoro-[1,2,4]triazolo[1,5-a]pyridin-2-yl)amino)cyclopentyl)amino]-[3,3'-bipyridine]-2(1H)-one Example 31 could also be prepared by reference to the following method.

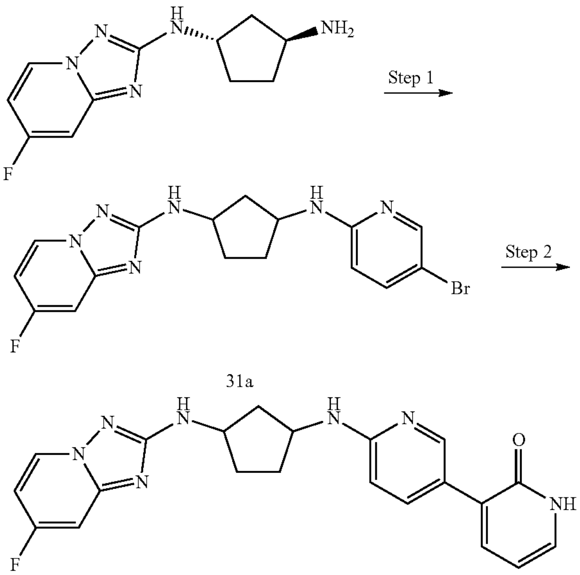

31a

31

Step 1: Under nitrogen protection, (1S,3S)-N3-(7-fluoro-[1,2,4]triazolo[1,5-a]pyridin-2-yl)cyclopentane-1,3-diamine (200 mg, 0.9 mmol), 5-bromo-2-fluoropyridine (195 mg, 1.1 mmol) and N,N-diisopropylethylamine (330 mg, 2.6 mmol) were dissolved in dimethyl sulfoxide (5 mL), and the reaction was heated to 130° C. and stirred for 16 hours. The reaction was filtered, the filtrate was concentrated, and the residue was separated by silica gel column chromatography (elution system A) to obtain N1-(5-bromopyridin-2-yl)-$N^3$-(7-fluoro-[1,2,4]triazolo[1,5-a]pyridin-2-yl)cyclopentane-1,3-diamine 31a (200 mg), yield: 60%. MS m/z (ESI): 391.0 $[M+H]^+$.

Step 2: Under nitrogen protection, 31a (170 mg, 0.4 mmol), (2-oxo-1H-pyridin-3-yl)boronic acid (60 mg, 0.4 mmol) and sodium carbonate (92 mg, 0.9 mmol) were dissolved in 1,4-dioxane (5 mL) and water (1 mL), [1,1-bis(diphenylphosphino)ferrocene]palladium dichloride (64 mg, 0.1 mmol) was added, and the reaction was heated to 80° C. and stirred for 1 hour. The reaction was filtered, the filtrate was concentrated, and the residue was purified by preparative HPLC (formic acid system) to obtain 6'-(3-((7-fluoro-[1,2,4]triazolo[1,5-a]pyridin-2-yl)amino)cyclopentyl)amino]-[3,3'-bipyridine]-2(1H)-one 31 (90 mg), yield: 51%. MS m/z (ESI): 406.1 $[M+H]^+$.

$^1$H NMR (400 MHz, DMSO-$d_6$) δ 11.66 (s, 1H), 8.66 (dd, 1H), 8.34 (d, 1H), 7.77 (dd, 1H), 7.54 (dd, 1H), 7.31-7.24 (m, 2H), 6.86 (td, 1H), 6.71 (dd, 2H), 6.46 (d, 1H), 6.23 (t, 1H), 4.31 (q, 1H), 4.15 (d, 1H), 2.13 (dt, 2H), 1.91 (dd, 2H), 1.52 (dd, 2H).

Example 32

6'-(((1S,3S)-3-((7-fluoro-[1,2,4]triazolo[1,5-a]pyridin-2-yl)amino)cyclopentyl)amino)-3-(2-hydroxypropan-2-yl)-2H-[1,3'-bipyridine]-2-one

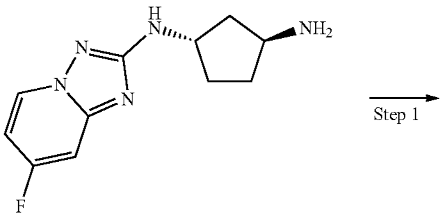

Reference example 2c

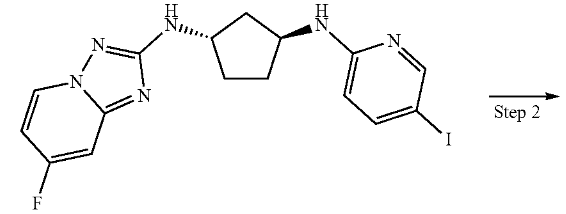

32a

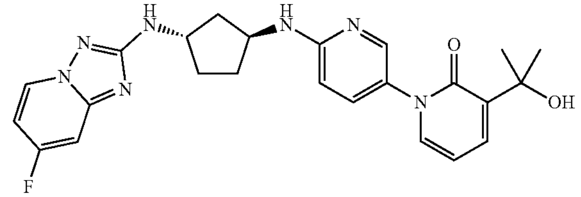

32

Step 1: Under nitrogen protection, reference example 2c (100 mg, 0.43 mmol), 2-fluoro-5-iodo-pyridine (142 mg, 0.64 mmol), and diisopropylethylamine (165 mg, 1.28 mmol) were dissolved in dimethyl sulfoxide (1.8 mL), and the reaction was heated to 130° C. and stirred for 16 hours. A saturated sodium chloride solution was added to the reaction liquid, and the mixture was extracted with ethyl acetate (25 mL×2). The organic phases were combined, dried, and concentrated, and the residue was separated by silica gel column chromatography to obtain (1S,3S)-N1-(7-fluoro-[1,2,4]triazolo[1,5-a]pyridin-2-yl)-$N^3$-(5-iodopyridin-2-yl)cyclopentane-1,3-diamine 32a (95 mg), yield: 51.00%. MS m/z (ESI): 439.0 $[M+H]^+$.

Step 2: Under nitrogen protection, 32a (50 mg, 0.11 mmol), 3-(2-hydroxypropan-2-yl)pyridin-2(1H)-one (35 mg, 0.23 mmol), cuprous iodide (22 mg, 0.11 mmol), trans-(1R,2R)—N,N'-dimethyl 1,2-cyclohexanediamine (16 mg, 0.11 mmol) and cesium carbonate (112 mg, 0.34 mmol) were dissolved in 1,4-dioxane (1 mL), and the reaction was heated to 105° C. and stirred for 2 hours. A saturated sodium chloride solution was added to the reaction liquid, and the mixture was extracted with ethyl acetate (25 mL×2). The organic phases were combined, dried, and concentrated, and the residue was subjected to reversed-phase HPLC to prepare 6'-(((1S,3S)-3-((7-fluoro-[1,2,4]triazolo[1,5-a]pyridin-2-yl)amino)cyclopentyl)amino)-3-(2-hydroxypropan-2-yl)-2H-[1,3'-bipyridine]-2-one 32 (25.1 mg), yield: 47.46%. MS m/z (ESI): 464.2 $[M+H]^+$.

$^1H$ NMR (400 MHz, DMSO-$d_6$) δ 8.70-8.62 (m, 1H), 7.91 (d, 1H), 7.65-7.59 (m, 1H), 7.56-7.52 (m, 1H), 7.42-7.37 (m, 1H), 7.30-7.24 (m, 1H), 6.91 (d, 1H), 6.89-6.83 (m, 1H), 6.75 (d, 1H), 6.53 (d, 1H), 6.34-6.28 (m, 1H), 5.33 (s, 1H), 4.38-4.24 (m, 1H), 4.22-4.09 (m, 1H), 2.22-2.07 (m, 2H), 2.04-1.81 (m, 2H), 1.64-1.37 (m, 8H).

Example 33

6-(6-(((1S,3S)-3-((7-fluoro-[1,2,4]triazolo[1,5-a]pyridin-2-yl)amino)cyclopentyl)amino)pyridin-3-yl)-2-methyl-5,6-dihydro-7H-pyrrolo[3,4-d]pyrimidin-7-one

33

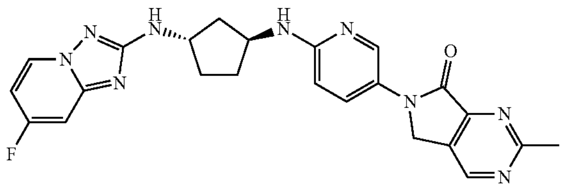

By reference to the synthesis method of reference example 2, the target product 6-(6-(((1S,3S)-3-((7-fluoro-[1,2,4]triazolo[1,5-a]pyridin-2-yl)amino)cyclopentyl)amino)pyridin-3-yl)-2-methyl-5,6-dihydro-7H-pyrrolo[3,4-d]pyrimidin-7-one 33 was synthesized. MS m/z (ESI): 460.2 $[M+H]^+$.

$^1H$ NMR (400 MHz, DMSO-$d_6$) δ 9.10 (s, 1H), 8.65 (dd, 1H), 8.36 (d, 1H), 7.87 (dd, 1H), 7.27 (dd, 1H), 6.86 (td, 1H), 6.75 (dd, 2H), 6.56 (d, 1H), 4.96 (s, 2H), 4.30 (q, 1H), 4.15 (q, 1H), 2.76 (s, 3H), 2.19-2.09 (m, 2H), 2.00-1.83 (m, 2H), 1.59-1.46 (m, 2H).

Example 49

2-(Tert-butyl)-6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one

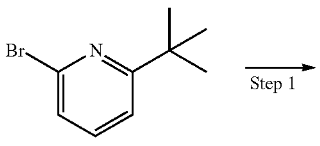

49a

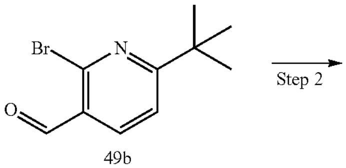

49b

-continued

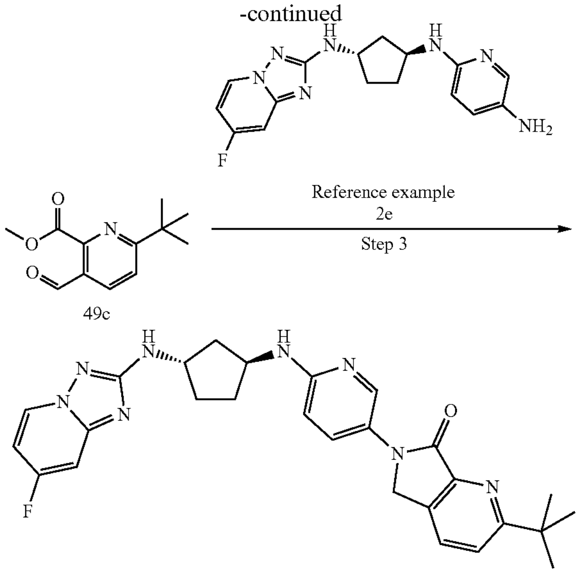

49c

49

Step 1: At −78° C., lithium diisopropylamide (2 M, 1.05 mL) was dropwise added to a solution of 2-bromo-6-tert-butylpyridine 49a (300 mg, 1.40 mmol) in tetrahydrofuran (5 mL). After the reaction was stirred at −78° C. for 1 hour, N,N-dimethylformamide (410 mg, 5.60 mmol) was dropwise added to the reaction liquid, and the reaction was slowly heated to room temperature and stirred for 1 hour. A saturated ammonium chloride solution was added to the reaction liquid, and the mixture was extracted with ethyl acetate (25 mL×2). The organic phases were combined, dried, and concentrated, and the residue was separated by silica gel column chromatography to obtain 2-bromo-6-(tert-butyl)nicotinaldehyde 49b (56 mg), yield: 16.51%. MS m/z (ESI): 242.0 $[M+H]^+$.

Step 2: Under carbon monoxide protection, 49b (53 mg, 0.22 mmol), [1,1-bis(diphenylphosphino)ferrocene]palladium dichloride (16 mg, 0.02 mmol), and triethylamine (44 mg, 0.44 mmol) were dissolved in a mixed solvent of N,N-dimethylformamide (1 mL) and methanol (2 mL), and the reaction was heated to 80° C. and stirred for 16 hours. A saturated sodium chloride solution was added to the reaction liquid, and the mixture was extracted with ethyl acetate (15 mL×2). The organic phases were combined, dried, and concentrated, and the residue was separated by silica gel column chromatography to obtain methyl 6-(tert-butyl)-3-formylpicolinate 49c (13 mg), yield: 26.84%. MS m/z (ESI): 222.1 $[M+H]^+$.

Step 3: Reference example 2e (23 mg, 0.07 mmol), 49c (13 mg, 0.06 mmol), and acetic acid (5 mg, 0.09 mmol) were dissolved in 1,2-dichloroethane (2 mL), and the reaction was heated to 60° C. and stirred for 1 hour. After the reaction liquid was brought back to room temperature, sodium triacetoxyborohydride (62 mg, 0.29 mmol) was added to the reaction liquid and stirred for 15 hours. A saturated ammonium chloride solution was added to the reaction liquid, and the mixture was extracted with dichloromethane (20 mL×2). The organic phases were combined, dried, and concentrated, and the residue was subjected to reversed-phase HPLC to prepare 2-(tert-butyl)-6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one 49 (15.8 mg), yield: 53.72%. MS m/z (ESI): 501.2 $[M+H]^+$.

$^1H$ NMR (400 MHz, DMSO-$d_6$) δ 8.70-8.62 (m, 1H), 8.34 (d, 1H), 8.02 (d, 1H), 7.89-7.80 (m, 1H), 7.68 (d, 1H), 7.31-7.22 (m, 1H), 6.90-6.82 (m, 1H), 6.75 (d, 1H), 6.68 (d, 1H), 6.56 (d, 1H), 4.86 (s, 2H), 4.35-4.23 (m, 1H), 4.22-4.08 (m, 1H), 2.22-2.07 (m, 2H), 2.03-1.81 (m, 2H), 1.63-1.42 (m, 2H), 1.37 (s, 9H).

Example 50

2-(6-((1S,3S)-3-((7-fluoro-[1,2,4]triazolo[1,5-a]pyridin-2-yl)amino)cyclopentyl)amino]pyridin-3-yl)-4-hydroxy-2,3-dihydro-1H-pyrrolo[3,4-c]pyridin-1-one

50

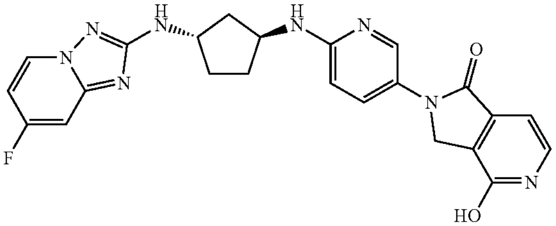

By reference to the synthesis method of reference example 2, 2-(6-((1S,3S)-3-((7-fluoro-[1,2,4]triazolo[1,5-a]pyridin-2-yl)amino)cyclopentyl)amino]pyridin-3-yl)-4-hydroxy-2,3-dihydro-1H-pyrrolo[3,4-c]pyridin-1-one 50 was synthesized. MS m/z (ESI): 461.1 $[M+H]^+$.

$^1H$ NMR (400 MHz, DMSO-$d_6$) δ 12.03 (s, 1H), 8.66 (dd, 1H), 8.32 (d, 1H), 7.80 (dd, 1H), 7.55 (d, 1H), 7.27 (dd, 1H), 6.86 (td, J=7.6, 2.8 Hz, 1H), 6.74 (d, J=7.3 Hz, 1H), 6.67 (d, 1H), 6.50 (dd, 2H), 4.73 (s, 2H), 4.28 (q, 1H), 4.15 (q, 1H), 2.14 (dq, 2H), 1.90 (dq, 2H), 1.51 (dd, 2H).

Example 51

2-(6-(((1S,3S)-3-((7-fluoro-[1,2,4]triazolo[1,5-a]pyridin-2-yl)amino)cyclopentyl)amino)pyridin-3-yl)-4,6-dimethyl-2,3-dihydro-1H-pyrrolo[3,4-c]pyridin-1-one

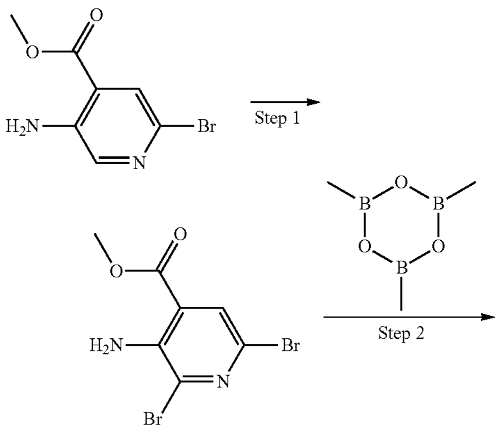

51a

-continued

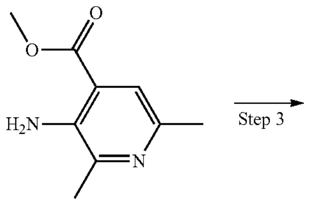

51b

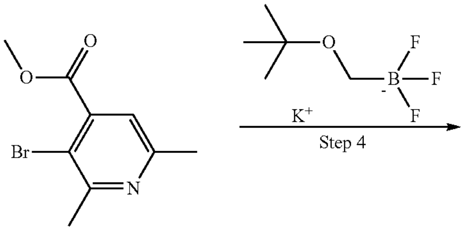

51c

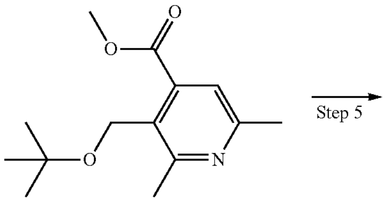

51d

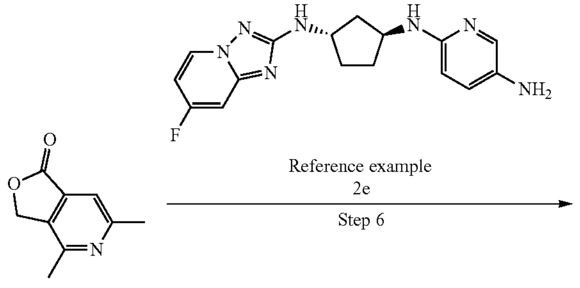

51e

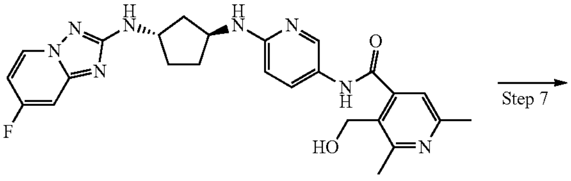

51f

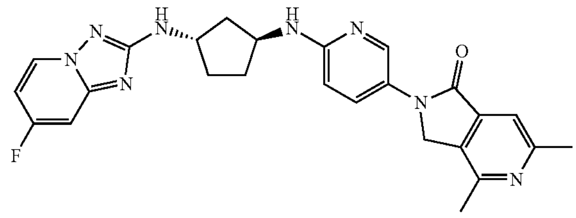

51

Step 1: At room temperature, methyl 5-amino-2-bromo-pyridine-4-carboxylate (10 g, 43.28 mmol) and N-bromo-succinimide (8.47 g, 47.61 mmol) were dissolved in 1, 2-dichloroethane (70 mL), and stirred for 16 hours. The reaction liquid was concentrated, and the residue was purified by silica gel column chromatography (elution system B) to obtain methyl 3-amino-2,6-dibromo-pyridine-4-carboxylate 51a (12.5 g), yield: 93.18%. MS m/z (ESI): 308.9, 310.9, 312.9 $[M+H]^+$.

Step 2: Under nitrogen protection, 51a (12.4 g, 40.01 mmol), a solution of 2,4,6-trimethyl-1,3,5,2,4,6-trioxatriborinane in tetrahydrofuran (3.5 M, 23 mL), 2-dicyclohexylphosphino-2',4',6'-triisopropylbiphenyl (1.91 g, 4.00 mmol), tris(dibenzylideneacetone)dipalladium (1.83 g, 2.0 mmol), and potassium phosphate (17.0 g, 80.01 mmol) were dissolved in 1,4-dioxane (100 mL), heated to 100° C. and stirred for 16 hours. The reaction liquid was filtered and concentrated. The residue was purified by silica gel column chromatography (elution system B) to obtain methyl 3-amino-2,6-dimethylisonicotine 51b (5 g), yield: 69.35%. MS m/z (ESI): 181.1 $[M+H]^+$.

Step 3: At room temperature, 51b (4.8 g, 26.64 mmol) and copper bromide (2.97 g, 13.32 mmol) were dissolved in acetonitrile (80 mL), and tert-butyl nitrite (8.24 g, 79.91 mmol) was added dropwise to the reaction liquid. The reaction was stirred at room temperature for 30 minutes, then heated to 60° C. and stirred for 1 hour. The reaction liquid was diluted with water (100 mL), and the aqueous phase was extracted with ethyl acetate (100 mLx3). The organic phase was concentrated, and the residue was purified by silica gel column chromatography (elution system B) to obtain methyl 3-bromo-2,6-dimethylisonicotine 51c (4.9 g), yield: 75.37%. MS m/z (ESI): 244.0, 246.0 $[M+H]^+$.

Step 4: Under nitrogen protection, 51c (500 mg, 2.05 mmol), potassium tert-butoxymethyltrifluoroborate (795.0 mg, 4.10 mmol), tris(dibenzylideneacetone)dipalladium (187.6 mg, 0.20 mmol), 2-dicyclohexylphosphino-2',6'-diisopropoxy-1,1'-biphenyl (191.2 mg, 0.41 mmol), and sodium carbonate (651.4 mg, 6.15 mmol) were dissolved in a mixed solvent of toluene (13 mL) and water (0.5 mL), and the reaction was heated to 120° C. and stirred for 16 hours. The reaction liquid was diluted with dichloromethane (40 mL), and the organic phase was washed with water and concentrated. The residue was purified by silica gel column chromatography (elution system B) to obtain methyl 3-(tert-butoxymethyl)-2,6-dimethylisonicotine 51d (300 mg), yield: 58.27%. MS m/z (ESI): 252.0 $[M+H]^+$.

Step 5: At room temperature, 51d (300 mg, 1.19 mmol) was dissolved in dichloromethane (7 mL), trifluoroacetic acid (409.02 mg, 3.59 mmol) was added dropwise to the reaction liquid, and the mixture was stirred for 1 hour. The reaction liquid was concentrated, the residue was diluted with ethyl acetate (50 mL), and the organic phase was washed with a saturated sodium bicarbonate solution and concentrated. The residue was purified by silica gel column chromatography (elution system B) to obtain 4,6-dimethylfuro[3,4-c]pyridin-1(3H)-one 51e (120 mg), yield: 61.61%. MS m/z (ESI): 164.1 $[M+H]^+$.

Step 6: Under nitrogen protection, reference example 2e (70 mg, 0.21 mmol) and 51e (69.8 mg, 0.43 mmol) were dissolved in 1,4-dioxane (5 mL), a solution of trimethylaluminum in toluene (2 M, 0.43 mL) was added dropwise to the reaction liquid, and the mixture was heated to 90° C. and stirred for 1 hour. The reaction liquid was added dropwise to methanol (10 mL) under stirring, and the mixed liquid was concentrated. The residue was purified by silica gel column chromatography (elution system A) to obtain N-(6-(((1S, 3S)-3-((7-fluoro-[1,2,4]triazolo[1,5-a]pyridin-2-yl)amino)cyclopentyl)amino)pyridin-3-yl)-3-(hydroxymethyl)-2,6-dimethylisonicotinamide 51f (30 mg), yield: 28.6%. MS m/z (ESI): 491.2 $[M+H]^+$.

Step 7: At room temperature, 51f (20 mg, 0.04 mmol) and triphenylphosphine (21.4 mg, 0.08 mmol) were dissolved in tetrahydrofuran (2 mL), diisopropyl azodicarboxylate (16.5 mg, 0.08 mmol) was added, and the mixture was stirred for 16 hours. The reaction liquid was concentrated, and the residue was purified by preparative HPLC (ammonium bicarbonate system) to obtain 2-(6-(((1S,3S)-3-((7-fluoro-[1,2,4]triazolo[1,5-a]pyridin-2-yl)amino)cyclopentyl) amino)pyridin-3-yl)-4,6-dimethyl-2,3-dihydro-1H-pyrrolo [3,4-c]pyridin-1-one 51 (1.2 mg), yield: 6.23%. MS m/z (ESI): 473.2 $[M+H]^+$.

$^1H$ NMR (400 MHz, DMSO-$d_6$) δ 8.69-8.62 (m, 1H), 8.36 (d, 1H), 7.86 (dd, 1H), 7.40 (s, 1H), 7.27 (dd, 1H), 6.86 (td, 1H), 6.72 (dd, 2H), 6.54 (d, 1H), 4.93 (s, 2H), 4.32-4.23 (m, 1H), 4.18-4.10 (m, 1H), 2.55 (s, 6H), 2.19-2.07 (m, 2H), 1.99-1.82 (m, 2H), 1.60-1.45 (m, 2H).

Example 52

1-(6-(((1S,3S)-3-((7-fluoro-[1,2,4]triazolo[1,5-a] pyridin-2-yl)amino)cyclopentyl)amino)pyridin-3-yl) piperidin-2-one

52

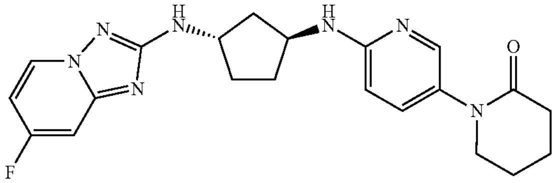

By reference to the synthesis method of example 32, the target product 1-(6-(((1S,3S)-3-((7-fluoro-[1,2,4]triazolo[1,5-a]pyridin-2-yl)amino)cyclopentyl)amino)pyridin-3-yl)piperidin-2-one 52 was synthesized. MS m/z (ESI): 410.2 $[M+H]^+$.

$^1H$ NMR (400 MHz, DMSO-$d_6$) δ 8.70-8.60 (m, 1H), 7.81 (d, 1H), 7.31-7.20 (m, 2H), 6.90-6.81 (m, 1H), 6.73 (d, 1H), 6.60 (d, 1H), 6.44 (d, 1H), 4.31-4.20 (m, 1H), 4.19-4.08 (m, 1H), 3.56-3.43 (m, 2H), 2.40-2.27 (m, 2H), 2.20-2.04 (m, 2H), 2.01-1.72 (m, 6H), 1.64-1.37 (m, 2H).

Example 53

4-(6-(((1S,3S)-3-((7-fluoro-[1,2,4]triazolo[1,5-a] pyridin-2-yl)amino)cyclopentyl)amino)pyridin-3-yl) morpholin-3-one

53

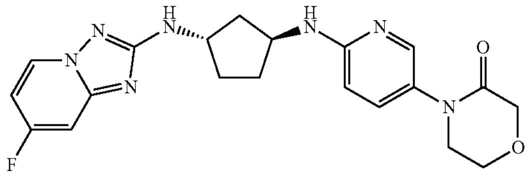

By reference to the synthesis method of example 32, the target product 4-(6-(((1S,3S)-3-((7-fluoro-[1,2,4]triazolo[1,5-a]pyridin-2-yl)amino)cyclopentyl)amino)pyridin-3-yl) morpholin-3-one 53 was synthesized. MS m/z (ESI): 412.2 $[M+H]^+$.

$^1H$ NMR (400 MHz, DMSO-$d_6$) δ 8.71-8.61 (m, 1H), 7.92 (d, 1H), 7.37-7.31 (m, 1H), 7.30-7.23 (m, 1H), 6.90-6.82 (m, 1H), 6.77-6.67 (m, 2H), 6.47 (d, 1H), 4.32-4.21 (m, 1H), 4.20-4.08 (m, 3H), 3.98-3.88 (m, 2H), 3.67-3.57 (m, 2H), 2.19-2.06 (m, 2H), 1.99-1.79 (m, 2H), 1.63-1.39 (m, 2H).

Example 54

5-(6-(((1S,3S)-3-((7-fluoro-[1,2,4]triazolo[1,5-a] pyridin-2-yl)amino)cyclopentyl)amino)pyridin-3-yl)-5-azaspiro[2.4]heptan-4-one

54

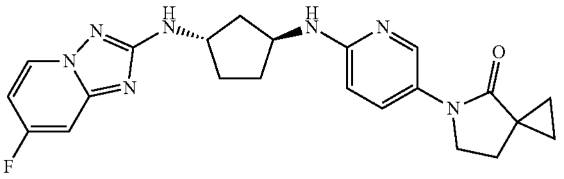

By reference to the synthesis method of example 32, the target product 5-(6-(((1S,3S)-3-((7-fluoro-[1,2,4]triazolo[1,5-a]pyridin-2-yl)amino)cyclopentyl)amino)pyridin-3-yl)-5-azaspiro[2.4]heptan-4-one 54 was synthesized. MS m/z (ESI): 422.2 $[M+H]^+$.

$^1H$ NMR (400 MHz, DMSO-$d_6$) δ 8.69-8.61 (m, 1H), 8.11 (d, 1H), 7.74-7.64 (m, 1H), 7.31-7.21 (m, 1H), 6.90-6.81 (m, 1H), 6.73 (d, 1H), 6.53 (d, 1H), 6.47 (d, 1H), 4.30-4.20 (m, 1H), 4.19-4.08 (m, 1H), 3.81 (t, 2H), 2.22-2.05 (m, 4H), 1.99-1.77 (m, 2H), 1.62-1.37 (m, 2H), 0.95-0.89 (m, 2H), 0.85-0.79 (m, 2H).

Example 55

6-(6-(((1S,3S)-3-((7-cyclopropyl-[1,2,4]triazolo[1,5-a]pyridin-2-yl)amino)cyclopentyl)amino)pyridin-3-yl)-5,6-dihydro-7H-pyrrolo[3,4-b]pyridin-7-one

55

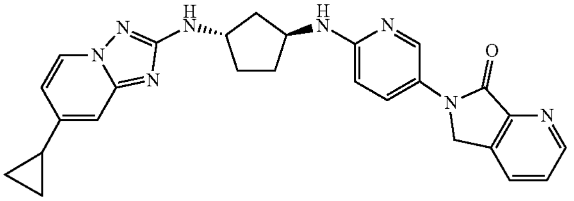

By reference to the synthesis method of reference example 3, 6-(6-(((1S,3S)-3-((7-cyclopropyl-[1,2,4]triazolo [1,5-a]pyridin-2-yl)amino)cyclopentyl)amino)pyridin-3-yl)-5,6-dihydro-7H-pyrrolo[3,4-b]pyridin-7-one 55 was synthesized. MS m/z (ESI): 467.2 $[M+H]^+$.

$^1H$ NMR (400 MHz, DMSO-$d_6$) δ 8.75 (d, 1H), 8.44-8.31 (m, 2H), 8.10 (d, 1H), 7.87 (dd, 1H), 7.61 (dd, 1H), 7.06 (s, 1H), 6.72-6.43 (m, 4H), 4.92 (s, 2H), 4.32-4.23 (m, 1H), 4.18-4.10 (m, 1H), 2.23-2.07 (m, 2H), 2.05-1.81 (m, 4H), 1.62-1.40 (m, 3H), 1.37-1.26 (m, 2H).

Example 56

6-(6-(((1S,3S)-3-((7-(difluoromethoxy)-[1,2,4]triazolo[1,5-a]pyridin-2-yl)amino)cyclopentyl)amino)pyridin-3-yl)-5,6-dihydro-7H-pyrrolo[3,4-b]pyridin-7-one

56

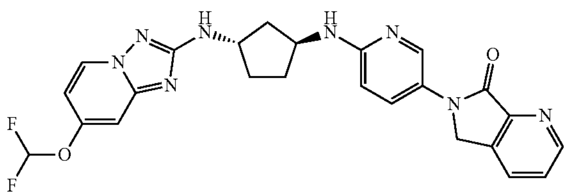

By reference to the synthesis method of reference example 3, 6-(6-(((1S,3S)-3-((7-(difluoromethoxy)-[1,2,4]triazolo[1,5-a]pyridin-2-yl)amino)cyclopentyl)amino)pyridin-3-yl)-5,6-dihydro-7H-pyrrolo[3,4-b]pyridin-7-one 56 was synthesized. MS m/z (ESI): 493.2 $[M+H]^+$.

$^1$H NMR (400 MHz, DMSO-$d_6$) δ 8.75 (dd, 1H), 8.63 (d, 1H), 8.35 (d, 1H), 8.11 (dd, 1H), 7.87 (dd, 1H), 7.65-7.58 (m, 1H), 7.42 (t, 1H), 7.14 (d, 1H), 6.78-6.66 (m, 3H), 6.55 (d, 1H), 4.92 (s, 2H), 4.32-4.23 (m, 1H), 4.20-4.07 (m, 1H), 2.20-2.08 (m, 2H), 2.01-1.82 (m, 2H), 1.60-1.43 (m, 2H).

Example 56 could also be synthesized by the following method:

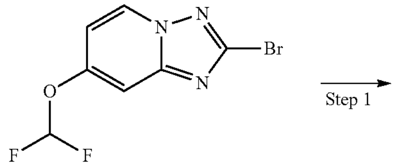

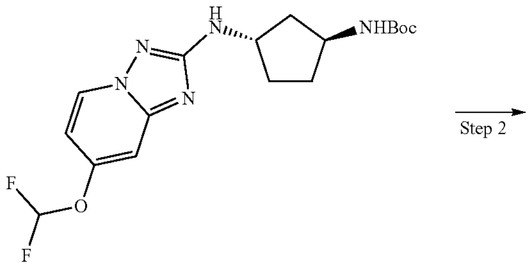

56a

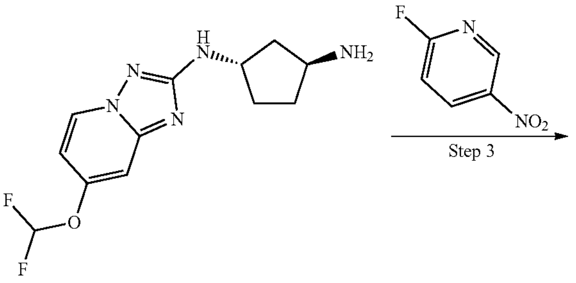

56b

-continued

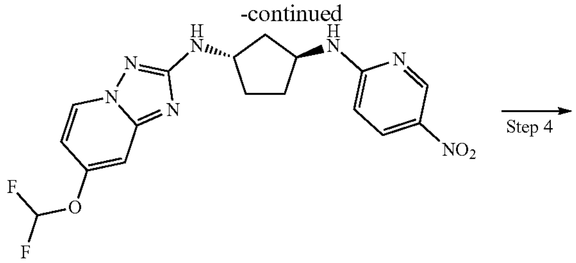

56c

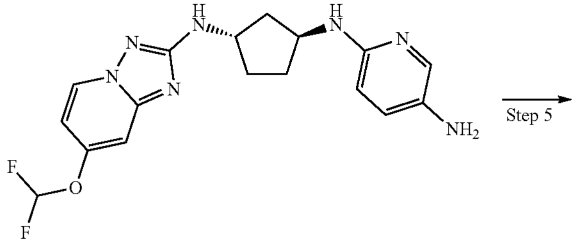

56d

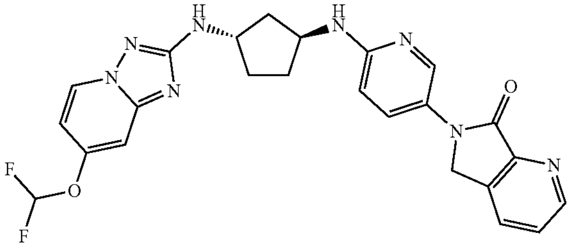

56

Step 1: Under nitrogen protection, 2-bromo-7-(difluoromethoxy)-[1,2,4]triazolo[1,5-a]pyridine (250 mg, 0.95 mmol), tert-butyl N-[(1S,3S)-3-aminocyclopentyl]carbamate (227.6 mg, 1.14 mmol), cesium carbonate (617.0 mg, 1.89 mmol), tris(dibenzylideneacetone)palladium (173.4 mg, 0.19 mmol), and 4,5-bis(diphenylphosphino)-9,9-dimethylxanthene (219.2 mg, 0.38 mmol) were dissolved in 1'4-dioxane (10 mL), heated to 130° C. by microwave and reacted for 2 hours. The reaction liquid was filtered, and the filtrate was concentrated. The residue was purified by silica gel column chromatography (elution system B) to obtain tert-butyl N-[(1S,3S)-3-[[7-(difluoromethoxy)-[1,2,4]triazolo[1,5-a]pyridin-2-yl]amino]cyclopentyl]carbamate 56a (170 mg), yield: 46.8%. MS m/z (ESI): 384.2 $[M+H]^+$.

Step 2: At room temperature, 56a (170 mg, 0.44 mmol) was dissolved in methanol (7 mL), hydrochloric acid (4 M, 4 mL) was added, and the mixture was stirred for half an hour. The reaction liquid was concentrated, and the residue was diluted with methanol. The mixture was adjusted pH=8-10 with a saturated sodium bicarbonate solution. After concentration, the residue was purified by silica gel column chromatography (elution system A) to obtain (1S,3S)-N3-[7-(difluoromethoxy)-[1,2,4]triazolo[1,5-a]pyridin-2-yl]cyclopentane-1,3-diamine 56b (120 mg), yield: 95.5%. MS m/z (ESI): 284.2 $[M+H]^+$.

Step 3: At room temperature, 56b (140 mg, 0.49 mmol), 2-fluoro-5-nitro-pyridine (77.2 mg, 0.54 mmol), and cesium carbonate (322.0 mg, 1.0 mmol) were dissolved in N,N-dimethylformamide (5 mL), heated to 80° C. and stirred for 3 hours. The reaction liquid was filtered, and the filtrate was concentrated. The residue was purified by silica gel column chromatography (elution system A) to obtain (1S,3S)-N3-[7-(difluoromethoxy)-[1,2,4]triazolo[1,5-a]pyridin-2-yl]-

N1-(5-nitro-2-pyridinyl)cyclopentane-1,3-diamine 56c (50 mg), yield: 25.0%. MS m/z (ESI): 406.2 [M+H]$^+$.

Step 4: In a hydrogen atmosphere, 56c (50 mg, 0.12 mmol) and palladium on carbon (13.1 mg, 0.012 mmol, purity: 10%) were dissolved in methanol (10 mL), and stirred for 1 hour at room temperature. The reaction liquid was filtered, and the filtrate was concentrated to obtain N2-[(1S,3S)-3-[[7-(difluoromethoxy)-[1,2,4]triazolo[1,5-a]pyridin-2-yl]amino]cyclopentyl]pyridine-2,5-diamine 56d (35 mg), yield: 75.6%. MS m/z (ESI): 376.1 [M+H]$^+$.

Step 5: At room temperature, 56d (35 mg, 0.09 mol), methyl 3-(bromomethyl)pyridine-2-carboxylate (20.0 mg, 0.065 mmol) and N,N-diisopropylethylamine (36.1 mg, 0.28 mmol) were dissolved in tert-butanol (5 mL), heated to 50° C. and stirred for 16 hours. The reaction liquid was concentrated, and the residue was purified by preparative thin layer chromatography (elution system A) to obtain 6-(6-(((1S,3S)-3-((7-(difluoromethoxy)-[1,2,4]triazolo[1,5-a]pyridin-2-yl)amino)cyclopentyl)amino)pyridin-3-yl)-5,6-dihydro-7H-pyrrolo[3,4-b]pyridin-7-one 56 (11 mg), yield: 24.0%. MS m/z (ESI): 493.2 [M+H]$^+$.

$^1$H NMR (400 MHz, DMSO-$d_6$) δ 8.75 (dd, 1H), 8.63 (d, 1H), 8.35 (d, 1H), 8.11 (dd, 1H), 7.87 (dd, 1H), 7.65-7.58 (m, 1H), 7.42 (t, 1H), 7.14 (d, 1H), 6.78-6.66 (m, 3H), 6.55 (d, 1H), 4.92 (s, 2H), 4.32-4.23 (m, 1H), 4.20-4.07 (m, 1H), 2.20-2.08 (m, 2H), 2.01-1.82 (m, 2H), 1.60-1.43 (m, 2H).

Example 57

4-methyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridin-1-one

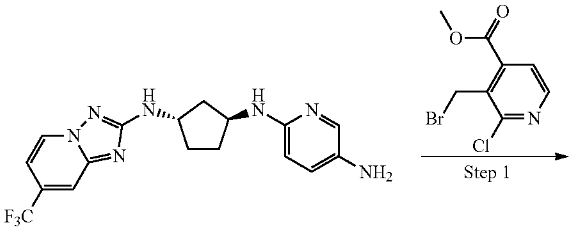

3g

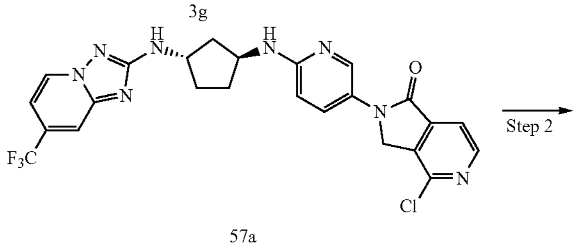

57a

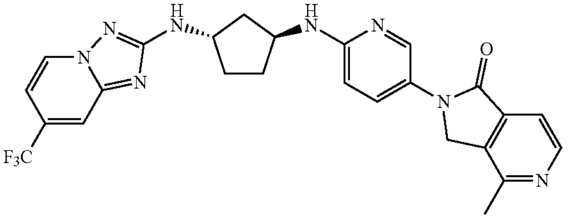

57

Step 1: At room temperature, reference example 3g (100 mg, 0.26 mmol), methyl 3-(bromomethyl)-2-chloroisonicotine (74.8 mg, 0.21 mmol), and N,N-diisopropylethylamine (102.7 mg, 0.79 mmol) were dissolved in a mixed solvent of tert-butanol (5 mL) and N,N-dimethylformamide (2 mL) and stirred for 16 hours. The reaction liquid was filtered and concentrated, and the residue was purified by silica gel column chromatography (elution system A) to obtain 4-chloro-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridin-1-one 57a (90 mg), yield: 64.21%. MS m/z (ESI): 529.1 [M+H]$^+$.

Step 2: Under nitrogen protection, 57a (90 mg, 0.17 mmol), a solution of 2,4,6-trimethyl-1,3,5,2,4,6-trioxatriborinane in tetrahydrofuran (3.5 M, 0.15 mL), 2-dicyclohexylphosphino-2',4',6'-triisopropylbiphenyl (16.2 mg, 0.034 mmol), tris(dibenzylideneacetone)dipalladium (15.6 mg, 0.017 mmol), and potassium phosphate (72.24 mg, 0.340 mmol) were dissolved in 1,4-dioxane (8 mL), heated to 100° C. and stirred for 5 hours. The reaction liquid was concentrated, and the residue was purified by thin layer chromatography (elution system A) to obtain 4-methyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridin-1-one 57 (56.6 mg), yield: 65.41%. MS m/z (ESI): 509.1 [M+H]$^+$.

$^1$H NMR (400 MHz, DMSO-$d_6$) δ 8.82 (d, 1H), 8.63 (d, 1H), 8.38 (d, 1H), 7.91-7.82 (m, 2H), 7.54 (d, 1H), 7.15 (dd, 1H), 7.03 (d, 1H), 6.73 (s, 1H), 6.57 (d, 1H), 4.98 (s, 2H), 4.37-4.14 (m, 2H), 2.57 (s, 3H), 2.21-2.10 (m, 2H), 2.03-1.86 (m, 2H), 1.64-1.44 (m, 2H).

Example 58

5-(6-(((1S,3S)-3-((7-(trifluoromethyl)-[1,2,4]triazolo[1,5-a]pyridin-2-yl)amino)cyclopentyl)amino)pyridin-3-yl)-5-azaspiro[2.4]heptan-4-one

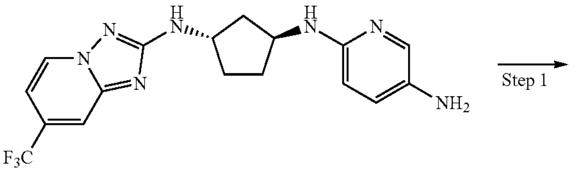

Reference example 3g

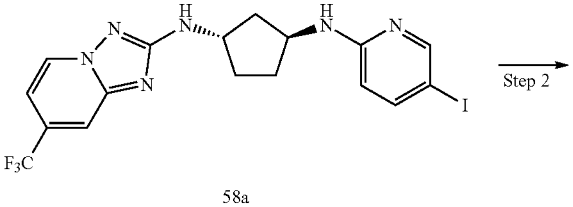

58a

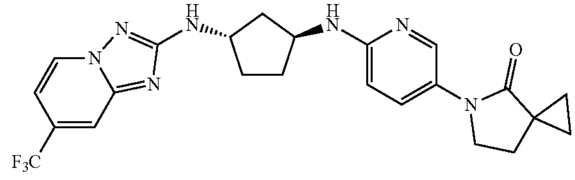

58

Step 1: Reference example 3g (70 mg, 0.19 mmol) was added to a solution of p-toluenesulfonic acid (96 mg, 0.56 mmol) in acetonitrile (1.5 mL), and the reaction liquid was cooled to 0° C. A solution of sodium nitrite (26 mg, 0.37 mmol) and potassium iodide (80 mg, 0.48 mmol) in water (0.5 mL) was added to the above reaction liquid, and the reaction was heated to room temperature and stirred for 48 hours. A saturated sodium chloride solution was added to the reaction liquid, and the aqueous phase was extracted with ethyl acetate (20 mL×2). The organic phases were combined, dried, and concentrated, and the residue was separated by silica gel column chromatography to obtain (1S,3S)-N1-(5-iodopyridin-2-yl)-N3-(7-(trifluoromethyl)-[1,2,4]triazolo[1,5-a]pyridin-2-yl)cyclopentane-1,3-diamine 58a (37 mg), yield: 40.85%. MS m/z (ESI): 489.1 $[M+H]^+$.

Step 2: By reference to the synthesis method of example 32, 5-(6-(((1S,3S)-3-((7-(trifluoromethyl)-[1,2,4]triazolo[1,5-a]pyridin-2-yl)amino)cyclopentyl)amino)pyridin-3-yl)-5-azaspiro[2.4]heptan-4-one 58 was synthesized. MS m/z (ESI): 472.2 $[M+H]^+$.

$^1$H NMR (400 MHz, DMSO-$d_6$) δ 8.82 (d, 1H), 8.11 (d, 1H), 7.85 (s, 1H), 7.74-7.64 (m, 1H), 7.19-7.10 (m, 1H), 7.02 (d, 1H), 6.54 (d, 1H), 6.47 (d, 1H), 4.32-4.11 (m, 2H), 3.87-3.74 (m, 2H), 2.23-2.07 (m, 4H), 2.00-1.80 (m, 2H), 1.65-1.38 (m, 2H), 0.95-0.90 (m, 2H), 0.85-0.79 (m, 2H).

Example 59

4,6-dimethyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridin-1-one

59

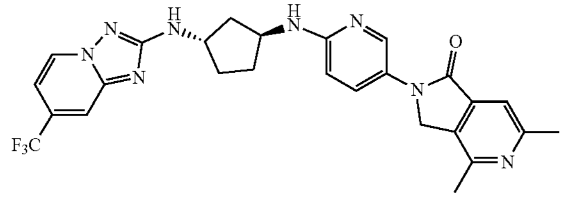

By reference to the synthesis method of reference example 3, 4,6-dimethyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridin-1-one 59 was synthesized. MS m/z (ESI): 523.2 $[M+H]^+$.

Example 60

3-methyl-N-(6-(((1S,3S)-3-((7-(trifluoromethyl)-[1,2,4]triazolo[1,5-a]pyridin-2-yl)amino)cyclopentyl)amino)pyridin-3-yl)methylpicolinamide

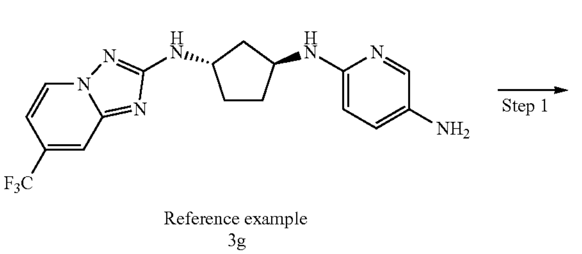

Reference example 3g

-continued

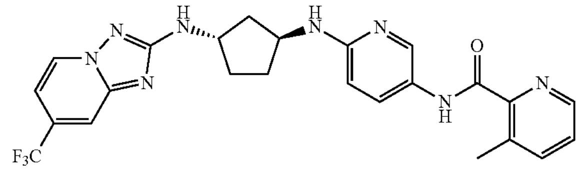

60

Step 1: Reference example 3g (50 mg, 0.13 mmol), 3-methyl 2-pyridinecarboxylic acid (20 mg, 0.15 mmol), and N-methylimidazole (33 mg, 0.4 mmol) were dissolved in acetonitrile (1.5 mL), N,N,N',N'-tetramethylchloroformamidinium hexafluorophosphate (56 mg, 0.2 mmol) was added to the above reaction liquid, and the mixture was stirred at room temperature for 2 hours. A saturated sodium chloride solution (20 mL) was added to the reaction liquid, and the aqueous phase was extracted with ethyl acetate (20 mL×3). The organic phases were combined, dried, and concentrated, and the residue was subjected to reversed-phase HPLC to prepare 3-methyl-N-(6-(((1S,3S)-3-((7-(trifluoromethyl)-[1,2,4]triazolo[1,5-a]pyridin-2-yl)amino)cyclopentyl)amino)pyridin-3-yl)methylpicolinamide 60 (9.7 mg), yield: 14.75%. MS m/z (ESI): 497.2 $[M+H]^+$.

$^1$H NMR (400 MHz, DMSO-$d_6$) δ 10.26 (s, 1H), 8.82 (d, 1H), 8.51 (d, 1H), 8.33 (d, 1H), 7.85 (s, 1H), 7.82-7.75 (m, 2H), 7.53-7.44 (m, 1H), 7.18-7.11 (m, 1H), 7.03 (d, 1H), 6.52-6.43 (m, 2H), 4.33-4.13 (m, 2H), 2.56 (s, 3H), 2.21-2.08 (m, 2H), 2.01-1.82 (m, 2H), 1.64-1.41 (m, 2H).

Example 61

3-fluoro-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one

61

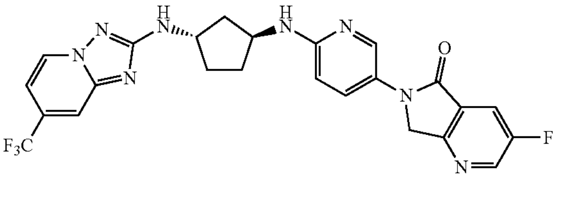

By reference to the synthesis method of reference example 3, 3-fluoro-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one 61 was synthesized. MS m/z (ESI): 513.2 $[M+H]^+$.

$^1$H NMR (400 MHz, DMSO-$d_6$) δ 8.87-8.76 (m, 2H), 8.36 (d, 1H), 8.10 (dd, 1H), 7.86 (dd, 2H), 7.15 (dd, 1H), 7.02 (d, 1H), 6.71 (d, 1H), 6.55 (d, 1H), 4.96 (d, 2H), 4.38-4.12 (m, 2H), 2.24-2.10 (m, 2H), 2.05-1.83 (m, 2H), 1.63-1.42 (m, 2H).

Example 62

N-methyl-N-(6-(((1S,3S)-3-((7-(trifluoromethyl)-[1,2,4]triazolo[1,5-a]pyridin-2-yl)amino)cyclopentyl)amino)pyridin-3-yl)methylpicolinamide

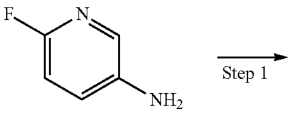

62a

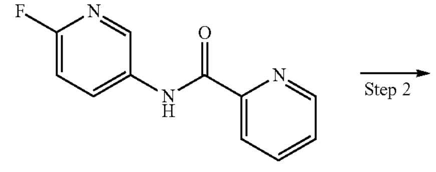

62b

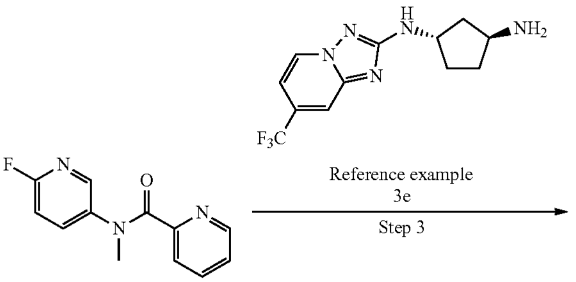

62c

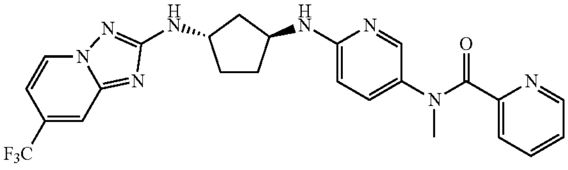

62

Step 1: 2-fluoro-5-aminopyridine 62a (500 mg, 4.46 mmol), pyridine-2-carboxylic acid (604 mg, 4.91 mmol), and N-methylimidazole (1.10 g, 13.38 mmol) were dissolved in acetonitrile (15 mL), N,N,N',N'-tetramethylchloroformamidinium hexafluorophosphate (1.88 g, 6.69 mmol) was added to the above reaction liquid, and the mixture was stirred at room temperature for 3 hours. A saturated sodium chloride solution (20 mL) was added to the reaction liquid, and the aqueous phase was extracted with ethyl acetate (20 mL×3). The organic phases were combined, dried, and concentrated, petroleum ether/ethyl acetate (v/v=1/1, 10 mL) was added to the residue, and the mixture was stirred at 60° C. for 30 minutes, cooled to room temperature, and filtered to obtain N-(6-fluoropyridin-3-yl)methylpicolinamide 62b (464 mg), yield: 47.90%. MS m/z (ESI): 218.1 $[M+H]^+$.

Step 2: At 0° C., sodium hydride (128 mg, 3.20 mmol, 60% content) was added to a solution of 62b (464 mg, 2.14 mmol) in tetrahydrofuran (10 mL), after 30 minutes, iodomethane (606 mg, 4.27 mmol) was added to the above reaction liquid, the reaction liquid was slowly heated to room temperature and stirred for 1.5 hours. A saturated sodium chloride solution (20 mL) was added to the reaction liquid, and the aqueous phase was extracted with ethyl acetate (20 mL). The organic phase was dried and concentrated, and the residue was separated by silica gel column chromatography to obtain N-(6-fluoropyridin-3-yl)-N-methylmethylpicolinamide 62c (53 mg), yield: 10.73%. MS m/z (ESI): 232.1 $[M+H]^+$.

Step 3: Reference example 3e (68 mg, 0.18 mmol), 62c (54 mg, 0.23 mmol) and N,N-diisopropylethylamine (69 mg, 0.54 mmol) were dissolved in dimethyl sulfoxide (1 mL), and the reaction was heated to 130° C. and stirred for 60 hours. The reaction liquid was filtered, and the filtrate was subjected to reversed-phase HPLC to prepare N-methyl-N-(6-(((1S,3S)-3-((7-(trifluoromethyl)-[1,2,4]triazolo[1,5-a]pyridin-2-yl)amino)cyclopentyl)amino)pyridin-3-yl)methylpicolinamide 62 (4.2 mg), yield: 4.73%. MS m/z (ESI): 497.2$[M+H]^+$.

$^1$H NMR (400 MHz, DMSO-$d_6$) δ 8.80 (d, 1H), 8.33 (d, 1H), 7.84 (s, 1H), 7.76-7.68 (m, 1H), 7.63 (s, 1H), 7.40 (d, 1H), 7.27-7.19 (m, 2H), 7.17-7.11 (m, 1H), 6.96 (d, 1H), 6.60 (d, 1H), 6.29 (d, 1H), 4.22-4.05 (m, 2H), 3.29 (s, 3H), 2.13-2.01 (m, 2H), 1.93-1.70 (m, 2H), 1.60-1.31 (m, 2H).

Example 63

3-(2-hydroxypropan-2-yl)-6'-(((1S,3S)-3-((7-(trifluoromethyl)-[1,2,4]triazolo[1,5-a]pyridin-2-yl)amino)cyclopentyl)amino)-2H-[1,3'-bipyridine]-2-one

63

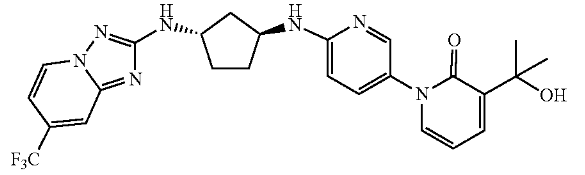

By reference to the synthesis method of example 58, 3-(2-hydroxypropan-2-yl)-6'-(((1S,3S)-3-((7-(trifluoromethyl)-[1,2,4]triazolo[1,5-a]pyridin-2-yl)amino)cyclopentyl)amino)-2H-[1,3'-bipyridine]-2-one 63 was synthesized. MS m/z (ESI): 514.2$[M+H]^+$.

$^1$H NMR (400 MHz, DMSO-$d_6$) δ 8.82 (d, 1H), 7.91 (d, 1H), 7.85 (s, 1H), 7.50 (d, 1H), 7.42-7.35 (m, 1H), 7.18-7.12 (m, 1H), 7.02 (d, 1H), 6.89 (d, 1H), 6.52 (d, 1H), 6.46 (d, 1H), 6.38-6.33 (m, 1H), 5.15 (s, 1H), 4.40-4.28 (m, 1H), 4.27-4.15 (m, 1H), 2.23-2.09 (m, 2H), 2.03-1.84 (m, 2H), 1.65-1.44 (m, 2H), 1.38 (s, 6H).

Example 65

5-carbonyl-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridine-3-carbonitrile

65

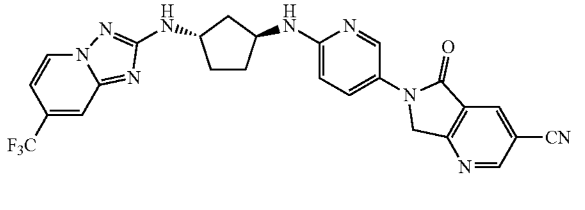

By reference to the synthesis method of reference example 3, 5-carbonyl-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridine-3-carbonitrile 65 was synthesized. MS m/z (ESI): 520.2 $[M+H]^+$.

$^1H$ NMR (400 MHz, DMSO-$d_6$) δ 9.24 (d, 1H), 8.82 (d, 1H), 8.71 (d, 1H), 8.37 (d, 1H), 7.87 (dd, 1H), 7.85 (s, 1H), 7.15 (dd, 1H), 7.03 (d, 1H), 6.74 (d, 1H), 6.56 (d, 1H), 5.09 (s, 2H), 4.34-4.29 (m, 1H), 4.23-4.18 (m, 1H), 2.18-2.12 (m, 2H), 2.01-1.88 (m, 2H), 1.59-1.49 (m, 2H).

Example 66

1-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-6-carbonitrile

66

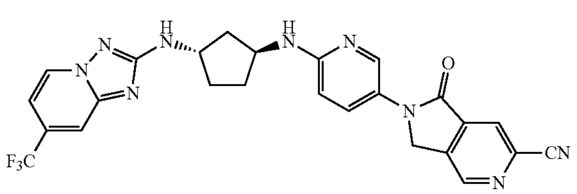

By reference to the synthesis method of reference example 3, 1-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-6-carbonitrile 66 was synthesized. MS m/z (ESI): 520.2 $[M+H]^+$.

$^1H$ NMR (400 MHz, DMSO-$d_6$) δ 9.12 (s, 1H), 8.82 (d, 1H), 8.41 (s, 1H), 8.35 (d, 1H), 7.86-7.82 (m, 2H), 7.15 (dd, 1H), 7.01 (d, 1H), 6.77 (d, 1H), 6.57 (d, 1H), 5.12 (s, 2H), 4.34-4.29 (m, 1H), 4.24-4.19 (m, 1H), 2.20-2.13 (m, 2H), 2.00-1.88 (m, 2H), 1.61-1.50 (m, 2H).

Example 67

2-methyl-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one

67

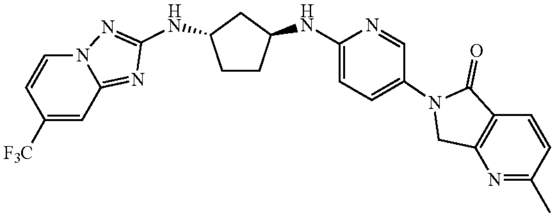

By reference to the synthesis method of reference example 3, 2-methyl-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one 67 was synthesized. MS m/z (ESI): 509.2 $[M+H]^+$.

$^1H$ NMR (400 MHz, DMSO-$d_6$) δ 8.82 (d, 1H), 8.35 (d, 1H), 8.01 (d, 1H), 7.91-7.78 (m, 2H), 7.42 (d, 1H), 7.14 (d, 1H), 7.01 (d, 1H), 6.64 (d, 1H), 6.55 (d, 1H), 4.90 (s, 2H), 4.33-4.27 (m, 1H), 4.23-4.18 (m, 1H), 2.62 (s, 3H), 2.18-2.13 (m, 2H), 2.00-1.89 (m, 2H), 1.60-1.49 (m, 2H).

Example 68

2-cyclopropyl-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one

68

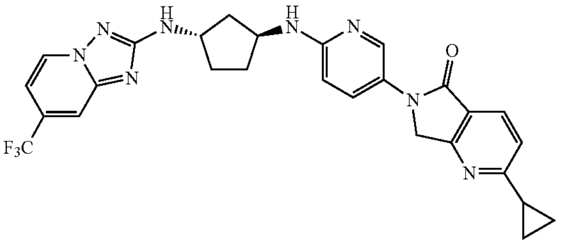

By reference to the synthesis method of reference example 3, 2-cyclopropyl-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one 68 was synthesized. MS m/z (ESI): 535.2 $[M+H]^+$.

$^1H$ NMR (400 MHz, DMSO-$d_6$) δ 8.82 (d, 1H), 8.32 (d, 1H), 7.96 (d, 1H), 7.88-7.83 (m, 2H), 7.46 (d, 1H), 7.14 (dd, 1H), 7.02 (d, 1H), 6.63 (d, 1H), 6.53 (d, 1H), 4.85 (s, 2H), 4.32-4.18 (m, 2H), 2.31-2.25 (m, 1H), 2.18-2.12 (m, 2H), 2.01-1.85 (m, 2H), 1.61-1.47 (m, 2H), 1.10-1.01 (m, 4H).

Example 69

(1S,3S)-N1-(5-(2-oxa-5-azaspiro[3.4]octan-5-yl)pyridin-2-yl)-N3-(7-fluoro-[1,2,4]triazolo[1,5-a]pyridin-2-yl)cyclopentane-1,3-diamine

69

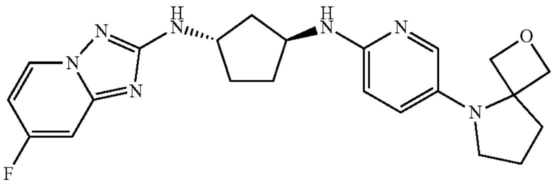

By reference to the synthesis method of example 58, (1S,3S)-N1-(5-(2-oxa-5-azaspiro[3.4]octan-5-yl)pyridin-2-yl)-N3-(7-fluoro-[1,2,4]triazolo[1,5-a]pyridin-2-yl)cyclopentane-1,3-diamine 69 was synthesized. MS m/z (ESI): 424.2 $[M+H]^+$.

Example 70

(1S,3S)-N1-(5-(2-oxa-5-azaspiro[3.4]octan-5-yl)pyridin-2-yl)-N3-(7-(trifluoromethyl)-[1,2,4]triazolo[1,5-a]pyridin-2-yl)cyclopentane-1,3-diamine

70

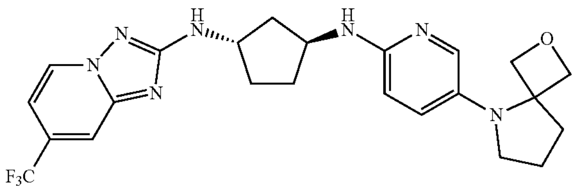

By reference to the synthesis method of example 58, (1S,3S)-N1-(5-(2-oxa-5-azaspiro[3.4]octan-5-yl)pyridin-2-yl)-N3-(7-(trifluoromethyl)-[1,2,4]triazolo[1,5-a]pyridin-2-yl)cyclopentane-1,3-diamine 70 was synthesized. MS m/z (ESI): 474.2 $[M+H]^+$.

Example 71

6-cyclopropyl-2-(6-(((1S,3S)-3-((7-(trifluoromethyl)-[1,2,4]triazolo[1,5-a]pyridin-2-yl)amino)cyclopentyl)amino)pyridin-3-yl)-1,2-dihydro-3H-pyrrolo[3,4-c]pyridin-3-one

71

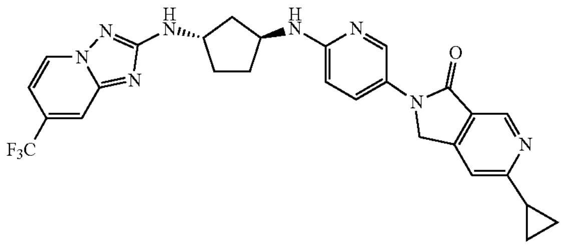

By reference to the synthesis method of reference example 3, 6-cyclopropyl-2-(6-(((1S,3S)-3-((7-(trifluoromethyl)-[1,2,4]triazolo[1,5-a]pyridin-2-yl)amino)cyclopentyl)amino)pyridin-3-yl)-1,2-dihydro-3H-pyrrolo[3,4-c]pyridin-3-one 71 was synthesized. MS m/z (ESI): 535.2 $[M+H]^+$.

Example 72

3-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-6-carbonitrile

72

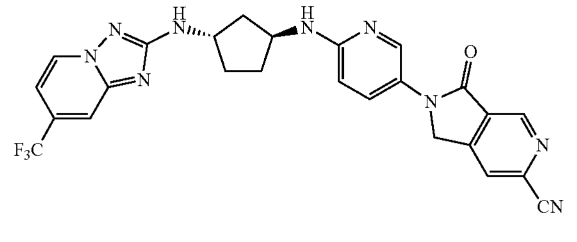

By reference to the synthesis method of reference example 3, 3-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-6-carbonitrile 72 was synthesized. MS m/z (ESI): 520.2 $[M+H]^+$.

Example 73

6'-(((1S,3S)-3-((7-(trifluoromethyl)-[1,2,4]triazolo[1,5-a]pyridin-2-yl)amino)cyclopentyl)amino)-[3,3'-bipyridine]-2(1H)-one

73

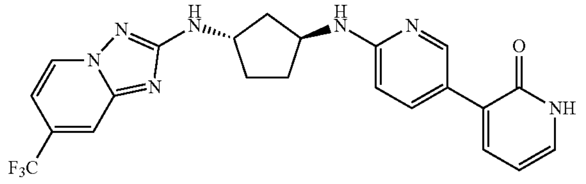

By reference to the synthesis method of example 31, 6'-(((1S,3S)-3-((7-(trifluoromethyl)-[1,2,4]triazolo[1,5-a]pyridin-2-yl)amino)cyclopentyl)amino)-[3,3'-bipyridine]-2(1H)-one 73 was synthesized. MS m/z (ESI): 456.2 $[M+H]^+$.

$^1$H NMR (400 MHz, DMSO-$d_6$) δ 11.63 (s, 1H), 8.81 (d, 1H), 8.35 (d, 1H), 7.84 (s, 1H), 7.77 (dd, 1H), 7.54 (dd, 1H), 7.28 (d, 1H), 7.14 (dd, 1H), 7.00 (d, 1H), 6.66 (d, 1H), 6.46 (d, 1H), 6.23 (t, 1H), 4.35-4.30 (m, 1H), 4.23-4.18 (m, 1H), 2.19-2.12 (m, 2H), 2.01-1.88 (m, 2H), 1.61-1.49 (d, 2H).

Example 75

3-fluoro-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one

75

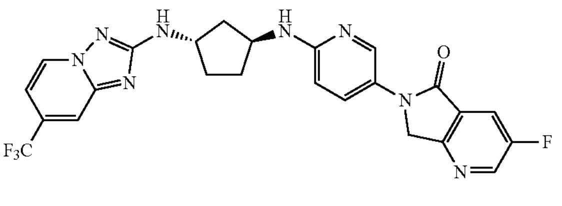

By reference to the synthesis method of reference example 3, 3-fluoro-6-(6-(((1S,3S)-3-((7-(trifluoromethyl)-[1,2,4]triazolo[1,5-a]pyridin-2-yl)amino)cyclopentyl)amino)pyridin-3-yl)-6,7-dihydro-5H-pyrrolo[3,4-b]pyridin-5-one 75 was synthesized. MS m/z (ESI): 513.2 $[M+H]^+$.

$^1$H NMR (400 MHz, DMSO-$d_6$) δ 8.87-8.76 (m, 2H), 8.36 (d, 1H), 8.10 (dd, 1H), 7.86 (dd, 2H), 7.15 (dd, 1H), 7.02 (d, 1H), 6.71 (d, 1H), 6.55 (d, 1H), 4.96 (d, 2H), 4.40-4.15 (m, 2H), 2.24-2.10 (m, 2H), 2.05-1.83 (m, 2H), 1.65-1.41 (m, 2H).

Example 76

1-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-4-carbonitrile

76

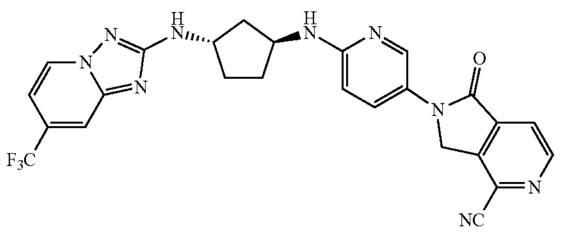

By reference to the synthesis method of reference example 3, 1-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-4-carbonitrile 76 was synthesized. MS m/z (ESI): 520.2 $[M+H]^+$.

$^1$H NMR (400 MHz, DMSO-$d_6$) δ 8.94 (d, 1H), 8.82 (d, 1H), 8.41 (d, 1H), 8.08 (d, 1H), 7.91-7.81 (m, 2H), 7.18-7.11 (m, 1H), 7.02 (d, 1H), 6.78 (d, 1H), 6.57 (d, 1H), 5.25 (s, 2H), 4.38-4.28 (m, 1H), 4.26-4.16 (m, 1H), 2.24-2.10 (m, 2H), 2.05-1.83 (m, 2H), 1.67-1.43 (m, 2H).

Example 77

3-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-7-carbonitrile

77

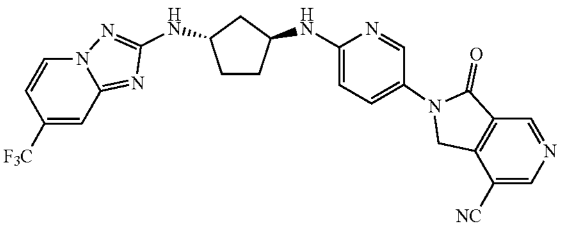

By reference to the synthesis method of reference example 3, 3-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-7-carbonitrile 77 was synthesized. MS m/z (ESI): 520.2 $[M+H]^+$.

Example 78

4-hydroxy-1-(6-(((1S,3S)-3-((7-(trifluoromethyl)-[1,2,4]triazolo[1,5-a]pyridin-2-yl)amino)cyclopentyl)amino)pyridin-3-yl)pyrimidin-2(1H)-one

78

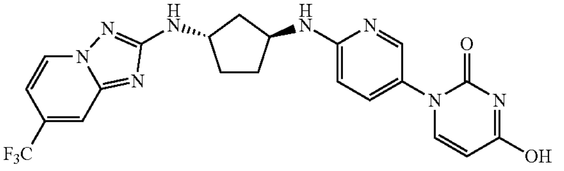

By reference to the synthesis method of example 58, 4-hydroxy-1-(6-(((1S,3S)-3-((7-(trifluoromethyl)-[1,2,4]triazolo[1,5-a]pyridin-2-yl)amino)cyclopentyl)amino)pyridin-3-yl)pyrimidin-2(1H)-one 78 was synthesized. MS m/z (ESI): 473.2 $[M+H]^+$.

$^1$H NMR (400 MHz, DMSO-$d_6$) δ 11.37 (s, 1H), 8.82 (d, 1H), 7.94 (d, 1H), 7.85 (s, 1H), 7.62 (d, 1H), 7.42-7.35 (m, 1H), 7.20-7.10 (m, 1H), 7.03 (d, 1H), 6.93 (d, 1H), 6.51 (d, 1H), 5.65-5.56 (m, 1H), 4.38-4.26 (m, 1H), 4.25-4.14 (m, 1H), 2.21-2.09 (m, 2H), 2.02-1.82 (m, 2H), 1.66-1.40 (m, 2H).

Example 79

5-(3-(2-hydroxypropan-2-yl)-1H-pyrazol-1-yl)-6'-(((1S,3S)-3-((7-(trifluoromethyl)-[1,2,4]triazolo[1,5-a]pyridin-2-yl)amino)cyclopentyl)amino)-2H-[1,3'-bipyridine]-2-one

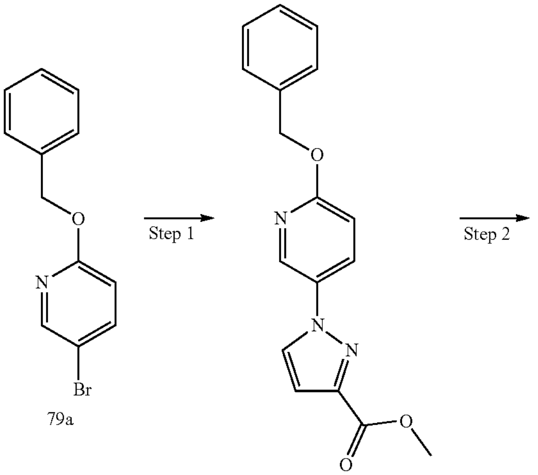

79a

79b

-continued

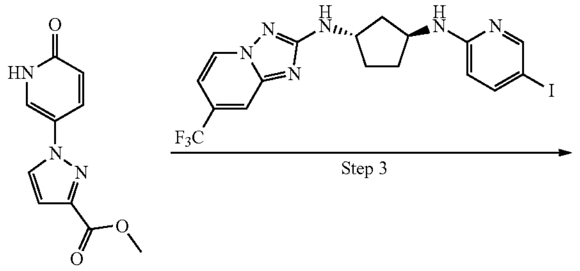

79c

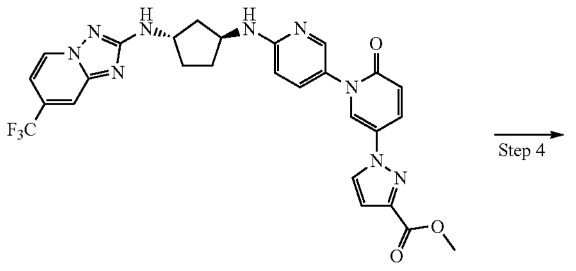

79d

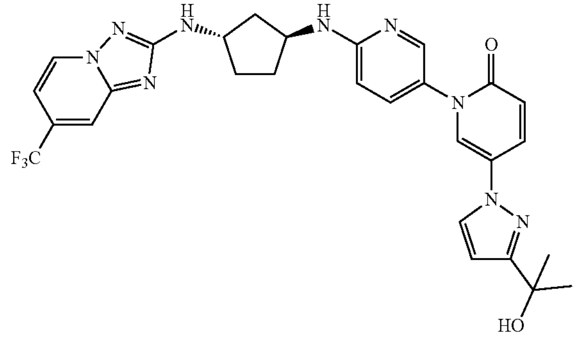

79

Step 1: Under nitrogen protection, 2-benzyloxy-5-bromopyridine 79a (2.0 g, 7.57 mmol), methyl 3-pyrazolecarboxylate (1.05 g, 8.33 mmol), cuprous iodide (288.4 mg, 1.51 mmol), L-proline (174.4 mg, 1.51 mmol) and potassium carbonate (3.14 g, 22.72 mmol) were dissolved in dimethyl sulfoxide (5 mL), and the reaction was heated to 120° C. and stirred for 5 hours. The reaction liquid was diluted with ethyl acetate, washed with a saturated sodium chloride aqueous solution, dried, and concentrated under reduced pressure. The residue was subjected to silica gel column chromatography (elution system B) to obtain methyl 1-(6-(benzyloxy)pyridin-3-yl)-1H-pyrazole-3-carboxylate 79b (230 mg), yield: 9.8%. MS m/z (ESI): 310.1 $[M+H]^+$.

Step 2: In a hydrogen atmosphere, 79b (230 mg, 0.743 mmol) and palladium on carbon (27 mg, 0.223 mmol) were dissolved in methanol (5 mL), and the reaction was stirred at room temperature for 16 hours. The reaction liquid was filtered, dried, and concentrated to obtain methyl 1-(6-oxo-1,6-dihydropyridin-3-yl)-1H-pyrazole-3-carboxylate 79c (60 mg), yield: 36.8%. MS m/z (ESI): 220.1 $[M+H]^+$.

Step 3: Under nitrogen protection, 79c (60 mg, 0.123 mmol), (26.9 mg, 0.123 mmol), cuprous iodide (23.4 mg, 0.123 mmol), trans-N,N'-dimethyl 1,2-cyclohexanediamine (17.5 mg, 0.123 mmol) and cesium carbonate (120 mg, 0.368 mmol) were dissolved in 1,4-dioxane (10 mL), and the reaction was heated to 100° C. and stirred for 16 hours. The reaction liquid was diluted with ethyl acetate, washed with a saturated sodium chloride aqueous solution, dried, and concentrated under reduced pressure. The residue was subjected to silica gel column chromatography (elution system B) to obtain methyl 1-(2-oxo-6'-(((1S,3S)-3-((7-(trifluoromethyl)-[1,2,4]triazolo[1,5-a]pyridin-2-yl)amino)cyclopentyl)amino)-2H-[1,3'-bipyridin]-5-yl)-1H-pyrazole-3-carboxylate 79d (60 mg), yield: 84.3%. MS m/z (ESI): 580.2 $[M+H]^+$.

Step 4: Under nitrogen protection at 0° C., 79d (60 mg, 0.103 mmol) was dissolved in anhydrous tetrahydrofuran (3 mL), a solution of methylmagnesium bromide in tetrahydrofuran (1 M, 0.5 mL) was dropwise added to the reaction liquid, and the reaction liquid was heated to room temperature and stirred for 1 hour. The reaction was quenched with methanol and concentrated, and the residue was purified by preparative HPLC (formic acid system) to obtain 5-(3-(2-hydroxypropan-2-yl)-1H-pyrazol-1-yl)-6'-(((1S,3S)-3-((7-(trifluoromethyl)-[1,2,4]triazolo[1,5-a]pyridin-2-yl)amino)cyclopentyl)amino)-2H-[1,3'-bipyridine]-2-one 79 (10.0 mg), yield: 16.7%. MS m/z (ESI): 580.2 $[M+H]^+$.

$^1H$ NMR (400 MHz, DMSO-$d_6$) δ 8.82 (d, 1H), 8.15 (d, 1H), 8.05-7.95 (m, 3H), 7.85 (s, 1H), 7.48 (dd, 1H), 7.15 (dd, 1H), 7.04 (d, 1H), 6.97 (d, 1H), 6.58 (dd, 2H), 6.42 (d, 1H), 4.96 (s, 2H), 4.37-4.19 (m, 2H), 2.17 (dd, 1H), 2.03-1.87 (m, 2H), 1.62-1.45 (m, 2H), 1.44 (s, 6H).

Example 81

4-(2-hydroxypropan-2-yl)-6'-(((1S,3S)-3-((7-(trifluoromethyl)-[1,2,4]triazolo[1,5-a]pyridin-2-yl)amino)cyclopentyl)amino)-2H-[1,3'-bipyridine]-2-one

81

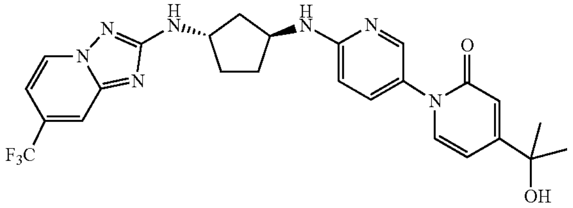

By reference to the synthesis method of example 58, the target product 4-(2-hydroxypropan-2-yl)-6'-(((1S,3S)-3-((7-(trifluoromethyl)-[1,2,4]triazolo[1,5-a]pyridin-2-yl)amino)cyclopentyl)amino)-2H-[1,3'-bipyridine]-2-one 81 was synthesized. MS m/z (ESI): 514.2 $[M+H]^+$.

$^1H$ NMR (400 MHz, DMSO-$d_6$) δ 8.82 (d, 1H), 7.91 (d, 1H), 7.85 (s, 1H), 7.50 (d, 1H), 7.42-7.35 (m, 1H), 7.17-7.11 (m, 1H), 7.02 (d, 1H), 6.89 (d, 1H), 6.52 (d, 1H), 6.46 (d, 1H), 6.38-6.33 (m, 1H), 5.15 (s, 1H), 4.39-4.27 (m, 1H), 4.27-4.15 (m, 1H), 2.21-2.10 (m, 2H), 2.04-1.84 (m, 2H), 1.66-1.44 (m, 2H), 1.38 (s, 6H).

Example 82

6-methyl-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one

82

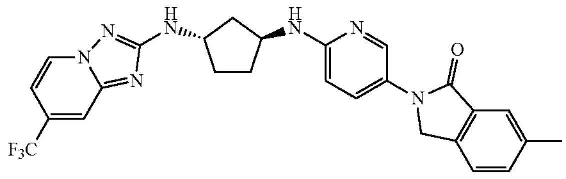

By reference to the synthesis method of reference example 3, 6-methyl-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one 82 was synthesized. MS m/z (ESI): 508.2 $[M+H]^+$.

$^1$H NMR (400 MHz, DMSO-$d_6$) δ 8.82 (d, 1H), 8.32 (d, 1H), 7.90-7.82 (m, 2H), 7.57-7.42 (m, 3H), 7.14 (dd, 1H), 7.01 (d, 1H), 6.61 (d, 1H), 6.54 (d, 1H), 4.85 (s, 2H), 4.38-4.15 (m, 2H), 2.42 (s, 3H), 2.22-2.11 (m, 2H), 2.01-1.91 (m, 2H), 1.66-1.44 (m, 2H).

Example 83

6-fluoro-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one

83

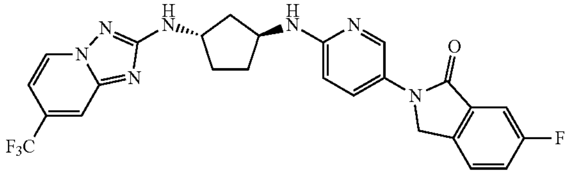

By reference to the synthesis method of reference example 3, 6-fluoro-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one 83 was synthesized. MS m/z (ESI): 512.2 $[M+H]^+$.

Example 84

2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one

84

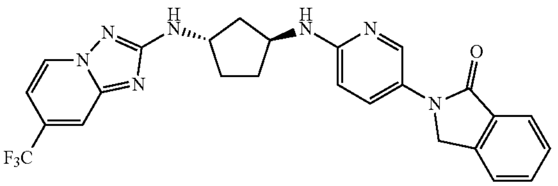

By reference to the synthesis method of reference example 3, 2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one 84 was synthesized. MS m/z (ESI): 494.2 $[M+H]^+$.

Example 85

5-methyl-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one

85

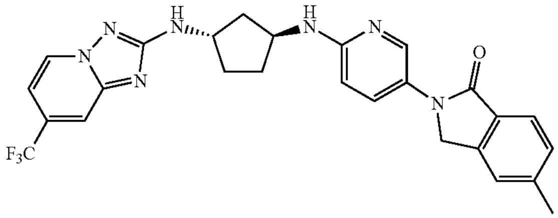

By reference to the synthesis method of reference example 3, 5-methyl-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one 85 was synthesized. MS m/z (ESI): 508.2 $[M+H]^+$.

Example 86

5-fluoro-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one

86

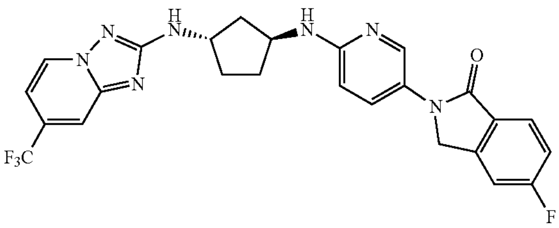

By reference to the synthesis method of reference example 3, 5-fluoro-2-(6-(((1S,3S)-3-((7-(trifluoromethyl)-[1,2,4]triazolo[1,5-a]pyridin-2-yl)amino)cyclopentyl)amino)pyridin-3-yl)isoindolin-1-one 86 was synthesized. MS m/z (ESI): 512.2 $[M+H]^+$.

Example 88

7-fluoro-2-(6-(((1S,3S)-3-((7-(trifluoromethyl)-[1,2,4]triazolo[1,5-a]pyridin-2-yl)amino)cyclopentyl)amino)pyridin-3-yl)-1,2-dihydro-3H-pyrrolo[3,4-c]pyridin-3-one

88

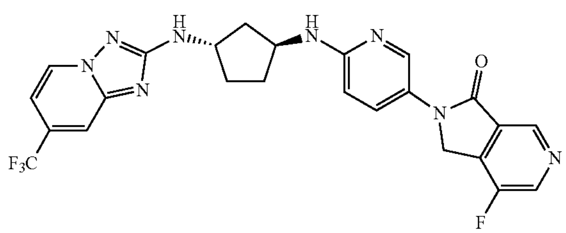

By reference to the synthesis method of reference example 3, 7-fluoro-2-(6-(((1S,3S)-3-((7-(trifluoromethyl)-[1,2,4]triazolo[1,5-a]pyridin-2-yl)amino)cyclopentyl)amino)pyridin-3-yl)-1,2-dihydro-3H-pyrrolo[3,4-c]pyridin-3-one 88 was synthesized. MS m/z (ESI): 513.2 [M+H]$^+$.

Example 89

6-methyl-2-(6-(((1S,3S)-3-((7-(trifluoromethyl)-[1,2,4]triazolo[1,5-a]pyridin-2-yl)amino)cyclopentyl)amino)pyridin-3-yl)-1,2-dihydro-3H-pyrrolo[3,4-c]pyridin-3-one

89

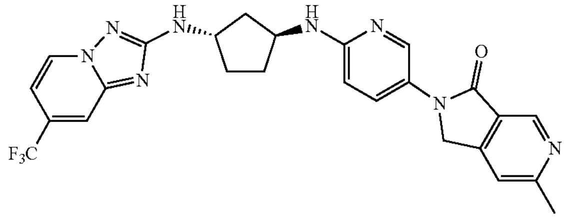

By reference to the synthesis method of reference example 3, 6-methyl-2-(6-(((1S,3S)-3-((7-(trifluoromethyl)-[1,2,4]triazolo[1,5-a]pyridin-2-yl)amino)cyclopentyl)amino)pyridin-3-yl)-1,2-dihydro-3H-pyrrolo[3,4-c]pyridin-3-one 89 was synthesized. MS m/z (ESI): 509.2 [M+H]$^+$.

$^1$H NMR (400 MHz, DMSO-$d_6$) δ 8.82 (d, 2H), 8.31 (d, 1H), 7.83 (dd, 2H), 7.55 (s, 1H), 7.14 (dd, 1H), 7.02 (d, 1H), 6.66 (d, 1H), 6.54 (d, 1H), 4.94 (s, 2H), 4.38-4.15 (m, 2H), 2.61 (s, 3H), 2.22-2.11 (m, 2H), 2.01-1.85 (m, 2H), 1.63-1.47 (m, 2H).

Example 90

6-methyl-1-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-4-carbonitrile

90

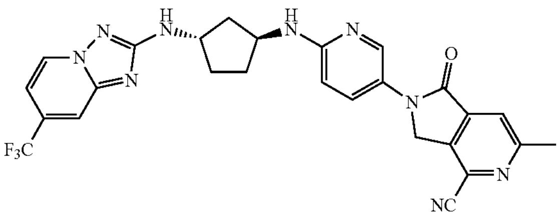

By reference to the synthesis method of reference example 3, 6-methyl-1-carbonyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridine-4-carbonitrile 90 was synthesized. MS m/z (ESI): 534.2 [M+H]$^+$.

$^1$H NMR (400 MHz, DMSO-$d_6$) δ 8.82 (d, 1H), 8.40 (d, 1H), 7.97 (s, 1H), 7.90-7.82 (m, 2H), 7.18-7.11 (m, 1H), 7.02 (d, 1H), 6.77 (d, 1H), 6.56 (d, 1H), 5.19 (s, 2H), 4.37-4.27 (m, 1H), 4.26-4.14 (m, 1H), 2.67 (s, 3H), 2.23-2.09 (m, 2H), 2.05-1.82 (m, 3H), 1.67-1.42 (m, 2H).

Example 91

2-methyl-6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one

91

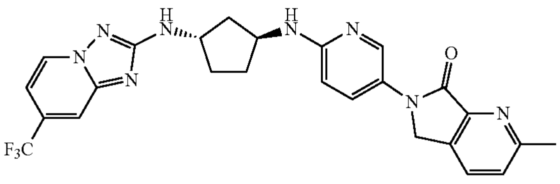

By reference to the synthesis method of reference example 3, 2-methyl-6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one 91 was synthesized. MS m/z (ESI): 509.2 [M+H]$^+$.

$^1$H NMR (400 MHz, DMSO-$d_6$) δ 8.82 (d, 1H), 8.34 (d, 1H), 7.98 (d, 1H), 7.87 (dd, 1H), 7.85 (s, 1H), 7.48 (d, 1H), 7.15 (d, 1H), 7.03 (d, 1H), 6.68 (d, 1H), 6.56 (d, 1H), 4.87 (s, 2H), 4.33-4.28 (m, 1H), 4.23-4.18 (m, 1H), 2.60 (s, 3H), 2.19-2.12 (m, 2H), 2.01-1.89 (m, 2H), 1.61-1.48 (m, 2H).

Example 112

6-(5-fluoro-6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one

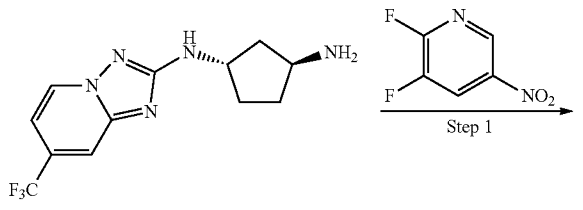

Reference example 3e

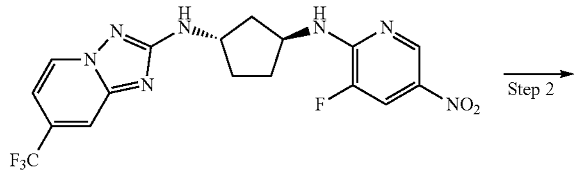

112a

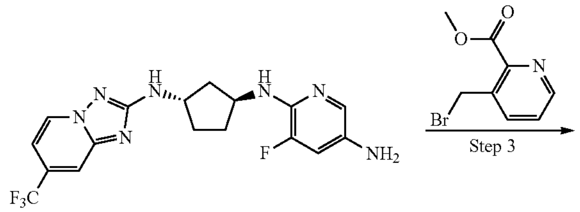

112b

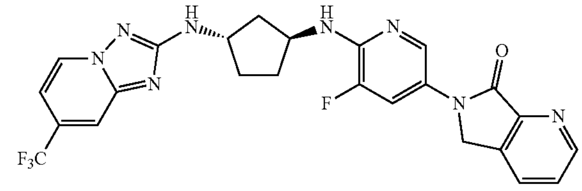

112

Step 1: Reference example 3e (150 mg, 0.53 mmol), 2,3-difluoro-5-nitro-pyridine (93 mg, 0.58 mmol), and cesium carbonate (428 mg, 1.31 mmol) were dissolved in N,N-dimethylformamide (3 mL), heated to 80° C. and stirred for 16 hours. The reaction liquid was filtered, and the filtrate was concentrated. The residue was purified by silica gel column chromatography (elution system B) to obtain (1S,3S)-N1-(3-fluoro-5-nitro-2-pyridinyl)-N3-[7-(trifluoromethyl)-[1,2,4]triazolo[1,5-a]pyridin-2-yl]cyclopentane-1,3-diamine 112a (180 mg), yield: 80.5%. MS m/z (ESI): 426.1 $[M+H]^+$.

Step 2: In a hydrogen atmosphere, 112a (158 mg, 0.37 mmol) and palladium on carbon (40 mg, 0.037 mmol, content: 10%) were dissolved in methanol (10 mL), and the reaction was stirred at room temperature for 2 hours. The reaction liquid was filtered, and the filtrate was concentrated to obtain 3-fluoro-N2-[(1S,3S)-3-[[7-(trifluoromethyl)-[1,2,4]triazolo[1,5-a]pyridin-2-yl]amino]cyclopentyl]pyridine-2,5-diamine 112b (131 mg), yield: 88.5%. MS m/z (ESI): 396.1 $[M+H]^+$.

Step 3: 112b (131 mg, 0.33 mmol), methyl 3-(bromomethyl)pyridine-2-carboxylate (85 mg, 0.28 mmol) and N,N-diisopropylethylamine (107 mg, 0.83 mmol) were dissolved in a mixed solvent of n-butanol (6 mL) and N,N-dimethylformamide (0.5 mL), heated to 40° C. and stirred for 11 hours, further heated to 110° C. and stirred for 5 hours. The reaction liquid was filtered, the filtrate was concentrated, and the residue was purified by preparative HPLC (formic acid system) to obtain 112 (100.4 mg), yield: 70.7%. MS m/z (ESI): 513.2 $[M+H]^+$.

$^1$H NMR (400 MHz, DMSO-$d_6$) δ 8.82 (d, 1H), 8.76 (dd, 1H), 8.24 (d, 1H), 8.12 (dd, 1H), 8.03 (dd, 1H), 7.85 (s, 1H), 7.63 (dd, 1H), 7.14 (dd, 1H), 7.01 (d, 1H), 6.66 (d, 1H), 4.96 (s, 2H), 4.59-4.15 (m, 2H), 2.24-2.10 (m, 2H), 2.04-1.93 (m, 2H), 1.68-1.51 (m, 2H).

Example 114

6-(6-(((1S,3S)-3-((7-(trifluoromethyl)-[1, 2, 4]triazolo[1,5-a]pyridin-2-yl)amino)cyclopentylamino)pyridin-3-yl)-6,7-dihydro-5H-pyrrolo[3,4-b]pyridin-5-one-7,7-d2

114

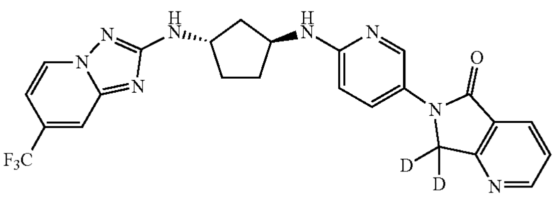

Example 12 (30 mg, 0.061 mmol) was dissolved in tetrahydrofuran (2 mL) and deuterium oxide (1 mL), a solution of 40% deuterated sodium oxide in deuterium oxide (62 mg, 0.607 mmol) was added, and the mixture was heated to 35° C. and stirred for 16 hours under nitrogen protection. The reaction liquid was cooled to room temperature and poured into 30 mL of water, and the mixture was extracted with ethyl acetate (30 mL×2). The organic phases were combined, washed successively with water (30 mL) and a saturated sodium chloride solution (30 mL), dried, filtered, and concentrated. The residue was purified by C18 chromatography (elution system C) to obtain 6-(6-(((1S,3S)-3-((7-(trifluoromethyl)-[1, 2, 4]triazolo[1,5-a]pyridin-2-yl)amino)cyclopentylamino)pyridin-3-yl)-6,7-dihydro-5H-pyrrolo[3,4-b]pyridin-5-one-7,7-d2 114 (8.7 mg), yield: 28.9%.

MS m/z (ESI): 497.1 $[M+H]^+$.

$^1$H NMR (400 MHz, DMSO-$d_6$) δ 8.83-8.79 (m, 2H), 8.37 (d, 1H), 8.14 (d, 1H), 7.90-7.84 (m, 2H), 7.56 (dd, 1H), 7.15 (d, 1H), 7.03 (d, 1H), 6.68 (d, 1H), 6.55 (d, 1H), 4.33-4.28 (m, 1H), 4.23-4.18 (m, 1H), 2.20-2.13 (m, 2H), 2.00-1.89 (m, 2H), 1.60-1.50 (m, 2H).

Example 164

6-(5-fluoro-6-(((1S, 3S)-3-((7-fluoro-[1,2,4]triazolo [1,5-a]pyridin-2-yl)amino)cyclopentyl)aminopyridin-3-yl)-5,6-dihydro-7H-pyrrolo[3,4-b]pyridin-7-one

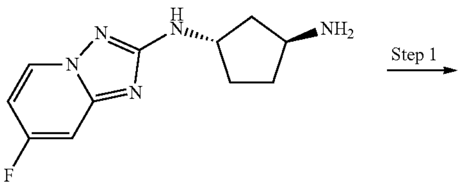

Reference example 2c

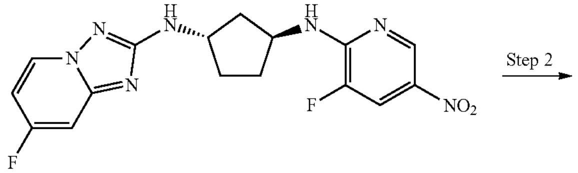

164a

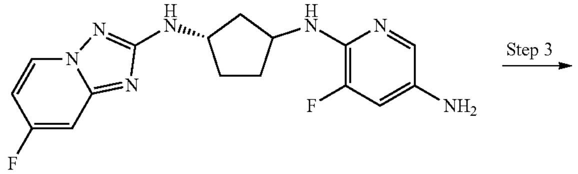

164b

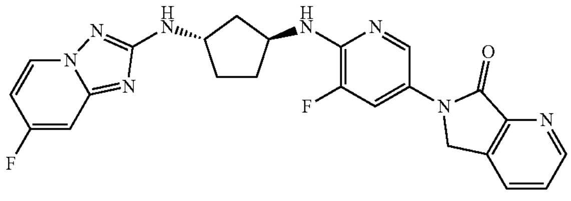

164

Step 1: Under nitrogen protection, reference example 2c (150 mg, 0.6 mmol), 2,3-difluoro-5-nitropyridine (123 mg, 0.7 mmol) and N,N-diisopropylethylamine (233 mg, 1.8 mmol) were dissolved in N,N-dimethylformamide (5 mL), and the reaction was stirred at 25° C. for 16 hours. The reaction was filtered, the filtrate was concentrated, and the residue was separated by silica gel column chromatography (elution system A) to obtain (1S,3S)-N1-(3-fluoro-5-nitropyridin-2-yl))-$N^3$-(7-fluoro-[1,2,4]triazolo[1,5-a]pyridin-2-yl)cyclopentane-1,3-diamine 164a (200 mg), yield: 87%. MS m/z (ESI): 376.2 $[M+H]^+$.

Step 2: In a hydrogen atmosphere, 164a (200 mg, 0.5 mmol) and palladium on carbon (70 mg, content: 10%) were dissolved in methanol (5 mL), and the reaction was heated to 50° C. and stirred for 2 hours. The reaction was filtered, and the filtrate was concentrated to obtain 3-fluoro-$N^2$-((1S, 3S)-3-((7-fluoro-[1,2,4]triazolo[1,5-a]pyridin-2-yl)amino) cyclopentyl)pyridine-2,5-diamine 164b (170 mg), yield: 97%. MS m/z (ESI): 346.2 $[M+H]^+$.

Step 3: Under nitrogen protection, 164b (90 mg, 0.25 mmol) and N,N-diisopropylethylamine (130 mg, 1 mmol) were dissolved in a mixed solution of N,N-dimethylformamide (2 mL) and tert-butanol (5 mL), and methyl 3-(bromomethyl)picolinate (50 mg, 0.23 mmol) was added under stirring. The reaction was stirred at 25° C. for 16 hours, then heated to 85° C. and stirred for 16 hours. The reaction was filtered, the filtrate was concentrated, and the residue was separated by preparative HPLC (formic acid system) to obtain 6-(5-fluoro-6-(((1S,3S)-3-((7-fluoro-[1,2,4]triazolo [1,5-a]pyridin-2-yl)amino)cyclopentyl)aminopyridin-3-yl)-5,6-dihydro-7H-pyrrolo[3,4-b]pyridin-7-one 164 (20 mg), yield: 17%. MS m/z (ESI): 463.2 $[M+H]^+$.

$^1H$ NMR (400 MHz, DMSO-$d_6$) δ 8.76 (dd, 1H), 8.65 (dd, 1H), 8.24 (d, 1H), 8.12 (dd, 1H), 8.03 (dd, 1H), 7.63 (dd, 1H), 7.27 (dd, 1H), 6.86 (td, 1H), 6.74 (d, 1H), 6.67 (d, 1H), 4.96 (s, 2H), 4.49 (q, 1H), 4.16 (q, 1H), 2.20-2.10 (m, 2H), 1.98 (dt, 2H), 1.63-1.52 (m, 2H).

Example 186

5'-fluoro-6'-(((1S,3S)-3-((7-fluoro-[1,2,4]triazolo[1, 5-a]pyridin-2-yl)amino)cyclopentyl)amino)-2H-[1, 3'-bipyridine]-2-one

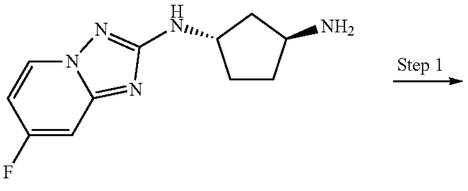

Reference example 2c

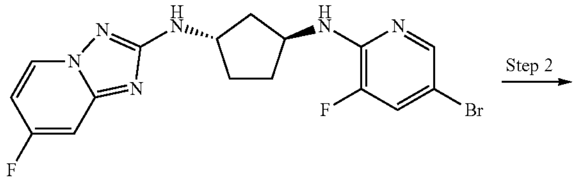

186a

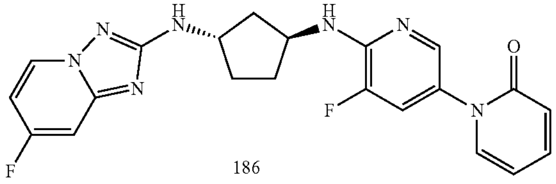

186

Step 1: Intermediate reference example 2c (60 mg, 0.26 mmol), 5-bromo-2,3-difluoropyridine (99 mg, 0.51 mmol) and N,N-diisopropylethylamine (132 mg, 1.02 mmol) were dissolved in dimethyl sulfoxide (2 mL), and the reaction was heated to 100° C. and stirred for 16 hours. A saturated sodium chloride solution was added to the reaction liquid, and the aqueous phase was extracted with ethyl acetate (20 mL×2). The organic phases were combined, dried, and concentrated, and the residue was separated by silica gel column chromatography to obtain (1S,3S)-N1-(5-bromo-3-fluoropyridin-2-yl)-$N^3$-(7-fluoro-[1,2,4]triazolo[1,5-a]pyridin-2-yl)cyclopentane-1,3-diamine 186a (75 mg), yield: 71.86%. MS m/z (ESI): 409.1 $[M+H]^+$.

Step 2: Under nitrogen protection, 186a (75 mg, 0.18 mmol), 2-pyridone (52 mg, 0.55 mmol), cuprous iodide (35 mg, 0.18 mmol), trans-(1R,2R)—N,N'-dimethyl 1,2-cyclohexanediamine (26 mg, 0.18 mmol), and cesium carbonate (119 mg, 0.37 mmol) were dissolved in 1,4-dioxane (1.5 mL), and the reaction was heated to 120° C. and stirred for 16 hours. A saturated ammonium chloride solution was added to the reaction liquid, and the aqueous phase was extracted with ethyl acetate (25 mL×2). The organic phases were combined, dried, and concentrated, and the residue was subjected to reversed-phase HPLC (formic acid system) to prepare 5'-fluoro-6'-(((1S,3S)-3-((7-fluoro-[1,2,4]triazolo[1,5-a]pyridin-2-yl)amino)cyclopentyl)amino)-2H-[1,3'-bipyridine]-2-one 186 (27.9 mg), yield: 35.95%. MS m/z (ESI): 424.2 [M+H]$^+$.

$^1$H NMR (400 MHz, DMSO-d$_6$) δ 8.71-8.61 (m, 1H), 7.84 (d, 1H), 7.68-7.62 (m, 1H), 7.58-7.53 (m, 1H), 7.52-7.46 (m, 1H), 7.30-7.24 (m, 1H), 6.94 (d, 1H), 6.90-6.82 (m, 1H), 6.75 (d, 1H), 6.46 (d, 1H), 6.32-6.25 (m, 1H), 4.62-4.42 (m, 1H), 4.24-4.09 (m, 1H), 2.22-2.07 (m, 2H), 2.05-1.88 (m, 2H), 1.69-1.48 (m, 2H).

Example 418

6'-(((1S,3S)-3-((6-(3-hydroxylazetidin-1-yl)pyrrolo[2,1-f][1,2,4]triazin-2-yl)amino)cyclopentyl)amino)-2H-[1,3'-bipyridine]-2-one

418

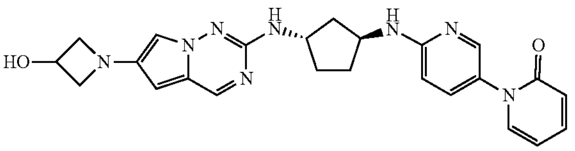

Example 418 could also be prepared by reference to the following method.

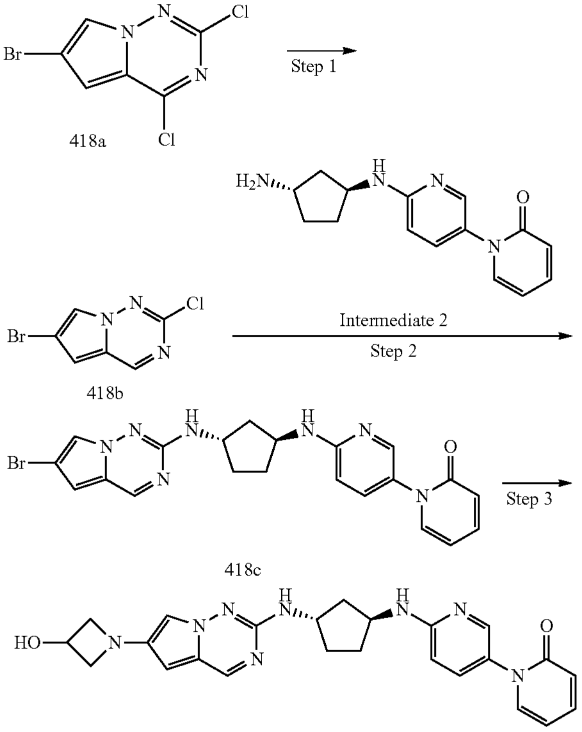

418a 418b 418c 418

Step 1: At room temperature, 6-bromo-2,4-dichloropyrrolo[2,1-f][1,2,4]triazine 418a (500 mg, 1.87 mmol) were dissolved in tetrahydrofuran (15 mL), and sodium borohydride (141.7 mg, 3.75 mmol) was added under stirring. Then, isopropanol (0.5 mL) was added and the mixture was stirred for 1 hour. The reaction liquid was filtered, and the filtrate was concentrated, and then dissolved in dichloromethane (20 mL). 2,3-dichloro-5,6-dicyanobenzoquinone (637.9 mg, 2.81 mmol) was added, and the reaction was stirred at room temperature for 1 hour. Dichloromethane (30 mL) was added to the reaction liquid, and the organic phase was washed with water (10 mL×3) and a saturated sodium chloride solution (10 mL), dried, and concentrated. The residue was separated by silica gel column chromatography (eluent system B) to obtain 6-bromo-2-chloropyrrolo[2,1-f][1,2,4]triazine 418b (320 mg), yield: 73.5%. MS m/z (ESI): 232.0 [M+H]$^+$.

Step 2: 418b (170 mg, 0.731 mmol), intermediate 2 (200 mg, 0.731 mmol) and potassium carbonate (202 mg, 1.46 mmol) were dissolved in N,N-dimethylformamide (5 mL), and the reaction was heated to 100° C. and stirred for 3 hours. The reaction liquid was filtered, and the residue was separated by silica gel column chromatography (eluent system B) to obtain 6'-(((1S,3S)-3-((6-bromopyrrolo[2,1-f][1,2,4]triazin-2-ylamino)cyclopentyl)amino)-2H-[1,3'-bipyridine]-2-one 418c (300 mg), yield: 88.0%. MS m/z (ESI): 466.1 [M+H]$^+$.

Step 3: Under nitrogen protection, 418c (100 mg, 0.214 mmol), 3-hydroxyazetidine hydrochloride (117.5 mg, 1.07 mmol), (2-di-tert-butylphosphino-2',4',6'-triisopropyl-1,1'-biphenyl)(2'-amino-1,1'-biphenyl-2-yl)palladium(II) methanesulfonate (34.1 mg, 0.043 mmol) and cesium carbonate (698.7 mg, 2.14 mmol) were dissolved in 1,4-dioxane (5 mL), heated to 100° C. and stirred for 16 hours. The reaction liquid was filtered, and purified by preparative HPLC (ammonium bicarbonate system) to obtain the target product 6'-(((1S,3S)-3-((6-(3-hydroxylazetidin-1-yl)pyrrolo[2,1-f][1,2,4]triazin-2-yl)amino)cyclopentyl)amino)-2H-[1,3'-bipyridine]-2-one 418 (15 mg), yield: 15.3%. MS m/z (ESI): 459.2 [M+H]$^+$.

$^1$H NMR (400 MHz, DMSO-d$_6$) δ 8.46 (s, 1H), 7.92 (d, 1H), 7.60 (dd, 1H), 7.48 (td, 1H), 7.40 (dd, 1H), 7.18 (d, 1H), 6.91 (d, 1H), 6.61 (d, 1H), 6.53 (d, 1H), 6.44 (d, 1H), 6.27 (t, 1H), 5.86 (d, 1H), 5.55 (d, 1H), 4.51 (m, 1H), 4.31 (m, 1H), 4.15 (m, 1H), 3.98 (t, 2H), 3.42 (t, 2H), 2.15-2.12 (m, 2H), 2.03-1.82 (m, 2H), 1.57-1.46 (m, 2H).

Example 422

6'-(((1S,3S)-3-((6-(3-hydroxy-3-methylazetidin-1-yl)pyrrolo[2,1-f][1,2,4]triazin-2-yl)amino)cyclopentyl)amino)-2H-[1,3'-bipyridine]-2-one

422

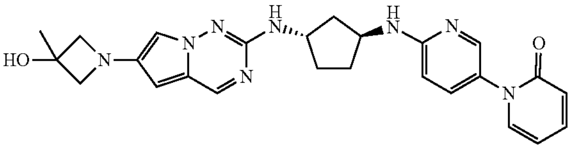

By reference to the synthesis method of example 418, 6'-(((1S,3S)-3-((6-(3-hydroxy-3-methylazetidin-1-yl)pyrrolo[2,1-f][1,2,4]triazin-2-yl)amino)cyclopentyl)amino)-2H-[1,3'-bipyridine]-2-one 422 was synthesized. MS m/z (ESI): 473.2 $[M+H]^+$.
$^1H$ NMR (400 MHz, DMSO-$d_6$) δ 8.46 (s, 1H), 7.92 (d, 1H), 7.60 (dd, 1H), 7.48 (td, 1H), 7.40 (dd, 1H), 7.19 (d, 1H), 6.91 (d, 1H), 6.61 (d, 1H), 6.53 (d, 1H), 6.44 (d, 1H), 6.27 (t, 1H), 5.86 (d, 1H), 5.45 (d, 1H), 4.30 (q, 1H), 4.15 (q, 1H), 3.66 (d, 2H), 3.52 (d, 2H), 2.15-2.12 (m, 2H), 2.03-1.82 (m, 2H), 1.57-1.45 (m, 2H), 1.24 (s, 3H).
For the synthesis method of the example, reference can be made to the above examples.
| Examples | Structure | MS m/z (ESI) |
|---|---|---|
| 1 | 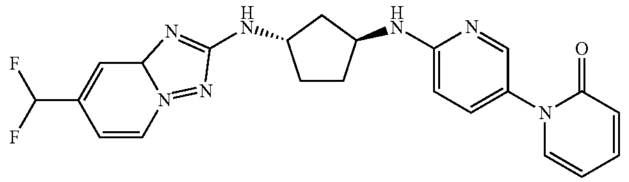 | 438.2 $[M + H]^+$ |
| 2 | 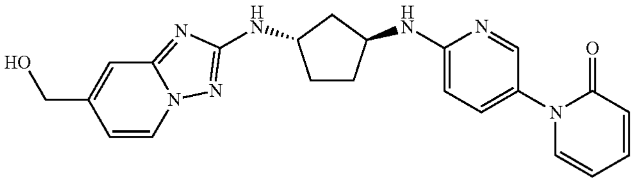 [SMILES: O=c1ccccn1-c1ccc(N[C@H]2CC[C@H](Nc3nc4cc(CO)ccn4n3)C2)nc1] | 418.2 $[M + H^+$ |
| 3 | 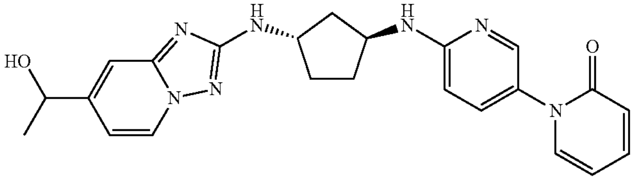 [SMILES: CC(O)c1ccn2nc(N[C@H]3CC[C@H](Nc4ccc(-n5ccccc5=O)cn4)C3)nc2c1] | 432.2 $[M + H]^+$ |
| 6 | 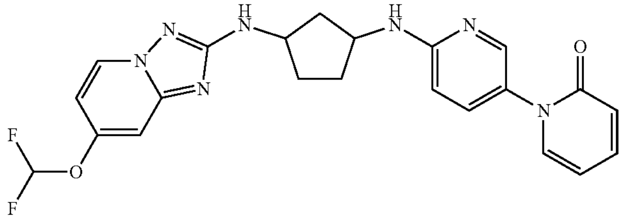 [SMILES: O=c1ccccn1-c1ccc(NC2CCC(Nc3nc4cc(OC(F)F)ccn4n3)C2)nc1] | 454.2 $[M + H]^+$ |
| 7 | 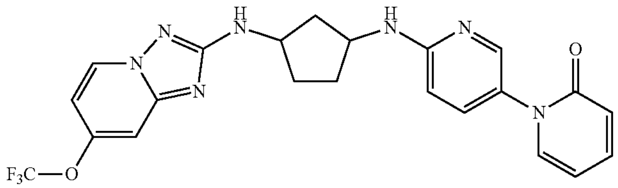 [SMILES: O=c1ccccn1-c1ccc(NC2CCC(Nc3nc4cc(OC(F)(F)F)ccn4n3)C2)nc1] | 472.2 $[M + H]^+$ |
| 8 | 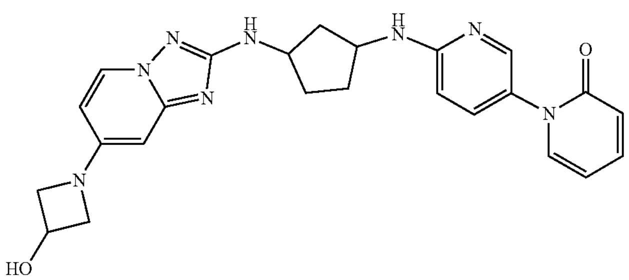 [SMILES: O=c1ccccn1-c1ccc(NC2CCC(Nc3nc4cc(N5CC(O)C5)ccn4n3)C2)nc1] | 459.2 $[M + H]^+$ |

-continued
| Examples | Structure | MS m/z (ESI) |
|---|---|---|
| 9 | 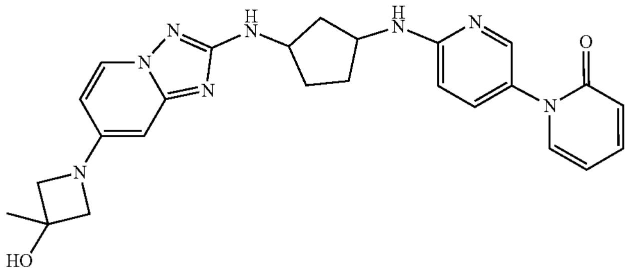 [SMILES: CC1(O)CN(c2ccn3nc(NC4CCC(Nc5ccc(-n6ccccc6=O)cn5)C4)nc3c2)C1] | 473.2 [M + H] + |
| 10 | 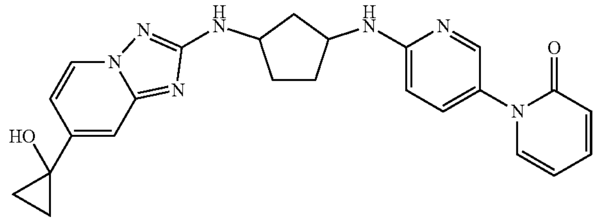 [SMILES: O=c1ccccn1-c1ccc(NC2CCC(Nc3nc4cc(C5(O)CC5)ccn4n3)C2)nc1] | 444.2 [M + H] + |
| 11 | 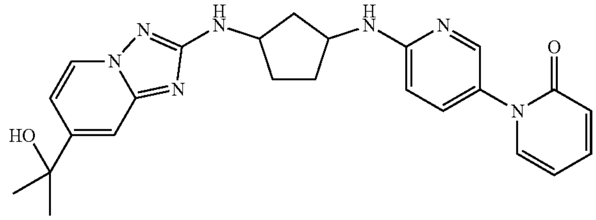 [SMILES: CC(C)(O)c1ccn2nc(NC3CCC(Nc4ccc(-n5ccccc5=O)cn4)C3)nc2c1] | 446.2 [M + H] + |
| 12 | 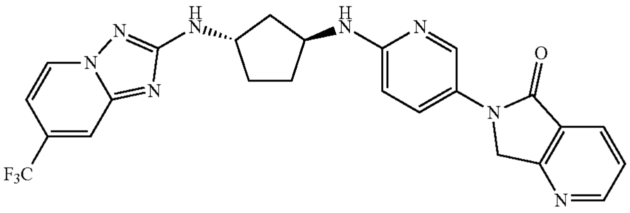 [SMILES: O=C1c2cccnc2CN1c1ccc(N[C@H]2CC[C@H](Nc3nc4cc(C(F)(F)F)ccn4n3)C2)nc1] | 495.2 [M + H] + |
| 13 | 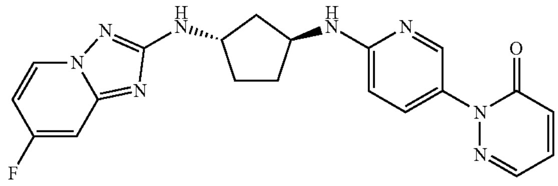 [SMILES: O=c1cccnn1-c1ccc(N[C@H]2CC[C@H](Nc3nc4cc(F)ccn4n3)C2)nc1] | 407.2 [M + H] + |
| 14 | 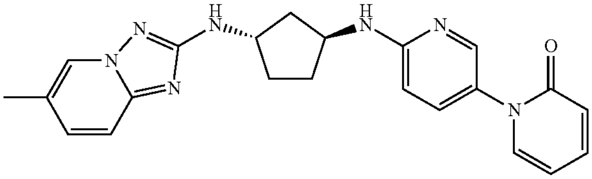 [SMILES: Cc1ccc2nc(N[C@H]3CC[C@H](Nc4ccc(-n5ccccc5=O)cn4)C3)nn2c1] | 402.2 [M + H]+ |
| 15 | 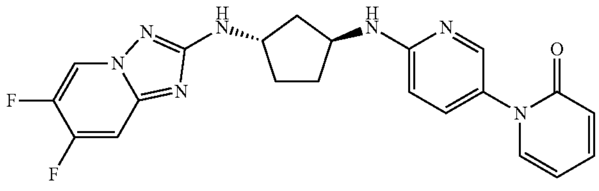 [SMILES: O=c1ccccn1-c1ccc(N[C@H]2CC[C@H](Nc3nc4cc(F)c(F)cn4n3)C2)nc1] | 424.2 [M + H]+ |

-continued
| Examples | Structure | MS m/z (ESI) |
| --- | --- | --- |
| 16 | 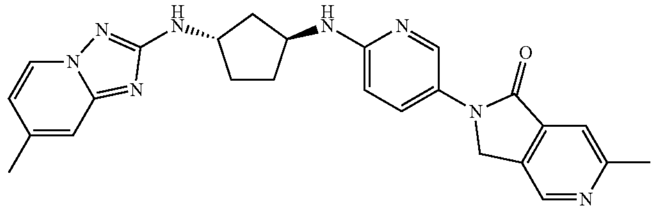 [SMILES: Cc1ccn2nc(N[C@H]3CC[C@H](Nc4ccc(N5Cc6cnc(C)cc6C5=O)cn4)C3)nc2c1] | 455.2 [M + H]+ |
| 17 | 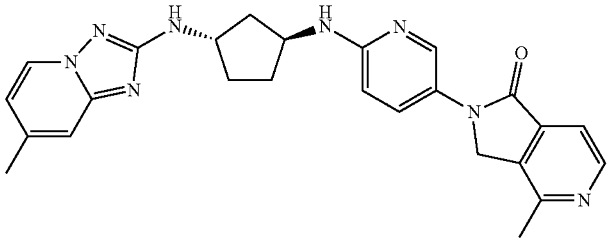 [SMILES: Cc1ccn2nc(N[C@H]3CC[C@H](Nc4ccc(N5Cc6c(ccnc6C)C5=O)cn4)C3)nc2c1] | 455.2 [M + H]+ |
| 19 | 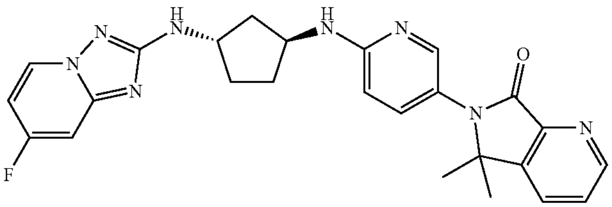 [SMILES: CC1(C)c2cccnc2C(=O)N1c1ccc(N[C@H]2CC[C@H](Nc3nc4cc(F)ccn4n3)C2)nc1] | 473.2 [M + H]+ |
| 20 | 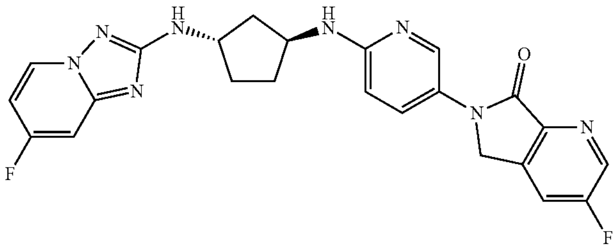 [SMILES: O=C1c2ncc(F)cc2CN1c1ccc(N[C@H]2CC[C@H](Nc3nc4cc(F)ccn4n3)C2)nc1] | 463.2 [M + H]+ |
| 24 | 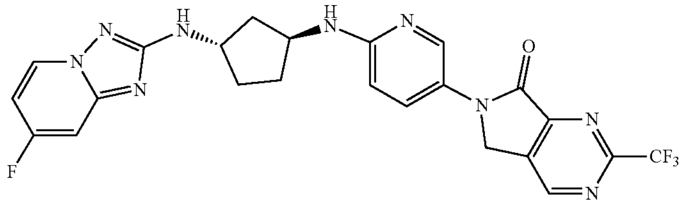 [SMILES: O=C1c2nc(C(F)(F)F)ncc2CN1c1ccc(N[C@H]2CC[C@H](Nc3nc4cc(F)ccn4n3)C2)nc1] | 514.2 [M + H]+ |
| 28 | 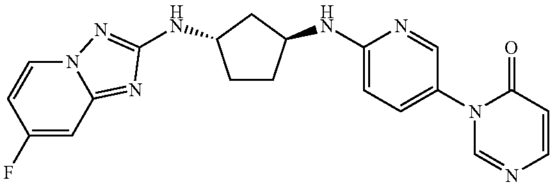 [SMILES: O=c1ccncn1-c1ccc(N[C@H]2CC[C@H](Nc3nc4cc(F)ccn4n3)C2)nc1] | 407.2 [M + H]+ |
| 29 | 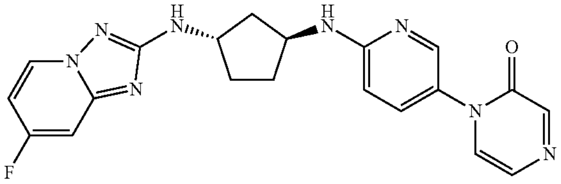 [SMILES: O=c1cnccn1-c1ccc(N[C@H]2CC[C@H](Nc3nc4cc(F)ccn4n3)C2)nc1] | 407.2 [M + H]+ |

-continued
| Examples | Structure | MS m/z (ESI) |
|---|---|---|
| 30 | 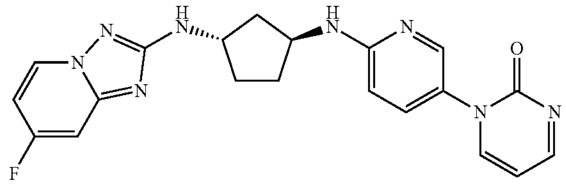 | 407.2 [M + H]+ |
| 31 | 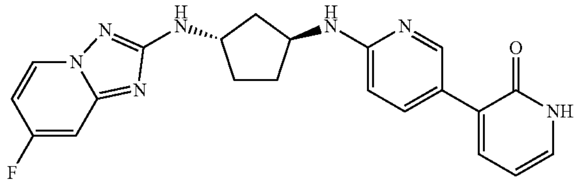 [SMILES: O=c1[nH]cccc1-c1ccc(N[C@H]2CC[C@H](Nc3nc4cc(F)ccn4n3)C2)nc1] | 406.2 [M + H]+ |
| 33 | 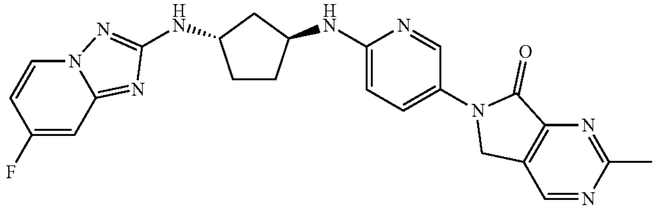 [SMILES: Cc1ncc2c(n1)C(=O)N(c1ccc(N[C@H]3CC[C@H](Nc4nc5cc(F)ccn5n4)C3)nc1)C2] | 460.2 [M + H]+ |
| 34 | 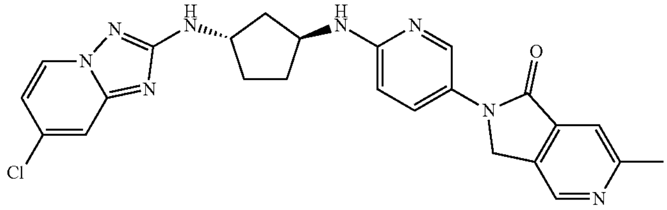 [SMILES: Cc1cc2c(cn1)CN(c1ccc(N[C@H]3CC[C@H](Nc4nc5cc(Cl)ccn5n4)C3)nc1)C2=O] | 475.2 [M + H]+ |
| 35 | 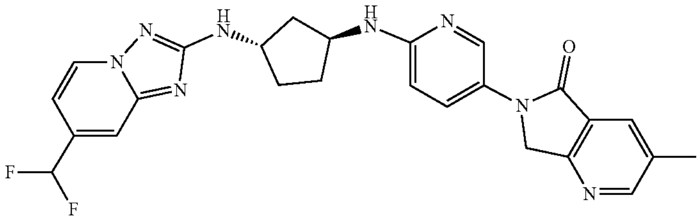 [SMILES: Cc1cnc2c(c1)C(=O)N(c1ccc(N[C@H]3CC[C@H](Nc4nc5cc(C(F)F)ccn5n4)C3)nc1)C2] | 491.2 [M + H]+ |
| 36 | 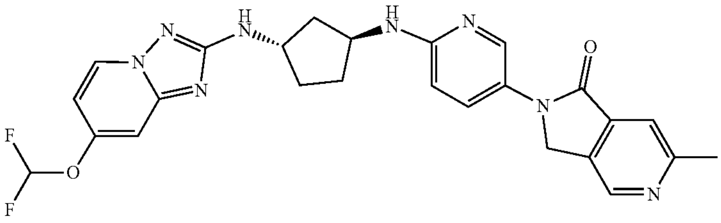 [SMILES: Cc1cc2c(cn1)CN(c1ccc(N[C@H]3CC[C@H](Nc4nc5cc(OC(F)F)ccn5n4)C3)nc1)C2=O] | 507.2 [M + H]+ |
| 37 | 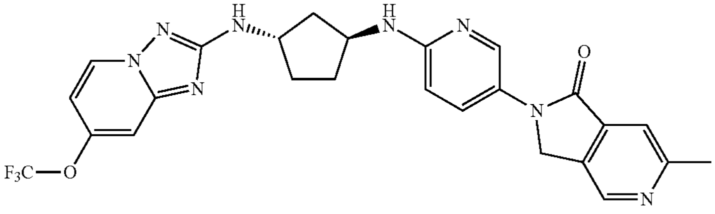 [SMILES: Cc1cc2c(cn1)CN(c1ccc(N[C@H]3CC[C@H](Nc4nc5cc(OC(F)(F)F)ccn5n4)C3)nc1)C2=O] | 525.2 [M + H]+ |

-continued
| Examples | Structure | MS m/z (ESI) |
|---|---|---|
| 38 | 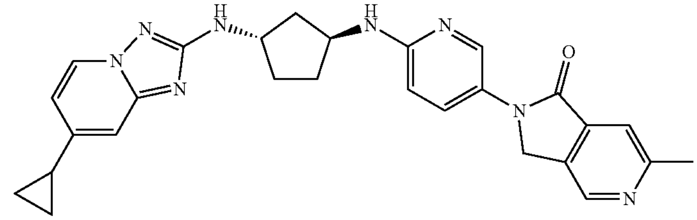 [SMILES: Cc1cc2c(cn1)CN(c1ccc(N[C@H]3CC[C@H](Nc4nc5cc(C6CC6)ccn5n4)C3)nc1)C2=O] | 481.2 [M + H]+ |
| 39 | 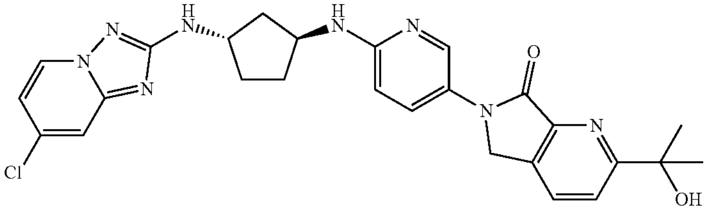 [SMILES: CC(C)(O)c1ccc2c(n1)C(=O)N(c1ccc(N[C@H]3CC[C@H](Nc4nc5cc(Cl)ccn5n4)C3)nc1)C2] | 519.2 [M + H]+ |
| 40 | 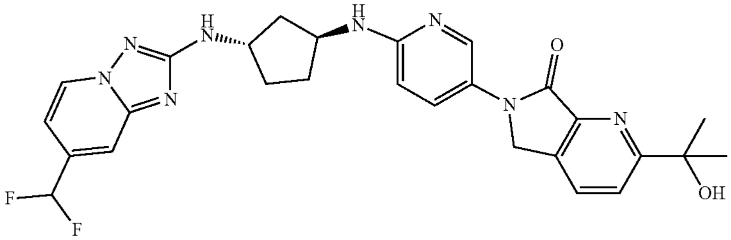 [SMILES: CC(C)(O)c1ccc2c(n1)C(=O)N(c1ccc(N[C@H]3CC[C@H](Nc4nc5cc(C(F)F)ccn5n4)C3)nc1)C2] | 535.2 [M + H]+ |
| 41 | 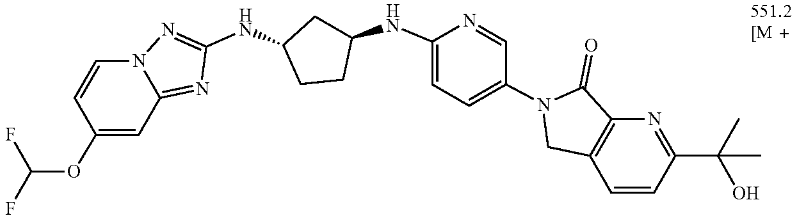 | 551.2 [M + H]+ |
| 42 | 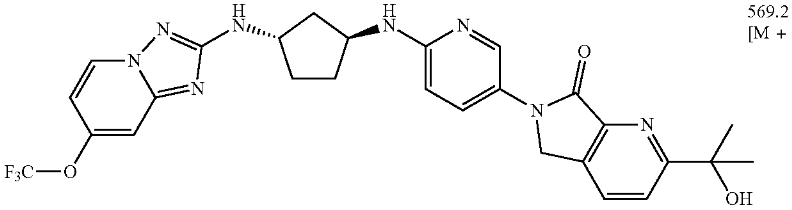 | 569.2 [M + H]+ |
| 43 | 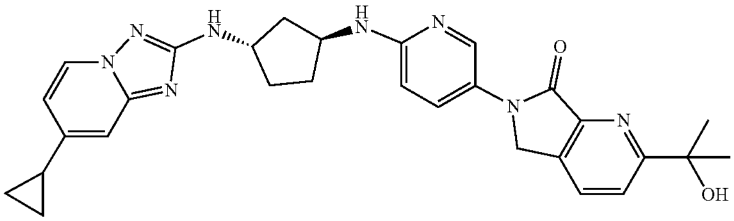 [SMILES: CC(C)(O)c1ccc2c(n1)C(=O)N(c1ccc(N[C@H]3CC[C@H](Nc4nc5cc(C6CC6)ccn5n4)C3)nc1)C2] | 525.3 [M + H]+ |
| 44 | 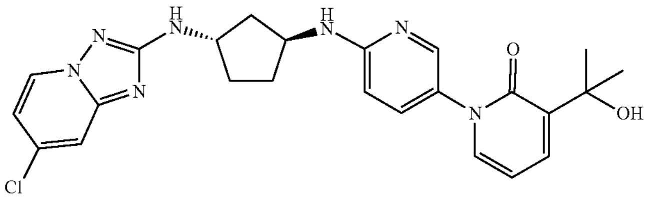 [SMILES: CC(C)(O)c1cccn(-c2ccc(N[C@H]3CC[C@H](Nc4nc5cc(Cl)ccn5n4)C3)nc2)c1=O] | 480.2 [M + H]+ |

-continued
| Examples | Structure | MS m/z (ESI) |
|---|---|---|
| 45 | 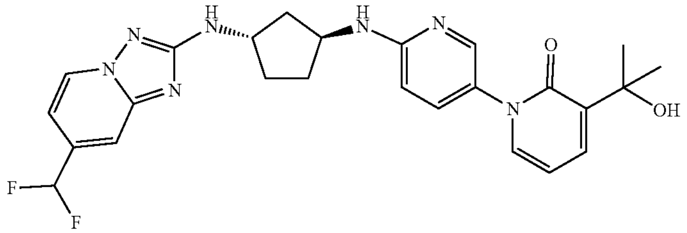 [SMILES: CC(C)(O)c1cccn(-c2ccc(N[C@H]3CC[C@H](Nc4nc5cc(C(F)F)ccn5n4)C3)nc2)c1=O] | 496.2 [M + H]+ |
| 46 | 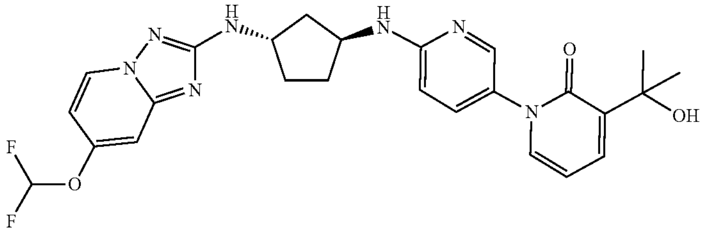 [SMILES: CC(C)(O)c1cccn(-c2ccc(N[C@H]3CC[C@H](Nc4nc5cc(OC(F)F)ccn5n4)C3)nc2)c1=O] | 512.2 [M + H]+ |
| 47 | 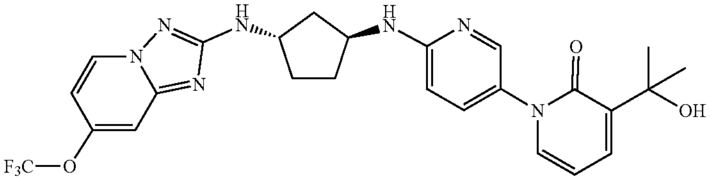 [SMILES: CC(C)(O)c1cccn(-c2ccc(N[C@H]3CC[C@H](Nc4nc5cc(OC(F)(F)F)ccn5n4)C3)nc2)c1=O] | 530.2 [M + H]+ |
| 48 | 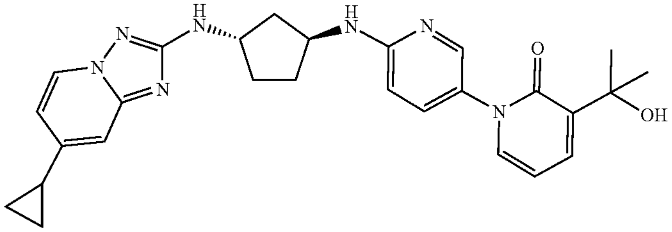 [SMILES: CC(C)(O)c1cccn(-c2ccc(N[C@H]3CC[C@H](Nc4nc5cc(C6CC6)ccn5n4)C3)nc2)c1=O] | 486.3 [M + H]+ |
| 64 | 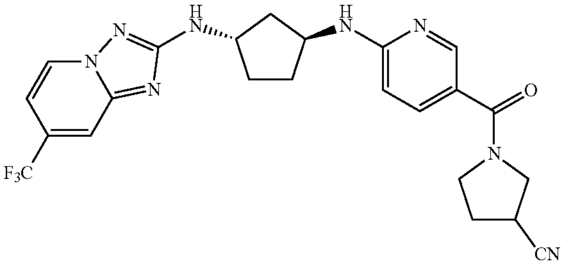 [SMILES: N#CC1CCN(C(=O)c2ccc(N[C@H]3CC[C@H](Nc4nc5cc(C(F)(F)F)ccn5n4)C3)nc2)C1] | 485.2 [M + H]+ |
| 74 | 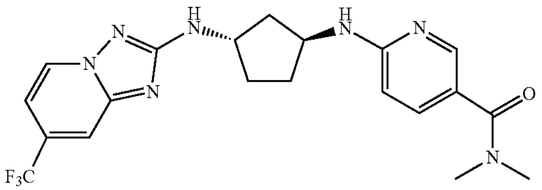 [SMILES: CN(C)C(=O)c1ccc(N[C@H]2CC[C@H](Nc3nc4cc(C(F)(F)F)ccn4n3)C2)nc1] | 434.2 [M + H]+ |

-continued
| Examples | Structure | MS m/z (ESI) |
| --- | --- | --- |
| 79 | 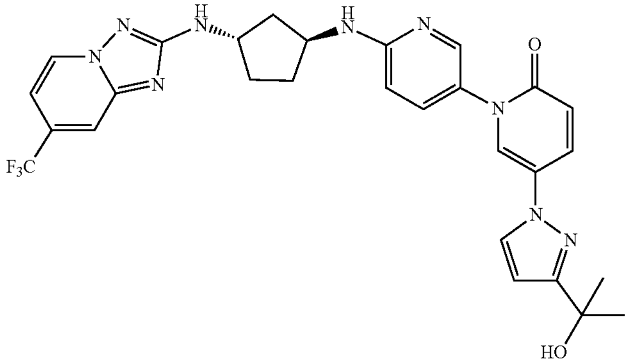 [SMILES: CC(C)(O)c1ccn(-c2ccc(=O)n(-c3ccc(N[C@H]4CC[C@H](Nc5nc6cc(C(F)(F)F)ccn6n5)C4)nc3)c2)n1] | 580.2 [M + H]+ |
| 80 | 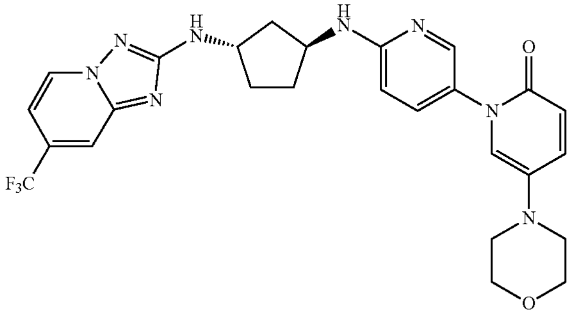 [SMILES: O=c1ccc(N2CCOCC2)cn1-c1ccc(N[C@H]2CC[C@H](Nc3nc4cc(C(F)(F)F)ccn4n3)C2)nc1] | 541.2 [M + H]+ |
| 87 | 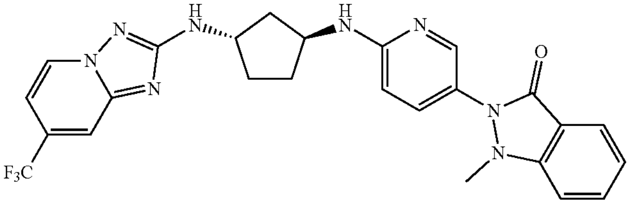 [SMILES: Cn1c2ccccc2c(=O)n1-c1ccc(N[C@H]2CC[C@H](Nc3nc4cc(C(F)(F)F)ccn4n3)C2)nc1] | 509.2 [M + H]+ |
| 92 | 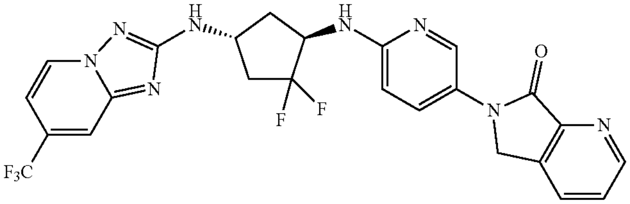 [SMILES: O=C1c2ncccc2CN1c1ccc(N[C@@H]2C[C@@H](Nc3nc4cc(C(F)(F)F)ccn4n3)CC2(F)F)nc1] | 531.2 [M + H]+ |
| 93 | 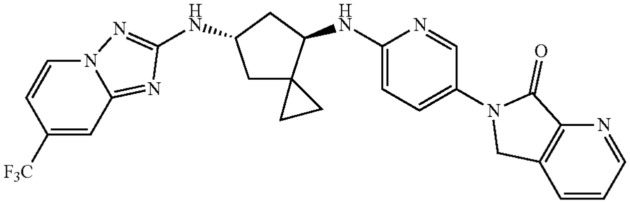 [SMILES: O=C1c2ncccc2CN1c1ccc(N[C@@H]2C[C@@H](Nc3nc4cc(C(F)(F)F)ccn4n3)CC23CC3)nc1] | 521.2 [M + H]+ |
| 94 | 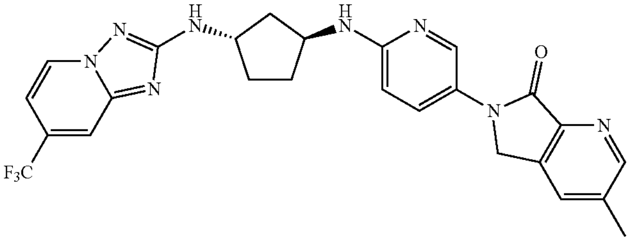 [SMILES: Cc1cnc2c(c1)CN(c1ccc(N[C@H]3CC[C@H](Nc4nc5cc(C(F)(F)F)ccn5n4)C3)nc1)C2=O] | 509.2 [M + H]+ |

-continued

| Examples | Structure | MS m/z (ESI) |
|---|---|---|
| | which was synthesized by reference to the method of reference example 3 | |
| 95 | 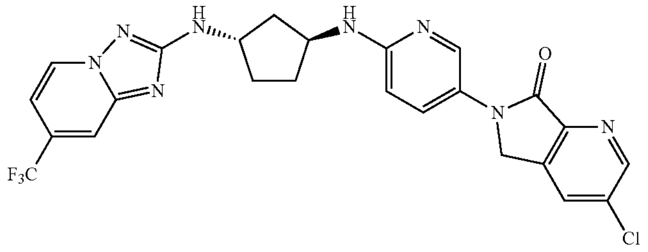 [SMILES: O=C1c2ncc(Cl)cc2CN1c1ccc(N[C@H]2CC[C@H](Nc3nc4cc(C(F)(F)F)ccn4n3)C2)nc1] | 529.2 [M + H]+ |
| | which was synthesized by reference to the method of reference example 3 | |
| 96 | 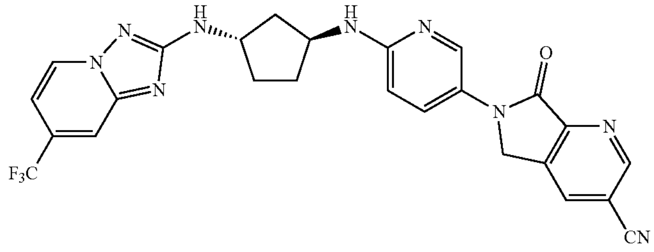 [SMILES: N#Cc1cnc2c(c1)CN(c1ccc(N[C@H]3CC[C@H](Nc4nc5cc(C(F)(F)F)ccn5n4)C3)nc1)C2=O] | 520.2 [M + H]+ |
| | which was synthesized by reference to the method of reference example 3 | |
| 97 | 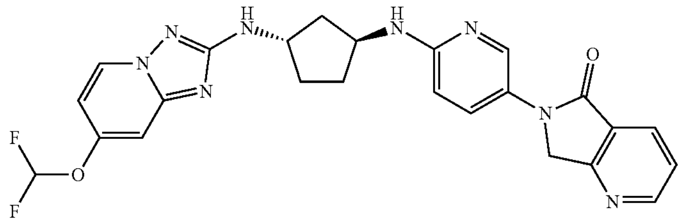 | 493.2 [M + H]+ |
| | which was synthesized by reference to the method of example 56 | |
| 98 | 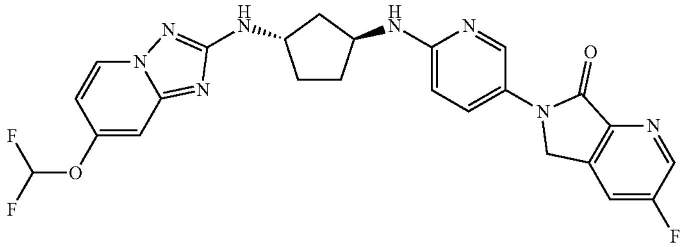 [SMILES: O=C1c2ncc(F)cc2CN1c1ccc(N[C@H]2CC[C@H](Nc3nc4cc(OC(F)F)ccn4n3)C2)nc1] | 511.2 [M + H]+ |
| | which was synthesized by reference to the method of example 56 | |

-continued

| Examples | Structure | MS m/z (ESI) |
|---|---|---|
| 99 | 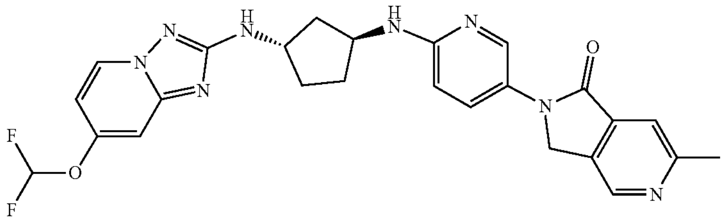 [SMILES: Cc1cc2c(cn1)CN(c1ccc(N[C@H]3CC[C@H](Nc4nc5cc(OC(F)F)ccn5n4)C3)nc1)C2=O] which was synthesized by reference to the method of example 56 | 507.2 $[M + H]^+$ |
| 100 | 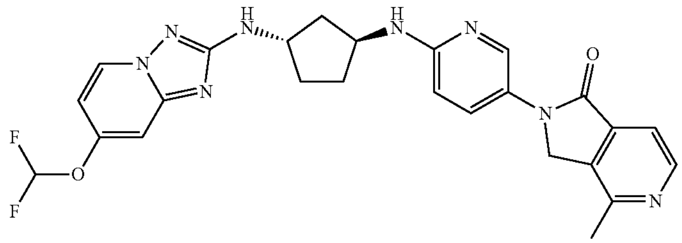 [SMILES: Cc1nccc2c1CN(c1ccc(N[C@H]3CC[C@H](Nc4nc5cc(OC(F)F)ccn5n4)C3)nc1)C2=O] which was synthesized by reference to the method of example 56 | 507.2 $[M + H]^+$ |
| 101 | 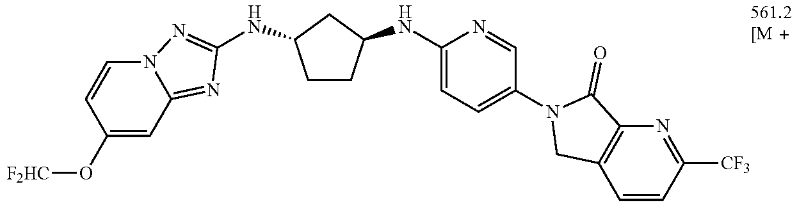 which was synthesized by reference to the method of example 56 | 561.2 $[M + H]^+$ |
| 102 | 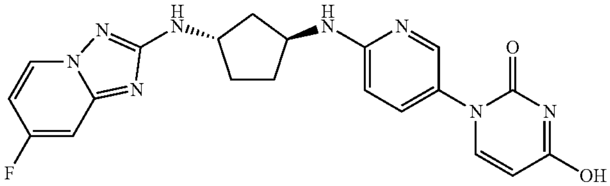 [SMILES: O=c1nc(O)ccn1-c1ccc(N[C@H]2CC[C@H](Nc3nc4cc(F)ccn4n3)C2)nc1] which was synthesized by reference to the method of example 58 | 423.1 $[M + H]^+$ |
| 103 | 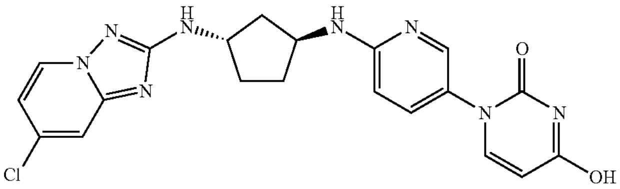 [SMILES: O=c1nc(O)ccn1-c1ccc(N[C@H]2CC[C@H](Nc3nc4cc(Cl)ccn4n3)C2)nc1] which was synthesized by reference to the method of example 58 | 439.1 $[M + H]^+$ |

-continued

| Examples | Structure | MS m/z (ESI) |
|---|---|---|
| 104 | 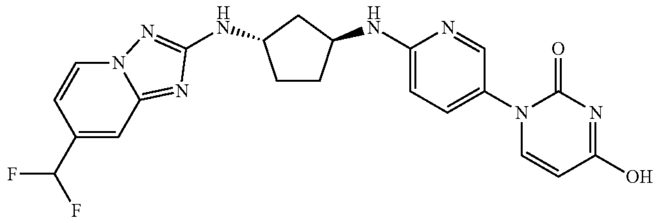 [SMILES: O=c1nc(O)ccn1-c1ccc(N[C@H]2CC[C@H](Nc3nc4cc(C(F)F)ccn4n3)C2)nc1] which was synthesized by reference to the method of example 58 | 455.2 [M + H]+ |
| 105 | 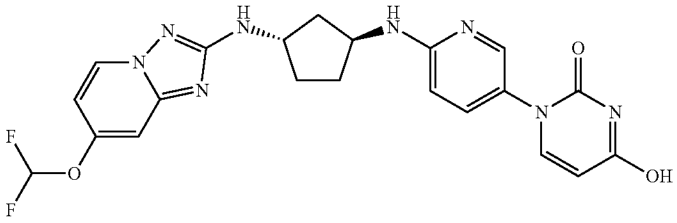 [SMILES: O=c1nc(O)ccn1-c1ccc(N[C@H]2CC[C@H](Nc3nc4cc(OC(F)F)ccn4n3)C2)nc1] which was synthesized by reference to the method of example 58 | 471.2 [M + H]+ |
| 106 | 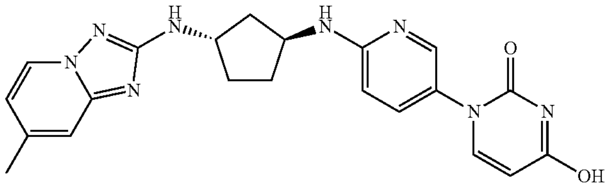 [SMILES: Cc1ccn2nc(N[C@H]3CC[C@H](Nc4ccc(-n5ccc(O)nc5=O)cn4)C3)nc2c1] which was synthesized by reference to the method of example 58 | 419.2 [M + H]+ |
| 107 | 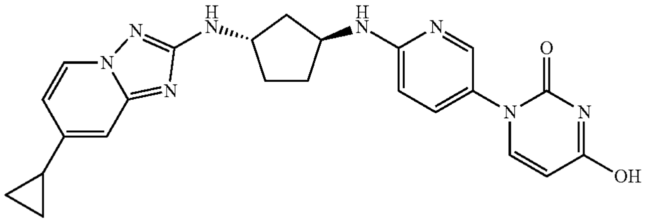 [SMILES: O=c1nc(O)ccn1-c1ccc(N[C@H]2CC[C@H](Nc3nc4cc(C5CC5)ccn4n3)C2)nc1] which was synthesized by reference to the method of example 58 | 445.2 [M + H]+ |
| 108 | 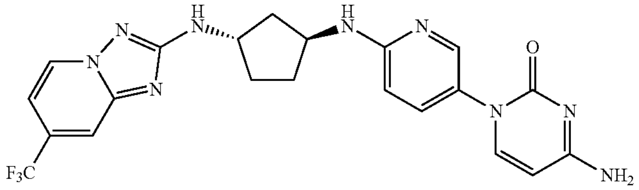 [SMILES: Nc1ccn(-c2ccc(N[C@H]3CC[C@H](Nc4nc5cc(C(F)(F)F)ccn5n4)C3)nc2)c(=O)n1] which was synthesized by reference to the method of example 58 | 472.2 [M + H]+ |

-continued

| Examples | Structure | MS m/z (ESI) |
| --- | --- | --- |
| 109 | 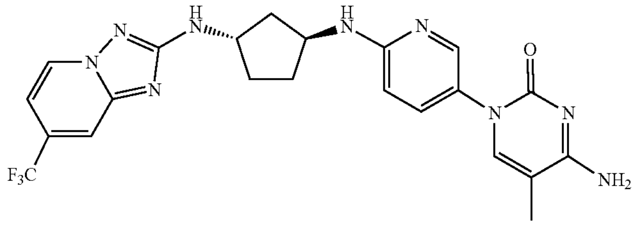 [SMILES: Cc1cn(-c2ccc(N[C@H]3CC[C@H](Nc4nc5cc(C(F)(F)F)ccn5n4)C3)nc2)c(=O)nc1N] which was synthesized by reference to the method of example 58 | 486.2 [M + H]+ |
| 110 | 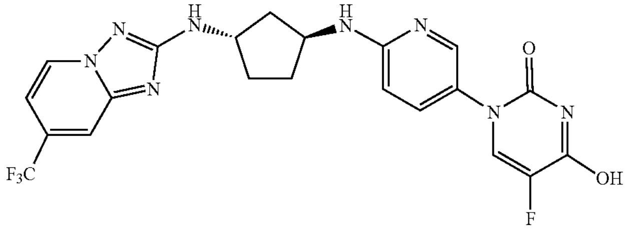 [SMILES: O=c1nc(O)c(F)cn1-c1ccc(N[C@H]2CC[C@H](Nc3nc4cc(C(F)(F)F)ccn4n3)C2)nc1] which was synthesized by reference to the method of example 58 | 491.2 [M + H]+ |
| 111 | 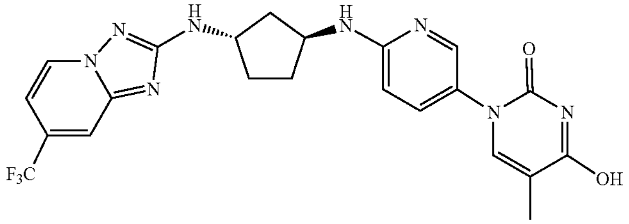 [SMILES: Cc1cn(-c2ccc(N[C@H]3CC[C@H](Nc4nc5cc(C(F)(F)F)ccn5n4)C3)nc2)c(=O)nc1O] which was synthesized by reference to the method of example 58 | 487.2 [M + H]+ |
| 113 | 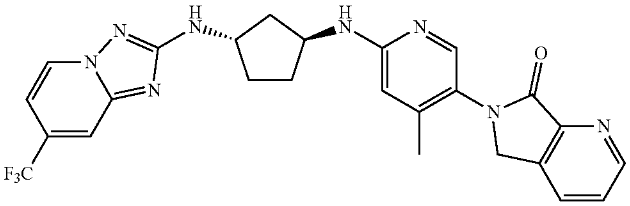 [SMILES: Cc1cc(N[C@H]2CC[C@H](Nc3nc4cc(C(F)(F)F)ccn4n3)C2)ncc1N1Cc2cccnc2C1=O] which was synthesized by reference to the method of example 112 | 509.2 [M + H]+ |
| 115 | 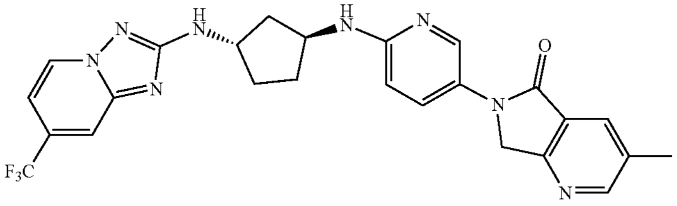 [SMILES: Cc1cnc2c(c1)C(=O)N(c1ccc(N[C@H]3CC[C@H](Nc4nc5cc(C(F)(F)F)ccn5n4)C3)nc1)C2] which was synthesized by reference to the method of reference example 3 | 509.2 [M + H]+ |

-continued

| Examples | Structure | MS m/z (ESI) |
|---|---|---|
| 116 | 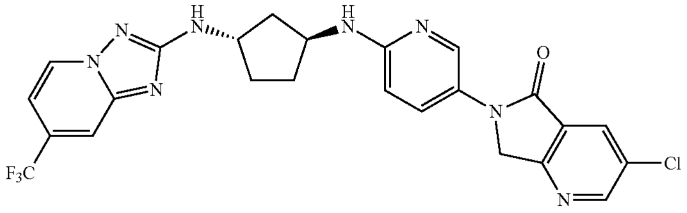 [SMILES: O=C1c2cc(Cl)cnc2CN1c1ccc(N[C@H]2CC[C@H](Nc3nc4cc(C(F)(F)F)ccn4n3)C2)nc1] which was synthesized by reference to the method of reference example 3 | 529.2 [M + H]+. |
| 117 | 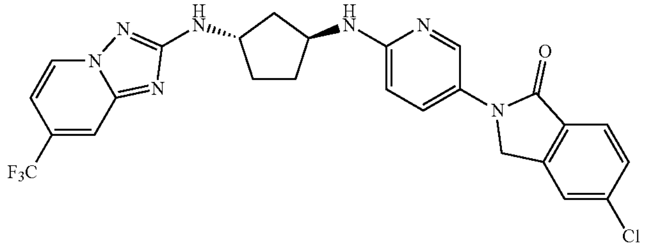 [SMILES: O=C1c2ccc(Cl)cc2CN1c1ccc(N[C@H]2CC[C@H](Nc3nc4cc(C(F)(F)F)ccn4n3)C2)nc1] which was synthesized by reference to the method of reference example 3 | 528.2 [M + H]+. |
| 118 | 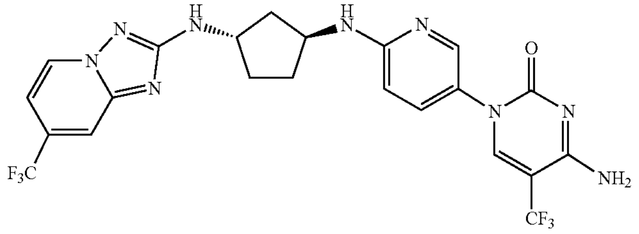 [SMILES: Nc1nc(=O)n(-c2ccc(N[C@H]3CC[C@H](Nc4nc5cc(C(F)(F)F)ccn5n4)C3)nc2)cc1C(F)(F)F] which was synthesized by reference to the method of example 58 | 540.2 [M + H]+ |
| 119 | 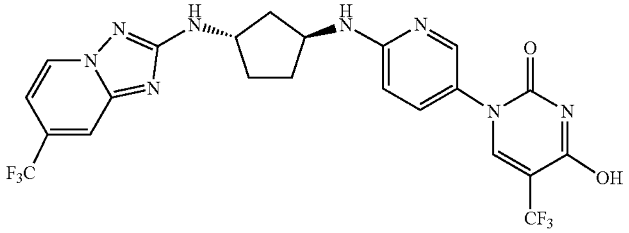 [SMILES: O=c1nc(O)c(C(F)(F)F)cn1-c1ccc(N[C@H]2CC[C@H](Nc3nc4cc(C(F)(F)F)ccn4n3)C2)nc1] which was synthesized by reference to the method of example 58 | 541.2 [M + H]+ |
| 120 | 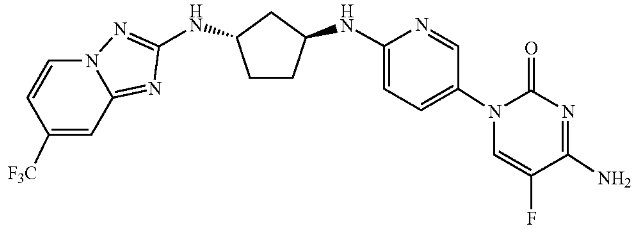 [SMILES: Nc1nc(=O)n(-c2ccc(N[C@H]3CC[C@H](Nc4nc5cc(C(F)(F)F)ccn5n4)C3)nc2)cc1F] which was synthesized by reference to the method of | 490.2 [M + H]+ |

-continued

| Examples | Structure | MS m/z (ESI) |
|---|---|---|
| | example 58 | |
| 121 | 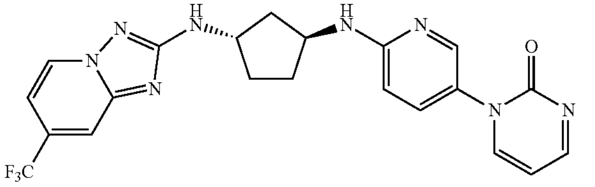 [SMILES: O=c1ncccn1-c1ccc(N[C@H]2CC[C@H](Nc3nc4cc(C(F)(F)F)ccn4n3)C2)nc1] | 457.2 [M + H]$^+$ |
| | which was synthesized by reference to the method of example 58 | |
| 122 | 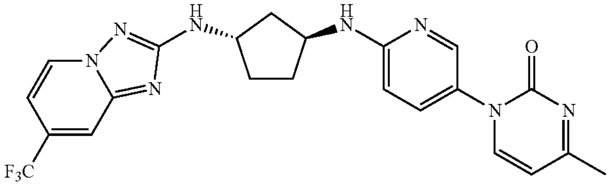 [SMILES: Cc1ccn(-c2ccc(N[C@H]3CC[C@H](Nc4nc5cc(C(F)(F)F)ccn5n4)C3)nc2)c(=O)n1] | 471.2 [M + H]$^+$ |
| | which was synthesized by reference to the method of example 58 | |
| 123 | 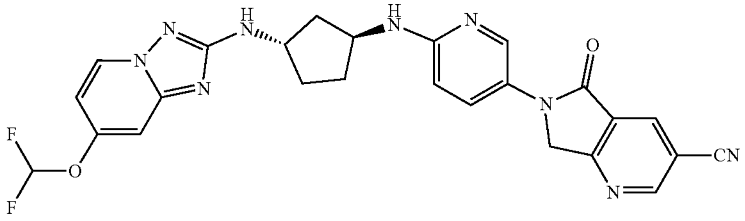 [SMILES: N#Cc1cnc2c(c1)C(=O)N(c1ccc(N[C@H]3CC[C@H](Nc4nc5cc(OC(F)F)ccn5n4)C3)nc1)C2] | 518.2 [M + H]$^+$ |
| | which was synthesized by reference to the method of example 56 | |
| 124 | 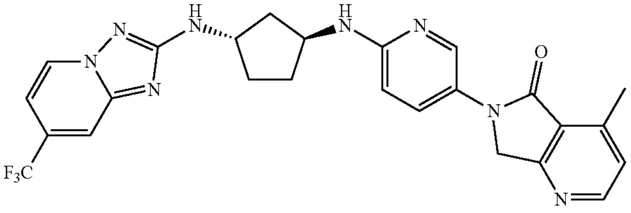 [SMILES: Cc1ccnc2c1C(=O)N(c1ccc(N[C@H]3CC[C@H](Nc4nc5cc(C(F)(F)F)ccn5n4)C3)nc1)C2] | 509.2 [M + H]$^+$ |
| | which was synthesized by reference to the method of reference example 3 | |
| 125 | 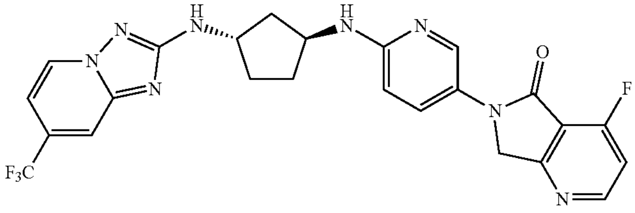 [SMILES: O=C1c2c(F)ccnc2CN1c1ccc(N[C@H]2CC[C@H](Nc3nc4cc(C(F)(F)F)ccn4n3)C2)nc1] | 513.2 [M + H]$^+$ |
| | which was synthesized by reference to the method of reference example 3 | |

-continued

| Examples | Structure | MS m/z (ESI) |
| --- | --- | --- |
| 126 | 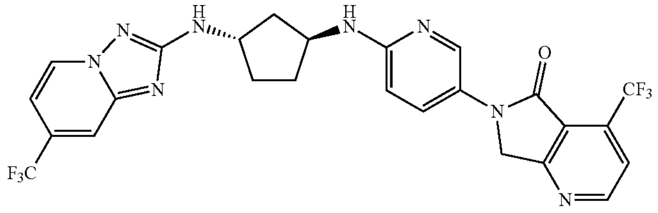 [SMILES: O=C1c2c(C(F)(F)F)ccnc2CN1c1ccc(N[C@H]2CC[C@H](Nc3nc4cc(C(F)(F)F)ccn4n3)C2)nc1] which was synthesized by reference to the method of reference example 3 | 563.2 $[M + H]^+$ |
| 127 | 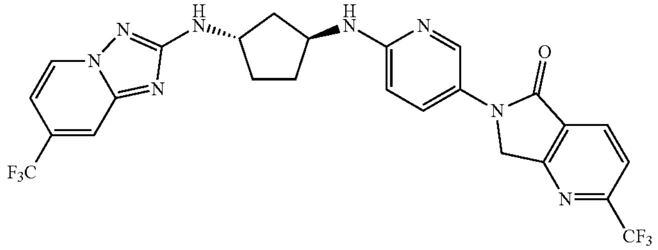 [SMILES: O=C1c2ccc(C(F)(F)F)nc2CN1c1ccc(N[C@H]2CC[C@H](Nc3nc4cc(C(F)(F)F)ccn4n3)C2)nc1] which was synthesized by reference to the method of reference example 3 | 563.2 [M + H]+ |
| 128 | 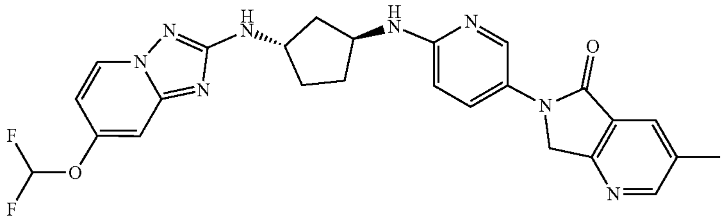 [SMILES: Cc1cnc2c(c1)C(=O)N(c1ccc(N[C@H]3CC[C@H](Nc4nc5cc(OC(F)F)ccn5n4)C3)nc1)C2] which was synthesized by reference to the method of example 56 | 507.2 $[M + H]^+$ |
| 129 | 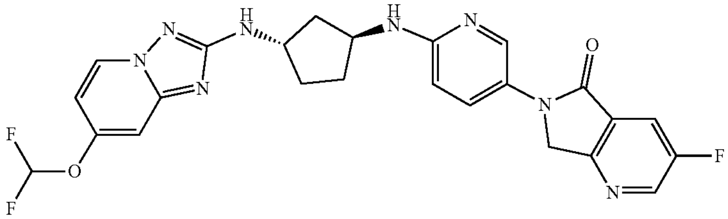 [SMILES: O=C1c2cc(F)cnc2CN1c1ccc(N[C@H]2CC[C@H](Nc3nc4cc(OC(F)F)ccn4n3)C2)nc1] which was synthesized by reference to the method of example 56 | 511.2 $[M + H]^+$ |
| 130 | 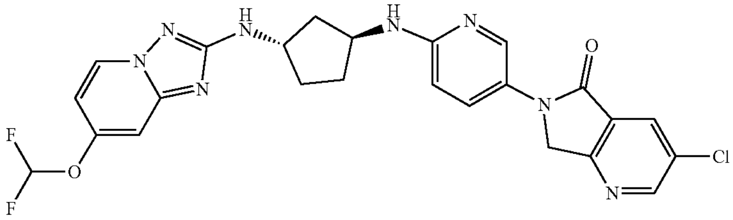 [SMILES: O=C1c2cc(Cl)cnc2CN1c1ccc(N[C@H]2CC[C@H](Nc3nc4cc(OC(F)F)ccn4n3)C2)nc1] which was synthesized by reference to the method of example 56 | 527.1 $[M + H]^+$ |

-continued
| Examples | Structure | MS m/z (ESI) |
|---|---|---|
| 131 | 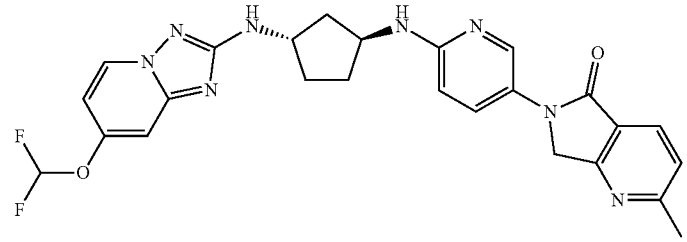 [SMILES: Cc1ccc2c(n1)CN(c1ccc(N[C@H]3CC[C@H](Nc4nc5cc(OC(F)F)ccn5n4)C3)nc1)C2=O] which was synthesized by reference to the method of example 56 | 507.2 [M + H]+ |
| 132 | 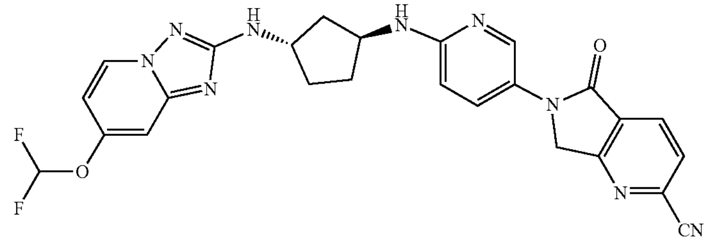 [SMILES: N#Cc1ccc2c(n1)CN(c1ccc(N[C@H]3CC[C@H](Nc4nc5cc(OC(F)F)ccn5n4)C3)nc1)C2=O] which was synthesized by reference to the method of example 56 | 518.2 [M + H]+ |
| 133 | 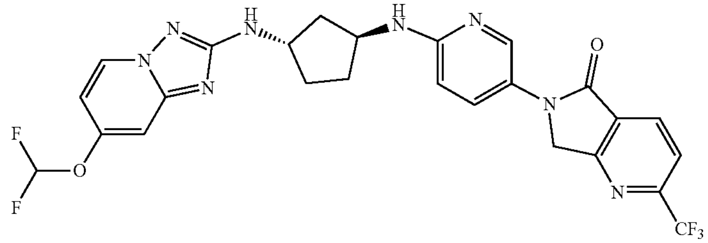 [SMILES: O=C1c2ccc(C(F)(F)F)nc2CN1c1ccc(N[C@H]2CC[C@H](Nc3nc4cc(OC(F)F)ccn4n3)C2)nc1] which was synthesized by reference to the method of example 56 | 561.2 [M + H]+ |
| 134 | 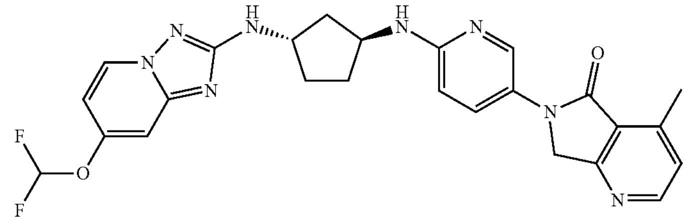 [SMILES: Cc1ccnc2c1C(=O)N(c1ccc(N[C@H]3CC[C@H](Nc4nc5cc(OC(F)F)ccn5n4)C3)nc1)C2] which was synthesized by reference to the method of example 56 | 507.2 [M + H]+ |
| 135 | 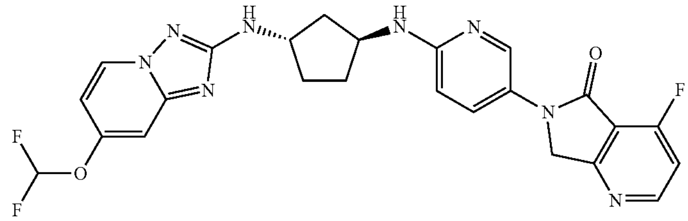 [SMILES: O=C1c2c(F)ccnc2CN1c1ccc(N[C@H]2CC[C@H](Nc3nc4cc(OC(F)F)ccn4n3)C2)nc1] | 511.2 [M + H]+ |

-continued
| Examples | Structure | MS m/z (ESI) |
|---|---|---|
| | which was synthesized by reference to the method of example 56 | |
| 136 | 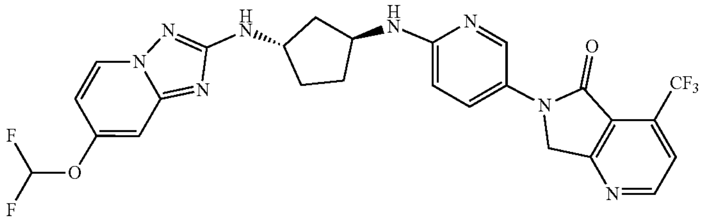 [SMILES: O=C1c2c(C(F)(F)F)ccnc2CN1c1ccc(N[C@H]2CC[C@H](Nc3nc4cc(OC(F)F)ccn4n3)C2)nc1] | 561.2 [M + H]+ |
| | which was synthesized by reference to the method of example 56 | |
| 137 | 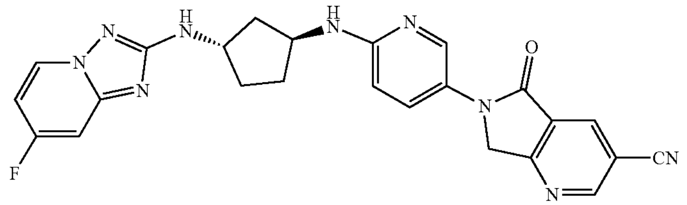 [SMILES: N#Cc1cnc2c(c1)C(=O)N(c1ccc(N[C@H]3CC[C@H](Nc4nc5cc(F)ccn5n4)C3)nc1)C2] | 470.2 [M + H]+ |
| | which was synthesized by reference to the method of example 56 | |
| 138 | 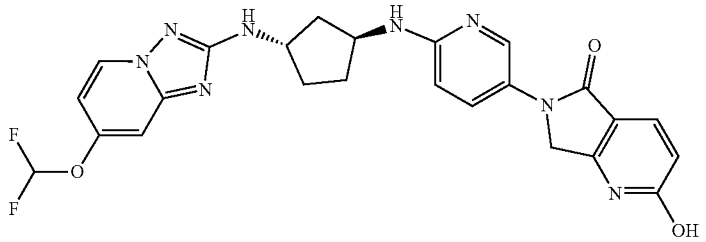 | 509.2 [M + H]+ |
| | which was synthesized by reference to the method of example 56 | |
| 139 | 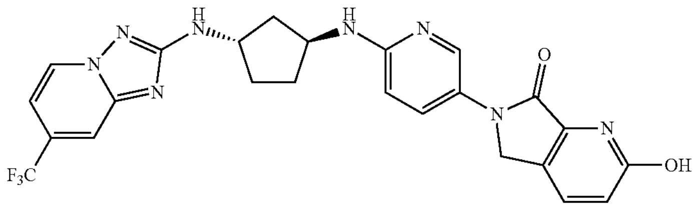 [SMILES: O=C1c2nc(O)ccc2CN1c1ccc(N[C@H]2CC[C@H](Nc3nc4cc(C(F)(F)F)ccn4n3)C2)nc1] | 511.2 [M + H]+ |
| 140 | 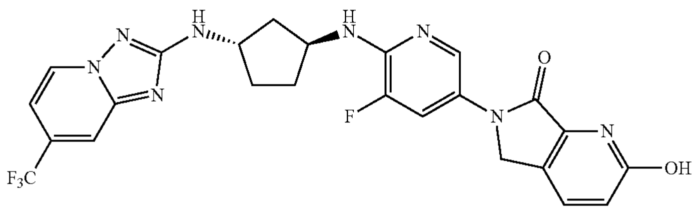 [SMILES: O=C1c2nc(O)ccc2CN1c1cnc(N[C@H]2CC[C@H](Nc3nc4cc(C(F)(F)F)ccn4n3)C2)c(F)c1] | 529.2 [M + H]+ |

-continued
| Examples | Structure | MS m/z (ESI) |
|---|---|---|
| 141 | 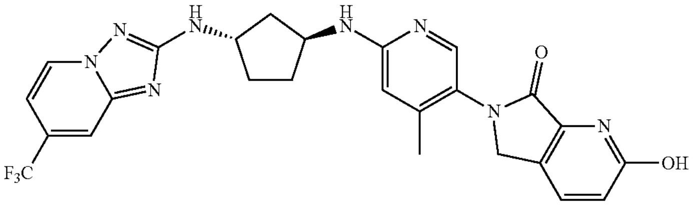 [SMILES: Cc1cc(N[C@H]2CC[C@H](Nc3nc4cc(C(F)(F)F)ccn4n3)C2)ncc1N1Cc2ccc(O)nc2C1=O] | 525.2 [M + H]+ |
| 142 | 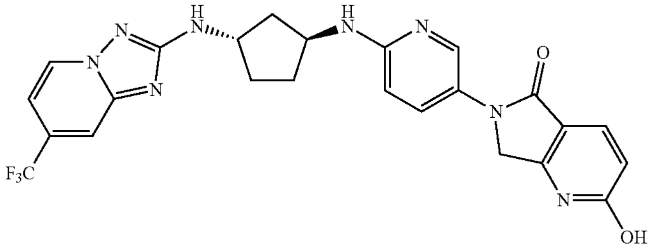 [SMILES: O=C1c2ccc(O)nc2CN1c1ccc(N[C@H]2CC[C@H](Nc3nc4cc(C(F)(F)F)ccn4n3)C2)nc1] | 511.2 [M + H]+ |
| 143 | 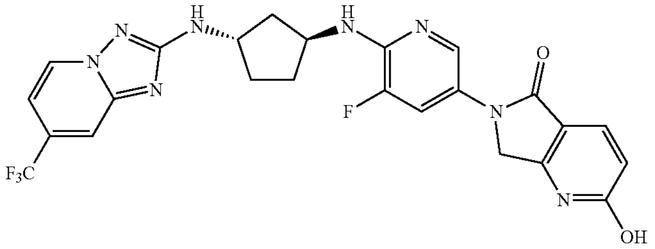 [SMILES: O=C1c2ccc(O)nc2CN1c1cnc(N[C@H]2CC[C@H](Nc3nc4cc(C(F)(F)F)ccn4n3)C2)c(F)c1] | 529.2 [M + H]+ |
| 144 | 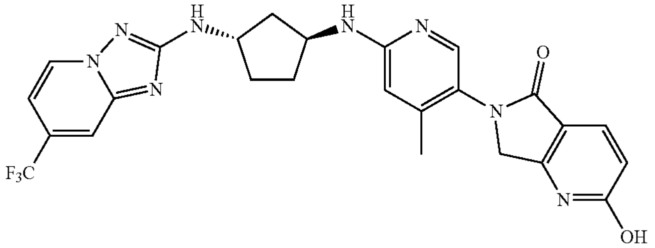 [SMILES: Cc1cc(N[C@H]2CC[C@H](Nc3nc4cc(C(F)(F)F)ccn4n3)C2)ncc1N1Cc2nc(O)ccc2C1=O] | 525.2 [M + H]+ |
| 145 | 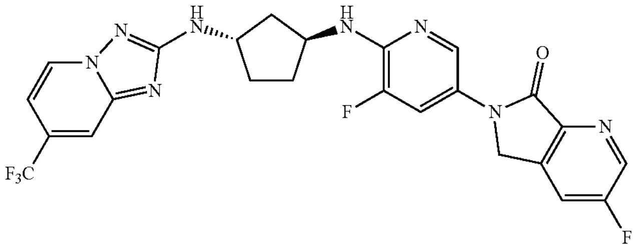 [SMILES: O=C1c2ncc(F)cc2CN1c1cnc(N[C@H]2CC[C@H](Nc3nc4cc(C(F)(F)F)ccn4n3)C2)c(F)c1] which was synthesized by reference to the method of example 112 | 531.2 [M + H]+ |
| 146 | 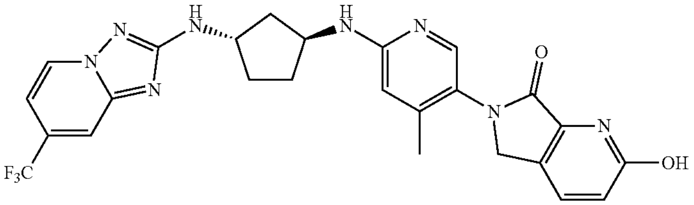 [SMILES: Cc1cc(N[C@H]2CC[C@H](Nc3nc4cc(C(F)(F)F)ccn4n3)C2)ncc1N1Cc2ccc(O)nc2C1=O] | 525.2 [M + H]+ |

-continued

| Examples | Structure | MS m/z (ESI) |
|---|---|---|
| | which was synthesized by reference to the method of example 112 | |
| 147 | 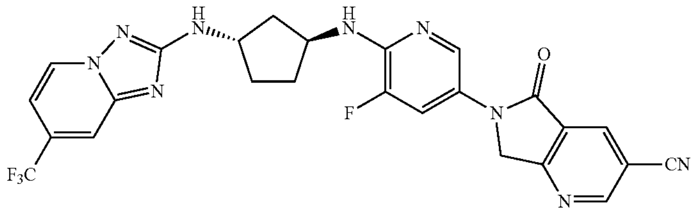 [SMILES: N#Cc1cnc2c(c1)C(=O)N(c1cnc(N[C@H]3CC[C@H](Nc4nc5cc(C(F)(F)F)ccn5n4)C3)c(F)c1)C2] | 538.2 $[M + H]^+$ |
| | which was synthesized by reference to example 112 | |
| 148 | 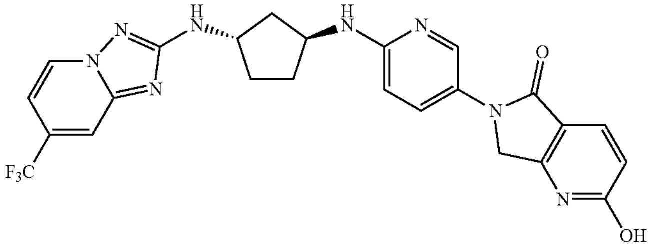 [SMILES: O=C1c2ccc(O)nc2CN1c1ccc(N[C@H]2CC[C@H](Nc3nc4cc(C(F)(F)F)ccn4n3)C2)nc1] | 520.2 $[M + H]^+$ |
| | which was synthesized by reference to the method of reference example 3 | |
| 149 | 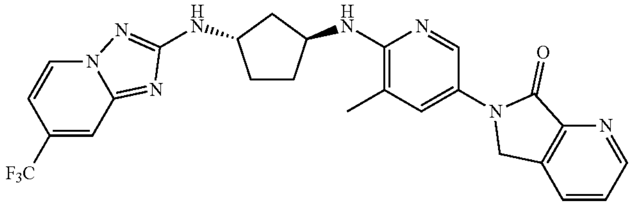 [SMILES: Cc1cc(N2Cc3cccnc3C2=O)cnc1N[C@H]1CC[C@H](Nc2nc3cc(C(F)(F)F)ccn3n2)C1] | 509.2 $[M + H]^+$ |
| | which was synthesized by reference to the method of example 112 | |
| 150 | 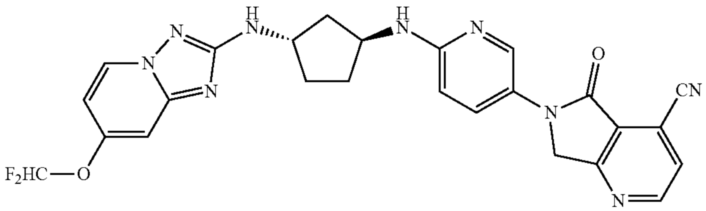 [SMILES: N#Cc1ccnc2c1C(=O)N(c1ccc(N[C@H]3CC[C@H](Nc4nc5cc(OC(F)F)ccn5n4)C3)nc1)C2] | 518.2 $[M + H]^+$ |
| | which was synthesized by reference to the method of example 56 | |
| 151 | 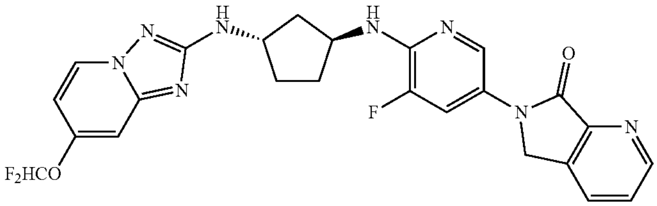 [SMILES: O=C1c2ncccc2CN1c1cnc(N[C@H]2CC[C@H](Nc3nc4cc(OC(F)F)ccn4n3)C2)c(F)c1] | 511.2 $[M + H]^+$ |

-continued

| Examples | Structure | MS m/z (ESI) |
|---|---|---|
| | which was synthesized by reference to the method of example 112 | |
| 152 | 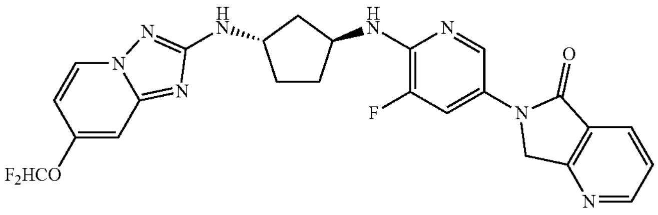 [SMILES: O=C1c2cccnc2CN1c1cnc(N[C@H]2CC[C@H](Nc3nc4cc(OC(F)F)ccn4n3)C2)c(F)c1] | 511.2 [M + H]+ |
| | which was synthesized by reference to the method of example 112 | |
| 153 | 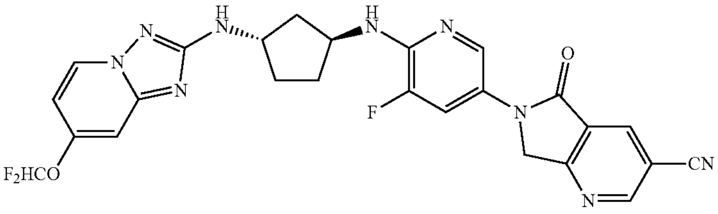 [SMILES: N#Cc1cnc2c(c1)C(=O)N(c1cnc(N[C@H]3CC[C@H](Nc4nc5cc(OC(F)F)ccn5n4)C3)c(F)c1)C2] | 536.2 [M + H]+ |
| | which was synthesized by reference to the method of example 112 | |
| 154 | 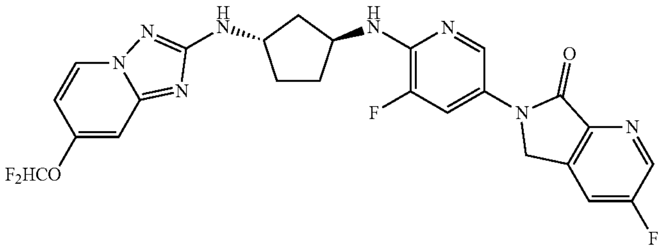 [SMILES: O=C1c2ncc(F)cc2CN1c1cnc(N[C@H]2CC[C@H](Nc3nc4cc(OC(F)F)ccn4n3)C2)c(F)c1] | 529.2 [M + H]+ |
| | which was synthesized by reference to the method of example 112 | |
| 155 | 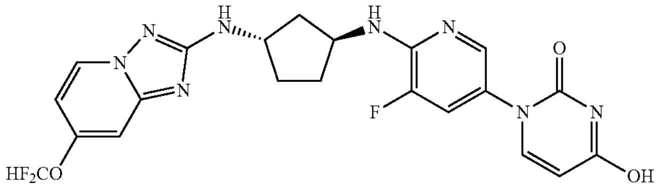 | 489.2 [M + H]+ |
| | which was synthesized by reference to the method of example 112 | |
| 156 | 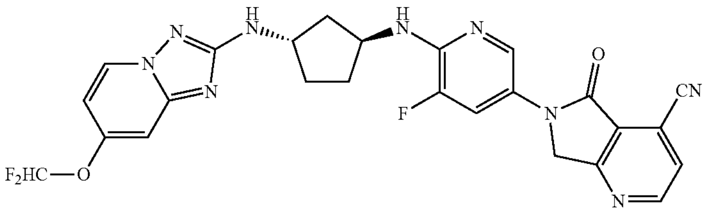 [SMILES: N#Cc1ccnc2c1C(=O)N(c1cnc(N[C@H]3CC[C@H](Nc4nc5cc(OC(F)F)ccn5n4)C3)c(F)c1)C2] | 536.2 [M + H]+ |

-continued

| Examples | Structure | MS m/z (ESI) |
|---|---|---|
| | which was synthesized by reference to the method of example 112 | |
| 157 | 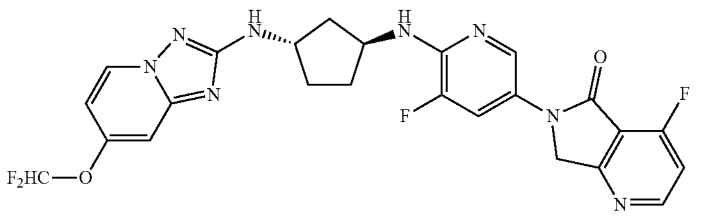 [SMILES: O=C1c2c(F)ccnc2CN1c1cnc(N[C@H]2CC[C@H](Nc3nc4cc(OC(F)F)ccn4n3)C2)c(F)c1] | 529.2 [M + H]+ |
| | which was synthesized by reference to the method of example 112 | |
| 158 | 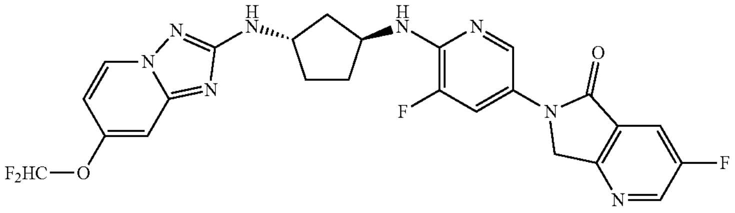 [SMILES: O=C1c2cc(F)cnc2CN1c1cnc(N[C@H]2CC[C@H](Nc3nc4cc(OC(F)F)ccn4n3)C2)c(F)c1] | 529.2 [M + H]+ |
| | which was synthesized by reference to the method of example 112 | |
| 159 | 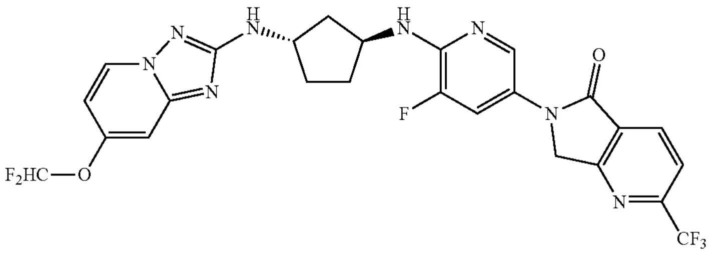 [SMILES: O=C1c2ccc(C(F)(F)F)nc2CN1c1cnc(N[C@H]2CC[C@H](Nc3nc4cc(OC(F)F)ccn4n3)C2)c(F)c1] | 579.2 [M + H]+ |
| | which was synthesized by reference to the method of example 112 | |
| 160 | 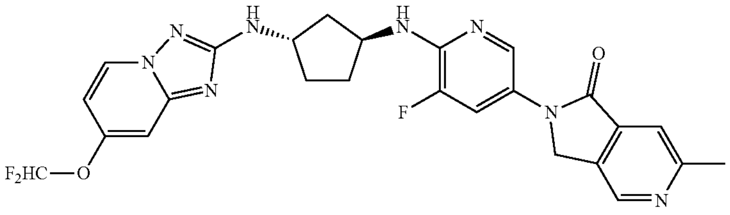 [SMILES: Cc1cc2c(cn1)CN(c1cnc(N[C@H]3CC[C@H](Nc4nc5cc(OC(F)F)ccn5n4)C3)c(F)c1)C2=O] | 525.2 [M + H]+ |
| | which was synthesized by reference to the method of example 112 | |
| 161 | 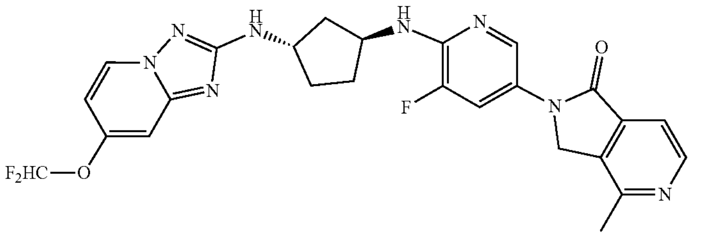 [SMILES: Cc1nccc2c1CN(c1cnc(N[C@H]3CC[C@H](Nc4nc5cc(OC(F)F)ccn5n4)C3)c(F)c1)C2=O] | 525.2 [M + H]+ |

-continued
| Examples | Structure | MS m/z (ESI) |
|---|---|---|
| | which was synthesized by reference to the method of example 112 | |
| 162 | 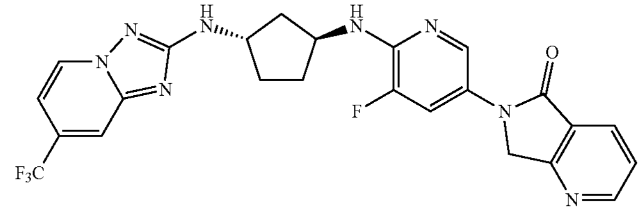 [SMILES: O=C1c2cccnc2CN1c1cnc(N[C@H]2CC[C@H](Nc3nc4cc(C(F)(F)F)ccn4n3)C2)c(F)c1] | 513.2 [M + H]+ |
| | which was synthesized by reference to example 112 | |
| 163 | 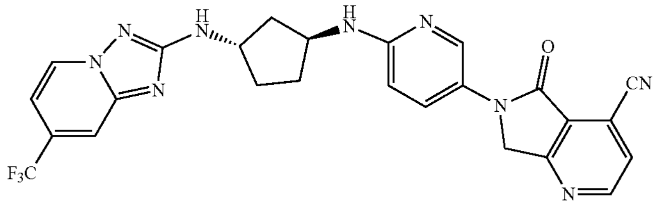 [SMILES: N#Cc1ccnc2c1C(=O)N(c1ccc(N[C@H]3CC[C@H](Nc4nc5cc(C(F)(F)F)ccn5n4)C3)nc1)C2] | 520.2 [M + H]+ |
| | which was synthesized by reference to the method of reference example 3 | |
| 165 | 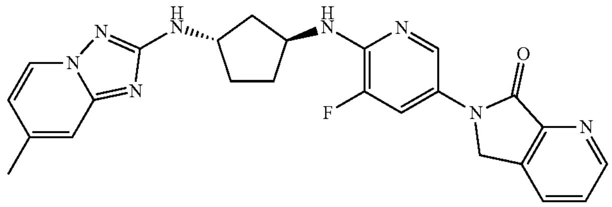 [SMILES: Cc1ccn2nc(N[C@H]3CC[C@H](Nc4ncc(N5Cc6cccnc6C5=O)cc4F)C3)nc2c1] | 459.2 [M + H]+ |
| 166 | 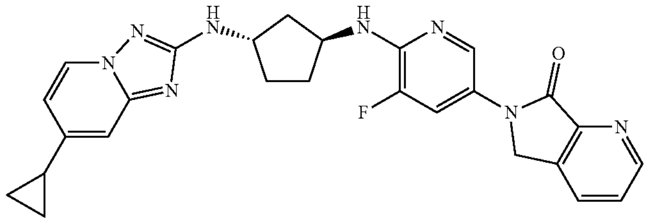 [SMILES: O=C1c2ncccc2CN1c1cnc(N[C@H]2CC[C@H](Nc3nc4cc(C5CC5)ccn4n3)C2)c(F)c1] | 485.2 [M + H]+ |
| 167 | 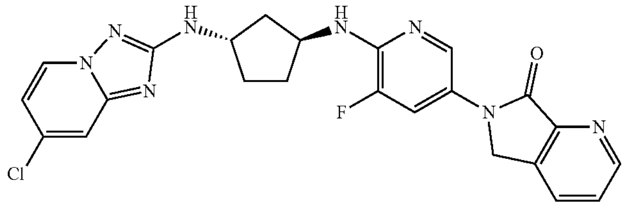 [SMILES: O=C1c2ncccc2CN1c1cnc(N[C@H]2CC[C@H](Nc3nc4cc(Cl)ccn4n3)C2)c(F)c1] | 479.1 [M + H]+ |
| 168 | 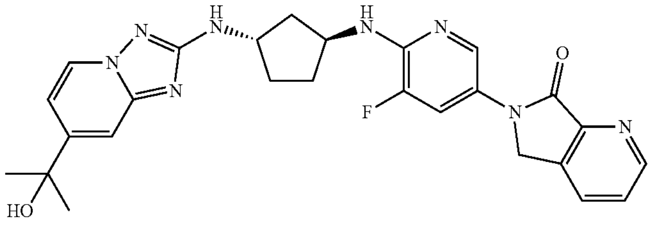 [SMILES: CC(C)(O)c1ccn2nc(N[C@H]3CC[C@H](Nc4ncc(N5Cc6cccnc6C5=O)cc4F)C3)nc2c1] | 503.2 [M + H]+ |

-continued
| Examples | Structure | MS m/z (ESI) |
|---|---|---|
| 169 | 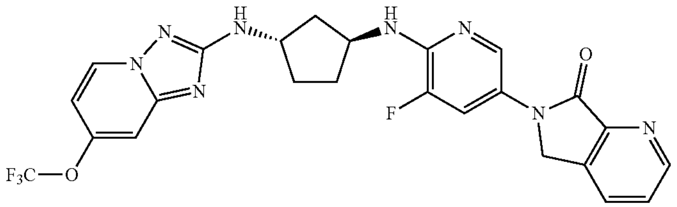 [SMILES: O=C1c2ncccc2CN1c1cnc(N[C@H]2CC[C@H](Nc3nc4cc(OC(F)(F)F)ccn4n3)C2)c(F)c1] | 529.2 [M + H]+ |
| 170 | 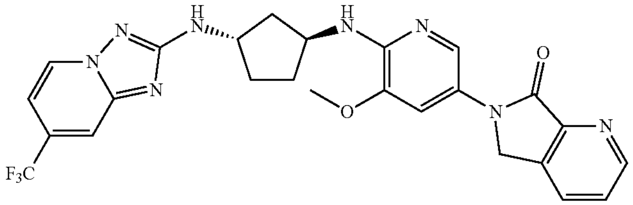 [SMILES: COc1cc(N2Cc3cccnc3C2=O)cnc1N[C@H]1CC[C@H](Nc2nc3cc(C(F)(F)F)ccn3n2)C1] | 525.2 [M + H]+ |
| 171 | 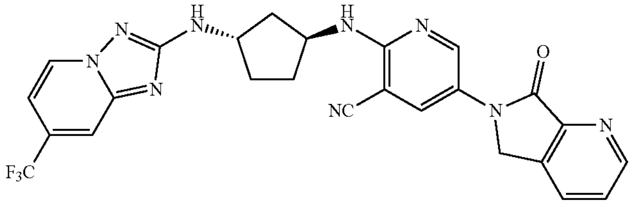 [SMILES: N#Cc1cc(N2Cc3cccnc3C2=O)cnc1N[C@H]1CC[C@H](Nc2nc3cc(C(F)(F)F)ccn3n2)C1] | 520.2 [M + H]+. |
| 172 | 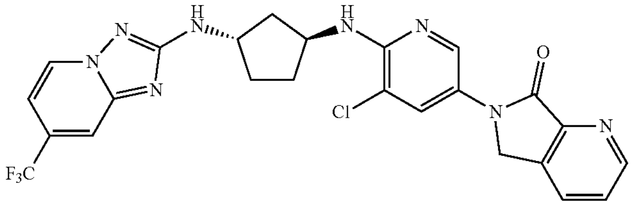 | 529.1 [M + H]+. |
| 173 | 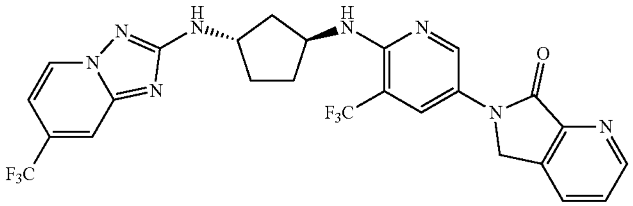 [SMILES: O=C1c2ncccc2CN1c1cnc(N[C@H]2CC[C@H](Nc3nc4cc(C(F)(F)F)ccn4n3)C2)c(Cl)c1] | 563.2 [M + H]+ |
| 174 | 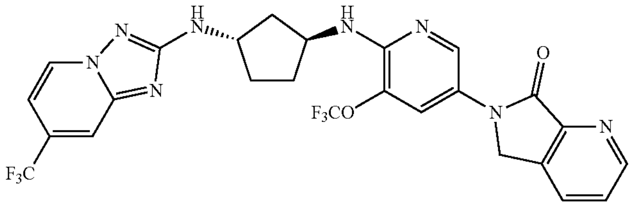 [SMILES: O=C1c2ncccc2CN1c1cnc(N[C@H]2CC[C@H](Nc3nc4cc(C(F)(F)F)ccn4n3)C2)c(OC(F)(F)F)c1] | 579.2 [M + H]+ |
| 175 | 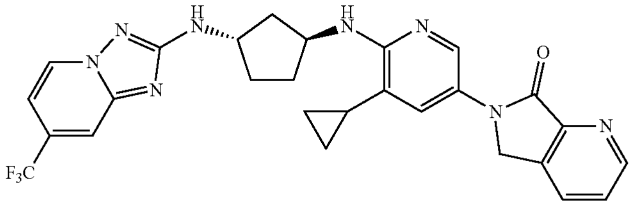 [SMILES: O=C1c2ncccc2CN1c1cnc(N[C@H]2CC[C@H](Nc3nc4cc(C(F)(F)F)ccn4n3)C2)c(C2CC2)c1] | 535.2 [M + H]+ |

-continued
| Examples | Structure | MS m/z (ESI) |
| --- | --- | --- |
| 176 | 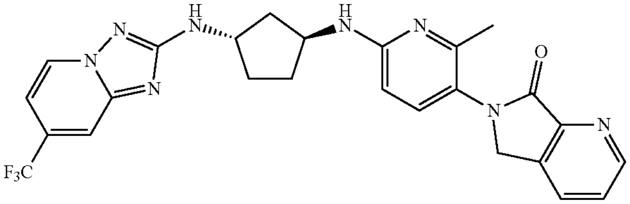 [SMILES: Cc1nc(N[C@H]2CC[C@H](Nc3nc4cc(C(F)(F)F)ccn4n3)C2)ccc1N1Cc2cccnc2C1=O] | 509.2 [M + H]$^+$ |
| 177 | 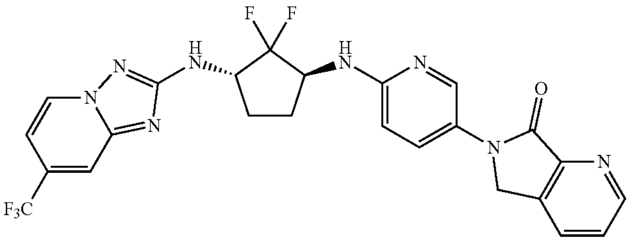 [SMILES: O=C1c2ncccc2CN1c1ccc(N[C@H]2CC[C@H](Nc3nc4cc(C(F)(F)F)ccn4n3)C2(F)F)nc1] | 531.2 [M + H]$^+$ |
| 178 | 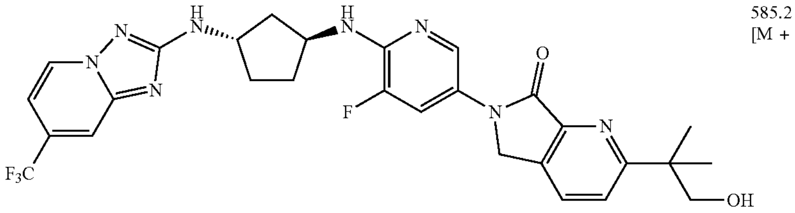 | 585.2 [M + H]$^+$ |
| 179 | 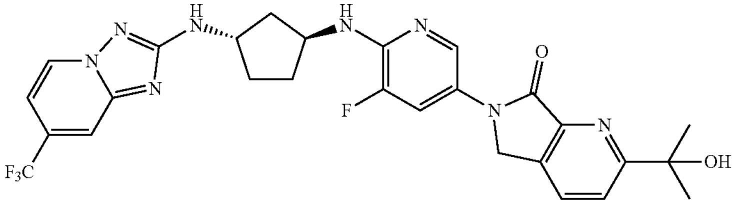 [SMILES: CC(C)(O)c1ccc2c(n1)C(=O)N(c1cnc(N[C@H]3CC[C@H](Nc4nc5cc(C(F)(F)F)ccn5n4)C3)c(F)c1)C2] | 571.2 [M + H]$^+$ |
| 180 | 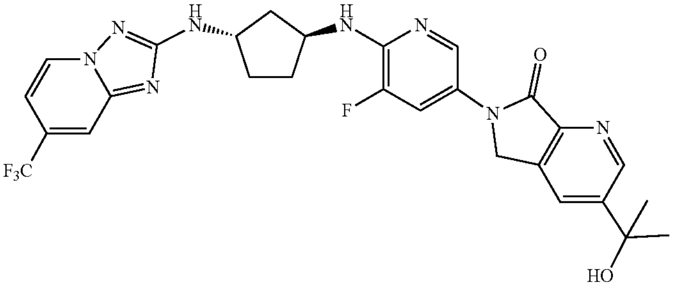 [SMILES: CC(C)(O)c1cnc2c(c1)CN(c1cnc(N[C@H]3CC[C@H](Nc4nc5cc(C(F)(F)F)ccn5n4)C3)c(F)c1)C2=O] | 571.2 [M + H]$^+$ |
| 181 | 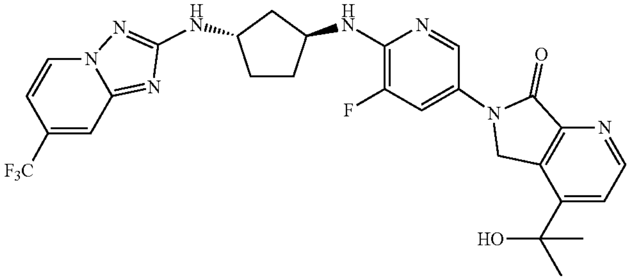 [SMILES: CC(C)(O)c1ccnc2c1CN(c1cnc(N[C@H]3CC[C@H](Nc4nc5cc(C(F)(F)F)ccn5n4)C3)c(F)c1)C2=O] | 571.2 [M + H]$^+$ |

-continued
| Examples | Structure | MS m/z (ESI) |
|---|---|---|
| 182 | 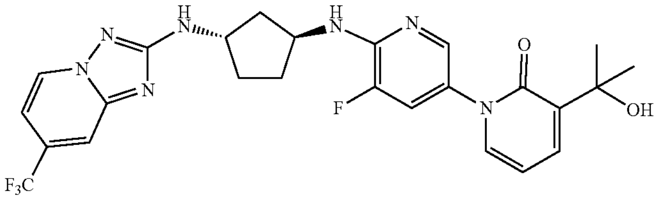 [SMILES: CC(C)(O)c1cccn(-c2cnc(N[C@H]3CC[C@H](Nc4nc5cc(C(F)(F)F)ccn5n4)C3)c(F)c2)c1=O] | 532.2 [M + H]+ |
| 183 | 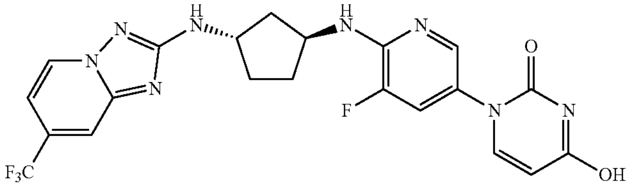 [SMILES: O=c1nc(O)ccn1-c1cnc(N[C@H]2CC[C@H](Nc3nc4cc(C(F)(F)F)ccn4n3)C2)c(F)c1] | 491.2 [M + H]+ |
| 184 | 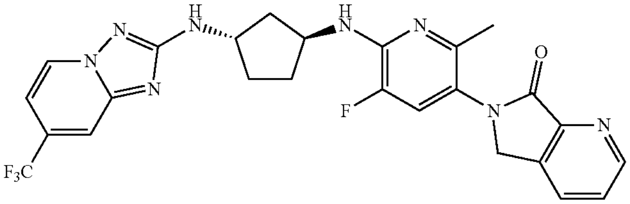 [SMILES: Cc1nc(N[C@H]2CC[C@H](Nc3nc4cc(C(F)(F)F)ccn4n3)C2)c(F)cc1N1Cc2cccnc2C1=O] | 527.2 [M + H]+ |
| 185 | 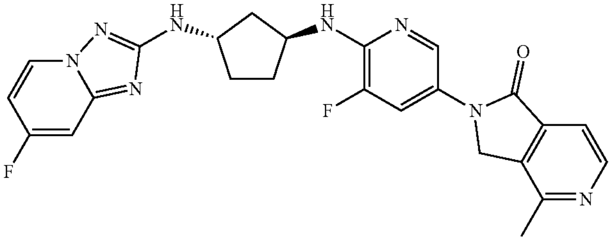 [SMILES: Cc1nccc2c1CN(c1cnc(N[C@H]3CC[C@H](Nc4nc5cc(F)ccn5n4)C3)c(F)c1)C2=O] | 477.2 [M + H]+ |
| 187 | 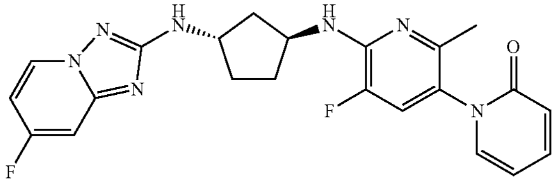 [SMILES: Cc1nc(N[C@H]2CC[C@H](Nc3nc4cc(F)ccn4n3)C2)c(F)cc1-n1ccccc1=O] | 438.2 [M + H]+ |
| 188 | 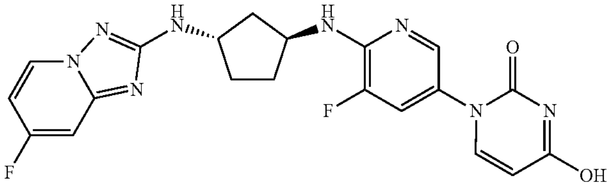 | 441.2 [M + H]+ |
| 189 | 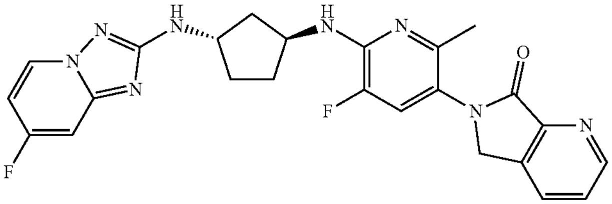 [SMILES: Cc1nc(N[C@H]2CC[C@H](Nc3nc4cc(F)ccn4n3)C2)c(F)cc1N1Cc2cccnc2C1=O] | 477.2 [M + H]+ |

-continued
| Examples | Structure | MS m/z (ESI) |
| --- | --- | --- |
| 190 | 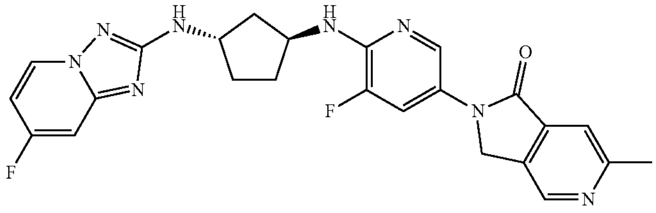 [SMILES: Cc1cc2c(cn1)CN(c1cnc(N[C@H]3CC[C@H](Nc4nc5cc(F)ccn5n4)C3)c(F)c1)C2=O] | 477.2 [M + H]$^+$ |
| 191 | 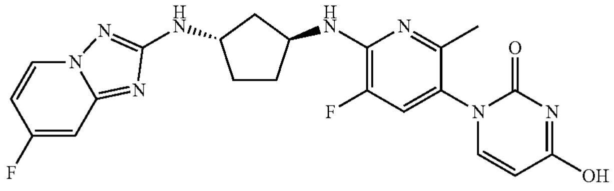 [SMILES: Cc1nc(N[C@H]2CC[C@H](Nc3nc4cc(F)ccn4n3)C2)c(F)cc1-n1ccc(O)nc1=O] | 455.2 [M + H]$^+$ |
| 192 | 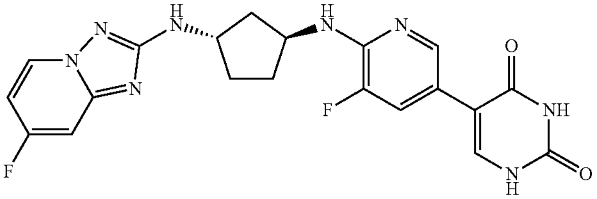 [SMILES: O=c1[nH]cc(-c2cnc(N[C@H]3CC[C@H](Nc4nc5cc(F)ccn5n4)C3)c(F)c2)c(=O)[nH]1] | 441.2 [M + H]$^+$. |
| 193 | 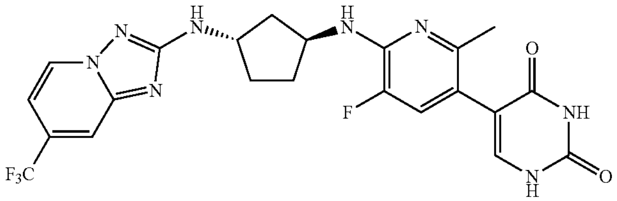 [SMILES: Cc1nc(N[C@H]2CC[C@H](Nc3nc4cc(C(F)(F)F)ccn4n3)C2)c(F)cc1-c1c[nH]c(=O)[nH]c1=O] | 505.2 [M + H]$^+$ |
| 194 | 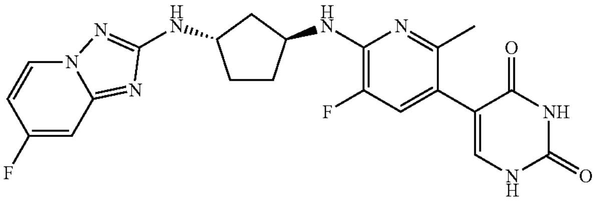 [SMILES: Cc1nc(N[C@H]2CC[C@H](Nc3nc4cc(F)ccn4n3)C2)c(F)cc1-c1c[nH]c(=O)[nH]c1=O] | 455.2 [M + H]$^+$ |
| 195 | 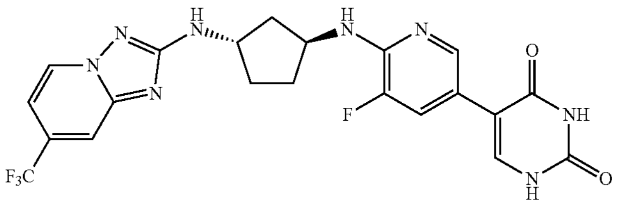 [SMILES: O=c1[nH]cc(-c2cnc(N[C@H]3CC[C@H](Nc4nc5cc(C(F)(F)F)ccn5n4)C3)c(F)c2)c(=O)[nH]1] | 491.2 [M + H]$^+$. |
| 196 | 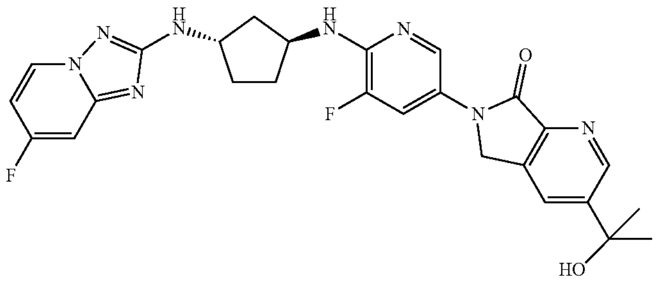 [SMILES: CC(C)(O)c1cnc2c(c1)CN(c1cnc(N[C@H]3CC[C@H](Nc4nc5cc(F)ccn5n4)C3)c(F)c1)C2=O] | 521.2 [M + H]$^+$ |

-continued
| Examples | Structure | MS m/z (ESI) |
| --- | --- | --- |
| 197 | 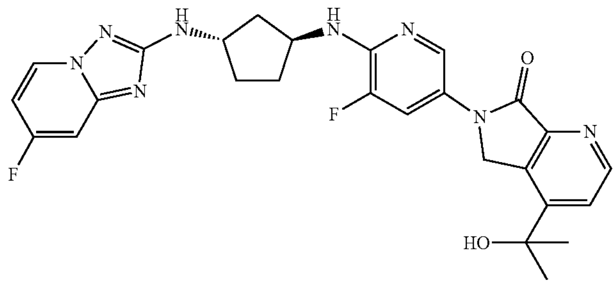 [SMILES: CC(C)(O)c1ccnc2c1CN(c1cnc(N[C@H]3CC[C@H](Nc4nc5cc(F)ccn5n4)C3)c(F)c1)C2=O] | 521.2 [M + H]+ |
| 198 | 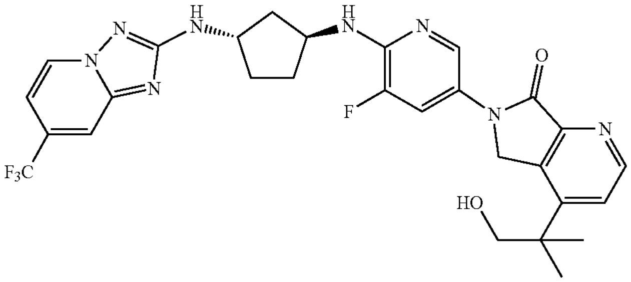 [SMILES: CC(C)(CO)c1ccnc2c1CN(c1cnc(N[C@H]3CC[C@H](Nc4nc5cc(C(F)(F)F)ccn5n4)C3)c(F)c1)C2=O] | 585.2 [M + H]+ |
| 199 | 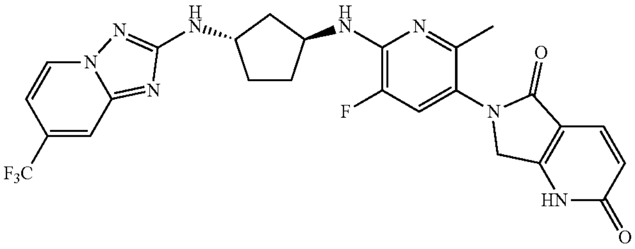 [SMILES: Cc1nc(N[C@H]2CC[C@H](Nc3nc4cc(C(F)(F)F)ccn4n3)C2)c(F)cc1N1Cc2[nH]c(=O)ccc2C1=O] | 543.2 [M + H]+ |
| 200 | 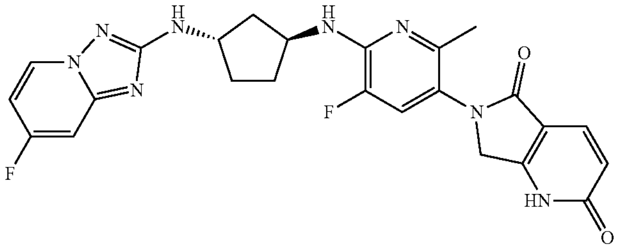 [SMILES: Cc1nc(N[C@H]2CC[C@H](Nc3nc4cc(F)ccn4n3)C2)c(F)cc1N1Cc2[nH]c(=O)ccc2C1=O] | 493.2 [M + H]+ |
| 201 | 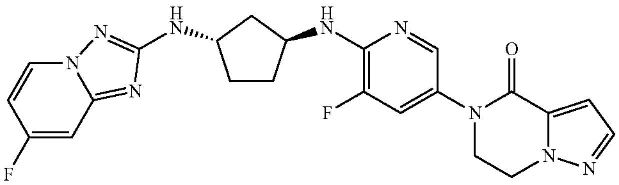 [SMILES: O=C1c2ccnn2CCN1c1cnc(N[C@H]2CC[C@H](Nc3nc4cc(F)ccn4n3)C2)c(F)c1] | 466.2 [M + H]+ |
| 202 | 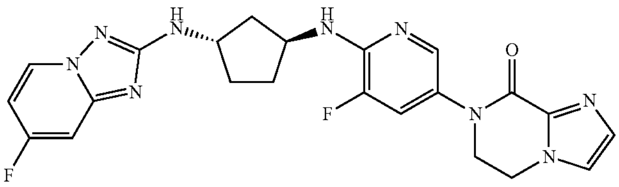 | 466.2 [M + H]+ |

-continued
| Examples | Structure | MS m/z (ESI) |
|---|---|---|
| 203 | 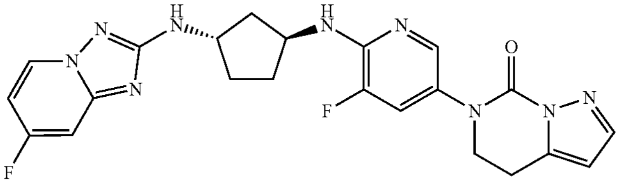 [SMILES: O=C1N(c2cnc(N[C@H]3CC[C@H](Nc4nc5cc(F)ccn5n4)C3)c(F)c2)CCc2ccnn21] | 466.2 [M + H]+ |
| 204 | 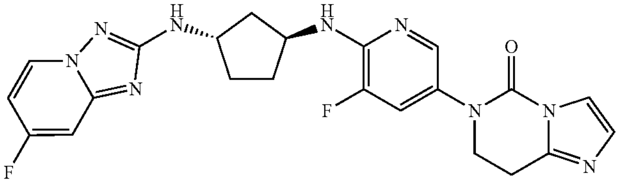 [SMILES: O=C1N(c2cnc(N[C@H]3CC[C@H](Nc4nc5cc(F)ccn5n4)C3)c(F)c2)CCc2nccn21] | 466.2 [M + H]+ |
| 205 | 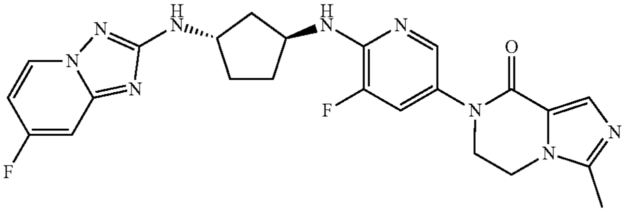 [SMILES: Cc1ncc2n1CCN(c1cnc(N[C@H]3CC[C@H](Nc4nc5cc(F)ccn5n4)C3)c(F)c1)C2=O] | 480.2 [M + H]+ |
| 206 | 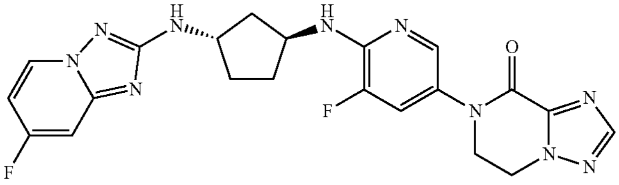 [SMILES: O=C1c2ncnn2CCN1c1cnc(N[C@H]2CC[C@H](Nc3nc4cc(F)ccn4n3)C2)c(F)c1] | 467.2 [M + H]+ |
| 207 | 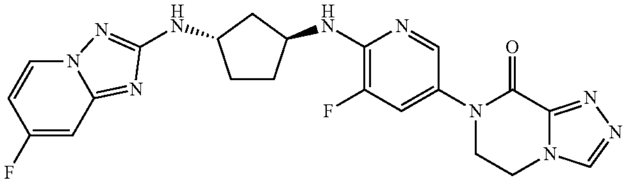 [SMILES: O=C1c2nncn2CCN1c1cnc(N[C@H]2CC[C@H](Nc3nc4cc(F)ccn4n3)C2)c(F)c1] | 467.2 [M + H]+ |
| 208 | 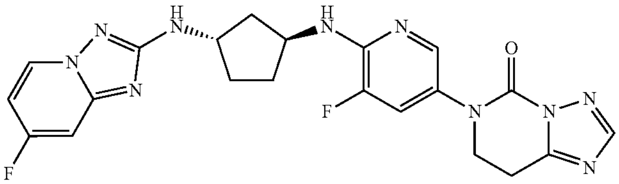 [SMILES: O=C1N(c2cnc(N[C@H]3CC[C@H](Nc4nc5cc(F)ccn5n4)C3)c(F)c2)CCc2ncnn21] | 467.2 [M + H]+ |
| 209 | 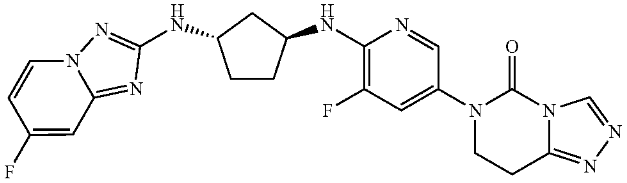 [SMILES: O=C1N(c2cnc(N[C@H]3CC[C@H](Nc4nc5cc(F)ccn5n4)C3)c(F)c2)CCc2nncn21] | 467.2 [M + H]+ |
| 210 | 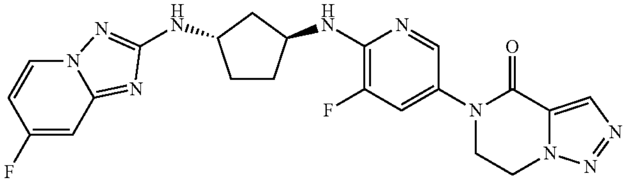 [SMILES: O=C1c2cnnn2CCN1c1cnc(N[C@H]2CC[C@H](Nc3nc4cc(F)ccn4n3)C2)c(F)c1] | 467.2 [M + H]+ |

-continued
| Examples | Structure | MS m/z (ESI) |
|---|---|---|
| 211 | 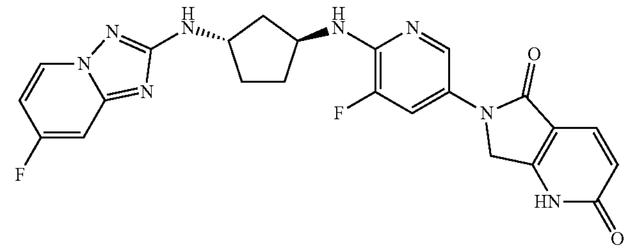 [SMILES: O=C1c2ccc(=O)[nH]c2CN1c1cnc(N[C@H]2CC[C@H](Nc3nc4cc(F)ccn4n3)C2)c(F)c1] | 479.2 [M + H]$^+$ |
| 212 | 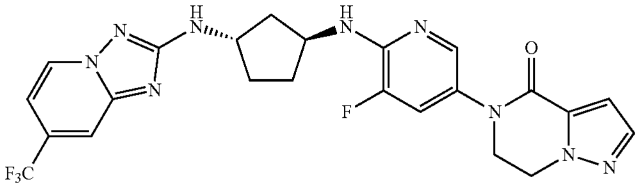 | 516.2 [M + H]$^+$. |
| 213 | 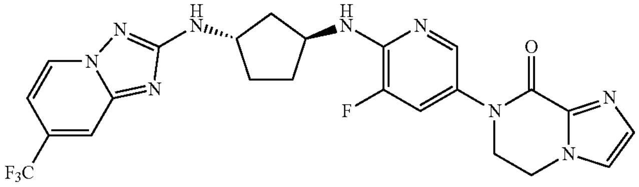 | 516.2 [M + H]$^+$. |
| 214 | 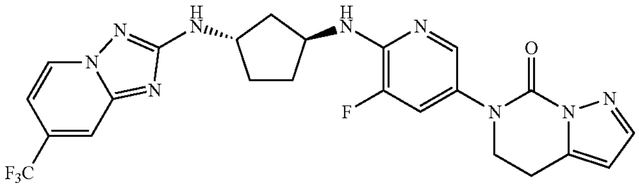 [SMILES: O=C1N(c2cnc(N[C@H]3CC[C@H](Nc4nc5cc(C(F)(F)F)ccn5n4)C3)c(F)c2)CCc2ccnn21] | 516.2 [M + H]+ |
| 215 | 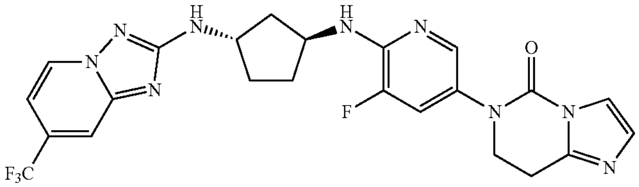 | 516.2 [M + H]$^+$ |
| 216 | 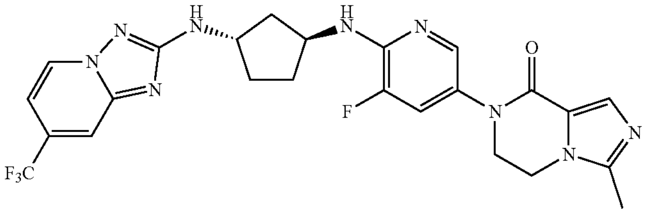 [SMILES: Cc1ncc2n1CCN(c1cnc(N[C@H]3CC[C@H](Nc4nc5cc(C(F)(F)F)ccn5n4)C3)c(F)c1)C2=O] | 530.2 [M + H]$^+$ |
| 217 | 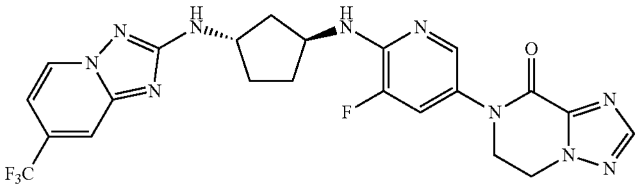 | 517.2 [M + H]$^+$ |

-continued
| Examples | Structure | MS m/z (ESI) |
| --- | --- | --- |
| 218 | 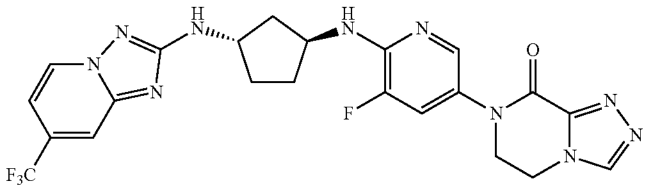 [SMILES: O=C1c2nncn2CCN1c1cnc(N[C@H]2CC[C@H](Nc3nc4cc(C(F)(F)F)ccn4n3)C2)c(F)c1] | 517.2 [M + H]+ |
| 219 | 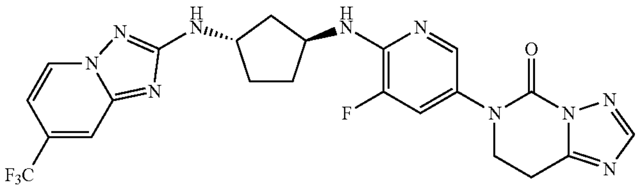 | 517.2 [M + H]+ |
| 220 | 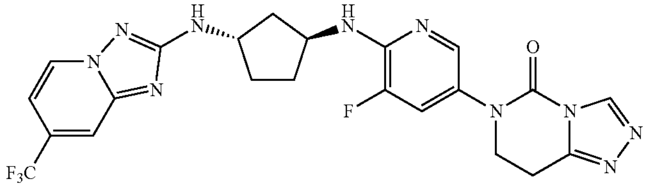 [SMILES: O=C1N(c2cnc(N[C@H]3CC[C@H](Nc4nc5cc(C(F)(F)F)ccn5n4)C3)c(F)c2)CCc2nncn21] | 517.2 [M + H]+ |
| 221 | 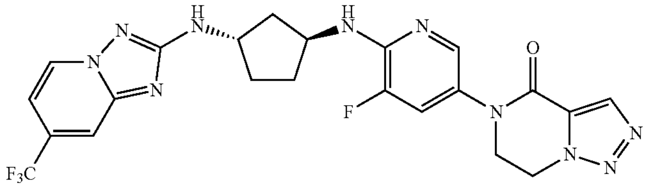 [SMILES: O=C1c2cnnn2CCN1c1cnc(N[C@H]2CC[C@H](Nc3nc4cc(C(F)(F)F)ccn4n3)C2)c(F)c1] | 417.2 [M + H]+ |
| 222 | 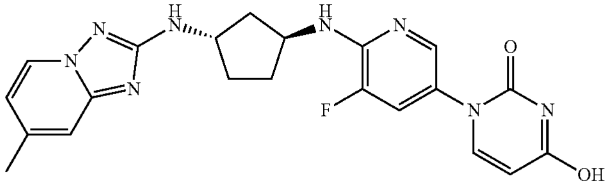 | 437.2 [M + H]+ |
| 223 | 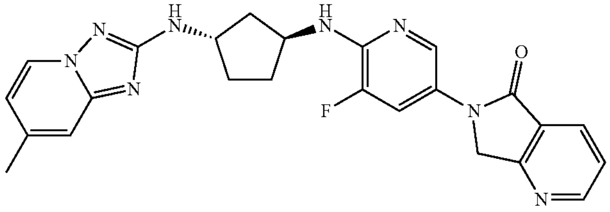 [SMILES: Cc1ccn2nc(N[C@H]3CC[C@H](Nc4ncc(N5Cc6ncccc6C5=O)cc4F)C3)nc2c1] | 459.2 [M + H]+ |
| 224 | 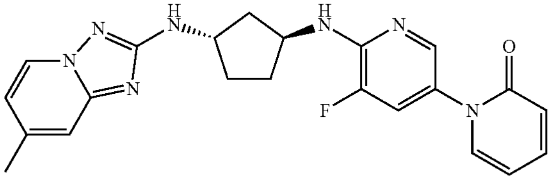 [SMILES: Cc1ccn2nc(N[C@H]3CC[C@H](Nc4ncc(-n5ccccc5=O)cc4F)C3)nc2c1] | 420.2 [M + H]+ |

-continued
| Examples | Structure | MS m/z (ESI) |
|---|---|---|
| 225 | 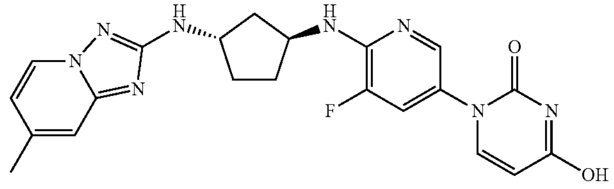 [SMILES: Cc1ccn2nc(N[C@H]3CC[C@H](Nc4ncc(-n5ccc(O)nc5=O)cc4F)C3)nc2c1] | 437.2 [M + H]$^+$ |
| 226 | 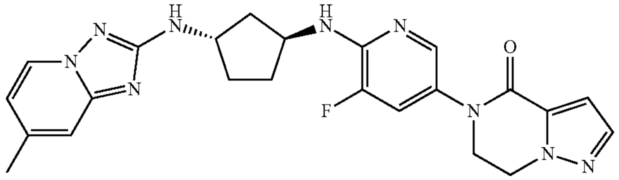 | 462.2 [M + H]$^+$ |
| 227 | 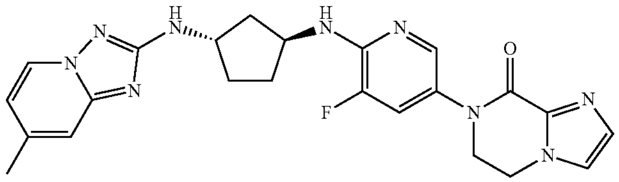 [SMILES: Cc1ccn2nc(N[C@H]3CC[C@H](Nc4ncc(N5CCn6ccnc6C5=O)cc4F)C3)nc2c1] | 462.2 [M + H]$^+$ |
| 228 | 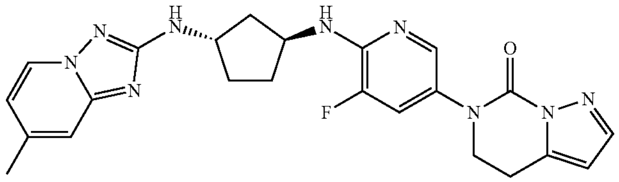 [SMILES: Cc1ccn2nc(N[C@H]3CC[C@H](Nc4ncc(N5CCc6ccnn6C5=O)cc4F)C3)nc2c1] | 462.2 [M + H]$^+$ |
| 229 | 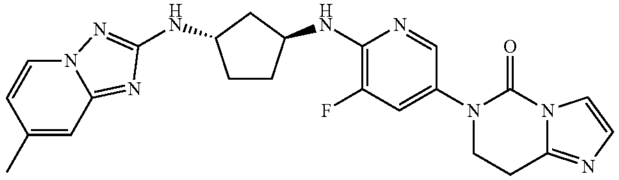 [SMILES: Cc1ccn2nc(N[C@H]3CC[C@H](Nc4ncc(N5CCc6nccn6C5=O)cc4F)C3)nc2c1] | 462.2 [M + H]$^+$ |
| 230 | 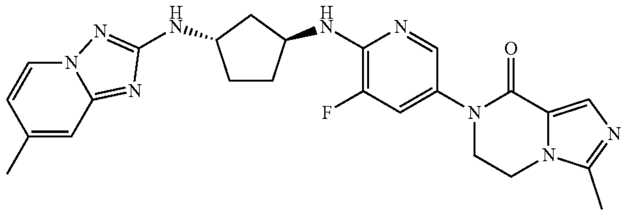 [SMILES: Cc1ccn2nc(N[C@H]3CC[C@H](Nc4ncc(N5CCn6c(cnc6C)C5=O)cc4F)C3)nc2c1] | 476.2 [M + H]$^+$ |
| 231 | 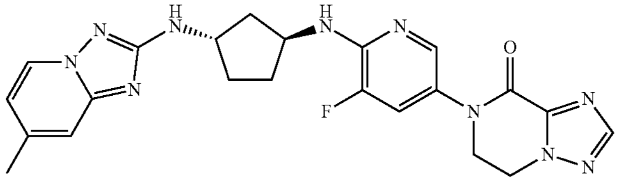 [SMILES: Cc1ccn2nc(N[C@H]3CC[C@H](Nc4ncc(N5CCn6ncnc6C5=O)cc4F)C3)nc2c1] | 463.2 [M + H]$^+$ |
| 232 | 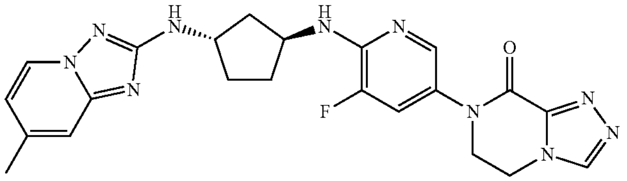 [SMILES: Cc1ccn2nc(N[C@H]3CC[C@H](Nc4ncc(N5CCn6cnnc6C5=O)cc4F)C3)nc2c1] | 463.2 [M + H]$^+$ |

-continued
| Examples | Structure | MS m/z (ESI) |
|---|---|---|
| 233 | 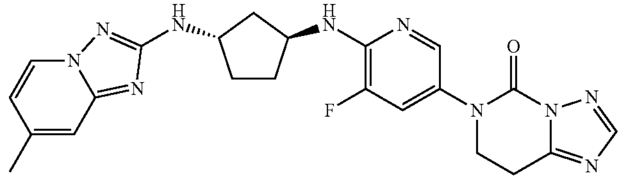 [SMILES: Cc1ccn2nc(N[C@H]3CC[C@H](Nc4ncc(N5CCc6ncnn6C5=O)cc4F)C3)nc2c1] | 463.2 [M + H]$^+$ |
| 234 | 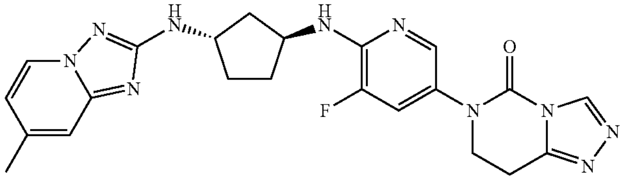 [SMILES: Cc1ccn2nc(N[C@H]3CC[C@H](Nc4ncc(N5CCc6nncn6C5=O)cc4F)C3)nc2c1] | 463.2 [M + H]$^+$ |
| 235 | 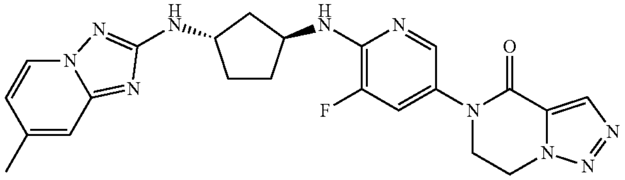 [SMILES: Cc1ccn2nc(N[C@H]3CC[C@H](Nc4ncc(N5CCn6nncc6C5=O)cc4F)C3)nc2c1] | 463.2 [M + H]$^+$ |
| 236 | 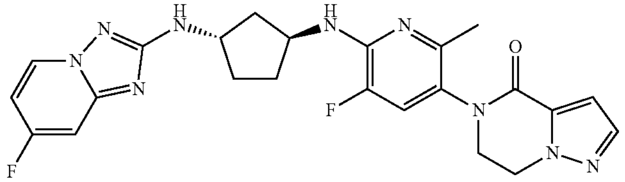 [SMILES: Cc1nc(N[C@H]2CC[C@H](Nc3nc4cc(F)ccn4n3)C2)c(F)cc1N1CCn2nccc2C1=O] | 480.2 [M + H]$^+$ |
| 237 | 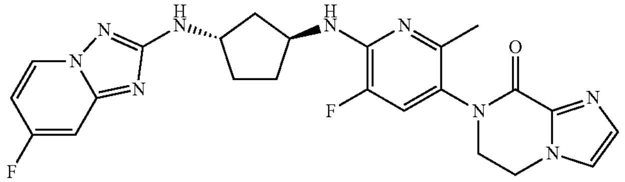 [SMILES: Cc1nc(N[C@H]2CC[C@H](Nc3nc4cc(F)ccn4n3)C2)c(F)cc1N1CCn2ccnc2C1=O] | 480.2 [M + H]$^+$ |
| 238 | 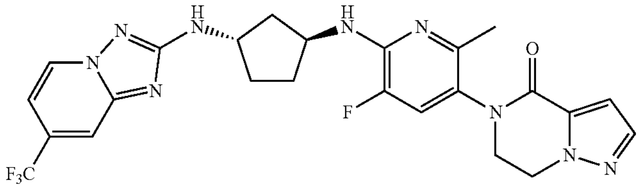 [SMILES: Cc1nc(N[C@H]2CC[C@H](Nc3nc4cc(C(F)(F)F)ccn4n3)C2)c(F)cc1N1CCn2nccc2C1=O] | 530.2 [M + H]$^+$ |
| 239 | 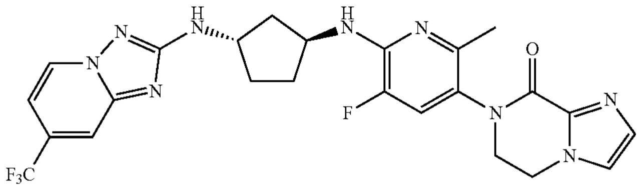 [SMILES: Cc1nc(N[C@H]2CC[C@H](Nc3nc4cc(C(F)(F)F)ccn4n3)C2)c(F)cc1N1CCn2ccnc2C1=O] | 530.2 [M + H]$^+$ |

-continued
| Examples | Structure | MS m/z (ESI) |
|---|---|---|
| 240 | 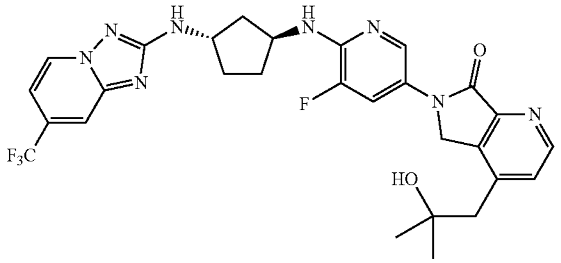 [SMILES: CC(C)(O)Cc1ccnc2c1CN(c1cnc(N[C@H]3CC[C@H](Nc4nc5cc(C(F)(F)F)ccn5n4)C3)c(F)c1)C2=O] | 585.2 [M + H]+ |
| 241 | 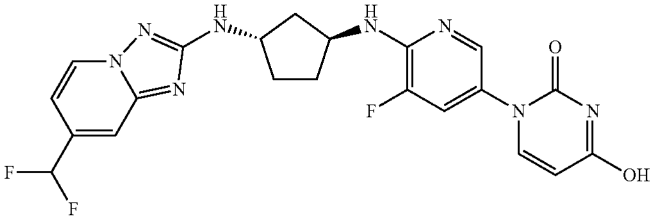 | 473.2 [M + H]+ |
| 242 | 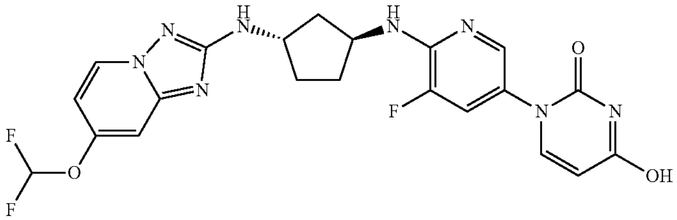 | 489.2 [M + H]+ |
| 243 | 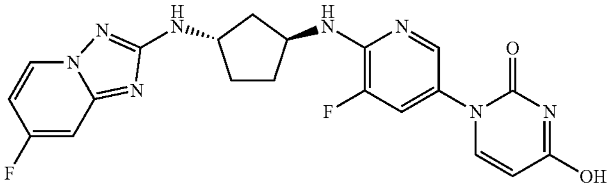 | 441.2 [M + H]+ |
| 244 | 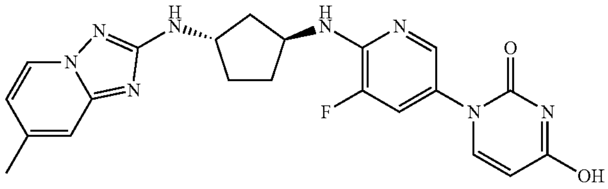 | 437.2 [M + H]+ |
| 245 | 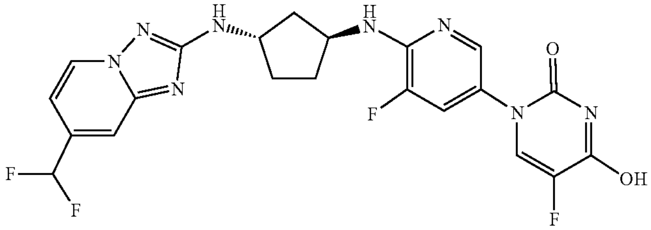 [SMILES: O=c1nc(O)c(F)cn1-c1cnc(N[C@H]2CC[C@H](Nc3nc4cc(C(F)F)ccn4n3)C2)c(F)c1] | 491.2 [M + H]+ |

-continued
| Examples | Structure | MS m/z (ESI) |
|---|---|---|
| 246 | 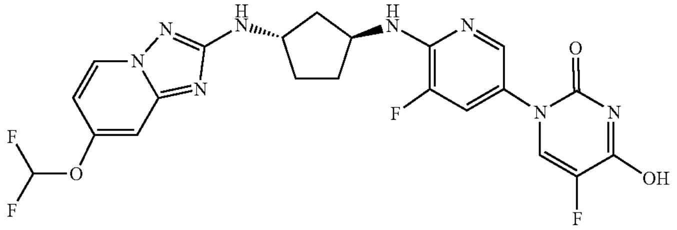 [SMILES: O=c1nc(O)c(F)cn1-c1cnc(N[C@H]2CC[C@H](Nc3nc4cc(OC(F)F)ccn4n3)C2)c(F)c1] | 507.1 [M + H]+ |
| 247 | 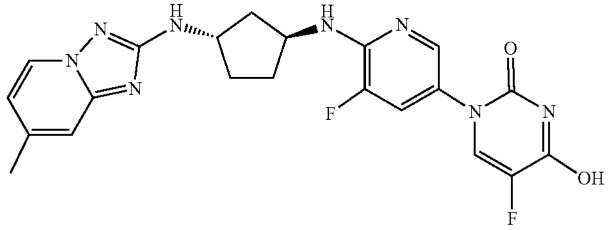 [SMILES: Cc1ccn2nc(N[C@H]3CC[C@H](Nc4ncc(-n5cc(F)c(O)nc5=O)cc4F)C3)nc2c1] | 455.2 [M + H]+ |
| 248 | 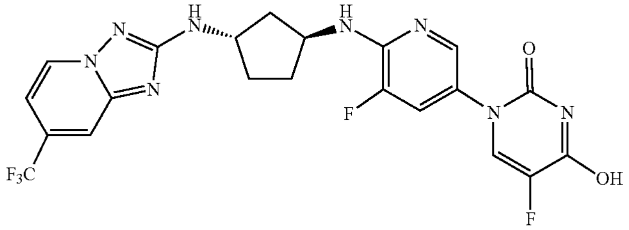 | 509.1 [M + H]+ |
| 249 | 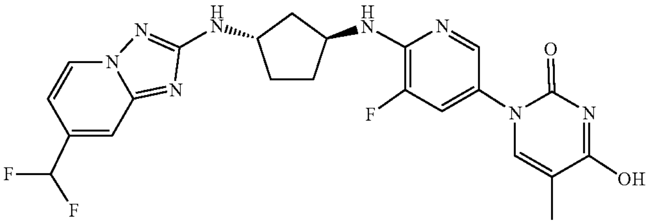 [SMILES: Cc1cn(-c2cnc(N[C@H]3CC[C@H](Nc4nc5cc(C(F)F)ccn5n4)C3)c(F)c2)c(=O)nc1O] | 487.2 [M + H]+ |
| 250 | 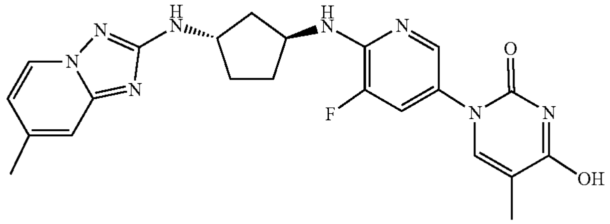 [SMILES: Cc1ccn2nc(N[C@H]3CC[C@H](Nc4ncc(-n5cc(C)c(O)nc5=O)cc4F)C3)nc2c1] | 451.2 [M + H]+ |
| 251 | 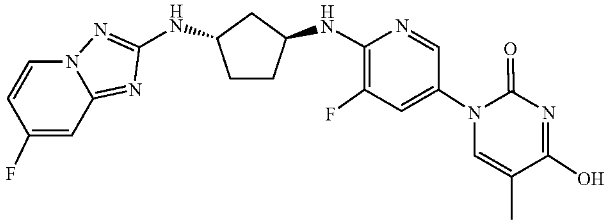 | 456.2 [M + H]+ |

-continued
| Examples | Structure | MS m/z (ESI) |
|---|---|---|
| 252 | 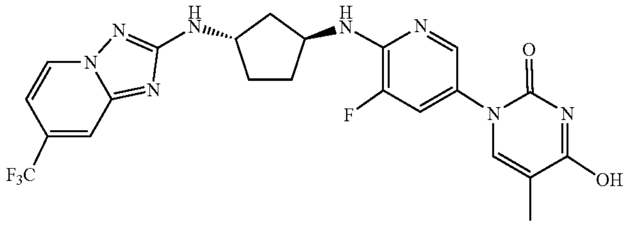 | 505.2 [M + H]+ |
| 253 | 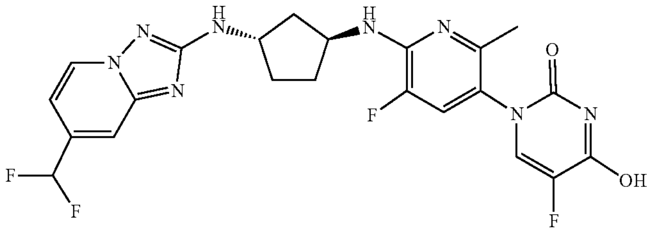 [SMILES: Cc1nc(N[C@H]2CC[C@H](Nc3nc4cc(C(F)F)ccn4n3)C2)c(F)cc1-n1cc(F)c(O)nc1=O] | 505.2 [M + H]+ |
| 254 | 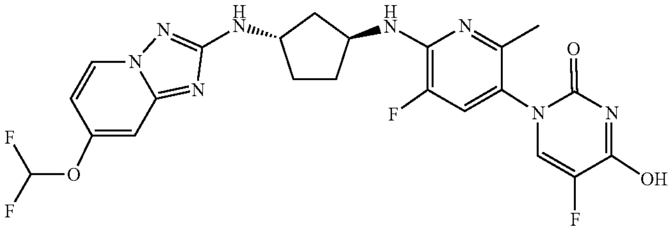 [SMILES: Cc1nc(N[C@H]2CC[C@H](Nc3nc4cc(OC(F)F)ccn4n3)C2)c(F)cc1-n1cc(F)c(O)nc1=O] | 521.2 [M + H]+ |
| 255 | 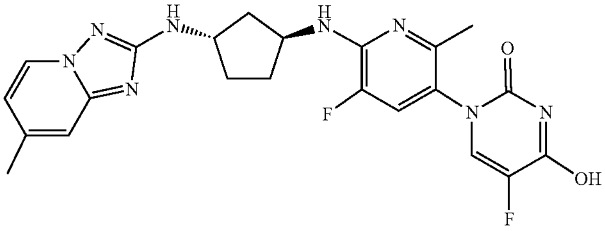 | 469.2 [M + H]+ |
| 256 | 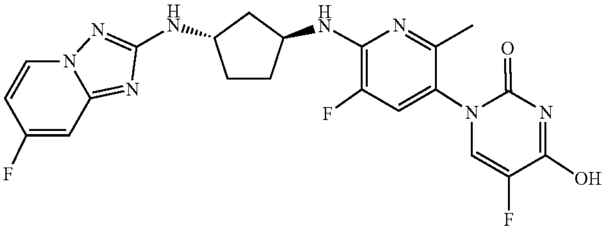 [SMILES: Cc1nc(N[C@H]2CC[C@H](Nc3nc4cc(F)ccn4n3)C2)c(F)cc1-n1cc(F)c(O)nc1=O] | 473.2 [M + H]+ |
| 257 | 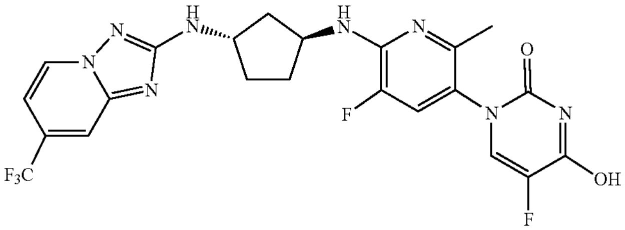 [SMILES: Cc1nc(N[C@H]2CC[C@H](Nc3nc4cc(C(F)(F)F)ccn4n3)C2)c(F)cc1-n1cc(F)c(O)nc1=O] | 523.2 [M + H]+ |

-continued
| Examples | Structure | MS m/z (ESI) |
|---|---|---|
| 258 | 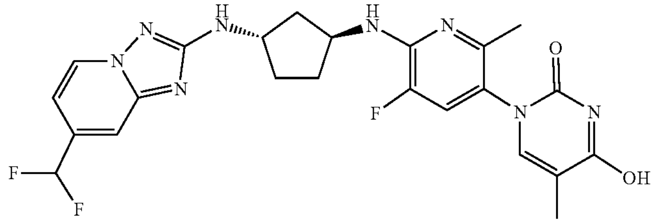 [SMILES: Cc1cn(-c2cc(F)c(N[C@H]3CC[C@H](Nc4nc5cc(C(F)F)ccn5n4)C3)nc2C)c(=O)nc1O] | 501.2 [M + H]+ |
| 259 | 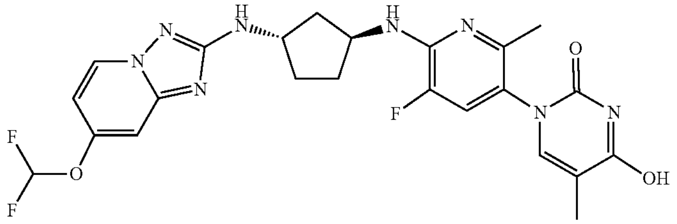 [SMILES: Cc1cn(-c2cc(F)c(N[C@H]3CC[C@H](Nc4nc5cc(OC(F)F)ccn5n4)C3)nc2C)c(=O)nc1O] | 517.2 [M + H]+ |
| 260 | 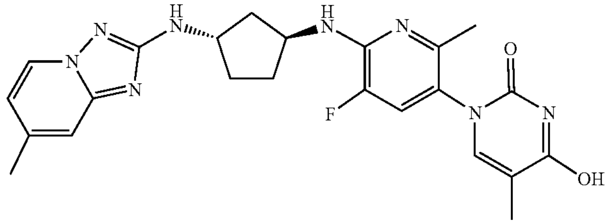 | 465.2 [M + H]+ |
| 261 | 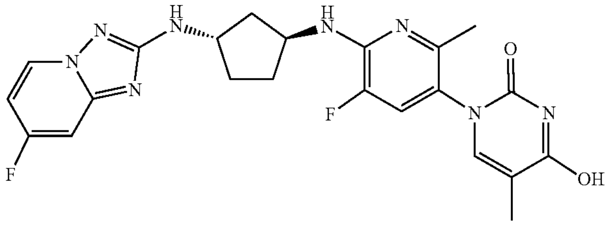 | 469.2 [M + H]+ |
| 262 | 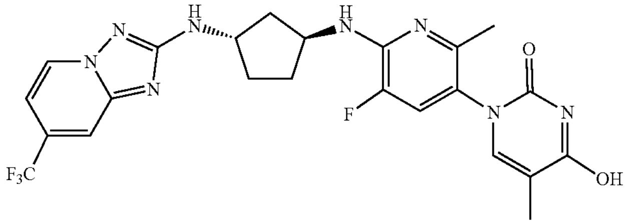 [SMILES: Cc1cn(-c2cc(F)c(N[C@H]3CC[C@H](Nc4nc5cc(C(F)(F)F)ccn5n4)C3)nc2C)c(=O)nc1O] | 519.2 [M + H]+ |
| 263 | 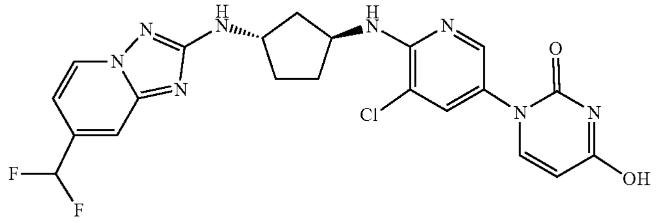 [SMILES: O=c1nc(O)ccn1-c1cnc(N[C@H]2CC[C@H](Nc3nc4cc(C(F)F)ccn4n3)C2)c(Cl)c1] | 489.1 [M + H]+ |

-continued
| Examples | Structure | MS m/z (ESI) |
|---|---|---|
| 264 | 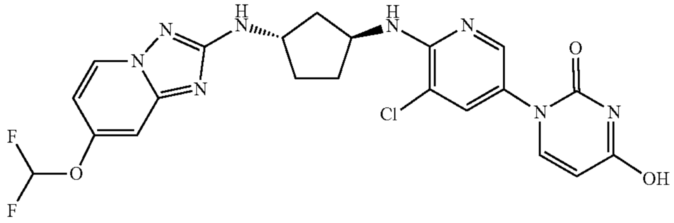 [SMILES: O=c1nc(O)ccn1-c1cnc(N[C@H]2CC[C@H](Nc3nc4cc(OC(F)F)ccn4n3)C2)c(Cl)c1] | 505.1 [M + H]+ |
| 265 | 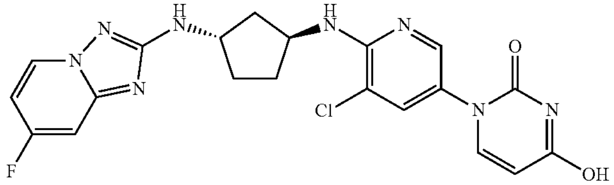 | 457.1 [M + H]+ |
| 266 | 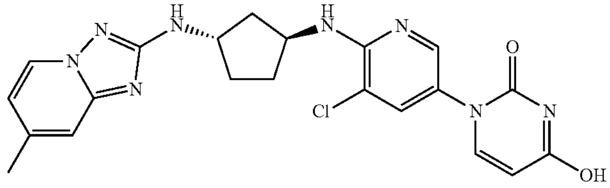 [SMILES: Cc1ccn2nc(N[C@H]3CC[C@H](Nc4ncc(-n5ccc(O)nc5=O)cc4Cl)C3)nc2c1] | 453.2 [M + H]+ |
| 267 | 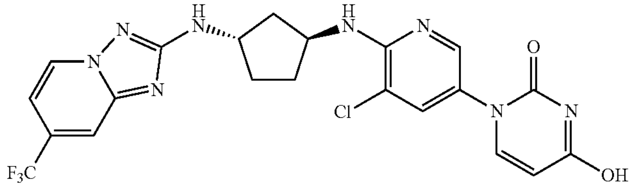 | 507.1 [M + H]+ |
| 268 | 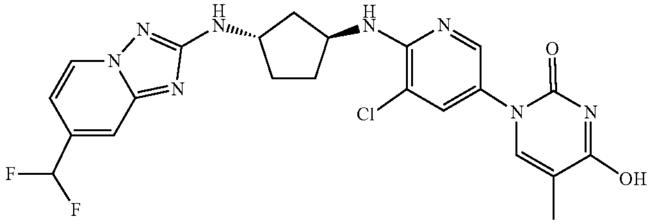 [SMILES: Cc1cn(-c2cnc(N[C@H]3CC[C@H](Nc4nc5cc(C(F)F)ccn5n4)C3)c(Cl)c2)c(=O)nc1O] | 503.1 [M + H]+ |
| 269 | 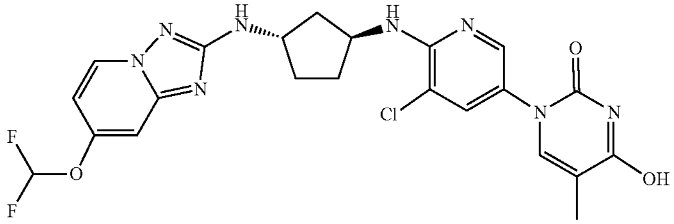 [SMILES: Cc1cn(-c2cnc(N[C@H]3CC[C@H](Nc4nc5cc(OC(F)F)ccn5n4)C3)c(Cl)c2)c(=O)nc1O] | 519.1 [M + H]+ |
| 270 | 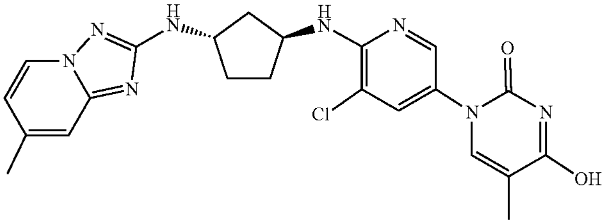 | 467.2 [M + H]+ |

-continued
| Examples | Structure | MS m/z (ESI) |
|---|---|---|
| 271 | 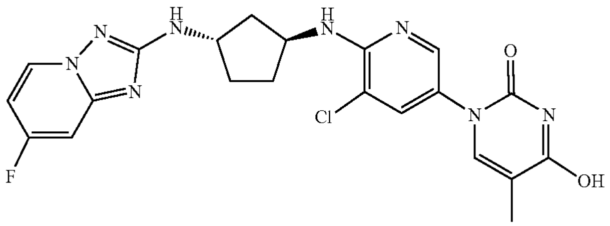 | 471.1 [M + H]+ |
| 272 | 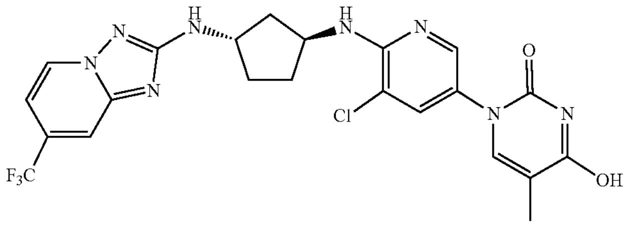 [SMILES: Cc1cn(-c2cnc(N[C@H]3CC[C@H](Nc4nc5cc(C(F)(F)F)ccn5n4)C3)c(Cl)c2)c(=O)nc1O] | 521.1 $[M + H]^+$ |
| 273 | 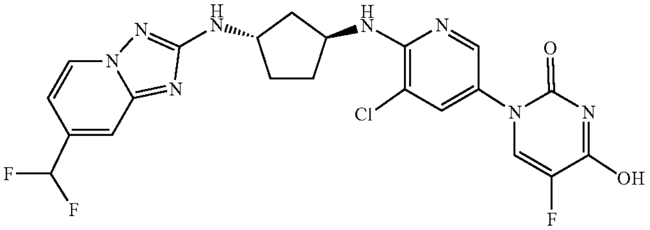 [SMILES: O=c1nc(O)c(F)cn1-c1cnc(N[C@H]2CC[C@H](Nc3nc4cc(C(F)F)ccn4n3)C2)c(Cl)c1] | 507.1 $[M + H]^+$ |
| 274 | 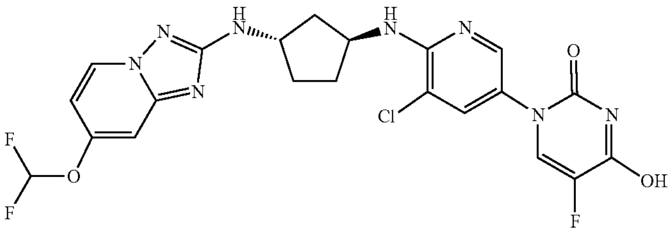 [SMILES: O=c1nc(O)c(F)cn1-c1cnc(N[C@H]2CC[C@H](Nc3nc4cc(OC(F)F)ccn4n3)C2)c(Cl)c1] | 523.1 $[M + H]^+$ |
| 275 | 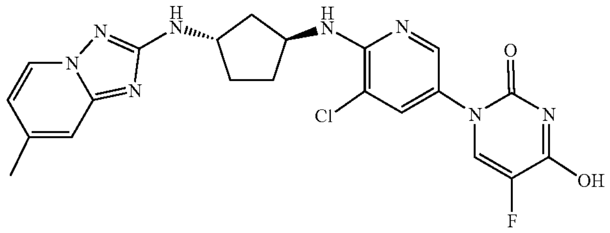 | 471.1 $[M + H]^+$ |
| 276 | 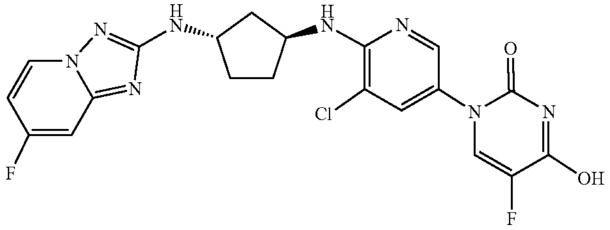 [SMILES: O=c1nc(O)c(F)cn1-c1cnc(N[C@H]2CC[C@H](Nc3nc4cc(F)ccn4n3)C2)c(Cl)c1] | 475.1 $[M + H]^+$ |

-continued
| Examples | Structure | MS m/z (ESI) |
| --- | --- | --- |
| 277 | 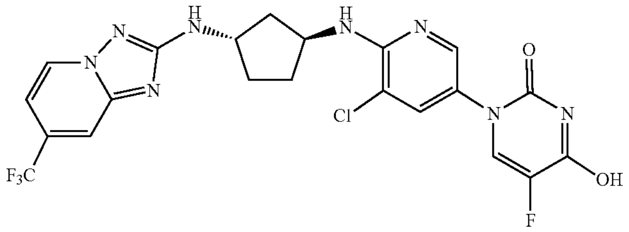 | 525.1 [M + H]+ |
| 278 | 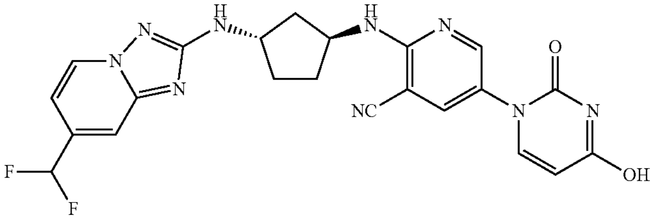 [SMILES: N#Cc1cc(-n2ccc(O)nc2=O)cnc1N[C@H]1CC[C@H](Nc2nc3cc(C(F)F)ccn3n2)C1] | 480.2 [M + H]+ |
| 279 | 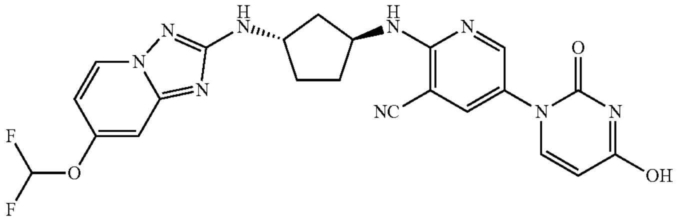 [SMILES: N#Cc1cc(-n2ccc(O)nc2=O)cnc1N[C@H]1CC[C@H](Nc2nc3cc(OC(F)F)ccn3n2)C1] | 496.2 [M + H]+ |
| 280 | 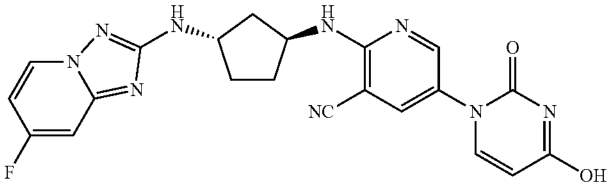 [SMILES: N#Cc1cc(-n2ccc(O)nc2=O)cnc1N[C@H]1CC[C@H](Nc2nc3cc(F)ccn3n2)C1] | 448.2 [M + H]+ |
| 281 | 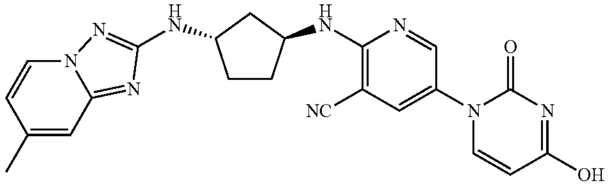 | 444.2 [M + H]+ |
| 282 | 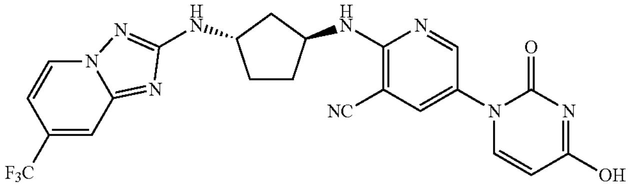 [SMILES: N#Cc1cc(-n2ccc(O)nc2=O)cnc1N[C@H]1CC[C@H](Nc2nc3cc(C(F)(F)F)ccn3n2)C1] | 498.2 [M + H]+ |
| 283 | 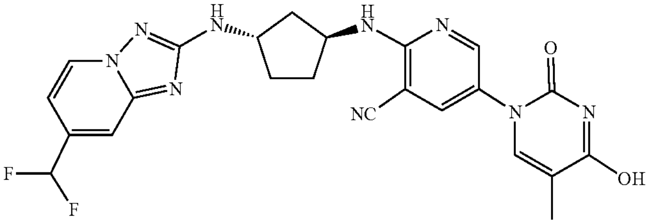 [SMILES: Cc1cn(-c2cnc(N[C@H]3CC[C@H](Nc4nc5cc(C(F)F)ccn5n4)C3)c(C#N)c2)c(=O)nc1O] | 494.2 [M + H]+ |

-continued
| Examples | Structure | MS m/z (ESI) |
|---|---|---|
| 284 | 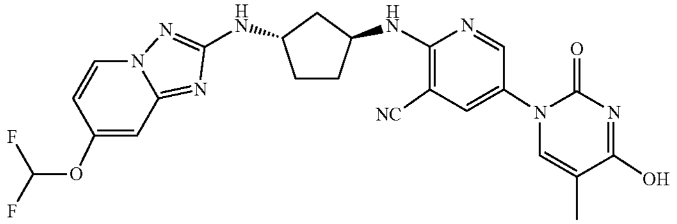 | 510.2 [M + H]$^+$ |
| 285 | 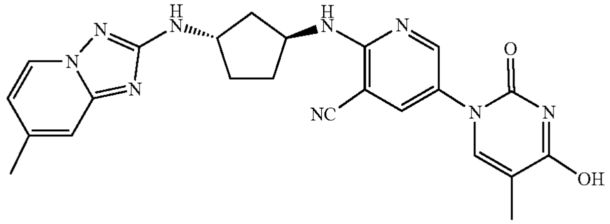 | 458.2 [M + H]$^+$ |
| 286 | 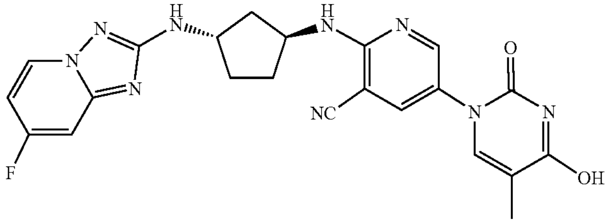 | 462.2 [M + H]$^+$ |
| 287 | 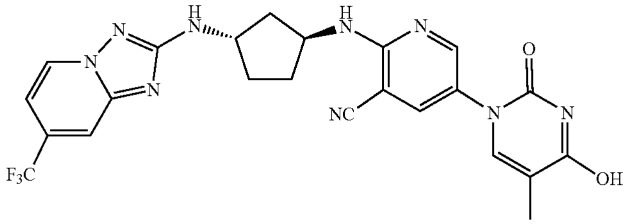 | 512.2 [M + H]$^+$ |
| 288 | 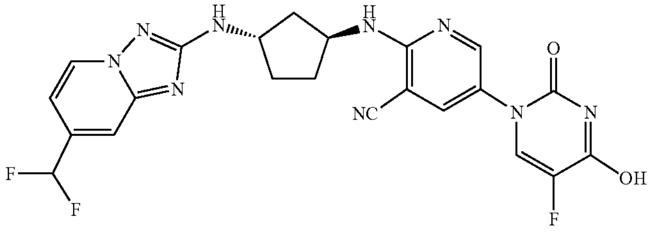 | 498.2 [M + H]$^+$ |
| 289 | 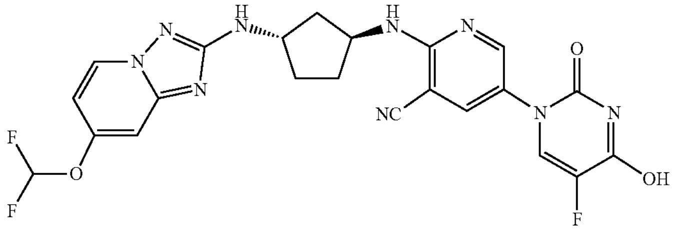 [SMILES: N#Cc1cc(-n2cc(F)c(O)nc2=O)cnc1N[C@H]1CC[C@H](Nc2nc3cc(OC(F)F)ccn3n2)C1] | 514.2 [M + H]$^+$ |

-continued
| Examples | Structure | MS m/z (ESI) |
| --- | --- | --- |
| 290 | 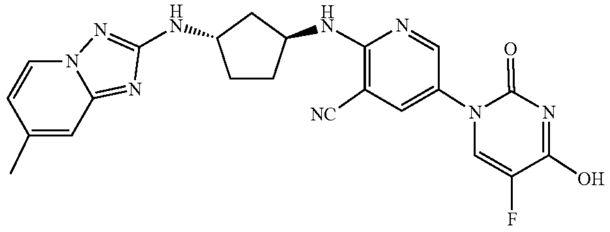 | 462.2 [M + H]+ |
| 291 | 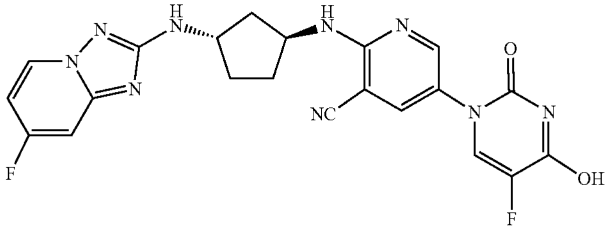 | 466.2 [M + H]+ |
| 292 | 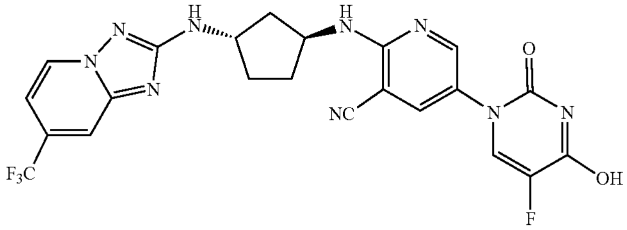 | 516.1 [M + H]+ |
| 293 | 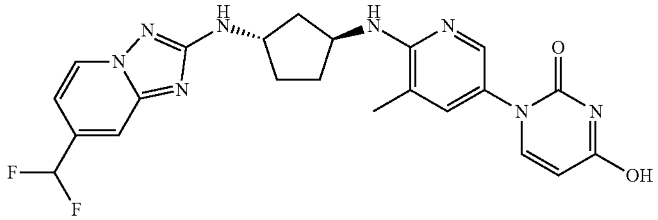 [SMILES: Cc1cc(-n2ccc(O)nc2=O)cnc1N[C@H]1CC[C@H](Nc2nc3cc(C(F)F)ccn3n2)C1] | 469.2 [M + H]+ |
| 294 | 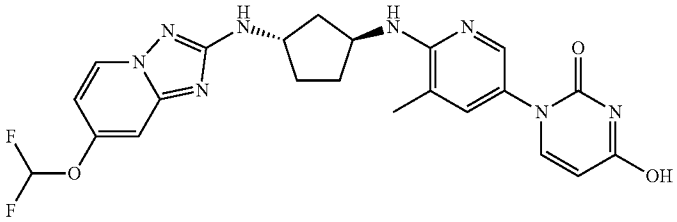 [SMILES: Cc1cc(-n2ccc(O)nc2=O)cnc1N[C@H]1CC[C@H](Nc2nc3cc(OC(F)F)ccn3n2)C1] | 485.2 [M + H]+ |
| 295 | 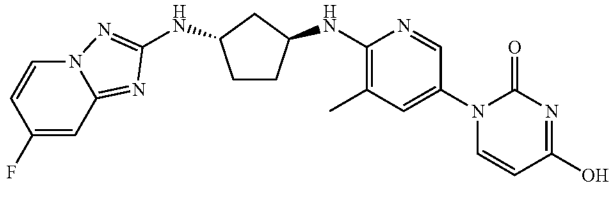 [SMILES: Cc1cc(-n2ccc(O)nc2=O)cnc1N[C@H]1CC[C@H](Nc2nc3cc(F)ccn3n2)C1] | 437.2 [M + H]+ |
| 296 | 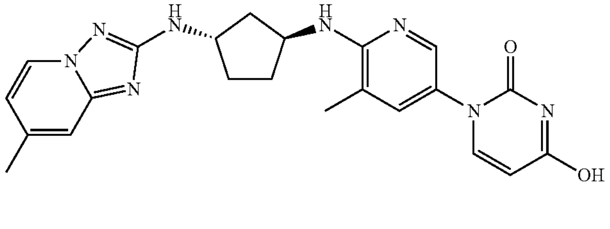 [SMILES: Cc1ccn2nc(N[C@H]3CC[C@H](Nc4ncc(-n5ccc(O)nc5=O)cc4C)C3)nc2c1] | 433.2 [M + H]+ |

-continued
| Examples | Structure | MS m/z (ESI) |
| --- | --- | --- |
| 297 | 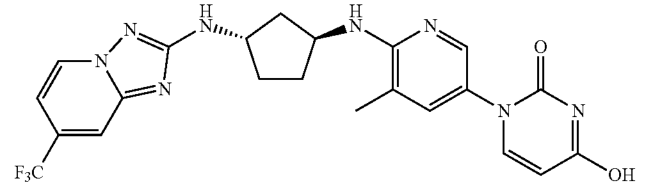 [SMILES: Cc1cc(-n2ccc(O)nc2=O)cnc1N[C@H]1CC[C@H](Nc2nc3cc(C(F)(F)F)ccn3n2)C1] | 487.2 [M + H]+ |
| 298 | 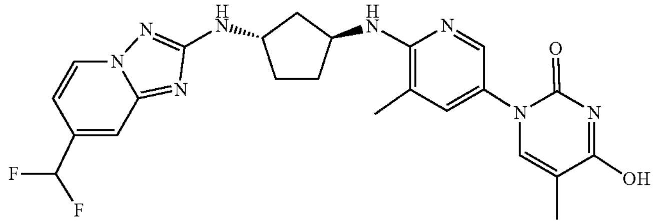 | 483.2 [M + H]+ |
| 299 | 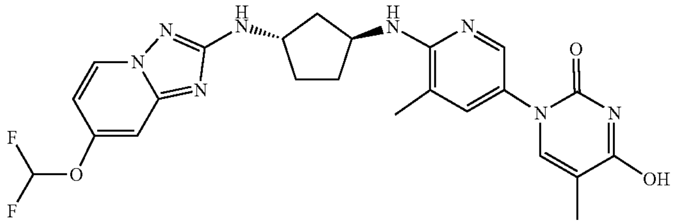 | 499.2 [M + H]+ |
| 300 | 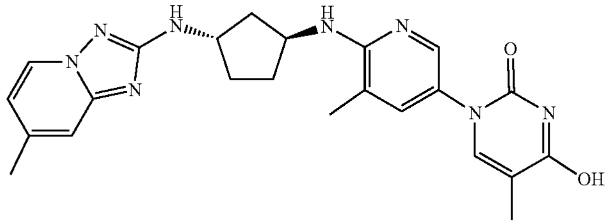 | 447.2 [M + H]+ |
| 301 | 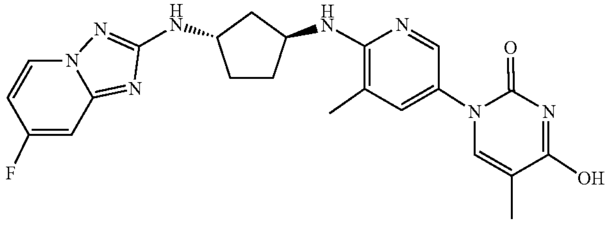 | 451.2 [M + H]+ |
| 302 | 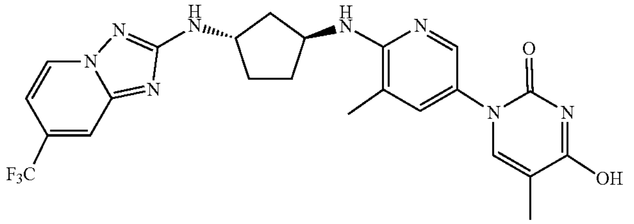 [SMILES: Cc1cn(-c2cnc(N[C@H]3CC[C@H](Nc4nc5cc(C(F)(F)F)ccn5n4)C3)c(C)c2)c(=O)nc1O] | 501.2 [M + H]+ |

-continued
| Examples | Structure | MS m/z (ESI) |
| --- | --- | --- |
| 303 | 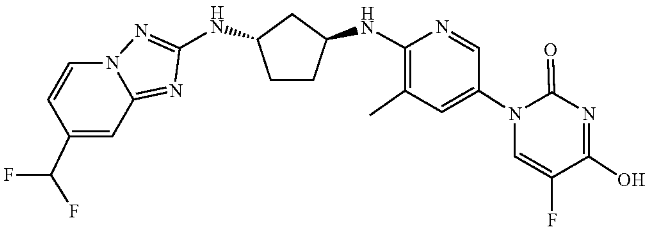 [SMILES: Cc1cc(-n2cc(F)c(O)nc2=O)cnc1N[C@H]1CC[C@H](Nc2nc3cc(C(F)F)ccn3n2)C1] | 487.2 [M + H]+ |
| 304 | 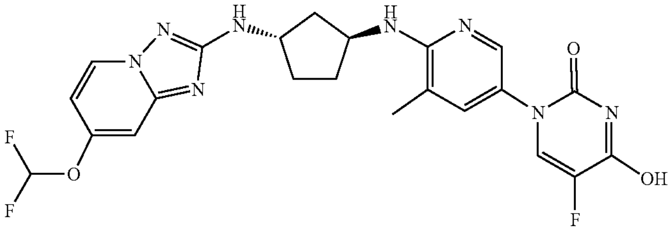 [SMILES: Cc1cc(-n2cc(F)c(O)nc2=O)cnc1N[C@H]1CC[C@H](Nc2nc3cc(OC(F)F)ccn3n2)C1] | 503.2 [M + H]+ |
| 305 | 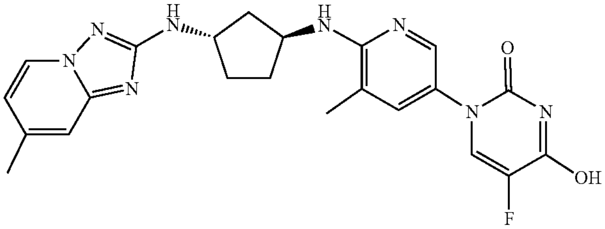 | 451.2 [M + H]+ |
| 306 | 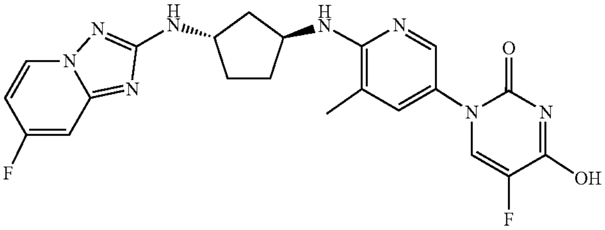 | 455.2 [M + H]+ |
| 307 | 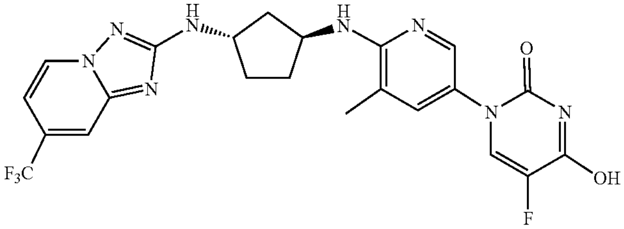 [SMILES: Cc1cc(-n2cc(F)c(O)nc2=O)cnc1N[C@H]1CC[C@H](Nc2nc3cc(C(F)(F)F)ccn3n2)C1] | 505.2 [M + H]+ |
| 308 | 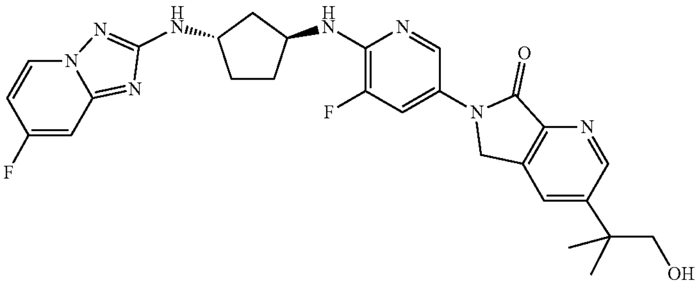 [SMILES: CC(C)(CO)c1cnc2c(c1)CN(c1cnc(N[C@H]3CC[C@H](Nc4nc5cc(F)ccn5n4)C3)c(F)c1)C2=O] | 535.2 [M + H]+ |

-continued
| Examples | Structure | MS m/z (ESI) |
| --- | --- | --- |
| 309 | 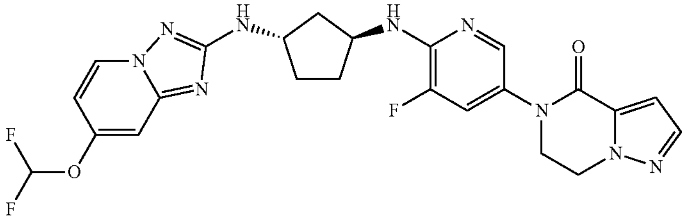 [SMILES: O=C1c2ccnn2CCN1c1cnc(N[C@H]2CC[C@H](Nc3nc4cc(OC(F)F)ccn4n3)C2)c(F)c1] | 514.2 [M + H]+ |
| 310 | 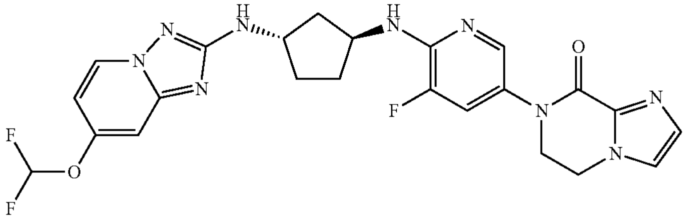 [SMILES: O=C1c2nccn2CCN1c1cnc(N[C@H]2CC[C@H](Nc3nc4cc(OC(F)F)ccn4n3)C2)c(F)c1] | 514.2 [M + H]+ |
| 311 | 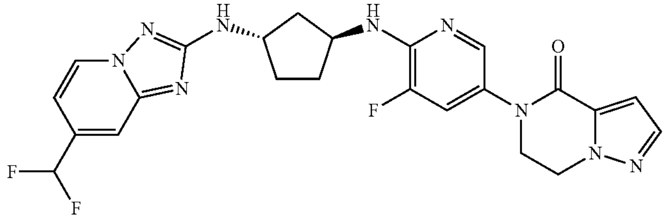 [SMILES: O=C1c2ccnn2CCN1c1cnc(N[C@H]2CC[C@H](Nc3nc4cc(C(F)F)ccn4n3)C2)c(F)c1] | 498.2 [M + H]+ |
| 312 | 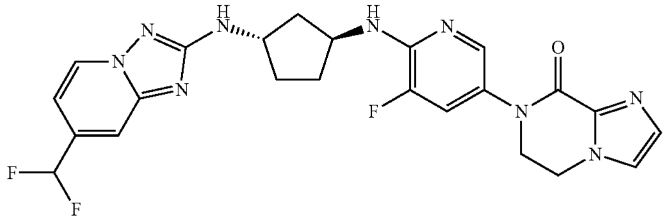 [SMILES: O=C1c2nccn2CCN1c1cnc(N[C@H]2CC[C@H](Nc3nc4cc(C(F)F)ccn4n3)C2)c(F)c1] | 498.2 [M + H]+ |
| 313 | 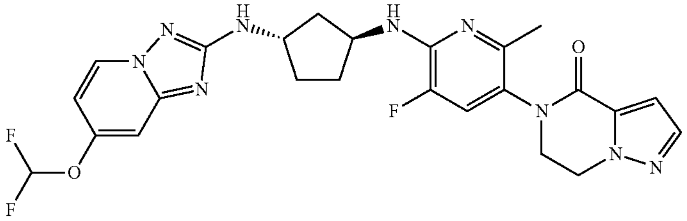 [SMILES: Cc1nc(N[C@H]2CC[C@H](Nc3nc4cc(OC(F)F)ccn4n3)C2)c(F)cc1N1CCn2nccc2C1=O] | 528.2 [M + H]+ |
| 314 | 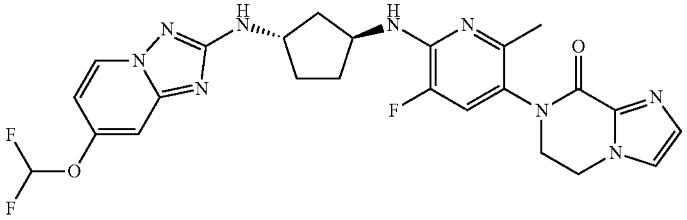 [SMILES: Cc1nc(N[C@H]2CC[C@H](Nc3nc4cc(OC(F)F)ccn4n3)C2)c(F)cc1N1CCn2ccnc2C1=O] | 528.2 [M + H]+ |

-continued
| Examples | Structure | MS m/z (ESI) |
|---|---|---|
| 315 | 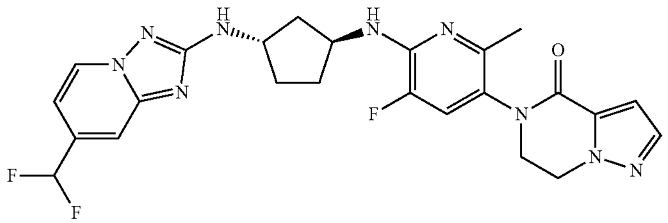 [SMILES: Cc1nc(N[C@H]2CC[C@H](Nc3nc4cc(C(F)F)ccn4n3)C2)c(F)cc1N1CCn2nccc2C1=O] | 512.2 [M + H]+ |
| 316 | 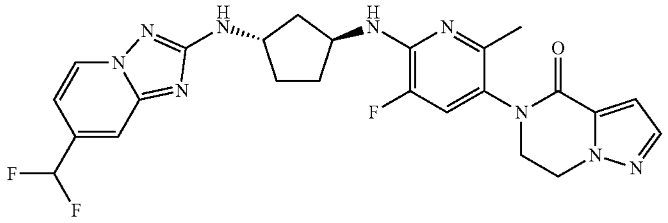 [SMILES: Cc1nc(N[C@H]2CC[C@H](Nc3nc4cc(C(F)F)ccn4n3)C2)c(F)cc1N1CCn2nccc2C1=O] | 512.2 [M + H]+ |
| 317 | 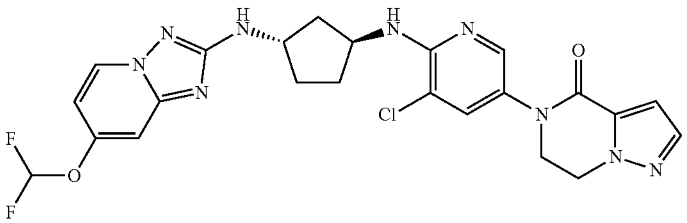 [SMILES: O=C1c2ccnn2CCN1c1cnc(N[C@H]2CC[C@H](Nc3nc4cc(OC(F)F)ccn4n3)C2)c(Cl)c1] | 530.2 [M + H]+ |
| 318 | 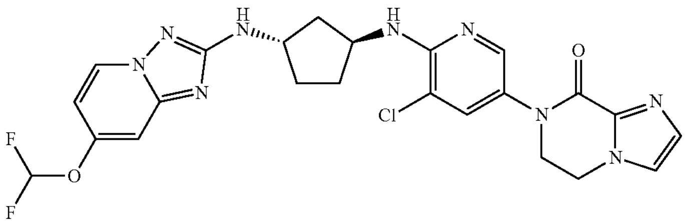 [SMILES: O=C1c2nccn2CCN1c1cnc(N[C@H]2CC[C@H](Nc3nc4cc(OC(F)F)ccn4n3)C2)c(Cl)c1] | 530.2 [M + H]+ |
| 319 | 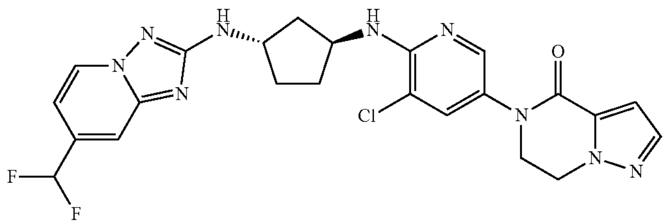 [SMILES: O=C1c2ccnn2CCN1c1cnc(N[C@H]2CC[C@H](Nc3nc4cc(C(F)F)ccn4n3)C2)c(Cl)c1] | 514.2 [M + H]+ |
| 320 | 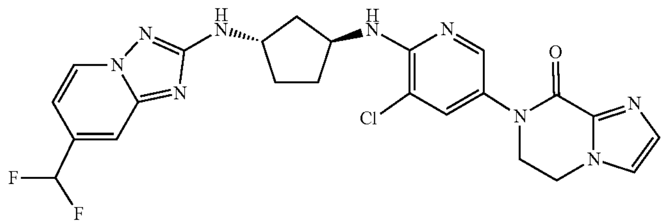 [SMILES: O=C1c2nccn2CCN1c1cnc(N[C@H]2CC[C@H](Nc3nc4cc(C(F)F)ccn4n3)C2)c(Cl)c1] | 514.2 [M + H]+ |
| 321 | 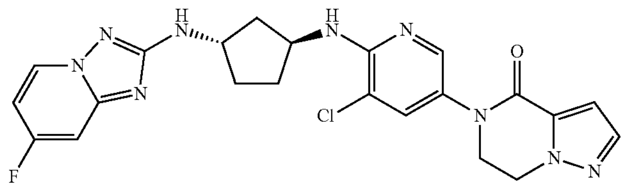 [SMILES: O=C1c2ccnn2CCN1c1cnc(N[C@H]2CC[C@H](Nc3nc4cc(F)ccn4n3)C2)c(Cl)c1] | 482.2 [M + H]+ |

-continued
| Examples | Structure | MS m/z (ESI) |
|---|---|---|
| 322 | 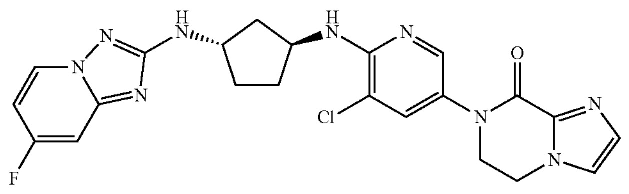 [SMILES: O=C1c2nccn2CCN1c1cnc(N[C@H]2CC[C@H](Nc3nc4cc(F)ccn4n3)C2)c(Cl)c1] | 482.2 [M + H]+ |
| 323 | 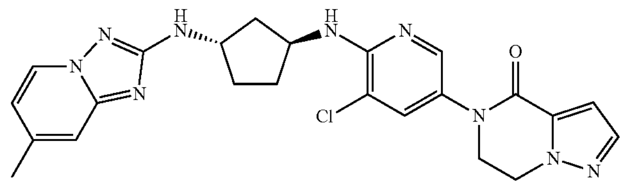 | 478.2 [M + H]+ |
| 324 | 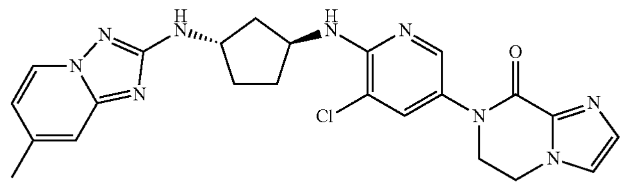 | 478.2 [M + H]+ |
| 325 | 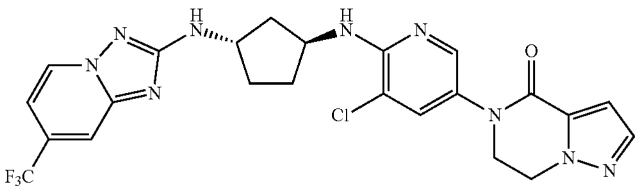 [SMILES: O=C1c2ccnn2CCN1c1cnc(N[C@H]2CC[C@H](Nc3nc4cc(C(F)(F)F)ccn4n3)C2)c(Cl)c1] | 532.2 [M + H]+ |
| 326 | 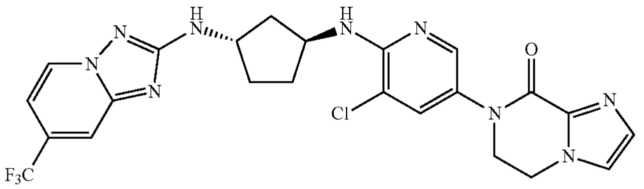 [SMILES: O=C1c2nccn2CCN1c1cnc(N[C@H]2CC[C@H](Nc3nc4cc(C(F)(F)F)ccn4n3)C2)c(Cl)c1] | 532.2 [M + H]+ |
| 327 | 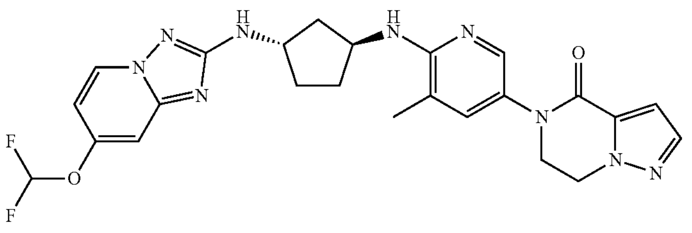 [SMILES: Cc1cc(N2CCn3nccc3C2=O)cnc1N[C@H]1CC[C@H](Nc2nc3cc(OC(F)F)ccn3n2)C1] | 510.2 [M + H]+ |
| 328 | 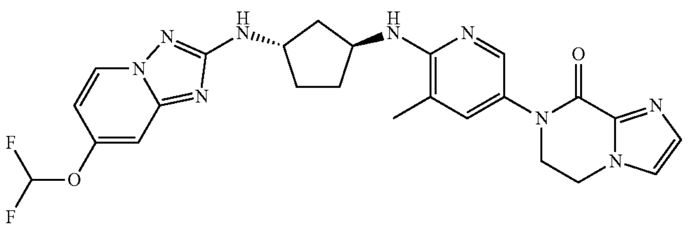 [SMILES: Cc1cc(N2CCn3ccnc3C2=O)cnc1N[C@H]1CC[C@H](Nc2nc3cc(OC(F)F)ccn3n2)C1] | 510.2 [M + H]+ |

-continued
| Examples | Structure | MS m/z (ESI) |
|---|---|---|
| 329 | 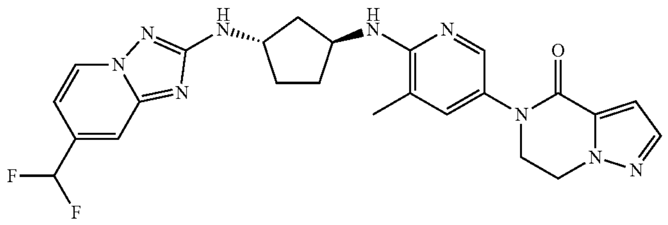 | 494.2 [M + H]$^+$ |
| 330 | 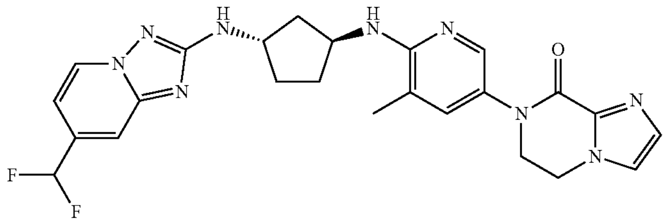 [SMILES: Cc1cc(N2CCn3ccnc3C2=O)cnc1N[C@H]1CC[C@H](Nc2nc3cc(C(F)F)ccn3n2)C1] | 494.2 [M + H]$^+$ |
| 331 | 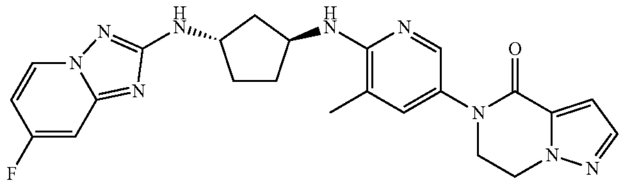 [SMILES: Cc1cc(N2CCn3nccc3C2=O)cnc1N[C@H]1CC[C@H](Nc2nc3cc(F)ccn3n2)C1] | 462.2 [M + H]$^+$ |
| 332 | 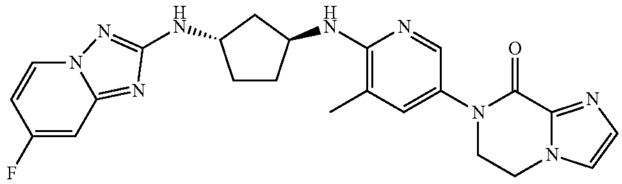 [SMILES: Cc1cc(N2CCn3ccnc3C2=O)cnc1N[C@H]1CC[C@H](Nc2nc3cc(F)ccn3n2)C1] | 462.2 [M + H]$^+$ |
| 333 | 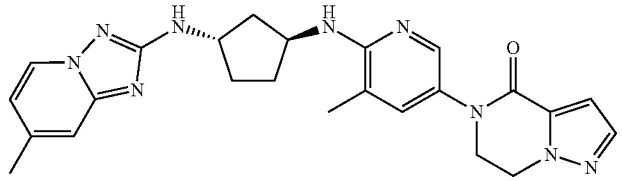 [SMILES: Cc1ccn2nc(N[C@H]3CC[C@H](Nc4ncc(N5CCn6nccc6C5=O)cc4C)C3)nc2c1] | 458.2 [M + H]$^+$ |
| 334 | 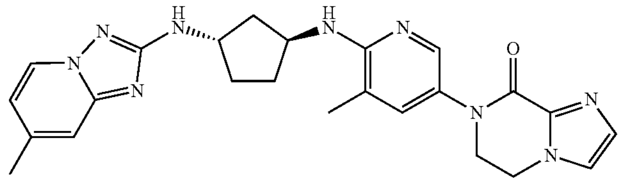 [SMILES: Cc1ccn2nc(N[C@H]3CC[C@H](Nc4ncc(N5CCn6ccnc6C5=O)cc4C)C3)nc2c1] | 458.2 [M + H]$^+$ |
| 335 | 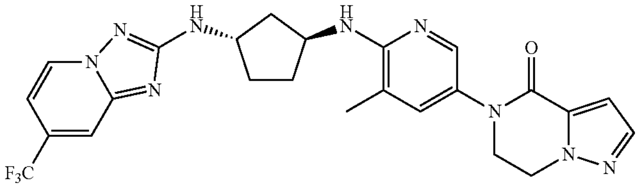 | 512.2 [M + H]$^+$ |

-continued
| Examples | Structure | MS m/z (ESI) |
| --- | --- | --- |
| 336 | 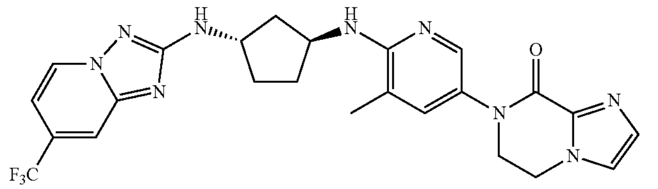 | 512.2 [M + H]+ |
| 337 | 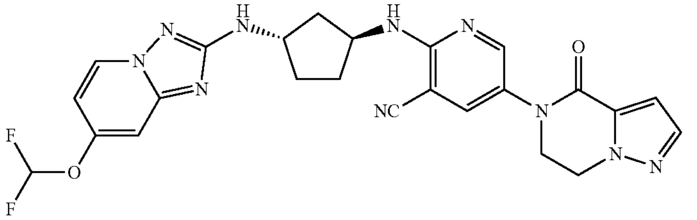 [SMILES: N#Cc1cc(N2CCn3nccc3C2=O)cnc1N[C@H]1CC[C@H](Nc2nc3cc(OC(F)F)ccn3n2)C1] | 521.2 [M + H]+ |
| 338 | 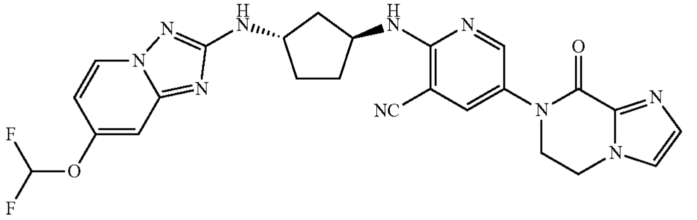 [SMILES: N#Cc1cc(N2CCn3ccnc3C2=O)cnc1N[C@H]1CC[C@H](Nc2nc3cc(OC(F)F)ccn3n2)C1] | 521.2 [M + H]+ |
| 339 | 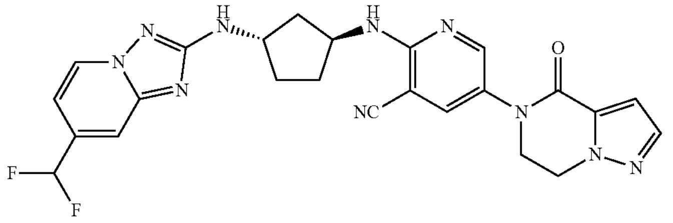 | 505.2 [M + H]+ |
| 340 | 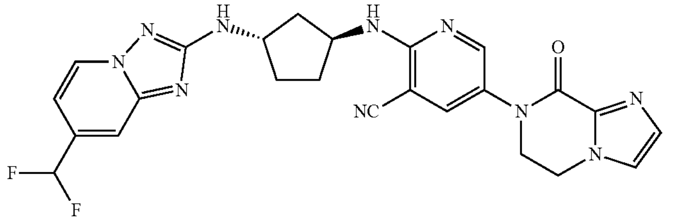 [SMILES: N#Cc1cc(N2CCn3ccnc3C2=O)cnc1N[C@H]1CC[C@H](Nc2nc3cc(C(F)F)ccn3n2)C1] | 505.2 [M + H]+ |
| 341 | 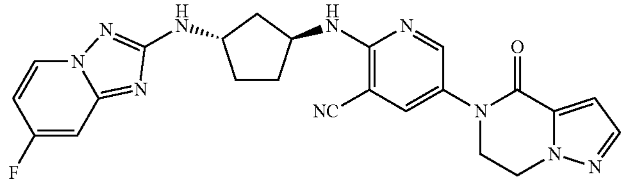 | 473.2 [M + H]+ |
| 342 | 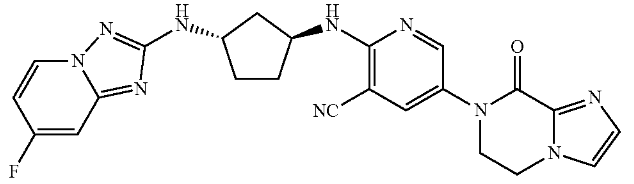 | 473.2 [M + H]+ |

-continued
| Examples | Structure | MS m/z (ESI) |
| --- | --- | --- |
| 343 | 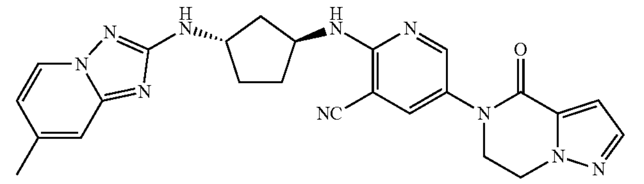 [SMILES: Cc1ccn2nc(N[C@H]3CC[C@H](Nc4ncc(N5CCn6nccc6C5=O)cc4C#N)C3)nc2c1] | 469.2 [M + H]+ |
| 344 | 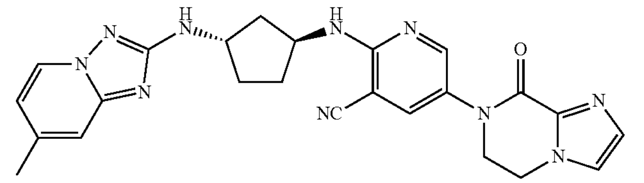 [SMILES: Cc1ccn2nc(N[C@H]3CC[C@H](Nc4ncc(N5CCn6ccnc6C5=O)cc4C#N)C3)nc2c1] | 469.2 [M + H]+ |
| 345 | 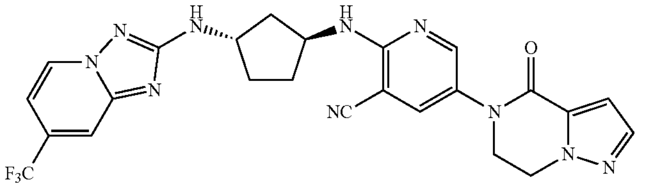 | 523.2 [M + H]+ |
| 346 | 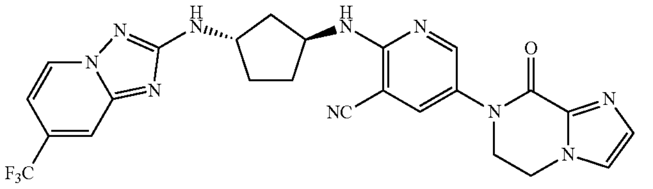 | 523.2 [M + H]+ |
| 347 | 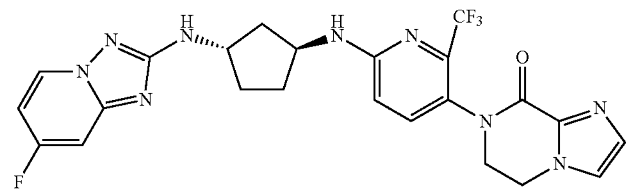 [SMILES: O=C1c2nccn2CCN1c1ccc(N[C@H]2CC[C@H](Nc3nc4cc(F)ccn4n3)C2)nc1C(F)(F)F] | 516.2 [M + H]+ |
| 348 | 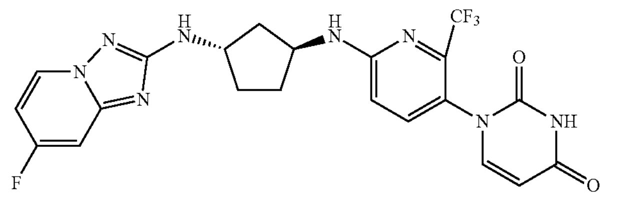 [SMILES: O=c1ccn(-c2ccc(N[C@H]3CC[C@H](Nc4nc5cc(F)ccn5n4)C3)nc2C(F)(F)F)c(=O)[nH]1] | 516.2 [M + H]+ |
| 349 | 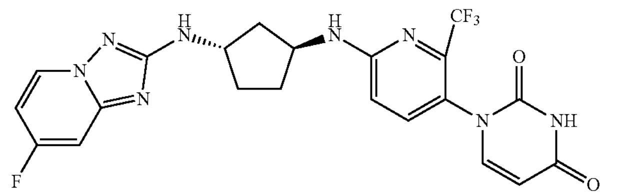 [SMILES: O=c1ccn(-c2ccc(N[C@H]3CC[C@H](Nc4nc5cc(F)ccn5n4)C3)nc2C(F)(F)F)c(=O)[nH]1] | 491.2 [M + H]+ |

-continued
| Examples | Structure | MS m/z (ESI) |
|---|---|---|
| 350 | 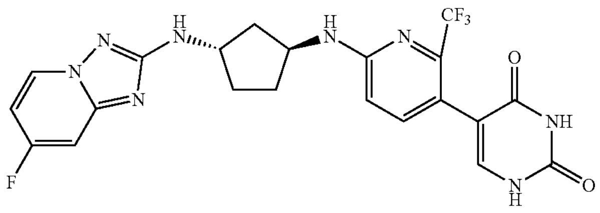 | 491.2 [M + H]$^+$ |
| 351 | 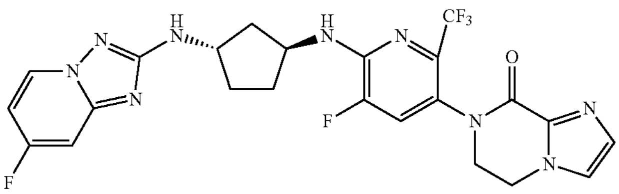 [SMILES: O=C1c2nccn2CCN1c1cc(F)c(N[C@H]2CC[C@H](Nc3nc4cc(F)ccn4n3)C2)nc1C(F)(F)F] | 534.2 [M + H]$^+$ |
| 352 | 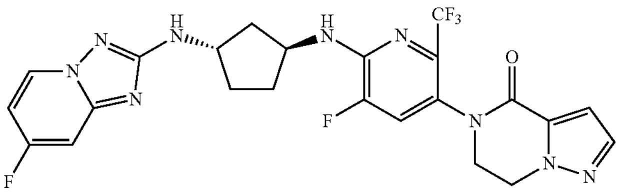 [SMILES: O=C1c2ccnn2CCN1c1cc(F)c(N[C@H]2CC[C@H](Nc3nc4cc(F)ccn4n3)C2)nc1C(F)(F)F] | 534.2 [M + H]$^+$ |
| 353 | 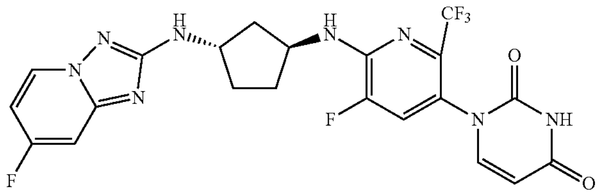 [SMILES: O=c1ccn(-c2cc(F)c(N[C@H]3CC[C@H](Nc4nc5cc(F)ccn5n4)C3)nc2C(F)(F)F)c(=O)[nH]1] | 509.1 [M + H]$^+$ |
| 354 | 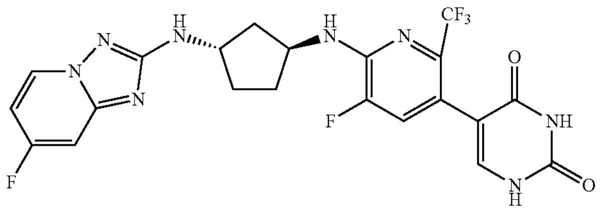 [SMILES: O=c1[nH]cc(-c2cc(F)c(N[C@H]3CC[C@H](Nc4nc5cc(F)ccn5n4)C3)nc2C(F)(F)F)c(=O)[nH]1] | 509.1 [M + H]$^+$ |
| 355 | 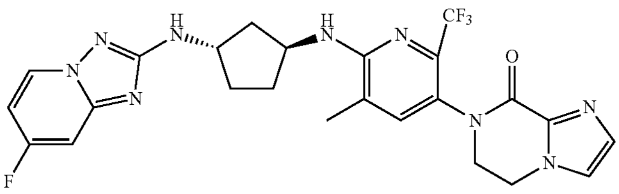 | 530.2 [M + H]$^+$ |
| 356 | 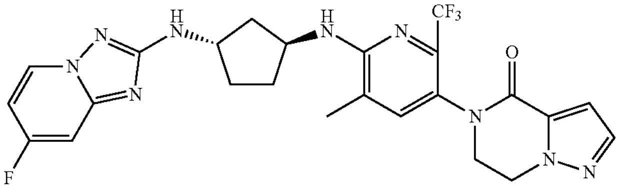 [SMILES: Cc1cc(N2CCn3nccc3C2=O)c(C(F)(F)F)nc1N[C@H]1CC[C@H](Nc2nc3cc(F)ccn3n2)C1] | 530.2 [M + H]$^+$ |

-continued
| Examples | Structure | MS m/z (ESI) |
|---|---|---|
| 357 | 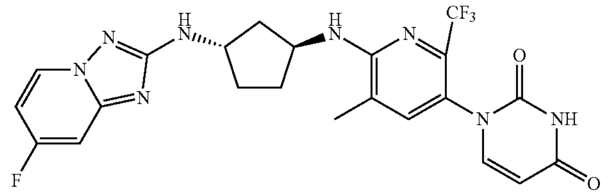 [SMILES: Cc1cc(-n2ccc(=O)[nH]c2=O)c(C(F)(F)F)nc1N[C@H]1CC[C@H](Nc2nc3cc(F)ccn3n2)C1] | 505.2 [M + H]$^+$ |
| 358 | 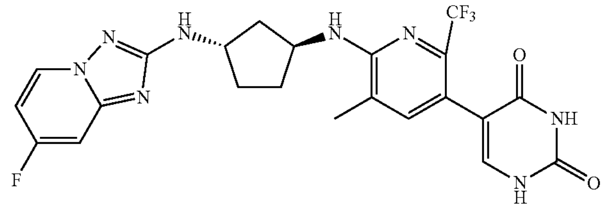 [SMILES: Cc1cc(-c2c[nH]c(=O)[nH]c2=O)c(C(F)(F)F)nc1N[C@H]1CC[C@H](Nc2nc3cc(F)ccn3n2)C1] | 505.2 [M + H]$^+$ |
| 359 | 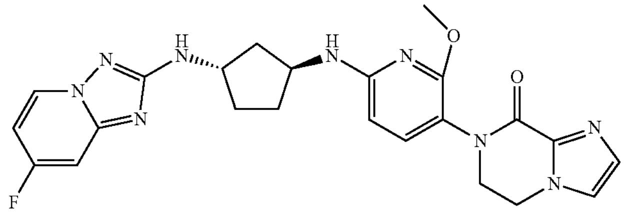 [SMILES: COc1nc(N[C@H]2CC[C@H](Nc3nc4cc(F)ccn4n3)C2)ccc1N1CCn2ccnc2C1=O] | 478.2 [M + H]$^+$ |
| 360 | 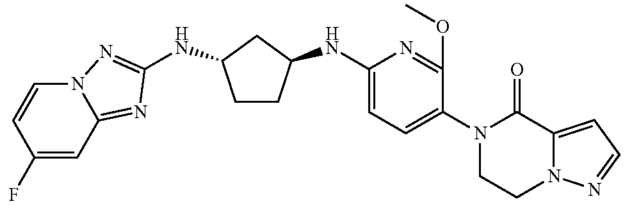 [SMILES: COc1nc(N[C@H]2CC[C@H](Nc3nc4cc(F)ccn4n3)C2)ccc1N1CCn2nccc2C1=O] | 478.2 [M + H]$^+$ |
| 361 | 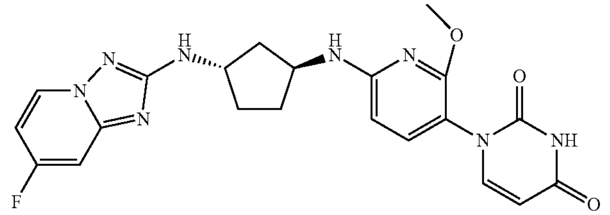 [SMILES: COc1nc(N[C@H]2CC[C@H](Nc3nc4cc(F)ccn4n3)C2)ccc1-n1ccc(=O)[nH]c1=O] | 453.2 [M + H]$^+$ |
| 362 | 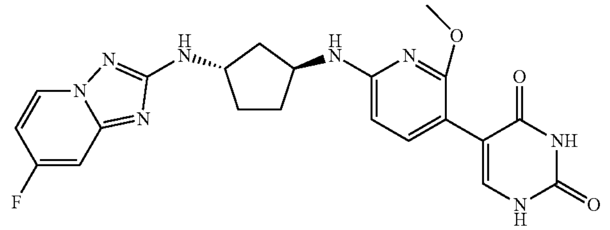 [SMILES: COc1nc(N[C@H]2CC[C@H](Nc3nc4cc(F)ccn4n3)C2)ccc1-c1c[nH]c(=O)[nH]c1=O] | 453.2 [M + H]$^+$ |
| 363 | 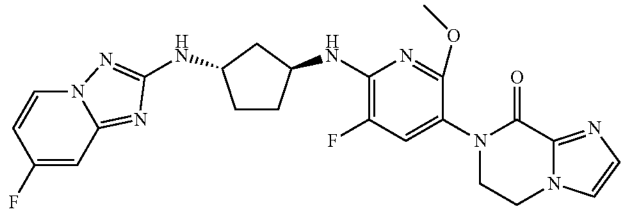 [SMILES: COc1nc(N[C@H]2CC[C@H](Nc3nc4cc(F)ccn4n3)C2)c(F)cc1N1CCn2ccnc2C1=O] | 496.2 [M + H]$^+$ |

-continued
| Examples | Structure | MS m/z (ESI) |
| --- | --- | --- |
| 364 | 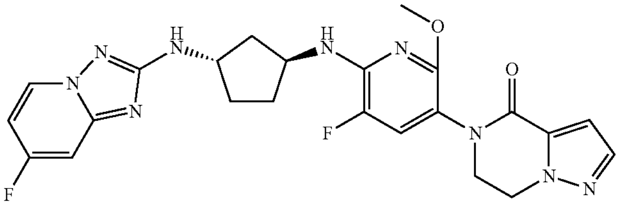 [SMILES: COc1nc(N[C@H]2CC[C@H](Nc3nc4cc(F)ccn4n3)C2)c(F)cc1N1CCn2nccc2C1=O] | 496.2 [M + H]+ |
| 365 | 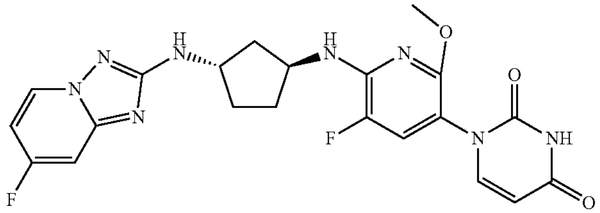 [SMILES: COc1nc(N[C@H]2CC[C@H](Nc3nc4cc(F)ccn4n3)C2)c(F)cc1-n1ccc(=O)[nH]c1=O] | 471.2 [M + H]+ |
| 366 | 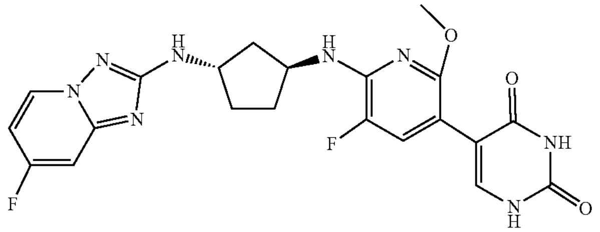 [SMILES: COc1nc(N[C@H]2CC[C@H](Nc3nc4cc(F)ccn4n3)C2)c(F)cc1-c1c[nH]c(=O)[nH]c1=O] | 471.2 [M + H]+ |
| 367 | 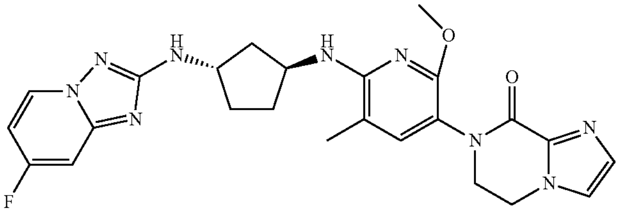 | 492.2 [M + H]+ |
| 368 | 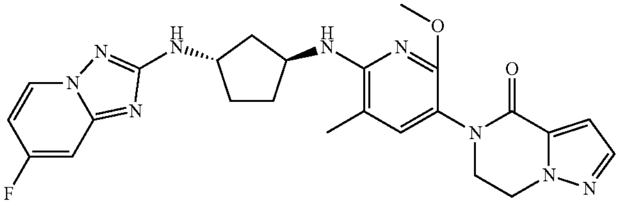 | 492.2 [M + H]+ |
| 369 | 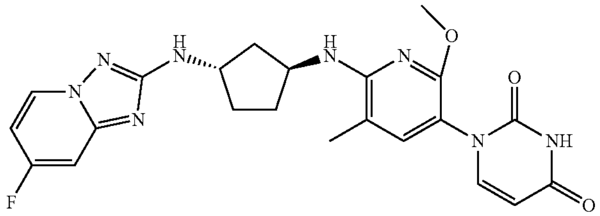 [SMILES: COc1nc(N[C@H]2CC[C@H](Nc3nc4cc(F)ccn4n3)C2)c(C)cc1-n1ccc(=O)[nH]c1=O] | 467.2 [M + H]+ |
| 370 | 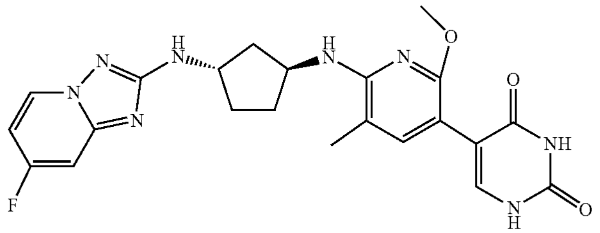 | 467.2 [M + H]+ |

-continued
| Examples | Structure | MS m/z (ESI) |
|---|---|---|
| 371 | 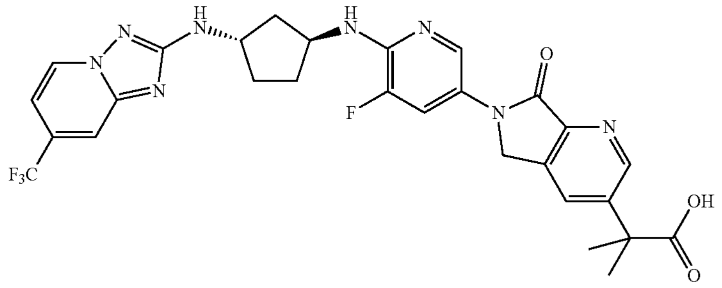 [SMILES: CC(C)(C(=O)O)c1cnc2c(c1)CN(c1cnc(N[C@H]3CC[C@H](Nc4nc5cc(C(F)(F)F)ccn5n4)C3)c(F)c1)C2=O] | 599.2 [M + H]$^+$ |
| 372 | 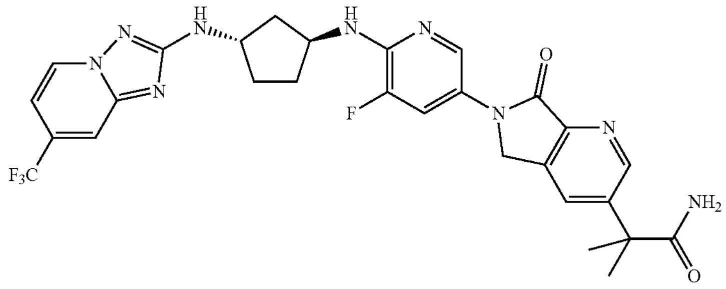 [SMILES: CC(C)(C(N)=O)c1cnc2c(c1)CN(c1cnc(N[C@H]3CC[C@H](Nc4nc5cc(C(F)(F)F)ccn5n4)C3)c(F)c1)C2=O] | 598.2 [M + H]$^+$ |
| 373 | 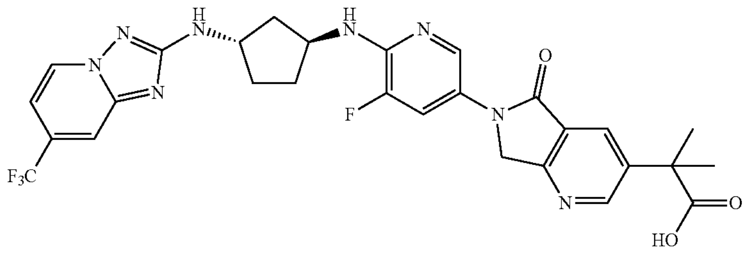 [SMILES: CC(C)(C(=O)O)c1cnc2c(c1)C(=O)N(c1cnc(N[C@H]3CC[C@H](Nc4nc5cc(C(F)(F)F)ccn5n4)C3)c(F)c1)C2] | 599.2 [M + H]$^+$ |
| 374 | 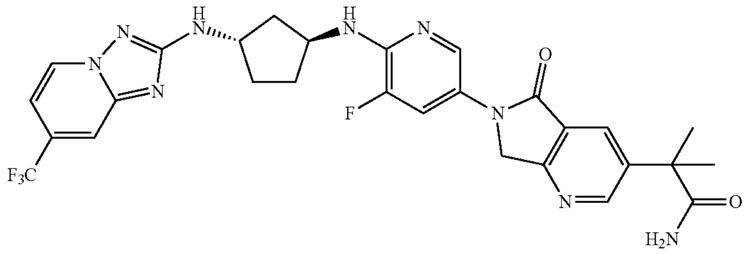 [SMILES: CC(C)(C(N)=O)c1cnc2c(c1)C(=O)N(c1cnc(N[C@H]3CC[C@H](Nc4nc5cc(C(F)(F)F)ccn5n4)C3)c(F)c1)C2] | 598.2 [M + H]$^+$ |
| 375 | 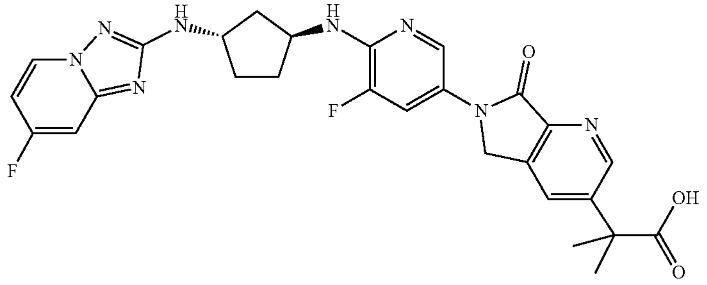 [SMILES: CC(C)(C(=O)O)c1cnc2c(c1)CN(c1cnc(N[C@H]3CC[C@H](Nc4nc5cc(F)ccn5n4)C3)c(F)c1)C2=O] | 549.2 [M + H]$^+$ |

-continued
| Examples | Structure | MS m/z (ESI) |
|---|---|---|
| 376 | 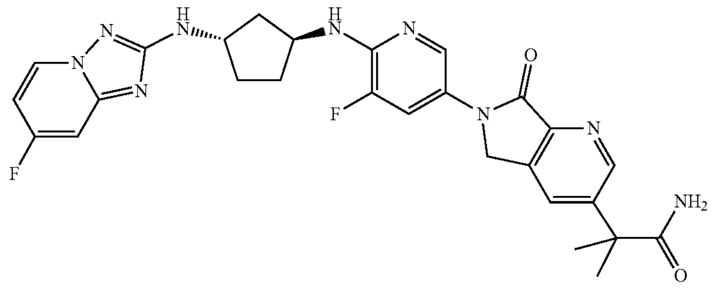 [SMILES: CC(C)(C(N)=O)c1cnc2c(c1)CN(c1cnc(N[C@H]3CC[C@H](Nc4nc5cc(F)ccn5n4)C3)c(F)c1)C2=O] | 548.2 [M + H]+ |
| 377 | 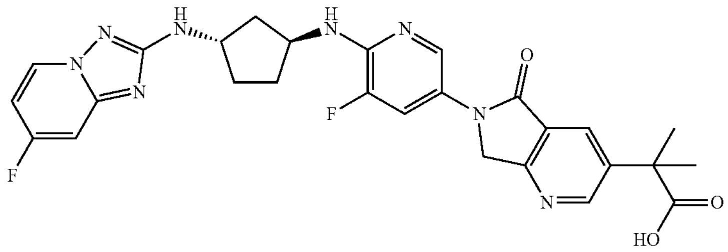 [SMILES: CC(C)(C(=O)O)c1cnc2c(c1)C(=O)N(c1cnc(N[C@H]3CC[C@H](Nc4nc5cc(F)ccn5n4)C3)c(F)c1)C2] | 549.2 [M + H]+ |
| 378 | 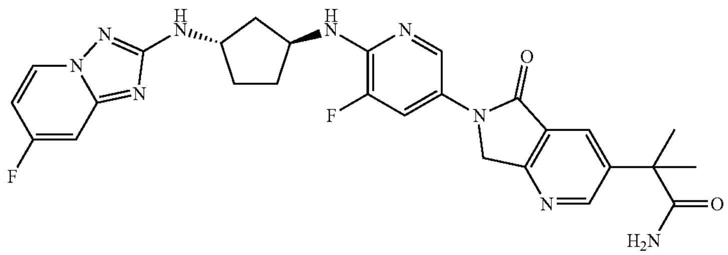 [SMILES: CC(C)(C(N)=O)c1cnc2c(c1)C(=O)N(c1cnc(N[C@H]3CC[C@H](Nc4nc5cc(F)ccn5n4)C3)c(F)c1)C2] | 548.2 [M + H]+ |
| 379 | 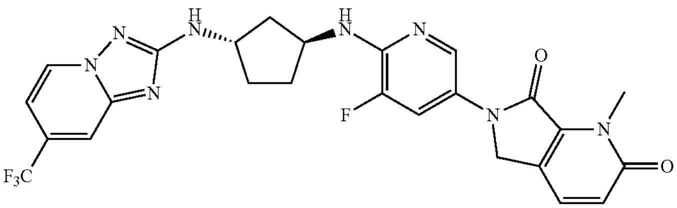 [SMILES: Cn1c2c(ccc1=O)CN(c1cnc(N[C@H]3CC[C@H](Nc4nc5cc(C(F)(F)F)ccn5n4)C3)c(F)c1)C2=O] | 543.2 [M + H]+ |
| 380 | 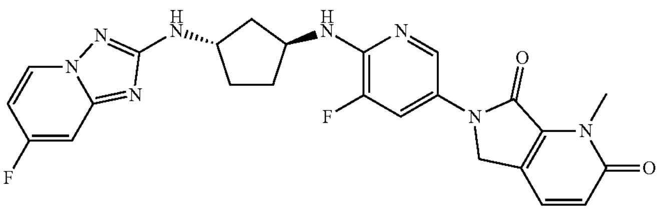 [SMILES: Cn1c2c(ccc1=O)CN(c1cnc(N[C@H]3CC[C@H](Nc4nc5cc(F)ccn5n4)C3)c(F)c1)C2=O] | 493.2 [M + H]+ |
| 381 | 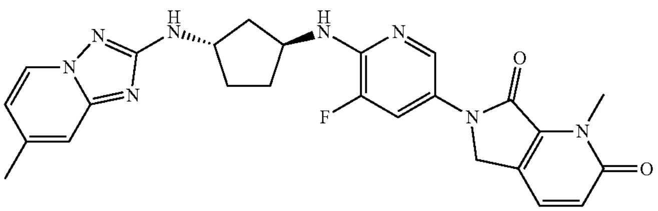 [SMILES: Cc1ccn2nc(N[C@H]3CC[C@H](Nc4ncc(N5Cc6ccc(=O)n(C)c6C5=O)cc4F)C3)nc2c1] | 489.2 [M + H]+ |

-continued
| Examples | Structure | MS m/z (ESI) |
|---|---|---|
| 382 | 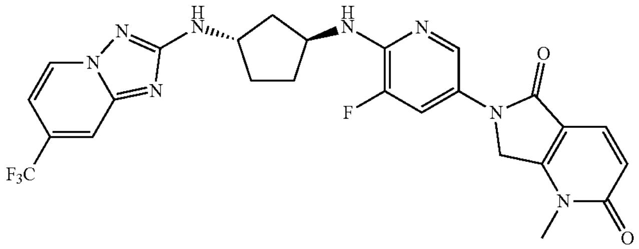 [SMILES: Cn1c2c(ccc1=O)C(=O)N(c1cnc(N[C@H]3CC[C@H](Nc4nc5cc(C(F)(F)F)ccn5n4)C3)c(F)c1)C2] | 543.2 [M + H]+ |
| 383 | 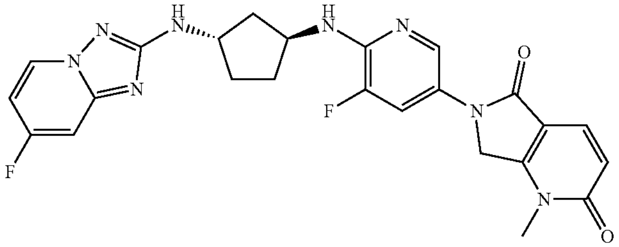 [SMILES: Cn1c2c(ccc1=O)C(=O)N(c1cnc(N[C@H]3CC[C@H](Nc4nc5cc(F)ccn5n4)C3)c(F)c1)C2] | 493.2 [M + H]+ |
| 384 | 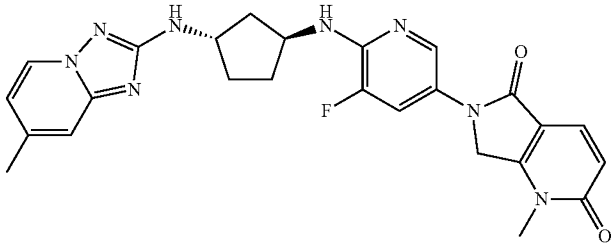 [SMILES: Cc1ccn2nc(N[C@H]3CC[C@H](Nc4ncc(N5Cc6c(ccc(=O)n6C)C5=O)cc4F)C3)nc2c1] | 489.2 [M + H]+ |
| 385 | 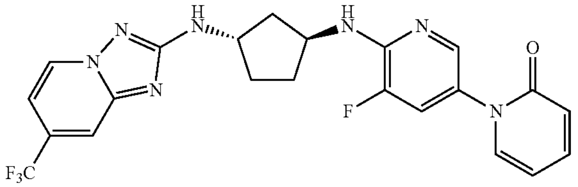 [SMILES: O=c1ccccn1-c1cnc(N[C@H]2CC[C@H](Nc3nc4cc(C(F)(F)F)ccn4n3)C2)c(F)c1] | 474.2 [M + H]+ |
| 386 | 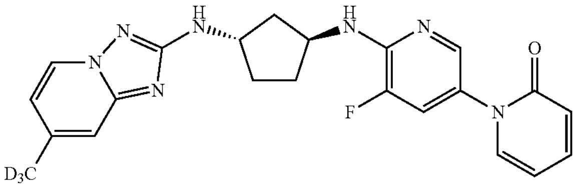 [SMILES: [2H]C([2H])([2H])c1ccn2nc(N[C@H]3CC[C@H](Nc4ncc(-n5ccccc5=O)cc4F)C3)nc2c1] | 423.2 [M + H]+ |
| 387 | 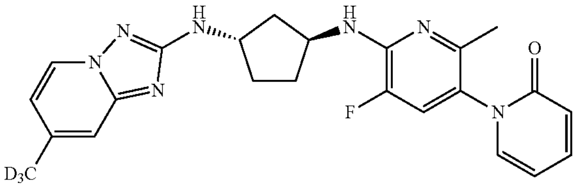 [SMILES: [2H]C([2H])([2H])c1ccn2nc(N[C@H]3CC[C@H](Nc4nc(C)c(-n5ccccc5=O)cc4F)C3)nc2c1] | 437.2 [M + H]+ |
| 388 | 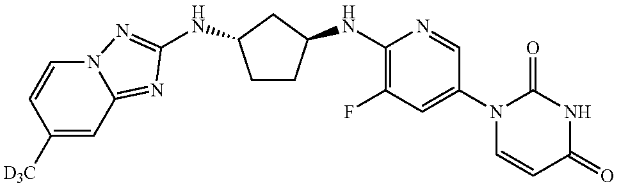 [SMILES: [2H]C([2H])([2H])c1ccn2nc(N[C@H]3CC[C@H](Nc4ncc(-n5ccc(=O)[nH]c5=O)cc4F)C3)nc2c1] | 440.2 [M + H]+ |

-continued
| Examples | Structure | MS m/z (ESI) |
|---|---|---|
| 389 | 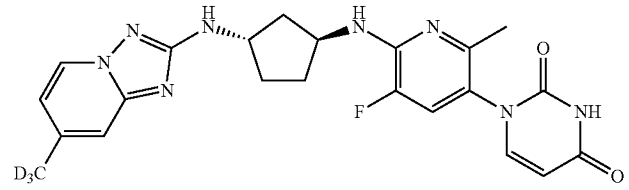 [SMILES: [2H]C([2H])([2H])c1ccn2nc(N[C@H]3CC[C@H](Nc4nc(C)c(-n5ccc(=O)[nH]c5=O)cc4F)C3)nc2c1] | 454.2 [M + H]+ |
| 390 | 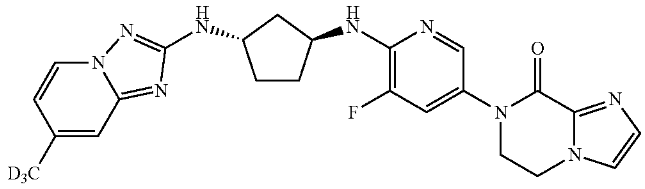 [SMILES: [2H]C([2H])([2H])c1ccn2nc(N[C@H]3CC[C@H](Nc4ncc(N5CCn6ccnc6C5=O)cc4F)C3)nc2c1] | 465.2 [M + H]+ |
| 391 | 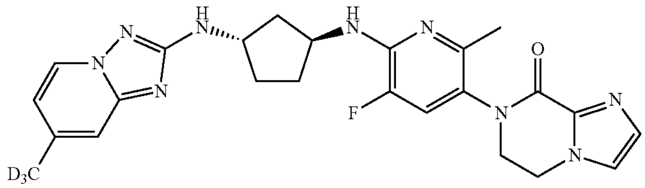 [SMILES: [2H]C([2H])([2H])c1ccn2nc(N[C@H]3CC[C@H](Nc4nc(C)c(N5CCn6ccnc6C5=O)cc4F)C3)nc2c1] | 479.2 [M + H]+ |
| 392 | 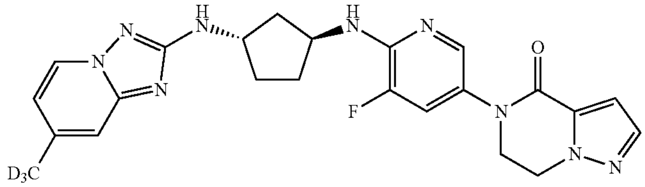 [SMILES: [2H]C([2H])([2H])c1ccn2nc(N[C@H]3CC[C@H](Nc4ncc(N5CCn6nccc6C5=O)cc4F)C3)nc2c1] | 465.2 [M + H]+ |
| 393 | 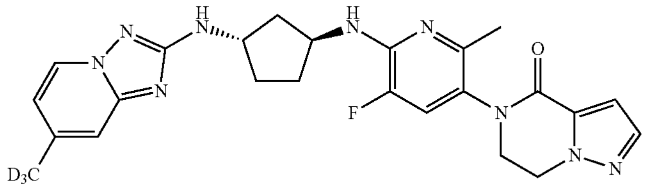 [SMILES: [2H]C([2H])([2H])c1ccn2nc(N[C@H]3CC[C@H](Nc4nc(C)c(N5CCn6nccc6C5=O)cc4F)C3)nc2c1] | 479.2 [M + H]+ |
| 394 | 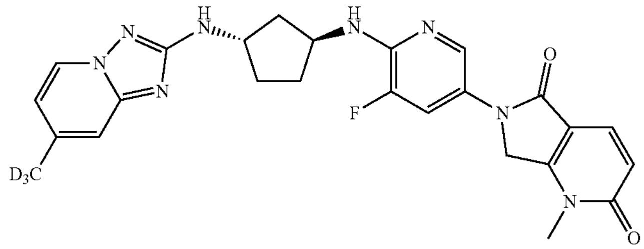 | 492.2 [M + H]+ |
| 395 | 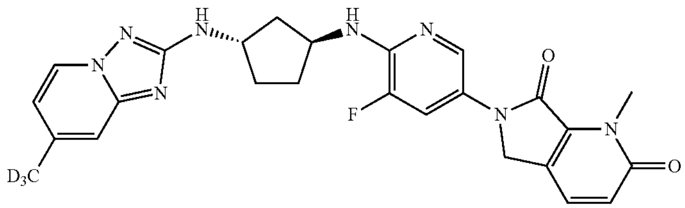 | 492.2 [M + H]+ |

-continued
| Examples | Structure | MS m/z (ESI) |
|---|---|---|
| 396 | 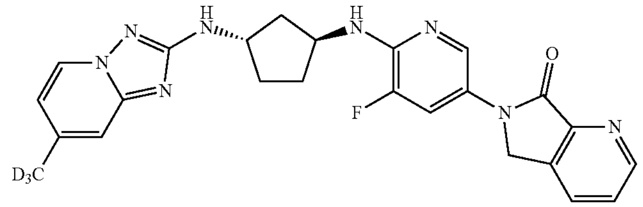 [SMILES: [2H]C([2H])([2H])c1ccn2nc(N[C@H]3CC[C@H](Nc4ncc(N5Cc6cccnc6C5=O)cc4F)C3)nc2c1] | 462.2 [M + H]+ |
| 397 | 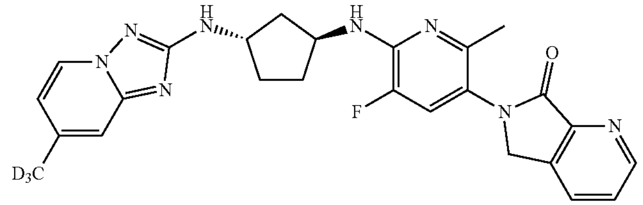 [SMILES: [2H]C([2H])([2H])c1ccn2nc(N[C@H]3CC[C@H](Nc4nc(C)c(N5Cc6cccnc6C5=O)cc4F)C3)nc2c1] | 476.2 [M + H]+ |
| 398 | 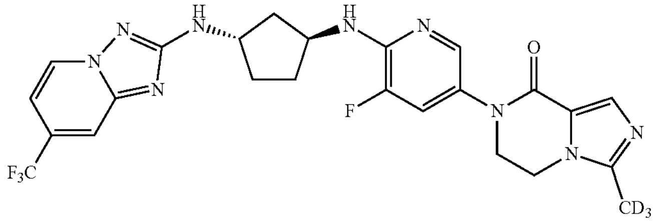 [SMILES: [2H]C([2H])([2H])c1ncc2n1CCN(c1cnc(N[C@H]3CC[C@H](Nc4nc5cc(C(F)(F)F)ccn5n4)C3)c(F)c1)C2=O] | 533.2 [M + H]+ |
| 399 | 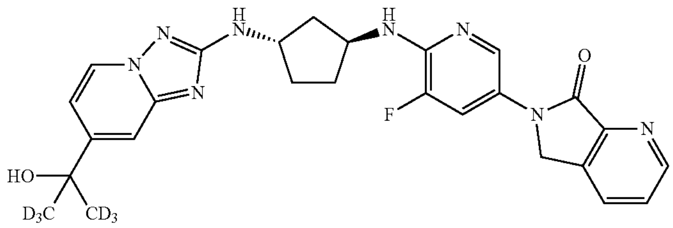 [SMILES: [2H]C([2H])([2H])C(O)(c1ccn2nc(N[C@H]3CC[C@H](Nc4ncc(N5Cc6cccnc6C5=O)cc4F)C3)nc2c1)C([2H])([2H])[2H]] | 509.2 [M + H]+ |
| 400 | 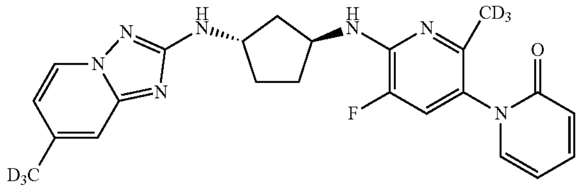 [SMILES: [2H]C([2H])([2H])c1ccn2nc(N[C@H]3CC[C@H](Nc4nc(C([2H])([2H])[2H])c(-n5ccccc5=O)cc4F)C3)nc2c1] | 440.2 [M + H]+ |
| 401 | 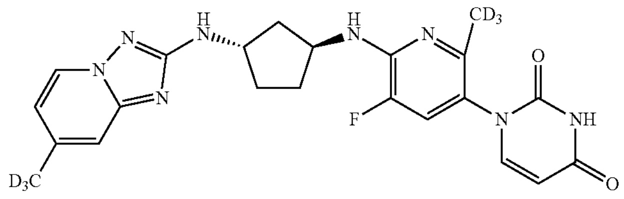 [SMILES: [2H]C([2H])([2H])c1ccn2nc(N[C@H]3CC[C@H](Nc4nc(C([2H])([2H])[2H])c(-n5ccc(=O)[nH]c5=O)cc4F)C3)nc2c1] | 457.2 [M + H]+ |
| 402 | 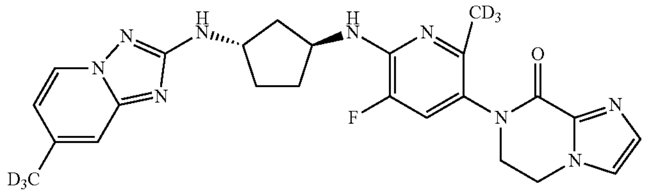 [SMILES: [2H]C([2H])([2H])c1ccn2nc(N[C@H]3CC[C@H](Nc4nc(C([2H])([2H])[2H])c(N5CCn6ccnc6C5=O)cc4F)C3)nc2c1] | 482.2 [M + H]+ |

-continued
| Examples | Structure | MS m/z (ESI) |
| --- | --- | --- |
| 403 | 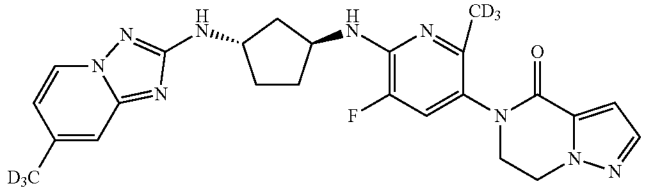 [SMILES: [2H]C([2H])([2H])c1ccn2nc(N[C@H]3CC[C@H](Nc4nc(C([2H])([2H])[2H])c(N5CCn6nccc6C5=O)cc4F)C3)nc2c1] | 482.2 [M + H]$^+$ |
| 404 | 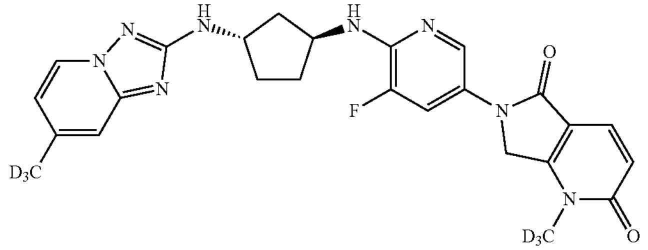 [SMILES: [2H]C([2H])([2H])c1ccn2nc(N[C@H]3CC[C@H](Nc4ncc(N5Cc6c(ccc(=O)n6C([2H])([2H])[2H])C5=O)cc4F)C3)nc2c1] | 495.2 [M + H]$^+$ |
| 405 | 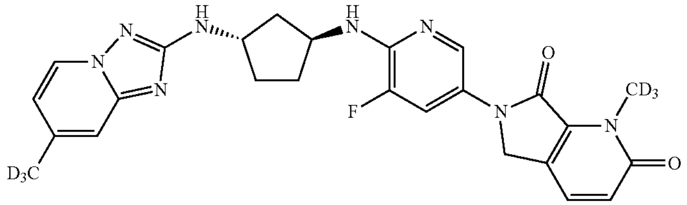 [SMILES: [2H]C([2H])([2H])c1ccn2nc(N[C@H]3CC[C@H](Nc4ncc(N5Cc6ccc(=O)n(C([2H])([2H])[2H])c6C5=O)cc4F)C3)nc2c1] | 495.2 [M + H]$^+$ |
| 406 | 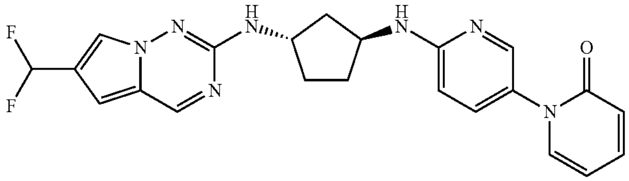 [SMILES: O=c1ccccn1-c1ccc(N[C@H]2CC[C@H](Nc3ncc4cc(C(F)F)cn4n3)C2)nc1] | 438.2 [M + H] $^+$ |
| 407 | 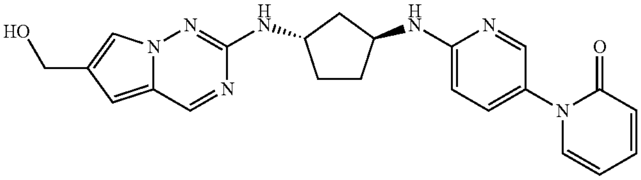 [SMILES: O=c1ccccn1-c1ccc(N[C@H]2CC[C@H](Nc3ncc4cc(CO)cn4n3)C2)nc1] | 418.2 [M + H] $^+$ |
| 408 | 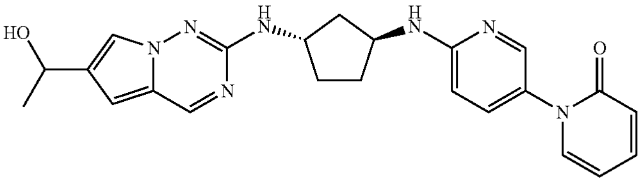 [SMILES: CC(O)c1cc2cnc(N[C@H]3CC[C@H](Nc4ccc(-n5ccccc5=O)cn4)C3)nn2c1] | 432.2 [M + H] $^+$ |
| 409 | 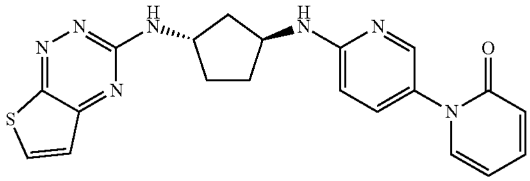 [SMILES: O=c1ccccn1-c1ccc(N[C@H]2CC[C@H](Nc3nnc4sccc4n3)C2)nc1] | 406.1 [M + H] $^+$ |

-continued
| Examples | Structure | MS m/z (ESI) |
|---|---|---|
| 410 | 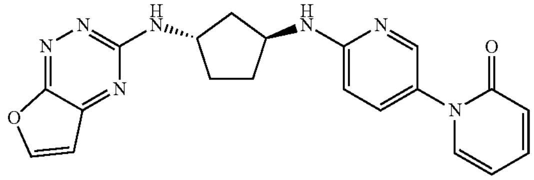 | 390.2 [M + H] + |
| 411 | 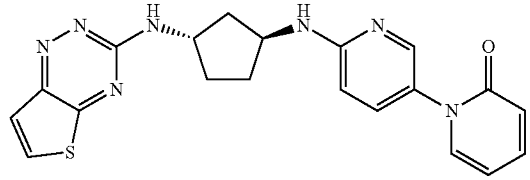 [SMILES: O=c1ccccn1-c1ccc(N[C@H]2CC[C@H](Nc3nnc4ccsc4n3)C2)nc1] | 406.1 [M + H] + |
| 412 | 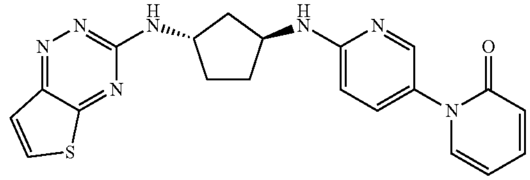 [SMILES: O=c1ccccn1-c1ccc(N[C@H]2CC[C@H](Nc3nnc4ccsc4n3)C2)nc1] | 390.2 [M + H] + |
| 413 | 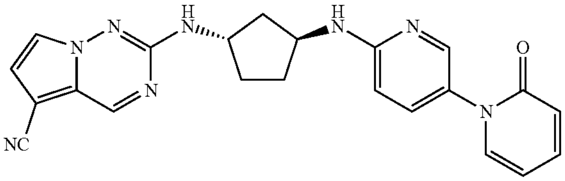 [SMILES: N#Cc1ccn2nc(N[C@H]3CC[C@H](Nc4ccc(-n5ccccc5=O)cn4)C3)ncc12] | 413.2 [M + H] + |
| 414 | 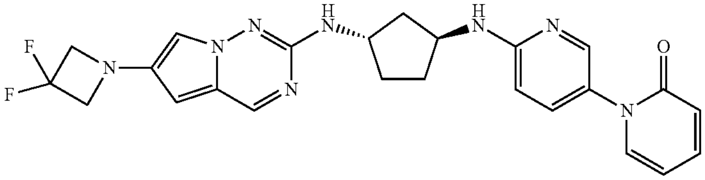 [SMILES: O=c1ccccn1-c1ccc(N[C@H]2CC[C@H](Nc3ncc4cc(N5CC(F)(F)C5)cn4n3)C2)nc1] | 478.2 [M + H] + |
| 415 | 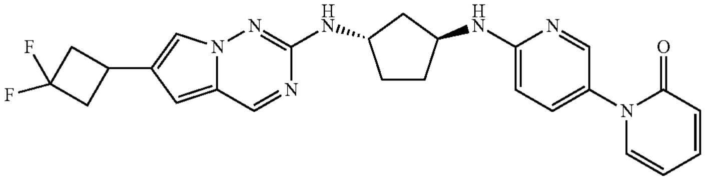 [SMILES: O=c1ccccn1-c1ccc(N[C@H]2CC[C@H](Nc3ncc4cc(C5CC(F)(F)C5)cn4n3)C2)nc1] | 479.2 [M + H] + |
| 416 | 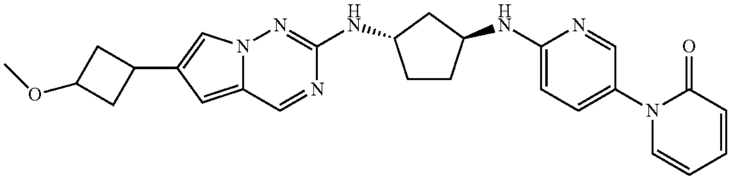 [SMILES: COC1CC(c2cc3cnc(N[C@H]4CC[C@H](Nc5ccc(-n6ccccc6=O)cn5)C4)nn3c2)C1] | 472.2 [M + H] + |
| 417 | 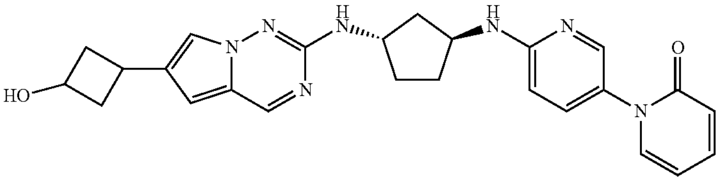 [SMILES: O=c1ccccn1-c1ccc(N[C@H]2CC[C@H](Nc3ncc4cc(C5CC(O)C5)cn4n3)C2)nc1] | 458.2 [M + H] + |

-continued
| Examples | Structure | MS m/z (ESI) |
|---|---|---|
| 418 | 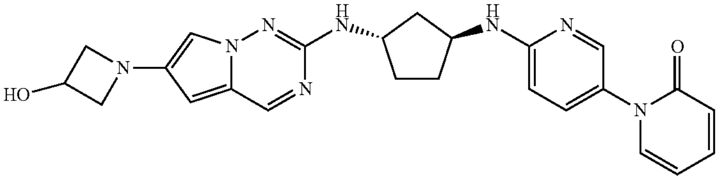 [SMILES: O=c1ccccn1-c1ccc(N[C@H]2CC[C@H](Nc3ncc4cc(N5CC(O)C5)cn4n3)C2)nc1] | 459.2 [M + H] + |
| 419 | 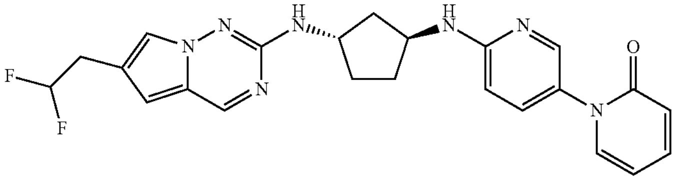 [SMILES: O=c1ccccn1-c1ccc(N[C@H]2CC[C@H](Nc3ncc4cc(CC(F)F)cn4n3)C2)nc1] | 452.2 [M + H] + |
| 420 | 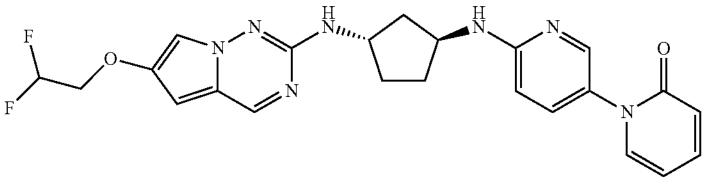 [SMILES: O=c1ccccn1-c1ccc(N[C@H]2CC[C@H](Nc3ncc4cc(OCC(F)F)cn4n3)C2)nc1] | 468.2 [M + H] + |
| 421 | 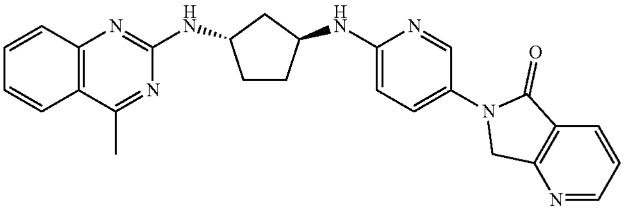 [SMILES: Cc1nc(N[C@H]2CC[C@H](Nc3ccc(N4Cc5ncccc5C4=O)cn3)C2)nc2ccccc12] | 452.2 [M + H] + |
| 423 | 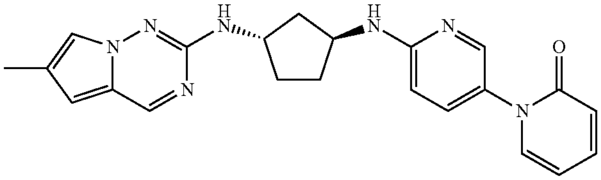 [SMILES: Cc1cc2cnc(N[C@H]3CC[C@H](Nc4ccc(-n5ccccc5=O)cn4)C3)nn2c1] | 402.2 [M + H]+ |
| 424 | 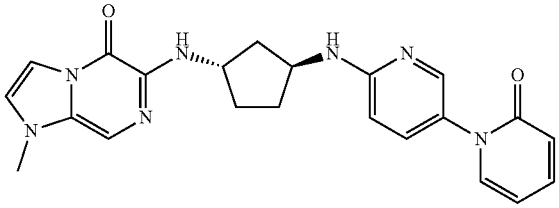 [SMILES: Cn1ccn2c(=O)c(N[C@H]3CC[C@H](Nc4ccc(-n5ccccc5=O)cn4)C3)ncc12] | 418.2 [M + H]+ |
| 425 | 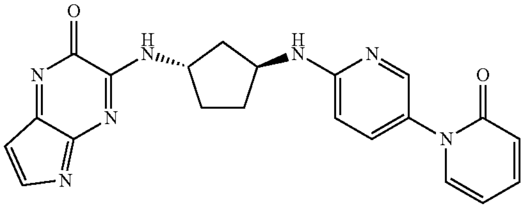 [SMILES: O=C1N=C2C=CN=C2N=C1N[C@H]1CC[C@H](Nc2ccc(-n3ccccc3=O)cn2)C1] | 402.2 [M + H]+ |

-continued

| Examples | Structure | MS m/z (ESI) |
|---|---|---|
| 426 | 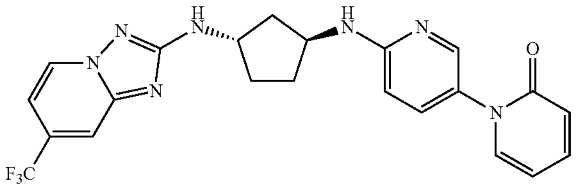 [SMILES: O=c1ccccn1-c1ccc(N[C@H]2CC[C@H](Nc3nc4cc(C(F)(F)F)ccn4n3)C2)nc1] | 456.2 [M + H]+ |
| 427 | 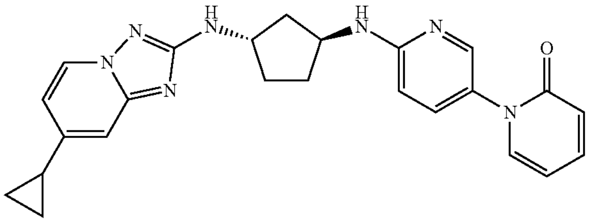 [SMILES: O=c1ccccn1-c1ccc(N[C@H]2CC[C@H](Nc3nc4cc(C5CC5)ccn4n3)C2)nc1] | 428.2 [M + H]+ |

The nuclear magnetic resonance characterization data of the relevant examples are shown in the following table:

| Examples | HNMR |
|---|---|
| 94 | $^1$H NMR (400 MHz, DMSO-d6) δ 8.82 (d, 1H), 8.59 (d, 1H), 8.34 (d,1H), 7.95-7.79 (m, 3H), 7.15 (dd, 1H), 7.03 (d, 1H), 6.68 (d, 1H), 6.55 (d, 1H), 4.88 (s, 2H), 4.31 (p, 1H), 4.20 (q, 1H), 2.44 (s,3H), 2.15 (tt, 2H), 1.98 (dt, 1H), 1.89 (dt, 1H), 1.54 (ddt, 2H). |
| 95 | $^1$H NMR (400 MHz, DMSO-d6) δ 8.82 (d, 1H), 8.79 (d, 1H), 8.34 (d, 1H), 8.30 (d, 1H), 7.89-7.82 (m, 2H), 7.14 (dd, 1H), 7.02 (d, 1H), 6.72 (d, 1H), 6.56 (d, 1H), 4.92 (s, 2H), 4.31 (q, 1H), 4.21 (h, 1H), 2.16 (qt, 2H), 1.98 (dt, 1H), 1.89 (dt, 1H), 1.59 (dd, 1H), 1.55-1.44 (m, 1H). |
| 96 | $^1$H NMR (400 MHz, DMSO-d6) δ 9.18 (s, 1H), 8.81 (d, 1H), 8.67 (s, 1H), 8.38 (d,1H), 7.88 (dd, 1H), 7.84 (s, 1H), 7.14 (dd, 1H), 7.01 (d, 1H), 6.76 (d, 1H), 6.57 (d, 1H), 4.99 (s, 2H), 4.32 (q, 1H), 4.21 (q, 1H), 2.16 (p, 2H), 2.06-1.96 (m, 1H), 1.94-1.83 (m, 1H), 1.68-1.43 (m, 2H). |
| 97 | $^1$H NMR (400 MHz, DMSO-$d_6$) δ 8.82-8.76 (m, 1H), 8.63 (d, 1H), 8.36 (d, 1H), 8.18-8.11 (m, 1H), 7.91-7.83 (m, 1H), 7.63-7.20 (m, 2H), 7.14 (d, 1H), 6.78-6.71 (m, 2H), 6.67 (d, 1H), 6.55 (d, 1H), 4.97 (s, 2H), 4.34-4.23 (m, 1H), 4.21-4.07 (m, 1H), 2.21-2.07 (m, 2H), 2.04-1.81 (m, 2H), 1.64-1.39 (m, 2H). |
| 98 | $^1$H NMR (400 MHz, DMSO-$d_6$) δ 8.76 (s, 1H), 8.63 (d, 1H), 8.33 (d, 1H), 8.12-8.05 (m, 1H), 7.88-7.81 (m, 1H), 7.63-7.20 (m, 1H), 7.14 (d, 1H), 6.78-6.50 (m, 4H), 4.93 (s, 2H), 4.37-4.23 (m, 1H), 4.20-4.07 (m, 1H), 2.22-2.06 (m, 2H), 2.03-1.79 (m, 2H), 1.66-1.40 (m, 2H). |
| 99 | $^1$H NMR (400 MHz, DMSO-$d_6$) δ 8.80 (s, 1H), 8.62 (d, 1H), 8.34 (d, 1H), 7.85 (dd, 1H), 7.59 (s, 1H), 7.41 (t, 1H), 7.13 (d, 1H), 6.74-6.71 (m, 2H), 6.68 (d, 1H), 6.55 (d, 1H), 4.97 (s, 2H), 4.31-4.27 (m, 1H), 4.18-4.13 (m, 1H), 2.60 (s, 3H), 2.18-2.11 (m, 2H), 1.98-1.93 (m, 1H), 1.90-1.85 (m, 1H), 1.59-1.48 (m, 2H). |
| 100 | $^1$H NMR (400 MHz, DMSO-$d_6$) δ 8.64-8.60 (m, 2H), 8.37 (d, 1H), 7.86 (dd, 1H), 7.54 (d, 1H), 7.41 (t, 1H), 7.13 (d, 1H), 6.74-6.71 (m, 2H), 6.68 (d, 1H), 6.55 (d, 1H), 4.98 (s, 2H), 4.32-4.27 (m, 1H), 4.18-4.13 (m, 1H), 2.57 (s, 3H), 2.17-2.11 (m, 2H), 1.98-1.93 (m, 1H), 1.90-1.85 (m, 1H), 1.59-1.48 (m, 2H). |
| 102 | $^1$H NMR (400 MHz, DMSO-$d_6$) δ 11.38 (s, 1H), 8.65 (dd, 1H), 7.93 (d, 1H), 7.63 (d, 1H), 7.38 (dd, 1H), 7.26 (dd, 1H), 6.92 (d, 1H), 6.86 (td, 1H), 6.74 (d, 1H), 6.50 (d, 1H), 5.61 (d, 1H), 4.30 (q, 1H), 4.15 (q, 1H), 2.14 (dq, 2H), 2.00-1.81 (m, 2H), 1.62-1.43 (m, 2H). |
| 103 | $^1$H NMR (400 MHz, DMSO-$d_6$) δ 11.29 (s, 1H), 8.55 (d, 1H), 7.87 (s, 1H), 7.55 (d, 1H), 7.47 (s, 1H), 7.32 (dd, 1H), 6.85 (t, 2H), 6.74 (d, 1H), 6.44 (d, 1H), 5.54 (d, 1H), 4.23 (d, 1H), 4.09 (d, 1H), 2.11-2.02 (m, 2H), 1.84 (dd, 2H), 1.46 (dd, 2H). |
| 104 | $^1$H NMR (400 MHz, DMSO-$d_6$) δ 11.37 (s, 1H), 8.72 (d, 1H), 7.94 (d, 1H), 7.67-7.57 (m, 2H), 7.39 (dd, Hz, 1H), 7.16 (d, 1H), 7.05-6.83 (m, 3H), 6.51 (d, 1H), 5.61 (dd, 1H), 4.31 (q, 1H), 4.18 (p, 1H), 2.15 (dq, 2H), 1.92 (dq, 2H), 1.53 (ddt, 2H). |
| 105 | $^1$H NMR (400 MHz, DMSO-$d_6$) δ 11.37 (s, 1H), 8.63 (d, 1H), 7.93 (d, 1H), 7.66-7.22 (m, 3H), 7.13 (d, 1H), 6.92 (d, 1H), 6.73 (dd, 2H), 6.50 (d, 1H), 5.61 (d, 1H), 4.30 (q, 1H), 4.15 (h, 1H), 2.14 (dq, 2H), 1.99-1.81 (m, 2H), 1.61-1.44 (m, 2H). |
| 106 | $^1$H NMR (400 MHz, DMSO-$d_6$) δ 11.37 (d, 1H), 8.43 (d, 1H), 7.94 (d, 1H), 7.62 (d, 1H), 7.38 (dd, 1H), 7.16 (s, 1H), 6.91 (d, 1H), 6.69 (dd, 1H), 6.50 (d, 2H), 5.61 (dd, 1H), 4.30 (q, 1H), 4.15 (q, 1H), 2.35 (s, 3H), 2.14 (dt, 2H), 2.00-1.82 (m, 2H), 1.60-1.43 (m, 2H). |
| 107 | $^1$H NMR (400 MHz, DMSO-$d_6$) δ 11.38 (s, 1H), 8.41 (d, 1H), 7.94 (s, 1H), 7.63 (d, 1H), 7.38 (dd, 1H), 7.08 (s, 1H), 6.92 (d, 1H), 6.53 (dd, 3H), 5.61 (dd, 1H), 4.29 (q, 1H), 4.14 |

-continued

| Examples | HNMR |
|---|---|
| | (d, 1H), 2.14 (q, 2H), 2.01-1.81 (m, 3H), 1.61-1.42 (m, 2H), 1.02 (p, , 2H), 0.79 (p, 2H). |
| 108 | $^1$H NMR (400 MHz, DMSO-$d_6$) δ 8.82(d, 1H), 7.85 (d, 2H), 7.55 (d, 1H), 7.33(dd, 1H), 7.22 (s, 1H), 7.15 (dd, 2H), 7.03 (d, 1H), 6.81 (d, 1H), 6.49 (d, 1H), 5.74 (d, 1H), 4.33-4.18 (m, 2H), 2.20-2.11 (m, 2H), 2.00-1.85 (m, 2H), 1.61-1.47 (m, 2H). |
| 109 | $^1$H NMR (400 MHz, DMSO-$d_6$) δ 8.83(d, 1H), 8.14 (s, 1H), 7.86 (d, 2H), 7.44 (s, 1H), 7.33(dd, 1H), 7.15 (dd, 1H), 7.03 (d, 1H), 6.80 (d, 2H), 6.48 (d, 1H), 4.33-4.16 (m, 2H), 2.20-2.12 (m, 2H), 2.01-1.85 (m, 2H), 1.85 (s, 3H), 1.61-1.47 (m, 2H). |
| 110 | $^1$H NMR (400 MHz, DMSO-$d_6$) δ 11.89(s, 1H), δ 8.82(d, 1H), 8.13 (d, 2H), 7.96 (d, 1H), 7.85(s, 1H), 7.40 (dd, 1H), 7.15 (dd, 1H), 7.04 (d, 1H), 6.96 (d, 1H), 6.50 (d, 1H), 4.35-4.15 (m, 2H), 2.23-2.08 (m, 2H), 2.01-1.85 (m, 2H), 1.61-1.47 (m, 2H). |
| 111 | $^1$H NMR (400 MHz, DMSO-$d_6$) δ 11.36 (s, 1H), δ 8.83 (d, 1H), 7.94 (d, 1H), 7.86 (s, 1H), 7.53 (d, 1H), 7.39 (dd, 1H), 7.15 (dd, 1H), 7.04 (d, 1H), 6.92 (d, 1H), 6.51 (d, 1H), 4.37-4.17 (m, 2H), 2.20-2.12 (m, 2H), 2.01-1.85 (m, 2H), 1.78 (s, 3H), 1.62-1.49 (m, 2H). |
| 113 | $^1$H NMR (400 MHz, DMSO-$d_6$) δ 8.82 (d, 1H), 8.78 (d, 1H), 8.11 (d, 1H), 7.94 (s, 1H), 7.85 (s, 1H), 7.63 (dd, 1H), 7.19-7.12 (m, 1H), 7.01 (d, 1H), 6.69 (d, 1H), 6.41 (s, 1H), 4.78 (s, 2H), 4.59-4.15 (m, 2H), 2.24-2.11 (m, 2H), 2.03 (s, 3H), 2.00-1.85 (m, 2H), 1.63-1.45 (m, 2H). |
| 115 | $^1$H NMR (400 MHz, DMSO-$d_6$) δ 8.81 (d, 1H), 8.64 (d, 1H), 8.36 (d, 1H), 7.95 (s, 1H), 7.87 (dd, 1H), 7.83 (s, 1H), 7.14 (dd, 1H), 6.98 (d, 1H), 6.62 (d, 1H), 6.55 (d, 1H), 4.91 (s, 2H), 4.33-4.28 (m, 1H), 4.24-4.19 (m, 1H), 2.43 (s, 3H), 2.18-2.12 (m, 2H), 2.00-1.94 (m, 1H), 1.93-1.88 (m 1H), 1.60-1.48 (m, 2H). |
| 116 | $^1$H NMR (400 MHz, DMSO-$d_6$) δ 8.86 (d, 1H), 8.82 (d, 1H), 8.36 (d, 1H), 8.28 (d, 1H), 7.89-7.83 (m, 2H), 7.15 (dd, 1H), 7.03 (d, 1H), 6.72 (d, 1H), 6.55 (d, 1H), 4.98 (s, 2H), 4.40-4.15 (m, 2H), 2.23-2.11 (m, 2H), 2.03-1.84 (m, 2H), 1.65-1.41 (m, 2H). |
| 117 | $^1$H NMR (400 MHz, DMSO-$d_6$) δ 8.82 (d, 1H), 8.31 (d, 1H), 7.88-7.81 (m, 2H), 7.79-7.70 (m, 2H), 7.58 (dd, 1H), 7.14 (dd, 1H), 7.01 (d, 1H), 6.65 (d, 1H), 6.54 (d, 1H), 4.91 (s, 2H), 4.36-4.13 (m, 2H), 2.24-2.08 (m, 2H), 2.02-1.84 (m, 2H), 1.63-1.44 (m, 2H). |
| 119 | $^1$H NMR (400 MHz, DMSO-$d_6$) δ 12.00 (s, 1H), 8 8.82 (d, 1H), 8.16 (d, 1H), 7.85 (s, 1H), 7.80 (d, 1H), 7.25 (d, 1H), 7.14 (dd, 1H), 7.02 (d, 1H), 6.85 (d, 1H), 6.52 (d, 1H), 4.34-4.18 (m, 2H), 2.20-2.12 (m, 2H), 2.02-1.88 (m, 2H), 1.62-1.48 (m, 2H). |
| 121 | $^1$H NMR (400 MHz, DMSO-$d_6$) δ 8.82 (d, 1H), 8.62 (dd, 1H), 8.15 (dd, 1H), 7.98 (d, 1H), 7.85 (d, 1H), 7.47 (dd, 1H), 7.15 (dd, 1H), 7.01 (dd, 2H), 6.57-6.41 (m, 2H), 4.34 (q, 1H), 4.21 (q, 1H), 2.20-2.11 (m, 2H), 1.94 (dq, 2H), 1.55 (ddt, 2H). |
| 122 | $^1$H NMR (400 MHz, DMSO-$d_6$) δ 8.82 (d, 1H), 7.99 (d, 1H), 7.95 (d, 1H), 7.86-7.82 (m, 1H), 7.43 (dd, 1H), 7.15 (dd, 1H), 7.00 (dd, 2H), 6.53 (d, 1H), 6.41 (d, 1H), 4.33 (q, 1H), 4.21 (dd, 1H), 2.32 (s, 3H), 2.16 (dd, 2H), 1.93 (dq, 2H), 1.55 (ddt, 2H). |
| 123 | $^1$H NMR (400 MHz, DMSO-$d_6$) δ 9.24 (d, 1H), 8.71 (d, 1H), 8.62 (d, 1H), 8.37 (d, 1H), 7.87 (dd, 1H), 7.42 (t, 1H), 7.13 (d, 1H), 6.75-6.71 (m, 3H), 6.56 (d, 1H), 5.09 (s, 2H), 4.32-4.27 (m, 1H), 4.17-4.12 (m, 1H), 2.18-2.11 (m, 2H), 1.98-1.94 (m, 1H), 1.90-1.85 (m, 1H), 1.58-1.48 (m, 2H). |
| 124 | $^1$H NMR (400 MHz, DMSO-$d_6$) δ 8.82 (d, 1H), 8.59 (d, 1H), 8.34 (d, 1H), 7.90-7.80 (m, 2H), 7.33 (d, 1H), 7.15 (dd, 1H), 7.04 (d, 1H), 6.66 (d, 1H), 6.54 (d, 1H), 4.88 (s, 2H), 4.38-4.13 (m, 2H), 2.65 (s, 3H), 2.25-2.09 (m, 2H), 2.04-1.84 (m, 2H), 1.65-1.41 (m, 2H). |
| 125 | $^1$H NMR (400 MHz, DMSO-$d_6$) δ 8.86-8.77 (m, 2H), 8.32 (d, 1H), 7.90-7.78 (m, 2H), 7.45 (dd, 1H), 7.15 (dd, 1H), 7.04 (d, 1H), 6.72 (d, 1H), 6.55 (d, 1H), 4.99 (s, 2H), 4.37-4.15 (m, 2H), 2.24-2.10 (m, 2H), 2.05-1.83 (m, 2H), 1.65-1.41 (m, 2H). |
| 126 | $^1$H NMR (400 MHz, DMSO-$d_6$) δ 9.04 (s, 1H), 8.82 (d, 1H), 8.36 (d, 1H), 7.93-7.81 (m, 3H), 7.18-7.10 (m, 1H), 7.03 (d, 1H), 6.73 (s, 1H), 6.55 (d, 1H), 5.06 (d, 2H), 4.39-4.11 (m, 2H), 2.25-2.09 (m, 2H), 2.04-1.84 (m, 2H), 1.65-1.41 (m, 2H). |
| 128 | $^1$H NMR (400 MHz, DMSO-$d_6$) δ 8.65-8.61 (m, 2H), 8.35 (d, 1H), 7.96 (s, 1H), 7.87 (dd, 1H), 7.13 (d, 1H), 6.75-6.70 (m, 2H), 6.64 (d, 1H), 6.54 (d, 1H), 4.91 (s, 2H), 4.31-4.26 (m, 1H), 4.17-4.12 (m, 1H), 2.42 (s, 3H), 2.18-2.11 (m, 2H), 1.97-1.93 (m, 1H), 1.90-1.85 (m, 1H), 1.59-1.47 (m, 2H). |
| 129 | $^1$H NMR (400 MHz, DMSO-$d_6$) δ 8.76 (s, 1H), 8.62 (d, 1H), 8.32 (d, 1H), 8.09 (dd, 1H), 7.85 (dd, 1H), 7.42 (t, 1H), 7.14 (d, 1H), 6.74-6.72 (m, 2H), 6.69 (d, 1H), 6.56 (d, 1H), 4.93 (s, 2H), 4.32-4.27 (m, 1H), 4.18-4.13 (m, 1H), 2.18-2.11 (m, 2H), 1.98-1.93 (m, 1H), 1.90-1.86 (m, 1H), 1.59-1.46 (m, 2H). |
| 130 | $^1$H NMR (400 MHz, DMSO-$d_6$) δ 8.85 (s, 1H), 8.62 (d, 1H), 8.35 (d, 1H), 8.29-8.23 (m, 1H), 7.86 (dd, 1H), 7.43 (t, 1H), 7.13 (d, 1H), 6.75-6.68 (m, 3H), 6.55 (d, 1H), 4.97 (s, 2H), 4.33-4.25 (m, 1H), 4.18-4.11 (m, 1H), 2.18-2.09 (m, 2H), 1.99-1.83 (m, 2H), 1.58-1.47 (m, 2H). |
| 131 | $^1$H NMR (400 MHz, DMSO-$d_6$) δ 8.62 (d, 1H), 8.35 (d, 1H), 8.01 (d, 1H), 7.86 (dd, 1H), 7.43 (t, 1H), 7.41 (d, 1H), 7.13 (d, 1H), 6.76-6.70 (m, 2H), 6.62 (d, 1H), 6.54 (d, 1H), 4.90 (s, 2H), 4.31-4.26 (m, 1H), 4.18-4.12 (m, 1H), 2.61 (s, 3H), 2.18-2.11 (m, 2H), 1.99-1.83 (m, 2H), 1.59-1.46 (m, 2H). |
| 132 | $^1$H NMR (400 MHz, DMSO-$d_6$) δ 8.63 (d, 1H), 8.42-8.35 (m, 2H), 8.20 (d, 1H), 7.89 (dd, 1H), 7.42 (t, 1H), 7.14 (d, 1H), 6.78-6.70 (m, 3H), 6.56 (d, 1H), 5.06 (s, 2H), 4.32-4.27 (m, 1H), 4.19-4.11 (m, 1H), 2.66 (s, 3H), 2.18-2.11 (m, 2H), 2.00-1.83 (m, 2H), 1.59-1.46 (m, 2H). |
| 133 | $^1$H NMR (400 MHz, DMSO-$d_6$) δ 8.63 (d, 1H), 8.42 (d, 1H), 8.38 (d, 1H), 8.07 (d, 1H), 7.89 (dd, 1H), 7.43 (t, 1H), 7.14 (d, 1H), 6.74 (dt, 3H), 6.57 (d, 1H), 5.09 (s, 2H), 4.32-4.26 (m, 1H), 4.19-4.13 (m, 1H), 2.18-2.11 (m, 2H), 2.00-1.84 (m, 2H), 1.59-1.46 (m, 2H). |

-continued

| Examples | HNMR |
|---|---|
| 134 | $^1$H NMR (400 MHz, DMSO-d$_6$) δ 8.63 (d, 1H), 8.59 (d, 1H), 8.34 (d, 1H), 7.85 (dd, 1H), 7.43 (t, 1H), 7.33 (d, 1H), 7.14 (d, 1H), 6.74 (dd, 2H), 6.64 (d, 1H), 6.54 (d, 1H), 4.88 (s, 2H), 4.32-4.27 (m, 1H), 4.18-4.13 (m, 1H), 2.66 (s, 3H), 2.16-2.11 (m, 2H), 2.03-1.83 (m, 2H), 1.59-1.46 (m, 2H). |
| 135 | $^1$H NMR (400 MHz, DMSO-d$_6$) δ 8.81 (t, 1H), 8.63 (d, 1H), 8.32 (d, 1H), 7.82 (dd, 1H), 7.48-7.44 (m, 1H), 7.43 (t, 1H), 7.14 (d, 1H), 6.79-6.67 (m, 3H), 6.54 (d, 1H), 4.99 (s, 2H), 4.32-4.27 (m, 1H), 4.17-4.12 (m, 1H), 2.18-2.11 (m, 2H), 2.01-1.83 (m, 2H), 1.59-1.46 (m, 2H). |
| 136 | $^1$H NMR (400 MHz, DMSO-d$_6$) δ 9.05 (d, 1H), 8.63 (d, 1H), 8.36 (s, 1H), 7.90-7.85 (m, 2H), 7.42 (t, 1H), 7.13 (d, 1H), 6.75-6.70 (m, 3H), 6.55 (d, 1H), 5.06 (s, 2H), 4.33-4.26 (m, 1H), 4.17-4.11 (m, 1H), 2.18-2.10 (m, 2H), 1.98-1.93 (m, 1H), 1.89-1.85 (m, 1H), 1.58-1.48 (m, 2H). |
| 137 | $^1$H NMR (400 MHz, DMSO-d$_6$) δ 9.24 (d, 1H), 8.71 (d, 1H), 8.69-8.60 (m, 1H), 8.37 (d, 1H), 7.87 (dd, 1H), 7.26 (dd, 1H), 6.85 (td, 1H), 6.72 (dd, 2H), 6.55 (d, 1H), 5.09 (s, 2H), 4.29 (p, 1H), 4.15 (q, 1H), 2.23-2.08 (m, 2H), 1.96 (dt, 1H), 1.86 (dt, 1H), 1.64-1.41 (m, 2H). |
| 138 | $^1$H NMR (400 MHz, DMSO-d$_6$) δ 8.62 (d, 1H), 8.39 (s, 1H), 8.19 (d, 1H), 7.71 (dd, 1H), 7.65 (d, 1H), 7.41 (t, 1H), 7.13 (d, 1H), 6.79-6.64 (m, 2H), 6.55 (d, 1H), 6.50 (d, 1H), 6.38 (d, 1H), 4.73 (s, 2H), 4.29-4.24 (m, 1H), 4.17-4.12 (m, 1H), 2.17-2.10 (m, 2H), 1.98-1.82 (m, 2H), 1.59-1.45 (m, 2H). |
| 140 | $^1$H NMR (400 MHz, DMSO-d$_6$) δ 8.83 (d, 1H), 8.41 (s, 1H), 8.18 (s, 1H), 7.95 (d, 1H), 7.86 (s, 1H), 7.79 (d, 1H), 7.15 (dd, 1H), 7.04 (d, 1H), 6.73-6.66 (m, 2H), 4.76 (s, 2H), 4.52-4.46 (m, 1H), 4.24-4.18 (m, 1H), 2.19-2.12 (m, 2H), 2.01-1.96 (m, 2H), 1.61-1.56 (m, 2H). |
| 143 | $^1$H NMR (400 MHz, DMSO-d$_6$) δ 8.82 (d, 1H), 8.41 (s, 1H), 8.08 (d, 1H), 7.88 (dd, 1H), 7.84 (s, 1H), 7.65 (d, 1H), 7.15 (dd, 1H), 7.01 (d, 1H), 6.53 (d, 1H), 6.37 (d, 1H), 4.75 (s, 2H), 4.50-4.45 (m, 1H), 4.24-4.19 (m, 1H), 2.17-2.12 (m, 2H), 2.00-1.94 (m, 2H), 1.62-1.55 (m, 2H). |
| 144 | $^1$H NMR (400 MHz, DMSO-d$_6$) δ 8.82 (d, 1H), 8.39 (s, 1H), 7.90 (s, 1H), 7.85 (s, 1H), 7.76 (d, 1H), 7.15 (dd, 1H), 7.02 (d, 1H), 6.70 (s, 1H), 6.68 (d, 1H), 6.38 (s, 1H), 4.57 (s, 2H), 4.32-4.27 (m, 1H), 4.22-4.17 (m, 1H), 2.18-2.13 (m, 2H), 2.01 (s, 3H), 1.99-1.88 (m, 2H), 1.60-1.49 (m, 2H). |
| 145 | $^1$H NMR (400 MHz, DMSO-d$_6$) δ 8.82 (d, 1H), 8.76 (t, 1H), 8.22 (d, 1H), 8.10 (dd, 1H), 8.00 (dd, 1H), 7.84 (s, 1H), 7.14 (dd, 1H), 7.01 (d, 1H), 6.67 (d, 1H), 4.96 (s, 2H), 4.51 (q, 1H), 4.22 (q, 1H), 2.21-2.12 (m, 2H), 1.99 (td, 2H), 1.59 (dt, 2H) |
| 147 | $^1$H NMR (400 MHz, DMSO-d$_6$) δ 9.25 (t, 1H), 8.82 (d, 1H), 8.74 (t, 1H), 8.28 (s, 1H), 8.04-7.98 (m, 1H), 7.85 (s, 1H), 7.15 (d, 1H), 7.03 (d, 1H), 6.72 (d, 1H), 5.12 (s, 2H), 4.50 (q, 1H), 4.26-4.17 (m, 1H), 2.21-2.11 (m, 2H), 1.99 (m, 2H), 1.60 (s, 2H). |
| 148 | $^1$H NMR (400 MHz, DMSO-d$_6$) δ 8.82 (d, 1H), 8.42-8.35 (m, 2H), 8.20 (d, 1H), 7.89 (dd, 1H), 7.86-7.83 (m, 1H), 7.15 (dd, 1H), 7.02 (d, 1H), 6.75 (d, 1H), 6.56 (d, 1H), 5.05 (s, 2H), 4.31 (q, 1H), 4.21 (q, 1H), 2.16 (dt, 2H), 2.00-1.87 (m, 2H), 1.55 (dt, 2H). |
| 149 | $^1$H NMR (400 MHz, DMSO-d$_6$) δ 8.82 (d, 1H), 8.75 (dd, 1H), 8.27 (d, 1H), 8.10 (dd, 1H), 7.87-7.82 (m, 1H), 7.77 (dd, 1H), 7.61 (dd, 1H), 7.15 (dd, 1H), 7.03 (d, 1H), 5.77 (d, 1H), 4.92 (s, 2H), 4.53 (q, 1H), 4.23 (q, 1H), 2.23-2.11 (m, 5H), 2.06-1.93 (m, 2H), 1.58 (qd, 2H). |
| 150 | $^1$H NMR (400 MHz, DMSO-d$_6$) δ 9.01 (d, 1H), 8.63 (d, 1H), 8.39 (d, 1H), 8.03 (d, 1H), 7.89 (dd, 1H), 7.42 (t, 1H), 7.14 (d, 1H), 6.81-6.70 (m, 3H), 6.56 (d, 1H), 5.05 (s, 2H), 4.30 (q, 1H), 4.15 (q, 1H), 2.21-2.10 (m, 2H), 1.92 (d, 2H), 1.53 (dd, 2H). |
| 151 | $^1$H NMR (400 MHz, DMSO-d$_6$) δ 8.79-8.74 (m, 1H), 8.62 (d, 1H), 8.24 (d, 1H), 8.12 (d, 1H), 8.03 (dd, 1H), 7.66-7.58 (m, 1H), 7.32 (d, 1H), 7.13 (d, 1H), 6.77-6.68 (m, 2H), 6.64 (d, 1H), 4.96 (s, 2H), 4.50 (q, 1H), 4.17 (q, 1H), 2.15 (qd, 2H), 1.97 (h, 2H), 1.63-1.53 (m, 2H). |
| 152 | $^1$H NMR (400 MHz, DMSO-d$_6$) δ 8.81 (dd, 1H), 8.63 (d, 1H), 8.27 (d, 1H), 8.16 (dd, 1H), 8.02 (dd, 1H), 7.62-7.54 (m, 1H), 7.33 (d, 1H), 7.14 (d, 1H), 6.73 (dd, 2H), 6.63 (dd, 1H), 5.00 (s, 2H), 4.49 (p, 1H), 4.15 (p, 1H), 2.14 (m, 2H), 1.97 (m, 2H), 1.64-1.51 (m, 2H). |
| 153 | $^1$H NMR (400 MHz, DMSO-d$_6$) δ 9.25 (d, 1H), 8.74 (d, 1H), 8.63 (d, 1H), 8.28 (d, 1H), 8.01 (dd, 1H), 7.51 (d, 1H), 7.14 (d, 1H), 6.77-6.67 (m, 3H), 5.12 (s, 2H), 4.49 (q, 1H), 4.16 (q, 1H), 2.20-2.09 (m, 2H), 1.97 (dt, 2H), 1.63-1.53 (m, 2H). |
| 154 | $^1$H NMR (400 MHz, DMSO-d$_6$) δ 8.77 (dd, 1H), 8.63 (d, 1H), 8.22 (d, 1H), 8.11 (dd, 1H), 8.00 (dd, 1H), 7.42 (t, 1H), 7.14 (d, 1H), 6.77-6.70 (m, 2H), 6.66 (dd, 1H), 4.97 (s, 2H), 4.50 (h, 1H), 4.16 (p, 1H), 2.20-2.10 (m, 2H), 1.97 (dq, 2H), 1.58 (dt, 2H). |
| 156 | $^1$H NMR (400 MHz, DMSO-d$_6$) δ 9.03 (d, 1H), 8.63 (d, 1H), 8.30 (d, 1H), 8.08-7.99 (m, 2H), 7.42 (t, 1H), 7.14 (d, 1H), 6.73 (dd, 3H), 5.08 (s, 2H), 4.50 (q, 1H), 4.16 (q, 1H), 2.21-2.09 (m, 2H), 1.97 (h, 2H), 1.63-1.54 (m, 2H). |
| 157 | $^1$H NMR (400 MHz, DMSO-d$_6$) δ 8.82 (dd, 1H), 8.62 (d, 1H), 8.23 (d, 1H), 7.95 (dd, 1H), 7.62-7.21 (m, 2H), 7.13 (d, 1H), 6.77-6.69 (m, 2H), 6.69-6.61 (m, 1H), 5.02 (s, 2H), 4.49 (q, 1H), 4.16 (q, 1H), 2.20-2.09 (m, 2H), 1.97 (h, 2H), 1.57 (tt, 2H). |
| 158 | $^1$H NMR (400 MHz, DMSO-d$_6$) δ 8.84 (dd, 1H), 8.63 (d, 1H), 8.27 (d, 1H), 8.13 (dd, 1H), 8.00 (dd, 1H), 7.42 (t, 1H), 7.14 (d, 1H), 6.73 (dd, 2H), 6.68 (d, 1H), 4.99 (d, 2H), 4.48 (q, 1H), 4.16 (q, 1H), 2.20-2.08 (m, 2H), 2.00-1.93 (m, 2H), 1.58 (dd, 2H). |
| 159 | $^1$H NMR (400 MHz, DMSO-d$_6$) δ 8.63 (d, 1H), 8.44 (d, 1H), 8.29 (d, 1H), 8.10-7.99 (m, 2H), 7.42 (t, 1H), 7.14 (d, 1H), 6.72 (dd, 3H), 5.12 (s, 2H), 4.49 (q, 1H), 4.16 (q, 1H), 2.14 (tt, 2H), 1.97 (h, 2H), 1.64-1.53 (m, 2H). |
| 160 | $^1$H NMR (400 MHz, DMSO-d$_6$) δ 8.81 (d, 1H), 8.63 (d, 1H), 8.23 (d, 1H), 8.00 (dd, 1H), 7.60 (d, 1H), 7.33 (d, 1H), 7.13 (d, 1H), 6.77-6.66 (m, 3H), 5.00 (s, 2H), 4.49 (q, 1H), 4.16 (q, 1H), 2.60 (s, 3H), 2.19-2.10 (m, 2H), 2.00-1.92 (m, 2H), 1.57 (q, 2H). |

-continued

| Examples | HNMR |
|---|---|
| 162 | $^1$H NMR (400 MHz, DMSO-$d_6$) δ 8.85-8.78 (m, 2H), 8.27 (d, 1H), 8.16 (dd, 1H), 8.02 (dd, 1H), 7.85 (s, 1H), 7.57 (dd, 1H), 7.15 (dd, 1H), 7.03 (d, 1H), 6.66 (d, 1H), 5.00 (s, 2H), 4.50 (q, 1H), 4.22 (q, 1H), 2.22-2.12 (m, 2H), 2.03-1.95 (m, 2H), 1.65-1.55 (m, 2H). |
| 163 | $^1$H NMR (400 MHz, DMSO-$d_6$) δ 9.01 (d, 1H), 8.82 (d, 1H), 8.40 (d, 1H), 8.03 (d, 1H), 7.90 (dd, 1H), 7.85 (s, 1H), 7.15 (dd, 1H), 7.04 (d, 1H), 6.76 (d, 1H), 6.56 (d, 1H), 5.05 (s, 2H), 4.32 (q, 1H), 4.21 (q, 1H), 2.16 (dq, 2H), 2.00-1.88 (m, 2H), 1.61-1.47 (m, 2H). |
| 165 | $^1$H NMR (400 MHz, DMSO-$d_6$) δ 8.76 (dd, 1H), 8.43 (d, 1H), 8.24 (d, 1H), 8.12 (dd, 1H), 8.03 (dd, 1H), 7.63 (dd, 1H), 7.18-7.12 (m, 1H), 6.67 (dd, 2H), 6.52 (d, 1H), 4.96 (s, 2H), 4.49 (q, 1H), 4.17 (s, 1H), 2.34 (s, 3H), 2.20-2.09 (m, 2H), 1.97 (dt, 2H), 1.63-1.50 (m, 2H). |
| 166 | $^1$H NMR (400 MHz, DMSO-$d_6$) δ 8.76 (dd, 1H), 8.41 (d, 1H), 8.24 (d, 1H), 8.12 (dd, 1H), 8.04 (dd, 1H), 7.63 (dd, 1H), 7.07 (d, 1H), 6.66 (d, 1H), 6.56 (dd, 1H), 6.52 (d, 1H), 4.96 (s, 2H), 4.51-4.46 (m, 1H), 4.18-4.13 (m, 1H), 2.19-2.09 (m, 2H), 2.03-1.93 (m, 3H), 1.63-1.45 (m, 2H), 1.04-0.99 (m, 2H), 0.87-0.77 (m, 2H). |
| 168 | $^1$H NMR (400 MHz, DMSO-$d_6$) δ 8.76 (dd, 1H), 8.47 (d, 1H), 8.24 (d, 1H), 8.12 (dd, 1H), 8.03 (dd, 1H), 7.63 (dd, 1H), 7.35 (d, 1H), 6.95 (dd, 1H), 6.71-6.63 (m, 1H), 6.56 (d, 1H), 5.28 (s, 1H), 4.96 (s, 2H), 4.50 (p, 1H), 4.17 (q, 1H), 2.14 (tt, 2H), 1.96 (dq, 2H), 1.63-1.52 (m, 2H), 1.44 (s, 6H). |
| 169 | $^1$H NMR (400 MHz, DMSO-$d_6$) δ 8.76 (dd, 1H), 8.73 (d, 1H), 8.24 (d, 1H), 8.12 (dd, 1H), 8.03 (dd, 1H), 7.63 (dd, 1H), 7.45 (d, 1H), 6.92 (dd, 1H), 6.88 (d, 1H), 6.67 (dd, 1H), 4.96 (s, 2H), 4.53-4.48 (m, 1H), 4.21-4.16 (m, 1H), 2.18-2.12 (m, 2H), 2.04-1.92 (m, 2H), 1.63-1.55 (m, 2H). |
| 170 | $^1$H NMR (400 MHz, DMSO-$d_6$) δ 8.83 (d, 1H), 8.76 (dd, 1H), 8.12 (dd, 1H), 7.96 (d, 1H), 7.86 (d, 1H), 7.66-7.60 (m, 2H), 7.15 (dd, 1H), 7.04 (d, 1H), 5.92 (d, 1H), 4.96 (s, 2H), 4.53-4.48 (m, 1H), 4.23-4.18 (m, 1H), 3.85 (s, 3H), 2.19-2.12 (m, 2H), 2.03-1.91 (m, 2H), 1.61-1.56 (m, 2H). |
| 171 | $^1$H NMR (400 MHz, DMSO-$d_6$) δ 8.83 (d, 1H), 8.77 (dd, 1H), 8.74 (d, 1H), 8.37 (d, 1H), 8.14 (dd, 1H), 7.89-7.83 (m, 1H), 7.64 (dd, 1H), 7.20-7.13 (m, 2H), 7.04 (d, 1H), 4.97 (s, 2H), 4.68-4.50 (m, 1H), 4.31-4.18 (m, 1H), 2.26-2.09 (m, 2H), 2.01 (t, 2H), 1.73-1.51 (m, 2H). |
| 172 | $^1$H NMR (400 MHz, DMSO-$d_6$) δ 8.83 (d, 1H), 8.76 (dd, 1H), 8.40 (d, 1H), 8.22 (d, 1H), 8.15-8.09 (m, 1H), 7.88-7.82 (m, 1H), 7.63 (dd, 1H), 7.15 (dd, 1H), 7.05 (d, 1H), 6.33 (d, 1H), 4.97 (s, 2H), 4.55 (q, 1H), 4.23 (q, 1H), 2.25-2.12 (m, 2H), 2.07-1.94 (m, 2H), 1.69-1.53 (m, 2H). |
| 173 | $^1$H NMR (400 MHz, DMSO-$d_6$) δ 8.83 (d, 1H), 8.80-8.74 (m, 1H), 8.67 (d, 1H), 8.38 (d, 1H), 8.14 (d, 1H), 7.86 (s, 1H), 7.68-7.60 (m, 1H), 7.19-7.12 (m, 1H), 7.05 (d, 1H), 6.10 (d, 1H), 5.01 (s, 2H), 4.76-4.63 (m, 1H), 4.31-4.15 (m, 1H), 2.24-2.10 (m, 2H), 2.09-1.95 (m, 2H), 1.72-1.52 (m, 2H). |
| 174 | $^1$H NMR (400 MHz, DMSO-$d_6$) δ 8.83 (d, 1H), 8.77 (d, 1H), 8.37 (d, 1H), 8.24 (s, 1H), 8.13 (d, 1H), 7.86 (s, 1H), 7.68-7.59 (m, 1H), 7.19-7.12 (m, 1H), 7.05 (d, 1H), 6.81 (d, 1H), 4.99 (s, 2H), 4.64-4.52 (m, 1H), 4.29-4.17 (m, 1H), 2.23-2.09 (m, 2H), 2.04-1.95 (m, 2H), 1.68-1.50 (m, 2H). |
| 175 | $^1$H NMR (400 MHz, DMSO-$d_6$) δ 8.83 (d, 1H), 8.75 (d, 1H), 8.26 (d, 1H), 8.10 (d, 1H), 7.86 (s, 1H), 7.63-7.60 (m, 2H), 7.16 (dd, 1H), 7.06 (d, 1H), 5.90 (d, 1H), 4.93 (s, 2H), 4.60-4.54 (m, 1H), 4.27-4.21 (m, 1H), 2.23-2.17 (m, 2H), 2.05-1.98 (m, 2H), 1.84-1.77 (m, 1H), 1.63-1.58 (m, 2H), 0.98-0.94 (m, 2H), 0.59-0.55 (m, 2H). |
| 176 | $^1$H NMR (400 MHz, DMSO-$d_6$) δ 8.84 (d, 1H), 8.77 (dd, 1H), 8.11 (d, 1H), 7.87 (s, 1H), 7.63 (dd, 1H), 7.39 (d, 1H), 7.16 (dd, 1H), 7.05 (d, 1H), 6.74 (d, 1H), 6.38 (d, 1H), 4.75 (s, 2H), 4.33-4.27 (m, 1H), 4.23-4.18 (m, 1H), 2.20-2.12 (m, 2H), 2.14 (s, 3H), 2.01-1.88 (m, 2H), 1.62-1.49 (m, 2H). |
| 179 | $^1$H NMR (400 MHz, DMSO-$d_6$) δ 8.83 (d, 1H), 8.24 (d, 1H), 8.07 (d, 1H), 8.01 (dd, 1H), 7.91 (d, 1H), 7.85 (d, 1H), 7.15 (dd, 1H), 7.04 (d, 1H), 6.68 (dd, 1H), 5.41 (s, 1H), 4.91 (s, 2H), 4.50 (q, 1H), 4.22 (q, 1H), 2.20-2.13 (m, 2H), 2.03-1.95 (m, 2H), 1.59 (dt, 2H), 1.49 (s, 6H). |
| 180 | $^1$H NMR (400 MHz, DMSO-$d_6$) δ 8.88 (d, 1H), 8.82 (d, 1H), 8.23 (d, 1H), 8.14 (d, 1H), 8.02 (dd, 1H), 7.89-7.81 (m, 1H), 7.15 (dd, 1H), 7.03 (d, 1H), 6.67 (d, 1H), 5.46 (s, 1H), 4.94 (s, 2H), 4.50 (q, 1H), 4.22 (q, 1H), 2.21-2.12 (m, 2H), 1.99 (dq, 2H), 1.66-1.56 (m, 2H), 1.52 (s, 6H). |
| 181 | $^1$H NMR (400 MHz, DMSO-$d_6$) δ 8.82 (d, 1H), 8.68 (d, 1H), 8.26 (d, 1H), 8.00 (dd, 1H), 7.89-7.82 (m, 1H), 7.56 (d, 1H), 7.15 (dd, 1H), 7.04 (d, 1H), 6.68 (d, 1H), 5.48 (s, 1H), 5.12 (s, 2H), 4.51 (q, 1H), 4.22 (q, 1H), 2.21-2.12 (m, 2H), 1.99 (td, 2H), 1.65-1.57 (m, 2H), 1.53 (s, 6H). |
| 182 | $^1$H NMR (400 MHz, DMSO-$d_6$) δ 8.82 (d, 1H), 7.88-7.82 (m, 2H), 7.64 (dd, 1H), 7.60-7.51 (m, 2H), 7.15 (dd, 1H), 7.04 (d, 1H), 6.93 (d, 1H), 6.32 (t, 1H), 5.29 (s, 1H), 4.53 (q, 1H), 4.22 (q, 1H), 2.16 (dt, 2H), 1.99 (t, 2H), 1.59 (dt, 2H), 1.44 (s, 6H). |
| 183 | $^1$H NMR (400 MHz, DMSO-$d_6$) δ 11.45 (d, 1H), 8.83 (d, 1H), 7.88 (d, 1H), 7.86 (s, 1H), 7.67 (d, 1H), 7.59-7.50 (m, 1H), 7.19-7.12 (m, 1H), 7.05 (d, 1H), 6.97 (d, 1H), 5.70-5.59 (m, 1H), 4.57-4.44 (m, 1H), 4.29-4.15 (m, 1H), 2.23-2.08 (m, 2H), 2.06-1.89 (m, 2H), 1.70-1.50 (m, 2H). |
| 184 | $^1$H NMR (400 MHz, DMSO-$d_6$) δ 8.83 (d, 1H), 8.78 (dd, 1H), 8.13 (dd, 1H), 7.86 (s, 1H), 7.64 (dd, 1H), 7.50 (d, 1H), 7.16 (dd, 1H), 7.05 (d, 1H), 6.74 (d, 1H), 4.78 (s, 2H), 4.58-4.53 (m, 1H), 4.20-4.24 (m, 1H), 2.22-2.12 (m, 2H), 2.15 (s, 3H), 2.00 (t, 2H), 1.64-1.56 (m, 2H). |

-continued

| Examples | HNMR |
|---|---|
| 192 | $^1$H NMR (400 MHz, DMSO-$d_6$) δ 11.35 (s, 1H), 11.27 (d, 1H), 8.69 (dd, 1H), 8.08 (d, 1H), 7.77 (dd, 2H), 7.30 (dd, 1H), 6.91 (td, 1H), 4.51-4.42 (m, 1H), 4.19-4.14 (m, 1H), 2.24-2.08 (m, 2H), 2.08-1.93 (m, 2H), 1.71-1.52 (m, 2H). |
| 195 | $^1$H NMR (400 MHz, DMSO-$d_6$) δ 11.25 (s, 1H), 11.11 (s, 1H), 8.82 (d, 1H), 7.99 (t, 1H), 7.85 (s, 1H), 7.60 (s, 1H), 7.52 (dd, 1H), 7.15 (dd, 1H), 7.03 (d, 1H), 6.64 (d, 1H), 4.56-4.42 (m, 1H), 4.26-4.14 (m, 1H), 2.22-2.06 (m, 2H), 2.04-1.87 (m, 2H), 1.65-1.51 (m, 2H). |
| 201 | $^1$H NMR (400 MHz, DMSO-$d_6$) δ 8.71-8.61 (m, 1H), 7.90 (d, 1H), 7.62 (d, 1H), 7.55-7.45 (m, 1H), 7.31-7.22 (m, 1H), 6.91-6.81 (m, 2H), 6.74 (d, 2H), 4.57-4.43 (m, 3H), 4.21-4.13 (m, 1H), 4.13-4.07 (m, 2H), 2.20-2.07 (m, 2H), 2.03-1.89 (m, 2H), 1.66-1.50 (m, 2H). |
| 202 | $^1$H NMR (400 MHz, DMSO-$d_6$) δ 8.70-8.62 (m, 1H), 7.88 (d, 1H), 7.53-7.46 (m, 1H), 7.42 (s, 1H), 7.31-7.23 (m, 1H), 7.17 (s, 1H), 6.90-6.81 (m, 1H), 6.78-6.65 (m, 2H), 4.54-4.44 (m, 1H), 4.43-4.36 (m, 2H), 4.22-4.11 (m, 1H), 4.09-4.01 (m, 2H), 2.20-2.08 (m, 2H), 2.03-1.89 (m, 2H), 1.65-1.51 (m, 2H). |
| 212 | $^1$H NMR (400 MHz, DMSO-$d_6$) δ 8.83 (d, 1H), 7.89 (d, 1H), 7.86 (s, 1H), 7.62 (d, 1H), 7.50 (dd, 1H), 7.15 (dd, 1H), 7.04 (d, 1H), 6.83 (d, 1H), 6.79-6.72 (m, 1H), 4.58-4.43 (m, 3H), 4.22 (d, 1H), 4.10 (dd, 2H), 2.21-2.09 (m, 2H), 2.04-1.92 (m, 2H), 1.65-1.51 (m, 2H). |
| 213 | $^1$H NMR (400 MHz, DMSO-$d_6$) δ 8.83 (d, 1H), 7.91-7.83 (m, 2H), 7.53-7.37 (m, 2H), 7.15 (dd, 2H), 7.04 (d, 1H), 6.74 (dd, 1H), 4.56-4.46 (m, 1H), 4.43-4.35 (m, 2H), 4.27-4.16 (m, 1H), 4.09-4.00 (m, 2H), 2.25-2.09 (m, 2H), 2.06-1.90 (m, 2H), 1.70-1.50 (m, 2H). |
| 426 | $^1$H NMR (400 MHz, DMSO-$d_6$) δ 8.83 (d, 1H), 7.92 (s, 1H), 7.86 (s, 1H), 7.60 (d, 1H), 7.52-7.44 (m, 1H), 7.40 (d, 1H), 7.15 (d, 1H), 7.05 (d, 1H), 6.94 (d, 1H), 6.53 (d, 1H), 6.44 (d, 1H), 6.27 (t, 1H), 4.40-4.29 (m, 1H), 4.27-4.12 (m, 1H), 2.22-2.09 (m, 2H), 2.03-1.82 (m, 2H), 1.66-1.43 (m, 2H). |
| 427 | $^1$H NMR (400 MHz, DMSO-$d_6$) δ 8.40 (d, 1H), 7.91 (d, 1H), 7.60 (dd, 1H), 7.47 (ddd, 1H), 7.39 (dd, 1H), 7.07 (d, 1H), 6.91 (d, 1H), 6.59-6.49 (m, 3H), 6.44 (dt, 1H), 6.26 (td, 1H), 4.36-4.25 (m, 1H), 4.20-4.08 (m, 1H), 2.20-2.07 (m, 2H), 2.02-1.81 (m, 3H), 1.61-1.42 (m, 2H), 1.07-0.98 (m, 2H), 0.84-0.74 (m, 2H). |

Biological Test and Evaluation

The present disclosure will be further described and explained below in conjunction with test examples, but these examples are not meant to limit the scope of the present disclosure.

Experimental Instruments and Reagents

1. Instruments:

Envision (PE-Cisbio: 2105-0020); Incubator (Boxun, BC-J80S); Centrifuge (Eppendorf: 5810R, Centrifuge 5720R); Ice maker (Xueke Electric Appliance, IMS-150); Water purifier (THERMO: Pacific TII+Micropure); Envision (PE-Cisbio: 2105-0020); Plate washer (Thermo: WELLWASH VERSA); Microplate shaker (Thermo: 88882006); Refrigerator (BCD-268TN, Haier); Biological safety cabinet (BSC-130011 A2, Shanghai Boxun Industrial Co., Ltd. Medical Equipment Factory); Ultra-clean workbench (CJ-2F, Suzhou Fengshi Experimental Animal Equipment Co., Ltd.); 5 mL pipettor (Research Plus, Eppendorf); 1 mL pipettor (Research Plus, Eppendorf); Thermostat water bath (HWS-12, Shanghai Yiheng Science); Electronic balance (BSA2202S-CW, CPA2202S, Sartorius); Ultrasonic cleaner (115F0032, Shanghai Kudos); Magnetic stirrer (08-2G, Chijiu); Fully automatic blood biochemical analyzer (HITACHI Model 7180, HITACHI).

2. Reagents:

PCSK9-His (Sino biology, 29698-H08H); Anti-His Tb (Revvity, 61HISTLF); Probe compound (Alexa Fluor 647 label, synthesized by Hansoh); DMSO (Sigma, D2650); HEPES buffer pH 7.5 (Beyotime, C0217); Sodium chloride solution (Beyotime, ST347); Calcium chloride solution (Beyotime, ST365); TWEEN 20 (Sigma, P9416); 10% BSA (Thermo, 37525); 384-well plate (Revvity, 6007299); Compound dilution plate (Biofil, VWP033096); 50 mL reagent reservoir (Corning, 4870); 50 mL centrifuge tube (Corning, 430829); 2.5 μL pipettor (Eppendorf, I36630F); 10 μL pipettor (Eppendorf, J13131F); 100 μL pipettor (Eppendorf, R22267J); 1000 μL pipettor (Eppendorf, 144804F); 10 μL 12-channel electronic pipettor (METTLER TOLEDO, 17013797); 300 μL 12-channel electronic pipettor (Eppendorf, 051743J); CircuLex Human PCSK9 ELISA kit (MBL: CY-8079); DMEM (Gibco: 31966-021); FBS (Sigma: S5394); Compound plate (Thermo: 1353506); Complete culture medium: DMEM+10% FBS+1×P/S; Experimental culture medium: DMEM+10% FBS; Cell strain: HepG2 (ATCC: HB-8065); Human LDL R Quantikine ELISA Kit (R&D: DLDLRO); PBS; Cell lysis buffer (Thermo: 78503); Protease inhibitor (Pierce: 78430); Alamethicin (Abcam); 7-Hydroxycoumarin (Sigma); Liver microsomes (XenoTech, Shanghai Quanyang Biotechnology Co., Ltd.), phosphate buffer (Gibco, Lot #SLBS7904 and Lot #SLBR3106V, pH 7.4), NADPH (reduced nicotinamide adenine dinucleotide phosphate, Shanghai Bide Pharmaceutical Technology Co., Ltd.), UDPGA (Sigma), Alamethicin (Abcam), methanol (Merck), and acetonitrile (Merck); High-fat feed (Western Diet, D12079B); Normal saline (MA0083-D, meilunbio); Solutol HS 15 (102483882, Sigma).

I. Binding Experiment

Test Example 1. Determination of the Binding Ability of the Compounds of the Present Disclosure to PCSK9 Protein 1. Experimental objective: To detect the action of compounds to bind PCSK9 protein by an HTRF method.

2. Experimental Method:

1) 1× experimental buffer was prepared from the following components: 20 mM HEPES, 150 mM NaCl, 1 mM CaCl2, 0.01% Tween20, and 0.01% BSA;

2) PCSK9-His working solution at a 2.5x final concentration (30 nM) was prepared with the 1× experimental buffer, except for the wells of Low control, 8 μL of the protein solution was added to each well of a 384-well plate, and 8 μL of 1× experimental buffer was added to the wells of Low control;

3) Preparation of compound working solution: The compounds in the stock solution were first diluted with DMSO in a uniform gradient (300 μM top, 3-fold, 10 dose), then the compounds diluted in the gradient were pipetted into 3.33 μL to 96.7 μL of the 1× experimental buffer and well mixed uniformly to obtain the prepared compound working solution (10×);

4) 2 μL of compound was pipetted into the corresponding well and incubated at 25° C. for 10 minutes;

5) Probe compound working solution at a 4x final concentration (90 nM) was prepared with the 1x experimental buffer, and well mixed uniformly, then 5 μL of the mixture was added to each well and incubated at 25° C. for 10 minutes;

6) Anti-His Tb working solution at a 4× final concentration (4×) was prepared with the 1× experimental buffer, then 5 μL of the mixture was added to each well and incubated at 25° C. for 2 hours;

7) Envision was used to read HTRF665/615 program.

3. Experimental data processing method: Four-parameter log(inhibitor) vs. response—Variable slope (four parameters) in XLit was used to perform non-linear fitting of the compound concentration and the corresponding inhibition rate, and $IC_{50}$ was calculated.

4. Experimental results:

| Examples | $IC_{50}$ (nM) |
|---|---|
| 28 | 17.4 |
| 29 | 18.4 |
| 52 | 60.5 |
| 53 | 43.6 |
| 65 | 13.9 |
| 66 | 25.9 |
| 67 | 14.0 |
| 68 | 9.8 |
| 73 | 31.0 |
| 76 | 13.9 |
| 78 | 10.1 |
| 79 | 24.9 |
| 82 | 11.8 |
| 83 | 11.5 |
| 84 | 6.3 |
| 85 | 12.2 |
| 86 | 14.8 |
| 87 | 12.1 |
| 88 | 28.3 |
| 89 | 10.5 |
| 90 | 12.3 |
| 91 | 10.4 |
| 94 | 9.5 |
| 95 | 10.2 |
| 96 | 13.5 |
| 97 | 2.5 |
| 98 | 6.6 |
| 99 | 6.9 |
| 100 | 8.4 |
| 102 | 13.3 |
| 103 | 10.8 |
| 104 | 13.9 |
| 105 | 9.1 |
| 106 | 10.6 |
| 107 | 21.3 |
| 108 | 15.3 |
| 109 | 16.1 |
| 110 | 18.7 |
| 111 | 16.2 |

-continued

| Examples | $IC_{50}$ (nM) |
|---|---|
| 112 | 8.3 |
| 113 | 7.4 |
| 114 | 8.9 |
| 115 | 9.9 |
| 116 | 16.4 |
| 117 | 18.3 |
| 119 | 23.0 |
| 121 | 16.7 |
| 122 | 16.1 |
| 123 | 11.5 |
| 124 | 6.7 |
| 125 | 7.2 |
| 126 | 9.4 |
| 128 | 8.5 |
| 129 | 6.6 |
| 130 | 7.8 |
| 131 | 6.7 |
| 132 | 10.0 |
| 133 | 7.8 |
| 134 | 6.8 |
| 135 | 5.4 |
| 136 | 7.8 |
| 137 | 15.9 |
| 138 | 8.8 |
| 139 | 36.3 |
| 142 | 15.7 |
| 143 | 13.6 |
| 144 | 15.6 |
| 145 | 10.6 |
| 147 | 8.8 |
| 148 | 17.2 |
| 149 | 7.1 |
| 150 | 10.4 |
| 151 | 8.1 |
| 152 | 6.7 |
| 153 | 12.2 |
| 154 | 6.8 |
| 157 | 8.9 |
| 158 | 16.0 |
| 159 | 16.8 |
| 160 | 7.7 |
| 162 | 5.9 |
| 163 | 6.3 |
| 164 | 7.2 |
| 165 | 7.5 |
| 166 | 7.9 |
| 168 | 10.6 |
| 169 | 9.4 |
| 170 | 13.3 |
| 171 | 10.6 |
| 172 | 8.4 |
| 173 | 26.0 |
| 174 | 96.4 |
| 175 | 16.9 |
| 176 | 9.08 |
| 179 | 17.3 |
| 180 | 8.1 |
| 181 | 7.2 |
| 182 | 29.3 |
| 183 | 8.8 |
| 184 | 8.0 |
| 186 | 8.5 |
| 190 | 8.5 |
| 192 | 8.4 |
| 193 | 6.9 |
| 195 | 9.6 |
| 196 | 8.7 |
| 197 | 7.5 |
| 201 | 7.7 |
| 202 | 8.7 |
| 212 | 6.9 |
| 213 | 9.5 |
| 216 | 11.0 |
| 223 | 7.2 |
| 224 | 8.5 |
| 225 | 8.6 |
| 226 | 7.1 |

-continued

| Examples | $IC_{50}$ (nM) |
|---|---|
| 227 | 8.1 |
| 238 | 8.0 |

5. Experimental conclusion: It can be seen from the data in the table that the example compounds shown in the present disclosure had a significant binding effect on the PCSK-9 protein.

II. Cell Function Experiment

Test Example 1. Determination of the Effect of the Compounds of the Present Disclosure on the Concentration of PCSK9 Secreted by HepG2 Cells 1. Experimental objective: To detect the inhibitory effect of the compounds on PCSK9.

2. Experimental method:

1) HepG2 cell strain was cultured in the complete culture medium at 37° C., 5% $CO_2$ to 70-90% confluence.
2) The cells were digested and resuspended in the experimental culture medium, inoculated at 25,000 cells/well/200 µL in a 96-well cell culture plate, and cultured at 37° C. and 5% CO2 for 20-24 hours.
3) The culture medium was removed from the cell culture plate, and the cell culture plate was washed once by adding 200 ul of the experimental culture medium to each well.
4) Preparation of positive control compound and compound to be tested: the positive control compound and the compound to be tested were diluted on the compound plate.
5) The diluted compound was added to the cell culture plate at 250 µL per well and incubated at 37° C. and 5% CO2 for 48 hours.
6) The cell culture medium was collected at 200 µL per well and cryopreserved at −80° C. for later use.
7) A sample of the cell culture medium was taken from the −80° C. cryopreservation condition, dissolved, vortexed, and centrifuged for later use.
8) Preparation of standard curve: corresponding volumes of Dilution buffer were successively added to respective standard tubes, and in the order of the concentrations of 10, 5, 2.5, 1.25, 0.625, 0.313, 0.16, 0 ng/mL, the standard was diluted in series by taking the corresponding volume from the original tube or the last concentration tube.
9) Preparation of washing liquid: 10x Wash buffer was diluted into 1x with Milli-Q for later use.
10) According to the standard curve wells and sample wells set according to a plate map, 100 µL/well of the corresponding standards and culture medium samples were added to the wells, with 2 replicate wells. A self-adhesive seal was applied, the plate was placed on a plate shaker at room temperature, gently shaken, uniformly mixed, and incubated for 1 hour.
11) The plate was placed on the plate washer, the washing liquid was set to 350 µL per well, and the plate was washed 4 times repeatedly.
12) 100 µL/well of an HRP-conjugated detection antibody was added, a self-adhesive seal was applied, and the plate was placed on the plate shaker, well mixed uniformly, and incubated for 1 hour.
13) The plate was placed on the plate washer, the washing liquid was set to 350 µL per well, and the plate was washed 4 times repeatedly.
14) 100 µL/well of Substrate reagent was added, and the plate was placed in the dark, applied with a self-adhesive seal, placed on the plate shaker, well mixed uniformly, and incubated for 10-20 minutes.
15) 100 µL of Stop solution (1N H2SO4) was added to each well and mixed uniformly.
16) The optical density (OD) value in each well was measured in sequence at a wavelength of 450 nm by the microplate reader. Detection was carried out within 30 min after the reaction was stopped.

3. Experimental data processing method: After the OD values were read by the microplate reader, the OD value of the 0-concentration standard in the standard group was subtracted from the OD values of the standards, control group, and samples to obtain the actual OD values for these wells. A standard curve was plotted with Graphpad and the concentration of the sample was calculated. If the dilution was performed during the sample detection, the calculated sample concentration was necessarily multiplied by the corresponding dilution ratio in the final calculation, which was the actual concentration of the sample. Inhibition rate=(actual concentration in control−actual concentration in sample)/actual concentration in control*100. According to the inhibition rates corresponding to the different concentrations, IC50 was derived by Graphpad.

4. Experimental results:

| Examples | $IC_{50}$ (µM) |
|---|---|
| 25 | 17.6 |
| 26 | 22.8 |
| 27 | 12.0 |
| 49 | 2.7 |
| 51 | 21.3 |
| 54 | 23.4 |
| 57 | 1.7 |
| 58 | 11.1 |
| 60 | 27.4 |
| 61 | 0.6 |
| 62 | 17.6 |
| 63 | 26.5 |
| 65 | 12.8 |
| 66 | 0.8 |
| 67 | 17.1 |
| 68 | 2.0 |
| 73 | 14.3 |
| 75 | 0.6 |
| 76 | 4.8 |
| 78 | 33.1 |
| 79 | 15.1 |
| 81 | 26.5 |
| 82 | 0.8 |
| 83 | 1.1 |
| 84 | 4.7 |
| 85 | 2.6 |
| 86 | 0.9 |
| 87 | 0.6 |
| 89 | 4.0 |
| 90 | 2.7 |
| 91 | 12.9 |
| 94 | 20.5 |
| 95 | 0.7 |
| 96 | 12.7 |
| 99 | 6.6 |
| 100 | 5.0 |
| 103 | 1.4 |
| 109 | 19.6 |
| 111 | 11.2 |
| 112 | 6.9 |
| 113 | 6.9 |

-continued

| Examples | $IC_{50}$ (μM) |
|---|---|
| 114 | 14.7 |
| 115 | 2.6 |
| 116 | 0.5 |
| 117 | 0.4 |
| 123 | 5.2 |
| 130 | 1.5 |
| 132 | 6.5 |
| 133 | 0.4 |
| 145 | 2.9 |
| 147 | 0.3 |
| 148 | 2.6 |
| 151 | 12.7 |
| 153 | 0.8 |
| 154 | 5.5 |
| 162 | 5.3 |
| 163 | 10.8 |
| 183 | 4.8 |
| 415 | 30.7 |
| 426 | 14.0 |
| 427 | 22.3 |

5. Experimental conclusion: It can be seen from the data in the table that the example compounds shown in the present disclosure showed a good inhibitory effect in the experiment of the effect on the concentration of PCSK9 secreted by HepG2 cells.

Test Example 2. Determination of the Effect of the Compounds of the Present Disclosure on the LDLR Level in HepG2 Cells 1. Experimental objective: To detect the effect of the compounds on the LDLR protein level.

2. Experimental method:

1) HepG2 cell strain was cultured in the complete culture medium at 37° C., 5% $CO_2$ to 70-90% confluence.

2) The cells were digested and resuspended in the experimental culture medium, inoculated at 25,000 cells/well/200 μL in a 96-well cell culture plate, and cultured at 37° C., 5% $CO_2$ for 20-24 hours.

3) The culture medium was removed from the cell culture plate, and the cell culture plate was washed once by adding 200 ul of the experimental culture medium to each well.

4) Preparation of positive control compound and compound to be tested: the positive control compound and the compound to be tested were diluted on the compound plate.

5) The diluted compound was added to the cell culture plate at 250 μL per well and incubated at 37° C. and 5% CO2 for 48 hours.

6) The cell culture medium was removed, the cells were washed with PBS, and 50 μL of the cell lysis buffer and the protein inhibitor were added.

7) After centrifugation, the lysate was removed and the sample was stored for later use.

8) Preparation of standard curve: corresponding volumes of Dilution buffer were successively added to respective standard tubes, and the standard was diluted in series by taking the corresponding volume from the original tube or the last concentration tube.

9) Preparation of washing liquid: 10× Wash buffer was diluted into 1× with Milli-Q for later use.

10) According to the standard curve wells and sample wells set according to a plate map, 80 μL/well of the corresponding standards and samples were added to the wells, with 2 replicate wells. A well in which no standard was added was used as a background value well. A self-adhesive seal was applied, the plate was placed on a plate shaker at room temperature, gently shaken, uniformly mixed, and incubated for 2 hours.

11) The plate was placed on the plate washer, the washing liquid was set to 350 μL per well, and the plate was washed 4 times repeatedly.

12) 200 μL of Human LDLR conjugate was added, a self-adhesive seal was applied, and the plate was placed on the plate shaker, well mixed uniformly, and incubated for 2 hours.

13) The plate was placed on the plate washer, the washing liquid was set to 350 μL per well, and the plate was washed 4 times repeatedly.

14) 200 μL/well of Substrate solution was added, and the plate was placed in the dark, applied with a self-adhesive seal, placed on the plate shaker, well mixed uniformly, and incubated for 20 minutes.

15) 50 μL/well of Stop solution was added and mixed uniformly over 20 min.

16) The optical density (OD) value in each well was measured in sequence at a wavelength of 450 nm by the microplate reader.

3. Experimental data processing method: After the OD values were read by the microplate reader, the OD value of the 0-concentration standard in the standard group was subtracted from the OD values of the standards, control group, and samples to obtain the actual OD values for these wells. A standard curve was plotted with Graphpad and the concentration of the sample was calculated. If the dilution was performed during the sample detection, the calculated sample concentration was necessarily multiplied by the corresponding dilution ratio in the final calculation, which was the actual concentration of the sample. Concentration increase %=(actual concentration in control−actual concentration in sample)/actual concentration in control*100.

4. Experimental results:

| Examples | LDLR expression level |
|---|---|
| 21 | 135% |
| 25 | 132% |

5. Experimental conclusion: It can be seen from the data in the table that the example compounds shown in the present disclosure showed an effect of significant increasing the LDLR concentration in the experiment of the effect on the concentration of LDLR on HepG2 cells.

III. Pharmacokinetic Experiment

Test Example 1. Pharmacokinetic Determination in Mice

1. Experimental objective: C57BL/6J mice were used as test animals to study the pharmacokinetic behavior of the compounds of the present disclosure in mice (plasma) after oral and intravenous administration.

2. Experimental scheme 2.1 Test drugs: the compounds of the present disclosure, made in house;

2.2 Test animals: C57 mice, male, purchased from Shanghai Bk Lab Animal Co., Ltd., with animal production license number (SCXK (Shanghai) 2013-0006 N0.311620400001794).

2.3 Drug preparation: Preparation of oral drug: 10% Solutol HS15

10 g of Solutol HS15 solid was weighed, dissolved in 90 mL of pure water, uniformly mixed, stirred, and ultrasonically treated to form a clear solution. The compound of the present disclosure was weighed and dissolved in this solution, uniformly shaken, and ultrasonically treated for 15 minutes to obtain a colorless clear solution with a concentration of 0.5 mg/mL. Preparation of intravenous drug: 5% DMSO+10% Solutol HS15+85% PBS, the compound of the present disclosure was weighed, 5% DMSO was first added on the basis of the proportion relative to the total volume of administration, and the mixture was vortexed and ultrasonically treated for 2 min until it was completely dissolved; 10% of Solutol HS15 was then added, and the mixture was vortexed and ultrasonically treated for 2 min until it was completely dissolved; and finally, 85% of PBS was added, and the mixture was vortexed, ultrasonically treated for 5 min, and filtered through a 0.22 um filter membrane to obtain a colorless and transparent clear solution with a concentration of 0.2 mg/mL.

2.4 Administration: 3 male C57 mice were fasted overnight and then respectively administered PO at a dose of 5 mg/kg and a volume of 10 mL/kg. 3 male C57 mice were fasted overnight and then respectively administered IV at a dose of 1 mg/kg and a volume of 5 mL/kg.

2.5 Sample collection: Before and after administration of mice, 0.04 mL of blood was collected from the orbit at 0.083 (iv), 0.25, 0.5, 1, 2, 4, 8, and 24 hours, and placed in EDTA-$K_2$ test tubes, which was centrifuged at 6000 rpm at 4° C. for 6 min to separate plasma which was stored at −80° C.; and the rats were fed 4 h after administration.

2.6 Determination results: The final determination results were obtained by using an LCMS/MS method.

3. Experimental results: The main pharmacokinetic parameters were calculated using WinNonlin 6.1.

| | Pharmacokinetic experiment (PO administration, 5 mpk) | | | | |
|---|---|---|---|---|---|
| Examples | Time to peak $t_{max}$ (h) | Plasma concentration $C_{max}$ (ng/mL) | Area under the curve $AUC_{0-\infty}$ (ng/mL × h) | Half-life $t_{1/2}$ (h) | Mean residence time MRT (h) |
| 12 | 0.25 | 4307.00 | 9514.00 | 2.90 | 2.80 |
| 65 | 4.00 | 7868.00 | 69985.00 | 4.00 | 5.80 |
| 78 | 0.25 | 7860.00 | 14010.00 | 3.60 | 1.70 |
| 89 | 0.25 | 10300.00 | 34342.00 | 2.70 | 3.10 |
| 99 | 0.25 | 7243.00 | 27909.00 | 2.70 | 3.40 |
| 110 | 1.00 | 2923.00 | 11253.00 | 3.00 | 2.60 |
| 112 | 1.00 | 5070.00 | 33812.00 | 2.20 | 4.70 |
| 114 | 0.50 | 2352.00 | 7233.00 | 3.10 | 3.00 |
| 123 | 2.00 | 9917.00 | 62189.00 | 2.40 | 4.30 |
| 130 | 1.00 | 5087.00 | 57882.00 | 3.60 | 6.10 |
| 131 | 0.50 | 7167.00 | 22429.00 | 3.40 | 2.70 |
| 132 | 0.50 | 8570.00 | 30627.00 | 2.90 | 3.00 |
| 133 | 2.00 | 11000.00 | 86787.70 | 5.00 | 5.80 |
| 145 | 1.00 | 6313.00 | 22625.00 | 3.30 | 3.10 |
| 151 | 0.50 | 3457.00 | 11256.00 | 1.40 | 2.30 |
| 154 | 1.00 | 2643.00 | 13322.00 | 2.50 | 3.70 |
| 159 | 2.00 | 7657.00 | 76792.00 | 9.80 | 10.70 |
| 183 | 0.70 | 6127.00 | 26693.00 | 3.00 | 3.50 |

4. Experimental conclusion:

The pharmacokinetic determination results in the C57BL/6J mice showed that the compounds of the present disclosure exhibited a good PK advantage.

Test Example 2. Pharmacokinetic Determination in Cynomolgus Monkeys

1. Study objective: Cynomolgus monkeys were used as test animals to study the pharmacokinetic behavior of the compounds of the present disclosure in cynomolgus monkeys (plasma) after oral administration at a dose of 5 mg/kg.

2. Experimental scheme:

2.1 Experimental drugs: The example compounds of the present disclosure, made in house.

2.2 Experimental animals: 3 cynomolgus monkeys per group, male, purchased from Guangxi Xiongsen, with animal production license number: SCXK (Guangxi) 2021-0004).

2.3 Formulation prescription: Preparation of oral drug: 10% Solutol HS15 in water 10 g of solid Solutol HS15 was weighed into a 100 ml volumetric flask, 90 ml of ddH2O was added, and the mixture was vortexed, uniformly mixed, and ultrasonically treated to obtain a clear solution. The compound was weighed and added to a 100 mL glass bottle, the solution was added, and the mixture was vortexed and ultrasonically treated for 10 minutes to obtain a white suspension with a concentration of 1 mg/mL.

2.4 Administration: After overnight fasting, 3 male cynomolgus monkeys were administered orally (p.o.) at a dose of 5 mg/kg and an administration volume of 5 mL/kg.

2.5 Sample collection: Blood collection: 0.3 mL of blood was collected from the forelimb vein of cynomolgus monkeys before administration and at 0.25, 0.5, 1, 2, 4, 6, 8 and 24 h after administration, and placed in an EDTA-$K_2$ anticoagulation tube, and the plasma was separated by centrifugation at 6000 rpm at 4° C. for 6 min and stored at −80° C.; the rats were fed 4 h after administration.

2.6 Sample treatment:

1) Acetonitrile (160 μL) was added to plasma sample (40 μL) for precipitation, and the mixture was mixed and centrifuged at 3500×g for 5-20 minutes.
2) The treated supernatant solution was taken and subjected to LC/MS/MS to analyze the concentrations of the compound to be tested. LC/MS/MS analysis instrument: AB Sciex API 4000 Qtrap.

Liquid phase analysis: Liquid phase conditions: Shimadzu LC-20AD pump

Chromatographic column: Agilent ZORBAX XDB-C18 (50×2.1 mm, 3.5 am), mobile phase: Liquid A: 0.1% aqueous formic acid, liquid B: acetonitrile, flow rate: 0.4 mL/min Elution time: 0-4.0 min, the eluent is as follows:

| Time/min | Liquid A | Liquid B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

3. Experimental results: The main pharmacokinetic parameters were calculated using WinNonlin 6.1.

4. Experimental conclusion: The pharmacokinetic determination results in the cynomolgus monkeys showed that the compounds of the present disclosure showed a good PK advantage, in which $AUC_{0-\infty}$(ng/mL×h) of the compound was 20000-50000, and the $AUC_{0-\infty}$ (ng/mL×h) of the advantageous compound was 30000-50000.

Test Example 3. Investigation on In Vitro Metabolic Stability of the Compounds of the Present Disclosure in Mouse, Rat and Human Liver Microsomes 1. Experimental objective: The purpose of this experiment was to evaluate the metabolic stability of the compounds in phase I and partially phase II in mouse, rat and human liver microsomes, respectively.

2. Experimental scheme 2.1 Drug preparation: 10 mM stock solution of the compound of the present disclosure was prepared in DMSO (or other suitable solution) and stored in a −20° C. refrigerator for later use. The compound of the present disclosure was made in house.

2.2 Experimental steps

1) Preparation of buffer: 4.01 mL of 1 M $K_2HPO_4·3H_2O$ (AR grade) and 0.99 mL of 1 M $KH_2PO_4$ (AR grade) were dissolved in ultrapure water and the volume was adjusted to 50 mL to prepare a phosphate buffer with a final concentration of 100 mM.

2) Preparation of compound working solution: Preparation of compound working solution: 2 μL of the compound stock solution was added to 998 μL of phosphate buffer to a final concentration of 20 μM. According to the properties of the compound, the preparation proportions could be adjusted appropriately to adjust the final concentration.

3) Preparation of liver microsome working solution: 156.3 μL of 20 mg/mL microsomes were diluted to 5 mL with 100 mM phosphate buffer, and the mixture was mixed well to reach a final concentration of 0.625 mg/mL.

4) Preparation of NADPH and UDPGA: 33.3 mg of NADPH and 25.8 mg of UDPGA were weighed and added to 2 mL of 100 mM phosphate buffer to reach a final concentration of 20 mM.

5) Preparation of pore-forming agent (Alamethicin): 1 mg of Alamethicin was weighed and added to 200 μL of methanol to prepare a 5 mg/mL solution. 10 μL of the solution was taken and added to 990 μL phosphate buffer (pH 7.4) to reach a final concentration of 50 μg/mL.

6) Preparation of reaction stop solution: The internal standard was diluted with acetonitrile (or other suitable solution) to use as a stop solution and stored in a 2° C.-8° C. refrigerator.

7) Incubation process: 400 μL of the prepared liver microsomes, 25 μL of the compound working solution (20 μM) and 25 μL of Alamethicin (50 μg/mL) were successively added to the 96-well plate, and the mixture was pre-incubated at 37° C. for 10 min. Then, 50 μL of prepared NADPH/UDPGA was added to start the reaction, and the mixture was incubated at 37° C. The total volume of the reaction system was 500 μL. The final contents of each component were as follows:

| Component | Content |
|---|---|
| Liver microsomes | 0.5 mg/mL |
| Compound | 1 μM |
| NADPH | 2 mM |
| UDPGA | 2 mM |
| Alamethicin | 2.5 μg/mL |

50 μL of samples were taken at 0, 5, 15, 30, 60 and 120 min, respectively, 200 μL of a cold stop solution containing the internal standard was added to stop the sample reaction, the mixture was centrifuged at 3500 rpm for 10 min, and the supernatant was taken and analyzed by LC-MS/MS.

2.4 Chromatographic analysis

1) Chromatographic Conditions:

Instruments: Shimadzu LC-20 AD; Chromatographic column: Phenomenex Gamin® C18 (50*4.6 mm, 5 μm particle size); mobile phase: A: 0.1% aqueous formic acid, B: acetonitrile; Elution gradient: 0.2-1.6 min, 5% A to 95% A, 3.0-3.1 min, 95% A to 5% A; Flow rate: 1.0 ml/min; Run time: 4.0 min; Injection volume: 5 μL.

2) Mass Spectrometry Conditions

Instruments: AP14000 liquid chromatography mass spectrometer, AB Sciex; Ion source: electrospray ionization source (ESI); Drying gas: N2, temperature 500° C.; Electrospray voltage: 5000 V; Detection mode: positive ion detection; Scanning mode: Reaction Monitoring (MRM) mode; Scanning time: 0.8401 s.

3. Data processing: The raw data were calculated according to the following formula:

$$\text{Residual rate }\% = \text{peak area ratio of compound to internal standard at any time point/peak area ratio of compound to internal standard at 0 min} \times 100$$

$$T_{1/2} = 0.693/Ke, \text{ in which } Ke \text{ is the elimination rate constant.}$$

The in vitro liver microsome intrinsic clearance rate ($CL_{int}$) and liver intrinsic clearance rate ($CL_{int,liver}$) were calculated by Ke.

$$CL_{int} = 0.693/T_{1/2}/\text{microsome protein content (microsome concentration during incubation, mg/ml)}$$

$$CL_{int,liver} = CL_{int} \times \text{amount of microsome protein in liver (mg/g)} \times \text{liver weight to body weight ratio}$$

-continued

In vivo liver clearance rate ($CL_{int,liver}$) was extrapolated from a well-stirred model $CL=(CL_{int,liver}\times fu\times Qh)/(CL_{int,liver}\times fu+Qh)$, in which fu is the free fraction in the blood, which defaults to 1, and the parameters in the formula were shown in the following table.

| Species | Body weight (Kg) | liver blood flow (mL/min/kg) | Amount of microsome protein (mg/g liver weight) | Liver weight to body weight ratio (g/kg body weight) |
|---|---|---|---|---|
| Mouse | 0.025 | 152 | 45 | 60 |
| Rat | 0.25 | 72 | 61 | 40 |
| Monkey | 5 | 44 | 45 | 32 |
| Dog | 12 | 55 | 55 | 32 |
| Human | 70 | 20 | 40 | 24 |

4. Experimental results:

| | Human | |
|---|---|---|
| Examples | $T_{1/2}$ min | Clint (ul/min/mg) |
| 78 | 794.22 | 1.75 |
| 110 | 4719.00 | 0.30 |
| 151 | 711.00 | 1.90 |
| 159 | 1208.57 | 1.15 |
| 164 | 936.86 | 1.48 |
| 183 | 1378.00 | 1.00 |
| 186 | 2124.40 | 0.70 |
| 188 | 757.70 | 1.80 |

5. Experimental conclusion: The results shown that the advantageous example compounds of the present disclosure showed stable metabolic effects in various specie liver microsomes, especially in human liver microsomes.

IV. Pharmacodynamic Experiment

Test Example 1. In Vivo Pharmacodynamic Study of the Compounds of the Present Disclosure in a Hyperlipidemia Animal Model of B6-hPCSK9 Transgenic Mice 1. Experimental objective: The compounds of the present disclosure were evaluated for in vivo pharmacodynamics in a hyperlipidemia animal model of B6-hPCSK9 transgenic mice.

2. Experimental operations and data processing 2.1 Animals: B6-hPCSK9 transgenic C57 mice, 6-8 weeks old, male, purchased from Jiangsu GemPharmatech Co., Ltd.

2.2 Animal model: After delivery to a barrier system, the animals were given one week for acclimatization and began to feed on the high-fat feed. The body weight and feed weight were weighed once a week, and the body weight and food intake thereof were recorded.

2.3 Grouping and administration a. The animals were grouped by a random grouping method.

c. According to the grouping results, administration with the test drug was started (mode of administration: oral administration; administration volume: 10 mL/kg; frequency of administration: once/day or single administration; administration cycle: 21 days; vehicle: 10% Solutol HS 15/90% Saline). Test drug: Compounds of the present disclosure, made in house.

d. After the test drug was administered, the body weight and feed weight were weighed twice a week and blood was taken once a week.

e. The data was processed with software such as Excel. Body weight change rate BWC (%)=(body weight at the end of animal treatment−body weight at the beginning of animal treatment)/body weight at the beginning of animal treatment×100%; food intake (g/mice/day)=(previous feed addition+previous feed residue−current feed residue)/number of animals/number of feeding days; and calculation of blood biochemical inhibition rate: with the blood biochemical results of the vehicle group detected in the same batch as the baseline, the data of each administration group were normalized, and the percentages of TC and LDL-C were then calculated according to the formulas: TC change percentage (%)=(TC value after administration−TC value before administration)/TC value before administration*100%; LDL-C change percentage (%)=(LDL-C value after administration−LDL-C value before administration)/LDL-C value before administration*100%. PCSK9 in plasma was detected by ELISA.

3. Experimental results:

| Pharmacodynamic experiment (PO administration) | | |
|---|---|---|
| Examples | Dosage | LDL-C reduction rate (%), Day 14 |
| Reference example 1 | 6 mpk | −31.52% |
| 12 | 10 mpk | −33.75% |
| 78 | 10 mpk | −37.98% |
| 112 | 10 mpk | −38.14% |
| 151 | 10 mpk | −31.09% |
| 154 | 10 mpk | −35.66% |
| 183 | 10 mpk | −48.90% |
| 186 | 10 mpk | −51.19% |
| 188 | 10 mpk | −47.11% |
| 201 | 10 mpk | −31.45% |
| 212 | 10 mpk | −60.08% |

4. Experimental conclusion: The example compounds shown in the present disclosure can effectively reduce LDL-C in the hyperlipidemia animal model of B6-hPCSK9 transgenic mice.

The invention claimed is:

1. A compound as represented by general formula (I-A), or a stereoisomer or pharmaceutically acceptable salt thereof:

(I-A)

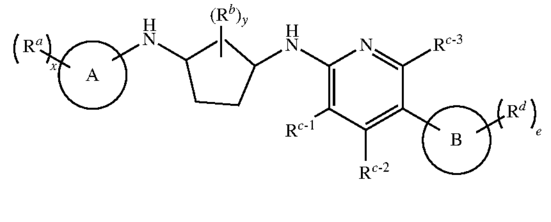

wherein ring A is selected from

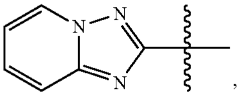
,
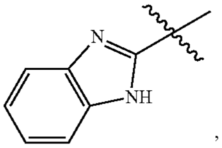
,
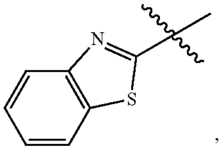
,
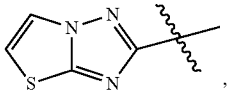
,
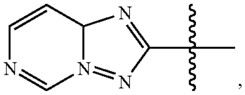
,
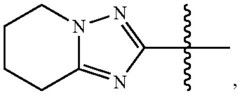
, or
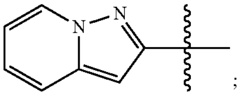
;

ring B is selected from

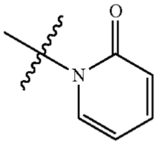
,
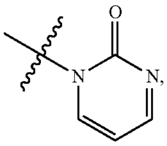
,
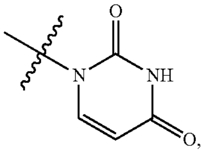
,
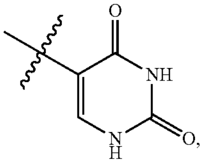
,
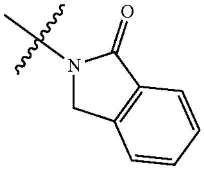
,
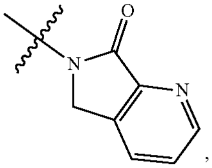
,
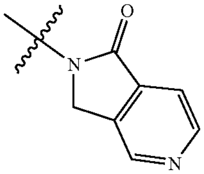
,
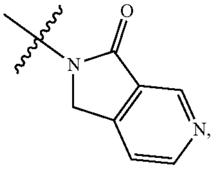
,
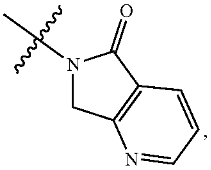
,
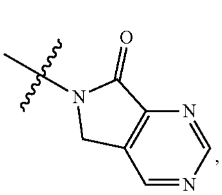
,
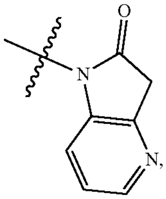
, -continued

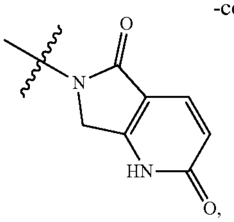
,
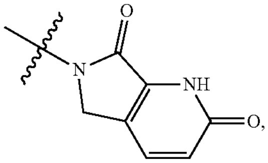
,
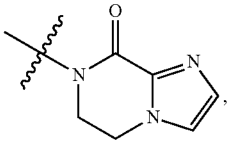
,
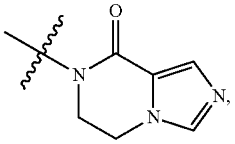
,
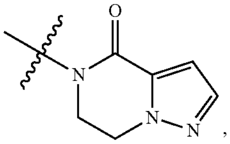
,
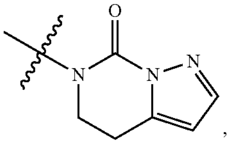
,
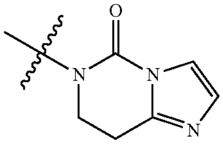
,
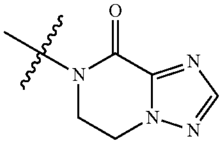
,
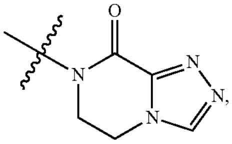
,
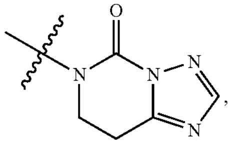
,
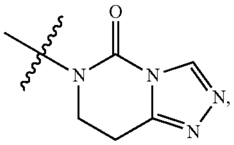
, or
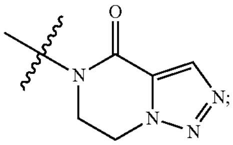
;

$R^a$ is selected from hydrogen, deuterium, halogen, amino, hydroxyl, cyano, $C_{1-6}$alkyl, $C_{2-6}$alkenyl, $C_{2-6}$alkynyl, oxo, thio, $C_{1-6}$alkylthio, $C_{1-6}$deuteroalkyl, $C_{1-6}$haloalkyl, $C_{1-6}$alkoxy, $C_{1-6}$haloalkoxy, $C_{1-6}$hydroxyalkyl, cyano-substituted $C_{1-6}$alkyl, $C_{3-8}$cycloalkyl or 3- to 8-membered heterocyclyl;

$R^b$ is selected from hydrogen, deuterium, halogen, amino, hydroxyl, cyano, $C_{1-6}$ alkyl, $C_{2-6}$alkenyl, $C_{2-6}$alkynyl, oxo, thio, $C_{1-6}$deuteroalkyl, $C_{1-6}$haloalkyl, $C_{1-6}$alkoxy, $C_{1-6}$haloalkoxy, $C_{1-6}$hydroxyalkyl, or cyano-substituted $C_{1-6}$alkyl;

$R^{c-1}$ is selected from halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl or 3- to 8-membered heterocyclyl;

$R^{c-2}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, or cyano-substituted $C_{1-3}$ alkyl;

$R^{c-3}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, or 3- to 8-membered heterocyclyl;

$R^d$ is selected from hydrogen, deuterium, halogen, amino, hydroxyl, cyano, nitro, $C_{1-6}$alkyl, $C_{1-6}$alkenyl, $C_{1-6}$alkynyl, oxo, thio, $C_{1-6}$deuteroalkyl, $C_{1-6}$haloalkyl, $C_{1-6}$alkoxy, $C_{1-6}$haloalkoxy, $C_{1-6}$hydroxyalkyl, cyano-substituted $C_{1-6}$alkyl, $C_{3-8}$cycloalkyl, 3- to 8-membered heterocyclyl, $C_{6-10}$ aryl, or $C_{5-12}$heteroaryl;

alternatively, any two adjacent or non-adjacent $R^d$ are connected to form $C_{3-8}$cycloalkyl or 3- to 8-membered heterocyclyl;

x is 0, 1, 2, or 3;

y is 0, 1, 2, or 3; and e is 0, 1, 2, or 3.

2. The compound or the stereoisomer or pharmaceutically acceptable salt thereof according to claim 1, wherein the compound is further represented by general formula (I-A-1):

(I-A-1)

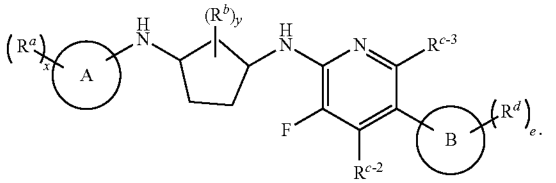

3. The compound or the stereoisomer or pharmaceutically acceptable salt thereof according to claim 1, wherein the compound is further represented by general formula (I-1-a):

(I-1-a)

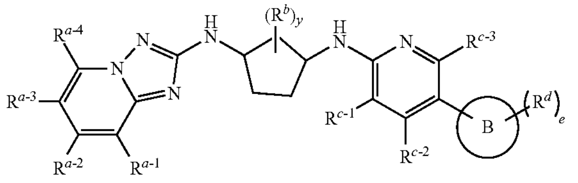

wherein $R^{a-1}$—$R^{a-4}$ are each independently selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, or 3- to 8-membered heterocyclyl.

4. The compound or the stereoisomer or pharmaceutically acceptable salt thereof according to claim 3, wherein the compound is further represented by general formula (I-1-a'):

(I-1-a')

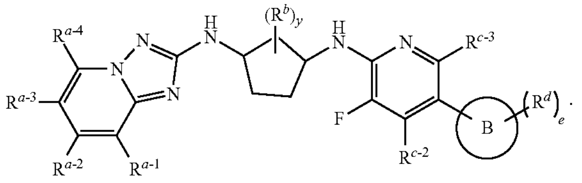

5. The compound or the stereoisomer or pharmaceutically acceptable salt thereof according to claim 1, wherein ring B is selected from

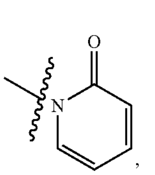 , 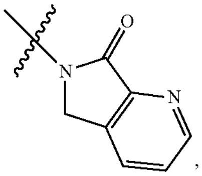 , 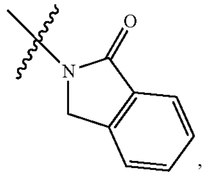 ,

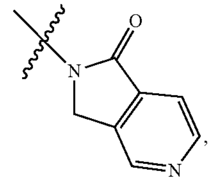 , 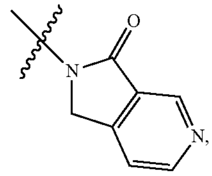

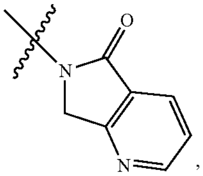 , 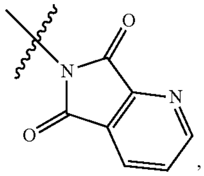 , or

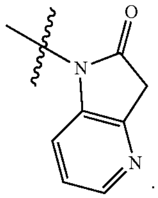 .

6. The compound or the stereoisomer or pharmaceutically acceptable salt thereof according to claim 1, wherein $R^a$ is selected from —H, —O—$CHF_2$, —O—$CF_3$, —O—$CF_2Cl$, —O—$CF_2Br$, —O—$CH_2$—$CHF_2$, —O—$CH_2$—$CF_3$—$CHF_2$, —$CF_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, or

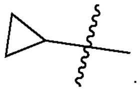 [SMILES: *C1CC1] .

7. The compound or the stereoisomer or pharmaceutically acceptable salt thereof according to claim 1, wherein $R^b$ is selected from —H or —F.

8. The compound or the stereoisomer or pharmaceutically acceptable salt thereof according to claim 1, wherein $R^{c-1}$ is selected from —F, —Cl, —O—$CH_3$, —CN, —$CF_3$, —$CH_3$, —O—$CF_3$, —O—$CH_3$, —O—$CH(CH_3)_2$, or

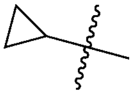 ;

And/or, wherein $R^{c-2}$ is selected from —H, —F, —Cl, —O—$CH_3$, —CN, —$CF_3$, —$CH_3$, —O—$CF_3$, —O—$CH_3$, or —O—$CH(CH_3)_2$;

And/or, wherein $R^{c-3}$ is selected from —H, —F, —Cl, —O—$CH_3$, —CN, —$CF_3$, —$CD_3$, —$CH_3$, —O—$CF_3$, —O—$CH_3$, —O—$CH(CH_3)_2$, or

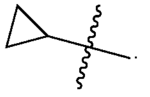

9. The compound or the stereoisomer or pharmaceutically acceptable salt thereof according to claim 1, wherein $R^d$ is selected from —H, -D, —F, —Cl, —CN, —$CH_3$, —$CF_3$, —$CH(CH_3)_2$, —$C(CH_3)_3$, —$C(CH_3)_2$—OH, —$C(CH_3)_2$—$CH_2$—OH, —O—$CH_3$, —$CH_2$—$NH_2$, —$CH_2$—OH, —$NH_2$, —OH, or

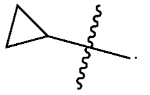 [SMILES: *C1CC1]

10. The compound or the stereoisomer or pharmaceutically acceptable salt thereof according to claim 3, wherein $R^{a-1}$—$R^{a-4}$ are each independently selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CH_2$—OH, —$CH_2$—$CHF_2$, —$CH(CH_3)$—OH, —$(CH_2)_3$—OH, —$C(CH_3)_2$—OH, —OH, —O—$CH_3$, —$CH_3$, —$CF_3$, —F, —Cl, —CN, —$NHCH_3$, —$NH_2$, —$CH_2$—$CF_3$, or

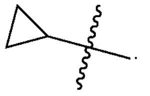 [SMILES: *C1CC1]

11. The compound as represented by general formula (I-A) or the stereoisomer or pharmaceutically acceptable salt thereof according to claim 1, wherein the compound is selected from the following compounds:

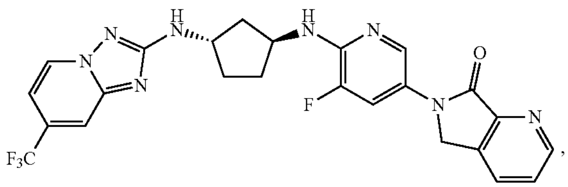

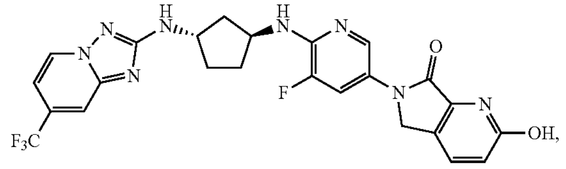

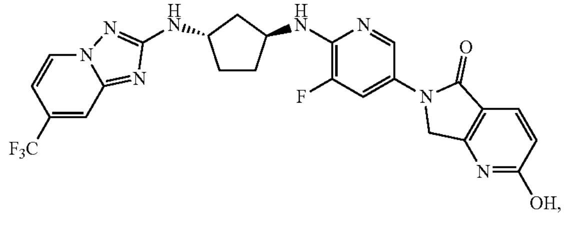

-continued

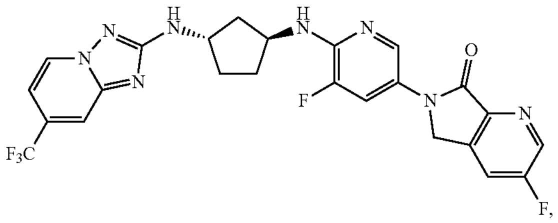

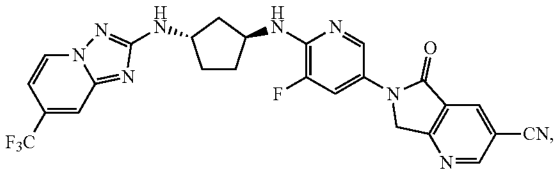

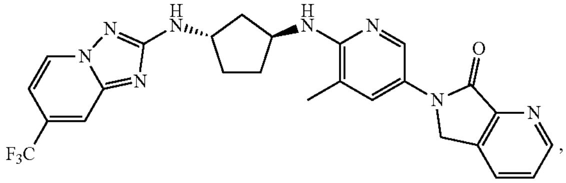

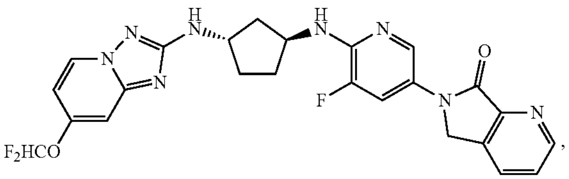

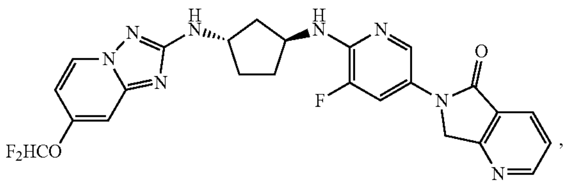

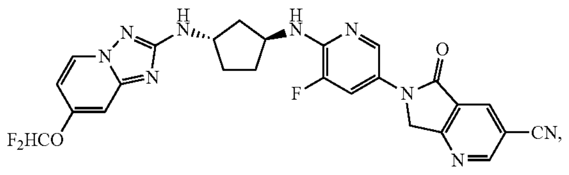

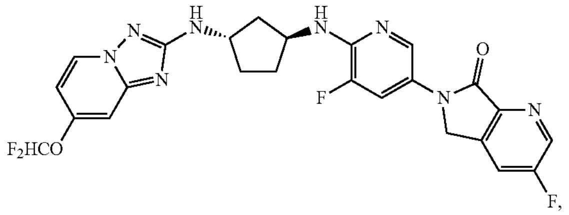

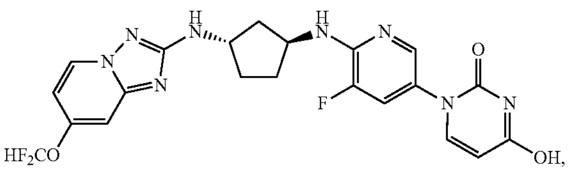

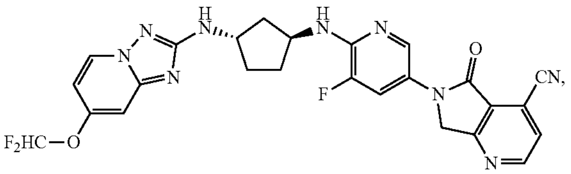

-continued
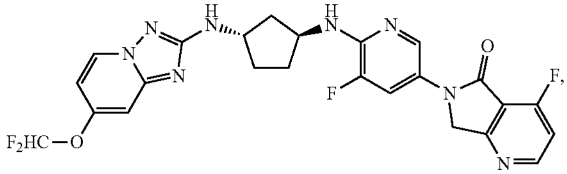
,
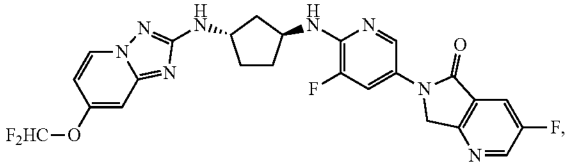
,
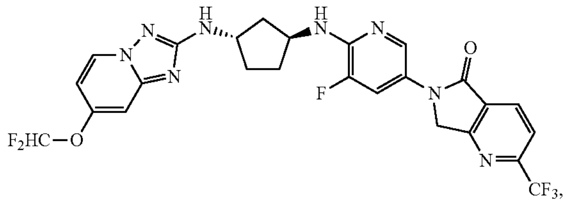
,
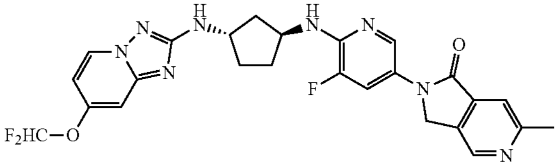
,
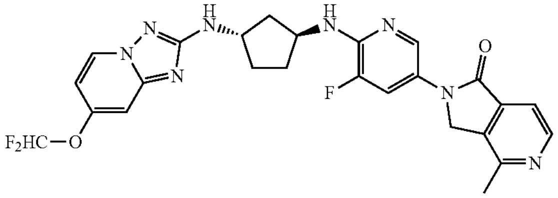
,
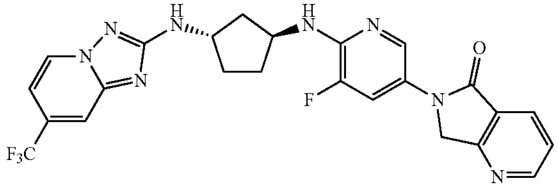
,
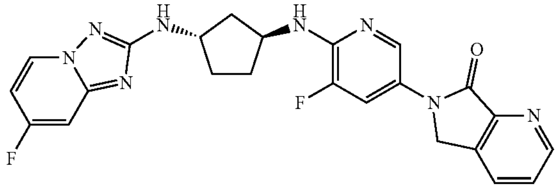
,
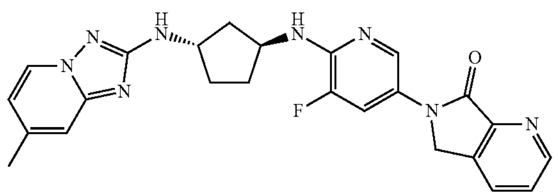
,
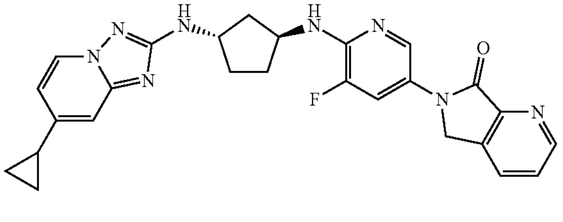
,
-continued
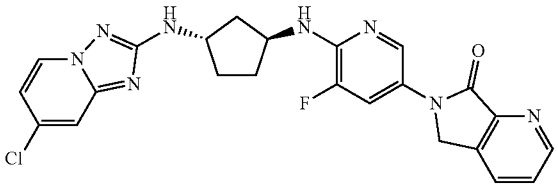
,
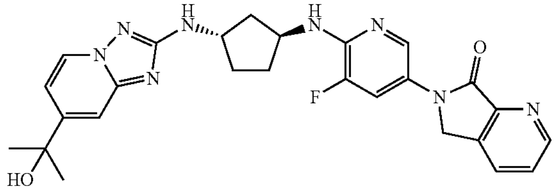
,
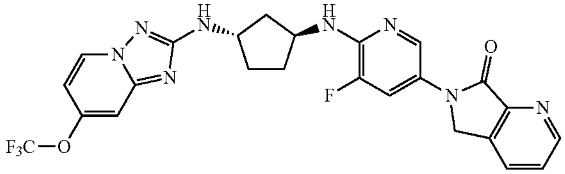
,
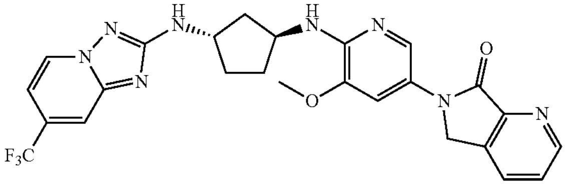
,
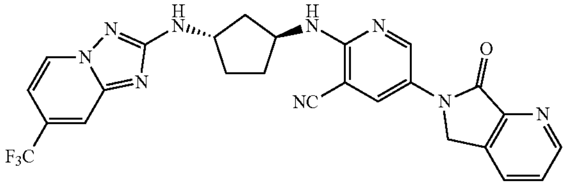
,
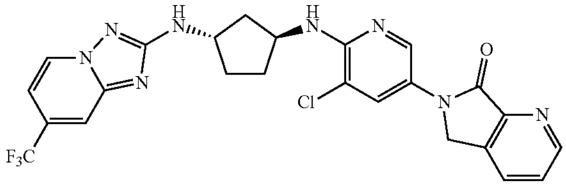
,
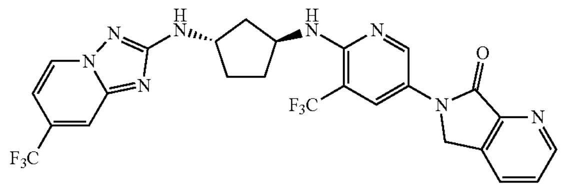
,
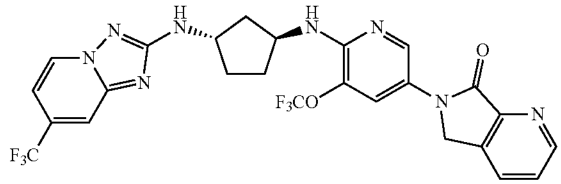
,
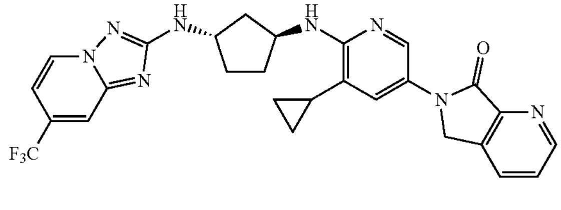
, -continued
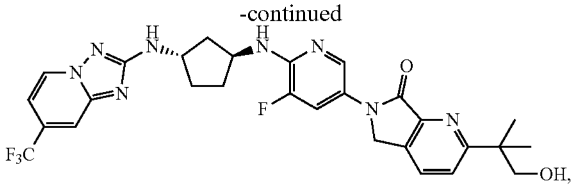,
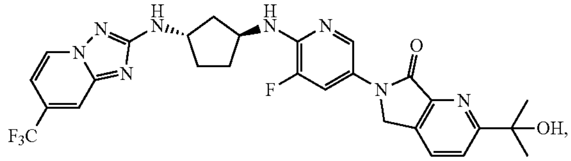,
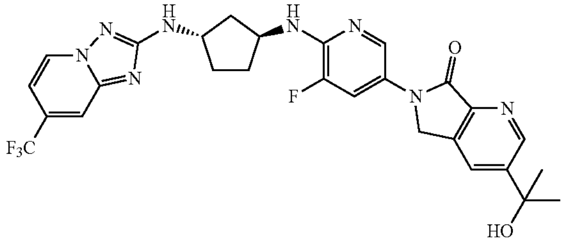,
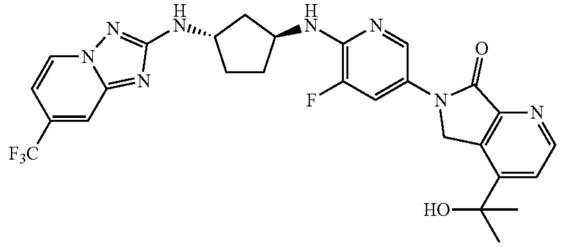,
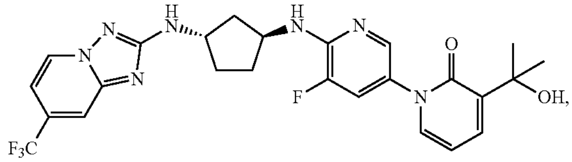,
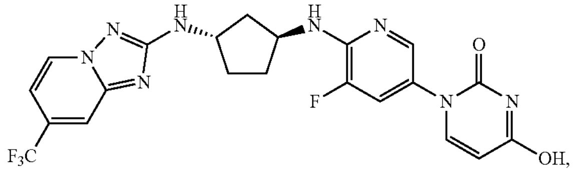,
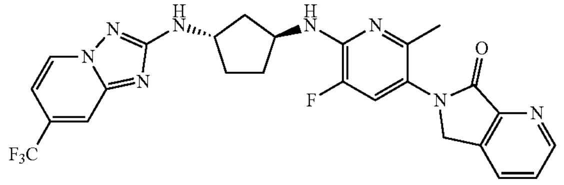,
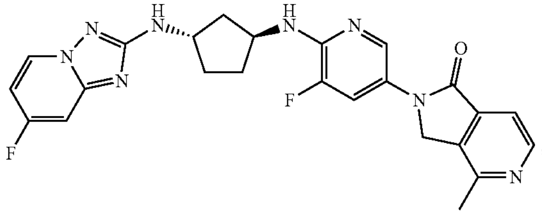,
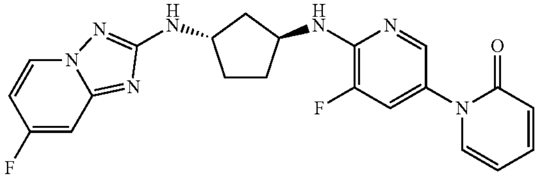,
-continued
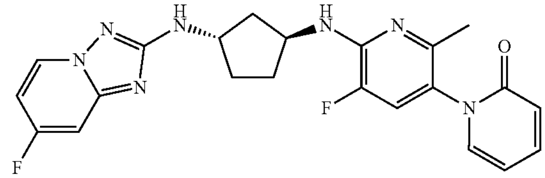,
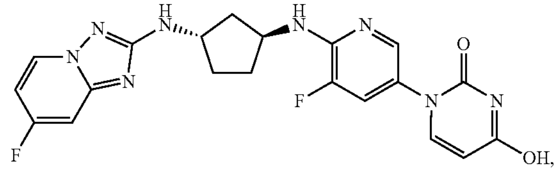,
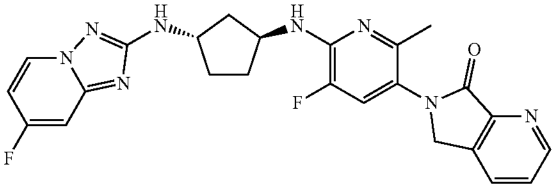,
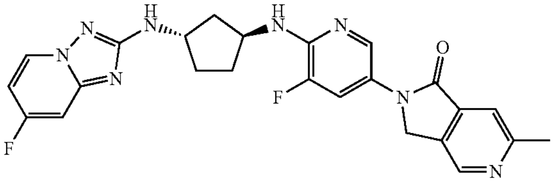,
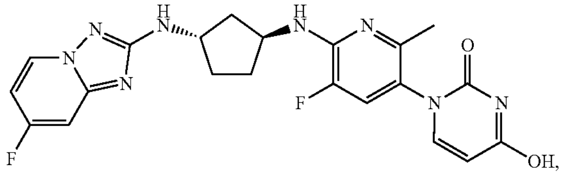,
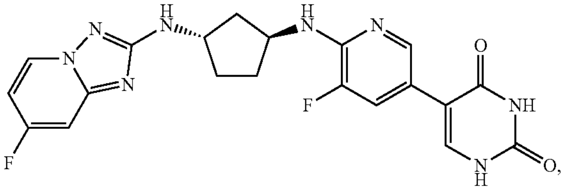,
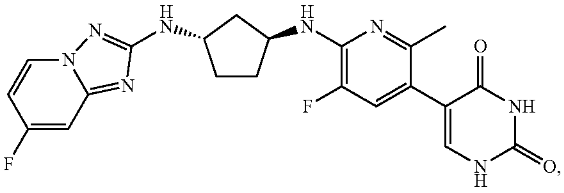,
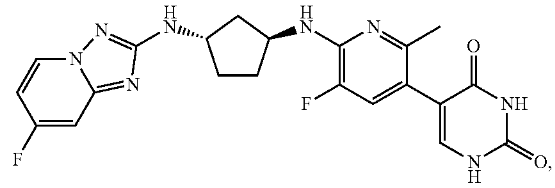,
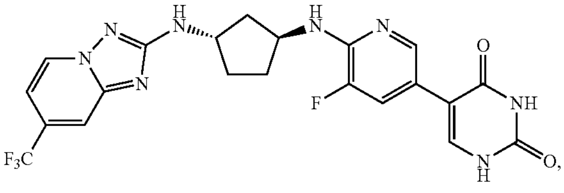, -continued
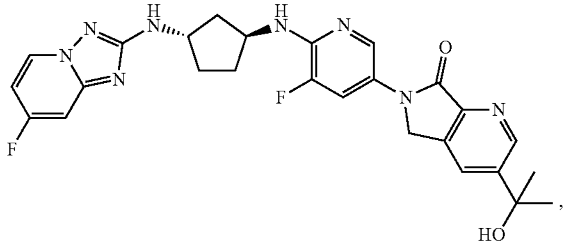,
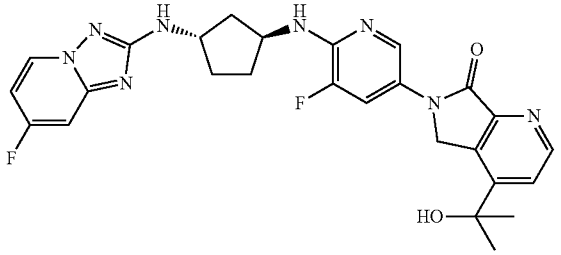,
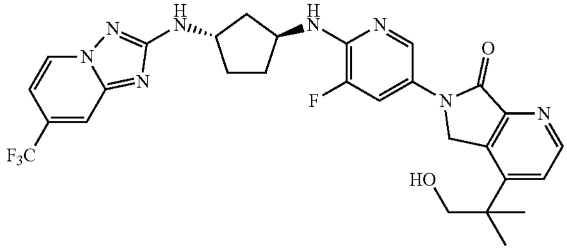,
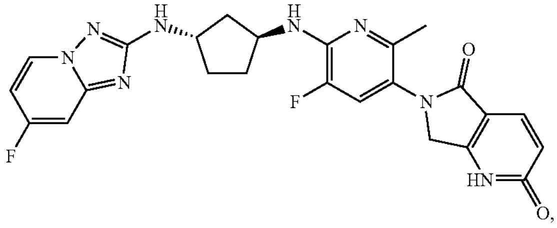,
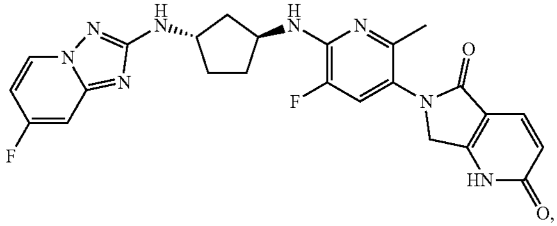,
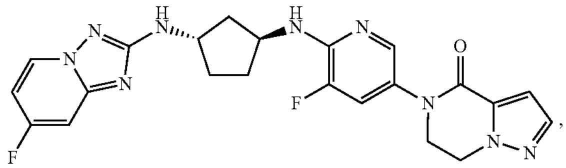,
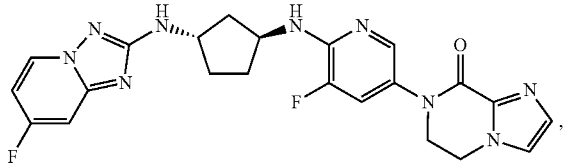,
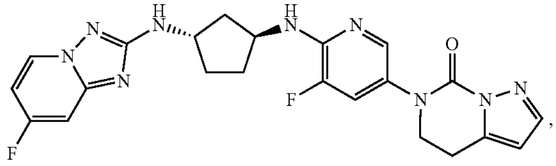,
-continued
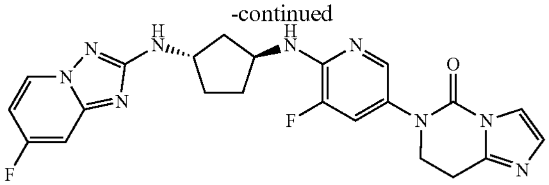,
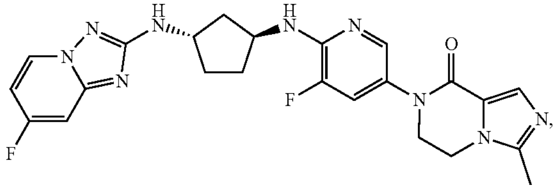,
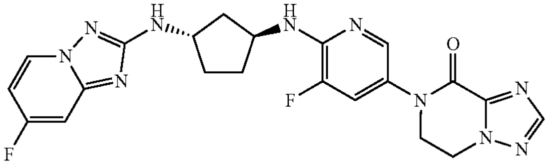,
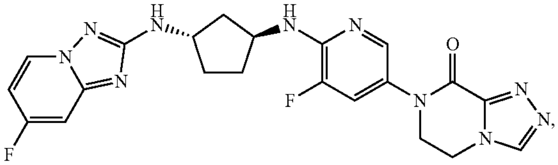,
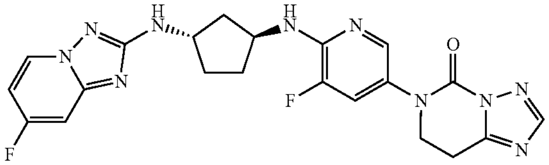,
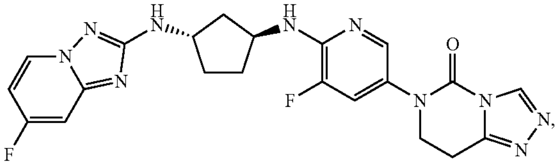,
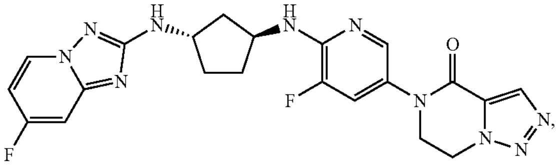,
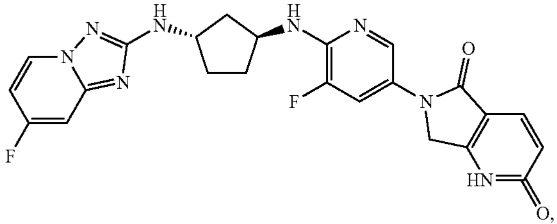,
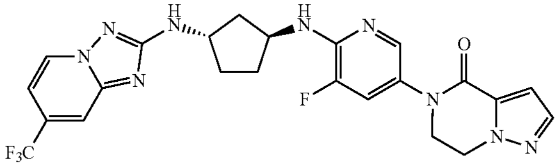,
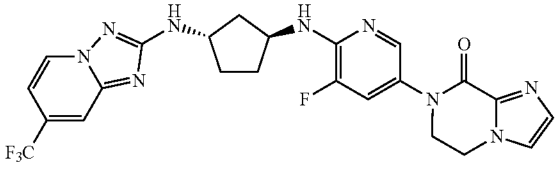, -continued
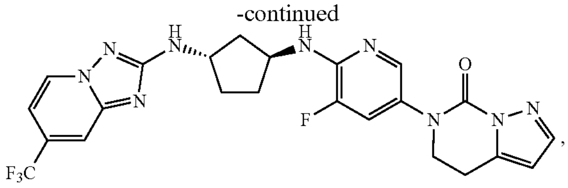
,
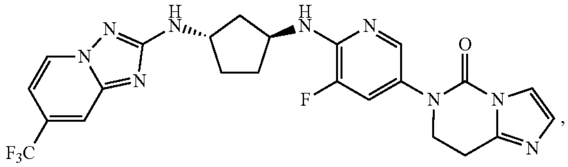
,
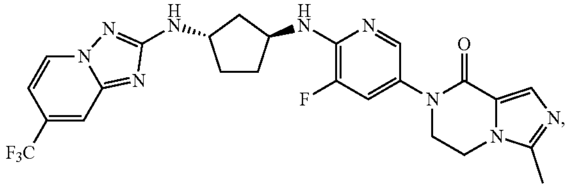
,
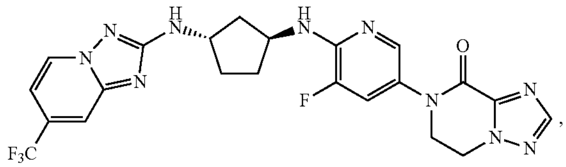
,
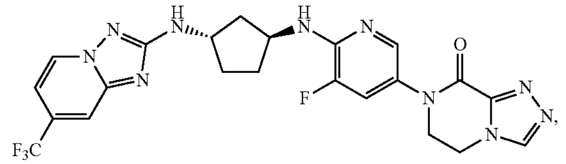
,
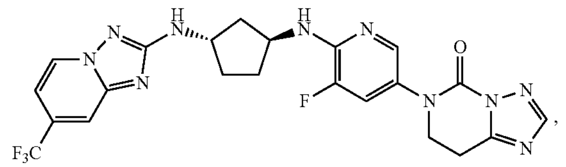
,
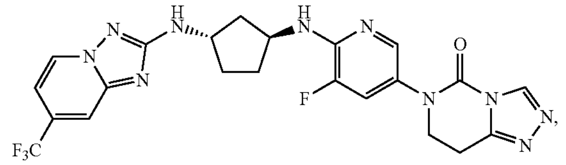
,
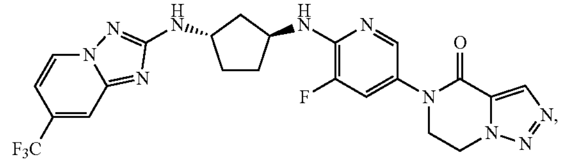
,
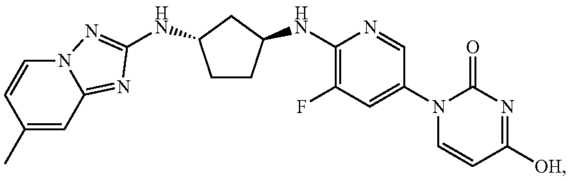
,
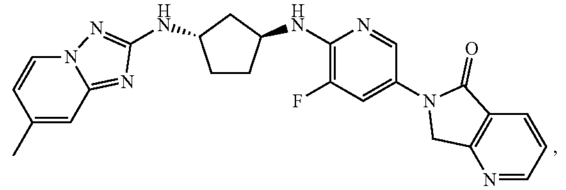
,
-continued
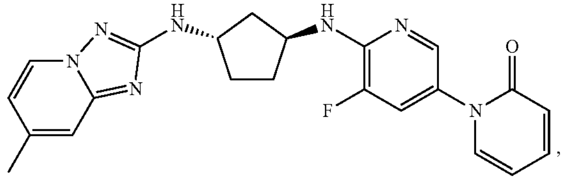
,
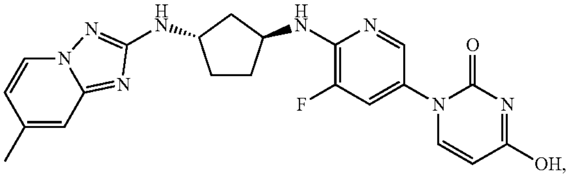
,
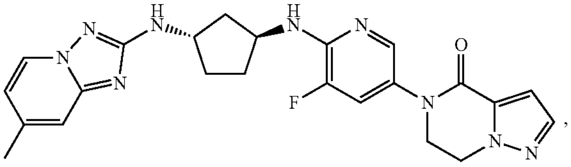
,
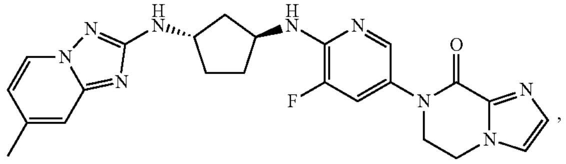
,
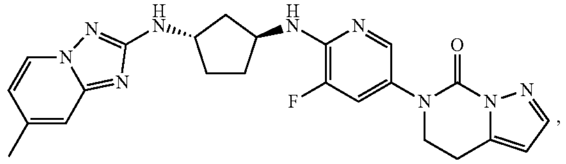
,
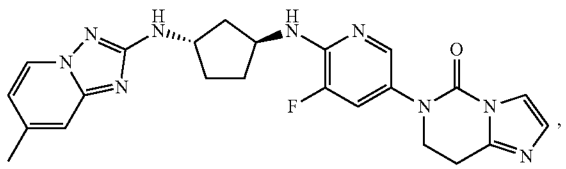
,
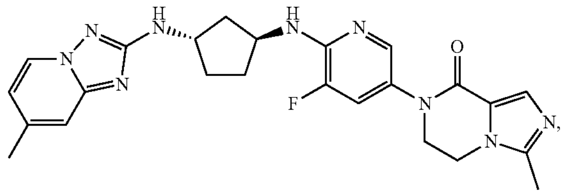
,
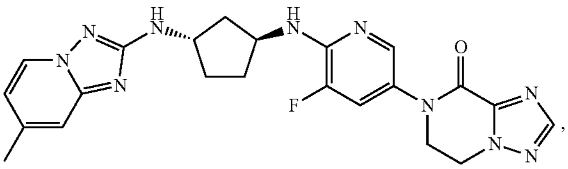
,
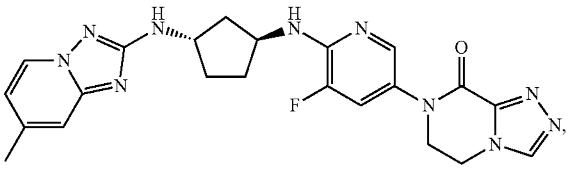
,
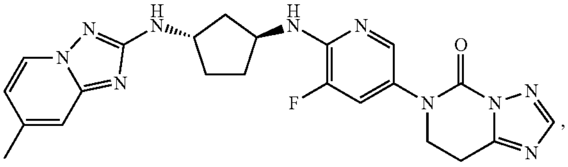
, -continued
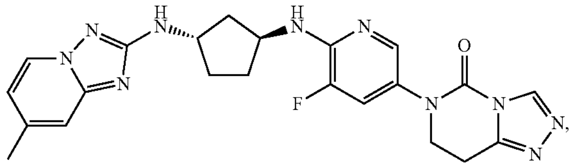,
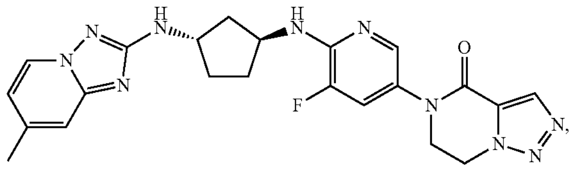,
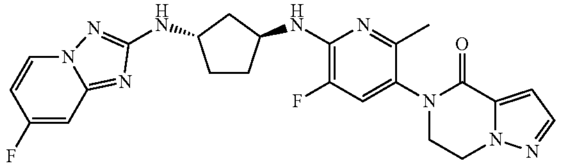,
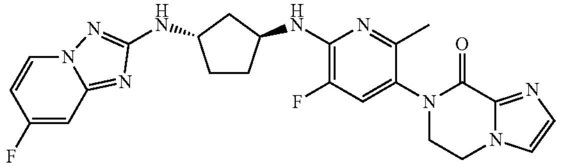,
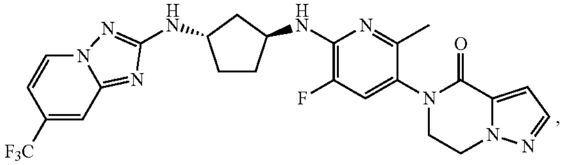,
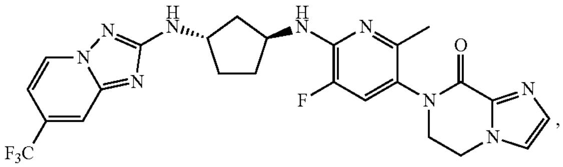,
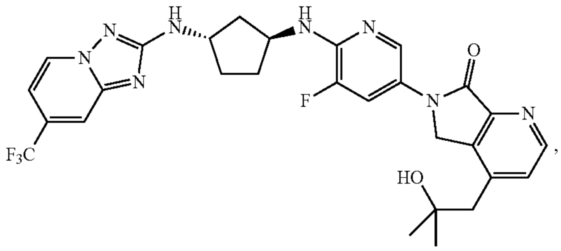,
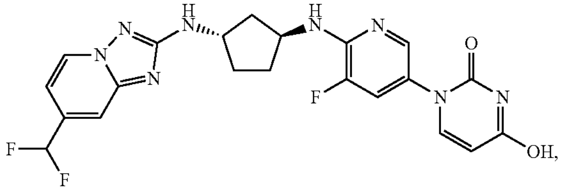,
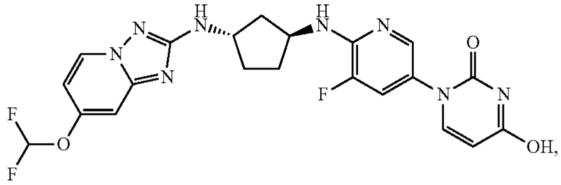,
-continued
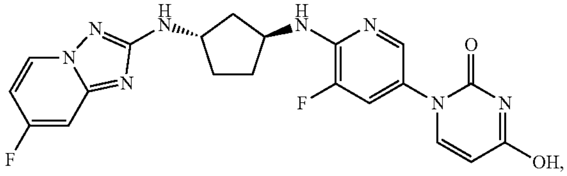,
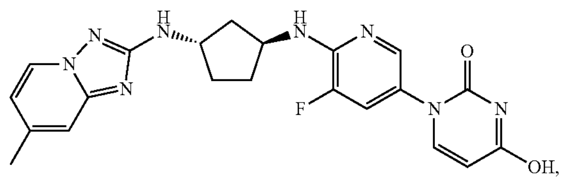,
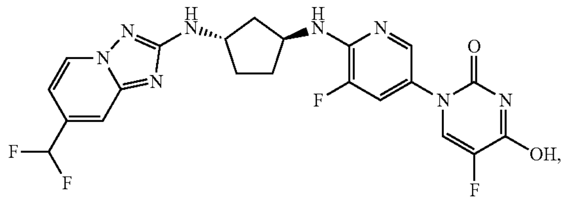,
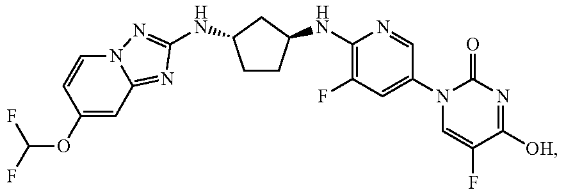,
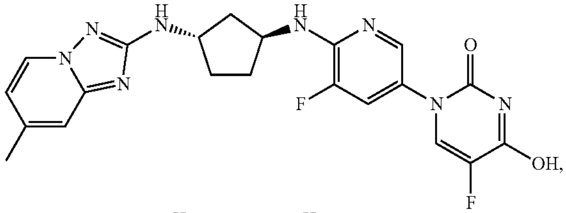,
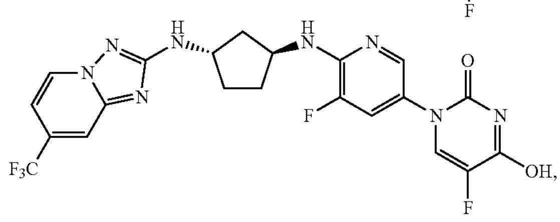,
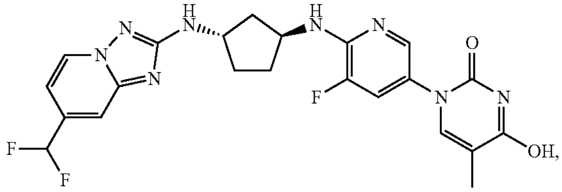,
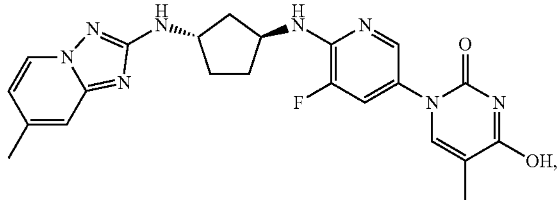, -continued
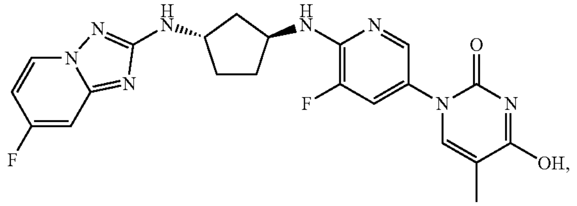,
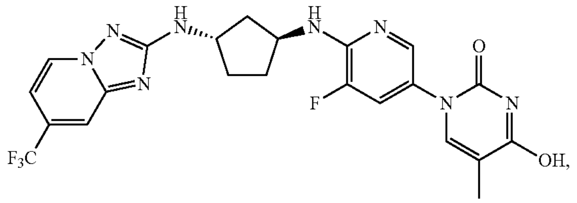,
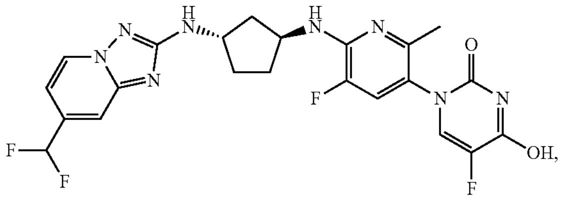,
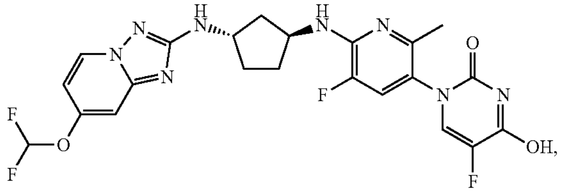,
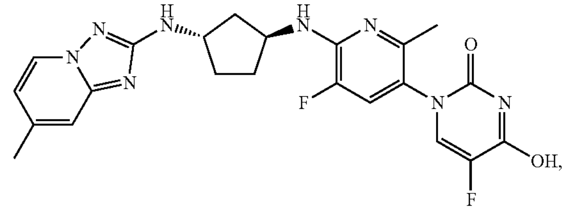,
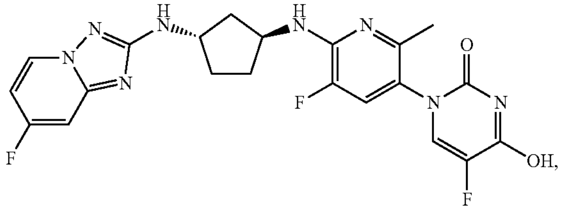,
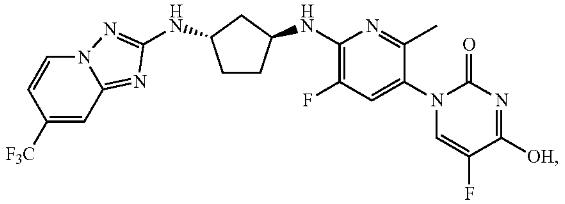,
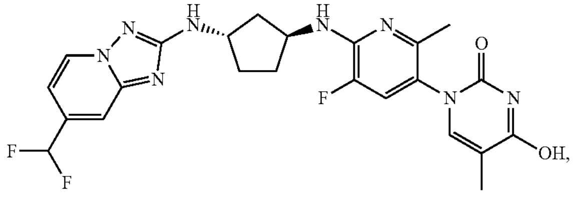,
-continued
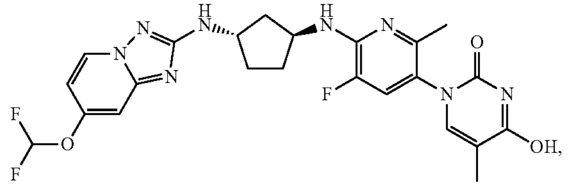,
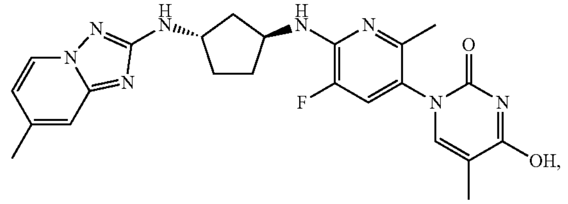,
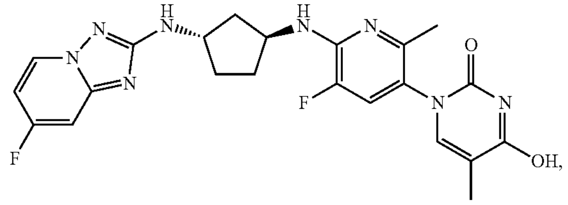,
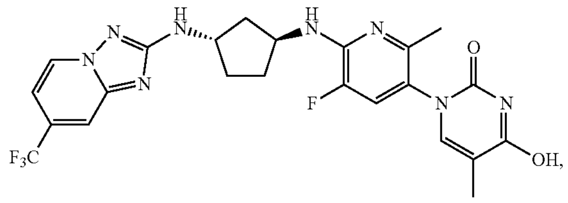,
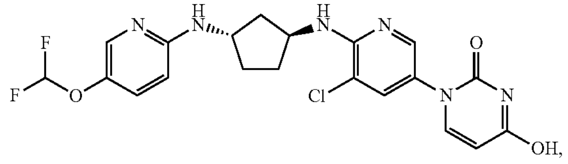,
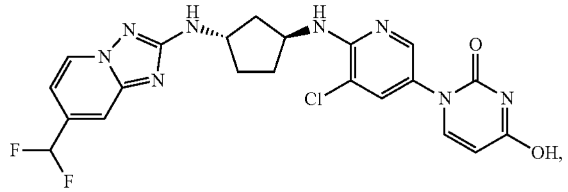,
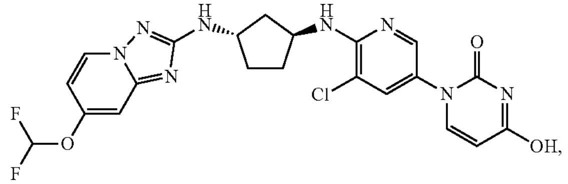,
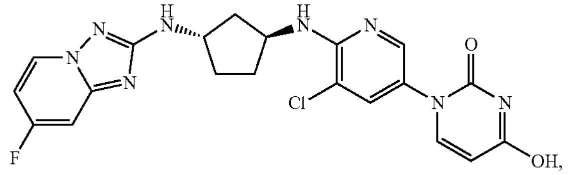,
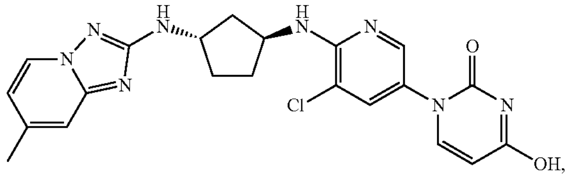, -continued
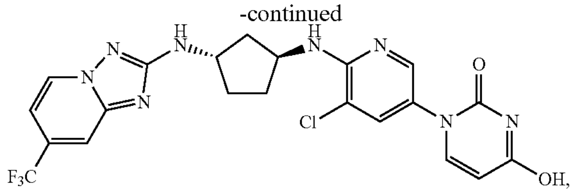
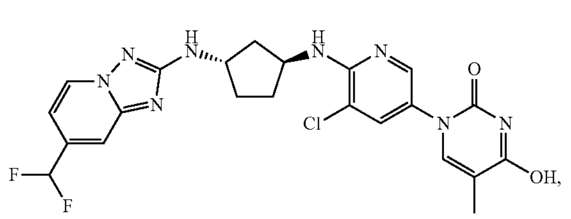
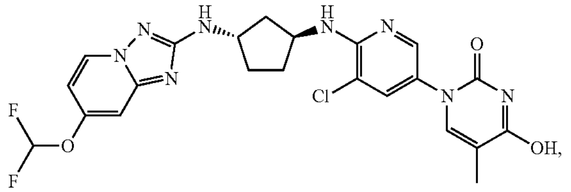
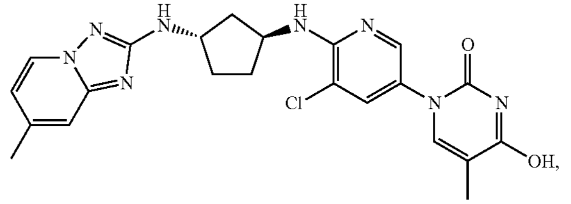
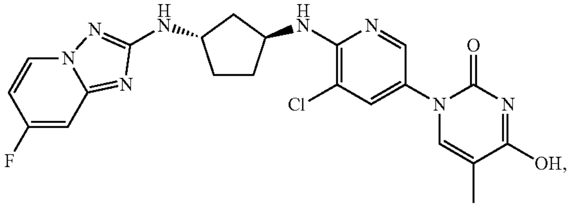
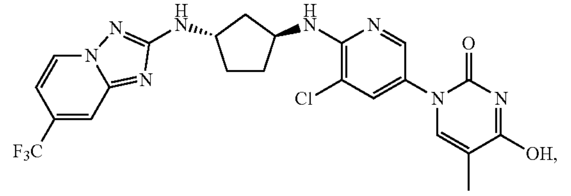
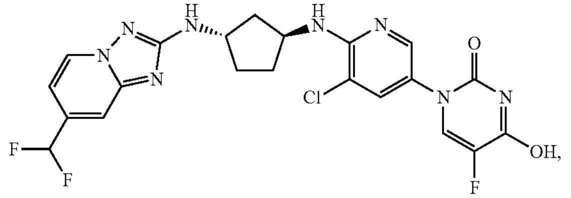
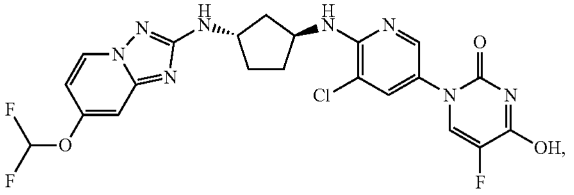
-continued
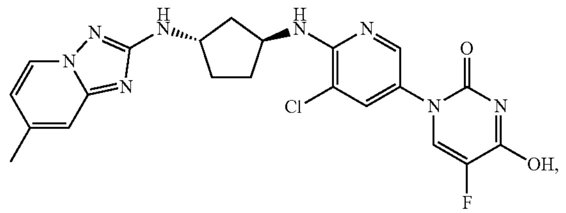
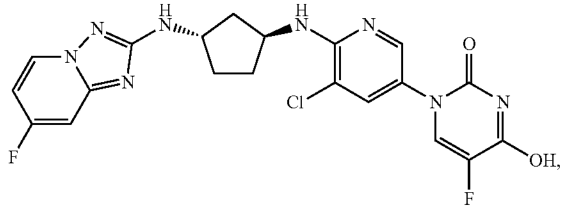
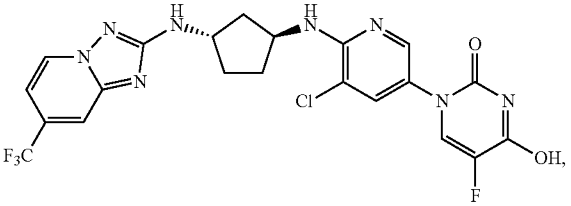
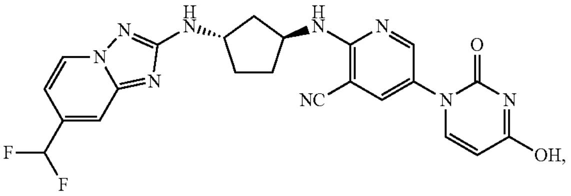
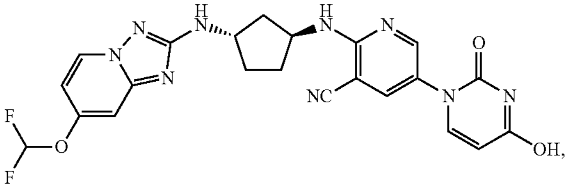
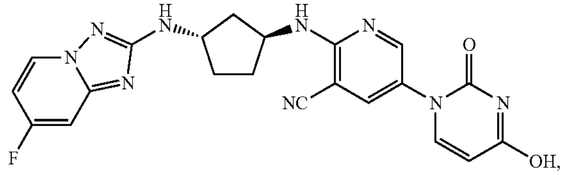
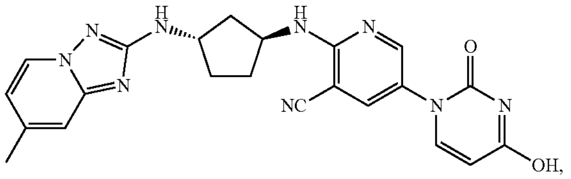
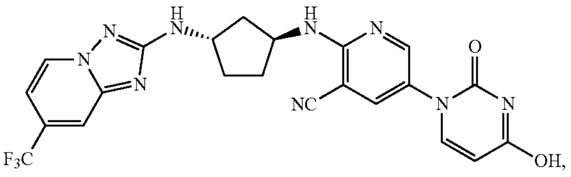
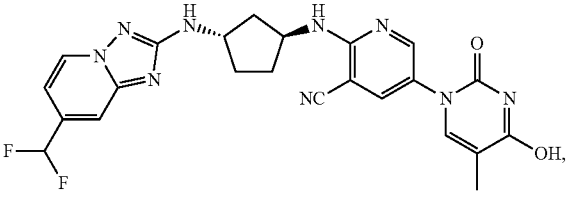

-continued
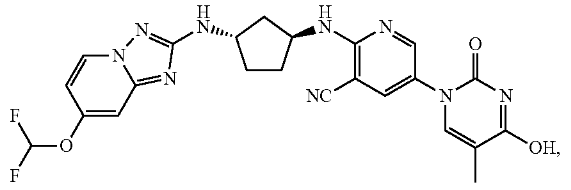
,
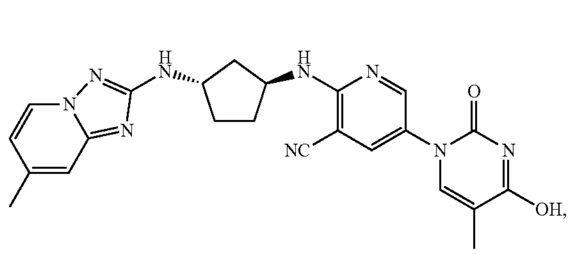
,
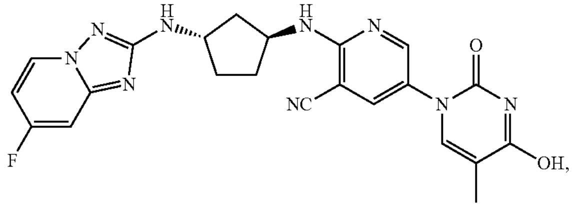
,
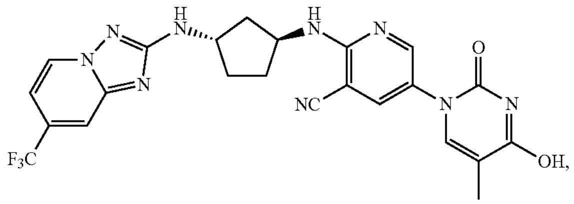
,
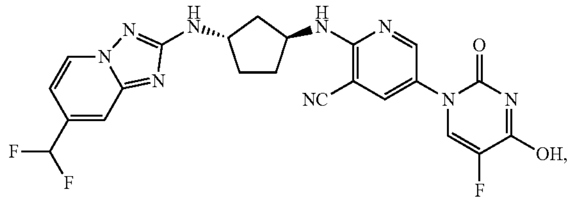
,
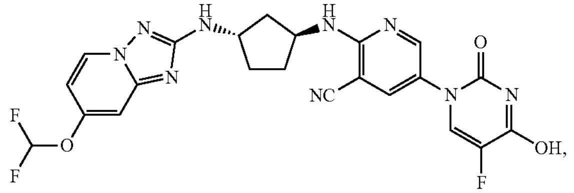
,
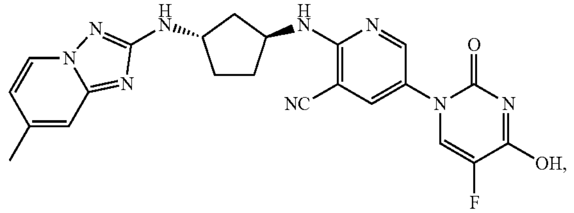
,
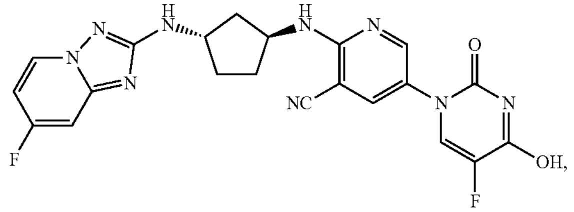
,
-continued
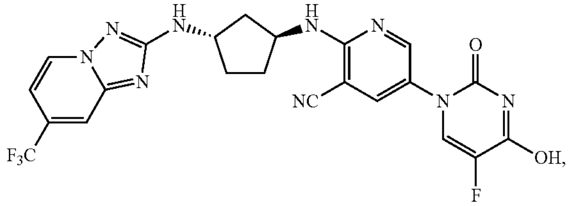
,
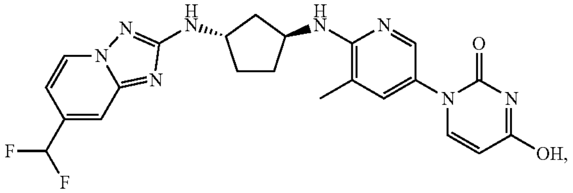
,
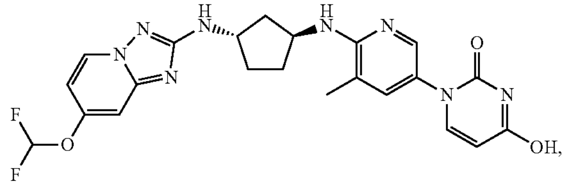
,
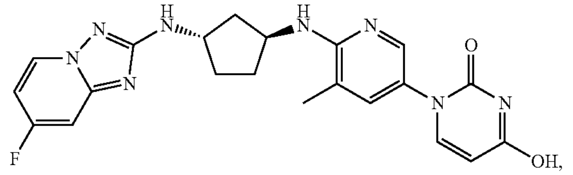
,
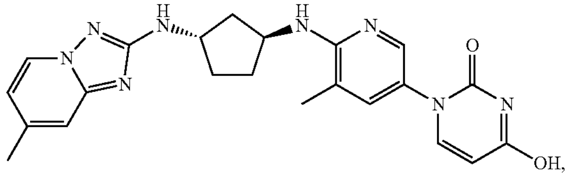
,
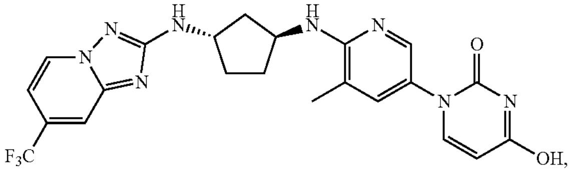
,
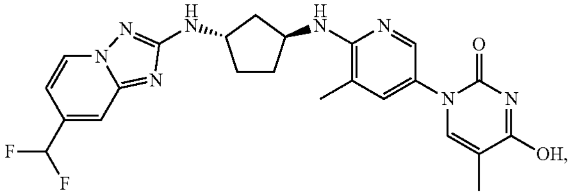
,
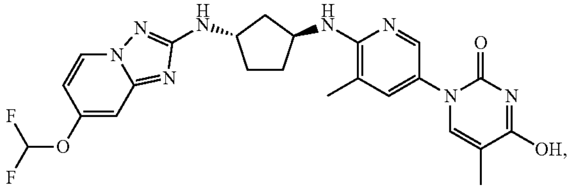
,
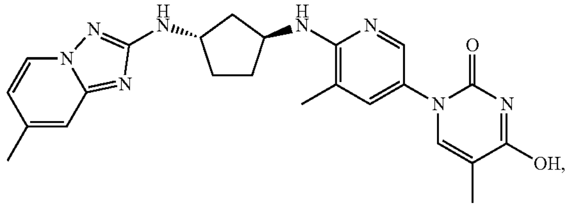
, -continued
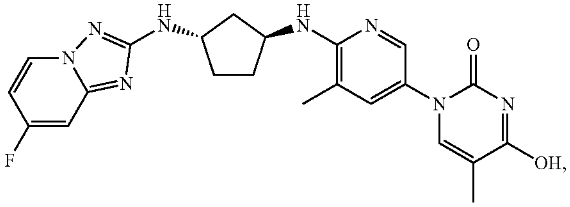
,
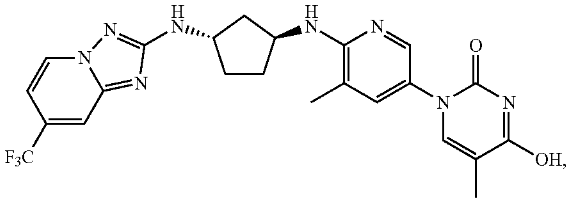
,
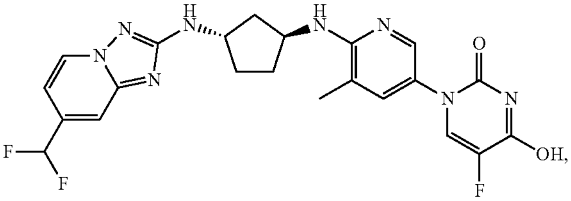
,
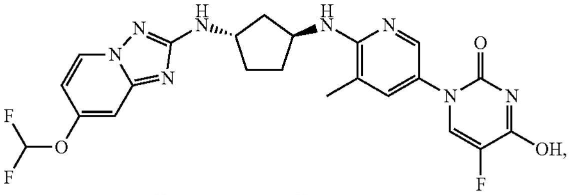
,
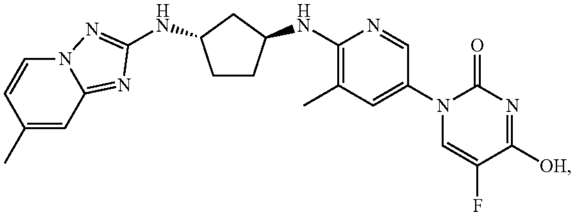
,
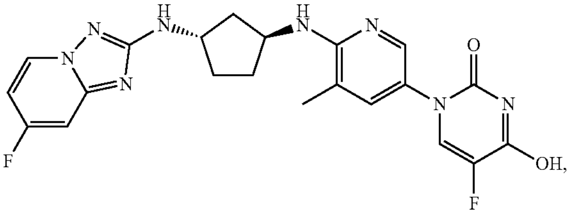
,
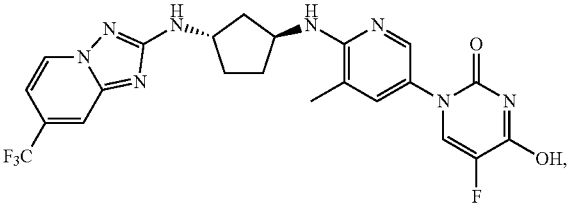
,
-continued
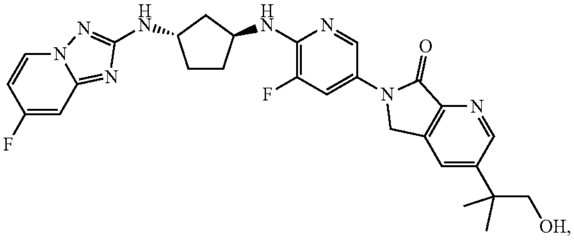
,
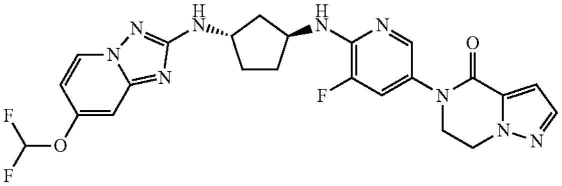
,
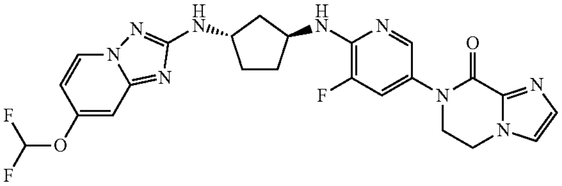
,
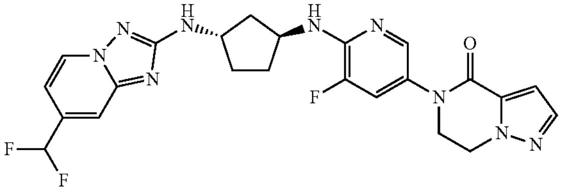
,
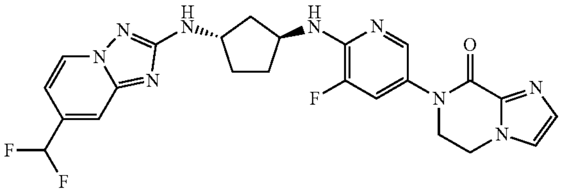
,
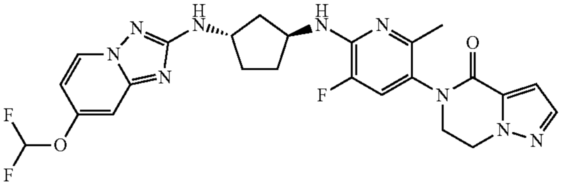
,
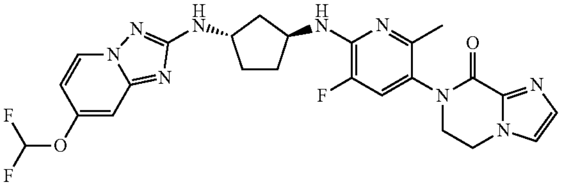
,
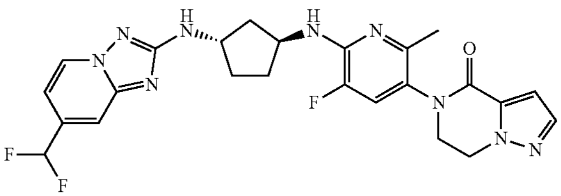
, -continued
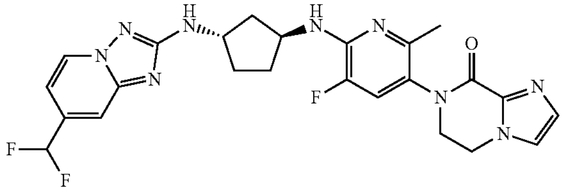,
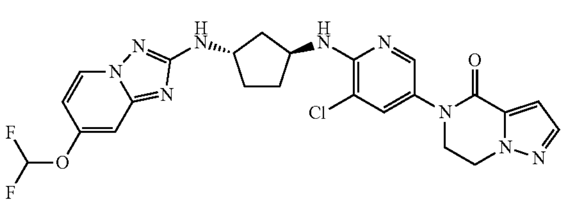,
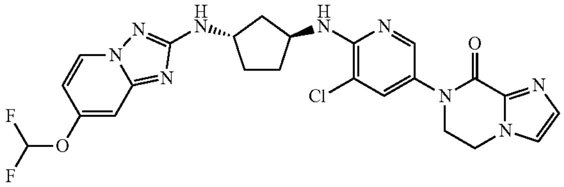,
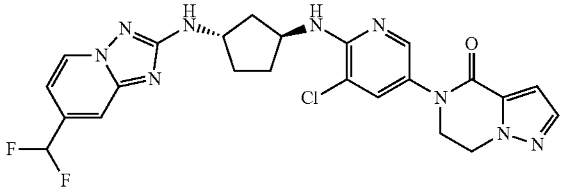,
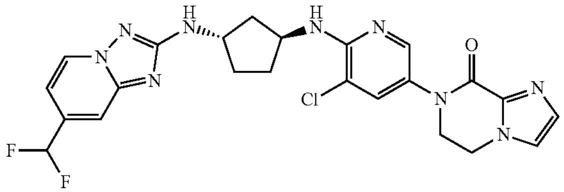,
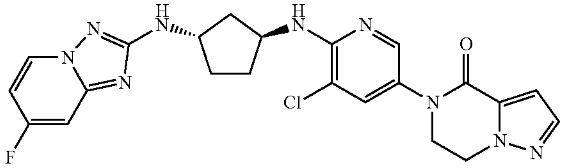,
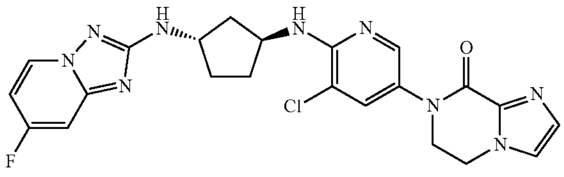,
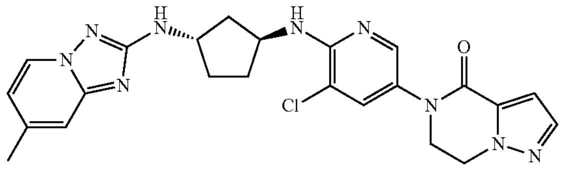,
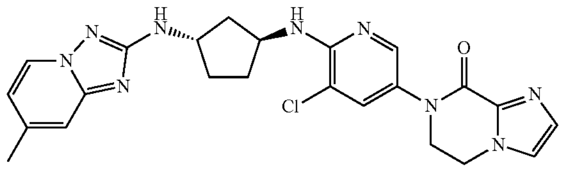,
-continued
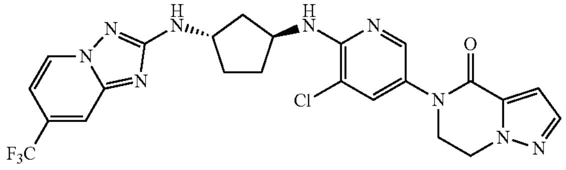,
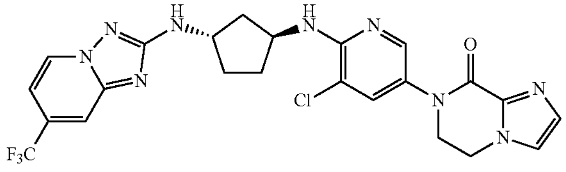,
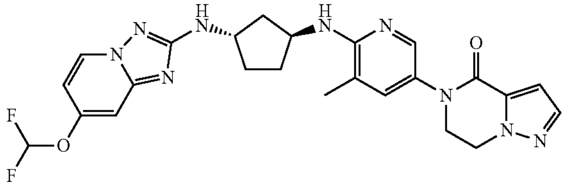,
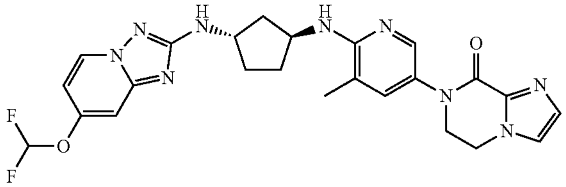,
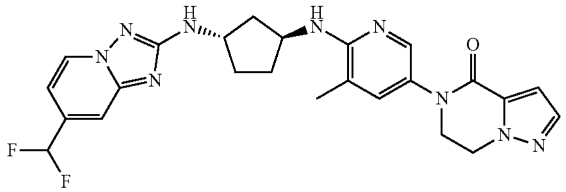,
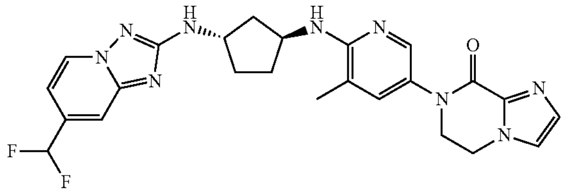,
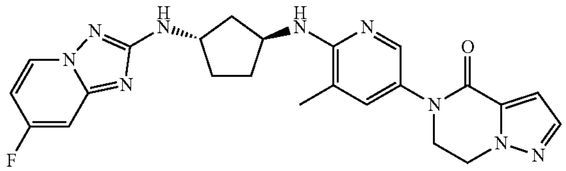,
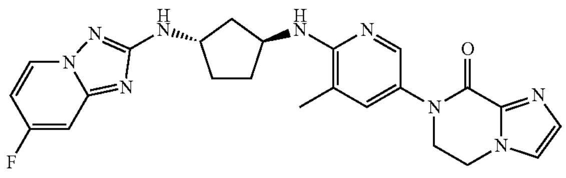,
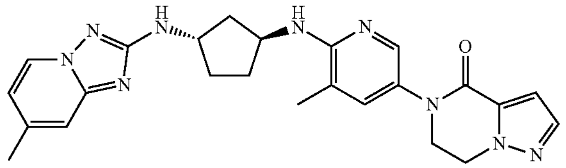, -continued
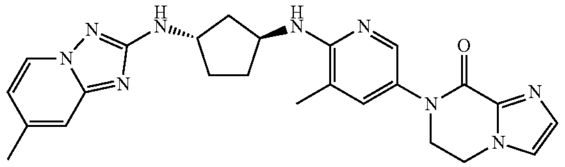
,
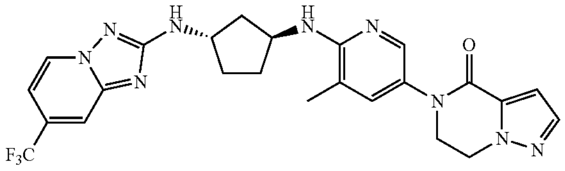
,
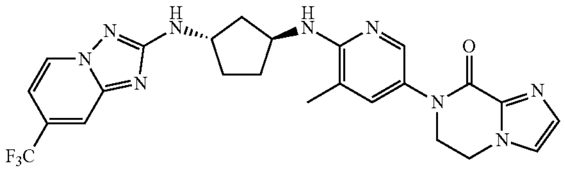
,
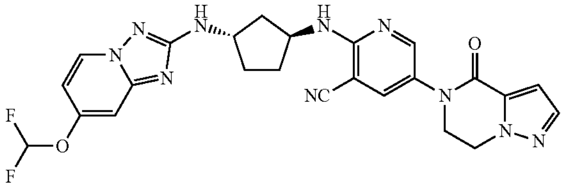
,
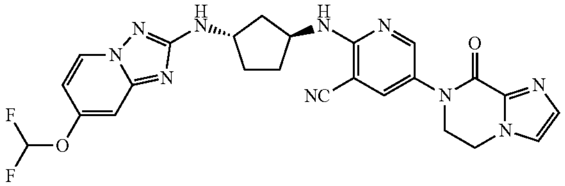
,
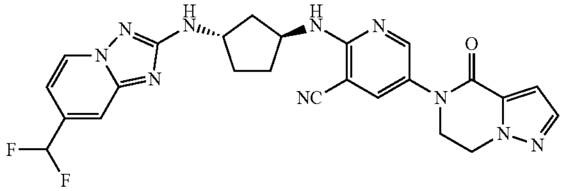
,
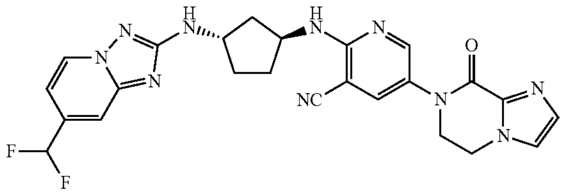
,
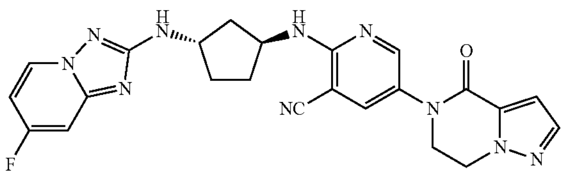
,
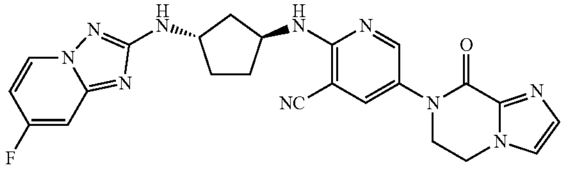
,
-continued
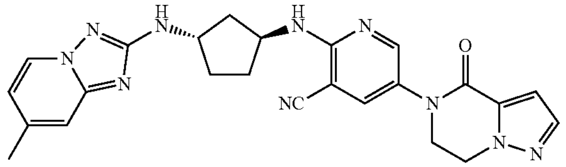
,
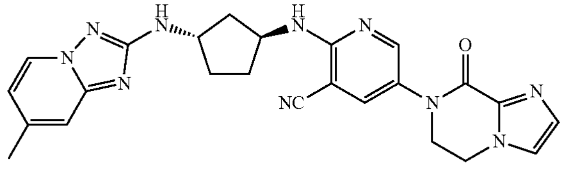
,
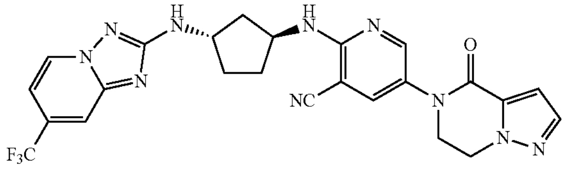
,
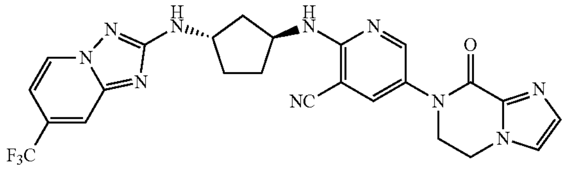
,
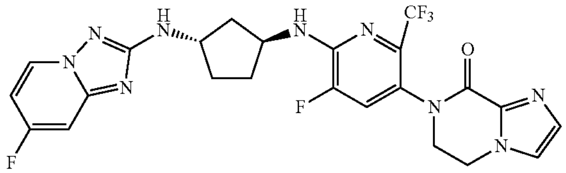
,
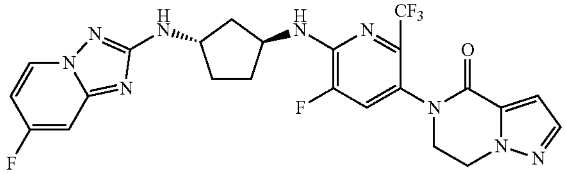
,
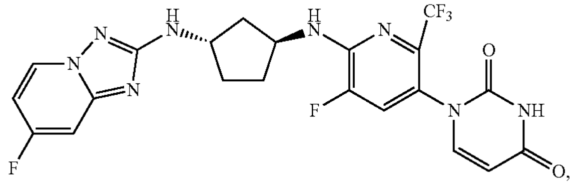
,
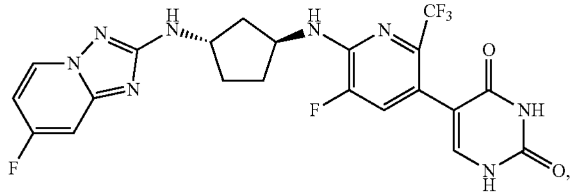
,
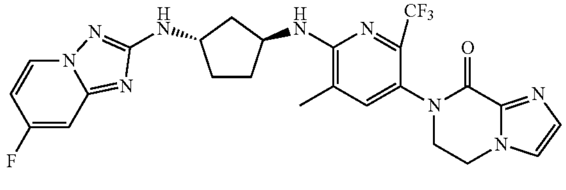
, -continued
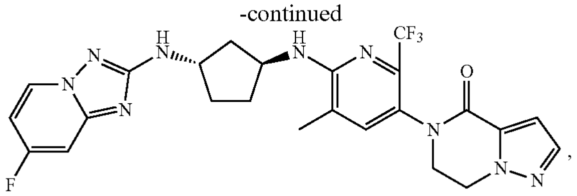
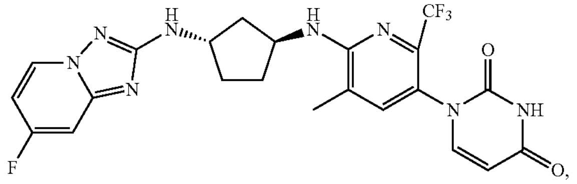
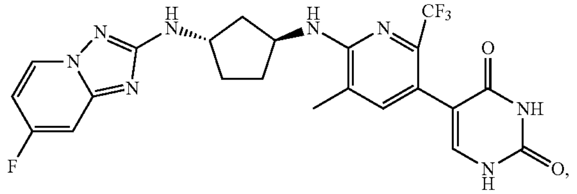
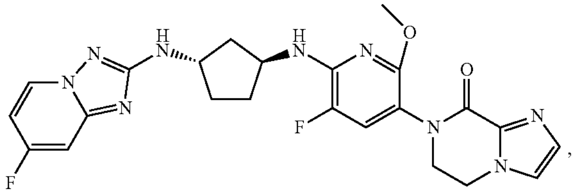
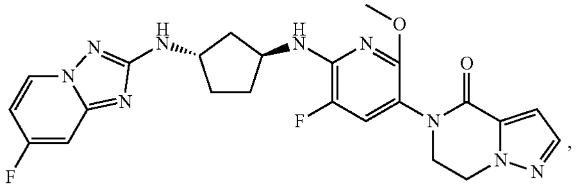
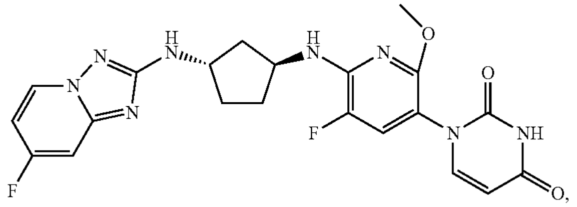
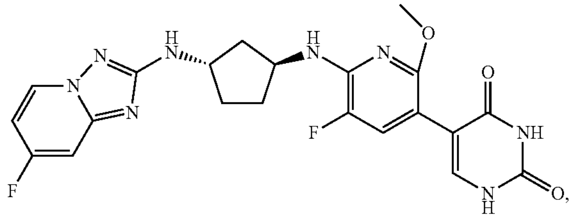
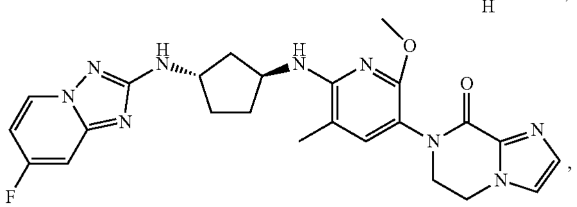
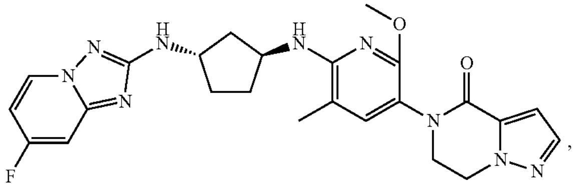
-continued
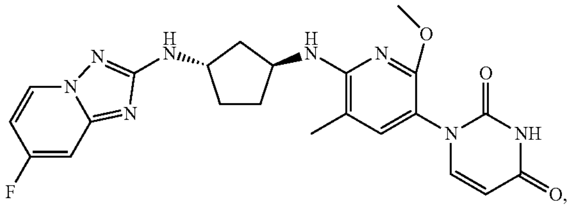
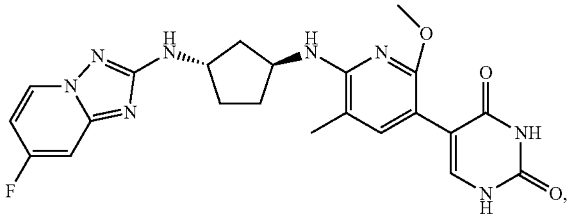
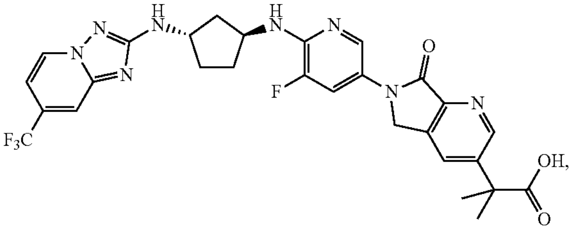
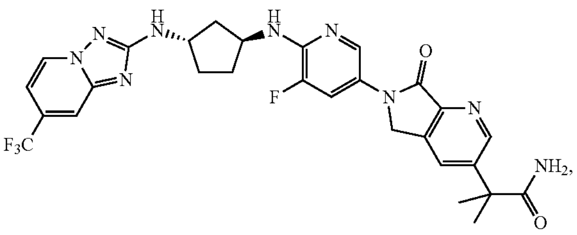
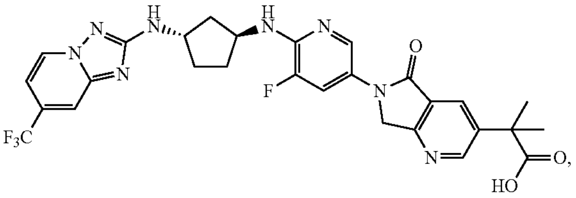
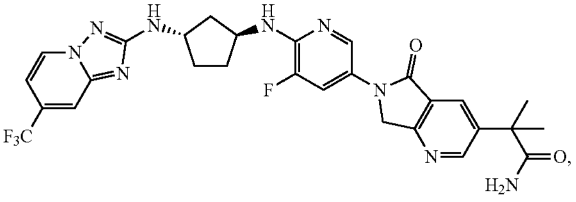
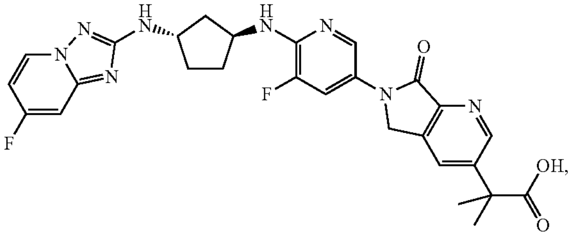

-continued
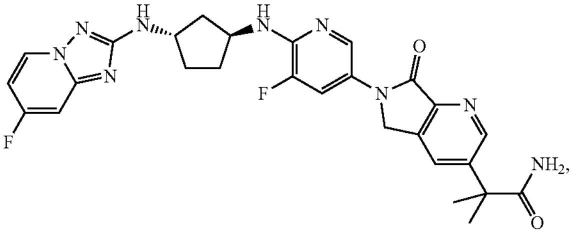,
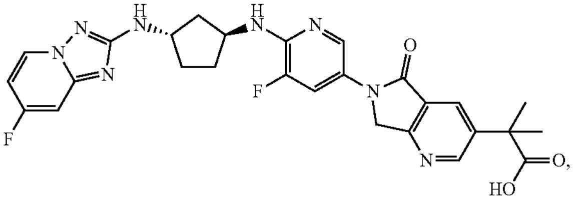,
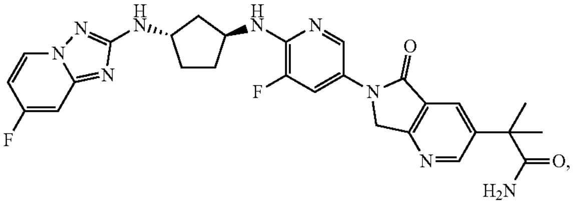,
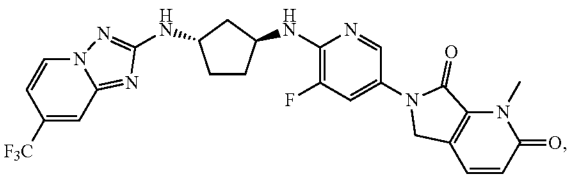,
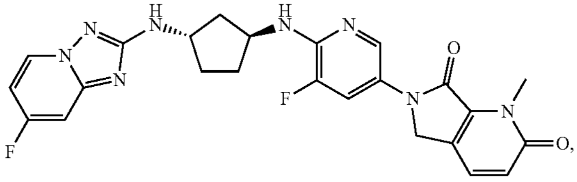,
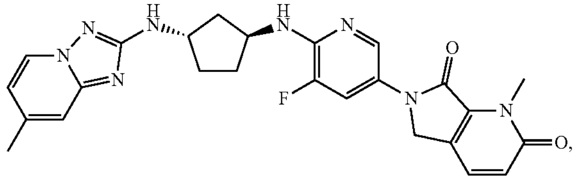,
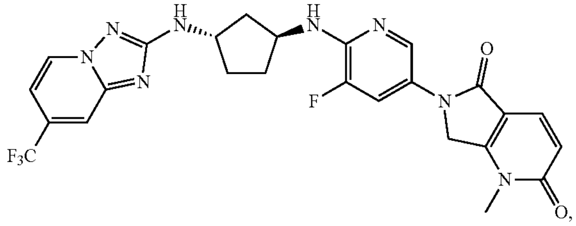,
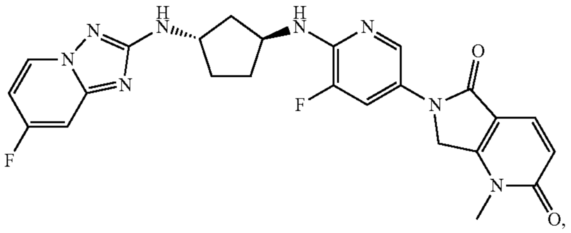,
-continued
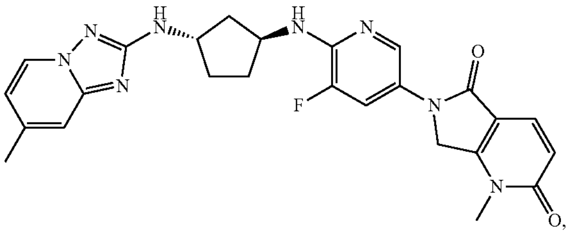,
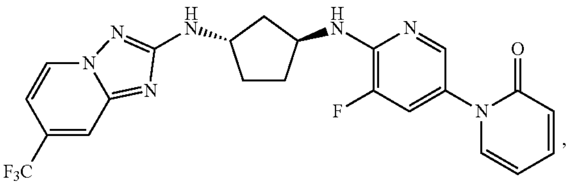,
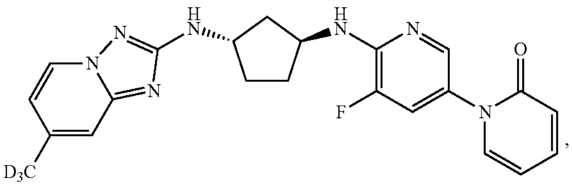,
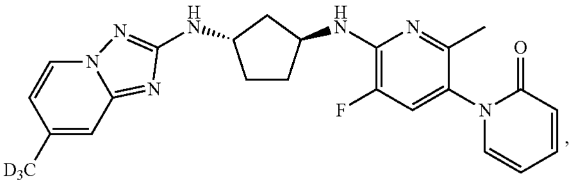,
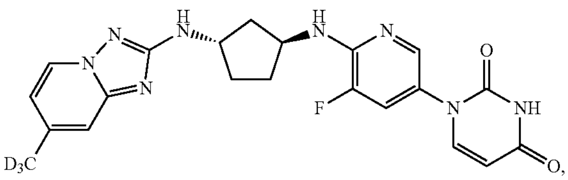,
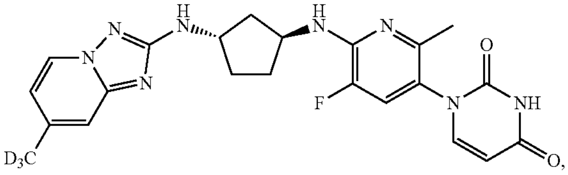,
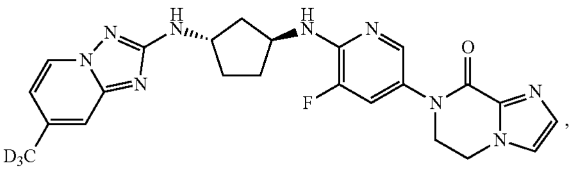,
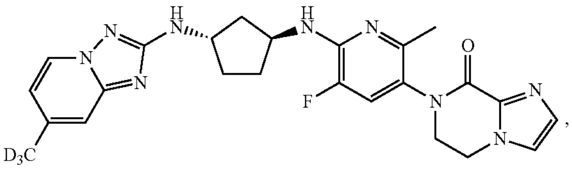,
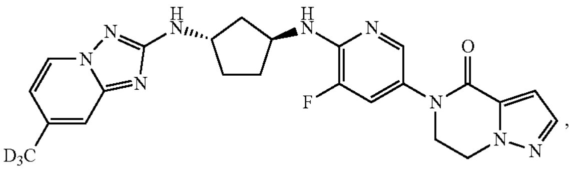, -continued

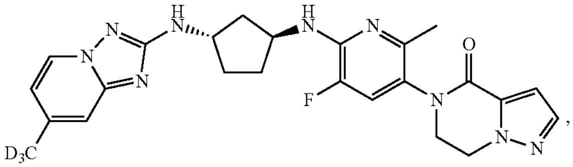,

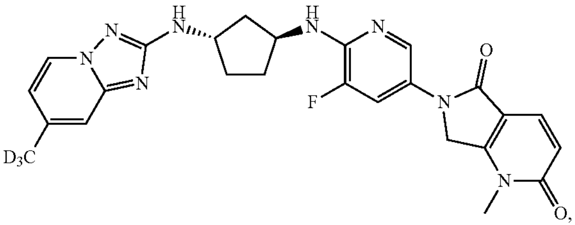,

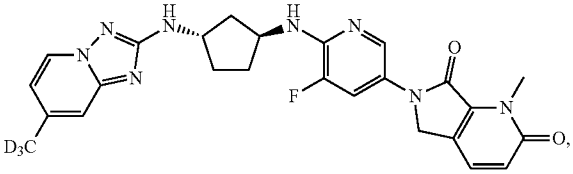,

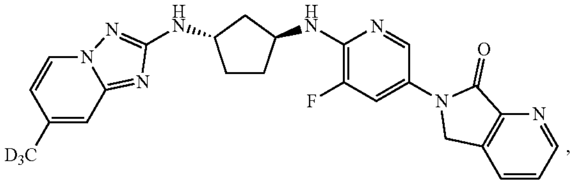,

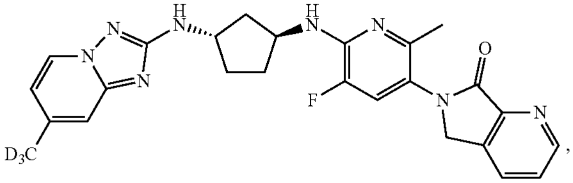,

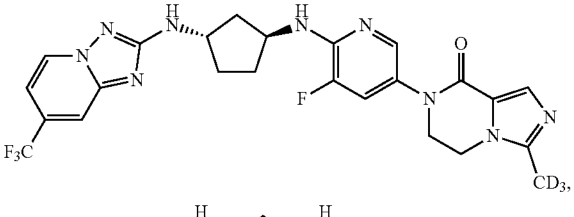,

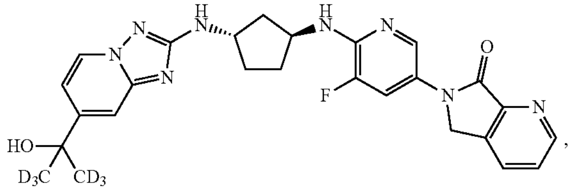,

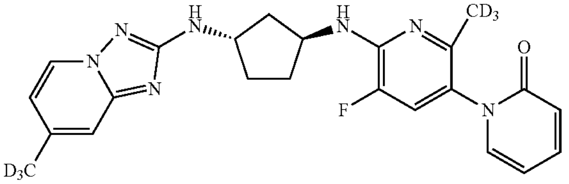,

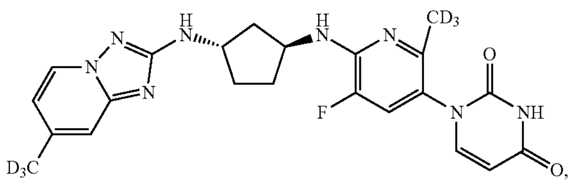,

-continued

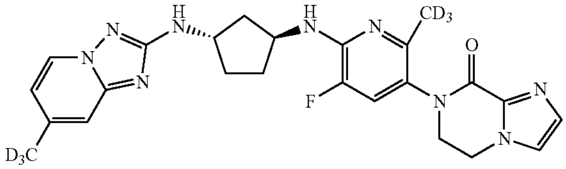,

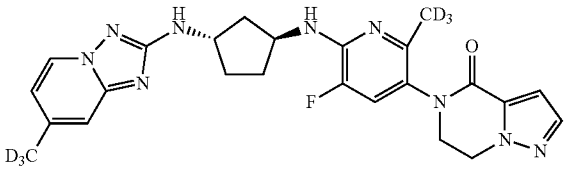,

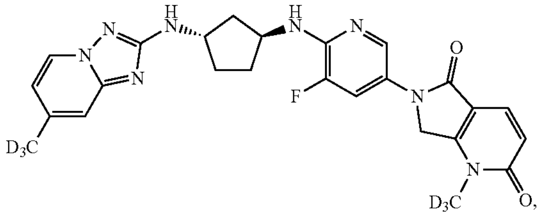, or

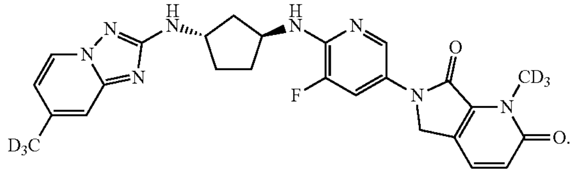.

12. A compound as represented by general formula (IV) or ah stereoisomer or pharmaceutically acceptable salt thereof, (IV)

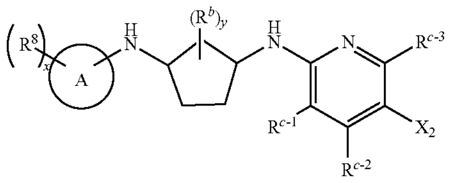

wherein $X_2$ is amino, nitro, halogen, boronic acid, or boronate; and $R^a$, $R^b$, $R^{c-1}$, $R^{c-2}$, $R^{c-3}$, x and y are each as defined in claim 1.

13. The compound as represented by general formula (IV) or the stereoisomer or pharmaceutically acceptable salt thereof according to claim 12, wherein the compound is selected from the following compounds:

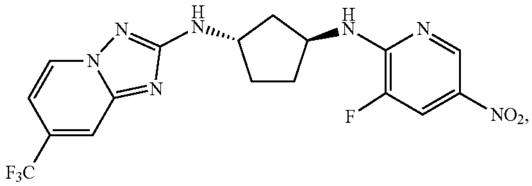,

-continued

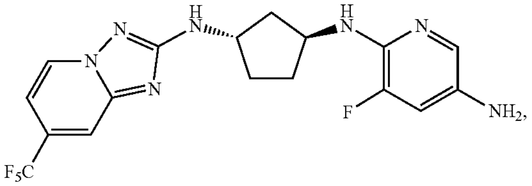

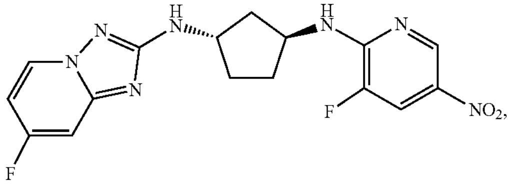

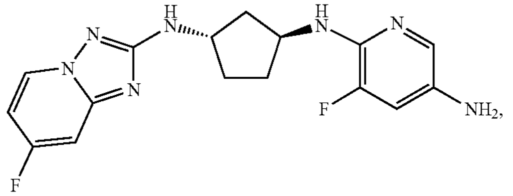

or

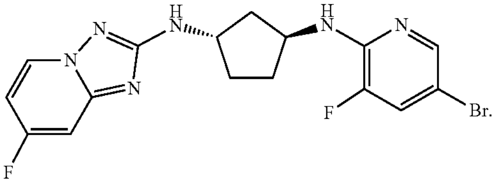

14. A pharmaceutical composition comprising a therapeutically effective dose of the compound as represented by general formula (I-A) or the stereoisomer or pharmaceutically acceptable salt thereof according to claim 1, and one or more pharmaceutically acceptable carriers, diluents, or excipients.

15. A pharmaceutical composition according to claim 14, wherein the weight percentage of the compound or the stereoisomer or pharmaceutically acceptable salt thereof in the composition is 0.1-95%.

16. A pharmaceutical composition according to claim 15, wherein the weight percentage of the compound or the stereoisomer or pharmaceutically acceptable salt thereof in the composition is 10-50%.

17. A pharmaceutical composition according to claim 15, wherein the compound is further represented by general formula (I-A'):

(I-A)

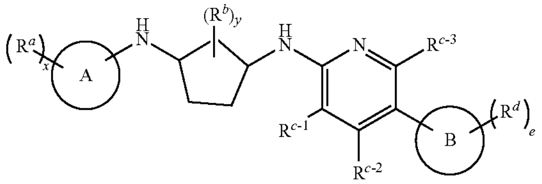

wherein ring A is selected from

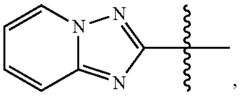

,

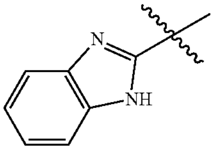

,

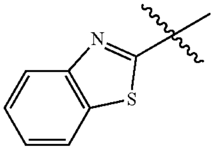

,

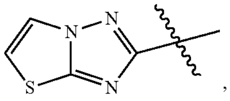

,

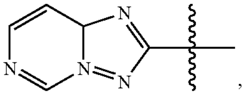

,

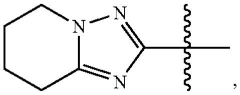

, or

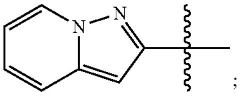

;

ring B is selected from

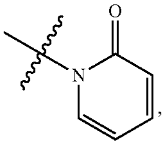

,

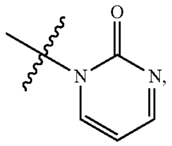

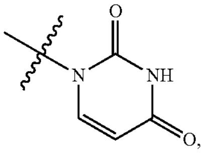

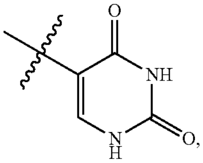

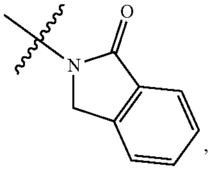

,

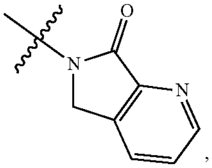

,

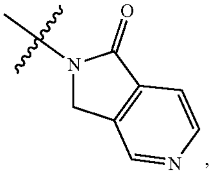

,

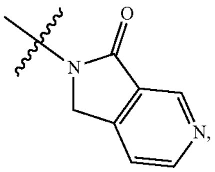

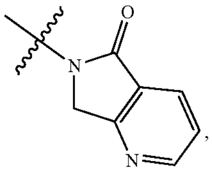

,

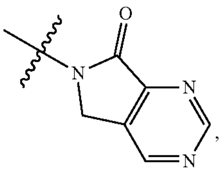

,

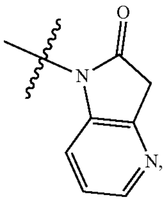

-continued

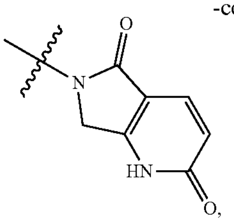
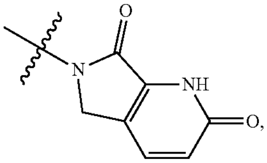
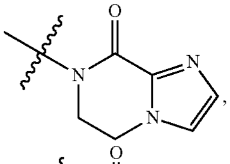
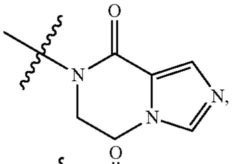
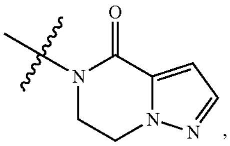
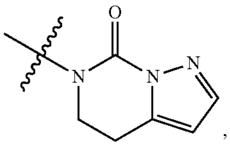
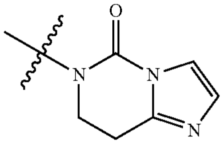
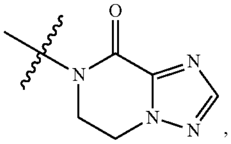
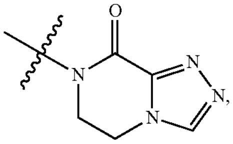
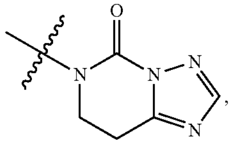
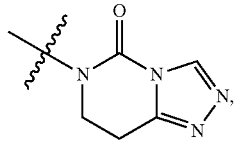
or
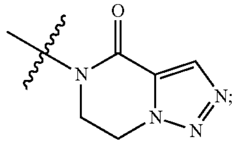

$R^a$ is selected from hydrogen, deuterium, halogen, amino, hydroxyl, cyano, $C_{1-6}$alkyl, $C_{2-6}$alkenyl, $C_{2-6}$alkynyl, oxo, thio, $C_{1-6}$alkylthio, $C_{1-6}$deuteroalkyl, $C_{1-6}$haloalkyl, $C_{1-6}$alkoxy, $C_{1-6}$haloalkoxy, $C_{1-6}$hydroxyalkyl, cyano-substituted $C_{1-6}$alkyl, $C_{3-8}$cycloalkyl or 3- to 8-membered heterocyclyl;

$R^b$ is selected from hydrogen, deuterium, halogen, amino, hydroxyl, cyano, $C_{1-6}$ alkyl, $C_{2-6}$alkenyl, $C_{2-6}$alkynyl, oxo, thio, $C_{1-6}$deuteroalkyl, $C_{1-6}$haloalkyl, $C_{1-6}$alkoxy, $C_{1-6}$haloalkoxy, $C_{1-6}$hydroxyalkyl, or cyano-substituted $C_{1-6}$alkyl;

$R^{c-1}$ is selected from halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, or 3- to 8-membered heterocyclyl;

$R^{c-2}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, or cyano-substituted $C_{1-3}$ alkyl;

$R^{c-3}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, or 3- to 8-membered heterocyclyl;

$R^d$ is selected from hydrogen, deuterium, halogen, amino, hydroxyl, cyano, nitro, $C_{1-6}$alkyl, $C_{1-6}$alkenyl, $C_{1-6}$alkynyl, oxo, thio, $C_{1-6}$deuteroalkyl, $C_{1-6}$haloalkyl, $C_{1-6}$alkoxy, $C_{1-6}$haloalkoxy, $C_{1-6}$hydroxyalkyl, cyano-substituted $C_{1-6}$alkyl, $C_{3-8}$ cycloalkyl, 3- to 8-membered heterocyclyl, $C_{6-10}$aryl, or $C_{5-12}$heteroaryl;

alternatively, any two adjacent or non-adjacent $R^d$ are connected to form $C_{3-8}$cycloalkyl or 3- to 8-membered heterocyclyl;

x is 0, 1, 2, or 3;

y is 0, 1, 2, or 3; and e is 0, 1, 2, or 3.

18. A pharmaceutical composition according to claim 17, wherein the compound is further represented by general formula (I-A-1):

(I-A-1)

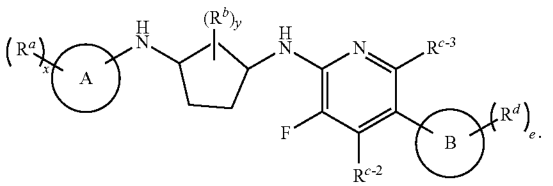

19. A pharmaceutical composition according to claim 17, wherein the compound is further represented by general formula (I-1-a):

(I-1-a)

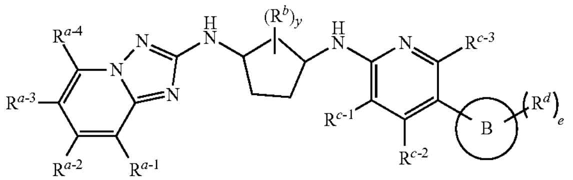

wherein $R^{a-1}$—$R^{a-4}$ are each independently selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, or 3- to 8-membered heterocyclyl.

20. A pharmaceutical composition according to claim 17, wherein the compound is further represented by general formula (I-1-a'):

(I-1-a')

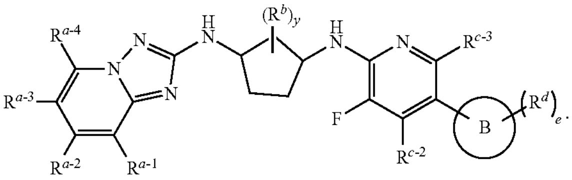

21. A pharmaceutical composition according to claim 17, wherein ring B is selected from

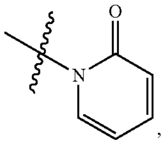, 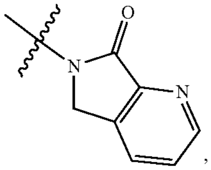, 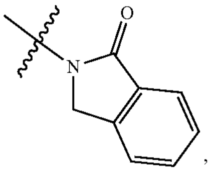, 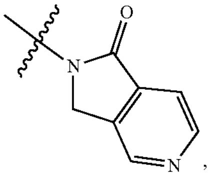, 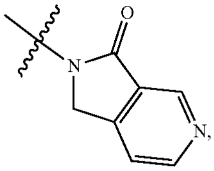, 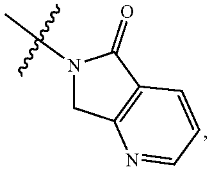, 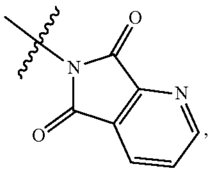, or 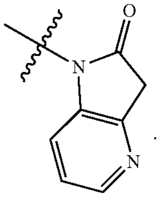.

22. A pharmaceutical composition according to claim 17, wherein $R^{a-1}$—$R^{a-4}$ are each independently selected from —H, —O—$CHF_2$, —O—$CF_3$, —O—$CF_2Cl$, —O—$CF_2Br$, —O—$CH_2$—$CHF_2$, —O—$CH_2$—$CF_3$, —$CHF_2$, —$CF_3$, —$CH_2$—OH, —$CH_2$—$CHF_2$, —CH($CH_3$)—OH, —$(CH_2)_3$—OH, —C$(CH_3)_2$—OH, —OH, —O—$CH_3$, —$CH_3$, —$CF_3$, —F, —Cl, —CN, —$NHCH_3$, —$NH_2$, —$CH_2$—$CF_3$, or

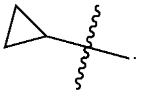 [SMILES: *C1CC1].

23. A pharmaceutical composition according to claim 17, wherein $R^b$ is selected from —H or —F.

24. A pharmaceutical composition according to claim 17, wherein $R^{c-2}$ is selected from —H, —F, —Cl, —O—$CH_3$, —CN, —$CF_3$, —$CH_3$, —O—$CF_3$, —O—$CH_3$, or —O—CH$(CH_3)_2$;

And/or, wherein $R^{c-3}$ is selected from —H, —F, —Cl, —O—$CH_3$, —CN, —$CF_3$, —$CD_3$, —$CH_3$, —O—$CF_3$, —O—$CH_3$, —O—CH$(CH_3)_2$, or

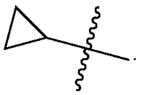 [SMILES: *C1CC1].

25. A pharmaceutical composition according to claim 17, wherein $R^d$ is selected from —H, -D, —F, —Cl, —CN, —$CH_3$, —$CF_3$, —CH$(CH_3)_2$, —C$(CH_3)_3$, —C$(CH_3)_2$—OH, —C$(CH_3)_2$—$CH_2$—OH, —O—$CH_3$, —$CH_2$—$NH_2$, —$CH_2$—OH, —$NH_2$, —OH, or

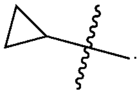.

26. A pharmaceutical composition according to claim 17, wherein the compound is selected from the following compounds:

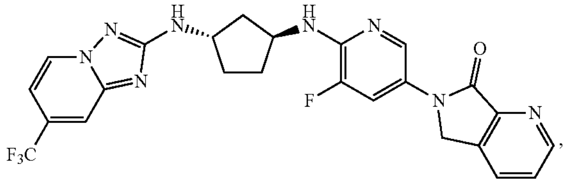,

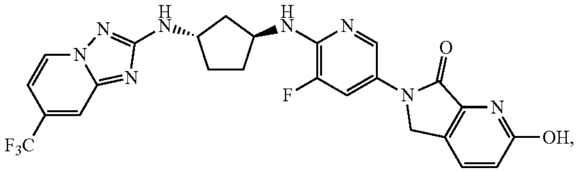,

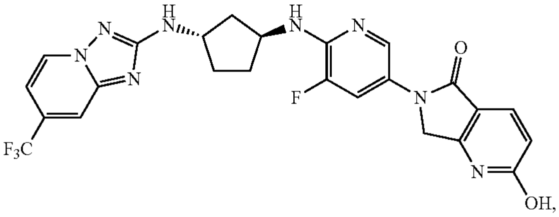,

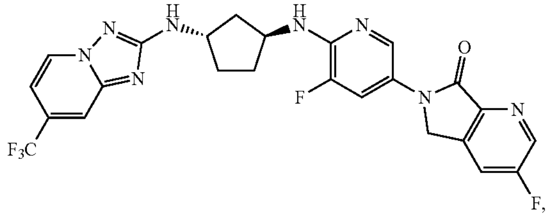,

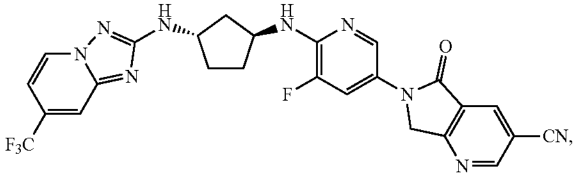,

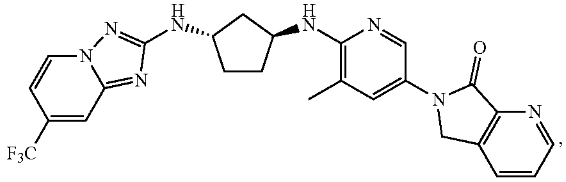,

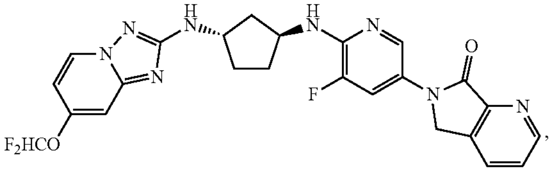,

-continued
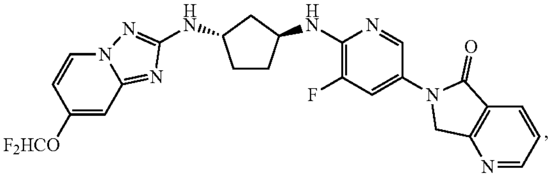
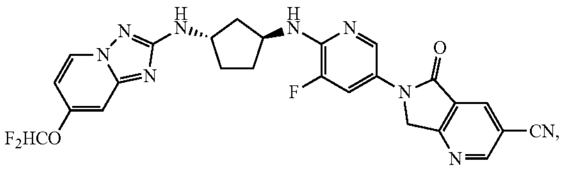
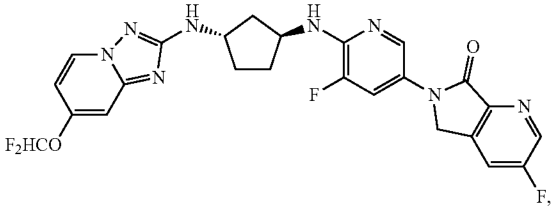
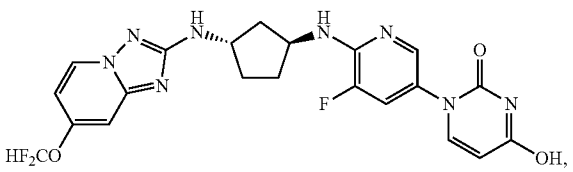
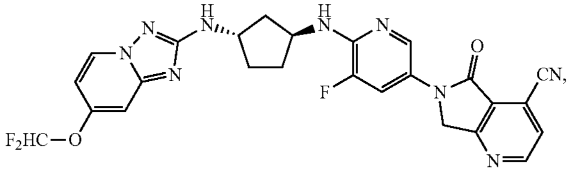
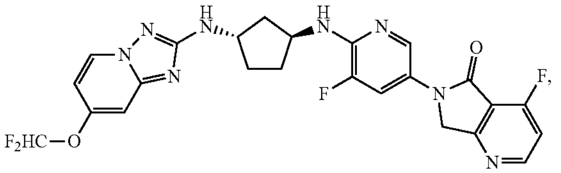
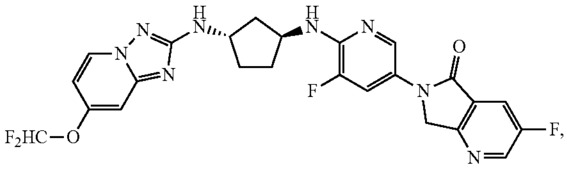
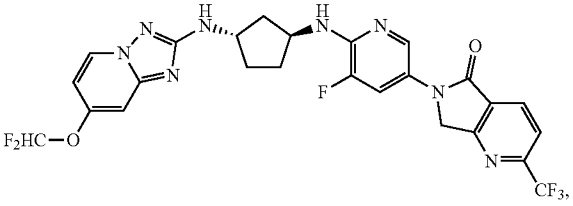
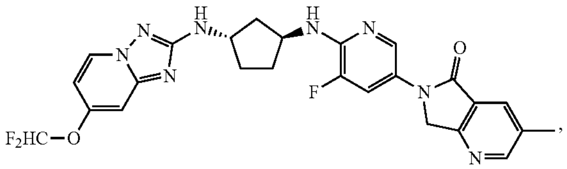
-continued
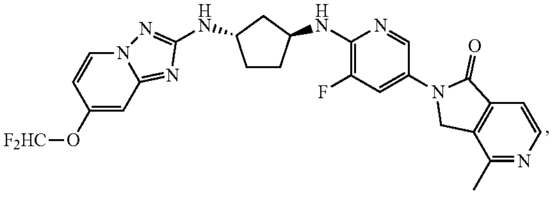
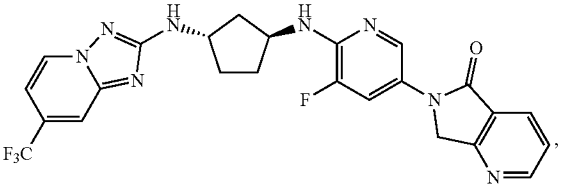
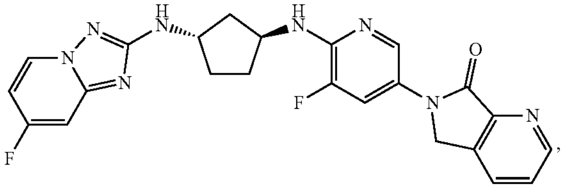
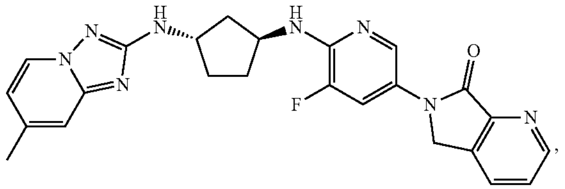
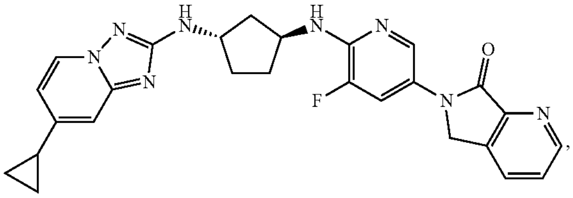
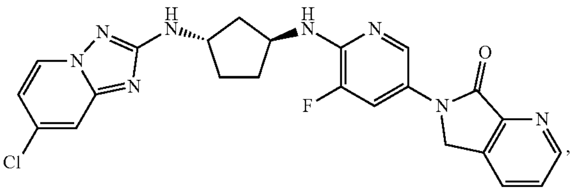
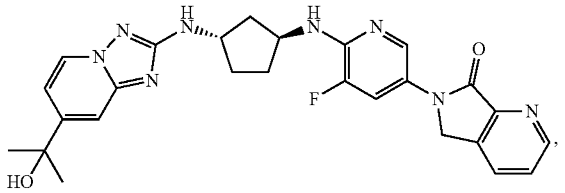
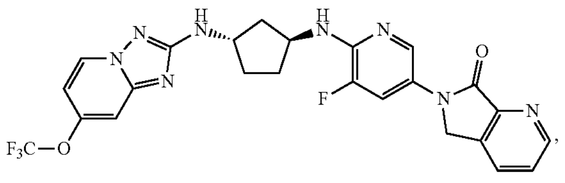
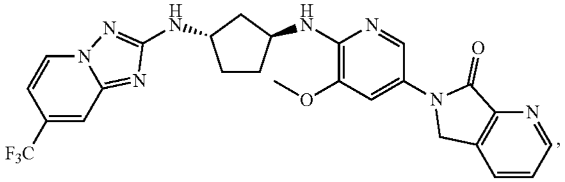

-continued
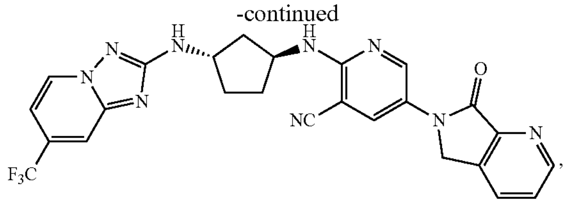
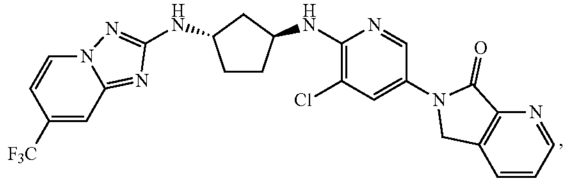
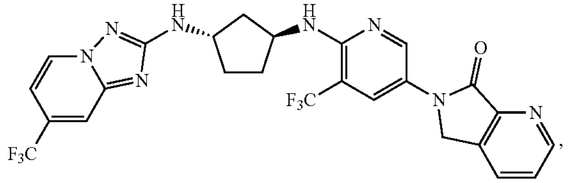
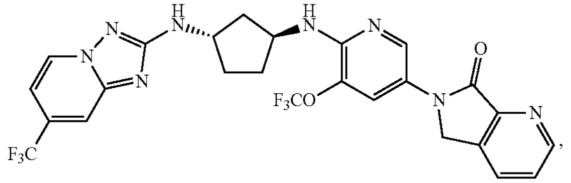
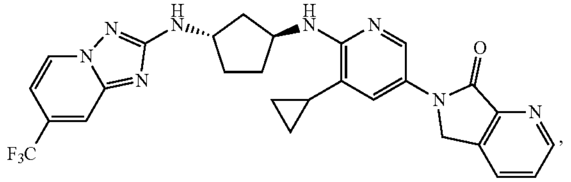
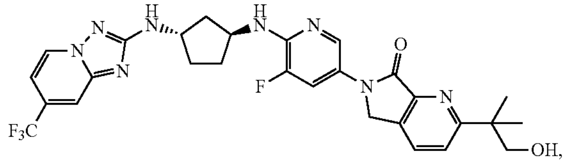
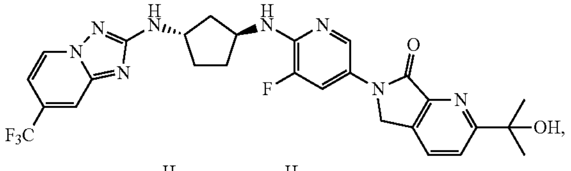
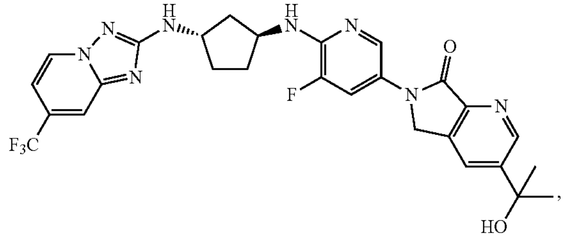
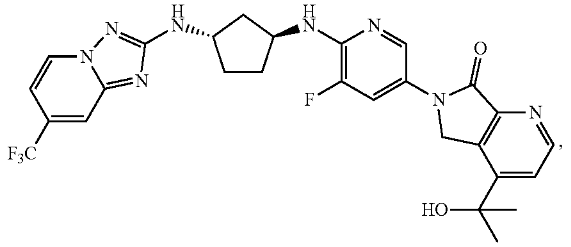
-continued
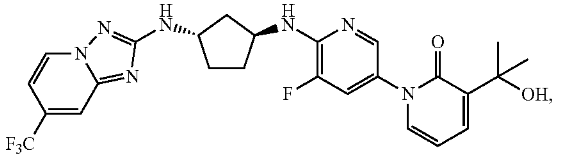
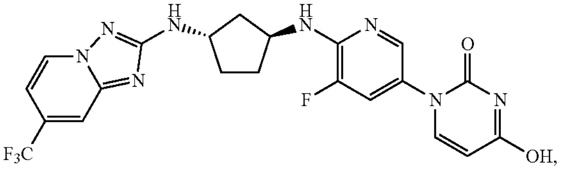
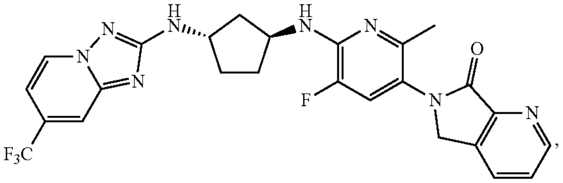
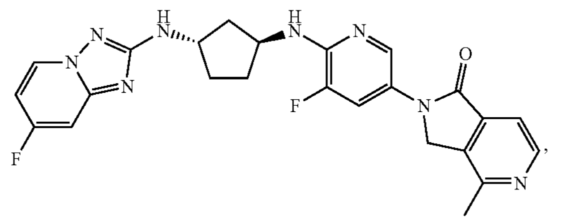
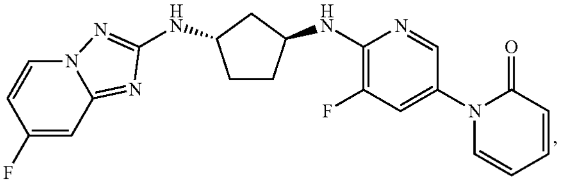
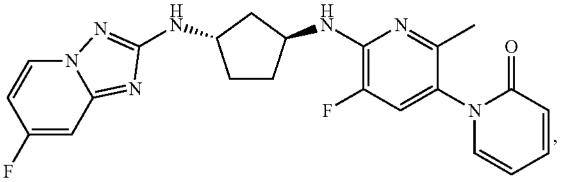
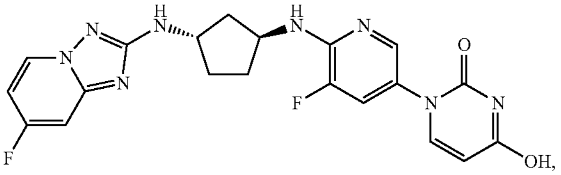
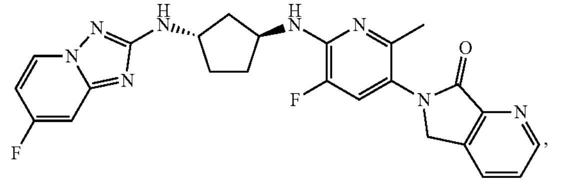
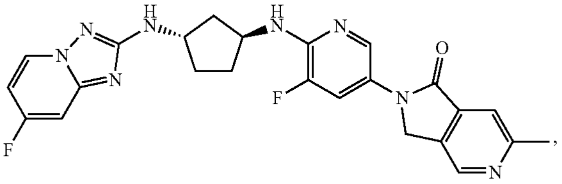

-continued
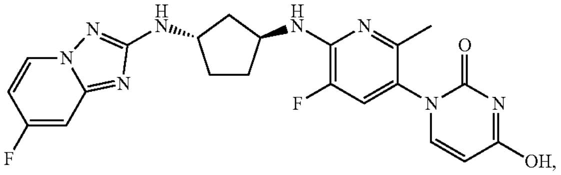
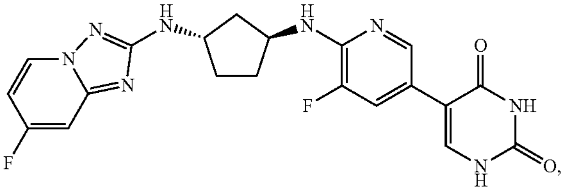
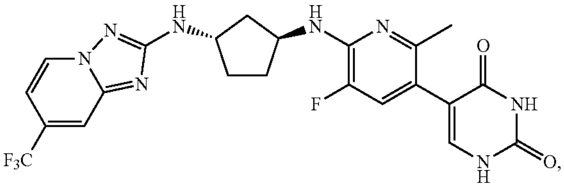
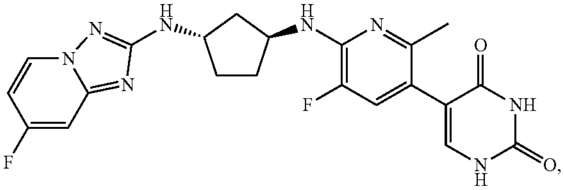
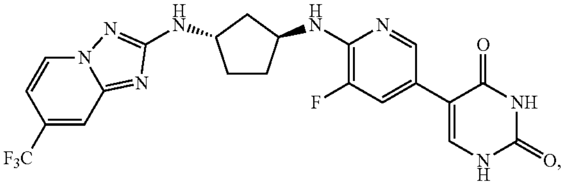
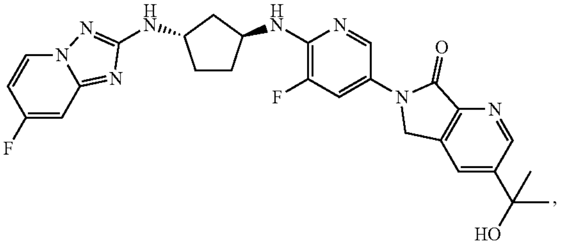
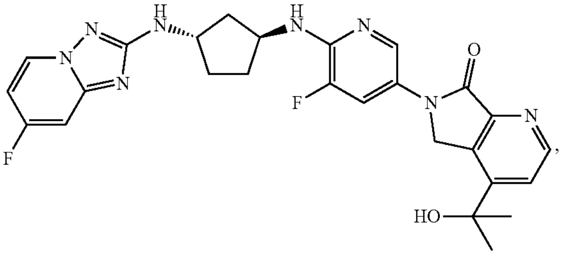
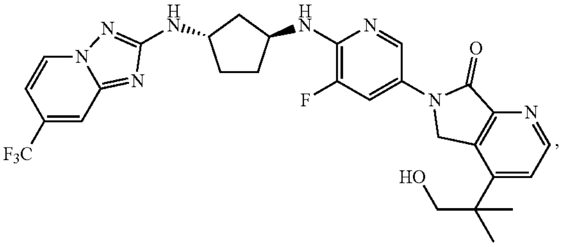
-continued
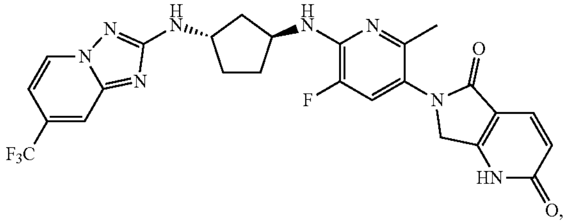
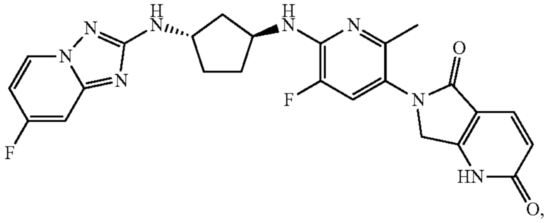
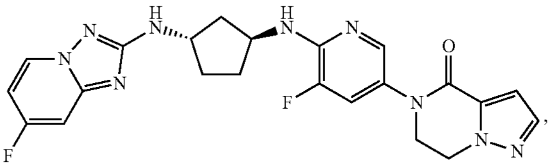
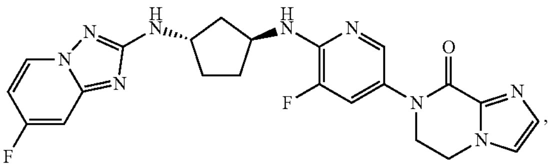
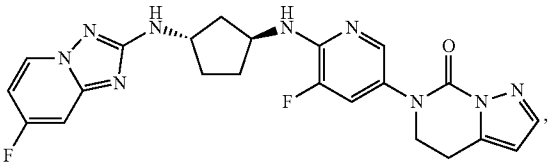
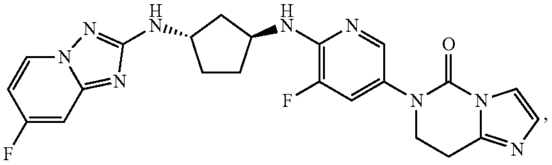
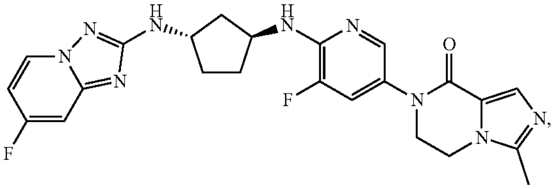
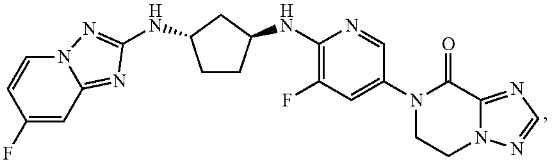
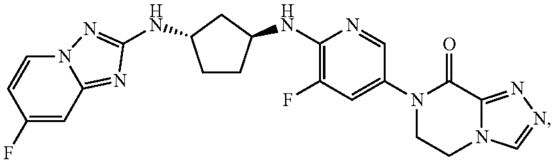

-continued
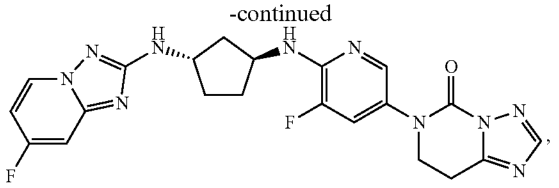,
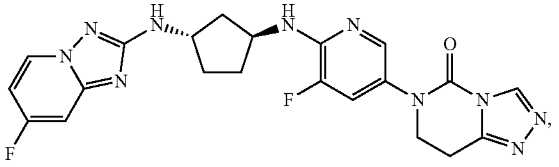,
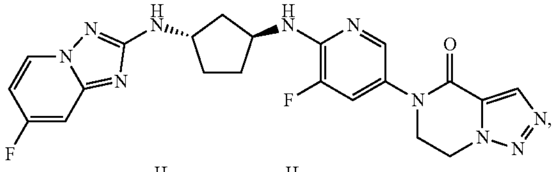,
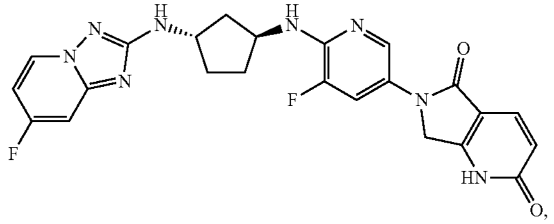,
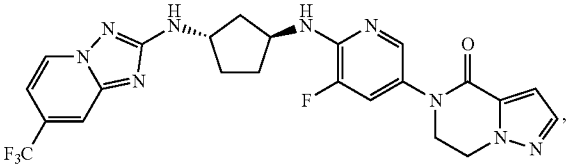,
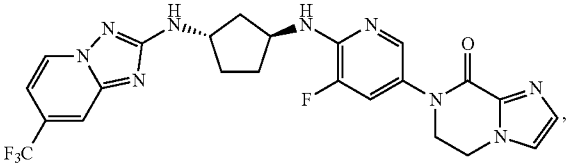,
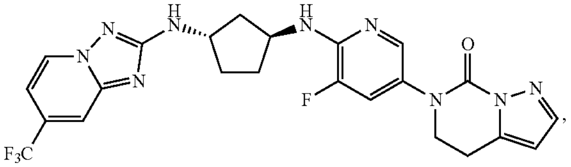,
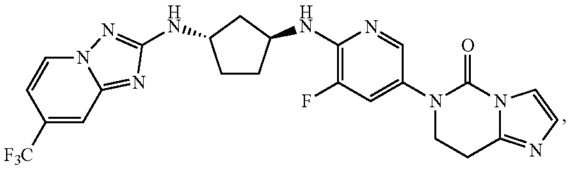,
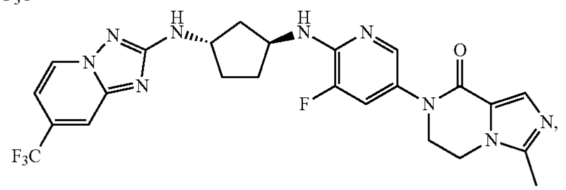,
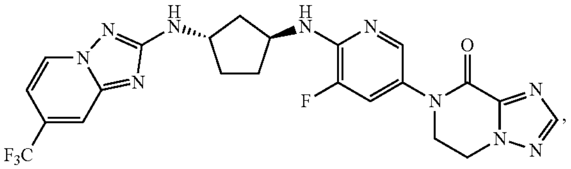,
-continued
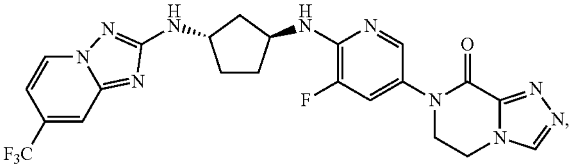,
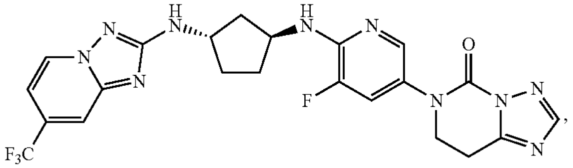,
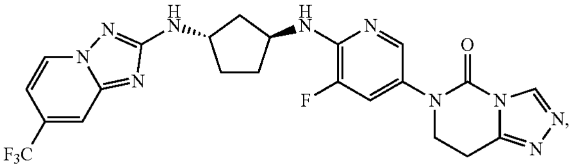,
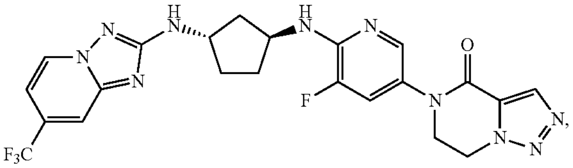,
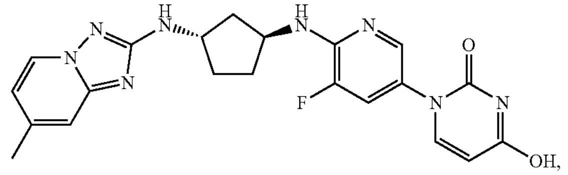,
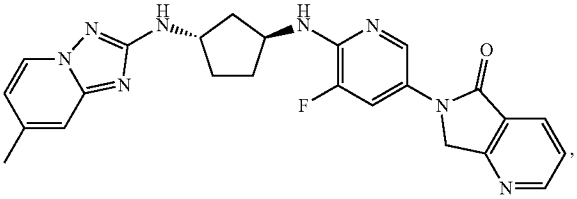,
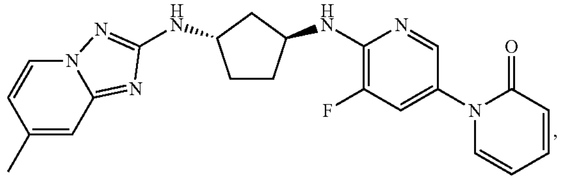,
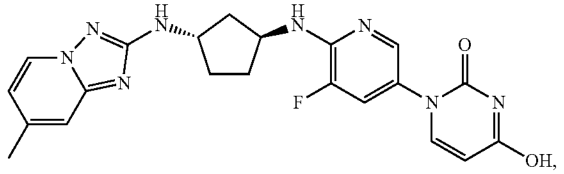,
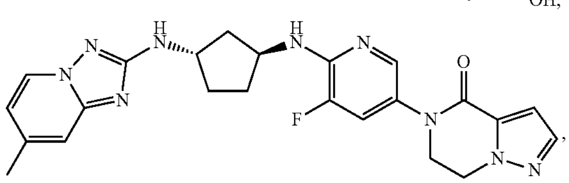,
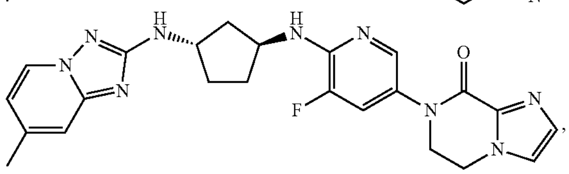, -continued
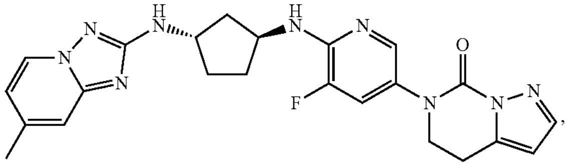,
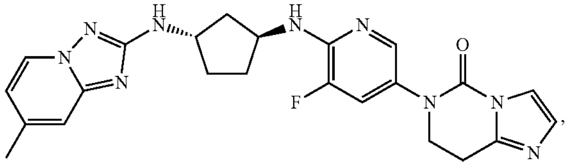,
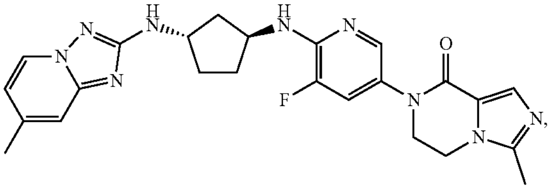,
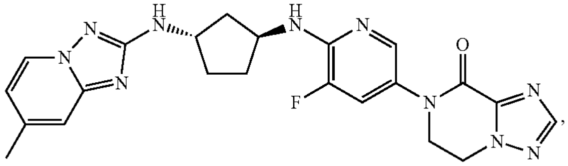,
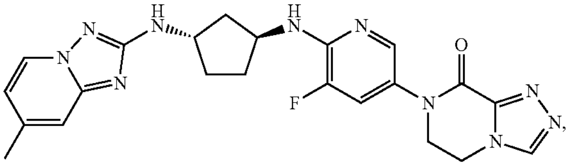,
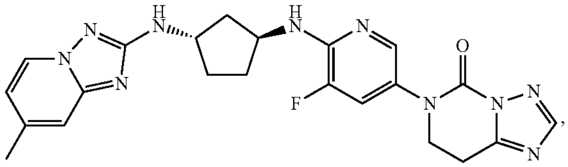,
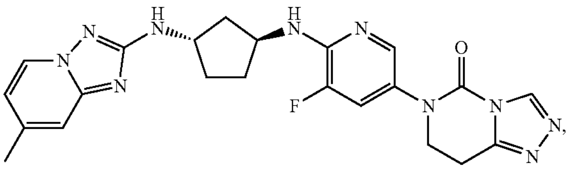,
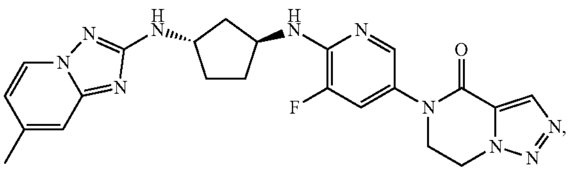,
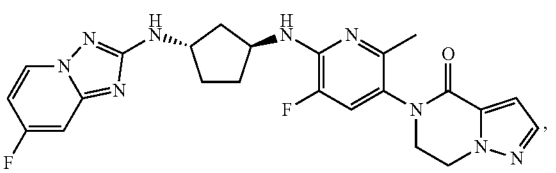,
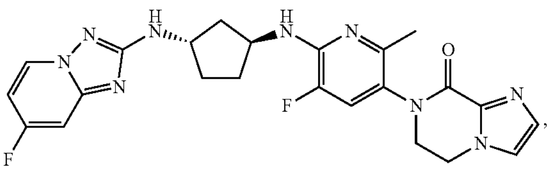,
-continued
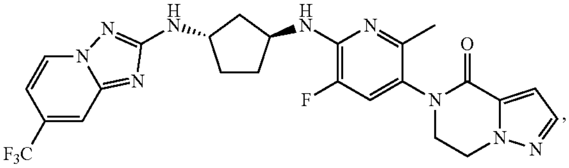,
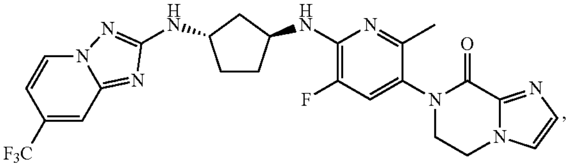,
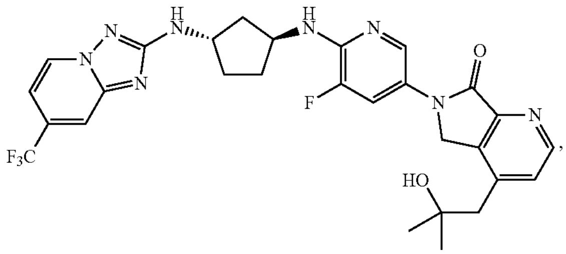,
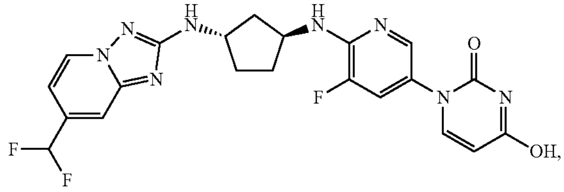,
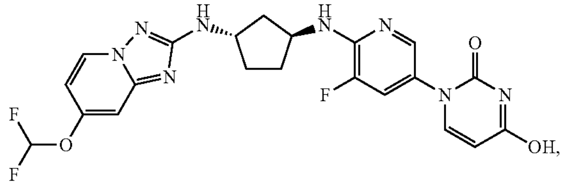,
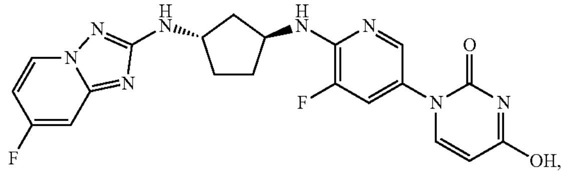,
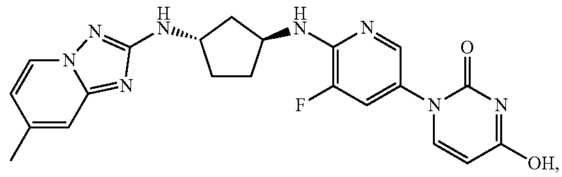,
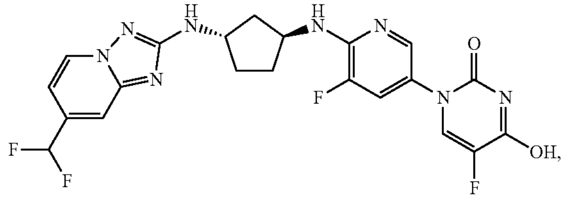,
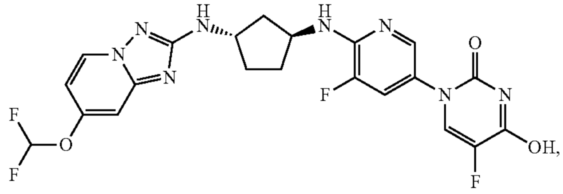, -continued
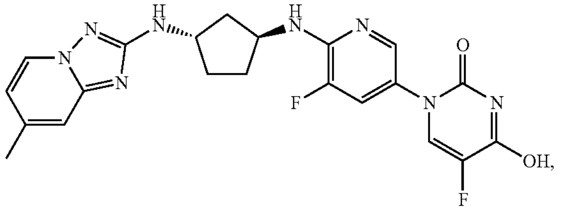
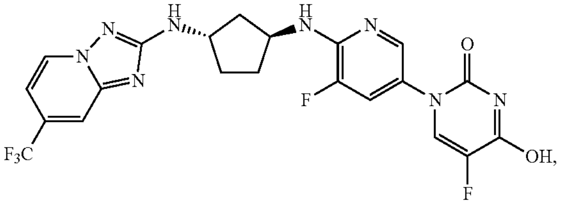
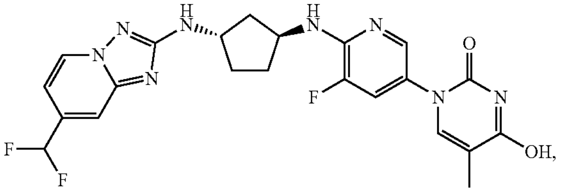
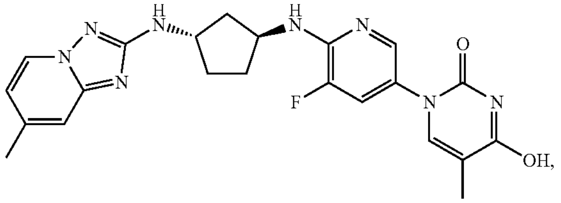
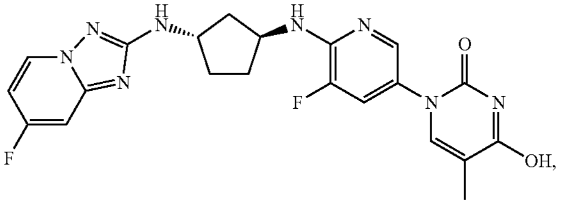
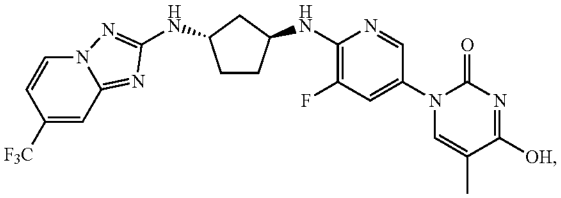
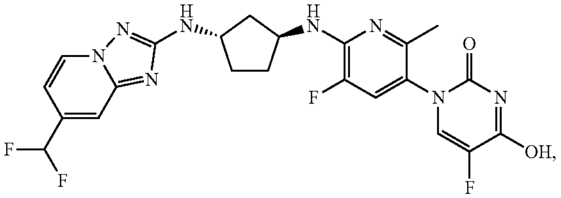
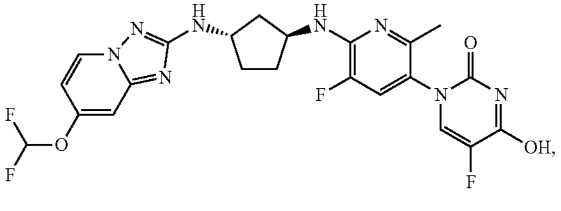
-continued
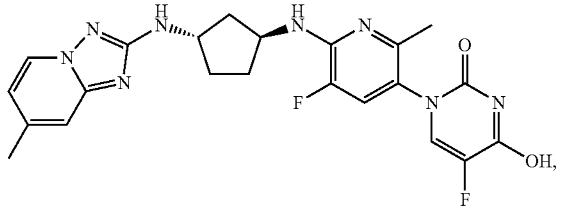
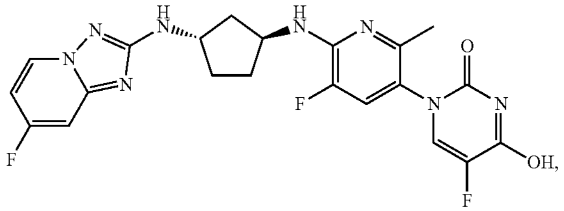
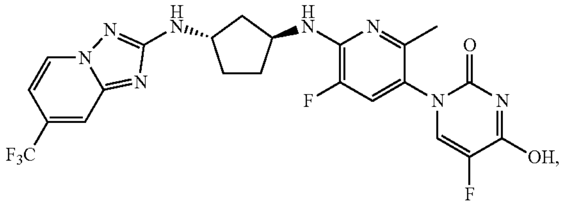
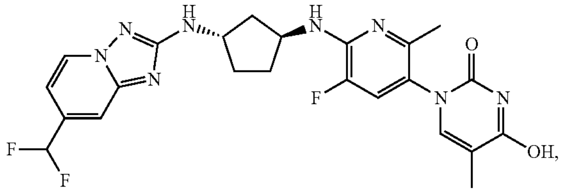
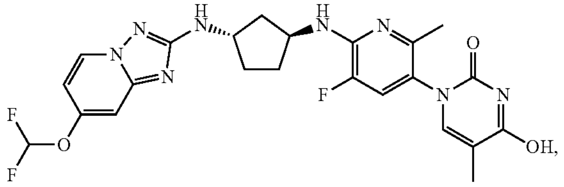
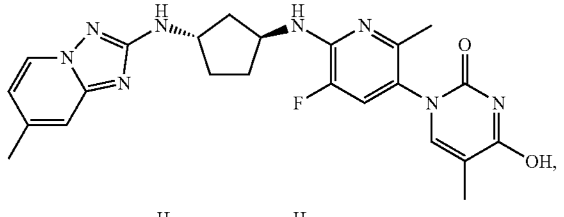
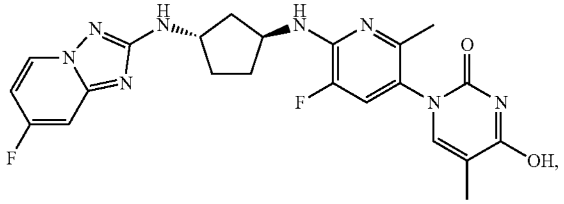
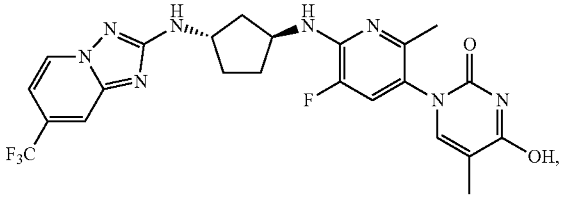

-continued
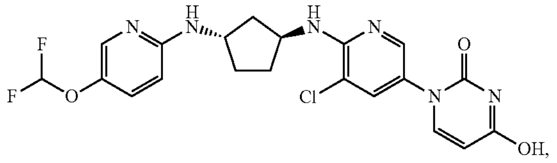
,
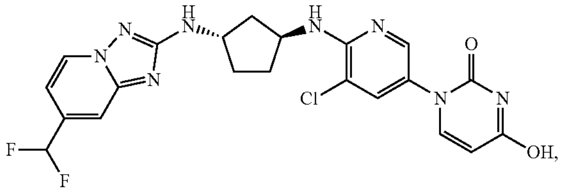
,
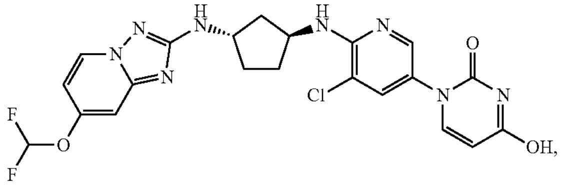
,
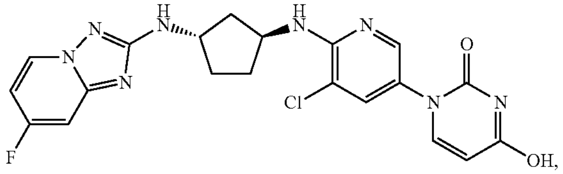
,
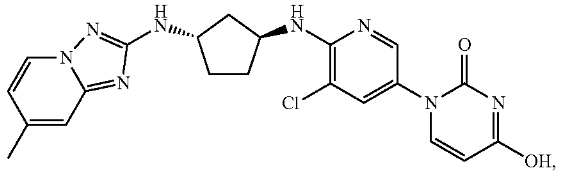
,
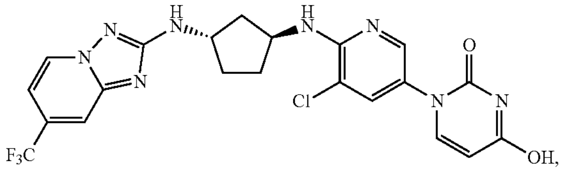
,
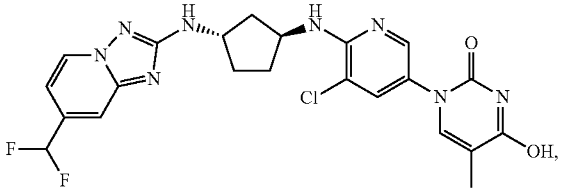
,
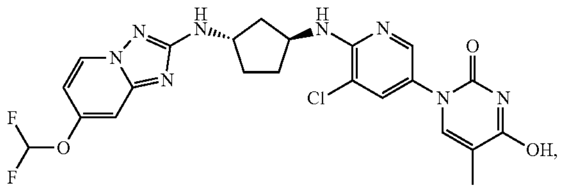
,
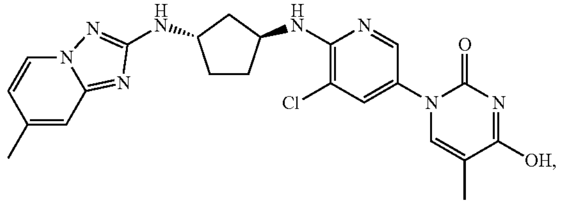
,
-continued
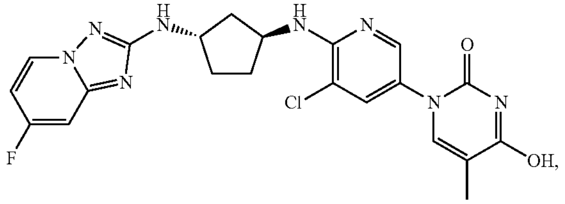
,
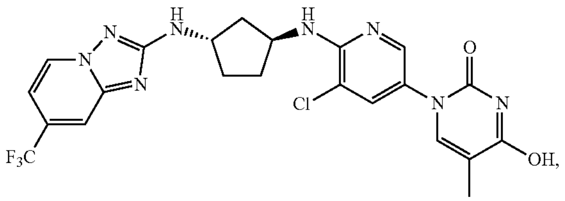
,
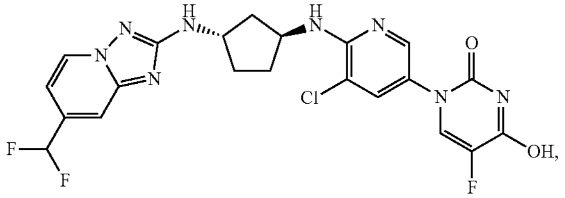
,
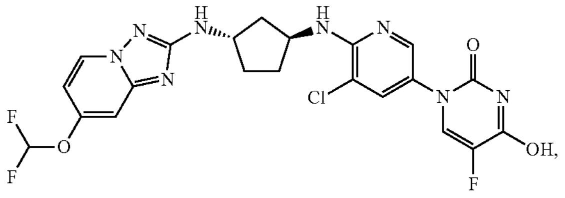
,
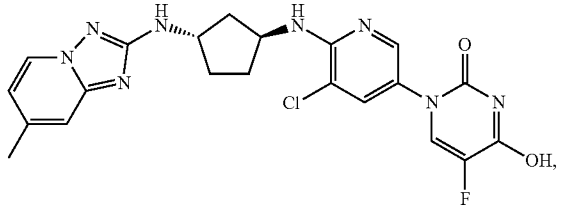
,
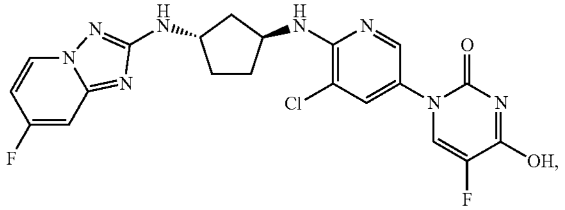
,
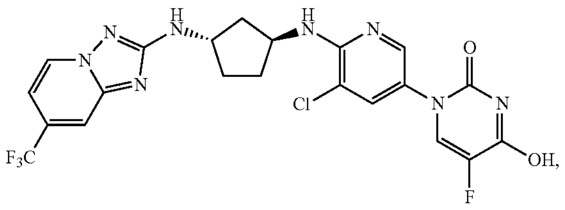
,
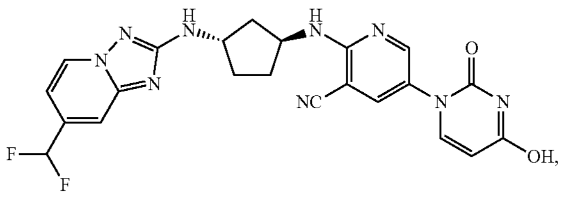
, -continued
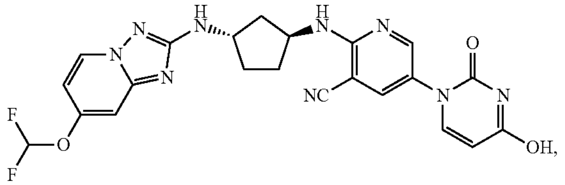
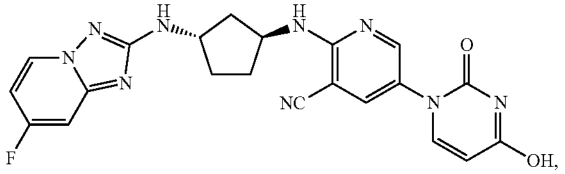
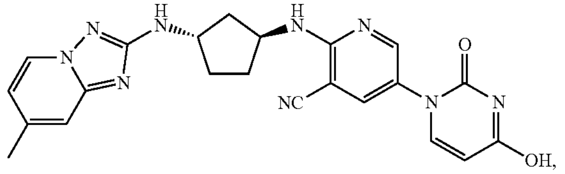
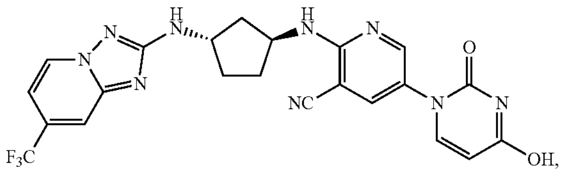
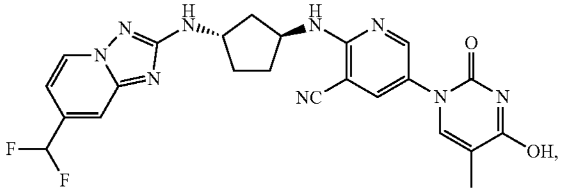
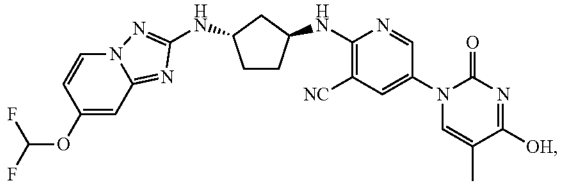
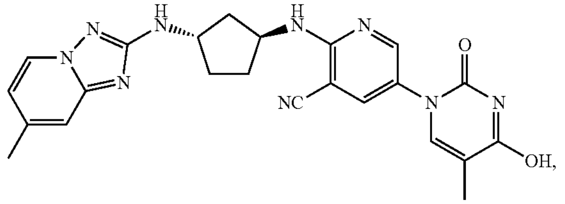
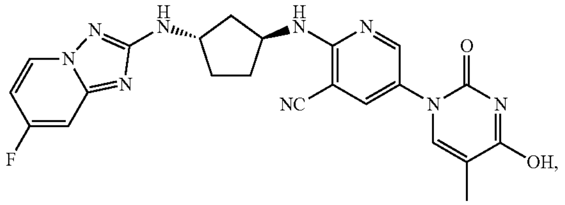
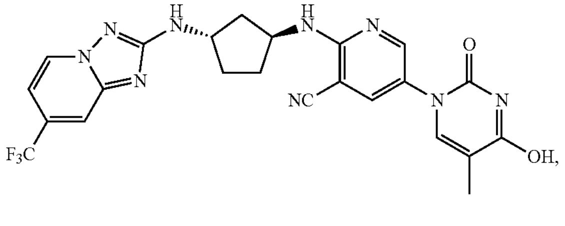
-continued
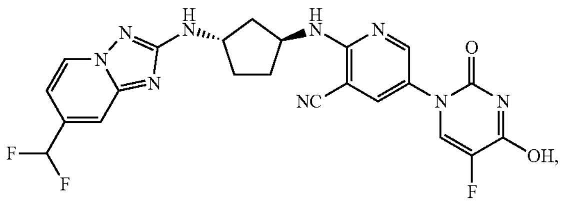
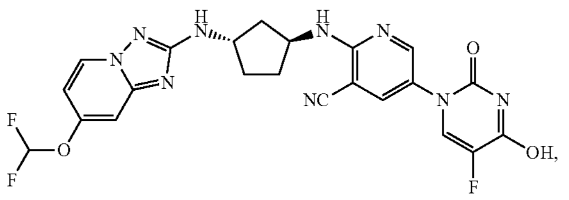
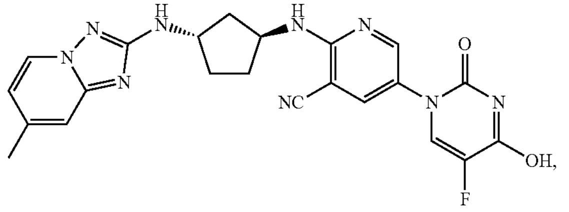
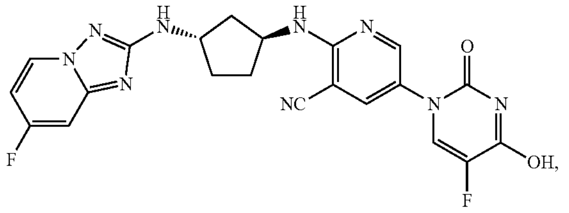
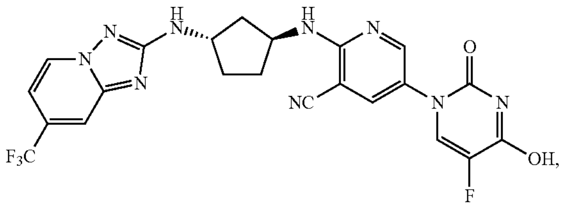
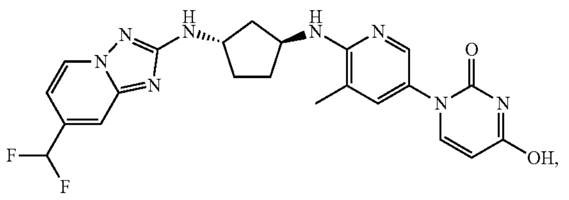
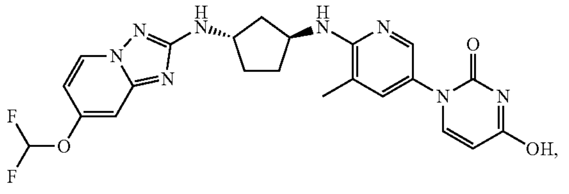
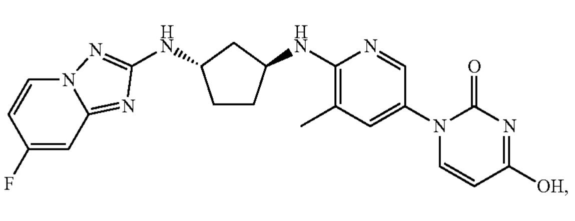

-continued
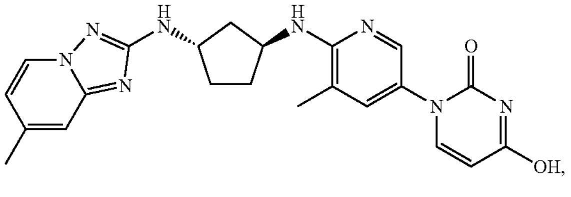
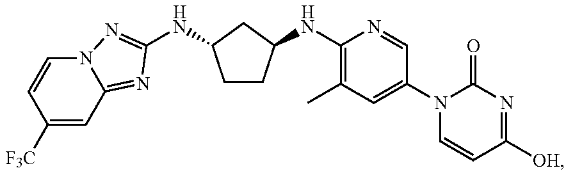
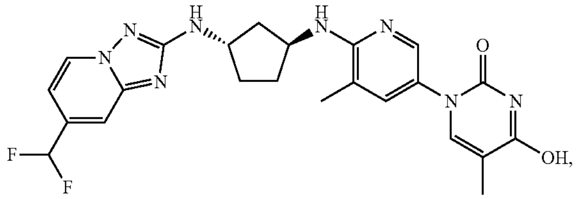
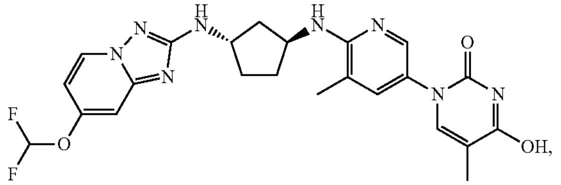
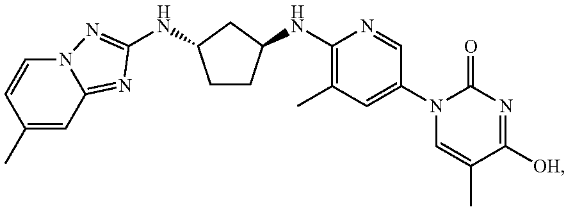
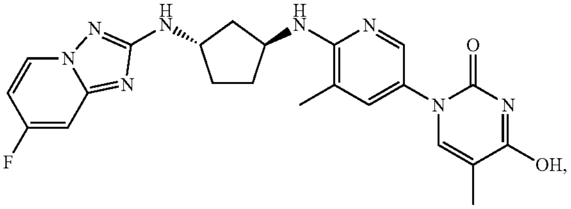
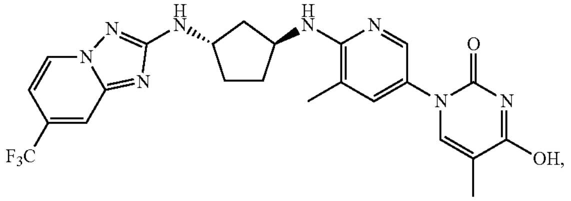
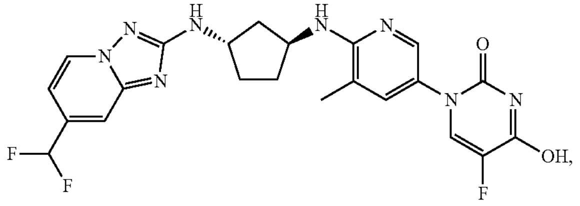
-continued
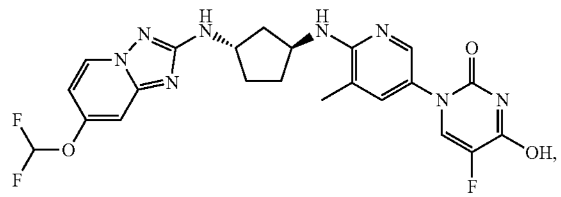
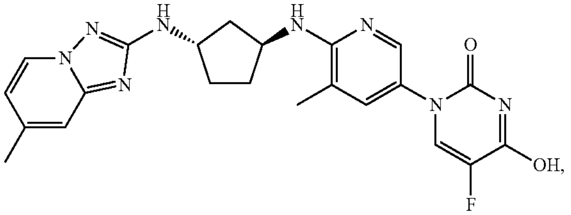
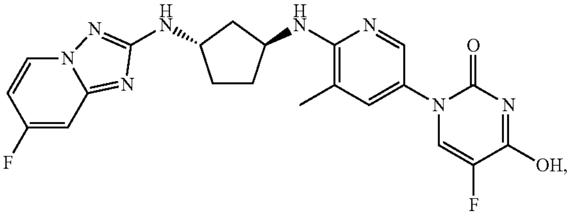
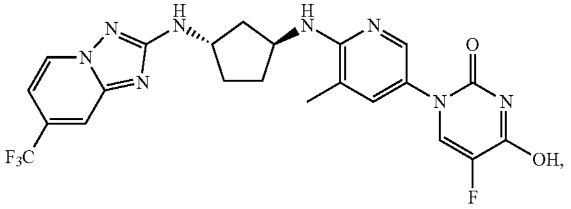
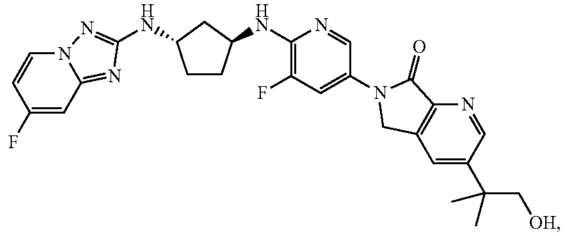
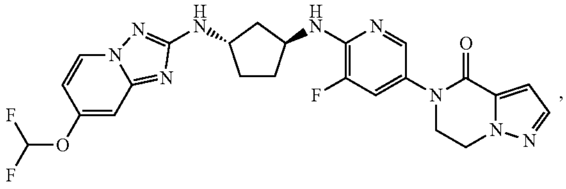
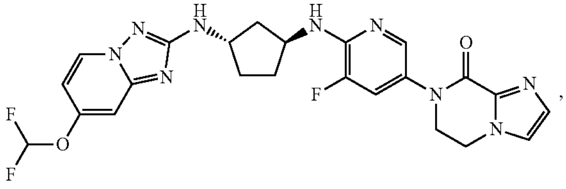
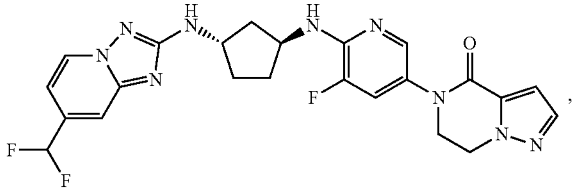

-continued
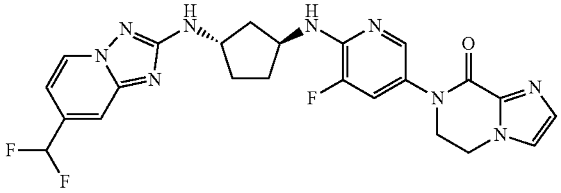,
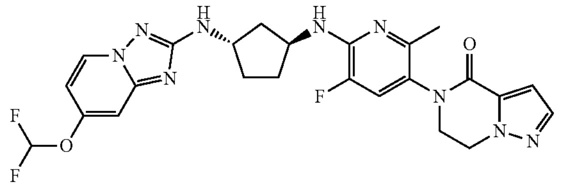,
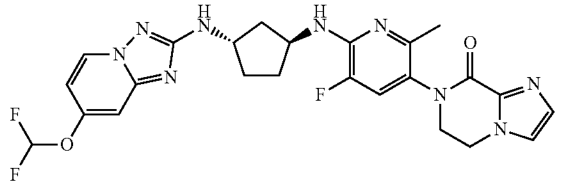,
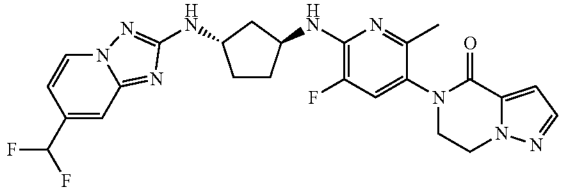,
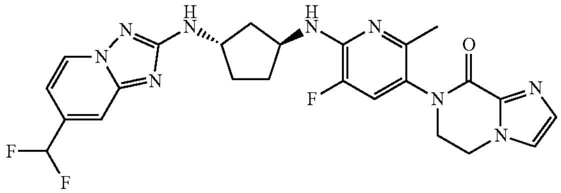,
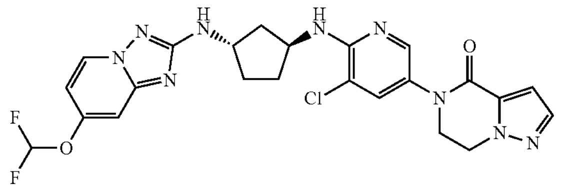,
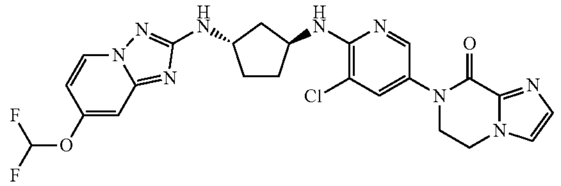,
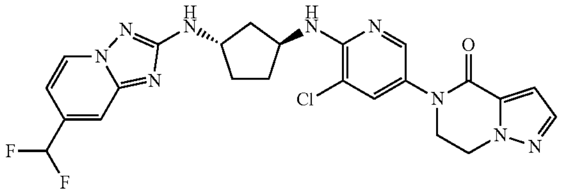,
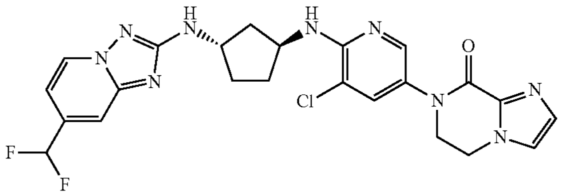,
-continued
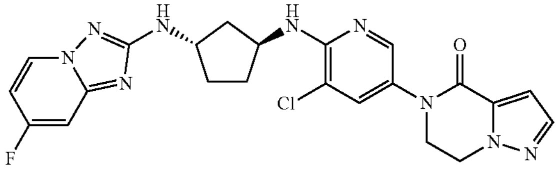,
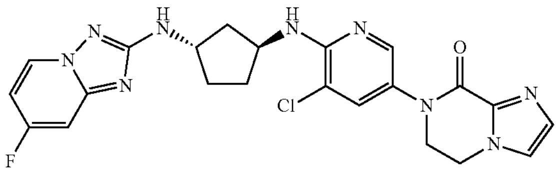,
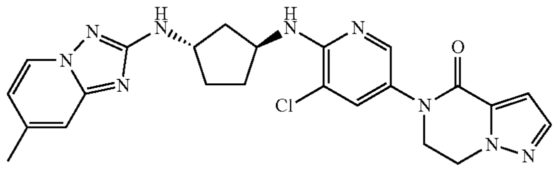,
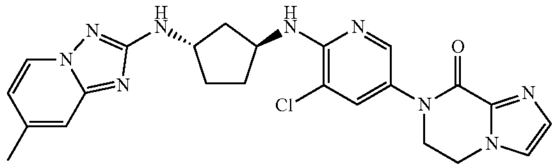,
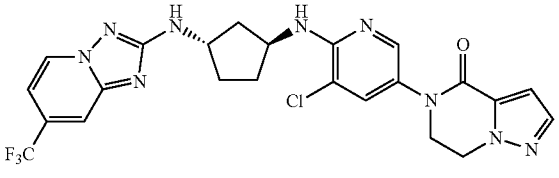,
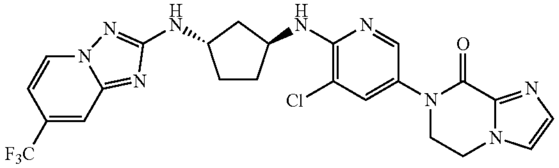,
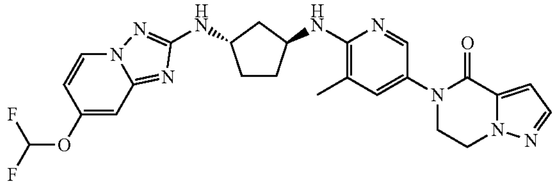,
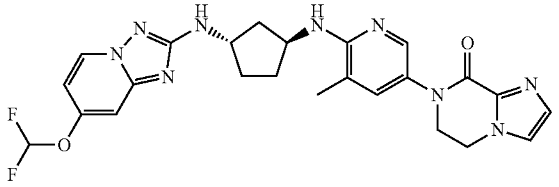,
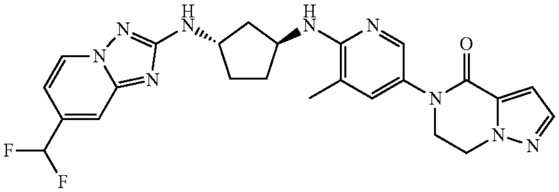, -continued
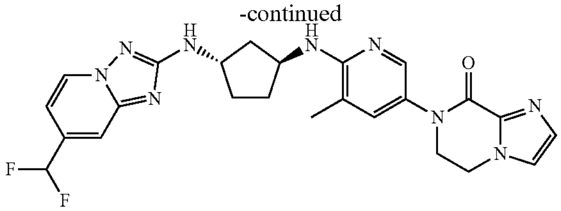,
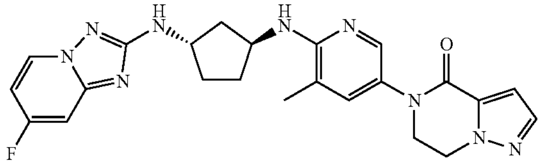,
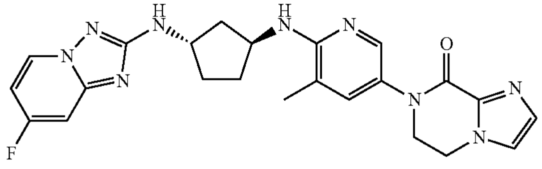,
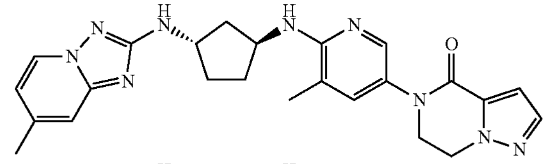,
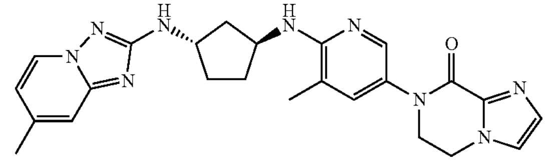,
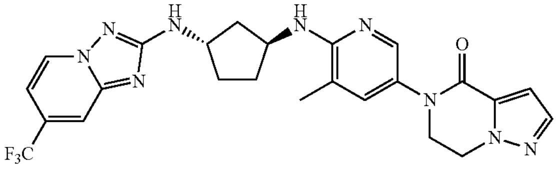,
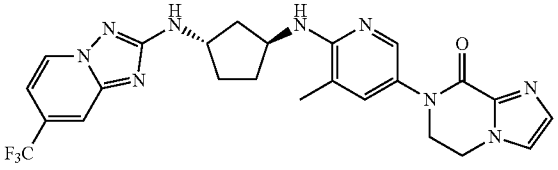,
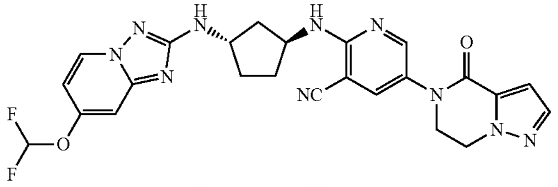,
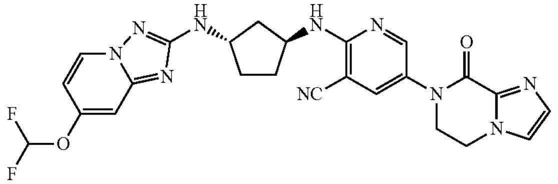,
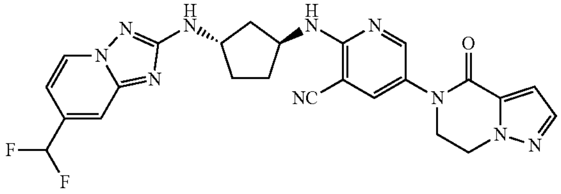,
-continued
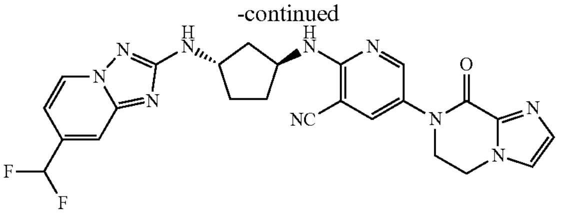,
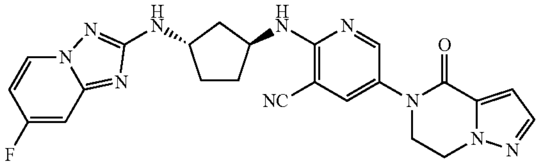,
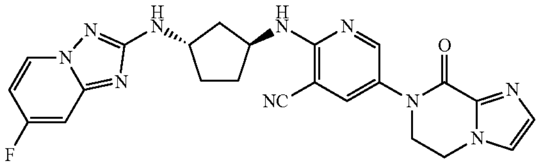,
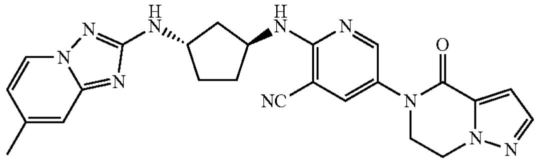,
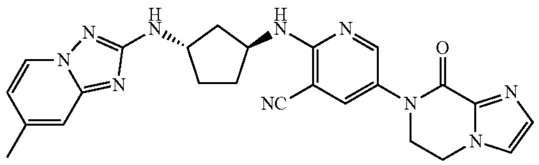,
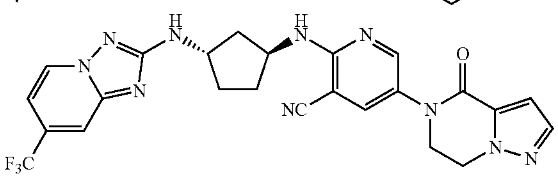,
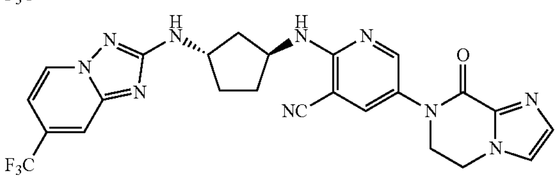,
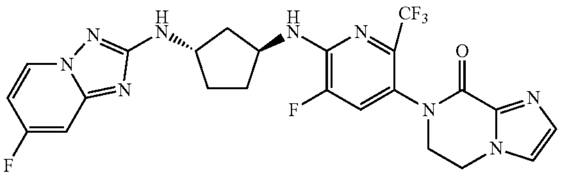,
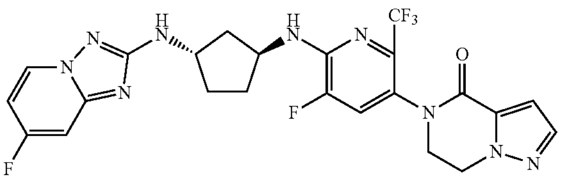,
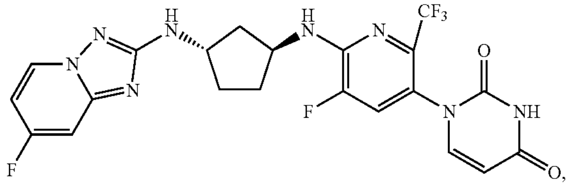, -continued
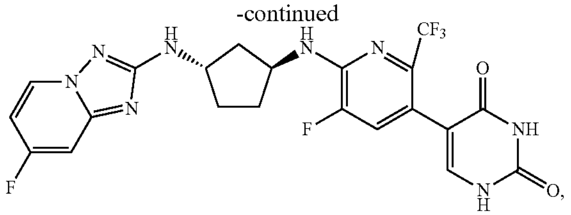
,
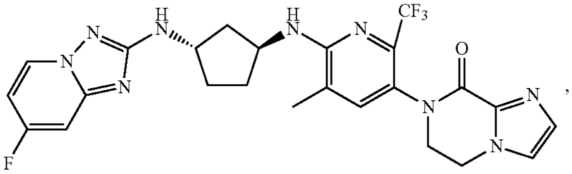
,
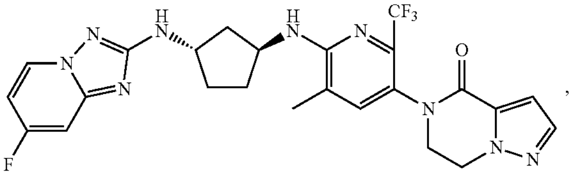
,
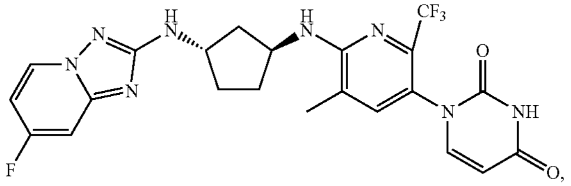
,
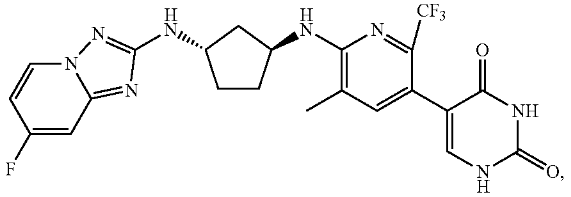
,
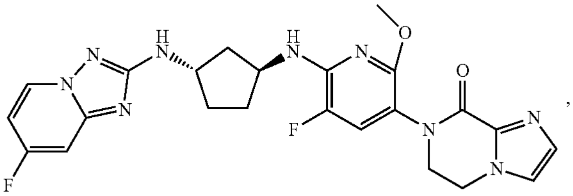
,
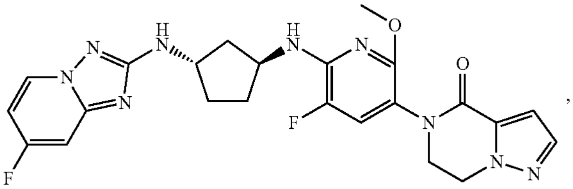
,
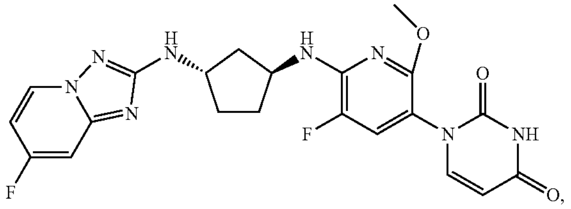
,
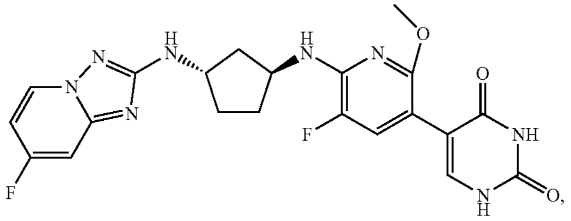
,
-continued
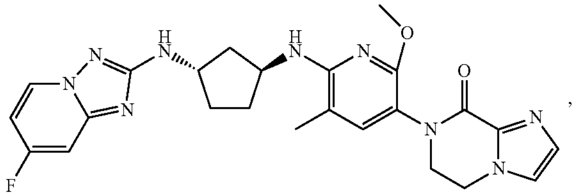
,
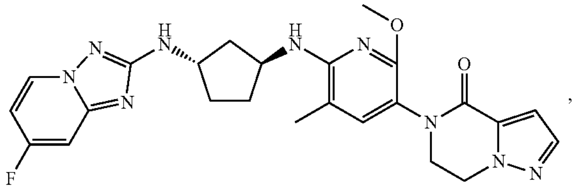
,
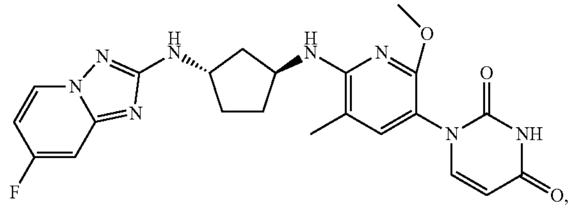
,
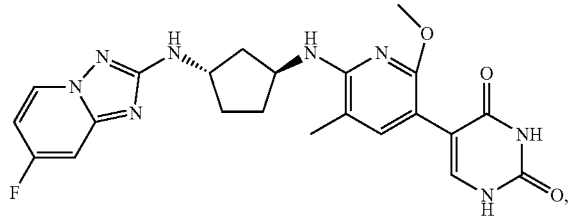
,
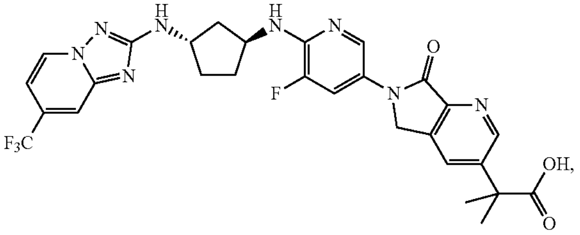
,
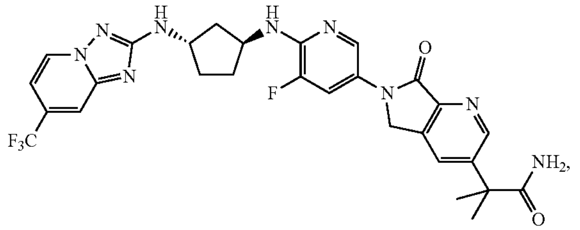
,
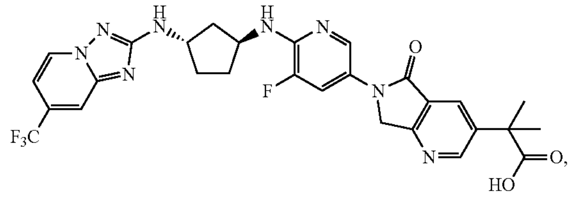
,
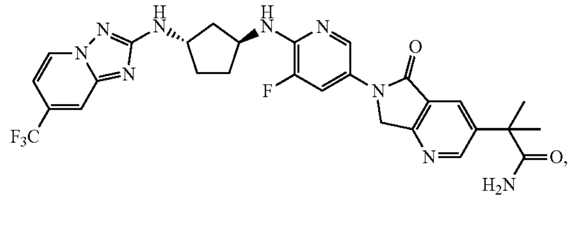
, -continued
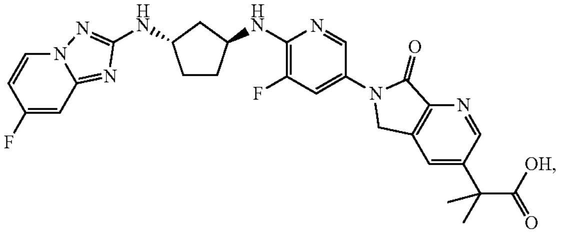
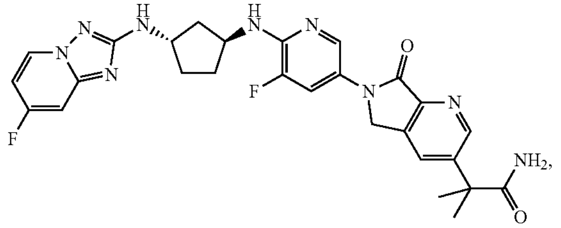
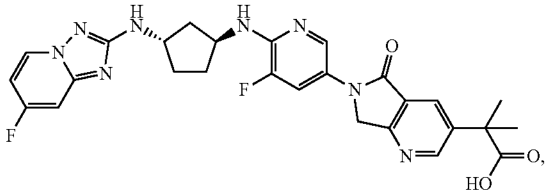
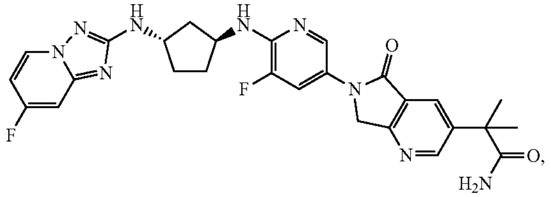
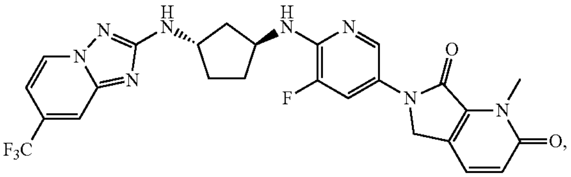
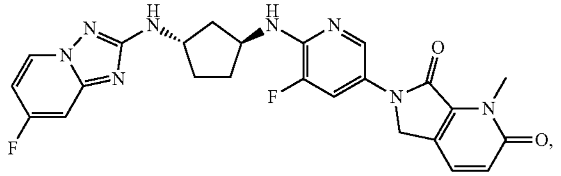
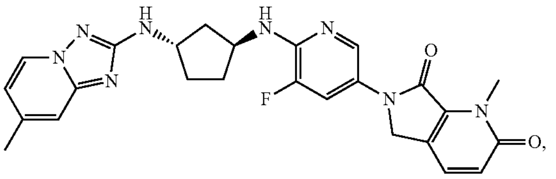
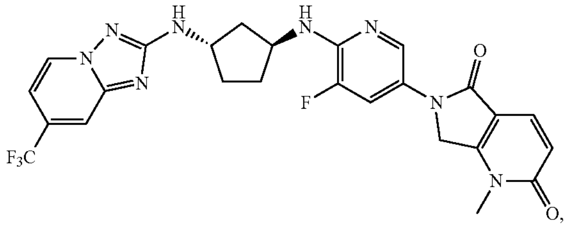
-continued
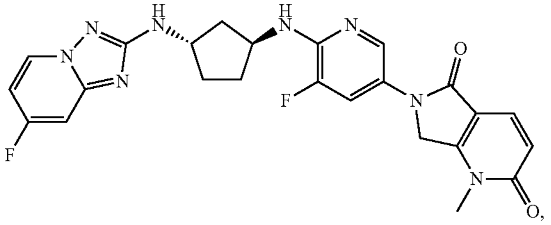
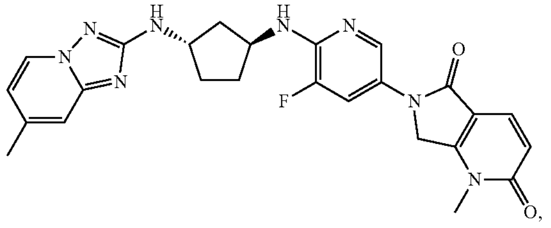
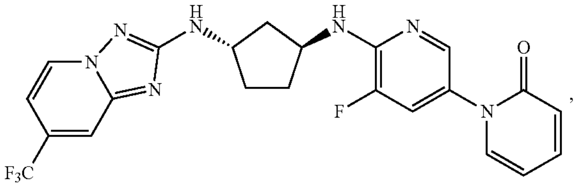
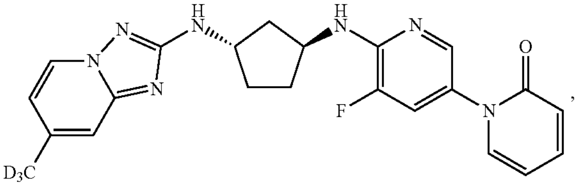
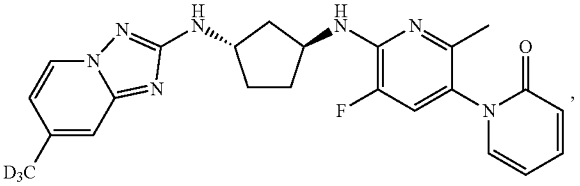
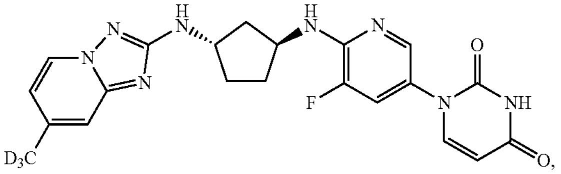
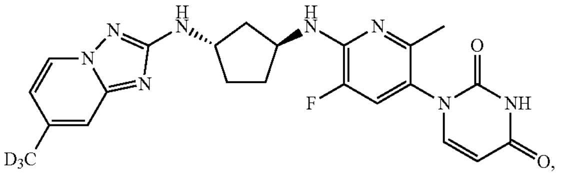
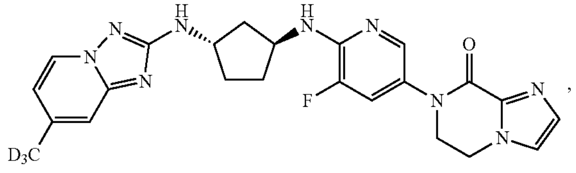
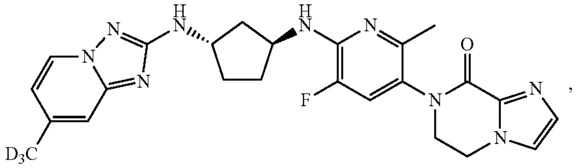

-continued
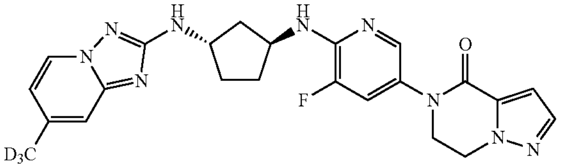
,
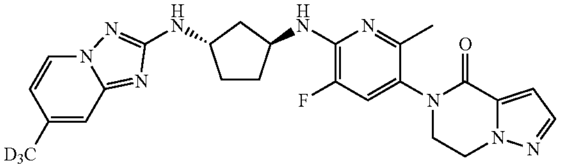
,
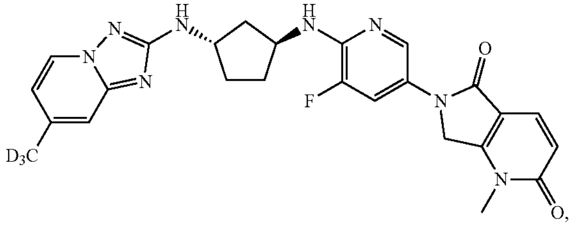
,
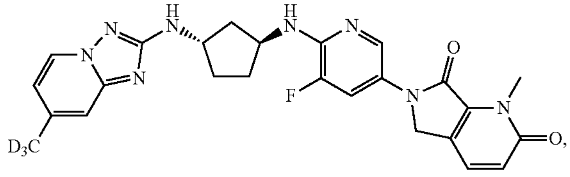
,
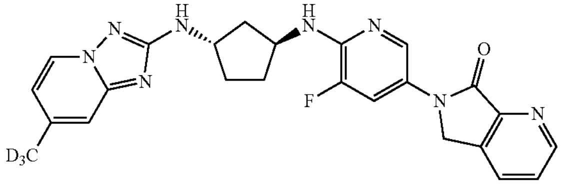
,
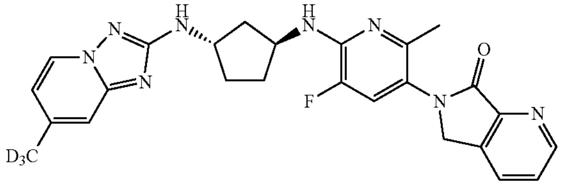
,
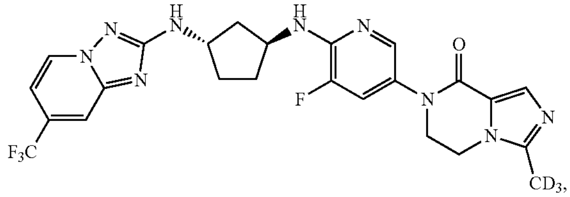
,
-continued
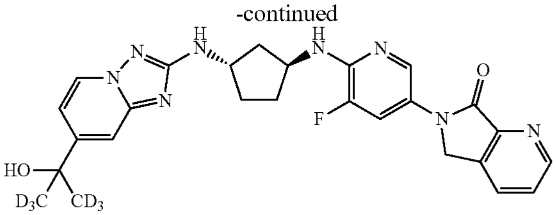
,
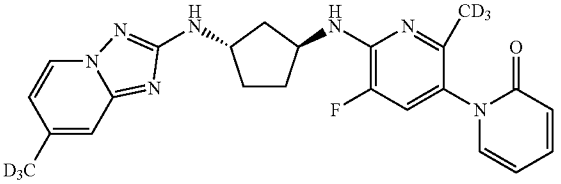
,
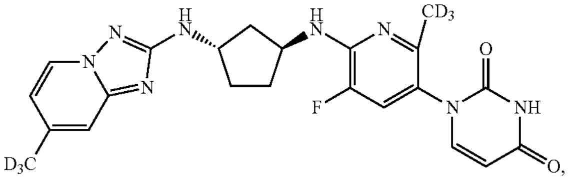
,
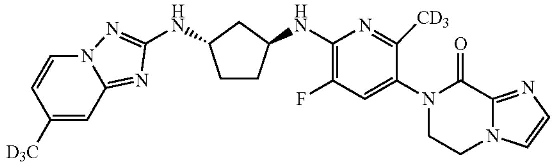
,
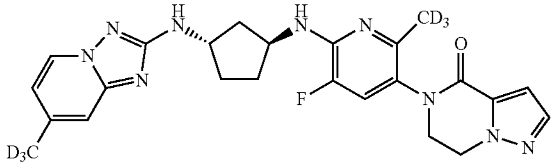
,
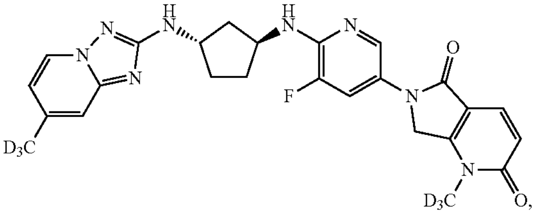
or
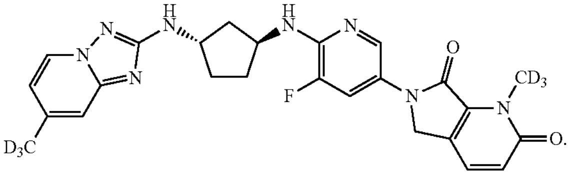 [SMILES: [2H]C([2H])([2H])c1ccn2nc(N[C@H]3CC[C@H](Nc4ncc(N5Cc6ccc(=O)n(C([2H])([2H])[2H])c6C5=O)cc4F)C3)nc2c1]
* * * * *